(12) United States Patent
Lauffer et al.

(10) Patent No.: US 8,232,406 B2
(45) Date of Patent: Jul. 31, 2012

(54) C-MET PROTEIN KINASE INHIBITORS

(75) Inventors: David J. Lauffer, Stow, MA (US);
Robert J. Davies, Watertown, MA (US);
Dean Stamos, Carlsbad, CA (US);
Alexander Aronov, Newton, MA (US);
David D. Deininger, Waltham, MA (US); Ronald Grey, Jr., Attleboro, MA (US); Jinwang Xu, Framingham, MA (US); Pan Li, Lexington, MA (US); Brian Ledford, Norton, MA (US); Luc Farmer, Foxborough, MA (US); Randy Scott Bethiel, Lexington, MA (US); Dylan Jacobs, Everett, MA (US); Kira McGinty, Schenectady, NY (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/942,395

(22) Filed: Nov. 9, 2010

(65) Prior Publication Data
US 2011/0059936 A1 Mar. 10, 2011

Related U.S. Application Data

(62) Division of application No. 11/726,170, filed on Mar. 21, 2007, now Pat. No. 7,872,031.

(60) Provisional application No. 60/784,937, filed on Mar. 22, 2006, provisional application No. 60/875,973, filed on Dec. 20, 2006.

(51) Int. Cl.
*A61K 31/4439* (2006.01)
(52) U.S. Cl. .................................. 546/268.4
(58) Field of Classification Search ............... 546/268.4
See application file for complete search history.

(56) References Cited

OTHER PUBLICATIONS

Suggitt et al. "50 Years of Preclinical Anticancer Drug Screening: Empirical to Target-Driven Approaches". 2005, Clinical Cancer Research,11,971-981.*
Voskoglou-Nomikos et al. "Clinical Predictive Value of the in vitro Cell line, Human Xenograft, and Mouse Allograft Preclinical Cancer Models". 2003, Clinical Cancer Research,9 ,4227-4239.*
Title A selective small molecule inhibitor of c-Met kinase inhibits c-Met-dependent phenotypes in vitro and exhibits cytoreductive antitumor activity in vivo. Author Christensen JG,Schreck R,Burrows J,Kuruganti P,Chan E,Le P,Chen J, Wang X,Ruslim L,Blake R,Lipson KE,Ramphal J,Do S,Cui JJ,Cherrington JM,Mendel DB Source Cancer Res 63(21) : 7345-55 2.
Title Hepatic gene expression of NK4, an HGF-antagonist/angiogenesis inhibitor, suppresses liver metastasis and invasive growth of colon cancer in mice. Author Wen J, Matsumoto K, Taniura N, Tomioka D, Nakamura T Source Cancer Gene Ther 11(6) : 419-430 2004.

Gaynor Davies et al. The HGF/SF Antagonist NK4 Reverses Fibroblast- and HGF-Induced Prostate Tumor Growth and Angiogenesis in Vivo. Int. J. Cancer: 106, 348-354 (2003).
Y Saga et al. Expression of HGF/NK4 in ovarian cancer cells suppresses intraperitoneal dissemination and extends host survival. Gene Therapy (2001) 8, 1450-1455.
Title c-Met: Structure, functions and potential for therapeutic inhibition Author Ma PC, Maulik G, Christensen J, Salgia R Source Cancer Metastasis Rev 22() : 309-325 2003.
Title c-Met and Hepatocyte Growth Factor: Potential as Novel Targets in Cancer Therapy. Author Sattler M, Salgia R Source Curr Oncol Rep 9(2) : 102-8 2007.
Title Hepatocyte growth factor/scatter factor and prostate cancer: a review. Author Hurle RA, Davies G, Parr C, Mason MD, Jenkins SA, Kynaston HG, Jiang WG Source Histol Histopathol 20(4) : 1339-1349 2005.
Title Inhibition of growth, invasion, and metastasis of human pancreatic carcinoma cells by NK4 in an orthotopic mouse model. Author Tomioka D,Maehara N,Kuba K,Mizumoto K,Tanaka M,Matsumoto K,Nakamura T Source Cancer Res 61(20) : 7518-24 2001.
Title C-Met overexpression in node-positive breast cancer identifies patients with poor clinical outcome independent of Her2/neu. Author Lengyel E, Prechtel D, Resau JH, Gauger K, Welk A, Lindemann K, Salanti G, Richter T, Knudsen B, Vande Woude GF, Harbeck N Source Int J Cancer 113(4) : 678-682 2004.
Title Growth and angiogenesis of human breast cancer in a nude mouse tumour model is reduced by NK4, a HGF/SF antagonist. Author Martin TA, Parr C, Davies G, Watkins G, Lane J, Matsumoto K, Nakamura T, Mansel RE, Jiang WG Source Carcinogenesis 24(8) : 1317-1323 2003.
Title Role of hepatocyte growth factor activator (HGF activator) in invasive growth of human glioblastoma cells in vivo. Author Uchinokura S, Miyata S, Fukushima T, Itoh H, Nakano S, Wakisaka S, Kataoka H Source Int J Cancer 118(3) : 583-592 2006.
Title Knockdown of c-Met by adenovirus-delivered small interfering RNA inhibits hepatocellular carcinoma growth in vitro and in vivo. Author Sheng-Zhou Zhang1,2, Fei-Yan Pan1, Jian-Feng Xu1, Jun Yuan1, Shi-Ying Guo1, Gu Dai1, Source Mol Cancer Ther 4(10) : 1577-1584 2005.

(Continued)

*Primary Examiner* — James O Wilson
*Assistant Examiner* — Brian McDowell
(74) *Attorney, Agent, or Firm* — Daniel A. Pearson

(57) ABSTRACT

The present invention relates to compounds useful of inhibitors of protein kinases. The invention also provides processes for preparing the compounds of this invention, pharmaceutically acceptable compositions comprising the compounds of the invention, and methods of using the compositions in the treatment of various disorders.

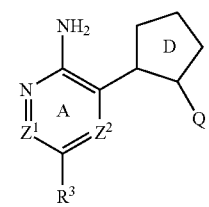

11 Claims, No Drawings

OTHER PUBLICATIONS

Title Inhibition of angiogenesis and HGF-cMET-elicited malignant processes in human hepatocellular carcinoma cells using adenoviral vector-mediated NK4 gene therapy. Author Heideman DA,Overmeer RM,van Beusechem VW, Lamers WH,Hakvoort TB,Snijders PJ,Craanen ME,Offerhaus GJ,Meijer CJ,Gerritsen WR Source Cancer Gene Ther 12(12) : 954-62 2005.

Title Suppression of tumor growth, invasion and angiogenesis of human gastric cancer by adenovirus-mediated expression of NK4. Author Heideman DA, Van Beusechem VW, Bloemena E, Snijders PJ, Craanen ME, Offerhaus GJ, Derksen PW, De Bruin M, Witlox MA, Molenaar B, Meijer CJ, Gerritsen WR Source J Gene Med 6(3) : 317-327 2004.

Title Functional expression and mutations of c-Met and its therapeutic inhibition with SU11274 and small interfering RNA in non-small cell lung cancer. Author Ma PC,Jagadeeswaran R,Jagadeesh S,Tretiakova MS,Nallasura V,Fox EA,Hansen M,Schaefer E,Naoki K,Lader A,Richards W,Sugarbaker D,Husain AN,Christensen JG,Salgia R Source Cancer Res 65(4) : 1479-88 2005.

* cited by examiner

US 8,232,406 B2

C-MET PROTEIN KINASE INHIBITORS

CROSS-REFERENCE TO RELATED APPLICATIONS

The present application is a divisional application of U.S. patent application Ser. No. 11/726,170 filed Mar. 21, 2007 now U.S. Pat. No. 7,872,031, which claims the benefit, under 35 U.S.C. §119, to U.S. Provisional Application No. 60/784, 937 filed Mar. 22, 2006 and U.S. Provisional Application No. 60/875,973 filed Dec. 20, 2006, the entire disclosures of each of which are incorporated herein by reference.

TECHNICAL FIELD OF THE INVENTION

The present invention relates to compounds useful as inhibitors of c-MET. The invention also provides pharmaceutically acceptable compositions comprising the compounds of the invention and methods of using the compositions in the treatment of various disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-MET, a receptor tyrosine kinase. c-MET, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-MET overexpression is implicated include, but are not limited to, gastric adenocarcinoma, renal cancer, small cell lung carcinoma, colorectal cancer, prostate cancer, brain cancer, liver cancer, pancreatic cancer, and breast cancer. c-MET is also implicated in atherosclerosis and lung fibrosis. Accordingly, there is a great need to develop compounds useful as inhibitors of c-MET protein kinase receptor.

SUMMARY OF THE INVENTION

It has been found that compounds of this invention, and pharmaceutically acceptable compositions thereof, are effective as inhibitors of c-MET. Accordingly, the invention features compounds having the formula:

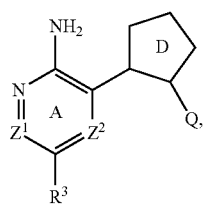

(I)

or a pharmaceutically acceptable salt thereof, wherein Ring A, ring D, $Z^1$, $Z^2$, $R^3$, and Q are as defined below.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, 75th Ed. 1994. Additionally, general principles of organic chemistry are described in "Organic Chemistry," Thomas Sorrell, University Science Books, Sausalito: 1999, and "March's Advanced Organic Chemistry," 5th Ed., Smith, M. B. and March, J., eds. John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group," as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments, aliphatic groups contain 1-4 carbon atoms. Suitable aliphatic groups include, but are not limited to, linear or branched, substituted or unsubstituted alkyl, alkenyl, or alkynyl groups. Further examples of aliphatic groups include methyl, ethyl, propyl, butyl, isopropyl, isobutyl, vinyl, and sec-butyl. The terms "alkyl" and the prefix "alk-," as used herein, are inclusive of both straight chain and branched saturated carbon chain. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloaliphatic" (or "carbocycle") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule, and wherein any individual ring in said bicyclic ring system has 3-7 members. Suitable cycloaliphatic groups include, but are not limited to, cycloalkyl, cycloalkenyl, and cycloalkynyl. Further examples of aliphatic groups include cyclopentyl, cyclopentenyl, cyclohexyl, cyclohexenyl, cycloheptyl, and cycloheptenyl.

The term "heterocycle," "heterocyclyl," "heterocycloaliphatic," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle," "heterocyclyl," "heterocycloaliphatic," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: tetrahydrofuran-2-yl, tetrahydrofuran-3-yl, tetrahydrothiophen-2-yl, tetrahydrothiophen-3-yl, 2-morpholino, 3-morpholino, 4-morpholino, 2-thiomorpholino, 3-thiomorpholino, 4-thiomorpholino, pyrrolidin-1-yl, pyrrolidin-2-yl, pyrrolidin-3-yl, tetrahydropiperazin-1-yl, tetrahydropiperazin-2-yl, tetrahydropiperazin-3-yl, piperidin-1-yl, piperidin-2-yl, piperidin-3-yl, piperidin-4-yl, pyrazolin-1-yl, pyrazolin-3-yl, pyrazolin-4-yl, pyrazolin-5-yl, thiazolidin-2-yl, thiazolidin-3-yl, thiazolidin-4-yl, thiazolidin-5-yl, imidazolidin-1-yl, imidazolidin-2-yl, imidazolidin-4-yl, imidazolidin-5-yl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydroimidazol-2-one.

The term "heteroatom" means one or more of oxygen, sulfur, nitrogen, phosphorus, or silicon, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or $NR^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to monocyclic, bicyclic, and tricyclic carbocyclic ring systems having a total of six to fourteen ring members, wherein at least one ring in the system is aromatic, wherein each ring in the system contains 3 to 7 ring members and that has a single point of attachment to the rest of the molecule. The term "aryl" may be used interchangeably with the term "aryl ring." Examples of aryl rings would include phenyl, naphthyl, and anthracene.

The term "heteroaryl," used alone or as part of a larger moiety as in "heteroaralkyl," or "heteroarylalkoxy," refers to monocyclic, bicyclic, and tricyclic ring systems having a total of five to fourteen ring members, wherein at least one ring in the system is aromatic, at least one ring in the system contains one or more heteroatoms, wherein each ring in the system contains 3 to 7 ring members and that has a single point of attachment to the rest of the molecule. The term "heteroaryl" may be used interchangeably with the term "heteroaryl ring" or the term "heteroaromatic." Further examples of heteroaryl rings include the following monocycles: furanyl (e.g., furan-2-yl or furan-3-yl); imidazolyl (e.g., N-imidazolyl, imidazol-2-yl, imidazol-4-yl, or imidazol-5-yl); isoxazolyl (e.g., isoxazol-3-yl, isoxazol-4-yl, isoxazol-5-yl); oxazolyl (e.g., oxazol-2-yl, oxazol-4-yl, or oxazol-5-yl); pyrrolyl (e.g., N-pyrrolyl, pyrrol-2-yl, or pyrrol-3-yl); pyridinyl (e.g., pyrid-2-yl, pyrid-3-yl, or pyrid-4-yl); pyrimidinyl (e.g., pyrimidin-2-yl, pyrimidin-4-yl, or pyrimidin-5-yl); pyridazinyl (e.g., pyridazin-3-yl, pyridazin-4-yl, pyridazin-5-yl, or pyridazin-6-yl); thiazolyl (e.g., thiazol-2-yl, thiazol-4-yl, or thiazol-5-yl); tetrazolyl (e.g., tetrazol-1-yl or tetrazol-5-yl); triazolyl (e.g., 2-triazolyl or 5-triazolyl), thienyl (e.g., thiophen-2-yl or thiophen-3-yl); pyrazolyl (e.g., pyrazol-2-yl, pyrazol-3-yl, or pyrazol-4-yl); isothiazolyl; 1,2,3-oxadiazolyl; 1,2,5-oxadiazolyl; 1,2,4-oxadiazolyl; 1,2,3-triazolyl; 1,2,3-thiadiazolyl; 1,3,4-thiadiazolyl; 1,2,5-thiadiazolyl; pyrazinyl; 1,3,5-triazinyl; and the following bicycles: benzimidazolyl; benzofuryl; benzothienyl; indolyl (e.g., 2-indolyl); purinyl; quinolinyl (e.g., 2-quinolinyl, 3-quinolinyl, or 4-quinolinyl); and isoquinolinyl (e.g., 1-isoquinolinyl, 3-isoquinolinyl, or 4-isoquinolinyl).

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of an aryl or heteroaryl group are selected from those listed in the definition of $R^1$, $R^2$, $R^3$, $R^4$, $J^M$, $J^Q$, or $J^R$ below. Other suitable substituents include: halogen; —$R^\circ$; —$OR^\circ$; —$SR^\circ$; 1,2-methylenedioxy; 1,2-ethylenedioxy; phenyl (Ph) optionally substituted with $R^\circ$; —O(Ph) optionally substituted with $R^\circ$; —$(CH_2)_{1\text{-}2}$(Ph), optionally substituted with $R^\circ$; —CH=CH(Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2R^\circ$; —$NR^\circ NR^\circ C(O)R^\circ$; —$NR^\circ NR^\circ C(O)N(R^\circ)_2$;

—NR°NR°CO$_2$R°; —C(O)C(O)R°; —C(O)CH$_2$C(O)R°; —CO$_2$R°; —C(O)R°; —C(S)R°; —C(O)N(R°)$_2$; —C(S)N(R°)$_2$; —OC(O)N(R°)$_2$; —OC(O)R°; —C(O)N(OR°)R°; —C(NOR°)R°; —S(O)$_2$R°; —S(O)$_2$OR°; —S(O)$_2$N(R°)$_2$; —S(O)R°; —NR°S(O)$_2$N(R°)$_2$; —NR°S(O)$_2$R°; —N(OR°)R°; —C(=NH)—N(R°)$_2$; —(CH$_2$)$_{0-2}$NHC(O)R°; -L-R°; -L-N(R°)$_2$; -L-SR°; -L-OR°; -L-(C$_{3-10}$ cycloaliphatic), -L-(C$_{6-10}$ aryl), -L-(5-10 membered heteroaryl), -L-(5-10 membered heterocyclyl), oxo, C$_{1-4}$ haloalkoxy, C$_{1-4}$ haloalkyl, -L-NO$_2$, -L-CN, -L-OH, -L-CF$_3$; or two substituents, together with the intervening atoms to which they are bound, form a 5-7 membered saturated, unsaturated, or partially saturated ring, wherein L is a C$_{1-6}$ alkylene group in which up to three methylene units are replaced by —NH—, —NR°—, —O—, —S—, —C(O)O—, —OC(O)—, —C(O)CO—, —C(O)—, —C(O)NH—, —C(O)NR°—, —C(=N—CN), —NHCO—, —NR°CO—, —NHC(O)O—, —NR°C(O)O—, —S(O)$_2$NH—, —S(O)$_2$NR°—, —NHS(O)$_2$—, —NR°S(O)$_2$—, —NHC(O)NH—, —NR°C(O)NH—, —NHC(O)NR°—, —NR°C(O)NR°, —OC(O)NH—, —OC(O)NR°—, —NHS(O)$_2$NH—, —NR°S(O)$_2$NH—, —NHS(O)$_2$NR°—, —NR°S(O)$_2$NR°—, —S(O)—, or —S(O)$_2$—, and wherein each independent occurrence of R° is selected from hydrogen, optionally substituted C$_{1-6}$ aliphatic, an unsubstituted 5-8 membered heteroaryl or heterocyclic ring, phenyl, —O(Ph), or —CH$_2$(Ph), or, two independent occurrences of R°, on the same substituent or different substituents, taken together with the atom(s) to which each R° group is bound, form a 5-8-membered heterocyclyl, aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of R° are selected from NH$_2$, NH(C$_{1-4}$aliphatic), N(C$_{1-4}$aliphatic)$_2$, halogen, C$_{1-4}$aliphatic, OH, O(C$_{1-4}$aliphatic), NO$_2$, CN, CO$_2$H, CO$_2$(C$_{1-4}$aliphatic), O(haloC$_{1-4}$ aliphatic), or haloC$_{1-4}$ aliphatic, wherein each of the foregoing C$_{1-4}$aliphatic groups of R° is unsubstituted.

In some embodiments, an aliphatic, cycloaliphatic, heteroaliphatic group, or a non-aromatic heterocyclic ring may contain one or more substituents. In some instances two substituents, on the same atom or on different atoms, together with the intervening atoms to which they are bound, form a 5-7 membered saturated, unsaturated, or partially saturated ring containing 0-3 heteroatoms selected from N, O, or S. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)$_2$, =NNHC(O)R*, =NNHCO$_2$(alkyl), =NNHS(O)$_2$ (alkyl), or =NR*, where each R* is independently selected from hydrogen or an optionally substituted C$_{1-6}$ aliphatic, or two R* on the same nitrogen are taken together with the nitrogen to form a 5-8 membered heterocyclyl or heteroaryl ring having 1-3 heteroatoms independently selected from nitrogen, oxygen, and sulfur. Optional substituents on the aliphatic group of R* are selected from NH$_2$, NH(C$_{1-4}$ aliphatic), N(C$_{1-4}$ aliphatic)$_2$, halogen, C$_{1-4}$ aliphatic, OH, O(C$_{1-4}$ aliphatic), NO$_2$, CN, CO$_2$H, CO$_2$(C$_{1-4}$ aliphatic), O(halo C$_{1-4}$ aliphatic), or halo (C$_{1-4}$ aliphatic), wherein each of the foregoing C$_{1-4}$aliphatic groups of R* is unsubstituted.

In some embodiments, optional substituents on the nitrogen of a non-aromatic heterocyclic ring include —R', —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R)$_2$, —C(=S)N(R$^+$)$_2$, —C(=NH)—N(R$^+$)$_2$, or —NR$^+$S(O)$_2$R$^+$; wherein R$^+$ is hydrogen, an optionally substituted C$_{1-6}$ aliphatic, optionally substituted phenyl, optionally substituted —O(Ph), optionally substituted —CH$_2$(Ph), optionally substituted —(CH$_2$)$_{1-2}$ (Ph); optionally substituted —CH=CH(Ph); or an unsubstituted 5-6 membered heteroaryl or heterocyclic ring having one to four heteroatoms independently selected from oxygen, nitrogen, or sulfur, or two independent occurrences of R$^+$, on the same substituent or different substituents, taken together with the atom(s) to which each R$^+$ group is bound, form a phenyl, 5-8-membered heterocyclyl, 5-8-membered heteroaryl, or a 3-8 membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R$^+$ are selected from —NH$_2$, —NH(C$_{1-4}$ aliphatic), —N(C$_{1-4}$ aliphatic)$_2$, halogen, C$_{1-4}$ aliphatic, —OH, —O(C$_{1-4}$ aliphatic), —NO$_2$, —CN, —C(O)OH, —C(O)O(C$_{1-4}$ aliphatic), —O(halo(C$_{1-4}$ aliphatic)), or halo(C$_{1-4}$ aliphatic), wherein each of the foregoing C$_{1-4}$aliphatic groups of R$^+$ is unsubstituted.

As detailed above, in some embodiments, two independent occurrences of R° (or R$^+$, or any other variable similarly defined herein), may be taken together with the atom(s) to which each variable is bound to form a phenyl, 5-8-membered heterocyclyl, 5-8-membered heteroaryl, or a 3-8 membered cycloalkyl ring. Exemplary rings that are formed when two independent occurrences of R° (or R', or any other variable similarly defined herein) are taken together with the atom(s) to which each variable is bound include, but are not limited to the following: a) two independent occurrences of R° (or R$^+$, or any other variable similarly defined herein) that are bound to the same atom and are taken together with that atom to form a ring, for example, N(R°)$_2$, where both occurrences of R° are taken together with the nitrogen atom to form a piperidin-1-yl, piperazin-1-yl, or morpholin-4-yl group; and b) two independent occurrences of R° (or R$^+$, or any other variable similarly defined herein) that are bound to different atoms and are taken together with both of those atoms to form a ring, for example where a phenyl group is substituted with two occurrences of OR°

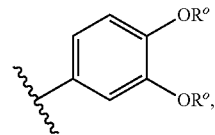

these two occurrences of R° are taken together with the oxygen atoms to which they are bound to form a fused 6-membered oxygen containing ring:

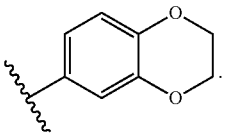

It will be appreciated that a variety of other rings can be formed when two independent occurrences of R° (or R$^+$, or any other variable similarly defined herein) are taken together with the atom(s) to which each variable is bound and that the examples detailed above are not intended to be limiting.

In some embodiments, a methylene unit of the alkyl or aliphatic chain is optionally replaced with another atom or group. Examples of such atoms or groups would include, but are not limited to, —NR°—, —O—, —S—, —C(O)O—, —OC(O)—, —C(O)CO—, —C(O)—, —C(O)NR°—, —C(=N—CN), —NR°CO—, —NR°C(O)O—, —S(O)$_2$NR°—, —NR°S(O)$_2$—, —NR°C(O)NR°—, —OC(O)NR°—, —NR°S(O)$_2$NR°—, —S(O)—, or —S(O)$_2$—, wherein R° is defined herein. Unless otherwise specified, the optional replacements form a chemically stable compound. Optional atom or group replacements can occur both within the chain and at either end of the chain; i.e. both at the point of attachment and/or also at the terminal end. Two optional replacements can also be adjacent to each other within a chain so long as it results in a chemically stable compound. Unless otherwise specified, if the replacement occurs at the terminal end, the replacement atom is bound to an H on the terminal end. For example, if one methylene unit of —CH$_2$CH$_2$CH$_3$ was optionally replaced with —O—, the resulting compound could be —OCH$_2$CH$_3$, —CH$_2$OCH$_3$, or —CH$_2$CH$_2$OH.

As described herein, a bond drawn from a substituent to the center of one ring within a multiple-ring system (as shown below) represents substitution of the substituent at any substitutable position in any of the rings within the multiple ring system. For example, Figure a represents possible substitution in any of the positions shown in Figure b.

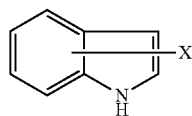

Figure a

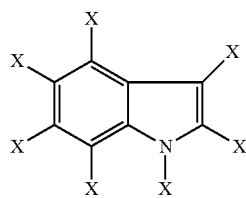

Figure b

This also applies to multiple ring systems fused to optional ring systems (which would be represented by dotted lines). For example, in Figure c, X is an optional substituent both for ring A and ring B.

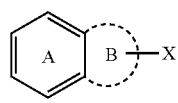

Figure c

If, however, two rings in a multiple ring system each have different substituents drawn from the center of each ring, then, unless otherwise specified, each substituent only represents substitution on the ring to which it is attached. For example, in Figure d, Y is an optionally substituent for ring A only, and X is an optional substituent for ring B only.

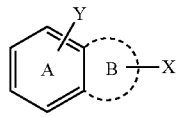

Figure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups in Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz).

The term "prodrug," as used herein, represents a compound that is transformed in vivo into a compound of formula I, I-A, I-B, I-C, I-D, or I-E, or a compound listed in Tables 1-5. Such a transformation can be affected, for example, by hydrolysis in blood or enzymatic transformation of the prodrug form to the parent form in blood or tissue. Prodrugs of the compounds of the invention may be, for example, esters. Esters that may be utilized as prodrugs in the present invention are phenyl esters, aliphatic (C$_1$-C$_{24}$) esters, acyloxymethyl esters, carbonates, carbamates, and amino acid esters. For example, a compound of the invention that contains an OH group may be acylated at this position in its prodrug form. Other prodrug forms include phosphates, such as, for example those phosphates resulting from the phosphorylation of an OH group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, and Judkins et al., *Synthetic Communications* 26(23):4351-4367, 1996, each of which is incorporated herein by reference.

Unless otherwise stated, structures depicted herein are also meant to include all isomeric (e.g., enantiomeric, diastereomeric, and geometric (or conformational)) forms of the structure; for example, the (R) and (S) configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays, or as c-MET inhibitors with improved therapeutic profile.

Description of Compounds of the Invention

In a first aspect, the invention features a compound having the formula:

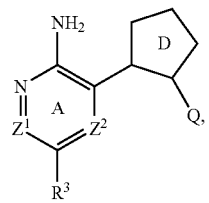

(I)

or a pharmaceutically acceptable salt thereof, wherein:
$Z^1$ is N or $CR^4$;
$Z^2$ is N or CH;
Ring D is the selected from:

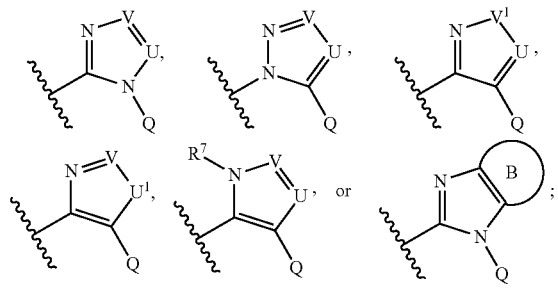

Ring B is a 5- or 6-membered aryl, cycloaliphatic, heteroaryl, or heterocyclyl ring, wherein said ring is optionally substituted with up to 4 occurrences of $R^B$ and said heteroaryl or heterocyclyl ring contains up to three heteroatoms selected from N, O, or S;
each $R^B$ is independently selected from halogen, $R^{B1}{}_5$—CN, —CO$_2R^{B1}$, —OC(O)$R^{B1}$, —OC(O)N($R^{B1}$), —NO$_2$, —N($R^{B1}$)$_2$, —NC(O)$R^{B1}$, —N($R^{B1}$)C(O)N($R^{B1}$)$_2$, —S$R^{B1}$, —S(O)$_2R^{B1}$, —S(O)$_2$N($R^{B1}$)$_2$, or —S(O)$R^{B1}$, wherein each $R^{B1}$ is, independently, hydrogen or $C_{1-4}$ aliphatic, or two $R^{B1}$ together with the atom to which they are bound, form a 3 membered carbocycle optionally substituted with 0-2 occurrences of $J^R$ or a 3-6 membered heterocyclyl containing 1-3 heteroatoms independently selected from N, O, or S and optionally substituted with 0-2 occurrences of $J^R$ on carbon and optionally substituted with $J^N$ on each substitutable ring nitrogen atom;
Q is $C_{6-10}$ aryl or 5-10 membered heteroaryl wherein each Q is optionally substituted with up to 5 occurrences of $J^Q$;
U is N or $CR^1$;
V is N or $CR^2$;
$U^1$ is O, $NR^5$, or S;
$V^1$ is O, $NR^6$, or S;
$R^1$ is hydrogen, halogen, —CN, —NH$_2$, —OH, $C_{1-2}$ haloalkyl, or selected from —NH($C_{1-4}$ aliphatic), —N($C_{1-4}$ aliphatic)$_2$, $C_{3-4}$ cycloalkyl, —($C_{1-2}$ aliphatic)-($C_{3-4}$ cycloalkyl), or $C_{1-4}$ aliphatic, each of which is optionally substituted with up to 2 occurrences of $J^R$;
$R^2$ is hydrogen, halogen, —CN, —NH$_2$, —NH($C_{1-4}$ aliphatic), —N($C_{1-4}$ aliphatic)$_2$, $C_{1-2}$ haloalkyl, $C_{3-4}$ cycloalkyl, or $C_{1-4}$ aliphatic;
$R^3$ is halogen or $R^A$, wherein $R^A$ is $C_{6-10}$ aryl, 5-10 membered heteroaryl, 5-12 membered heterocyclyl, or $C_{3-8}$ cycloaliphatic, each of which is optionally substituted with 0-3 occurrences of $J^M$;
$R^4$ is hydrogen, —CN, $C_{1-4}$ aliphatic, halogen or $C_{1-2}$ haloalkyl;
each of $R^5$, $R^6$, and $R^7$, is, independently, hydrogen or $J^N$;
each $J^M$ is independently selected from halogen, —NO$_2$, —CN, $C_{1-4}$ aliphatic, $C_{1-2}$ haloalkyl, —(CH$_2$)$_{0-2}$CH(R')$_2$, —OH, —OR', —(CR'''$_2$)$_q$NH$_2$, —(CR'''$_2$)$_q$NHR', —(CR'''$_2$)$_q$N(R)$_2$, —(CR'''$_2$)$_q$NHS(O)$_2$R', —(CR'''$_2$)$_q$NHC(O)R', —(CR'''$_2$)$_q$NHC(O)OR', —(CR'''$_2$)$_q$NHC(O)NH$_2$, —(CR'''$_2$)$_q$NHC(C)NHR', —(CR'''$_2$)$_q$NHC(O)N(R')$_2$, —(CR'''$_2$)$_q$NHC(NH)NH$_2$, —(CR'''$_2$)$_q$NHC(NH)NHR', —(CR'''$_2$)$_q$NHC(NR)N(R')$_2$, —(CR'''$_2$)$_q$NHS(O)$_2$NH$_2$, —(CR'''$_2$)$_q$NHS(O)$_2$NHR', —(CR'''$_2$)$_q$NHS(O)$_2$N(R)$_2$, —SH, —SR', —(CR'''$_2$)$_q$CO$_2$H, —(CR'''$_2$)$_q$CO$_2$R', —C(O)H, —(CR'''$_2$)$_q$C(O)R', —(CR'''$_2$)$_q$—C(O)—(CH$_2$)$_{0-2}$CH(R')$_2$, —(CR'''$_2$)$_q$—C(O)—(CH$_2$)$_{0-2}$NHCH(R)$_2$, —(CR'''$_2$)$_q$—C(O)—(CH$_2$)$_{0-2}$NR'CH(R')$_2$, —(CR'''$_2$)$_q$—C(O)NH$_2$, —(CR'''$_2$)$_q$—C(O)NHR', —(CR'''$_2$)$_q$—C(O)N(R')$_2$, —(CR'''$_2$)$_q$—C(O)N(OH)R', —(CR'''$_2$)$_q$—C(O)N(OR')R', —(CR'''$_2$)$_q$—C(O)N(OR')H, —(CR'''$_2$)$_q$—C(O)N(OH)H, —(CR'''$_2$)$_q$C(=NOH)R', —(CR'''$_2$)$_q$C(=NOR')H, —(CR'''$_2$)$_q$—C(NOR')R', —(CR'''$_2$)$_q$—S(O)$_2$R', —(CR'''$_2$)$_q$—S(O)$_2$OH, —(CR'''$_2$)$_q$—S(O)$_2$OR', —(CR'''$_2$)$_q$—S(O)$_2$NH$_2$, —(CR'''$_2$)$_q$—S(O)$_2$NHR', —(CR'''$_2$)$_q$—S(O)$_2$N(R')$_2$, —(CR'''$_2$)$_q$—S(O)R', —(CR'''$_2$)$_q$C(=NR')—NH$_2$, —(CR'''$_2$)$_q$C(=NR')—NHR', —(CR'''$_2$)$_q$C(=NR')—N(R')$_2$, —(CR'''$_2$)$_q$C(=NH)—NH$_2$, —(CR'''$_2$)$_q$C(=NH)—NHR', —(CR'''$_2$)$_q$C(=NH)—N(R')$_2$, $C_{6-10}$ aryl, 5-10 membered heteroaryl, 5-10 membered heterocyclyl, or $C_{3-8}$ cycloaliphatic, wherein q is selected from 0-4; or two $J^M$, together with the atom or atoms to which they are bound, form a 3-6 membered cycloaliphatic or heterocyclyl ring; wherein each of said cycloaliphatic or heterocyclyl is optionally substituted with up to 3 occurrences of $J^N$ or $J^R$;
each $J^N$ is independently selected from —(CR'''$_2$)$_q$C$_{1-4}$ aliphatic, —(CR'''$_2$)$_q$C$_{3-6}$ cycloalkyl, —(CR'''$_2$)$_q$phenyl, —(CR'''$_2$)$_q$C(O)C$_{1-4}$aliphatic, —(CR'''$_2$)$_q$C(O)C$_{1-2}$haloalkyl, —C(O)O(C$_{1-4}$alkyl), —(CR'''$_2$)$_q$C(O)NH$_2$, —(CR'''$_2$)$_q$C(O)NH(C$_{1-4}$aliphatic), —(CR'''$_2$)$_q$C(O)N(C$_{1-4}$aliphatic)$_2$, or —S(O)$_2$C$_{1-4}$aliphatic, wherein q' is 0-2 and each aliphatic or cycloaliphatic is optionally substituted with up to 2 occurrences of $J^R$;
each $J^Q$ is independently selected from halogen, —NO$_2$, —CN, $C_{1-4}$ aliphatic, $C_{1-4}$ haloalkyl, —OH, —OR'', —NH$_2$, —NHR'', —N(R'')$_2$, —SH, —SR'', —CO$_2$H, —CO$_2$R", —C(O)H, —C(O)R", —C(O)NH$_2$, —C(O)NHR", —C(O)N(R")$_2$, —C(O)N(OH)R", —C(O)N(OR")R", —C(O)N(OR")H, —C(O)N(OH)H, —C(NOH)R", —C(NOR")H, —C(NOR")R", —S(O)$_2$R", —S(O)$_2$OH, —S(O)$_2$OR", —S(O)$_2$NH$_2$, —S(O)$_2$NHR", —S(O)$_2$N(R")$_2$, —S(O)R", —C(=NR')—NH$_2$, —C(=NR')—NHR', —C(=NR')—N(R')$_2$, —C(=NH)—NH$_2$, —C(=NH)—NHR", —C(=NH)—N(R")$_2$, $C_{6-10}$ aryl, 5-10 membered heteroaryl, 5-10 membered heterocyclyl, or $C_{3-8}$ cycloaliphatic;

each $J^R$ is independently selected from halogen, —NO$_2$, —CN, $C_{1-4}$ aliphatic, $C_{1-4}$ haloalkyl, $C_{3-4}$ cycloalkyl, —OH, —NH$_2$, —O($C_{1-4}$ aliphatic), —N($C_{1-4}$ aliphatic)$_2$, or —NH($C_{1-4}$ aliphatic);

each R' is independently selected from unsubstituted $C_{1-6}$ aliphatic; or two R' groups, together with the atom(s) to which they are bound, form a 3-6 membered cycloaliphatic or heterocyclyl, each optionally substituted with up to 2 occurrences of $J^R$;

each R" is independently selected from unsubstituted $C_{1-6}$ aliphatic; or two R" groups, together with the atom to which they are bound, form a 3-6 membered heterocyclyl, optionally substituted with up to 2 occurrences of $J^R$; and each R''' is independently selected from hydrogen or $C_{1-4}$ aliphatic, or an R''' group and an R' group, together with the atoms to which they are bound, form a 3-6 membered cycloaliphatic or heterocyclyl, each optionally substituted with up to 2 occurrences of $J^R$.

In one embodiment,
$Z^1$ is N or $CR^4$;
$Z^2$ is N or CH;
Ring D is the selected from one of the 5-membered rings shown below:

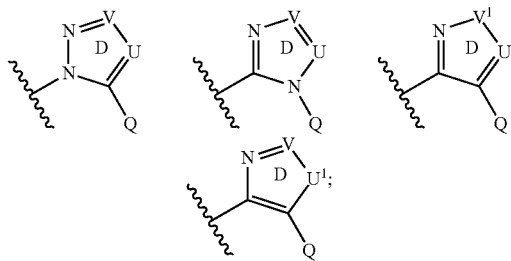

each of $R^5$ and $R^6$ is hydrogen, $C_{1-2}$ haloalkyl, or selected from $C_{3-4}$ cycloalkyl, —($C_{1-2}$ aliphatic)-($C_{3-4}$ cycloalkyl), or $C_{1-4}$ aliphatic, each of which is optionally substituted with up to 2 occurrences of $J^R$;

$R^3$ is a $C_{6-10}$ aryl, 5-10 membered heteroaryl, 5-10 membered heterocyclyl, or $C_{3-8}$ cycloaliphatic, each of which is optionally substituted with 0-3 occurrences of $J^M$;

each $J^Q$ is, independently, selected from halogen, —NO$_2$, —CN, $C_{1-4}$ aliphatic, $C_{1-4}$ haloalkyl, —OH, —OR", —NH$_2$, —NHR", —N(R")$_2$, —SH, —SR", —CO$_2$H, —CO$_2$R", —C(O)H, —C(O)R", —C(O)NH$_2$, —C(O)NHR", —C(O)N(R")$_2$, —C(O)N(OH)R", —C(O)N(OR")R", —C(O)N(OR")H, —C(O)N(OH)H, —C(NOH)R", —C(NOR")H, —C(NOR")R", —S(O)$_2$R", —S(O)$_2$OH, —S(O)$_2$OR", —S(O)$_2$NH$_2$, —S(O)$_2$NHR", —S(O)$_2$N(R")$_2$, —S(O)R", —C(=NR')—NH$_2$, —C(=NR')—NHR', —C(=NR')—N(R')$_2$, —C(=NH)—NH$_2$, —C(=NH)—NHR", —C(=NH)—N(R")$_2$, $C_{6-10}$ aryl, 5-10 membered heteroaryl, 5-10 membered heterocyclyl, or $C_{3-8}$ cycloaliphatic;

each $J^R$ is, independently, selected from halogen, —NO$_2$, —CN, $C_{1-4}$ aliphatic, $C_{1-4}$ haloalkyl, $C_{3-4}$ cycloalkyl, —OH, —NH$_2$, —O($C_{1-2}$ aliphatic), —N($C_{1-2}$ aliphatic)$_2$, or —NH($C_{1-2}$ aliphatic);

each $J^L$ is independently selected from halogen, —NO$_2$, —CN, $C_{1-4}$ aliphatic, $C_{1-4}$ haloalkyl, —OH, —NH$_2$, —O($C_{1-2}$ aliphatic), —N($C_{1-2}$ aliphatic)$_2$, or —NH($C_{1-2}$ aliphatic); and each $J^M$ is, independently, selected from halogen, —NO$_2$, —CN, $C_{1-4}$ aliphatic, $C_{1-2}$ haloalkyl, —OH, —OR', —(CR'''$_2$)$_q$NH$_2$, —(CR'''$_2$)$_q$NHR', —(CR'''$_2$)$_q$N(R')$_2$, —(CR''$_2$)$_q$NS(O)$_2$R', —(CR''$_2$)$_q$NHC(O)R', —(CR''$_2$)$_q$NHC(O)OR', —(CR''$_2$)$_q$NHC(O)NH$_2$, —(CR''$_2$)$_q$NHC(O)NHR', —(CR''$_2$)$_q$NHC(O)N(R')$_2$, —(CR''$_2$)$_q$NHS(O)$_2$NH$_2$, —(CR'''$_2$)$_q$NHS(O)$_2$NHR', —(CR''$_2$)$_q$NHS(O)$_2$N(R')$_2$, —SH, —SR', —CO$_2$H, —CO$_2$R', —C(O)H, —C(O)R', —C(O)NH$_2$, —C(O)NHR', —C(O)N(R')$_2$, —C(O)N(OH)R', —C(O)N(OR')R', —C(O)N(OR')H, —C(O)N(OH)H, —C(=NOH)R', —C(=NOR')H, —C(NOR')R', —S(O)$_2$R', —S(O)$_2$OH, —S(O)$_2$OR', —S(O)$_2$NH$_2$, —S(O)$_2$NHR', —S(O)$_2$N(R')$_2$, —S(O)R', —C(=NR')—NH$_2$, —C(=NR')—NHR', —C(=NR')—N(R')$_2$, —C(=NH)—NH$_2$, —C(=NH)—NHR', —C(=NH)—N(R')$_2$, $C_{6-10}$ aryl, 5-10 membered heteroaryl, 5-10 membered heterocyclyl, or $C_{3-8}$ cycloaliphatic, wherein q is selected from 0-4;

each R' is, independently, selected from unsubstituted $C_{1-6}$ aliphatic; or two R' groups, together with the atom to which they are bound, form a 3-6 membered heterocyclyl, optionally substituted with 0-2 occurrences of $J^R$;

each R" is, independently, selected from unsubstituted $C_{1-6}$ aliphatic; or two R" groups, together with the atom to which they are bound, form a 3-6 membered heterocyclyl, optionally substituted with 0-2 occurrences of $J^R$; and each R''' is, independently, selected from hydrogen or $C_{1-4}$ aliphatic.

In one embodiment for compounds of the invention, Ring D is selected from:

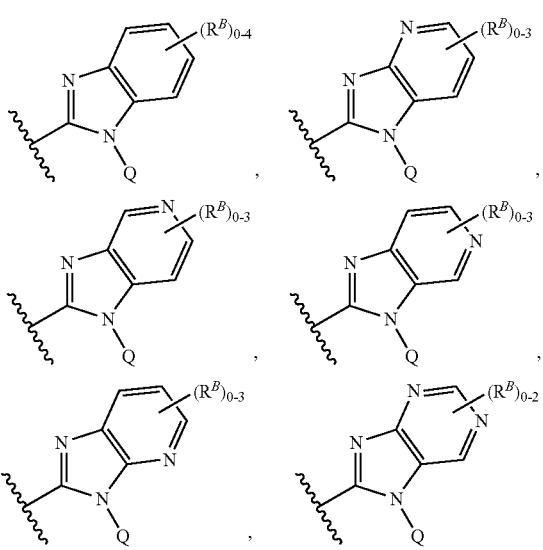

or 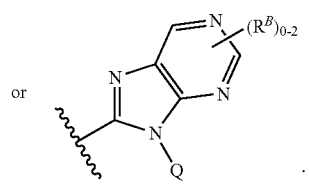
In another embodiment, Ring D is selected from:
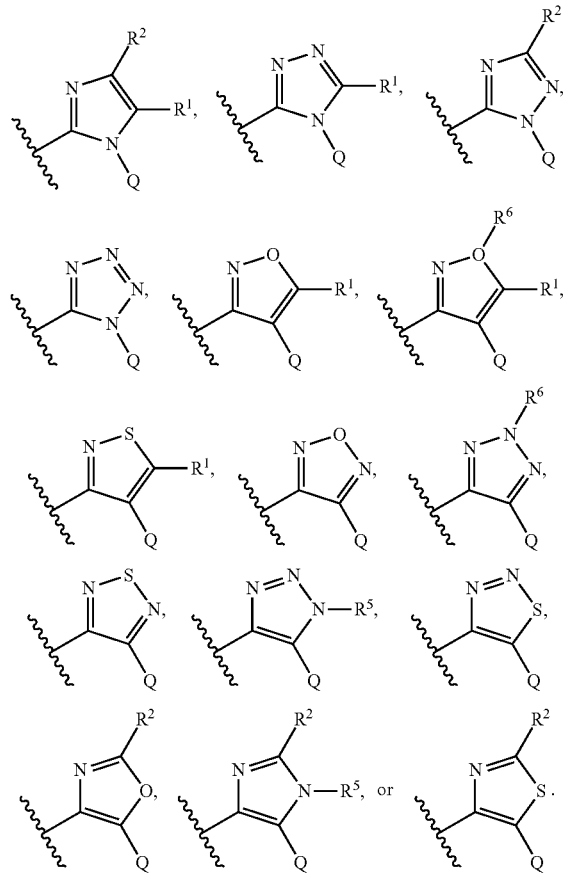
In a further embodiment, Ring D is
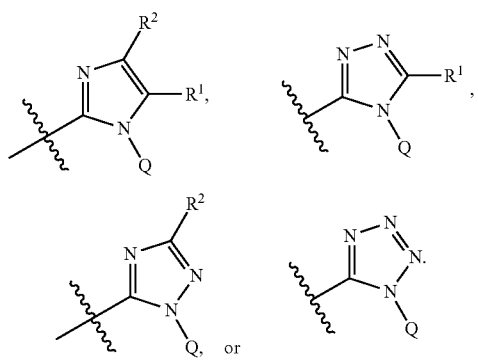
In an alternative embodiment, Ring D is selected from
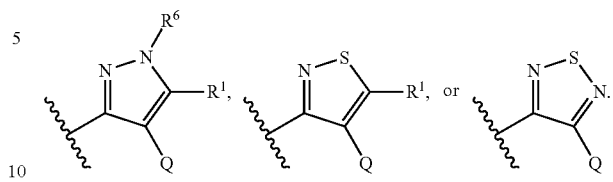
In another embodiment, Ring D is selected from
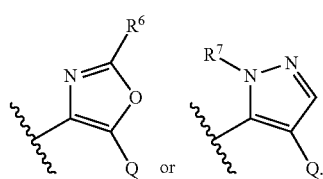
In another embodiment, Ring D is selected from
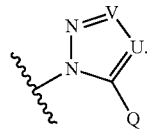
In a further embodiment, Ring D is
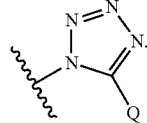
In one embodiment, Ring A is selected from
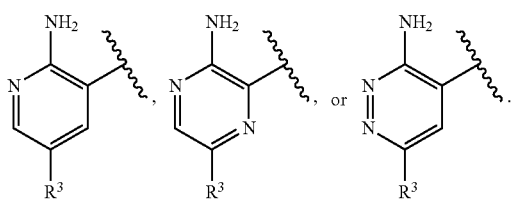
In a further embodiment, Ring A is
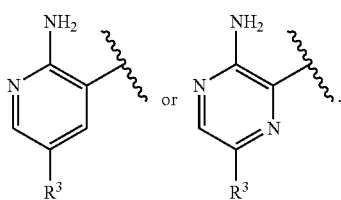

Compounds of the invention include those of formulae II or III:

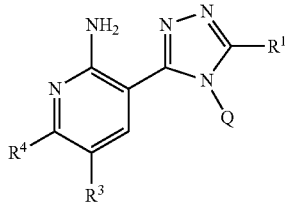
(II)

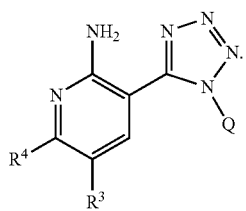
(III)

In one embodiment for compounds of the invention, $R^4$ is hydrogen.

In one embodiment for compounds of the invention, Q is

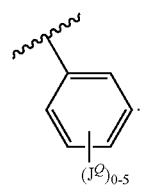

In a further embodiment, Q is

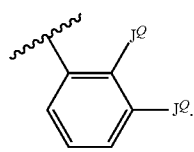

In yet a further embodiment, each $J^Q$ is, independently, fluoro or chloro, such as, for example, when Q is

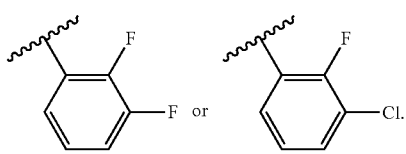

In one embodiment for compounds of the invention, $R^3$ is $R^A$, which is a $C_{6-10}$ aryl, a $C_{3-8}$ cycloaliphatic, or a monocyclic or bicyclic 5-10 membered heteroaryl or heterocyclyl containing 1-4 heteroatoms independently selected from N, O, or S, wherein said aryl, cycloaliphatic, heteroaryl, or heterocyclyl is optionally substituted with up to 3 occurrences of $J^M$.

In another embodiment, $R^A$ is phenyl optionally substituted with up to 3 occurrences of $J^M$. In another embodiment, $R^A$ is a 5-6 membered heteroaryl optionally substituted with up to 3 occurrences of $J^M$, such as, for example, an optionally substituted pyridyl, thienyl, thiazolyl, isothiazolyl, pyrrolyl, pyrazolyl, imidazolyl, triazolyl, furanyl, isoxazolyl, or oxazolyl. Further examples include 1H-pyrazol-4-yl substituted at the 1-position with $J^M$, thiophen-2-yl substituted at the 5-position with $J^M$, thiophen-3-yl substituted at the 5-position with $J^M$, furan-2-yl substituted at the 5-position with $J^M$, furan-3-yl substituted at the 5-position with $J^M$, 1H-pyrrol-3-yl substituted at the 1-position with $J^M$, 1H-1,2,3-triazol-4-yl substituted at the 1-position with $J^M$, or thiazol-5-yl substituted at the 2-position with $J^M$.

Examples of $J^M$ include those where $J^M$ is selected from phenyl, 5-8 membered heteroaryl, 5-10 membered heterocyclyl, or $C_{3-8}$cycloaliphatic; each optionally substituted with up to 3 occurrences of $J^N$ or $J^R$. In a further example, $J^M$ is an optionally substituted 5-10 membered heterocyclyl containing 1 or 2 nitrogen atoms, such as, for example an optionally substituted piperidine, piperazine or pyrrolidine or an optionally substituted bicyclooctane or bicyclononane containing 1 or 2 nitrogen atoms.

In another embodiment, $R^A$ is a $C_{8-10}$ bicyclic heteroaryl selected from:

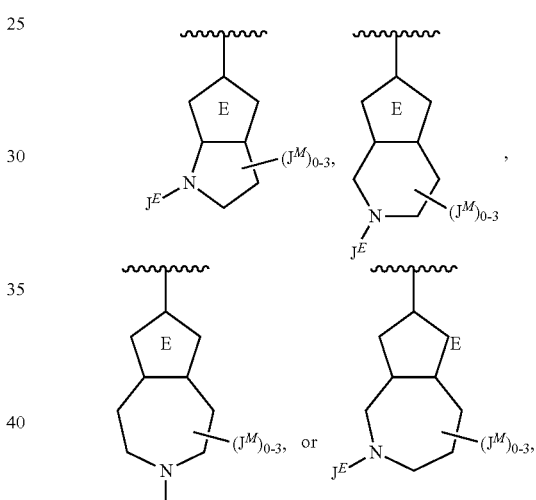

wherein Ring E is a 5-membered heteroaryl ring with 1 to 2 heteroatoms selected from N, O, or S; and $J^E$ is hydrogen or $J^N$.

In a further embodiment, Ring E is selected from thienyl, thiazolyl, pyrrolyl, imidazolyl, furanyl, or oxazolyl.

In another embodiment, $R^A$ is

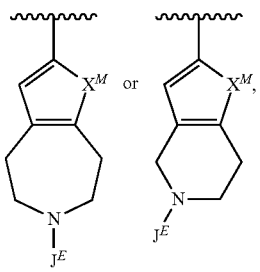

wherein $X^M$ is O or S.

In another embodiment, $R^A$ is a 5-7 membered heterocyclyl selected from:

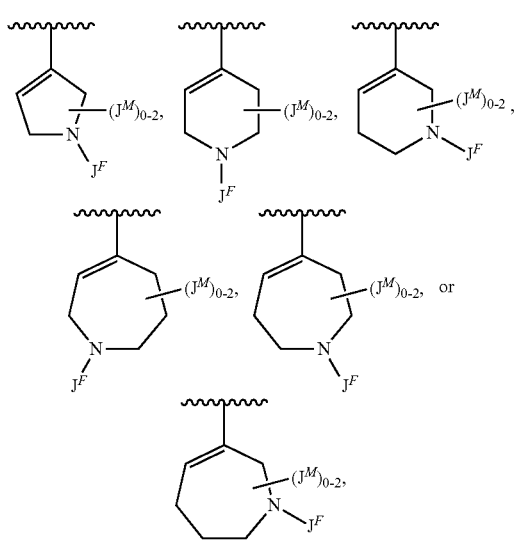

wherein J$^F$ is selected from C$_{1-4}$ aliphatic, —C$_{0-2}$aliphaticCH(R')$_2$, —(CR"$_2$)$_o$NH$_2$, —(CR'"$_2$)$_q$NHR', —(CR'"$_2$)$_q$N(R')$_2$, —(CR'"$_2$)$_q$NS(O)$_2$R', —(CR'"$_2$)$_q$NHC(O)R', —(CR'"$_2$)$_q$NHC(O)OR', —(CR'"$_2$)$_q$NHC(O)NH$_2$, —(CR'"$_2$)$_q$NHC(O)NHR', —(CR'"$_2$)$_q$NHC(O)N(R)$_2$, —(CR'"$_2$)$_q$NHC(NH)NH$_2$, —(CR'"$_2$)$_q$NHC(NH)NHR', —(CR'"$_2$)$_q$NHC(NH)N(R')$_2$, —(CR'"$_2$)$_q$NHS(O)$_2$NH$_2$, —(CR'"$_2$)$_q$NHS(O)$_2$NHR', —(CR'"$_2$)$_q$NHS(O)$_2$N(R')$_2$, —CO$_2$R', —C(O)H, —C(O)R', —C(O)—(CH$_2$)$_{0-2}$CH(R')$_2$, —C(O)NH$_2$, —C(O)NHR', —C(O)N(R')$_2$, —S(O)$_2$R', —S(O)$_2$NH$_2$, —S(O)$_2$NHR', —S(O)$_2$N(R)$_2$, C$_{6-10}$ aryl, 5-10 membered heteroaryl, 5-10 membered heterocyclyl, or C$_{3-8}$ cycloaliphatic, wherein q is selected from 0-4 and said aryl, heteroaryl, heterocyclyl, or cycloaliphatic of JF is optionally substituted with halogen, —NO$_2$, —CN, C$_{1-4}$ aliphatic, C$_{1-4}$ haloalkyl, C$_{3-4}$ cycloalkyl, —OH, —NH$_2$, —O(C$_{1-2}$ aliphatic), —N(C$_{1-2}$ aliphatic)$_2$, or —NH(C$_{1-2}$ aliphatic).

In a further embodiment, R$^A$ is

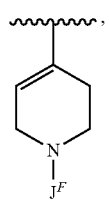

wherein J$^F$ is —C$_{0-2}$aliphaticCH(R')$_2$, —(CR'"$_2$)$_q$NH$_2$, —(CR'"$_2$)$_q$NHR', —(CR'"$_2$)$_q$N(R')$_2$, —C(O)R', —C(O)—(CH$_2$)$_{0-2}$CH(R')$_2$, or optionally substituted heterocyclyl.

For any of the compounds of the invention, J$^M$ is selected from halogen, —NO$_2$, —CN, C$_{1-4}$ aliphatic, C$_{1-2}$ haloalkyl, —OH, —OR', —(CR'"$_2$)$_q$NH$_2$, —(CR'"$_2$)$_q$NHR', —(CR'"$_2$)$_q$N(R')$_2$, —(CR'"$_2$)$_q$NS(O)$_2$R', —(CR'"$_2$)$_q$NHC(O)R', —(CR'"$_2$)$_q$NHC(O)OR', —(CR'"$_2$)$_q$NHC(O)NH$_2$, —(CR"$_2$)$_q$NHC(O)NHR', —(CR"$_2$)$_q$NHC(O)N(R')$_2$, —(CR'"$_2$)$_q$NHS(O)$_2$NH$_2$, —(CR'"$_2$)$_q$NHS(O)$_2$NHR', —(CR'"$_2$)$_q$NHS(O)$_2$N(R)$_2$, —SH, —SR', —CO$_2$H, —CO$_2$R', —C(O)H, —C(O)R', —C(O)NH$_2$, —C(O)NHR', —C(O)N(R')$_2$, —C(O)N(OH)R', —C(O)N(OR')R', —C(O)N(OR')H, —C(O)N(OH)H, —C(=NOH)R', —C(=NOR'), H, —C(NOR')R', —S(O)$_2$R', —S(O)$_2$OR', —S(O)$_2$NH$_2$, —S(O)$_2$NHR', —S(O)$_2$N(R)$_2$, —S(O)R', —C(=NR')—NH$_2$, —C(=NR')—NHR',
—C(=NR')—N(R')$_2$, —C(=NH)—NH$_2$, —C(=NH)—NHR', or —C(=NH)—N(R')$_2$.

In another embodiment, J$^M$ is selected from

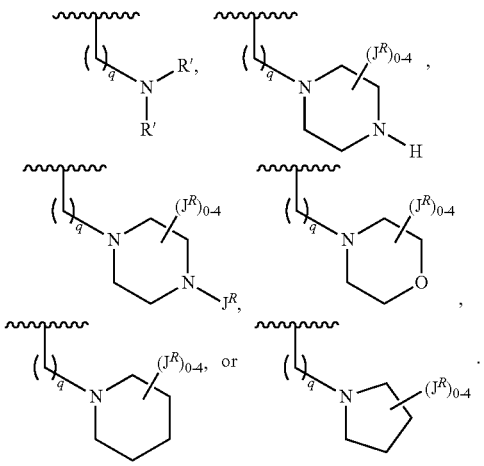

In another embodiment, q is 1 or 2.

In yet another embodiment, J$^M$ is not substituted on a ring position adjacent to Ring A.

In one embodiment for compounds of the invention, wherein R$^3$ is halogen, compounds of formula I are useful as intermediates for preparing compounds of formula I wherein R$^3$ is R$^A$.

In yet another embodiment for compounds of the invention, a substituted or unsubstituted C$_{1-4}$ or C$_{1-6}$ aliphatic group of R$^1$, R$^2$, R$^4$, R$^5$, R$^6$, J$^M$, J$^N$, J$^Q$, J$^R$, R', R", or R'" comprises two or more non-hydrogen atoms.

In another aspect, the invention features a compound having the formula:

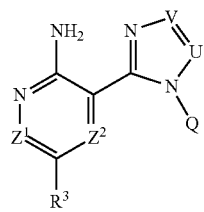

I-A

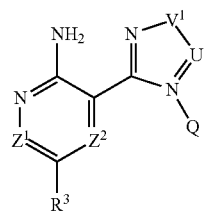

I-B

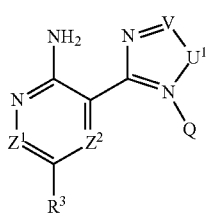

I-C

I-D
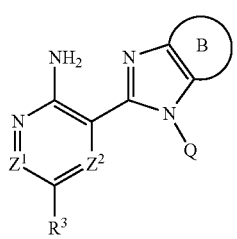
I-E
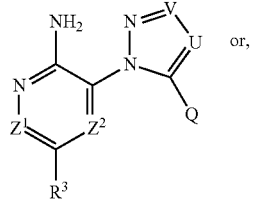  or,
wherein said compound is selected from the compounds of Tables 1, 2, 3, 4, or 5, respectively.
TABLE 1
Compounds of Formula 1-A
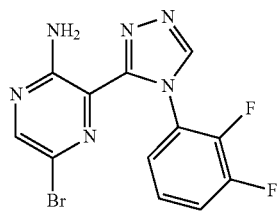
I-A-1
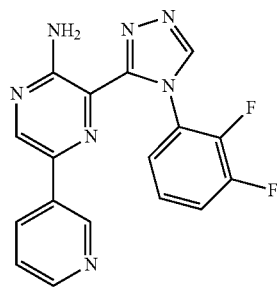
I-A-2
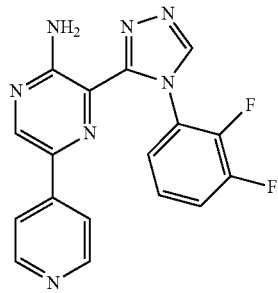
I-A-3
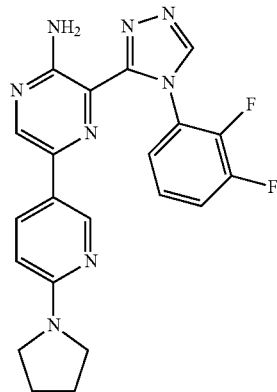
I-A-4
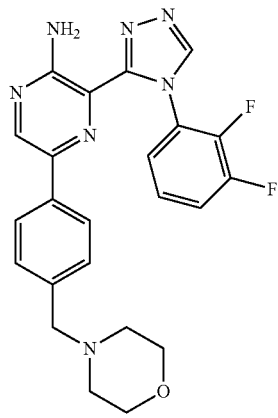
I-A-5
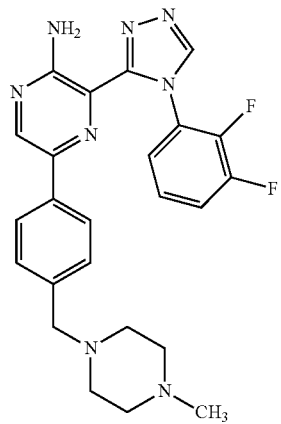
I-A-6

TABLE 1-continued
Compounds of Formula 1-A
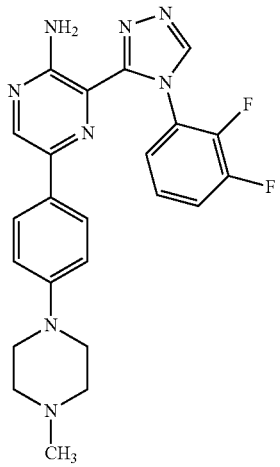
I-A-7
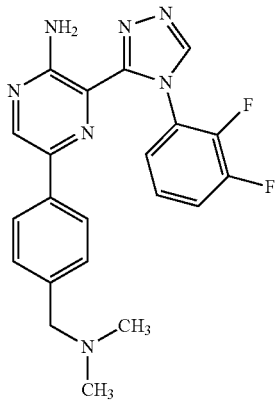
I-A-8
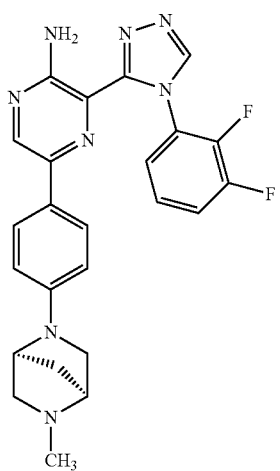
I-A-9
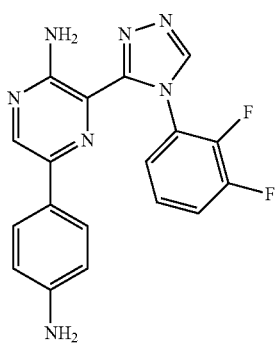
I-A-10
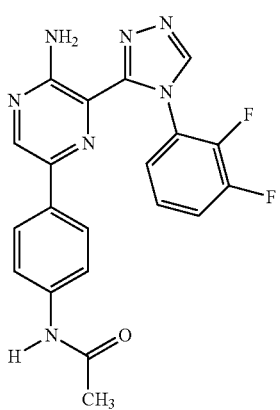
I-A-11
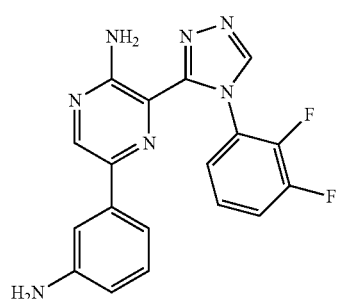
I-A-12

TABLE 1-continued
Compounds of Formula 1-A
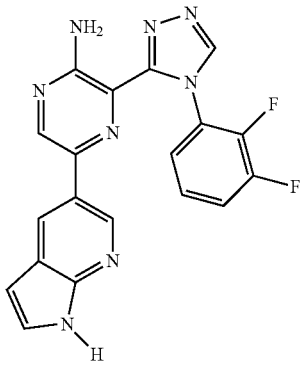
I-A-13
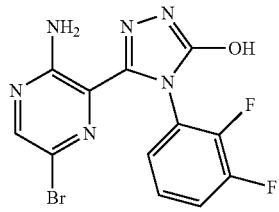
I-A-14
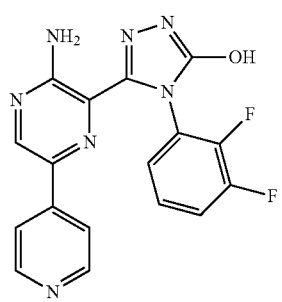
I-A-15
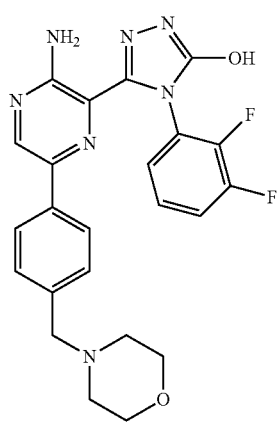
I-A-16
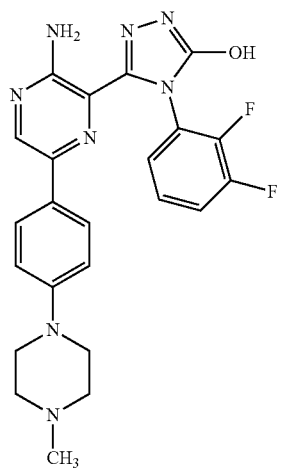
I-A-17
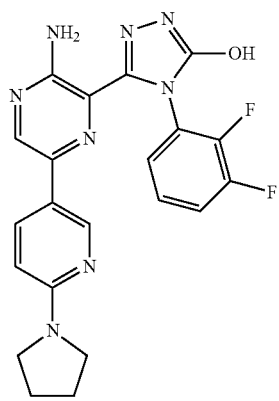
I-A-18

TABLE 1-continued
Compounds of Formula 1-A
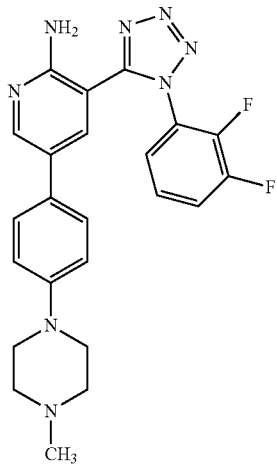
I-A-19
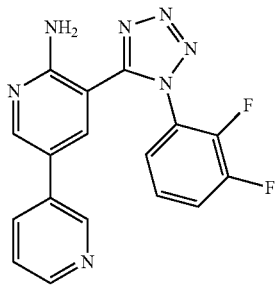
I-A-20
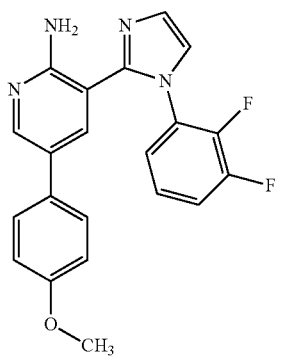
I-A-21
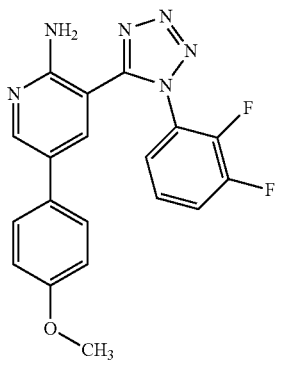
I-A-22
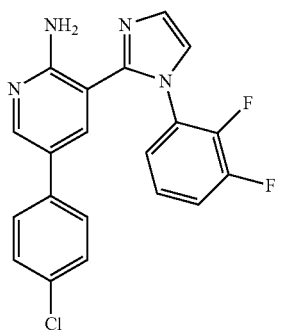
I-A-23
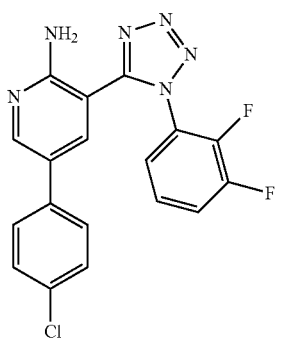
I-A-24

TABLE 1-continued
Compounds of Formula 1-A
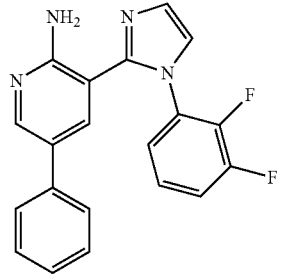
I-A-25
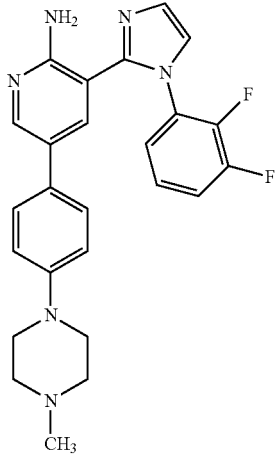
I-A-26
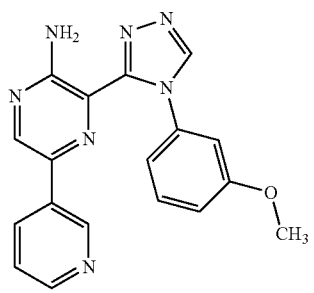
I-A-27
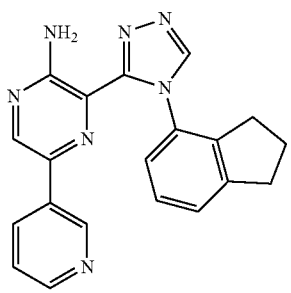
I-A-28
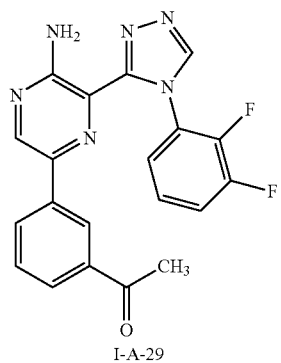
I-A-29
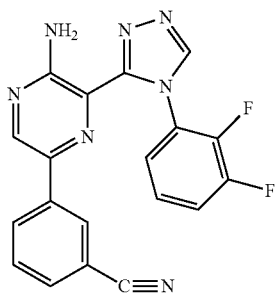
I-A-30
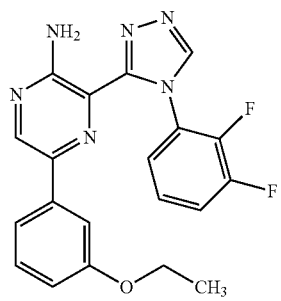
I-A-31
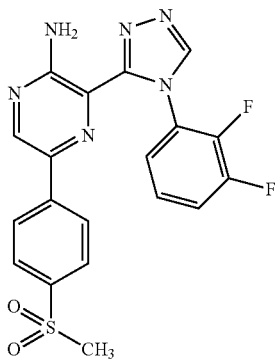
I-A-32

TABLE 1-continued
Compounds of Formula 1-A
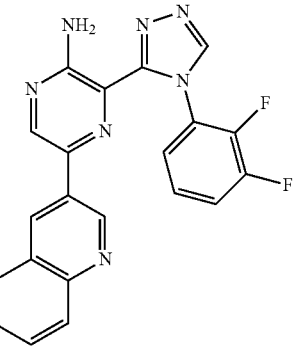
I-A-33
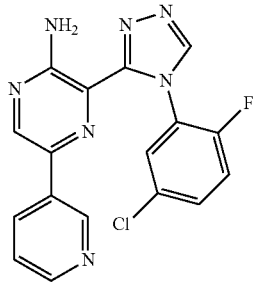
I-A-34
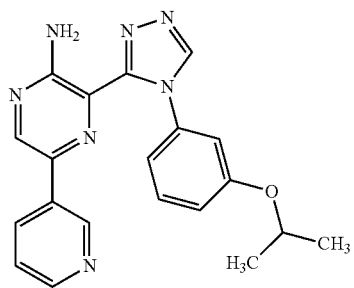
I-A-35
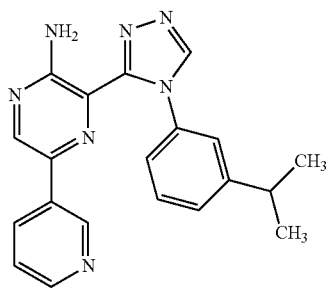
I-A-36
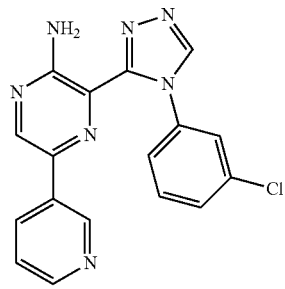
I-A-37
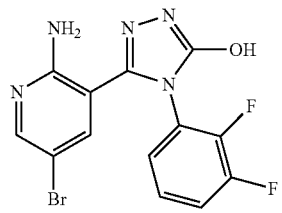
I-A-38
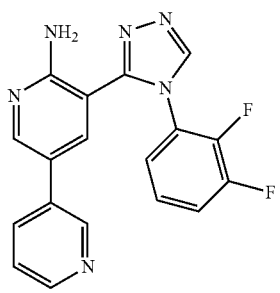
I-A-39
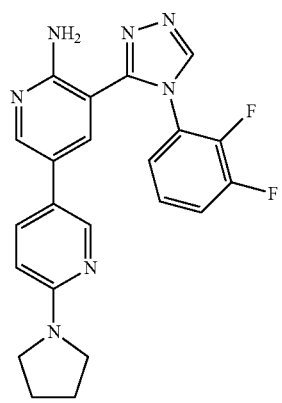
I-A-40

TABLE 1-continued
Compounds of Formula 1-A
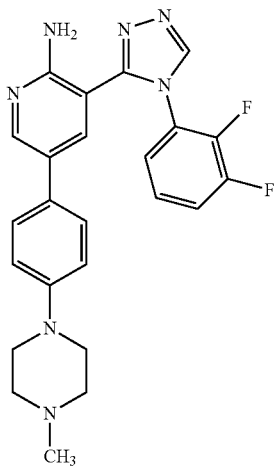
I-A-41
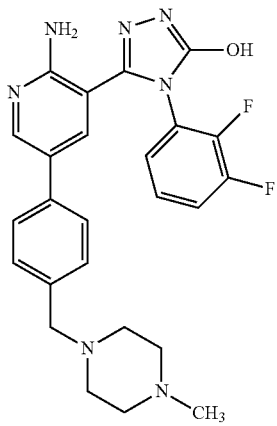
I-A-42
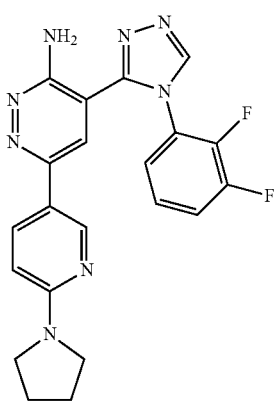
I-A-43
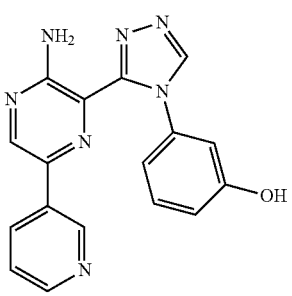
I-A-44
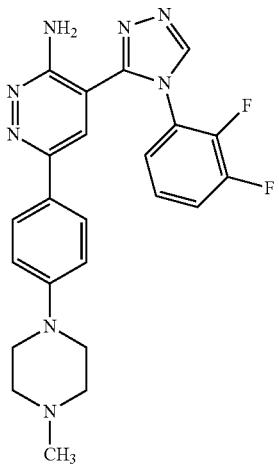
I-A-45
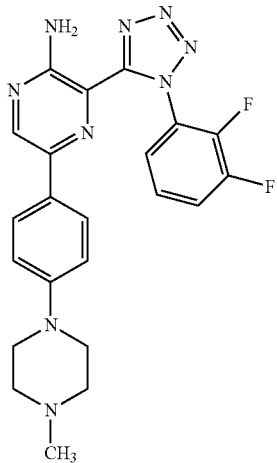
I-A-46

TABLE 1-continued
Compounds of Formula 1-A
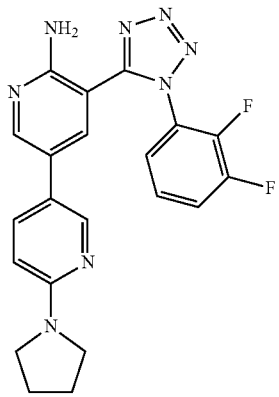
I-A-47
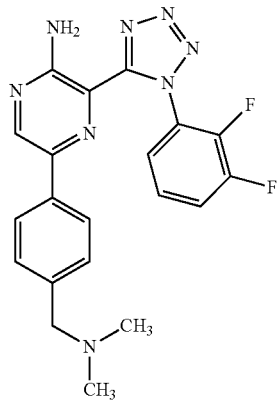
I-A-48
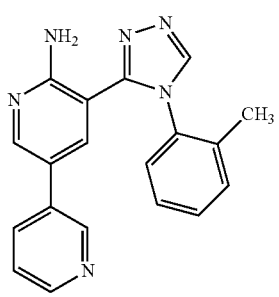
I-A-49
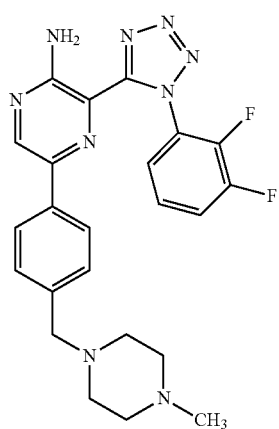
I-A-50
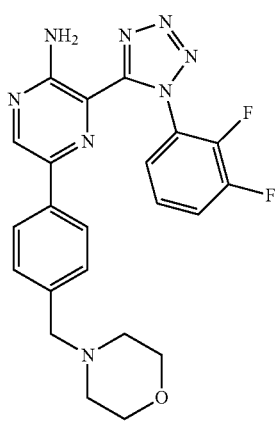
I-A-51
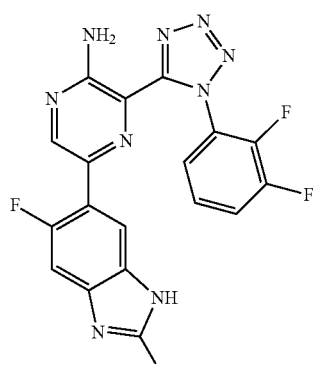
I-A-52

TABLE 1-continued
Compounds of Formula 1-A
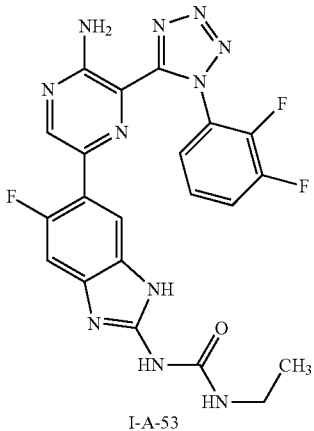
I-A-53
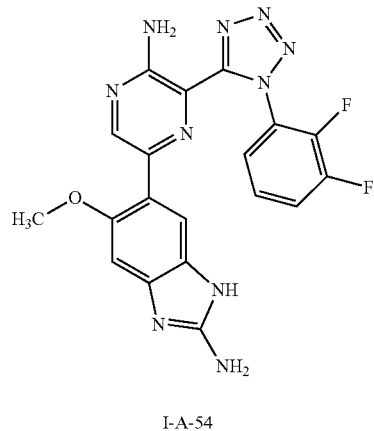
I-A-54
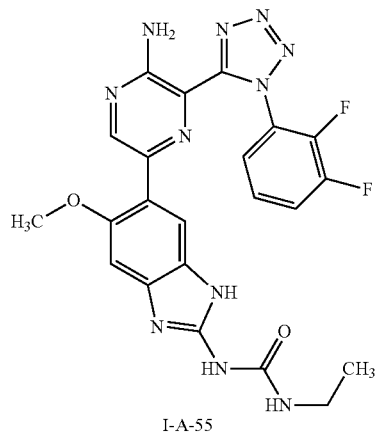
I-A-55
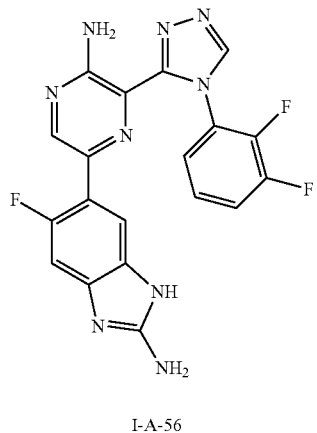
I-A-56
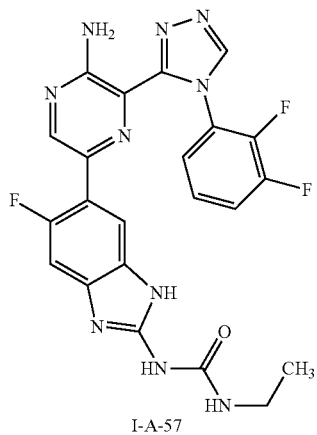
I-A-57
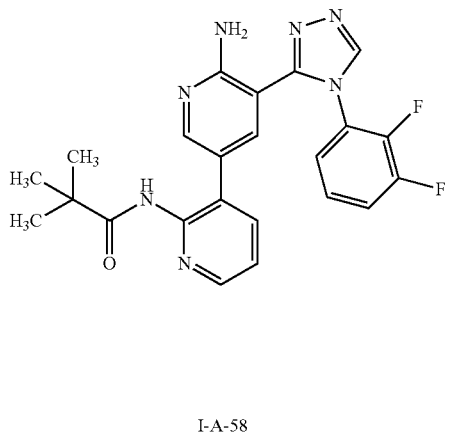
I-A-58
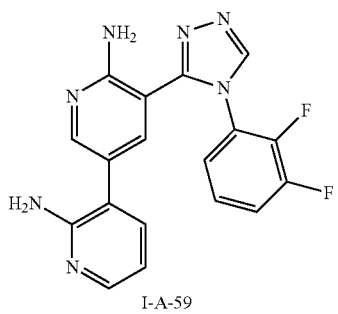
I-A-59
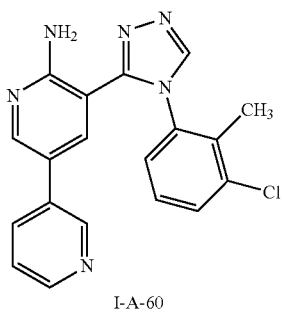
I-A-60

TABLE 1-continued
Compounds of Formula 1-A
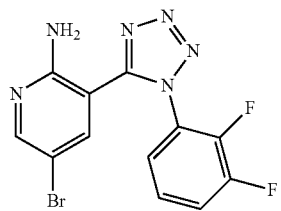
I-A-61
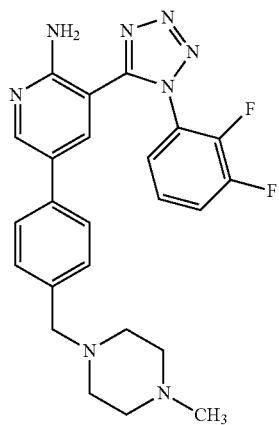
I-A-62
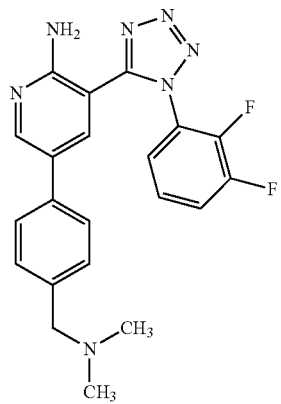
I-A-63
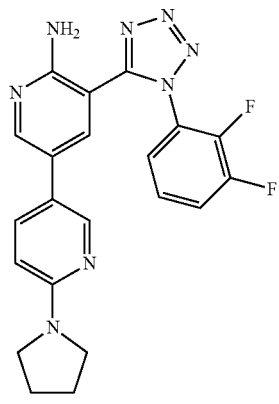
I-A-64
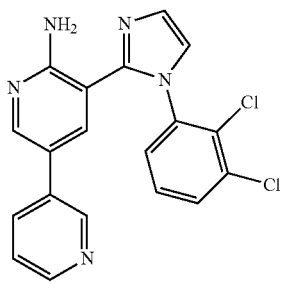
I-A-65
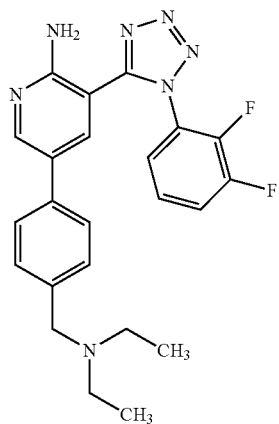
I-A-66

TABLE 1-continued
Compounds of Formula 1-A
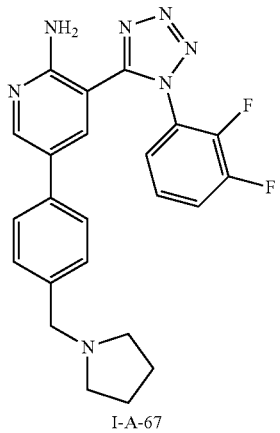
I-A-67
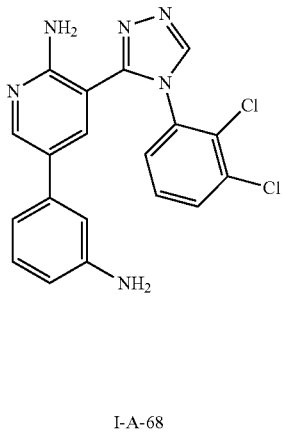
I-A-68
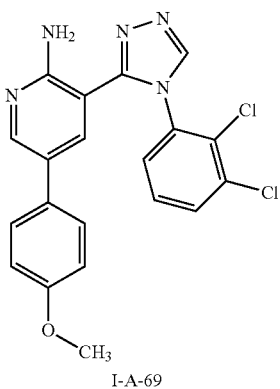
I-A-69
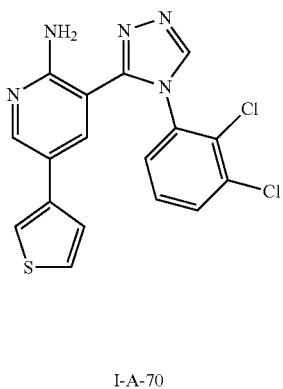
I-A-70
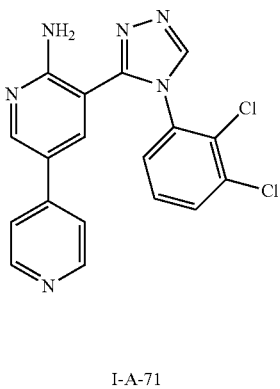
I-A-71
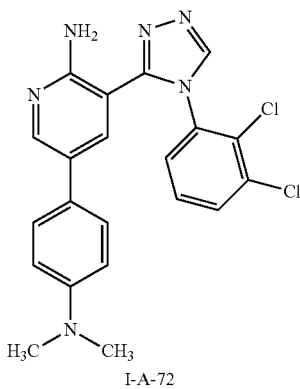
I-A-72
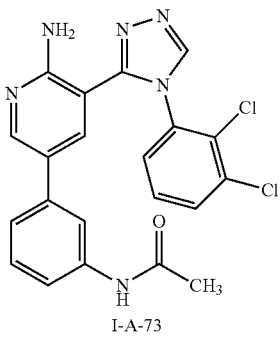
I-A-73
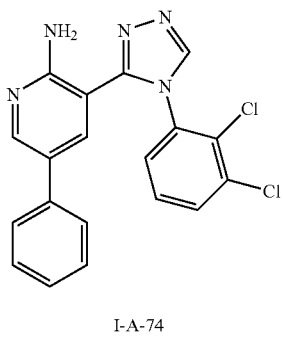
I-A-74

TABLE 1-continued
Compounds of Formula 1-A
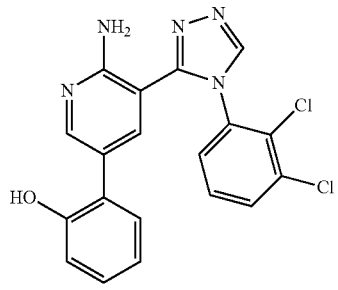
I-A-75
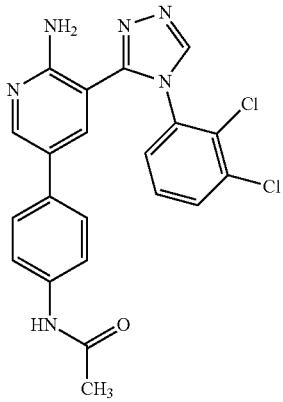
I-A-76
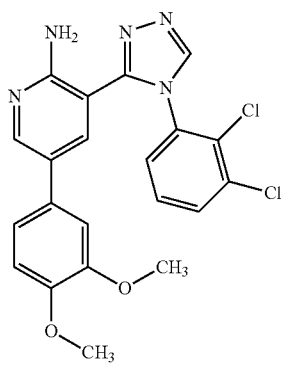
I-A-77
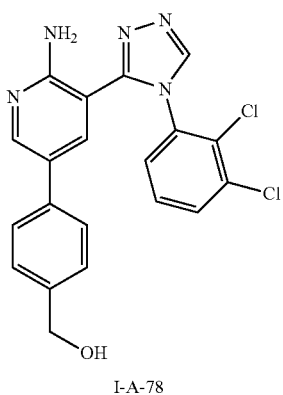
I-A-78
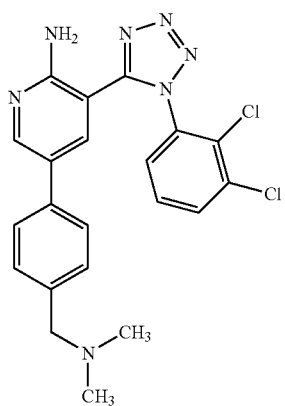
I-A-79
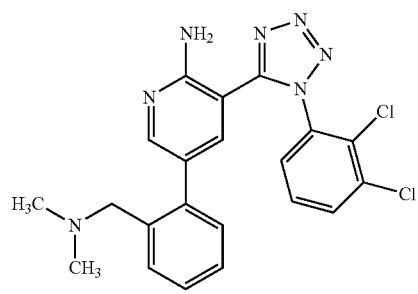
I-A-80

TABLE 1-continued
Compounds of Formula 1-A
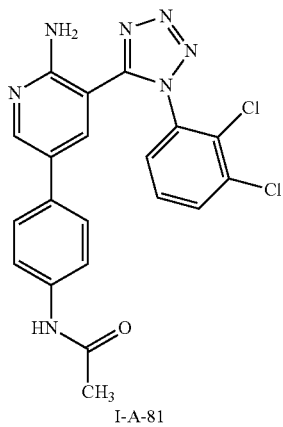
I-A-81
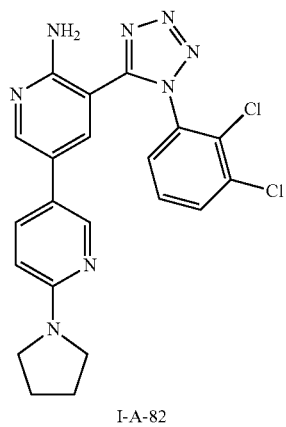
I-A-82
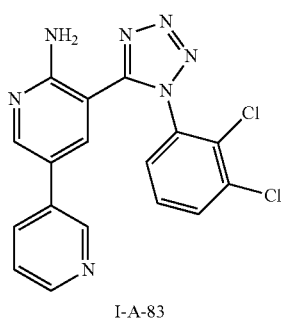
I-A-83
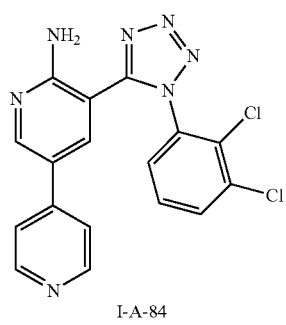
I-A-84
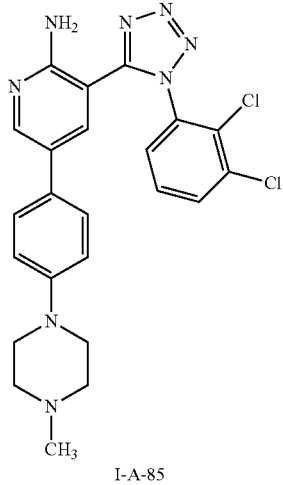
I-A-85
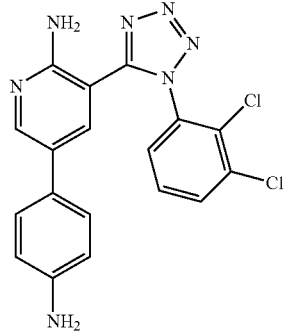
I-A-86
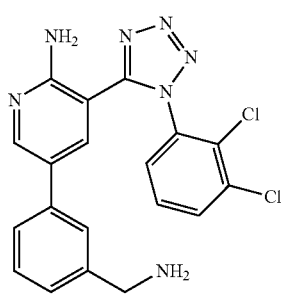
I-A-87
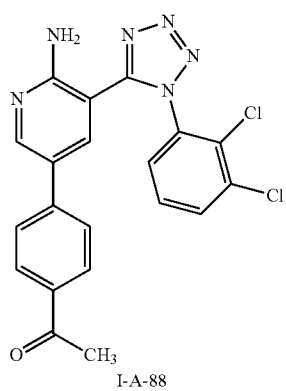
I-A-88

TABLE 1-continued
Compounds of Formula 1-A
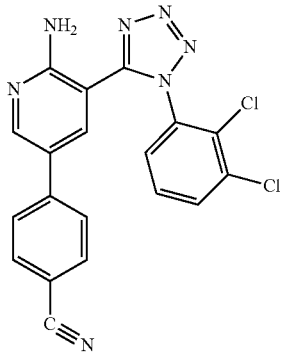
I-A-89
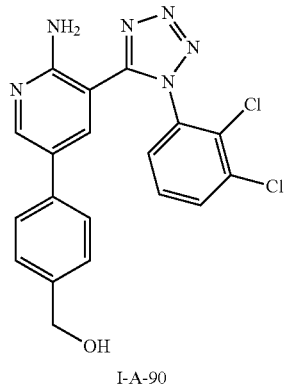
I-A-90
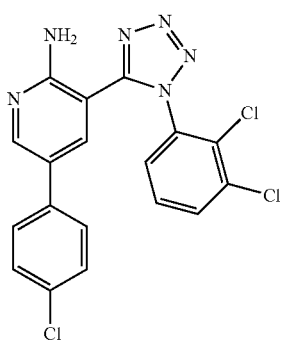
I-A-91
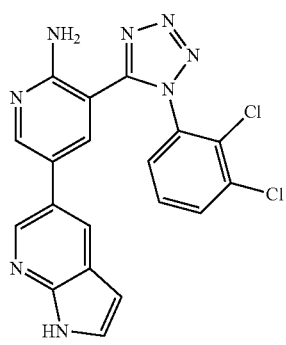
I-A-92
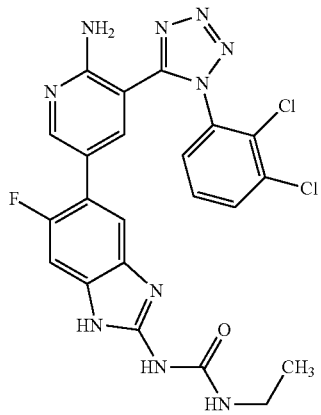
I-A-93
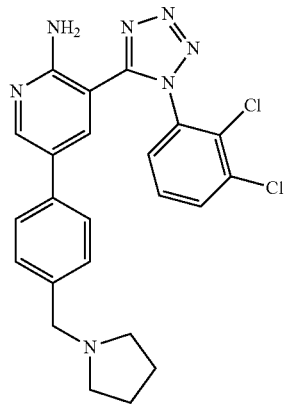
I-A-94

TABLE 1-continued
Compounds of Formula 1-A
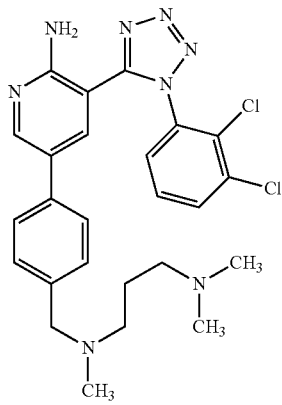
I-A-95
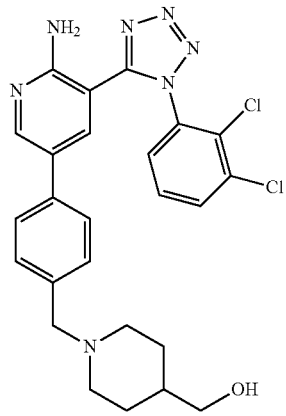
I-A-96
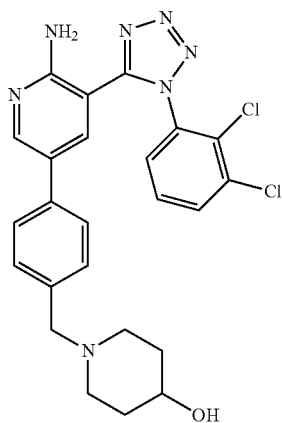
I-A-97
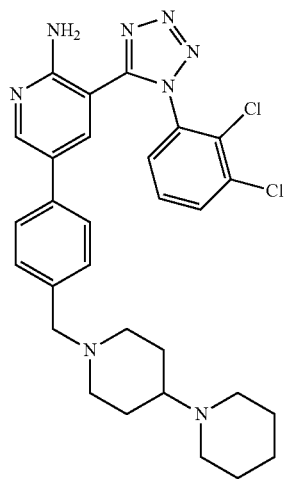
I-A-98
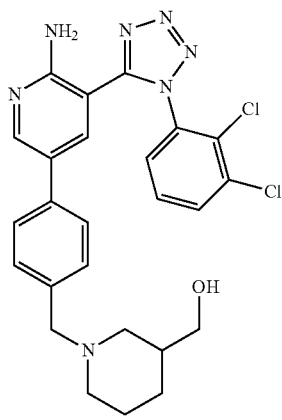
I-A-99
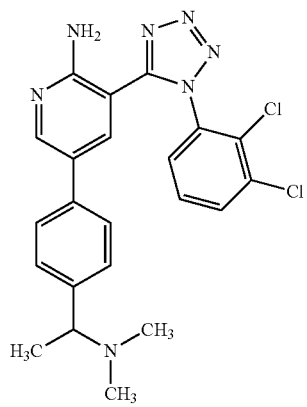
I-A-100

TABLE 1-continued
Compounds of Formula 1-A
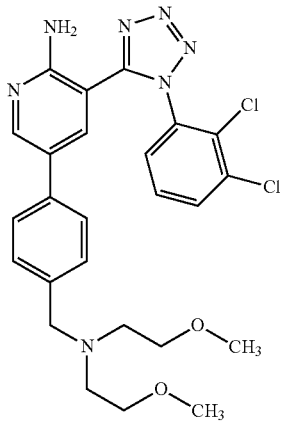
I-A-101
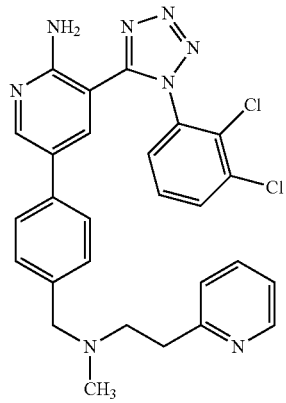
I-A-102
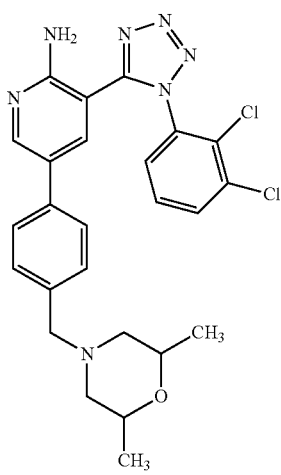
I-A-103
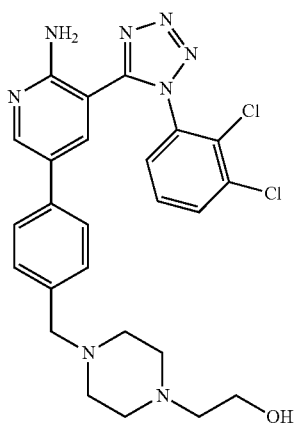
I-A-104
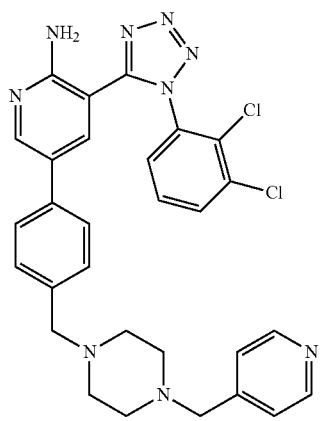
I-A-105
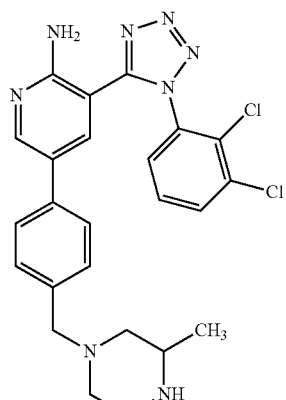
I-A-106

TABLE 1-continued
Compounds of Formula 1-A
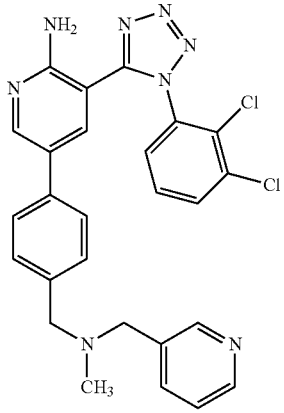
I-A-107
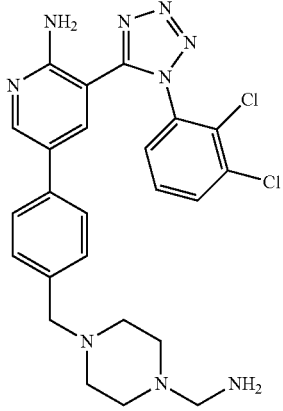
I-A-108
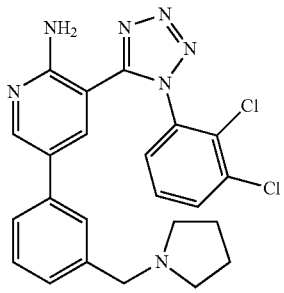
I-A-109
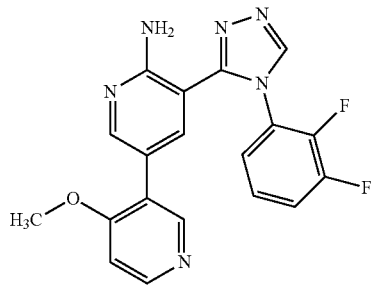
I-A-110
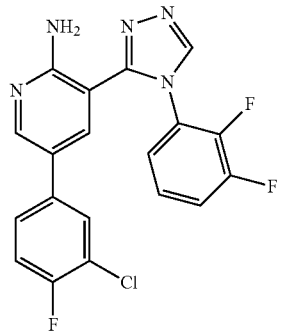
I-A-111
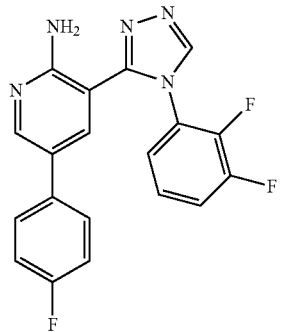
I-A-112
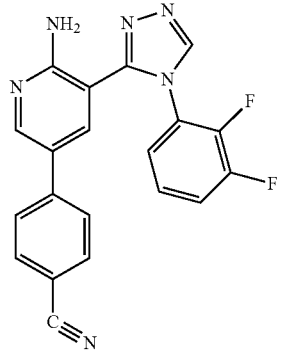
I-A-113
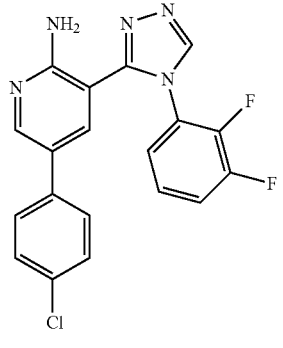
I-A-114

TABLE 1-continued
Compounds of Formula 1-A
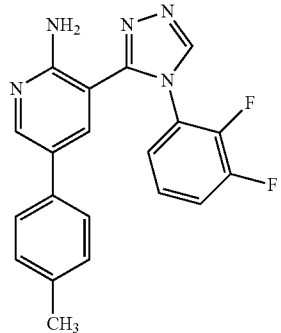
I-A-115
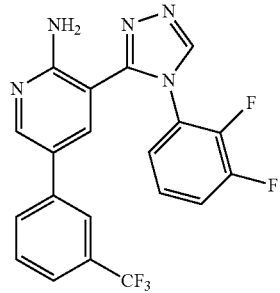
I-A-116
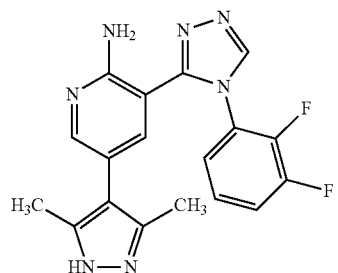
I-A-117
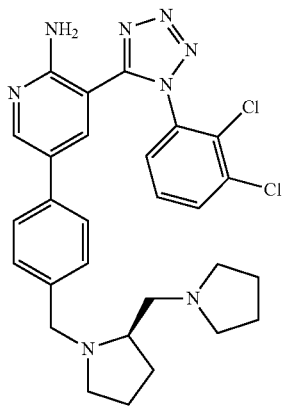
I-A-118
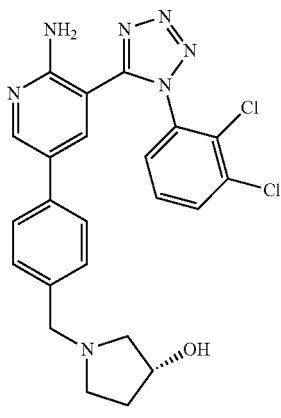
I-A-119
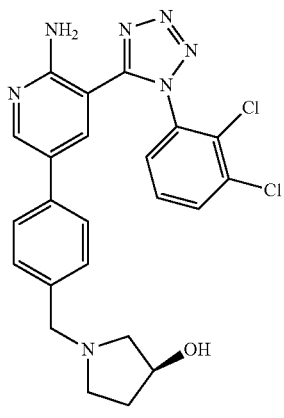
I-A-120

TABLE 1-continued
Compounds of Formula 1-A
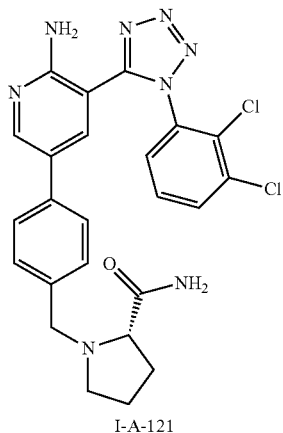
I-A-121
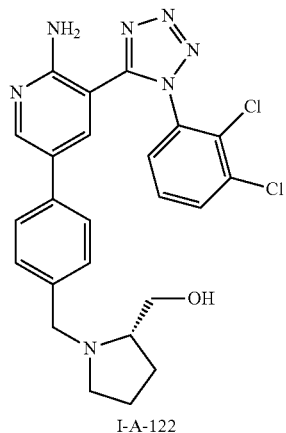
I-A-122
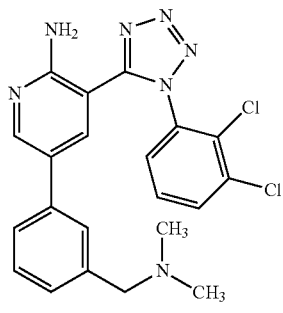
I-A-123
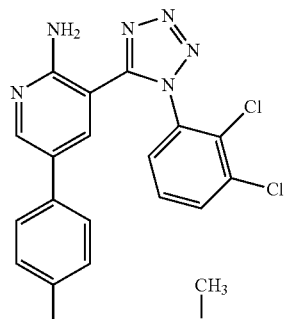
I-A-124
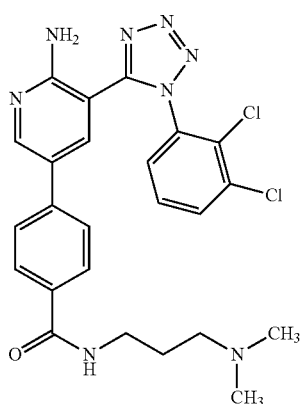
I-A-125
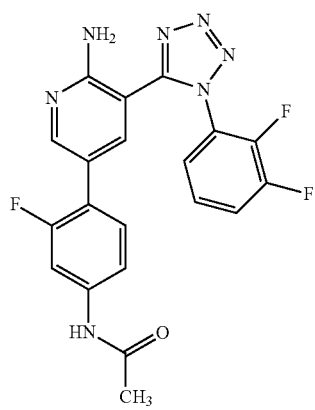
I-A-126

TABLE 1-continued
Compounds of Formula 1-A
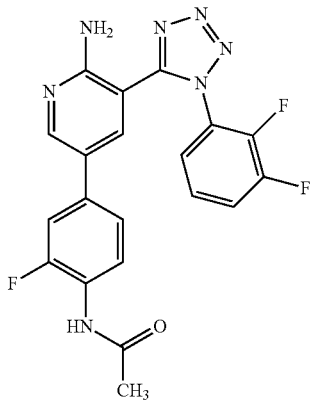
I-A-127
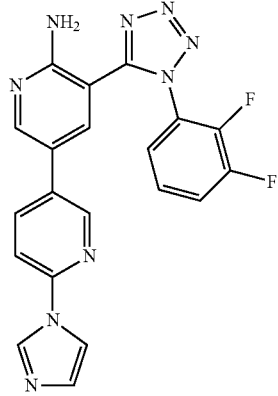
I-A-128
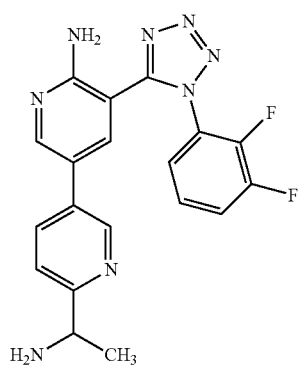
I-A-129
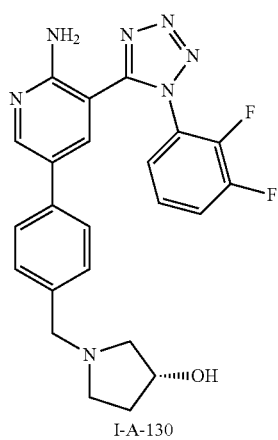
I-A-130
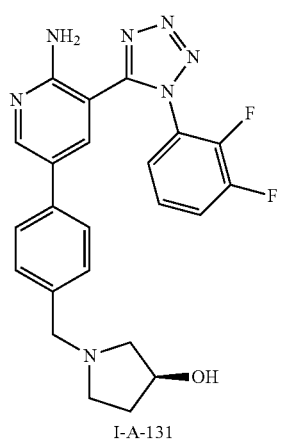
I-A-131
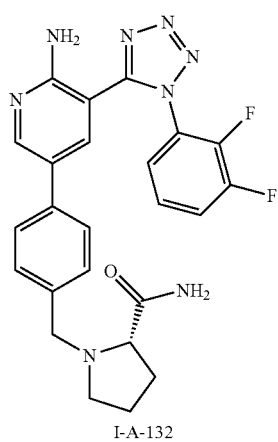
I-A-132

TABLE 1-continued
Compounds of Formula 1-A
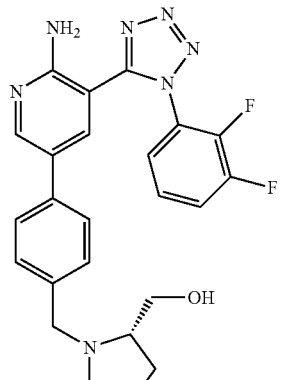
I-A-133
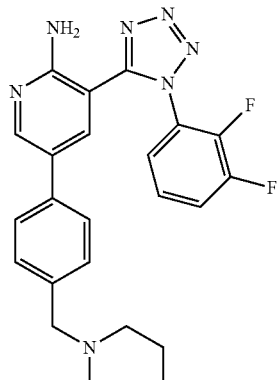
I-A-134
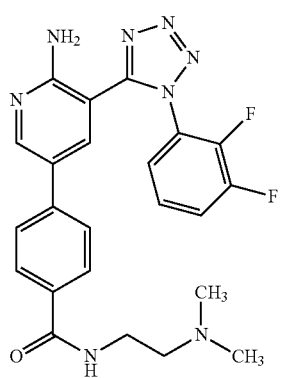
I-A-135
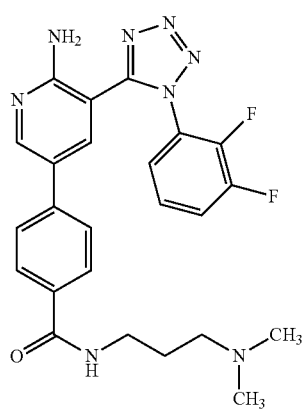
I-A-136
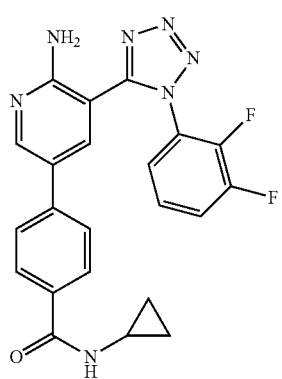
I-A-137
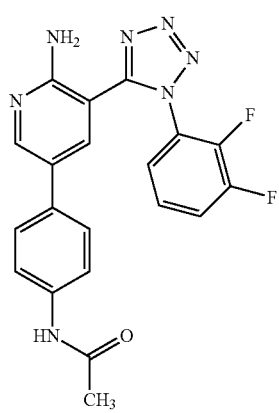
I-A-138

TABLE 1-continued
Compounds of Formula 1-A
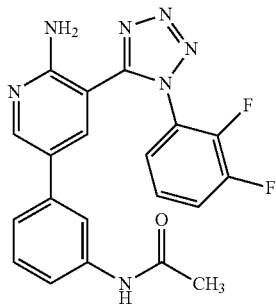
I-A-139
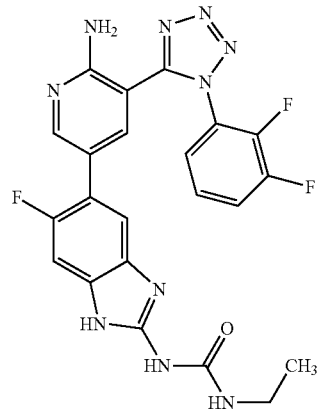
I-A-140
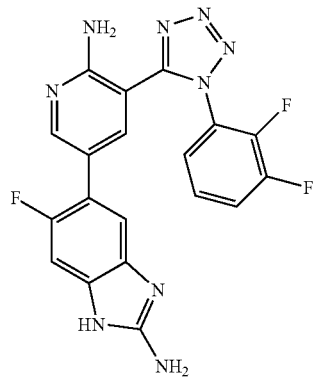
I-A-141
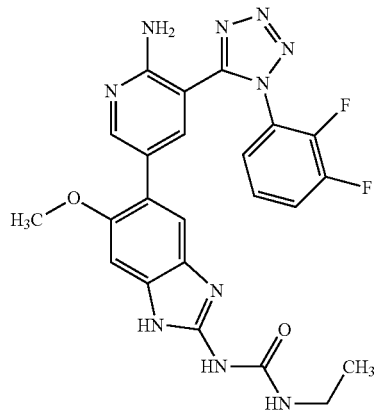
I-A-142
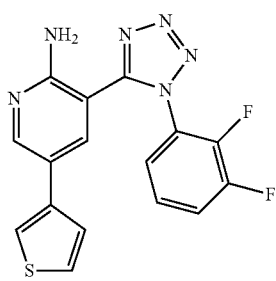
I-A-143
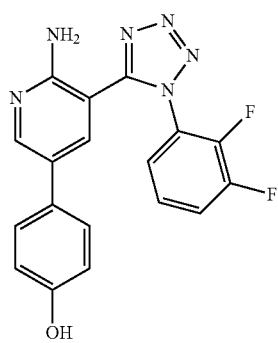
I-A-144

TABLE 1-continued
Compounds of Formula 1-A
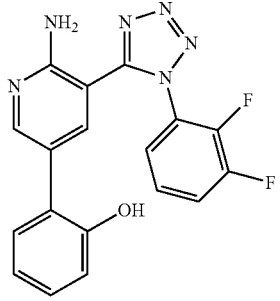
I-A-145
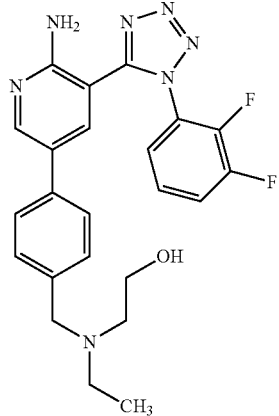
I-A-146
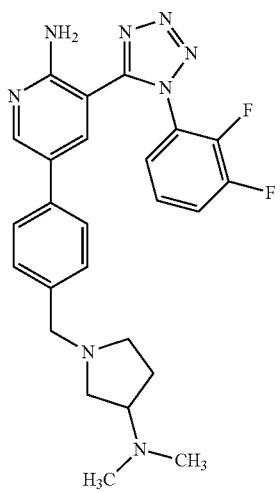
I-A-147
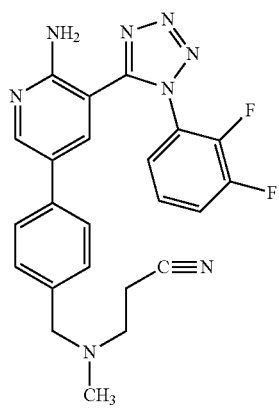
I-A-148
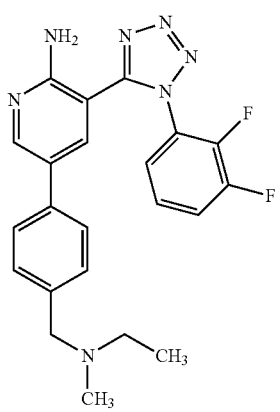
I-A-149
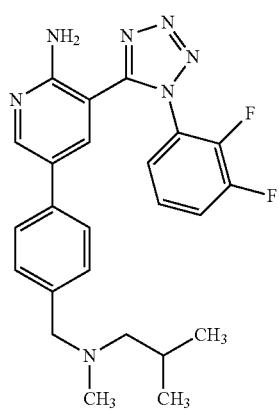
I-A-150

TABLE 1-continued
Compounds of Formula 1-A
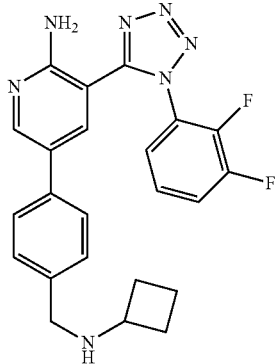
I-A-151
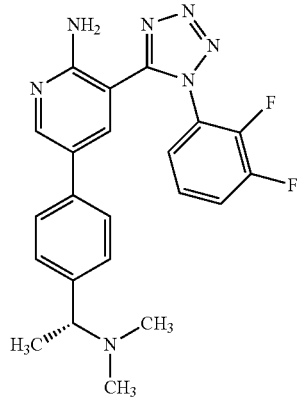
I-A-152
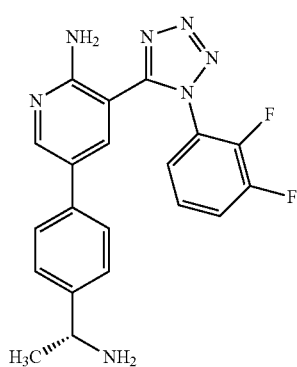
I-A-153
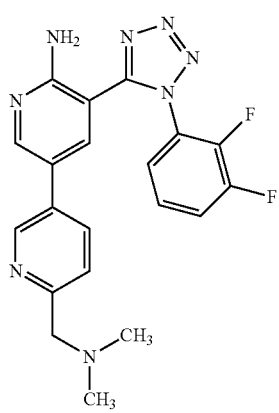
I-A-154
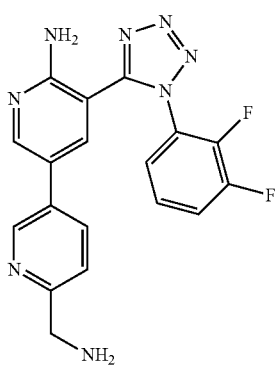
I-A-155
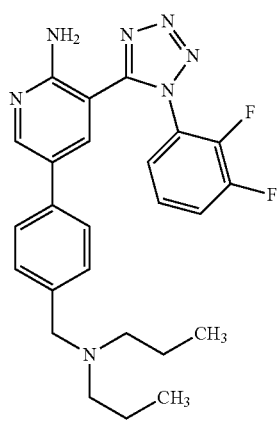
I-A-156

TABLE 1-continued
Compounds of Formula 1-A
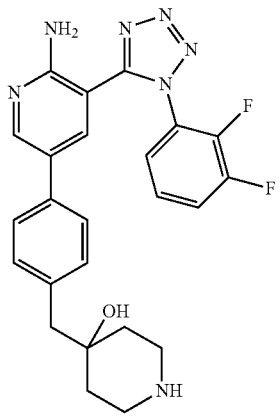
I-A-157
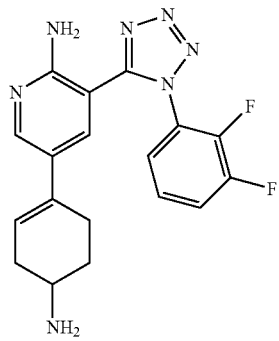
I-A-158
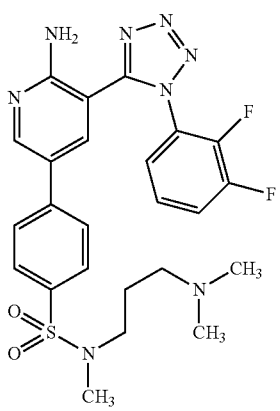
I-A-159
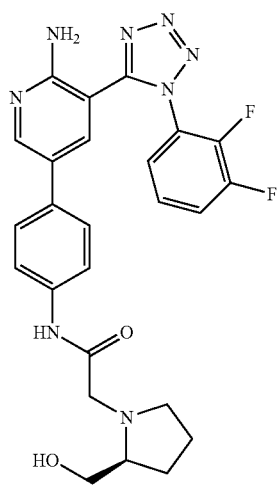
I-A-160
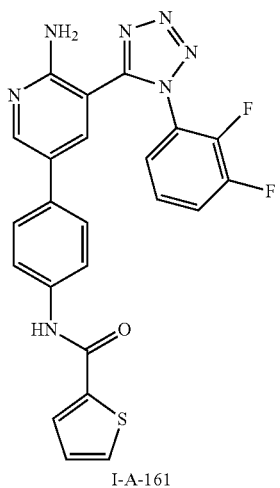
I-A-161
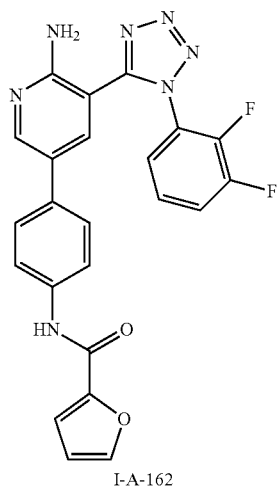
I-A-162

TABLE 1-continued
Compounds of Formula 1-A
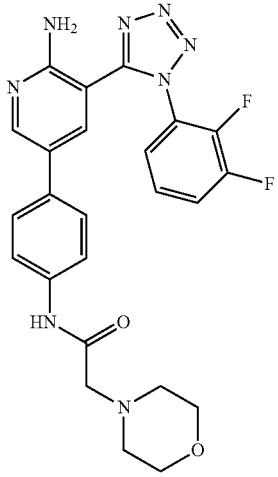
I-A-163
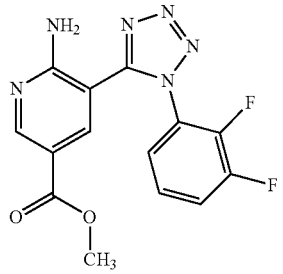
I-A-164
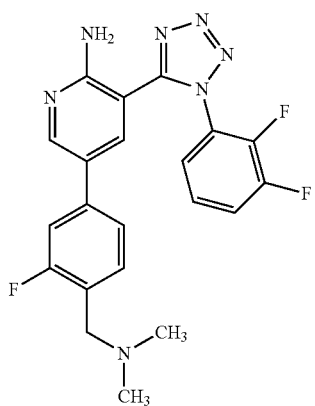
I-A-165
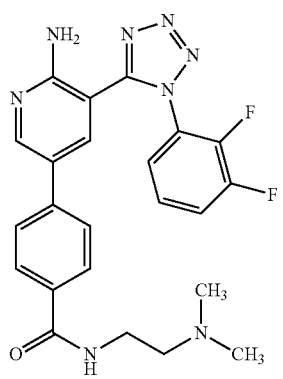
I-A-166
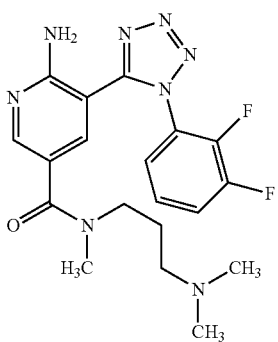
I-A-167
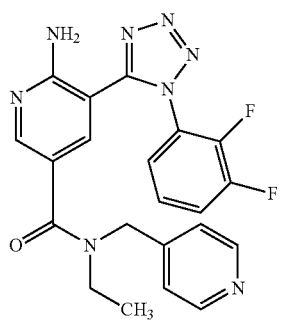
I-A-168

TABLE 1-continued
Compounds of Formula 1-A
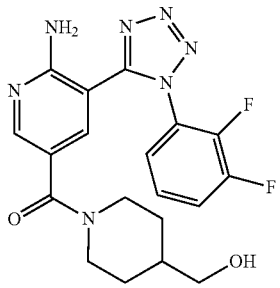
I-A-169
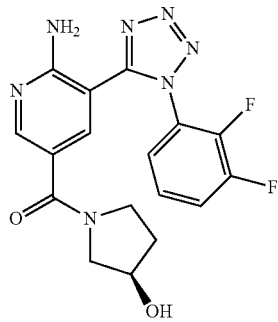
I-A-170
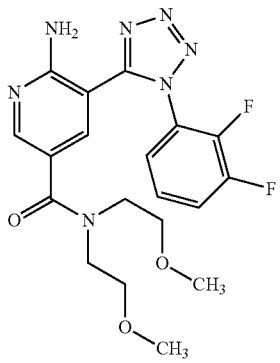
I-A-171
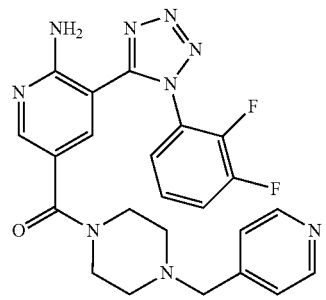
I-A-172
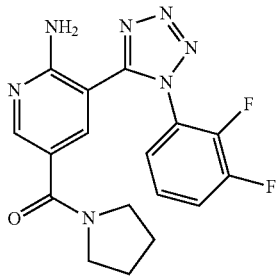
I-A-173
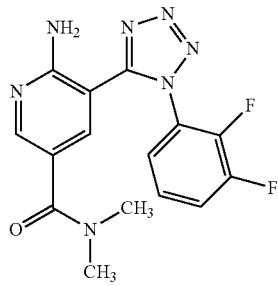
I-A-174
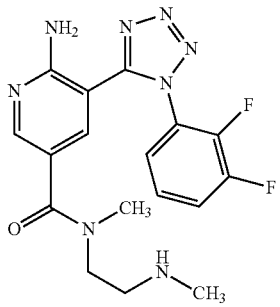
I-A-175
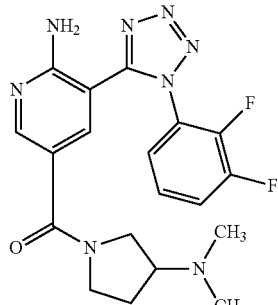
I-A-176

TABLE 1-continued
Compounds of Formula 1-A
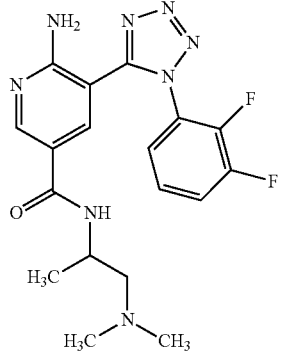
I-A-177
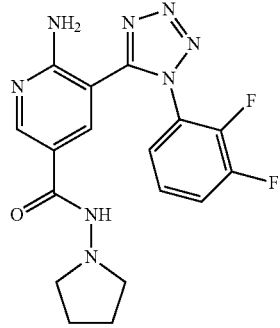
I-A-178
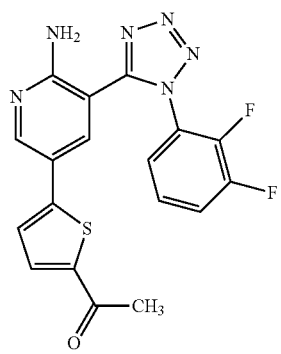
I-A-179
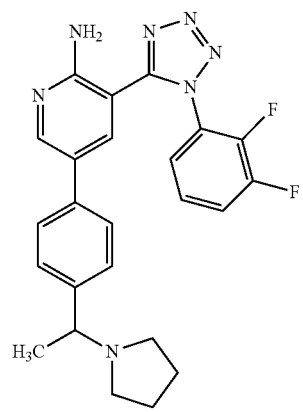
I-A-180
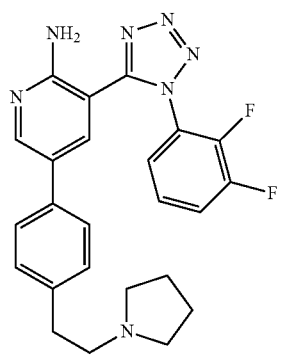
I-A-181
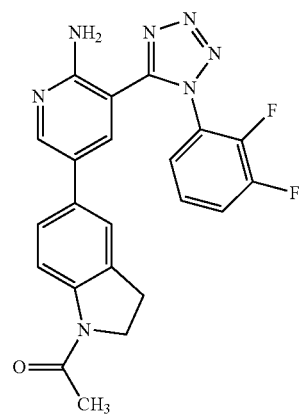
I-A-182

TABLE 1-continued
Compounds of Formula 1-A
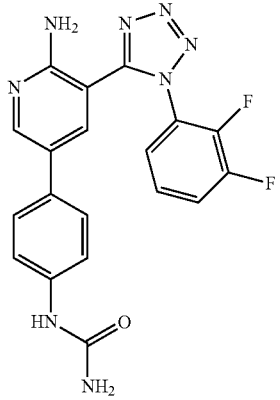
I-A-183
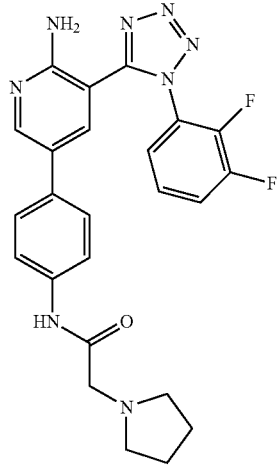
I-A-184
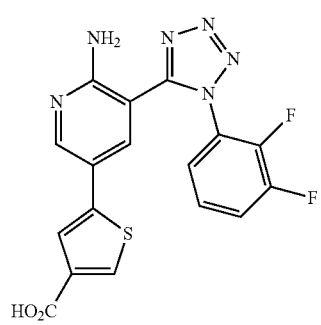
I-A-185
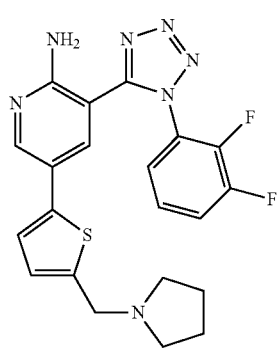
I-A-186
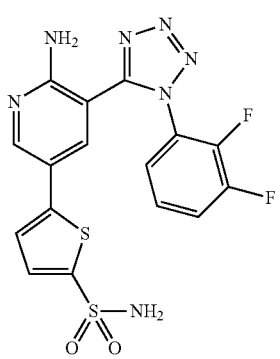
I-A-187
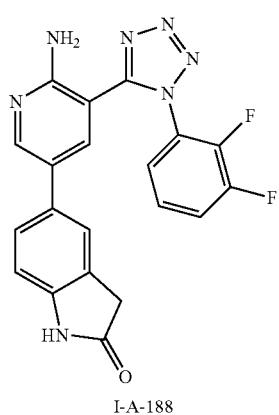
I-A-188

TABLE 1-continued
Compounds of Formula 1-A
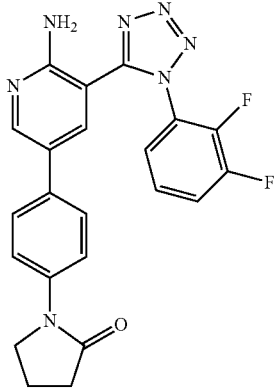
I-A-189
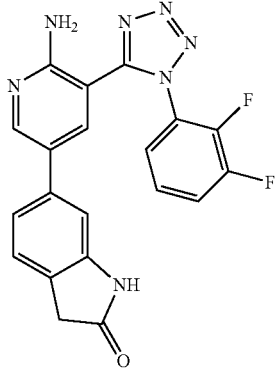
I-A-190
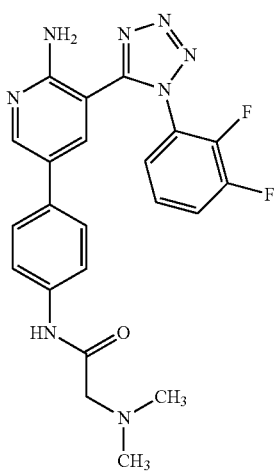
I-A-191
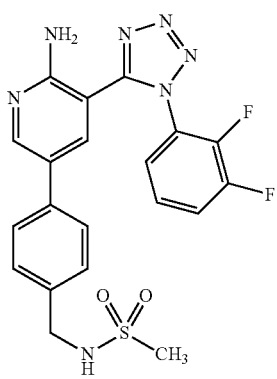
I-A-192
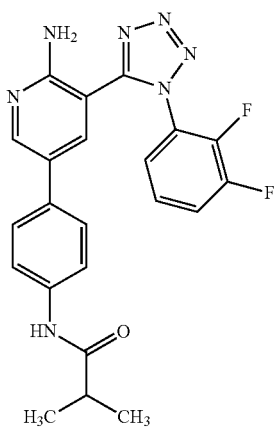
I-A-193
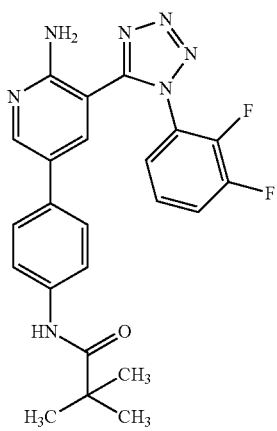
I-A-194

TABLE 1-continued
Compounds of Formula 1-A
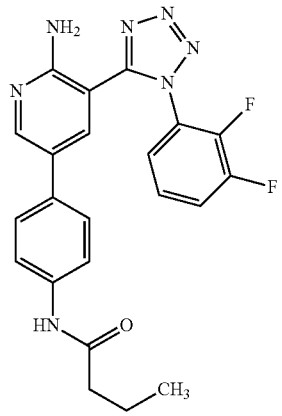
I-A-195
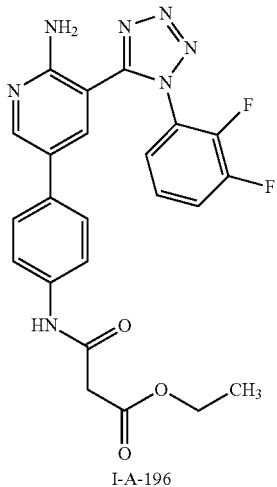
I-A-196
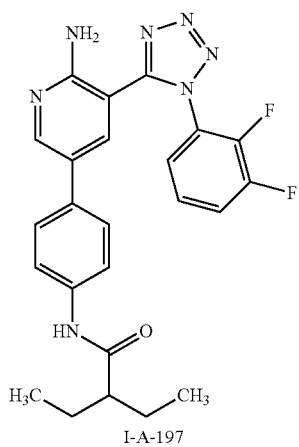
I-A-197
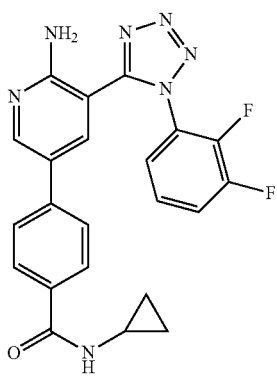
I-A-198
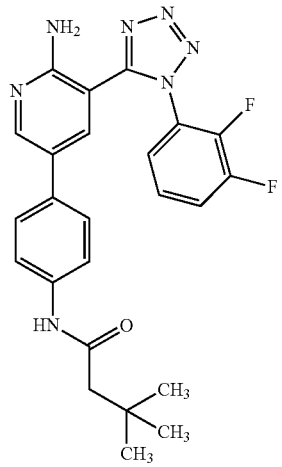
I-A-199
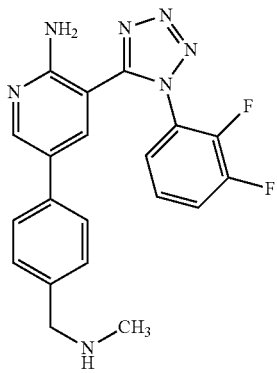
I-A-200

TABLE 1-continued
Compounds of Formula 1-A
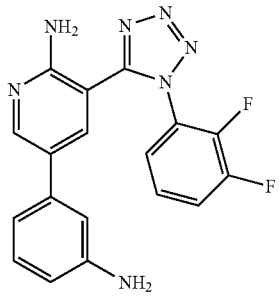
I-A-201
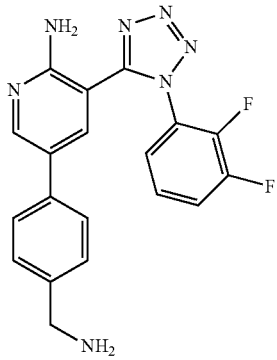
I-A-202
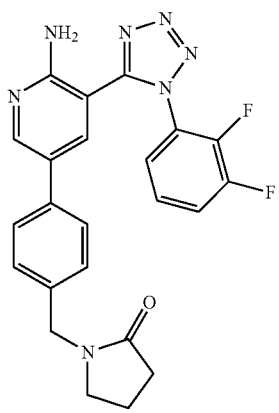
I-A-203
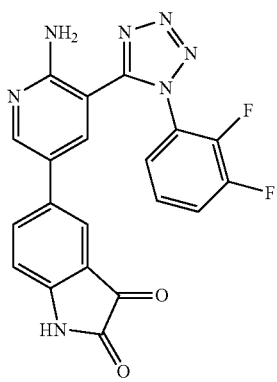
I-A-204
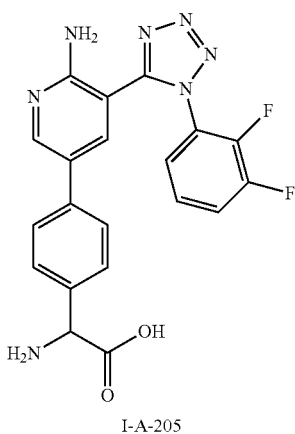
I-A-205
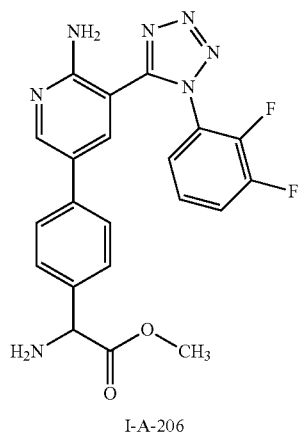
I-A-206

TABLE 1-continued
Compounds of Formula 1-A
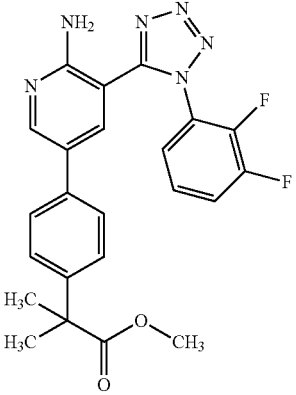
I-A-207
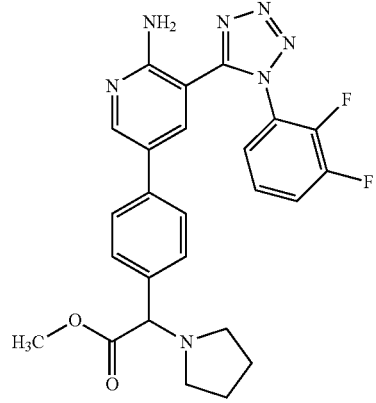
I-A-208
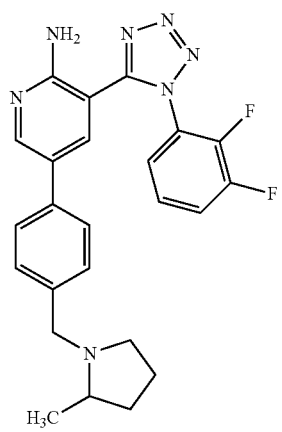
I-A-209
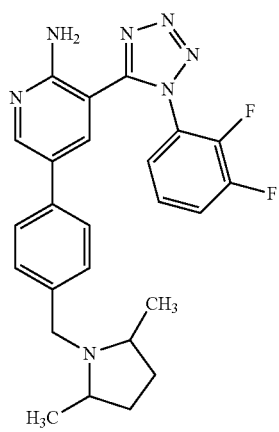
I-A-210
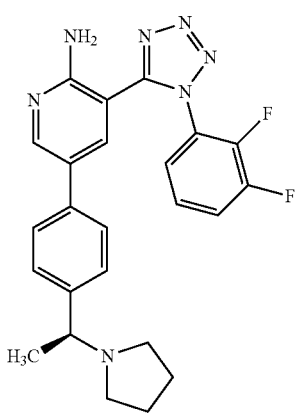
I-A-211
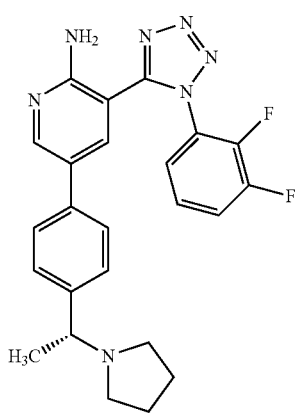
I-A-212

TABLE 1-continued
Compounds of Formula 1-A
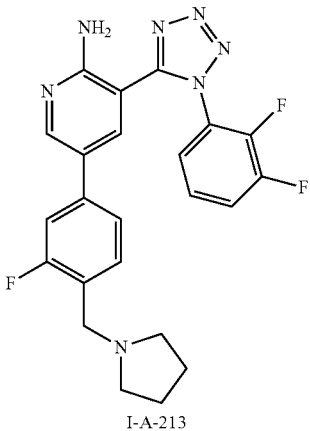
I-A-213
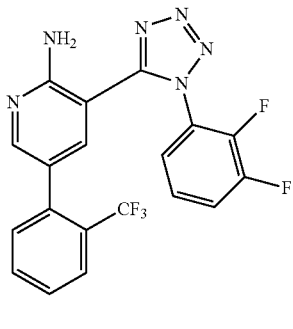
I-A-214
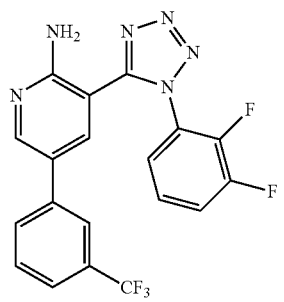
I-A-215
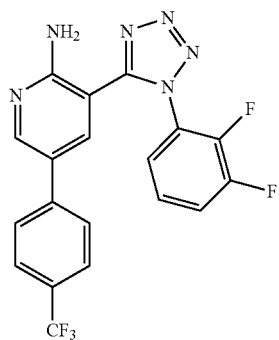
I-A-216
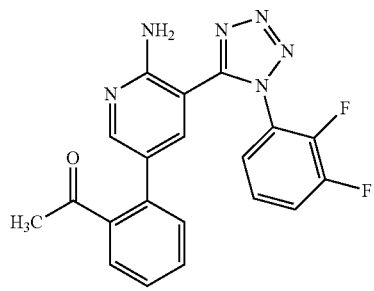
I-A-217
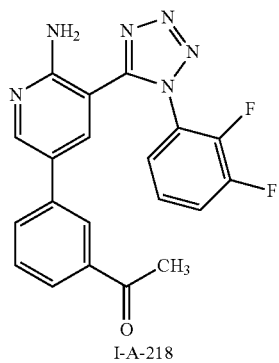
I-A-218
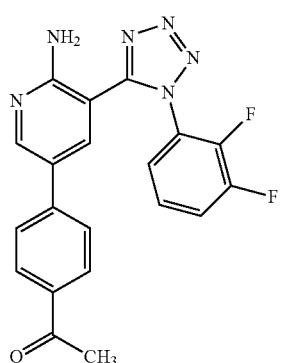
I-A-219
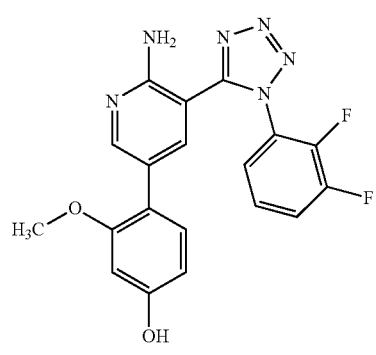
I-A-220

TABLE 1-continued
Compounds of Formula 1-A
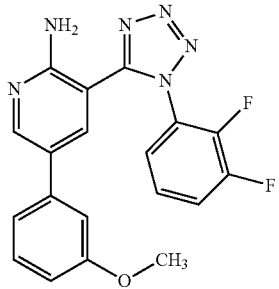
I-A-221
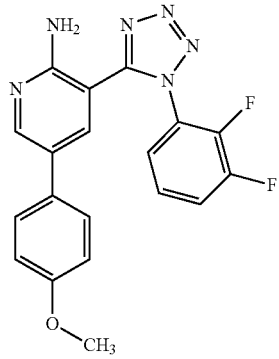
I-A-222
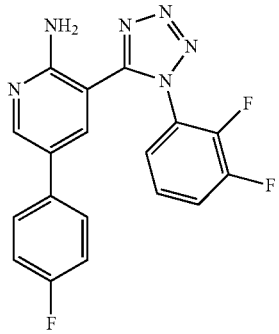
I-A-223
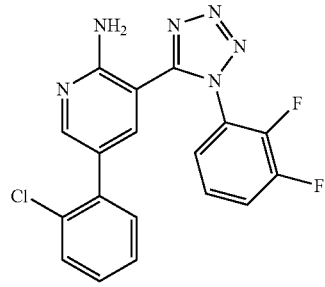
I-A-224
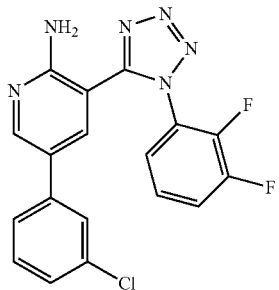
I-A-225
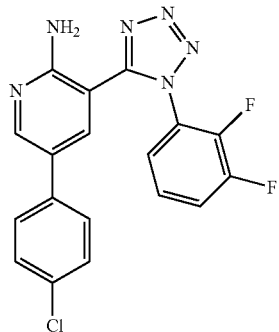
I-A-226
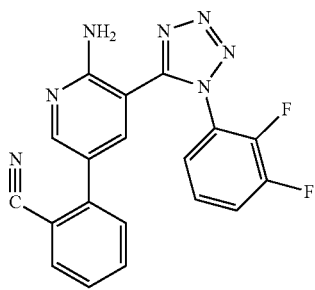
I-A-227
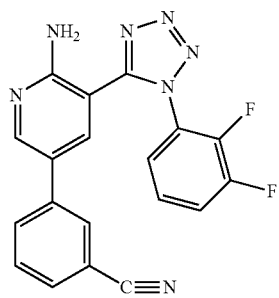
I-A-228

TABLE 1-continued
Compounds of Formula 1-A
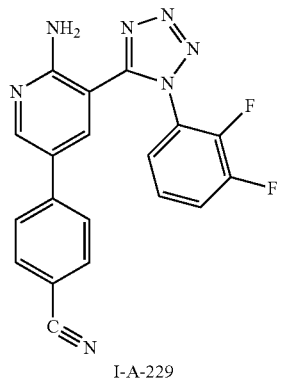
I-A-229
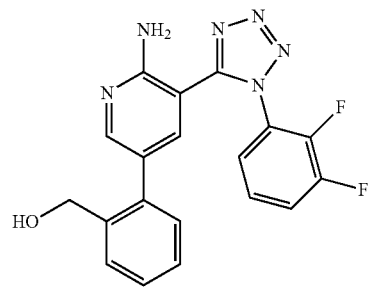
I-A-230
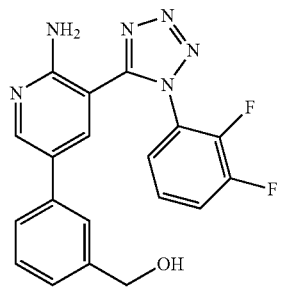
I-A-231
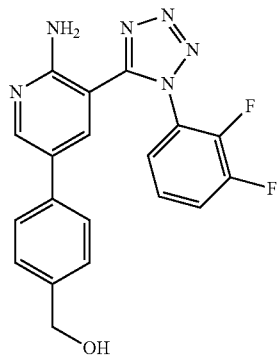
I-A-232
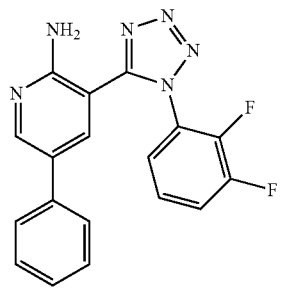
I-A-233
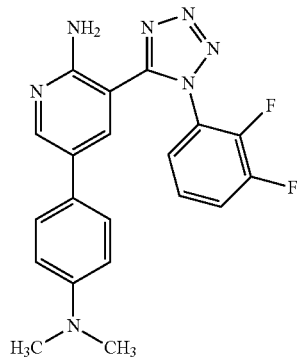
I-A-234
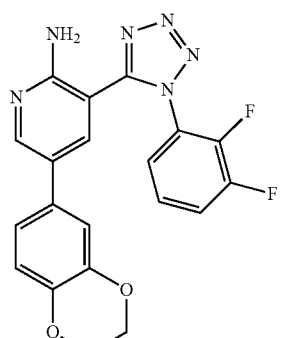
I-A-235
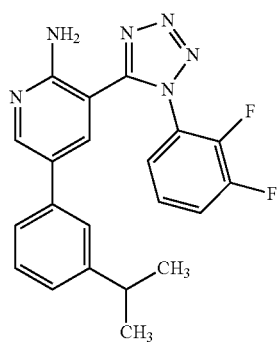
I-A-236

TABLE 1-continued
Compounds of Formula 1-A
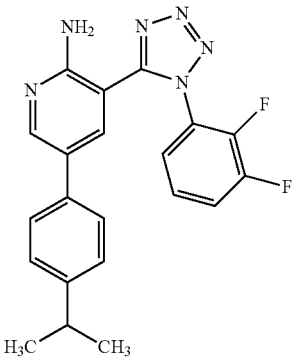
I-A-237
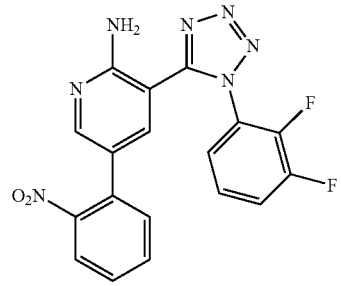
I-A-238
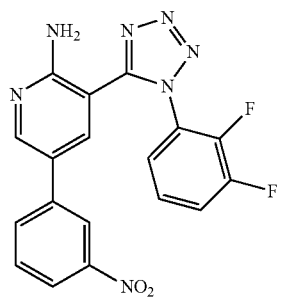
I-A-239
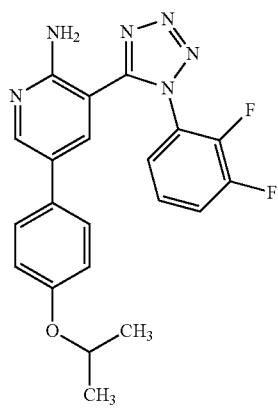
I-A-240
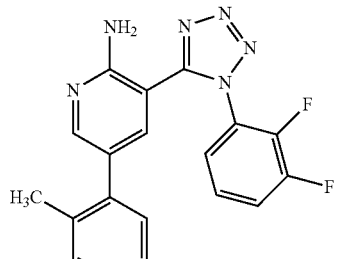
I-A-241
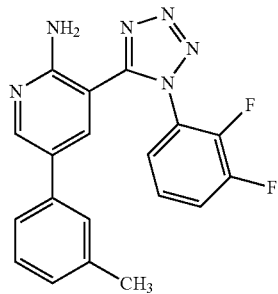
I-A-242
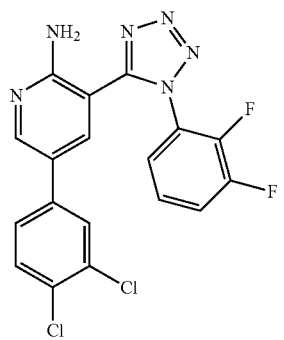
I-A-243
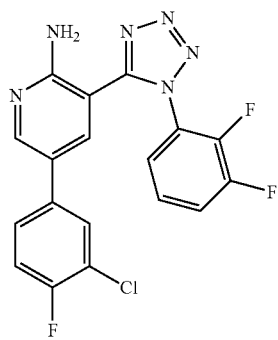
I-A-244

TABLE 1-continued
Compounds of Formula 1-A
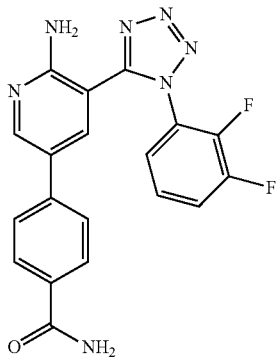
I-A-245
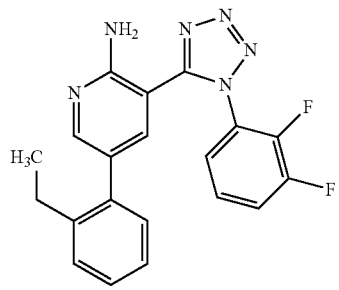
I-A-246
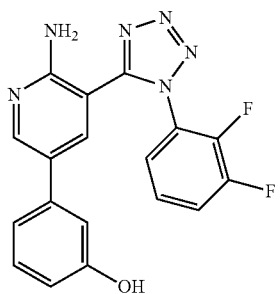
I-A-247
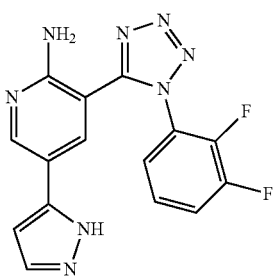
I-A-248
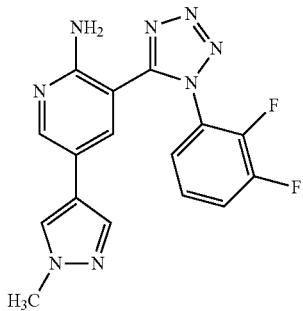
I-A-249
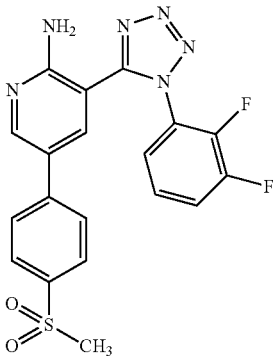
I-A-250
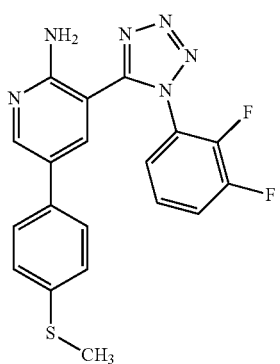
I-A-251
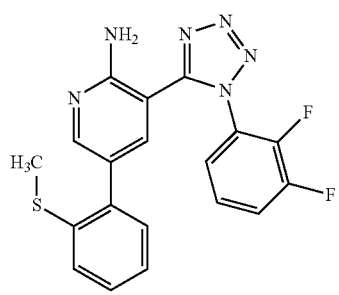
I-A-252

TABLE 1-continued
Compounds of Formula 1-A
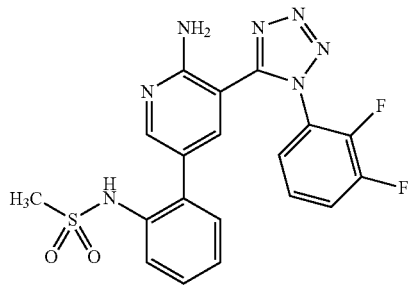
I-A-253
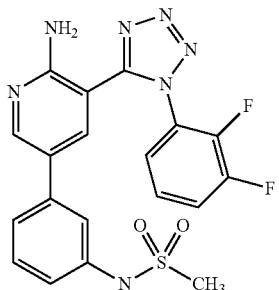
I-A-254
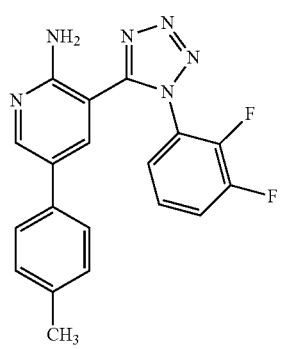
I-A-255
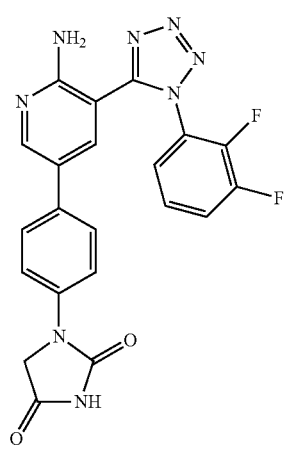
I-A-256
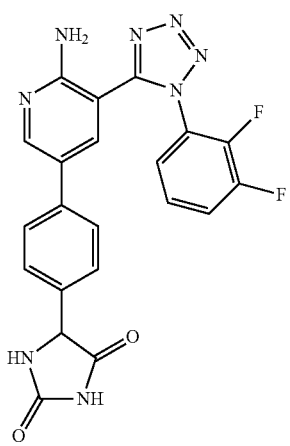
I-A-257
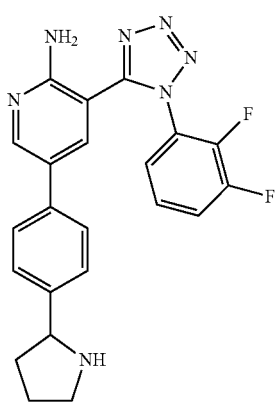
I-A-258

TABLE 1-continued
Compounds of Formula 1-A
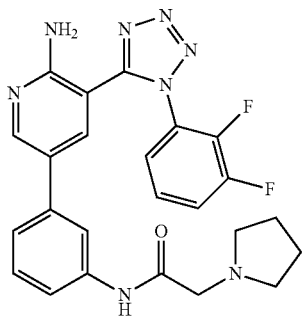
I-A-259
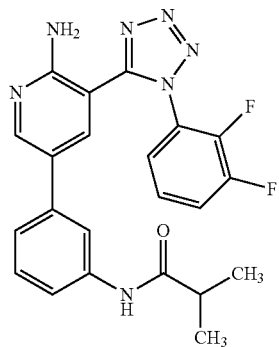
I-A-260
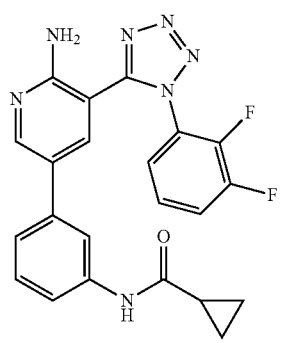
I-A-261
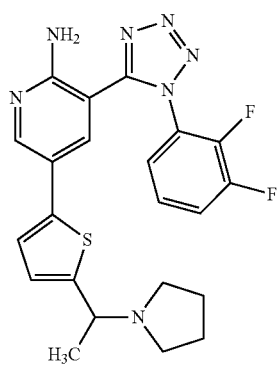
I-A-262
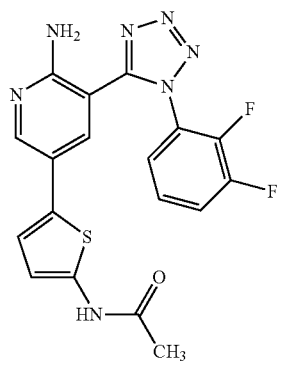
I-A-263
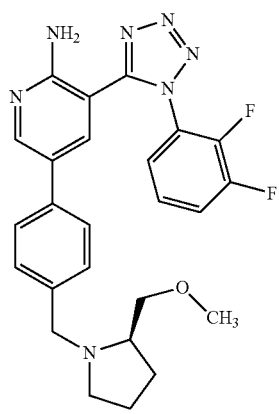
I-A-264

TABLE 1-continued
Compounds of Formula 1-A
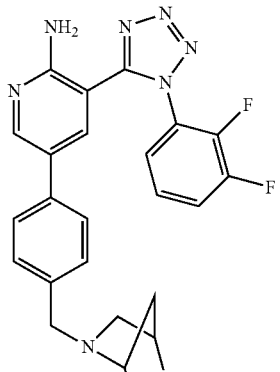
I-A-265
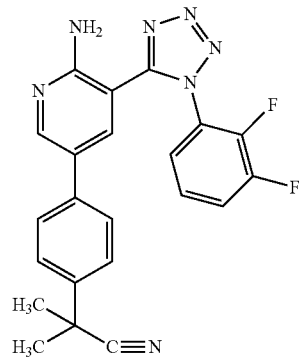
I-A-266
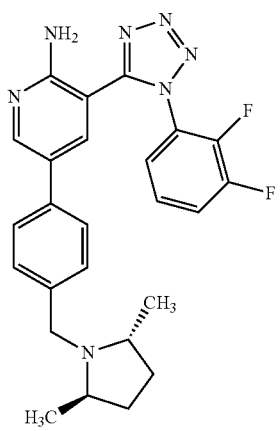
I-A-267
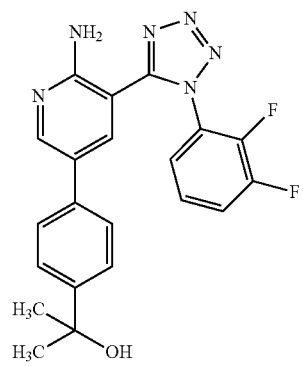
I-A-268
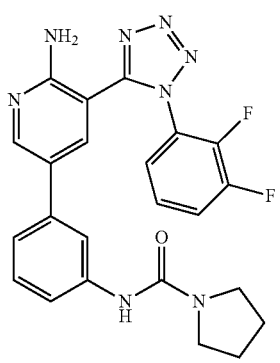
I-A-269
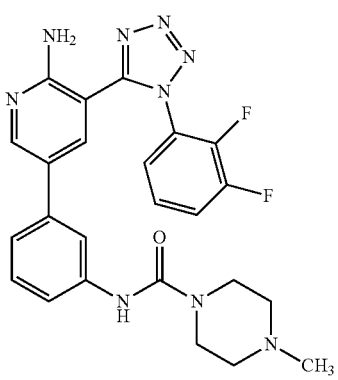
I-A-270

TABLE 1-continued
Compounds of Formula 1-A
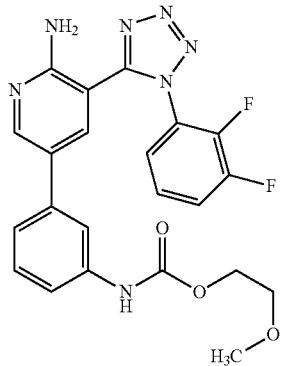
I-A-271
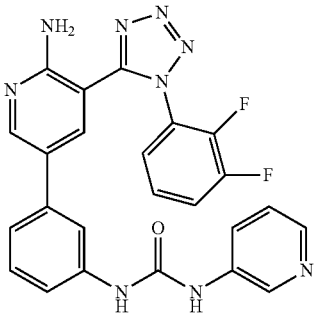
I-A-272
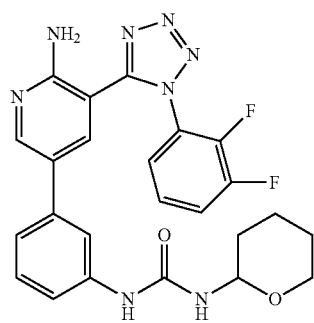
I-A-273
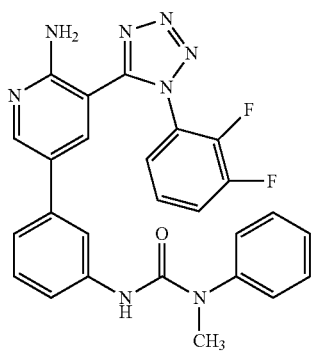
I-A-274
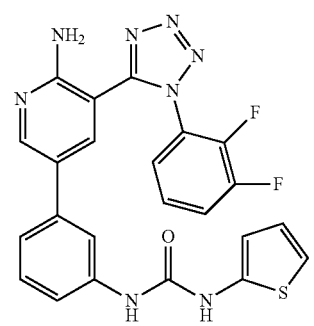
I-A-275
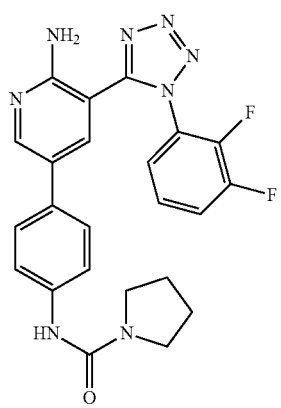
I-A-276

TABLE 1-continued
Compounds of Formula 1-A
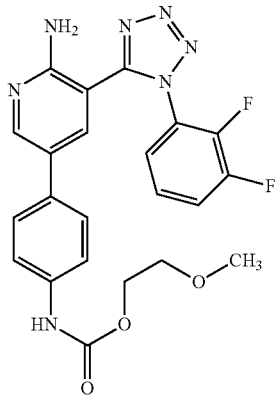
I-A-277
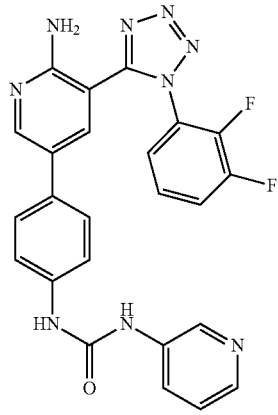
I-A-278
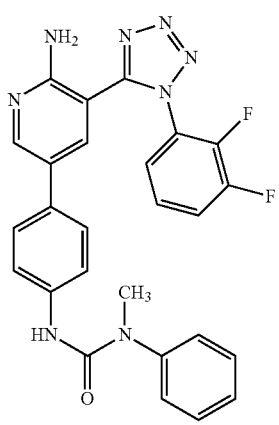
I-A-279
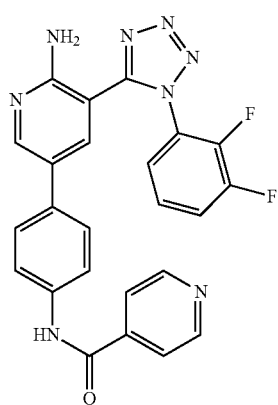
I-A-280
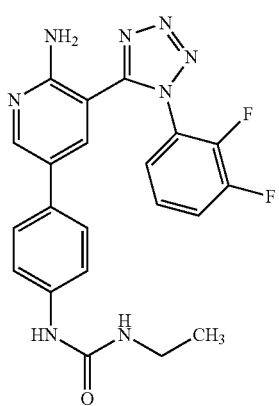
I-A-281
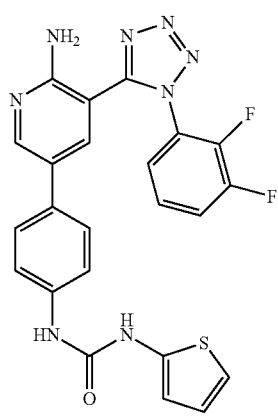
I-A-282

TABLE 1-continued
Compounds of Formula 1-A
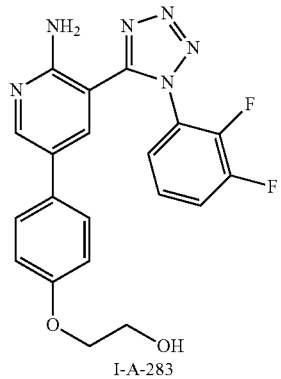
I-A-283
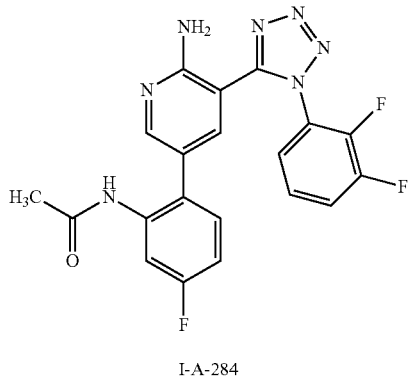
I-A-284
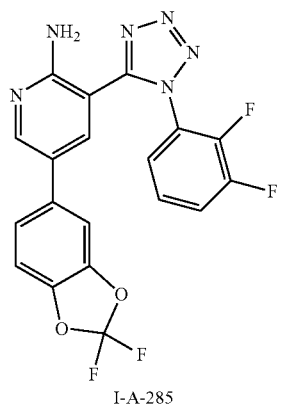
I-A-285
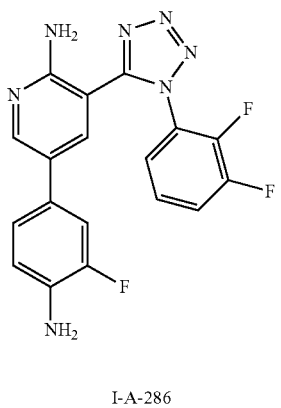
I-A-286
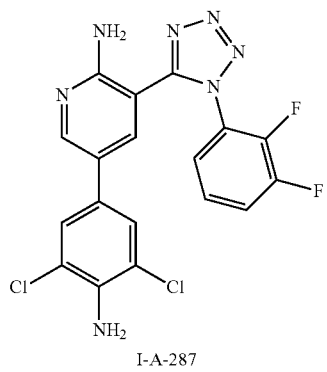
I-A-287
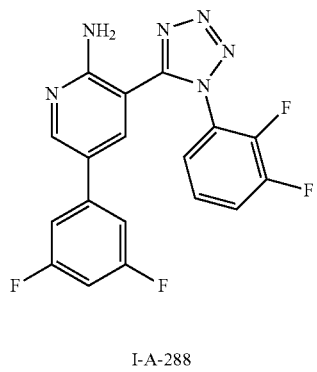
I-A-288
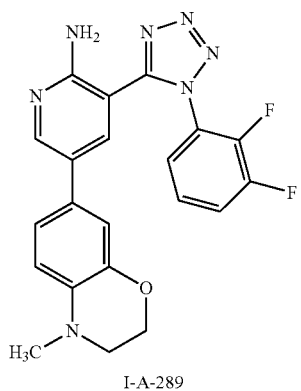
I-A-289
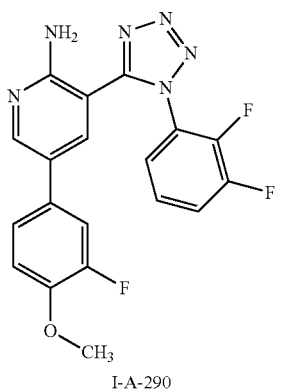
I-A-290

TABLE 1-continued
Compounds of Formula 1-A
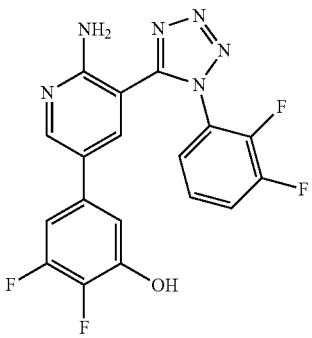
I-A-291
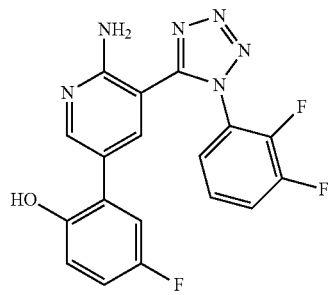
I-A-292
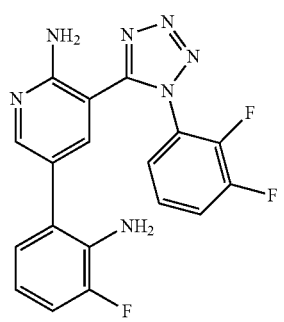
I-A-293
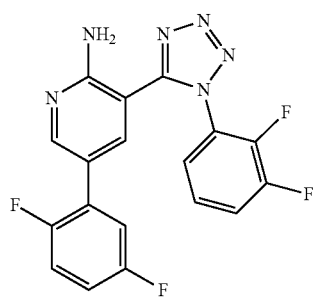
I-A-294
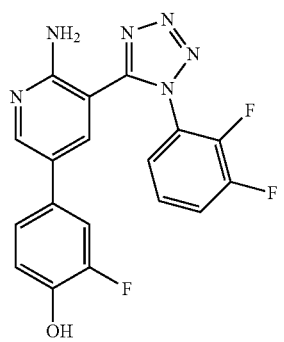
I-A-295
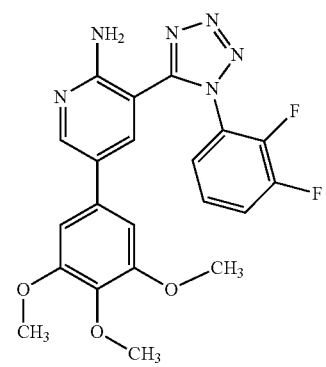
I-A-296
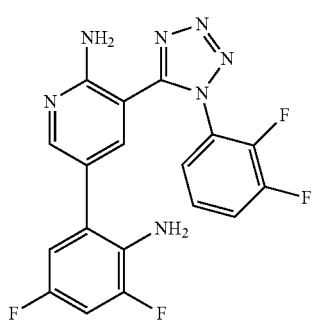
I-A-297
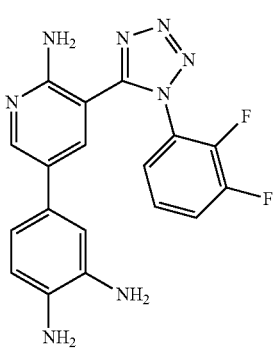
I-A-298

TABLE 1-continued
Compounds of Formula 1-A
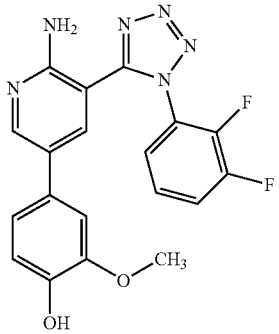
I-A-299
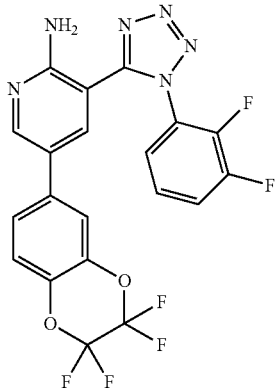
I-A-300
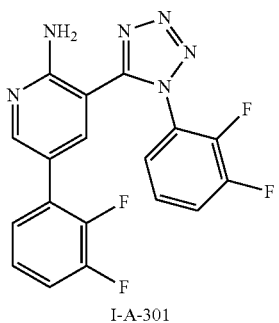
I-A-301
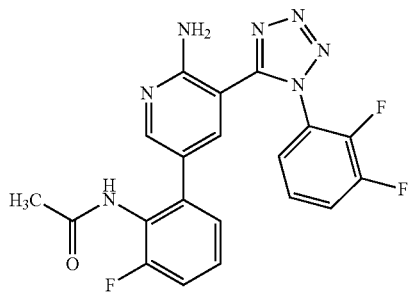
I-A-302
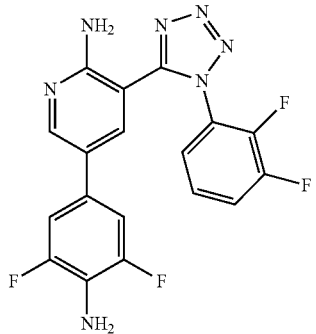
I-A-303
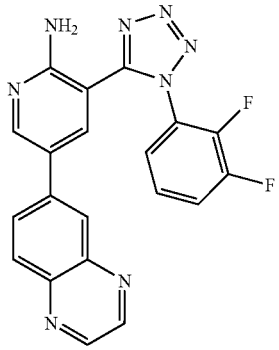
I-A-304
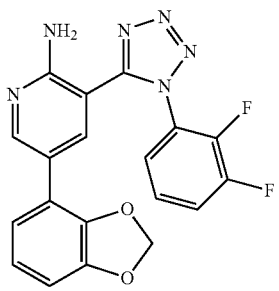
I-A-305
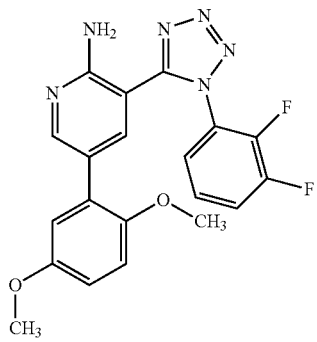
I-A-306

TABLE 1-continued
Compounds of Formula 1-A
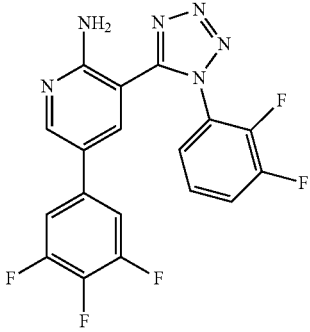
I-A-307
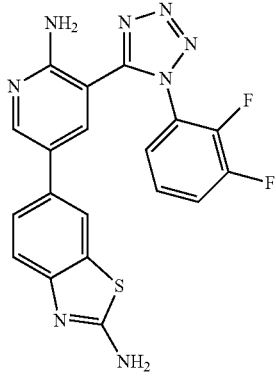
I-A-308
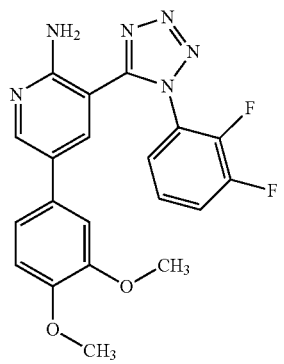
I-A-309
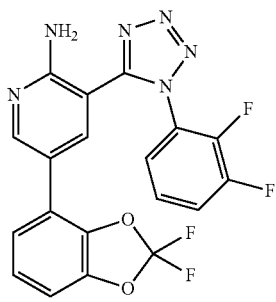
I-A-310
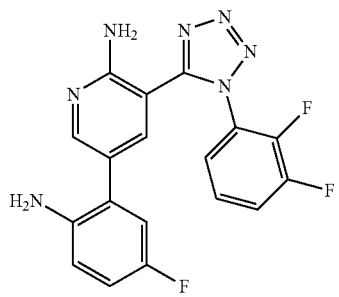
I-A-311
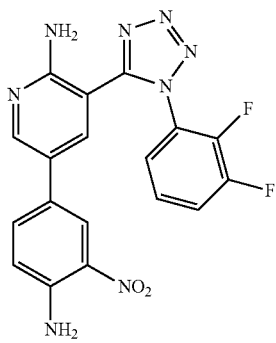
I-A-312
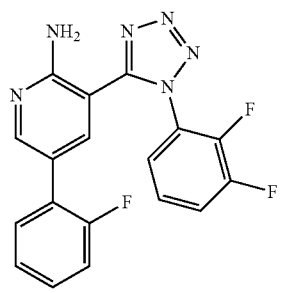
I-A-313
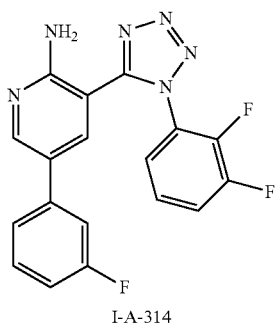
I-A-314

TABLE 1-continued
Compounds of Formula 1-A
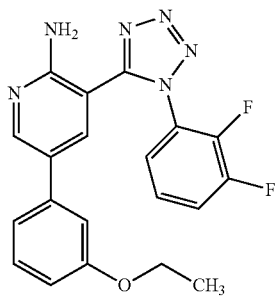
I-A-315
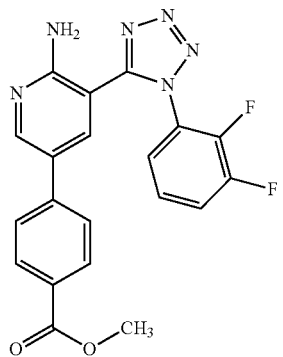
I-A-316
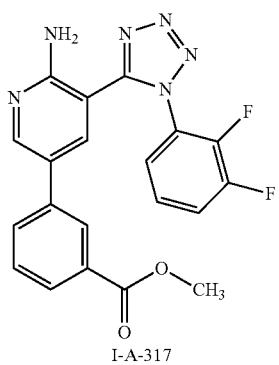
I-A-317
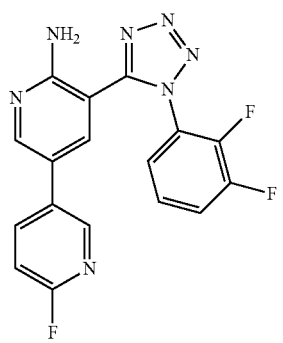
I-A-318
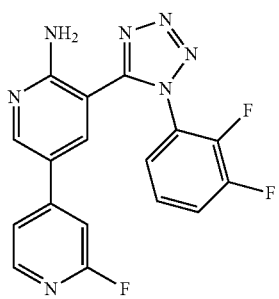
I-A-319
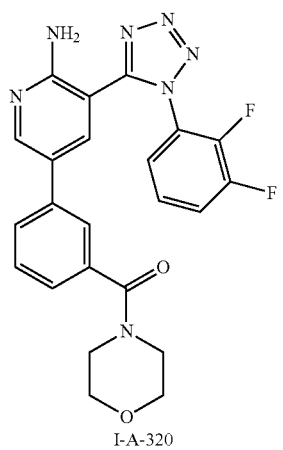
I-A-320
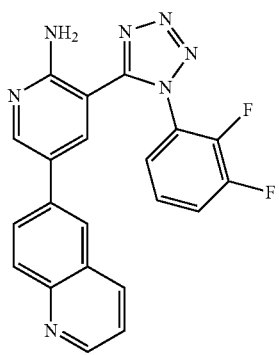
I-A-321
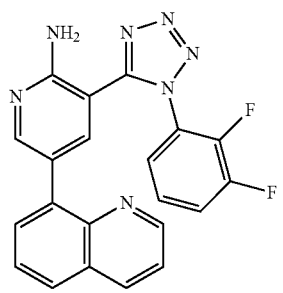
I-A322

TABLE 1-continued
Compounds of Formula 1-A
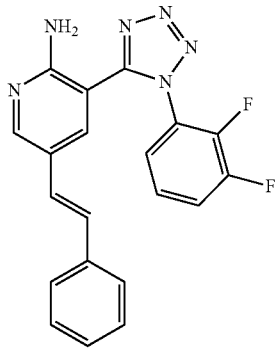
I-A-323
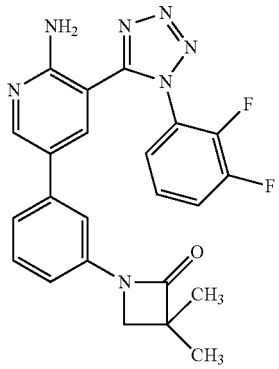
I-A-324
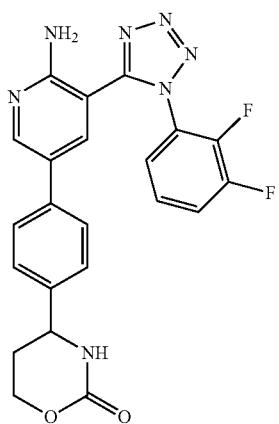
I-A-325
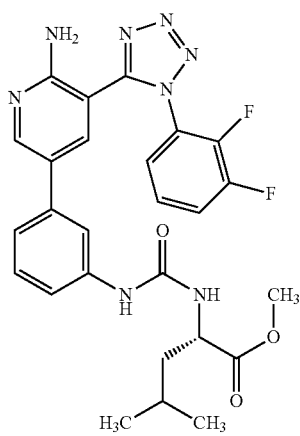
I-A-326
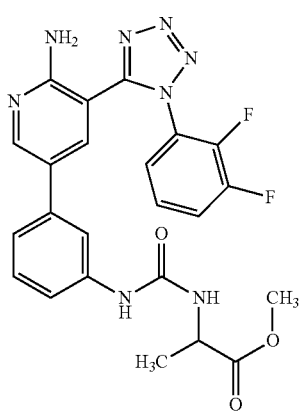
I-A-327
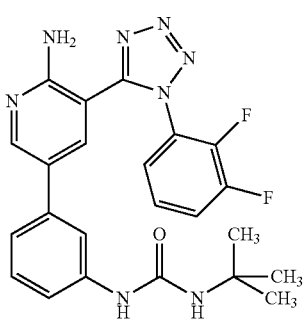
I-A-328

TABLE 1-continued
Compounds of Formula 1-A
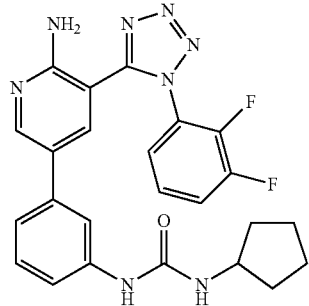
I-A-329
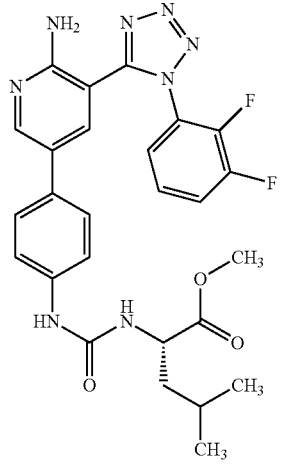
I-A-330
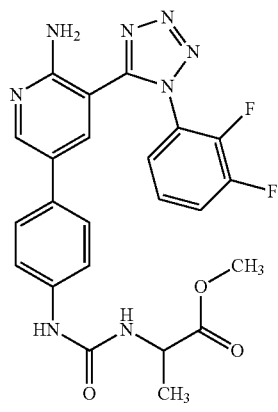
I-A-331
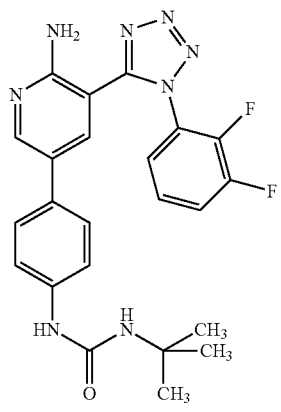
I-A-332
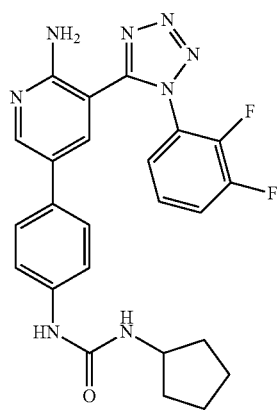
I-A-333
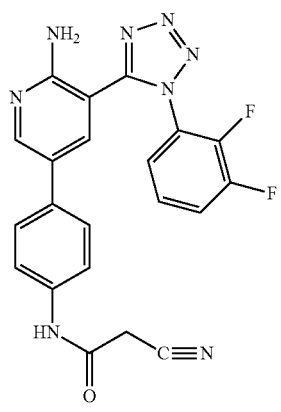
I-A-334

TABLE 1-continued
Compounds of Formula 1-A
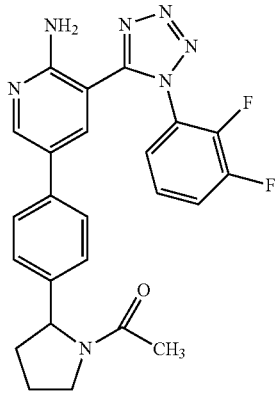
I-A-335
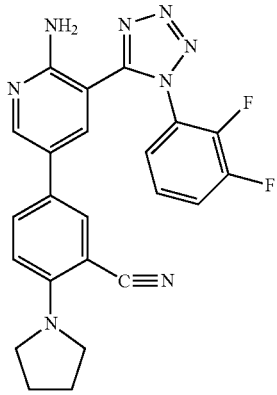
I-A-336
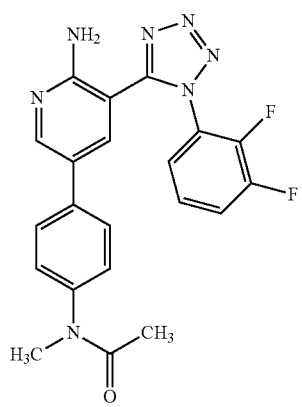
I-A-337
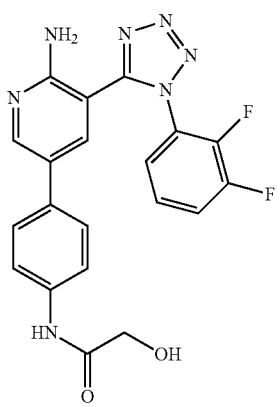
I-A-338
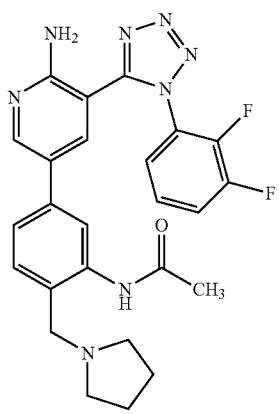
I-A-339
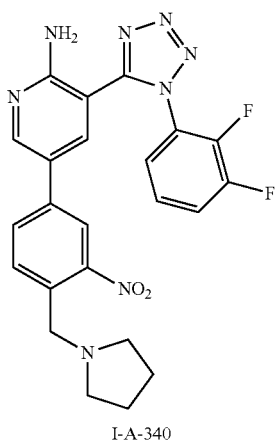
I-A-340

TABLE 1-continued
Compounds of Formula 1-A
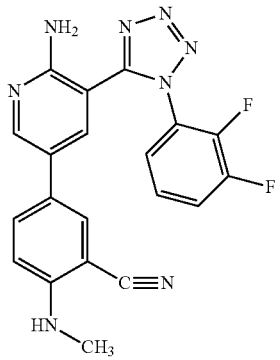
I-A-341
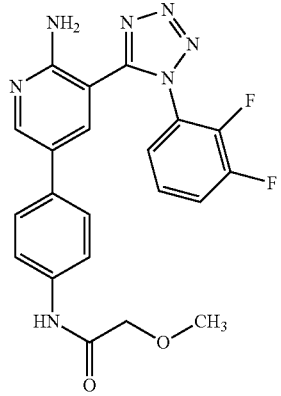
I-A-342
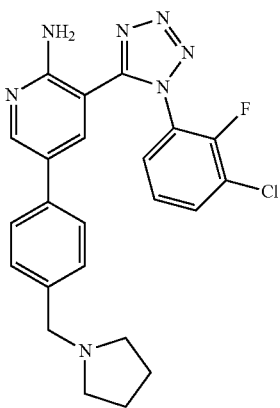
I-A-343
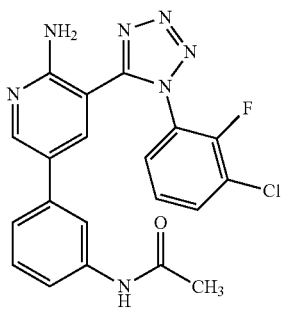
I-A-344
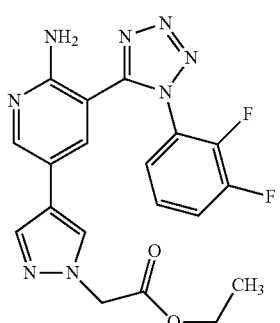
I-A-345
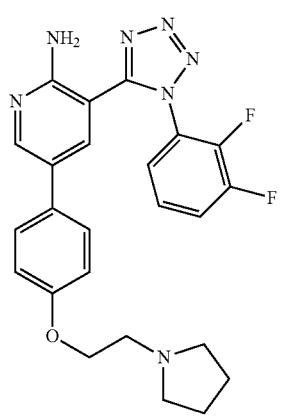
I-A-346

TABLE 1-continued
Compounds of Formula 1-A
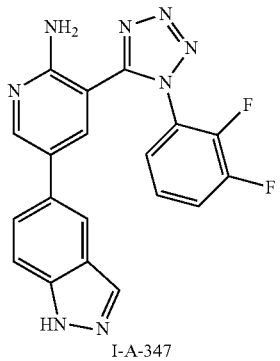
I-A-347
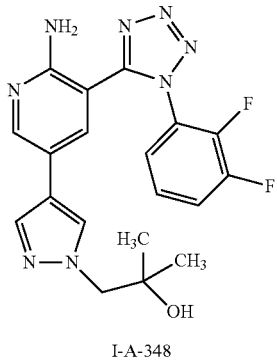
I-A-348
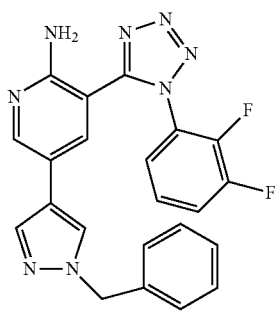
I-A-349
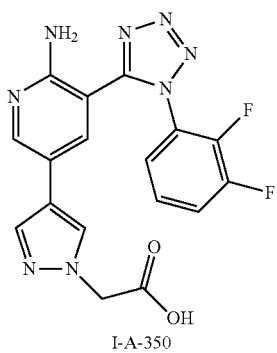
I-A-350
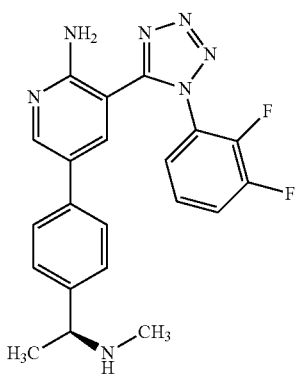
I-A-351
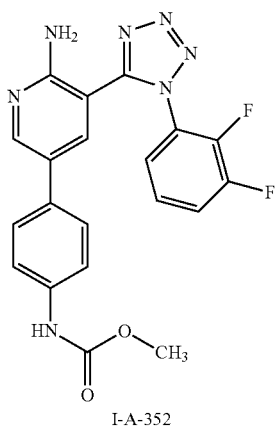
I-A-352
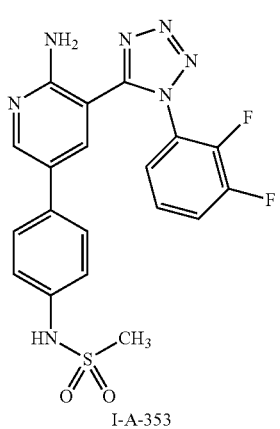
I-A-353
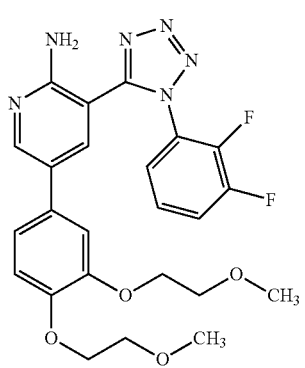
I-A-354

TABLE 1-continued
Compounds of Formula 1-A
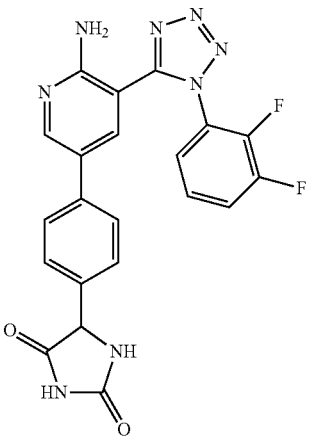
I-A-355
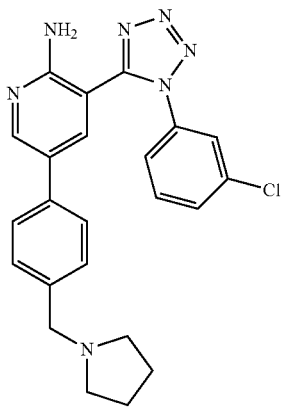
I-A-356
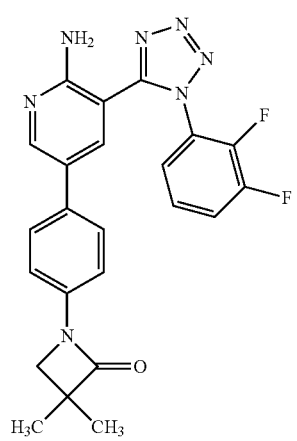
I-A-357
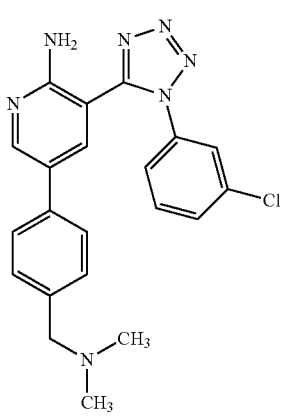
I-A-358
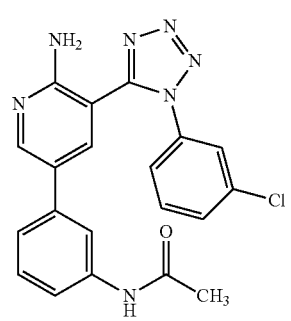
I-A-359
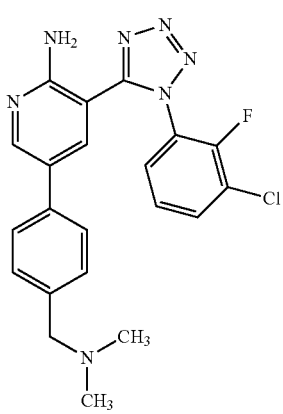
I-A-360

TABLE 1-continued
Compounds of Formula 1-A
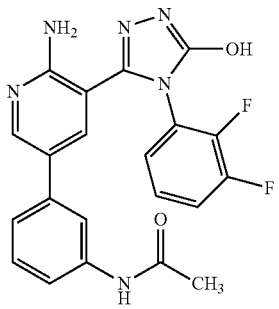
I-A-361
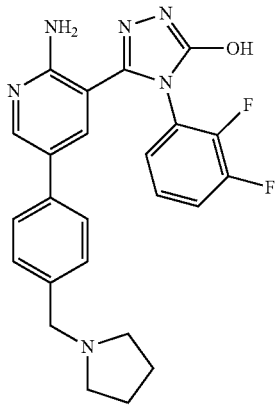
I-A-362
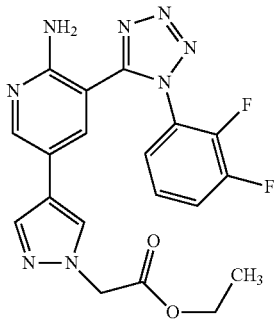
I-A-363
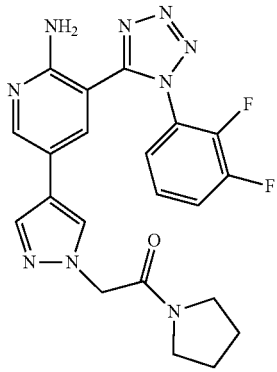
I-A-364
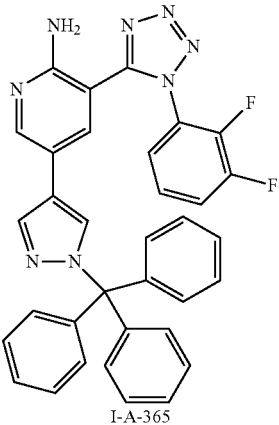
I-A-365
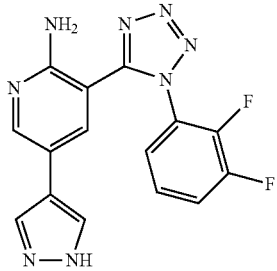
I-A-366
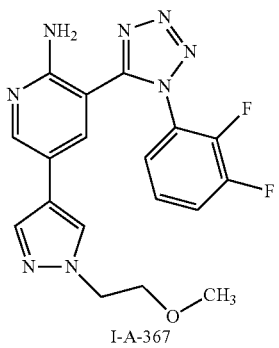
I-A-367
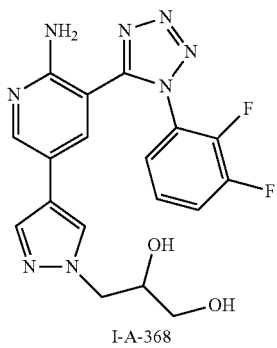
I-A-368

TABLE 1-continued
Compounds of Formula 1-A
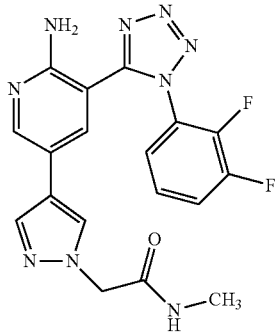
I-A-369
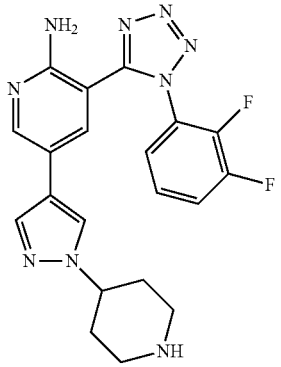
I-A-370
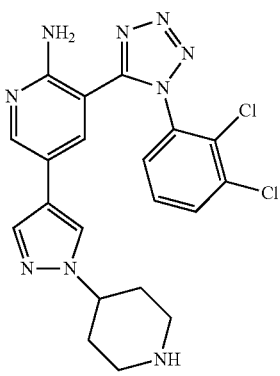
I-A-371
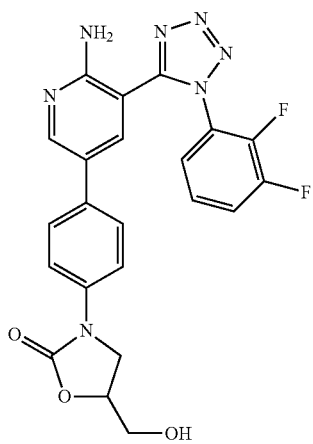
I-A-372
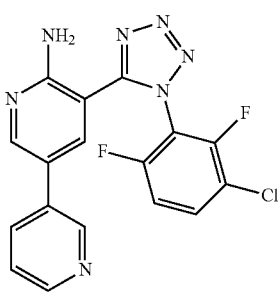
I-A-373
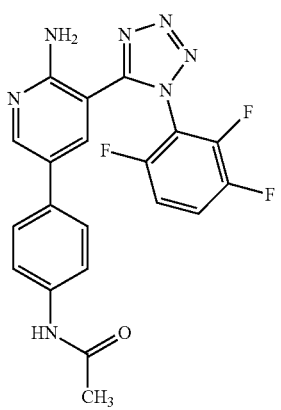
I-A-374

TABLE 1-continued
Compounds of Formula 1-A
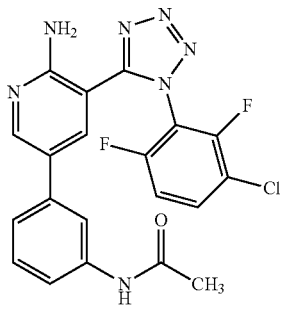
I-A-375
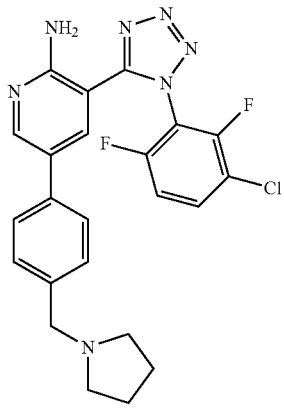
I-A-376
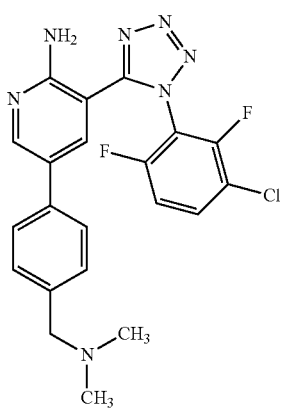
I-A-377
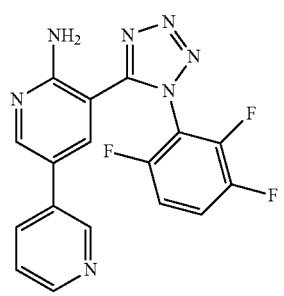
I-A-378
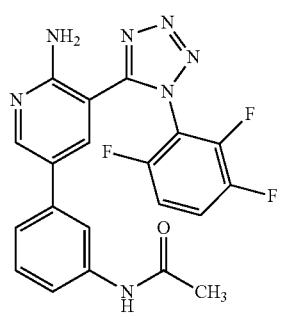
I-A-379
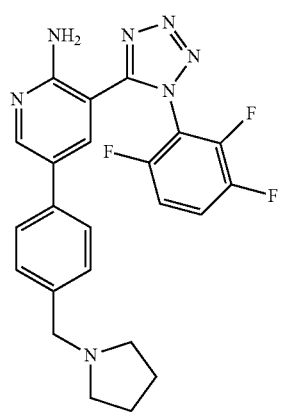
I-A-380

TABLE 1-continued
Compounds of Formula 1-A
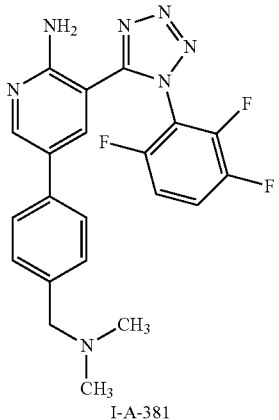
I-A-381
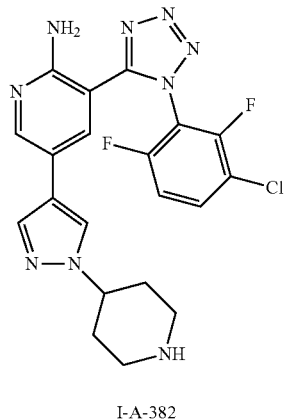
I-A-382
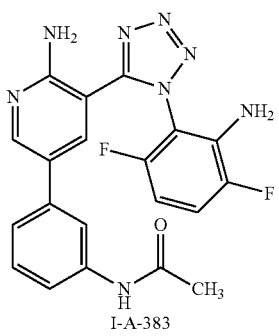
I-A-383
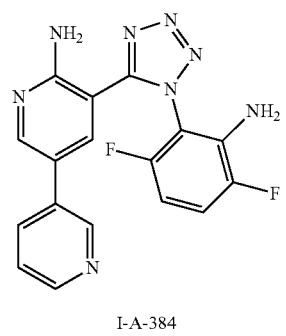
I-A-384
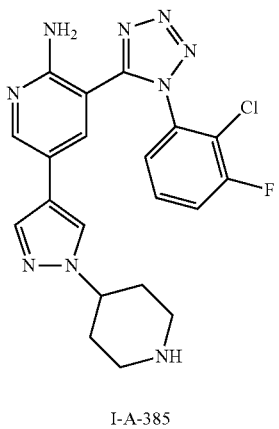
I-A-385
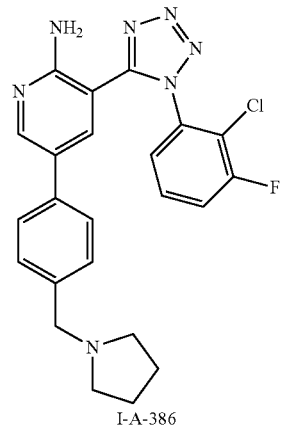
I-A-386
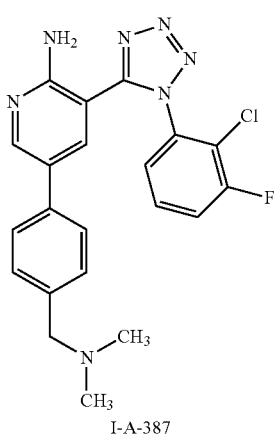
I-A-387
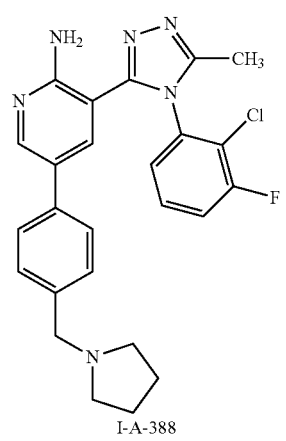
I-A-388

TABLE 1-continued
Compounds of Formula 1-A
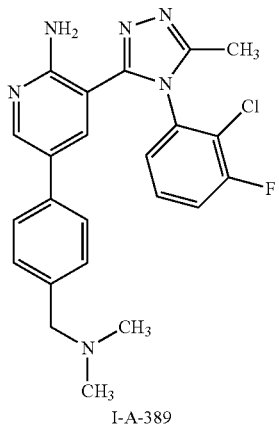
I-A-389
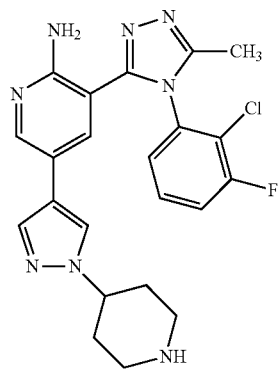
I-A-390
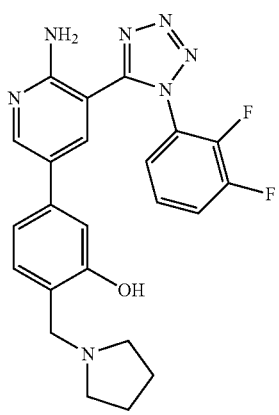
I-A-391
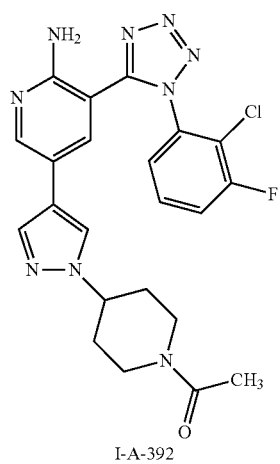
I-A-392
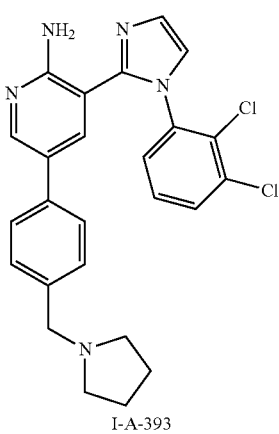
I-A-393
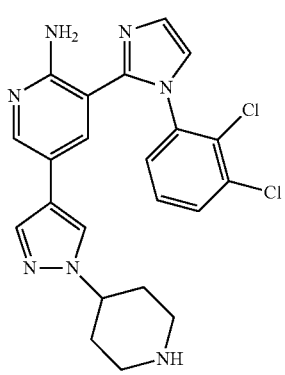
I-A-394

TABLE 1-continued
Compounds of Formula 1-A
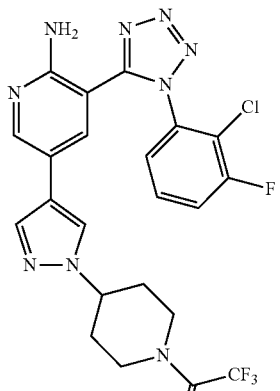
I-A-395
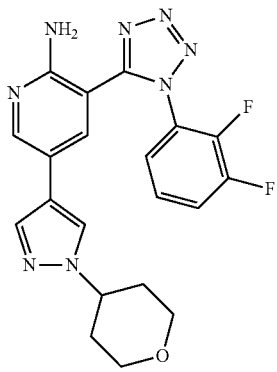
I-A-396
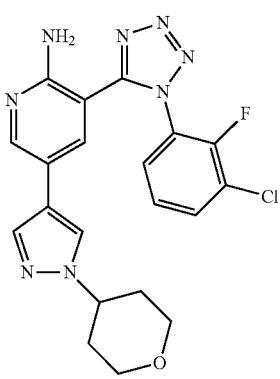
I-A-397
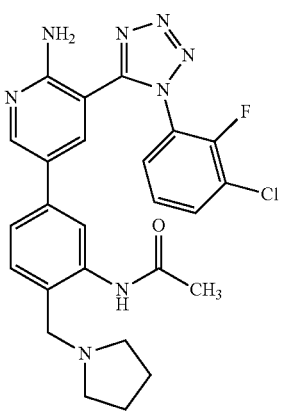
I-A-398
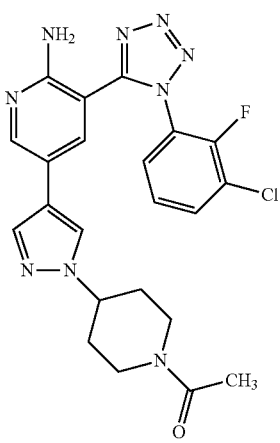
I-A-399
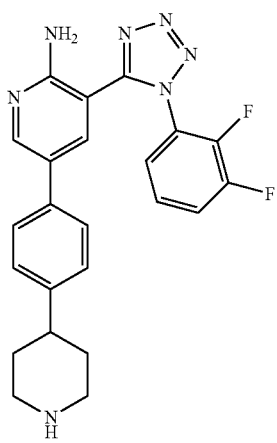
I-A-400

TABLE 1-continued
Compounds of Formula 1-A
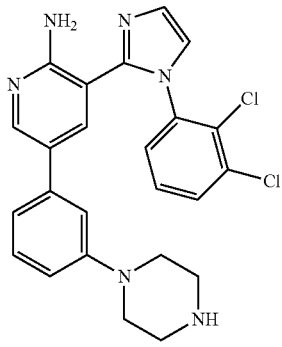
I-A-401
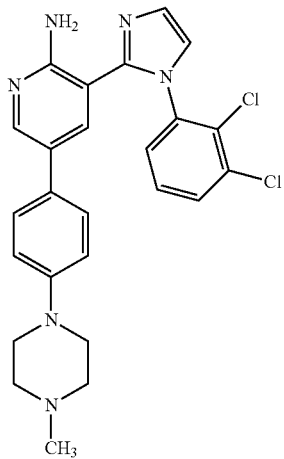
I-A-402
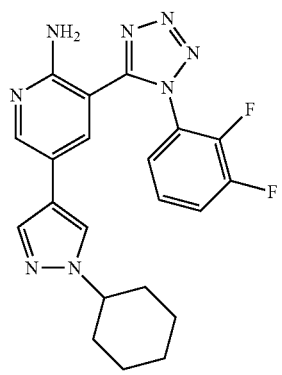
I-A-403
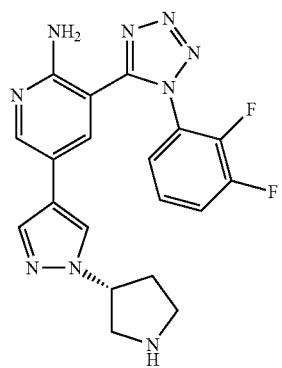
I-A-404
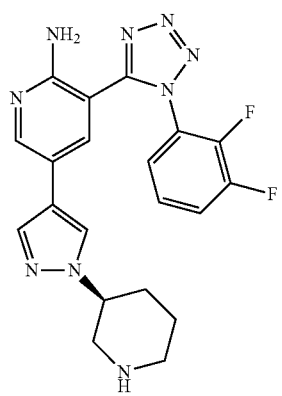
I-A-405
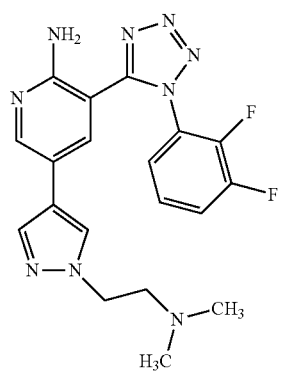
I-A-406

TABLE 1-continued
Compounds of Formula 1-A
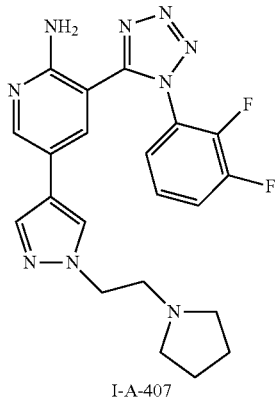
I-A-407
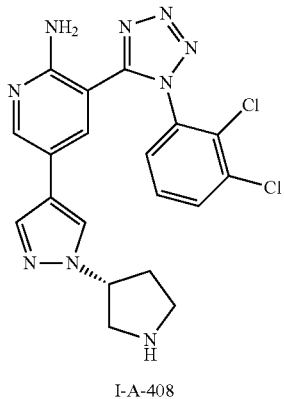
I-A-408
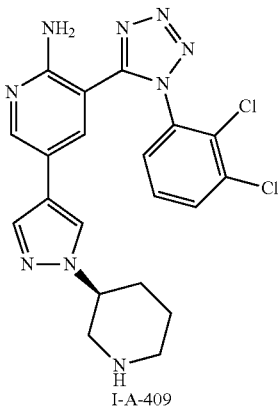
I-A-409
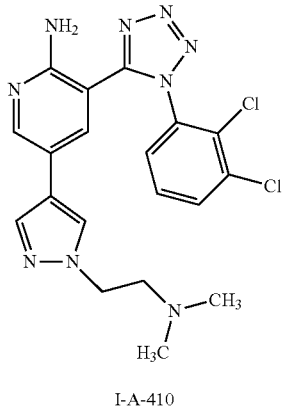
I-A-410
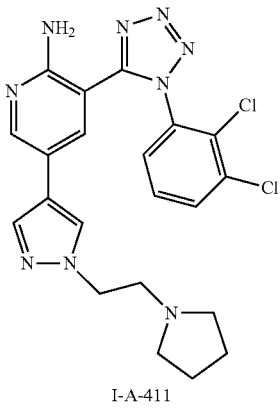
I-A-411
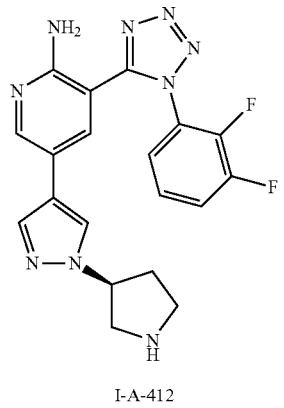
I-A-412
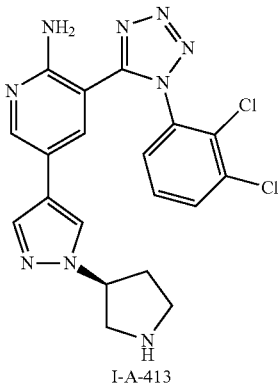
I-A-413
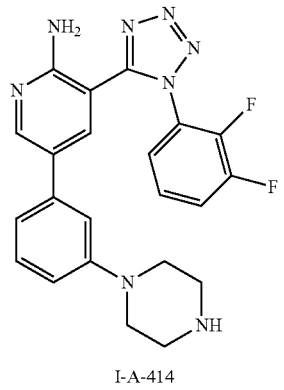
I-A-414

TABLE 1-continued
Compounds of Formula 1-A
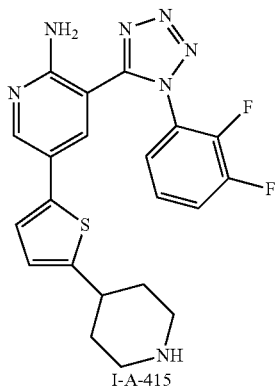
I-A-415
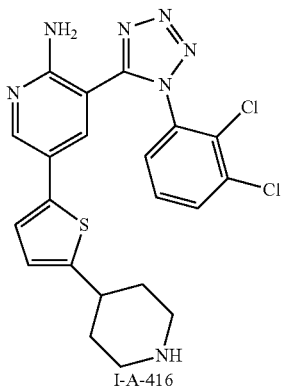
I-A-416
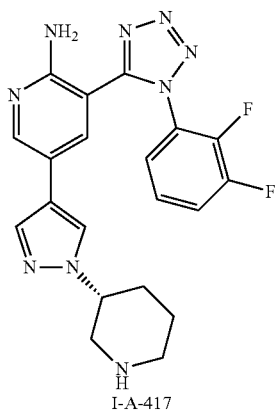
I-A-417
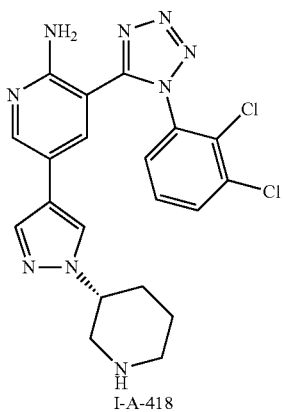
I-A-418
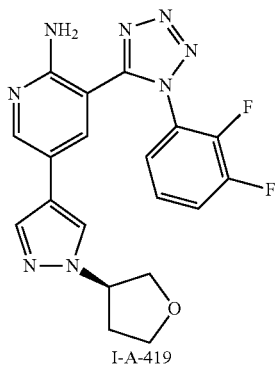
I-A-419
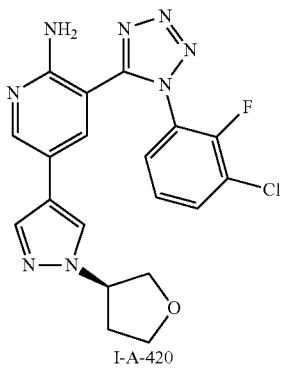
I-A-420
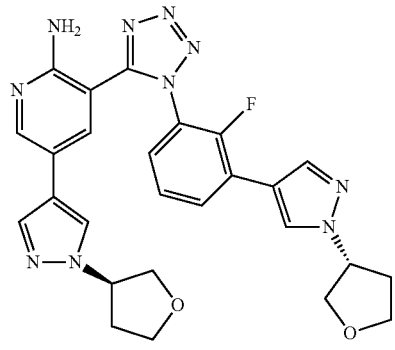
I-A-421
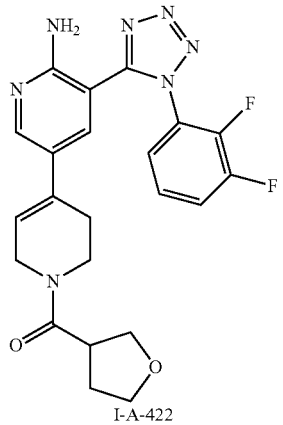
I-A-422

TABLE 1-continued
Compounds of Formula 1-A
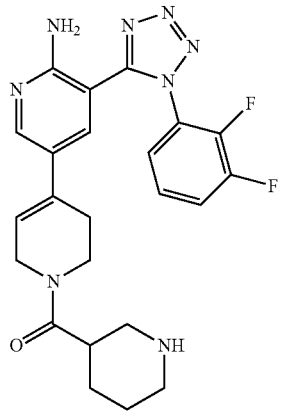
I-A-423
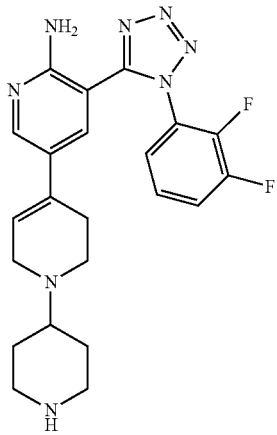
I-A-424
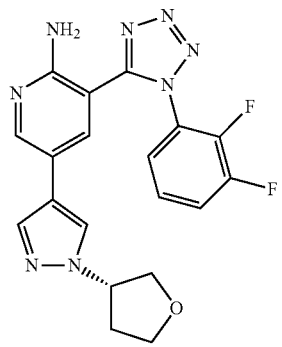
I-A-425
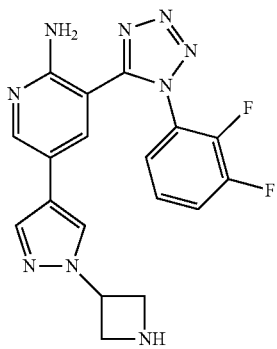
I-A-426
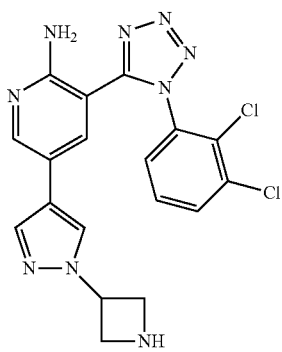
I-A-427
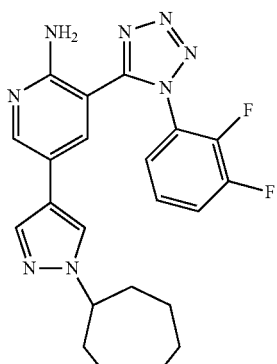
I-A-428

TABLE 1-continued
Compounds of Formula 1-A
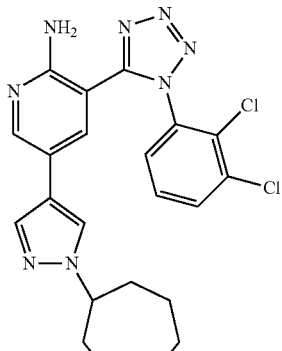
I-A-429
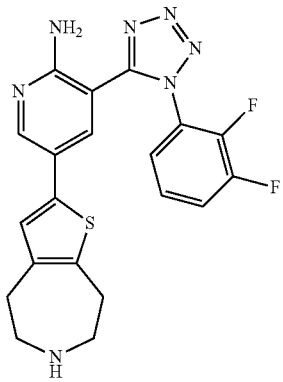
I-A-430
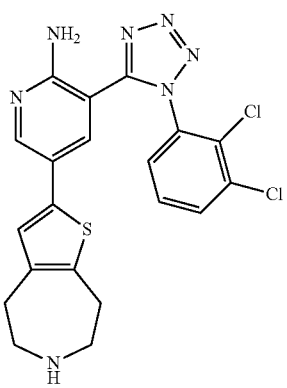
I-A-431
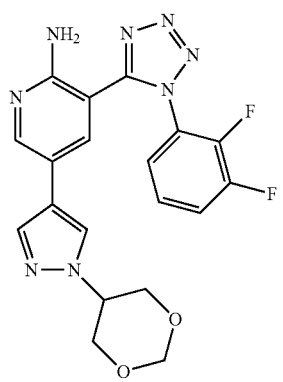
I-A-432
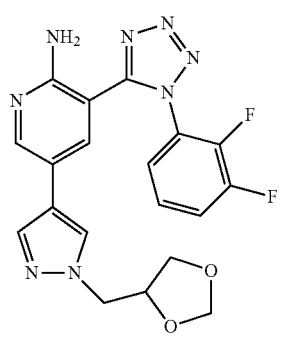
I-A-433
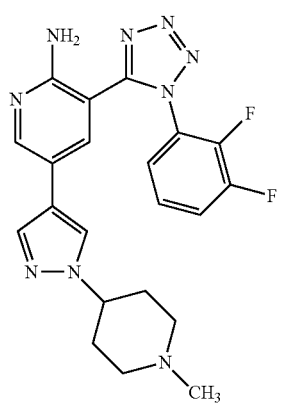
I-A-434

TABLE 1-continued
Compounds of Formula 1-A
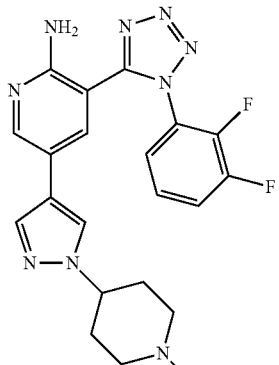
I-A-435
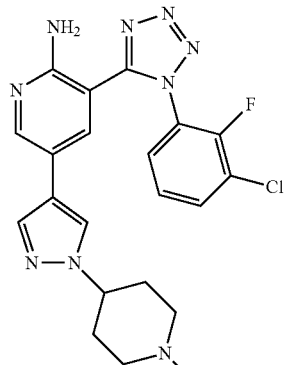
I-A-436
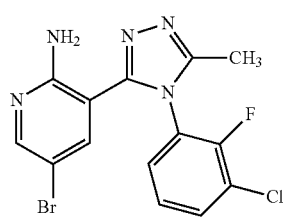
I-A-437
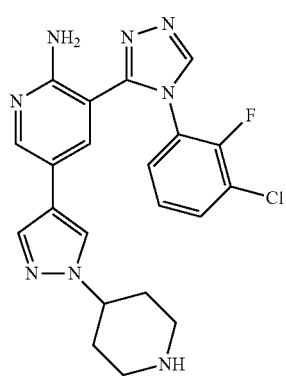
I-A-438
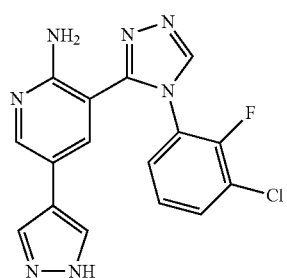
I-A-439
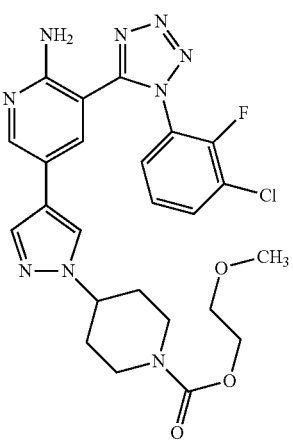
I-A-440

TABLE 1-continued
Compounds of Formula 1-A
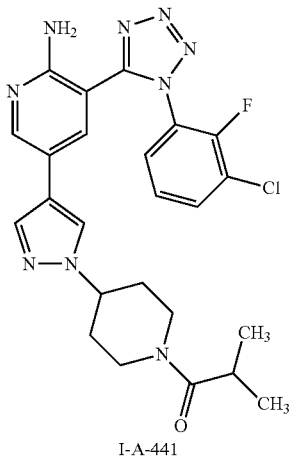
I-A-441
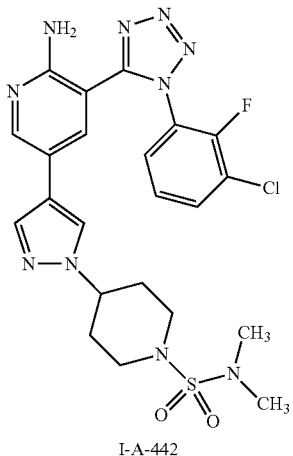
I-A-442
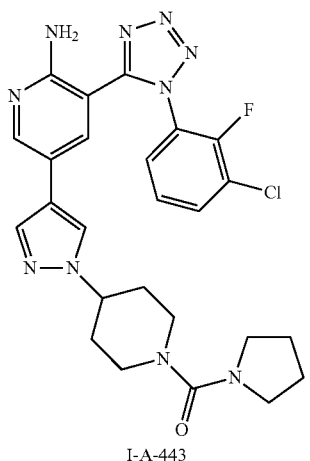
I-A-443
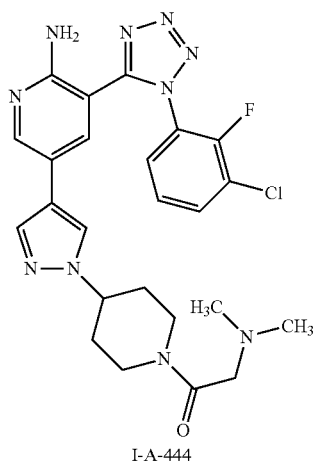
I-A-444
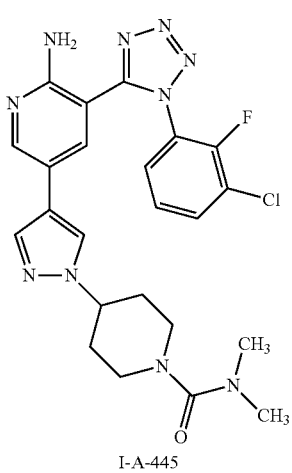
I-A-445
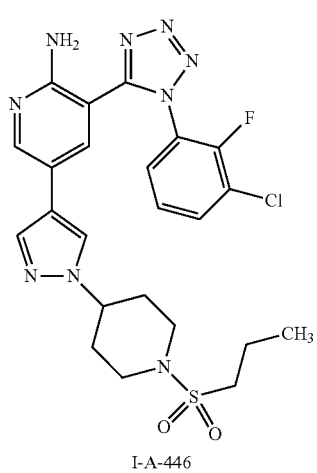
I-A-446

TABLE 1-continued
Compounds of Formula 1-A
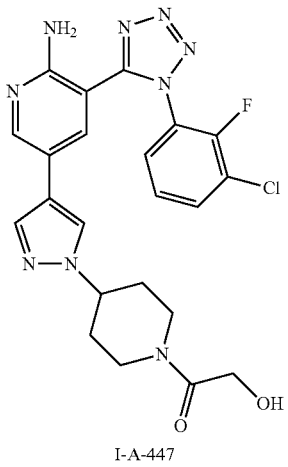
I-A-447
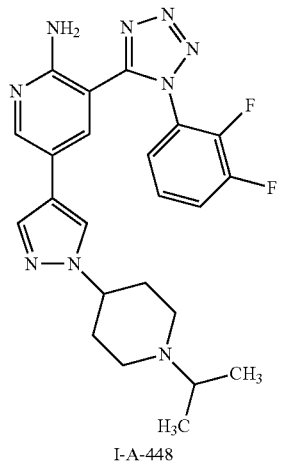
I-A-448
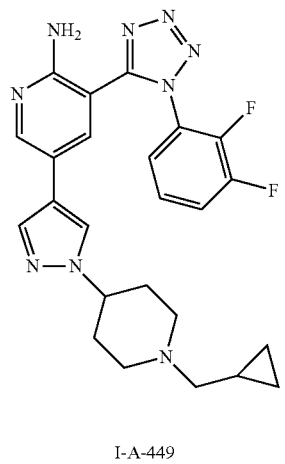
I-A-449
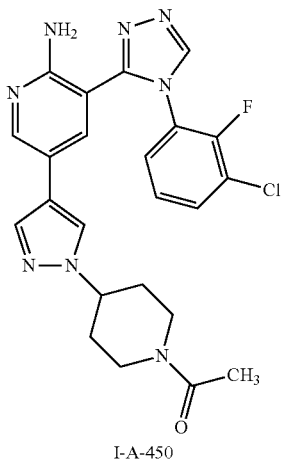
I-A-450
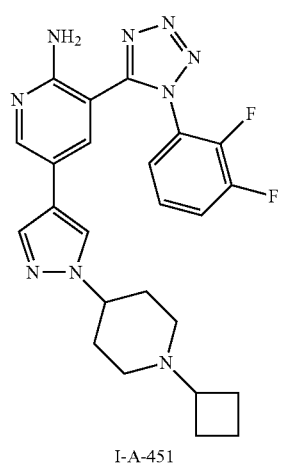
I-A-451
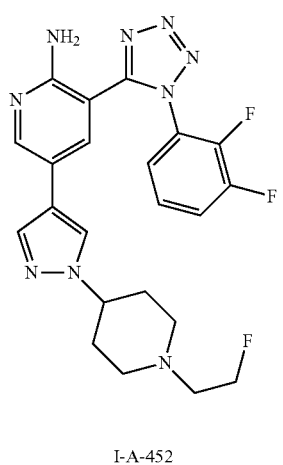
I-A-452

TABLE 1-continued
Compounds of Formula 1-A
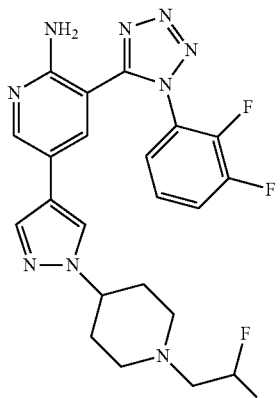
I-A-453
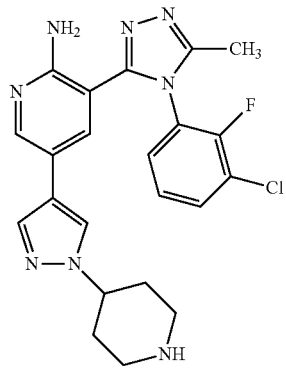
I-A-454
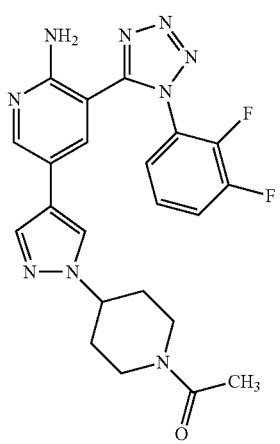
I-A-455
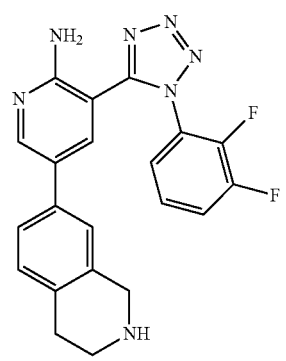
I-A-456
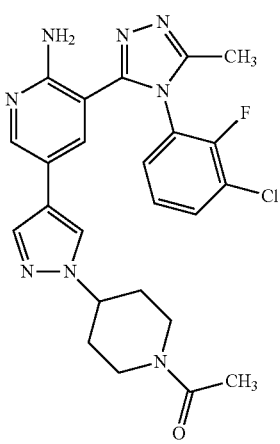
I-A-457
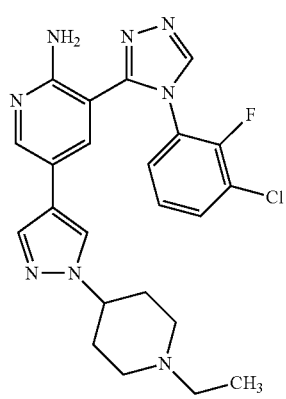
I-A-458

TABLE 1-continued
Compounds of Formula 1-A
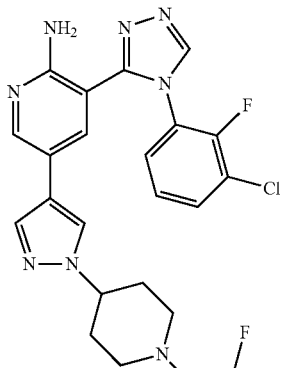
I-A-459
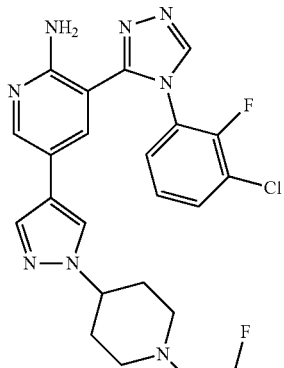
I-A-460
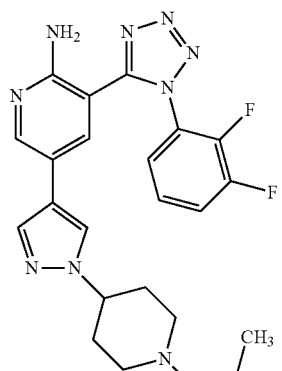
I-A-461
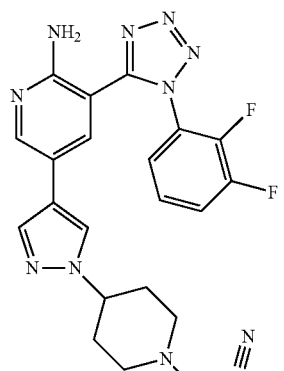
I-A-462
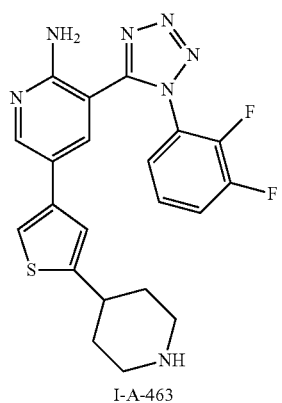
I-A-463
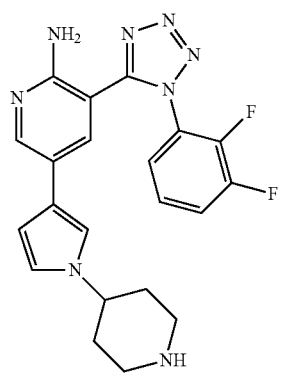
I-A-464

TABLE 1-continued
Compounds of Formula 1-A
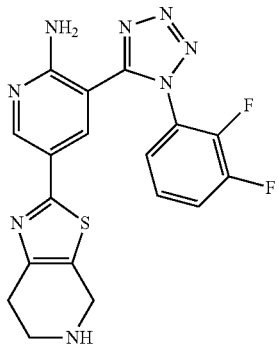
I-A-465
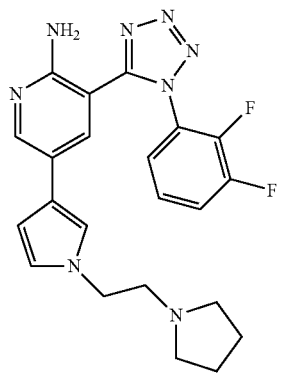
I-A-466
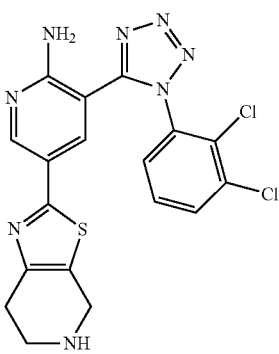
I-A-467
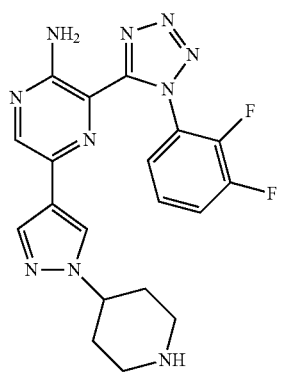
I-A-468
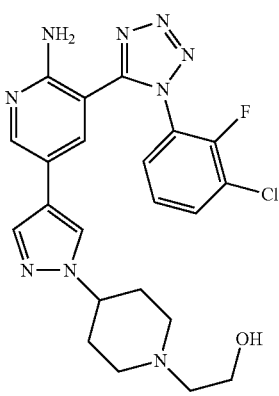
I-A-469
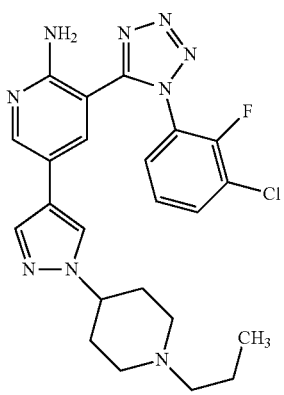
I-A-470

TABLE 1-continued
Compounds of Formula 1-A
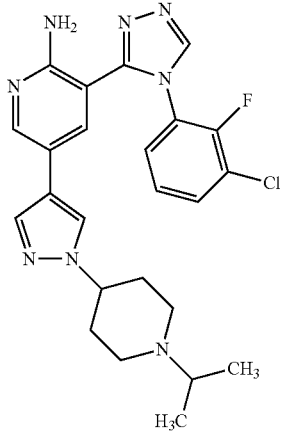
I-A-471
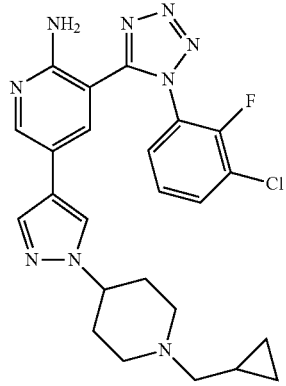
I-A-472
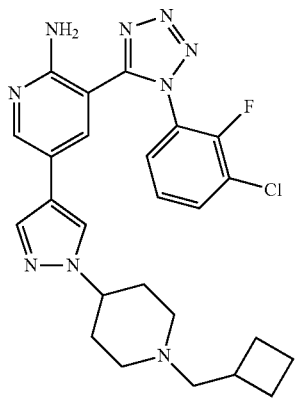
I-A-473
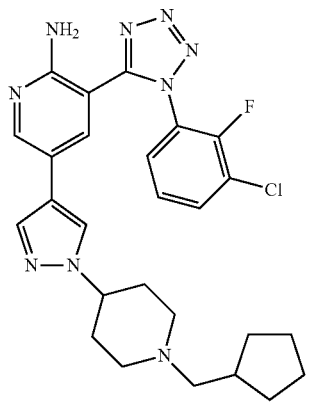
I-A-474
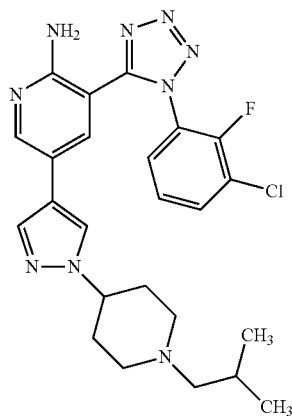
I-A-475
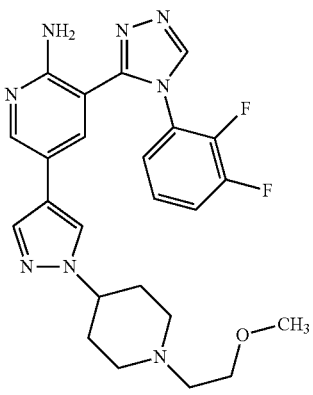
I-A-476

TABLE 1-continued
Compounds of Formula 1-A
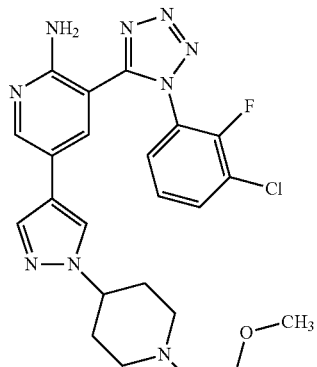
I-A-477
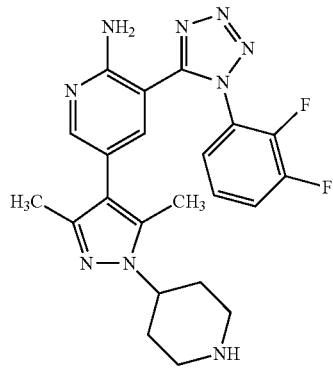
I-A-478
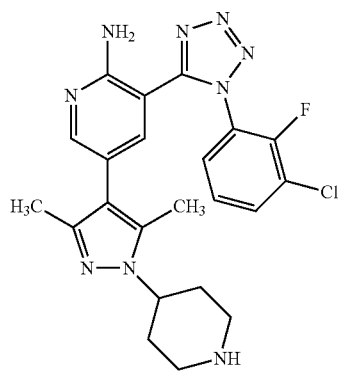
I-A-479
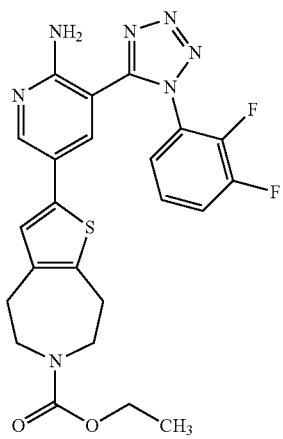
I-A-480
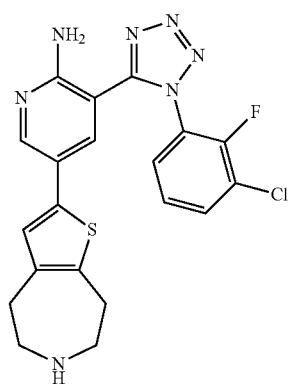
I-A-481
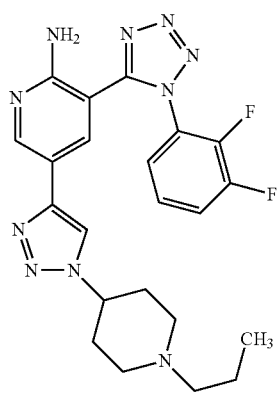
I-A-482

TABLE 1-continued
Compounds of Formula 1-A
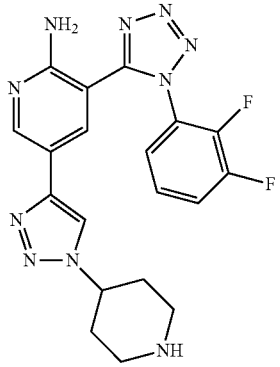
I-A-483
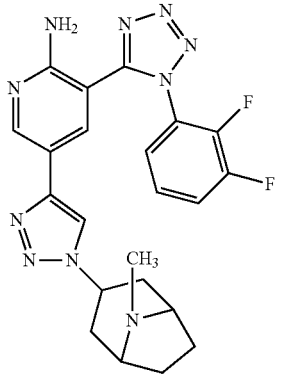
I-A-484
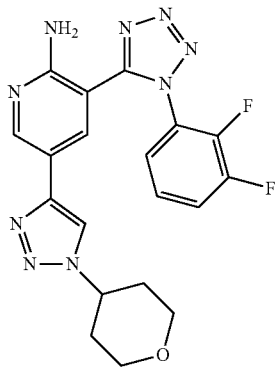
I-A-485
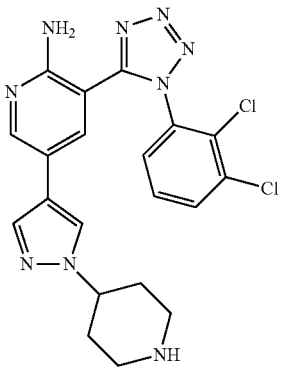
I-A-486
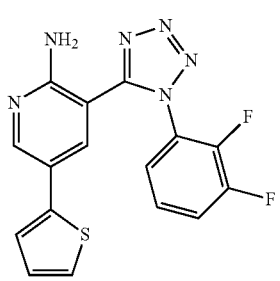
I-A-487
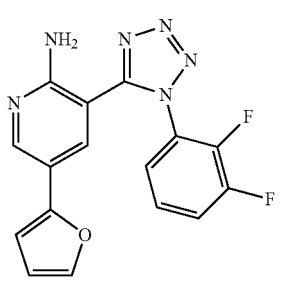
I-A-488
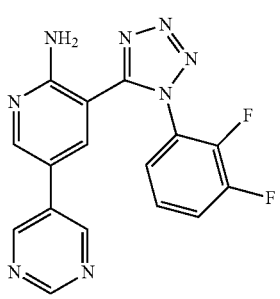
I-A-489
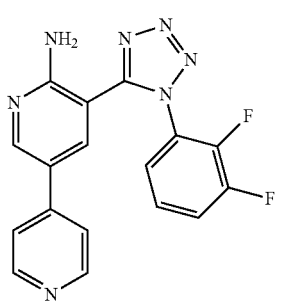
I-A-490

TABLE 1-continued
Compounds of Formula 1-A
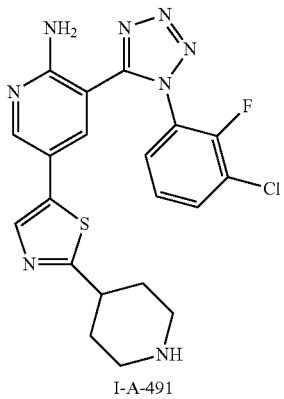
I-A-491
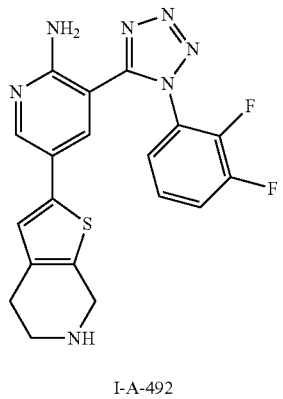
I-A-492
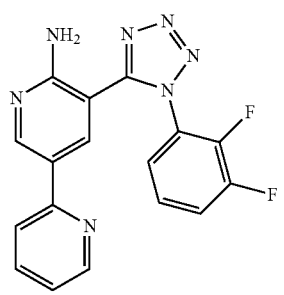
I-A-493
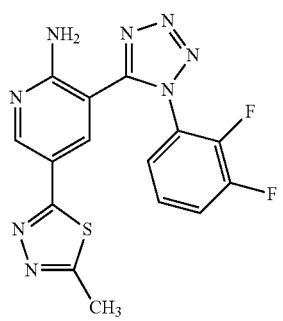
I-A-494
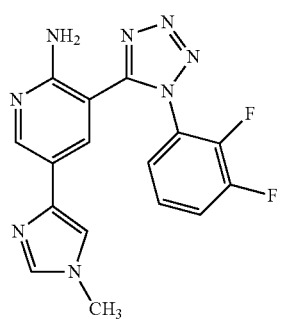
I-A-495
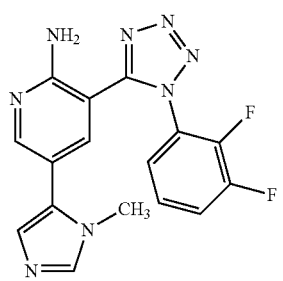
I-A-496
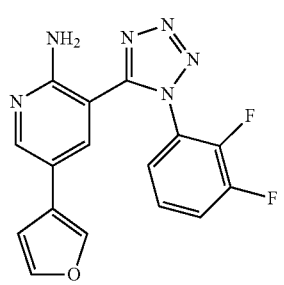
I-A-497
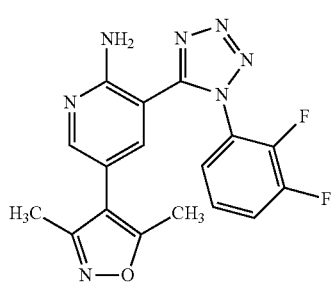
I-A-498

TABLE 1-continued
Compounds of Formula 1-A
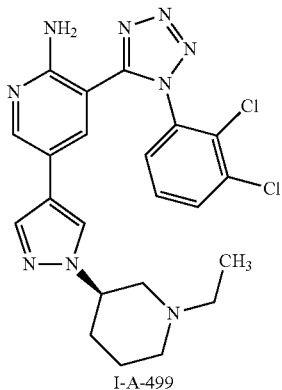
I-A-499
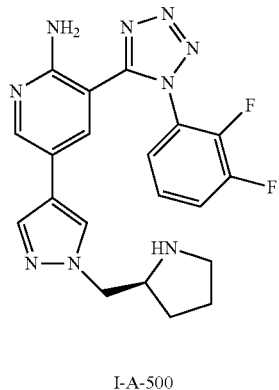
I-A-500
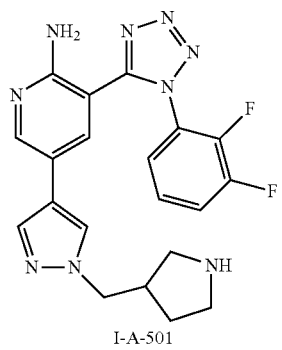
I-A-501
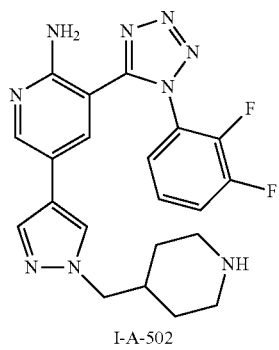
I-A-502
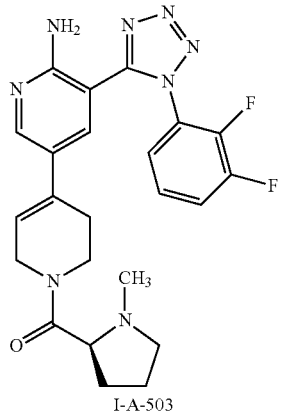
I-A-503
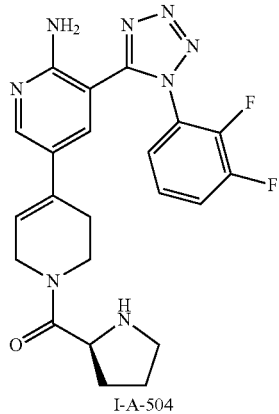
I-A-504
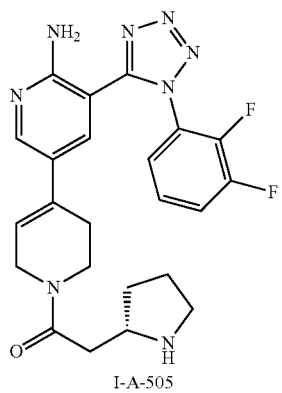
I-A-505
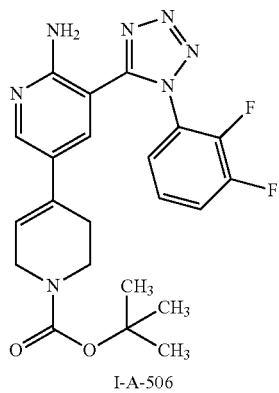
I-A-506

TABLE 1-continued
Compounds of Formula 1-A
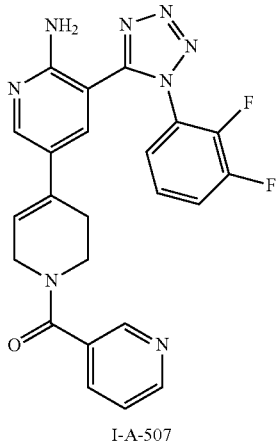
I-A-507
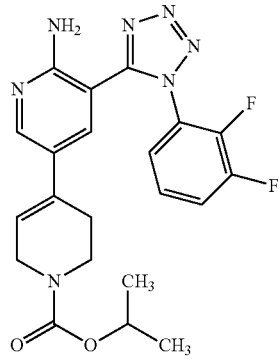
I-A-508
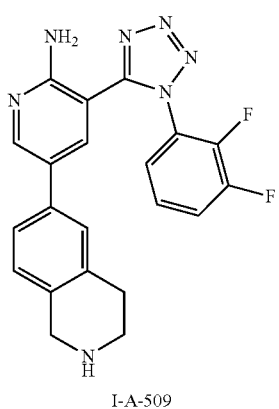
I-A-509
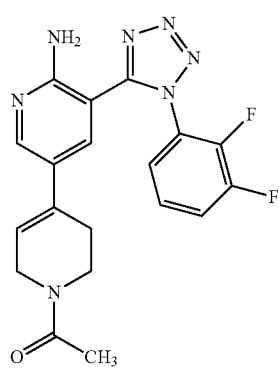
I-A-510
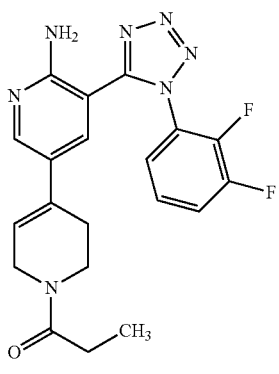
I-A-511
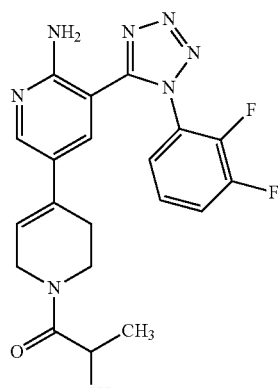
I-A-512

TABLE 1-continued
Compounds of Formula 1-A
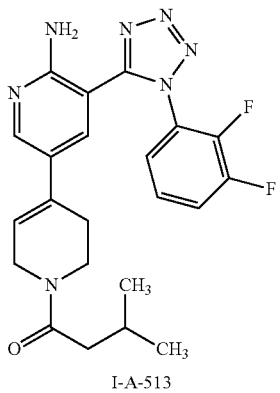
I-A-513
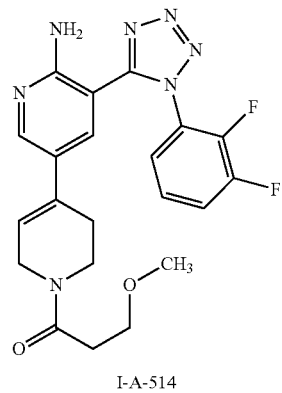
I-A-514
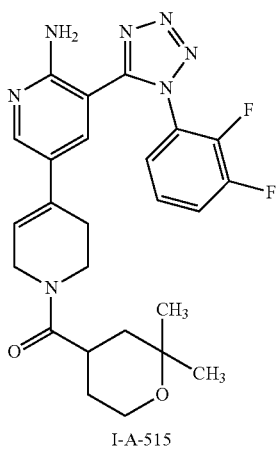
I-A-515
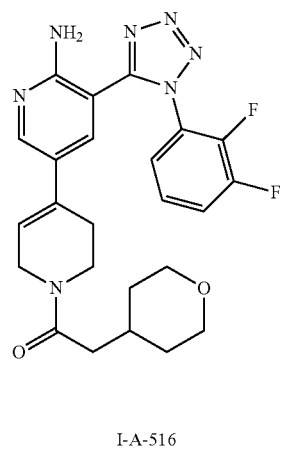
I-A-516
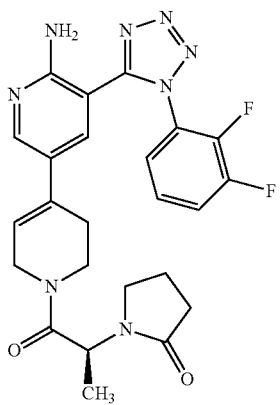
I-A-517
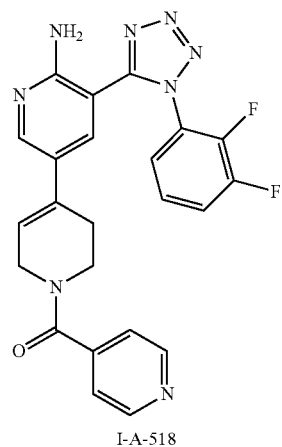
I-A-518

TABLE 1-continued
Compounds of Formula 1-A
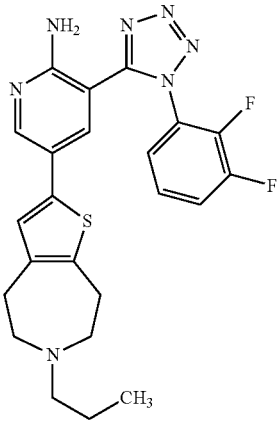
I-A-519
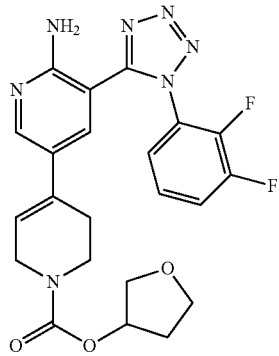
I-A-520
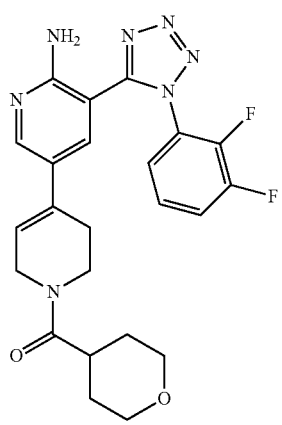
I-A-521
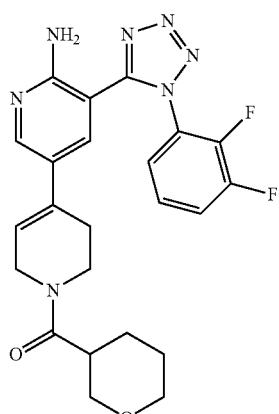
I-A-522
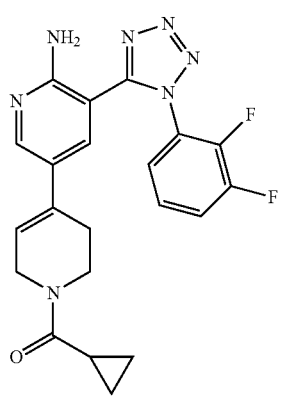
I-A-523
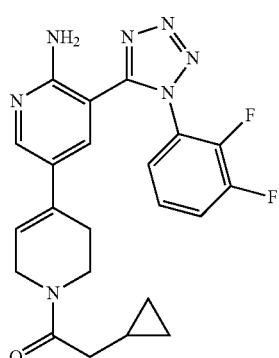
I-A-524

TABLE 1-continued
Compounds of Formula 1-A
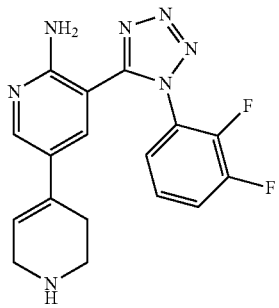
I-A-525
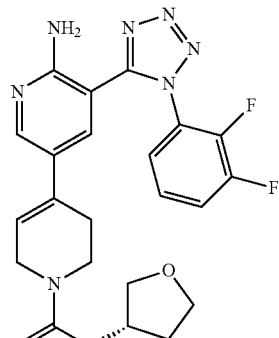
I-A-526
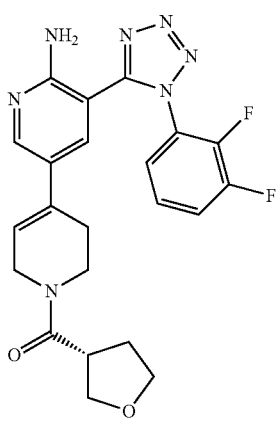
I-A-527
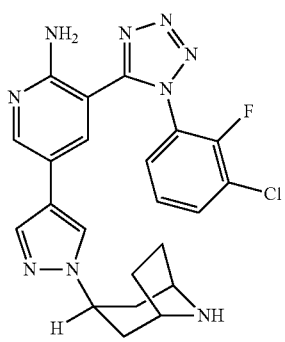
I-A-528
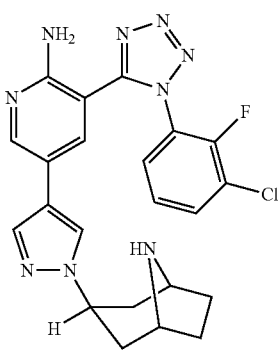
I-A-529
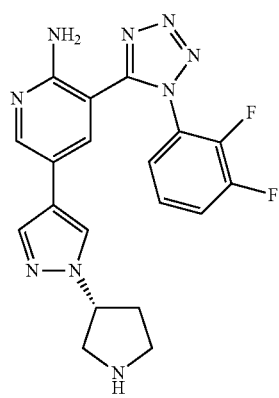
I-A-530

TABLE 1-continued
Compounds of Formula 1-A
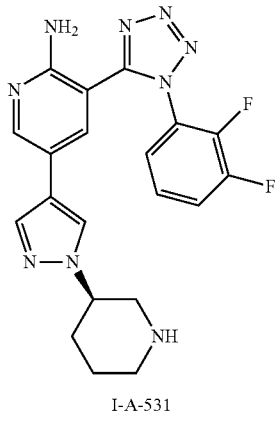
I-A-531
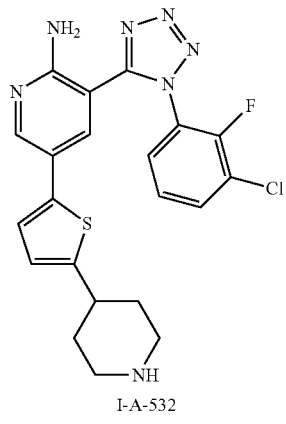
I-A-532
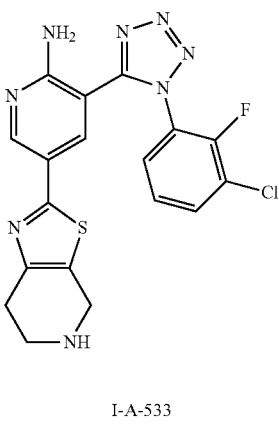
I-A-533
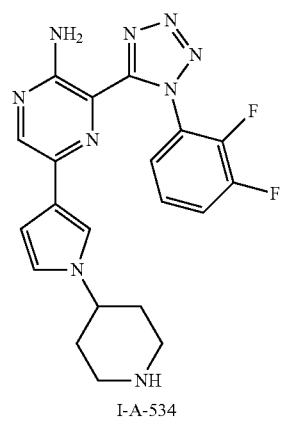
I-A-534
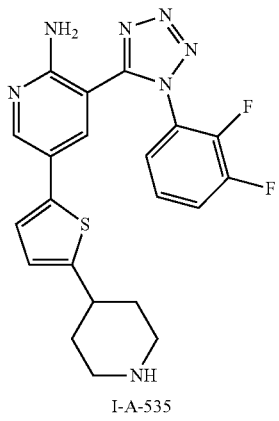
I-A-535
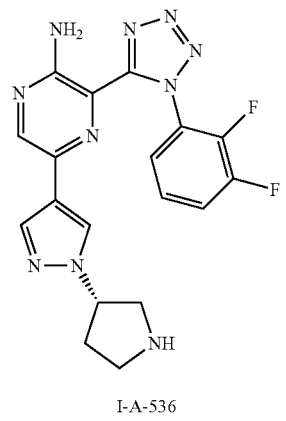
I-A-536

TABLE 1-continued
Compounds of Formula 1-A
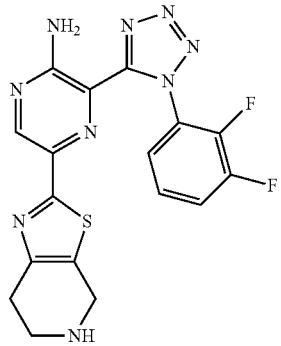
I-A-537
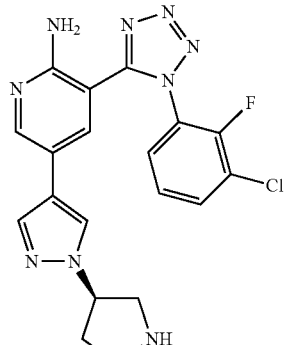
I-A-538
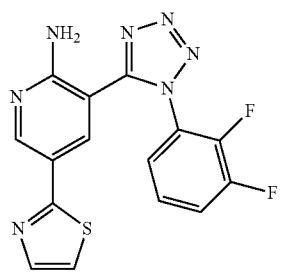
I-A-539
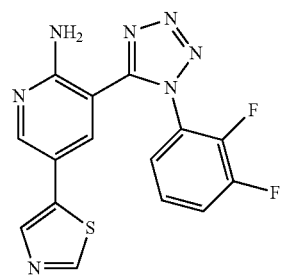
I-A-540
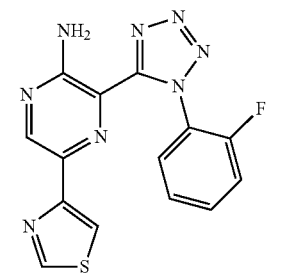
I-A-541
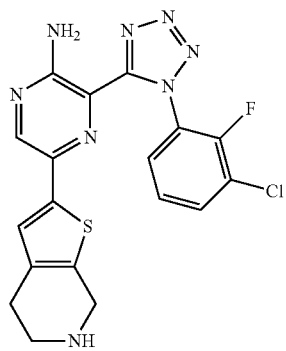
I-A-542
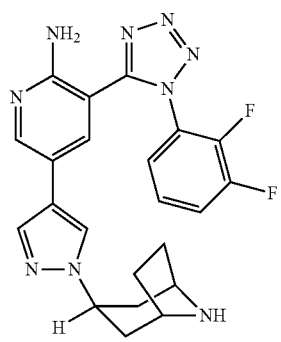
I-A-543
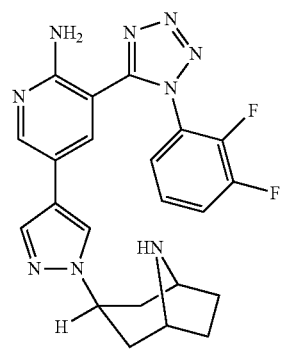
I-A-544

TABLE 1-continued
Compounds of Formula 1-A
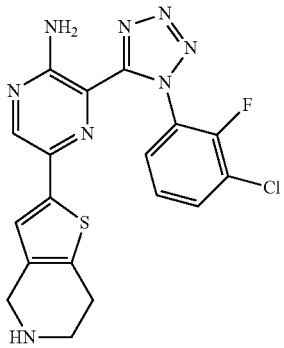
I-A-545
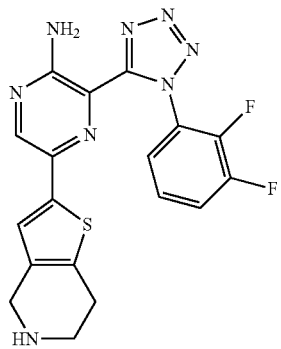
I-A-546
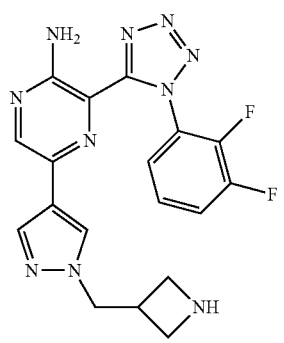
I-A-547
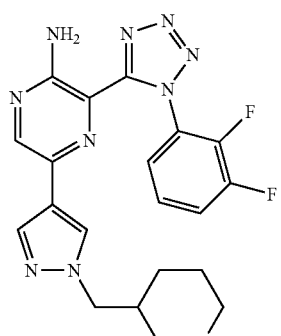
I-A-548
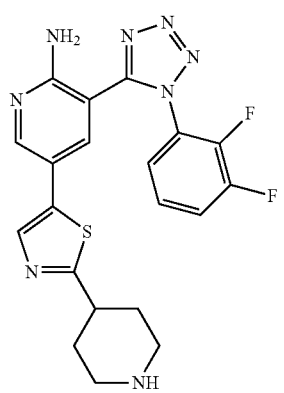
I-A-549
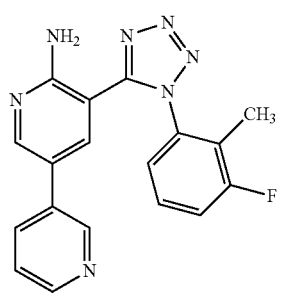
I-A-550
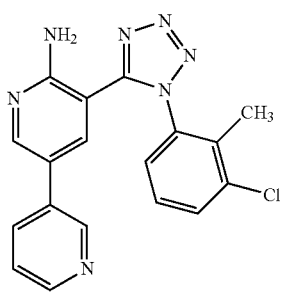
I-A-551
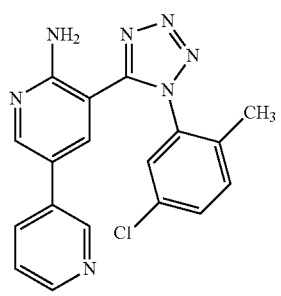
I-A-552

TABLE 1-continued
Compounds of Formula 1-A
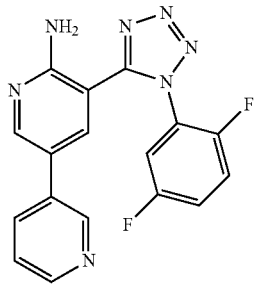
I-A-553
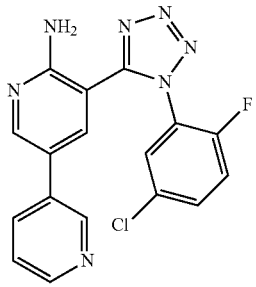
I-A-554
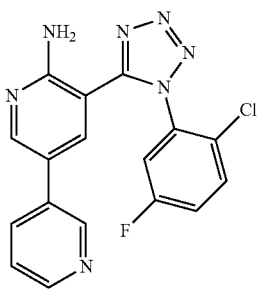
I-A-555
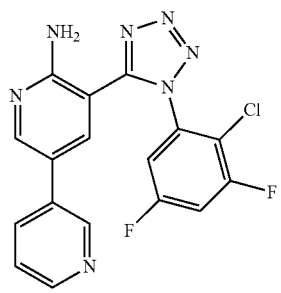
I-A-556
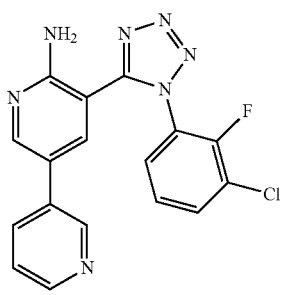
I-A-557
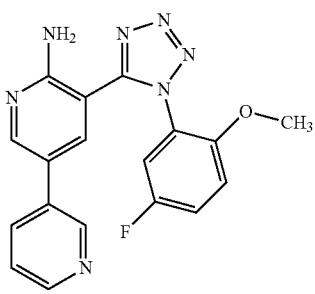
I-A-558
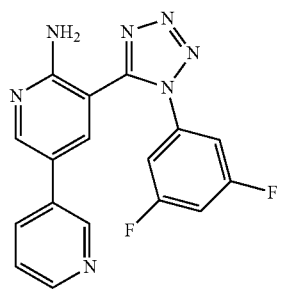
I-A-559
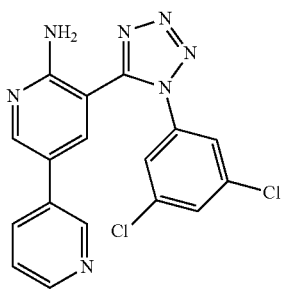
I-A-560
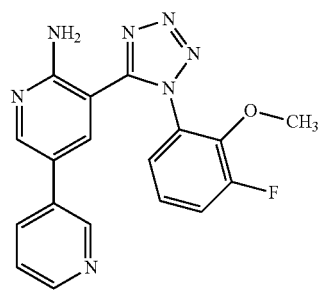
I-A-561
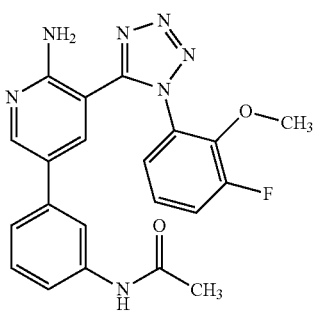
I-A-562

TABLE 1-continued
Compounds of Formula 1-A
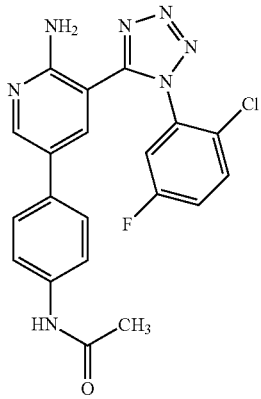
I-A-563
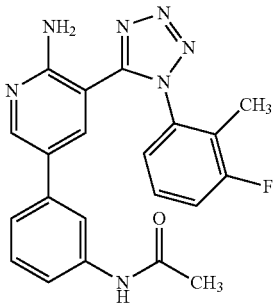
I-A-564
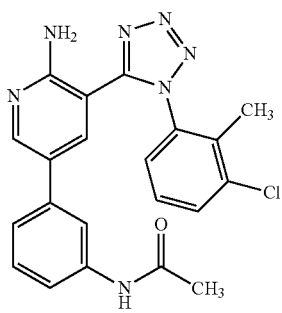
I-A-565
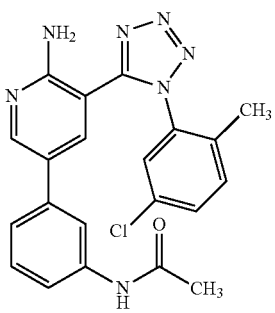
I-A-566
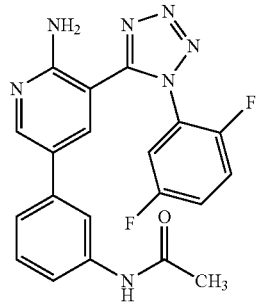
I-A-567
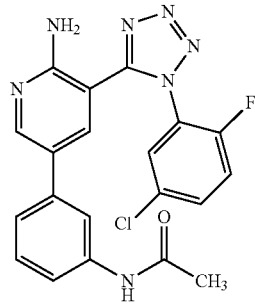
I-A-568
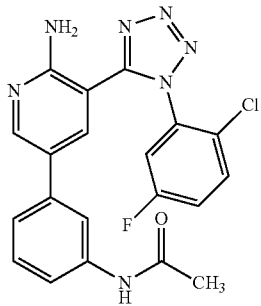
I-A-569
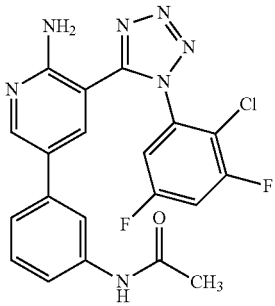
I-A-570

TABLE 1-continued
Compounds of Formula 1-A
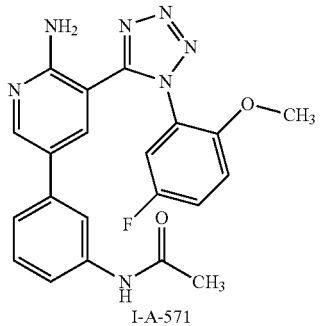
I-A-571
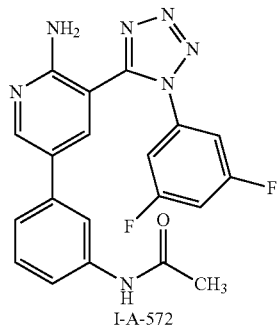
I-A-572
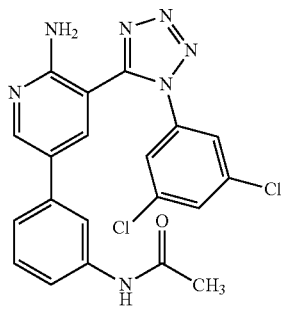
I-A-573
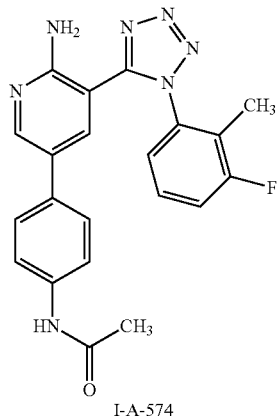
I-A-574
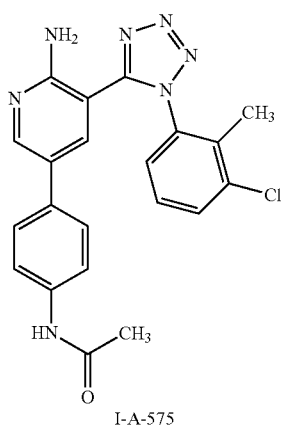
I-A-575
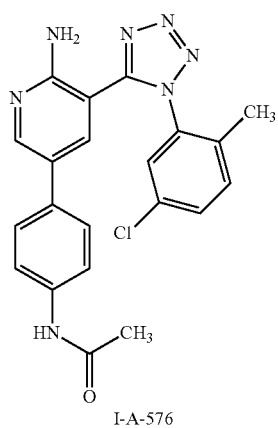
I-A-576
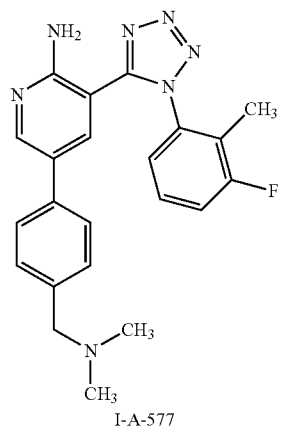
I-A-577
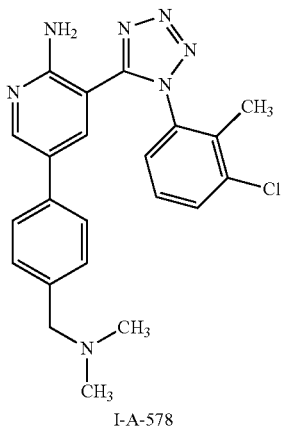
I-A-578

TABLE 1-continued
Compounds of Formula 1-A
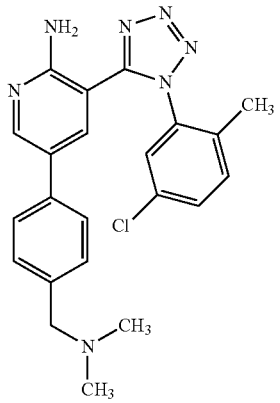
I-A-579
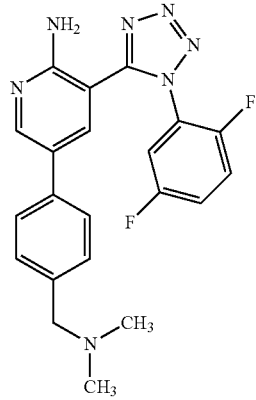
I-A-580
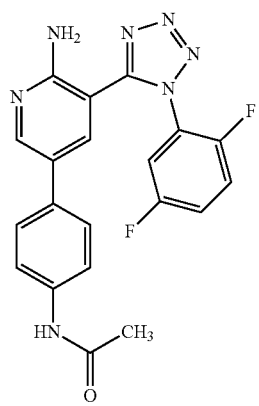
I-A-581
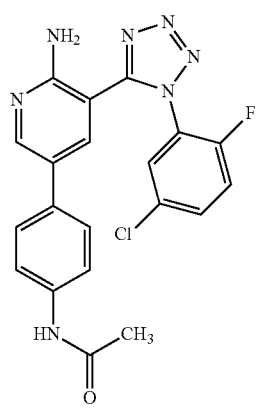
I-A-582
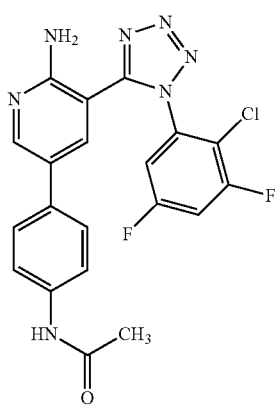
I-A-583
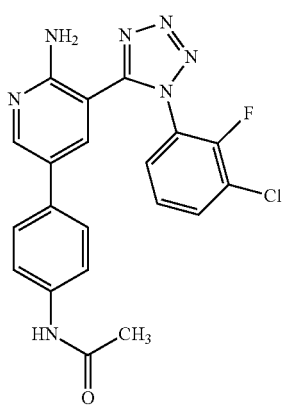
I-A-584

TABLE 1-continued
Compounds of Formula 1-A
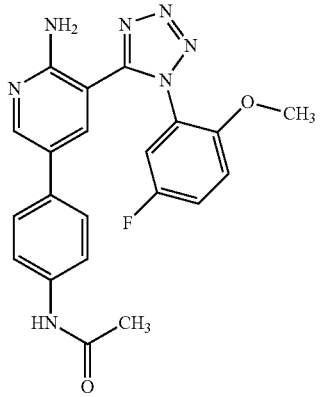
I-A-585
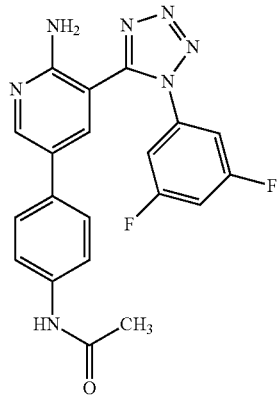
I-A-586
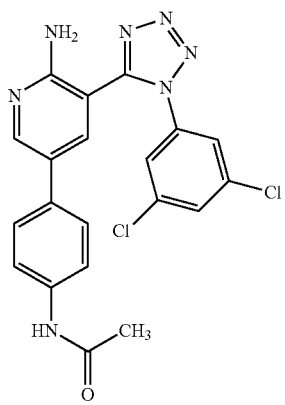
I-A-587
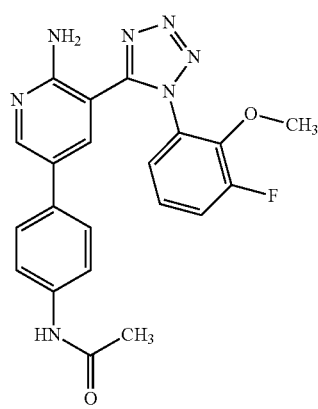
I-A-588
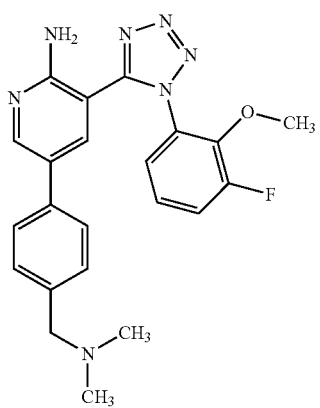
I-A-589
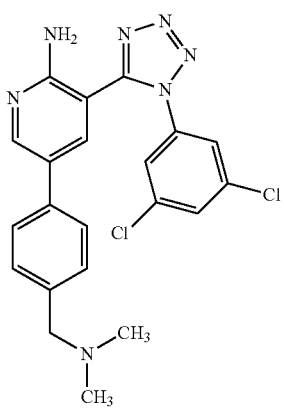
I-A-590

TABLE 1-continued
Compounds of Formula 1-A
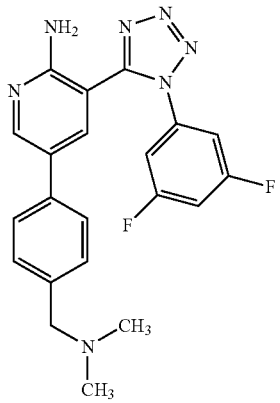
I-A-591
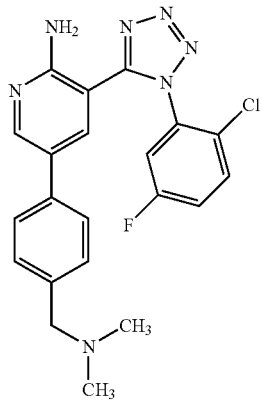
I-A-592
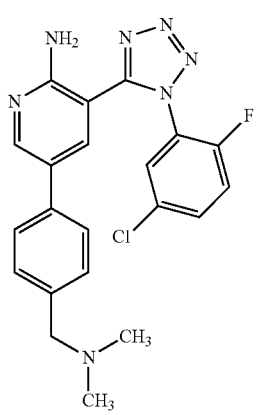
I-A-593
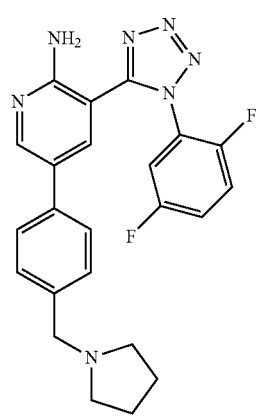
I-A-594
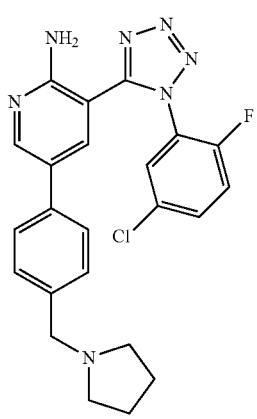
I-A-595
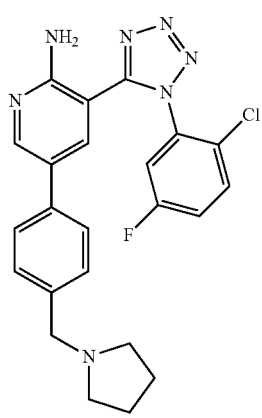
I-A-596

TABLE 1-continued
Compounds of Formula 1-A
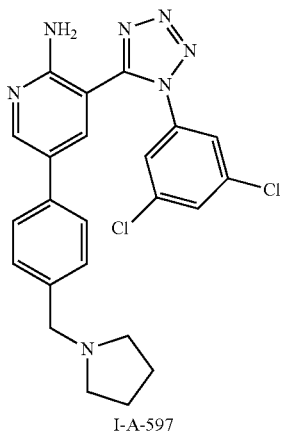
I-A-597
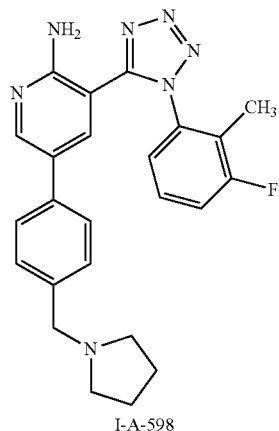
I-A-598
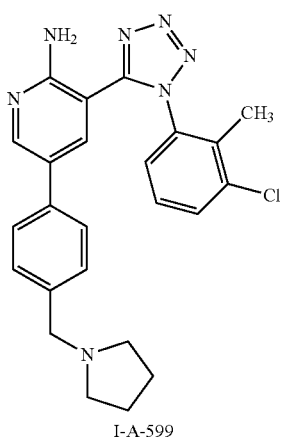
I-A-599
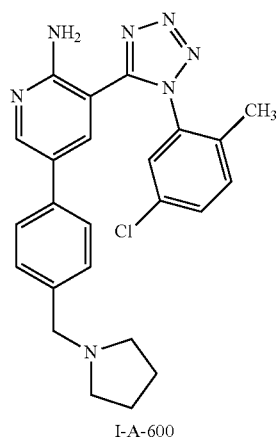
I-A-600
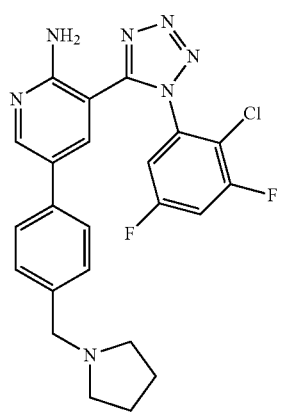
I-A-601
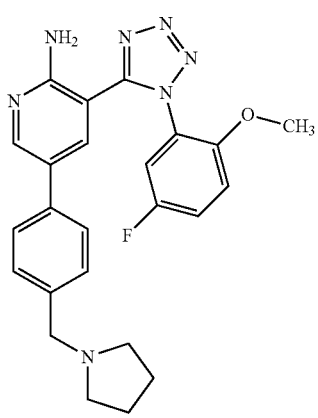
I-A-602

TABLE 1-continued
Compounds of Formula 1-A
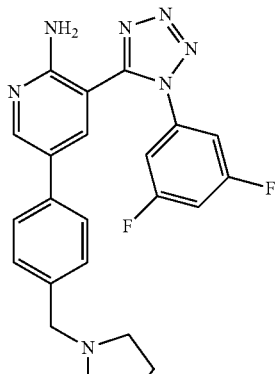
I-A-603
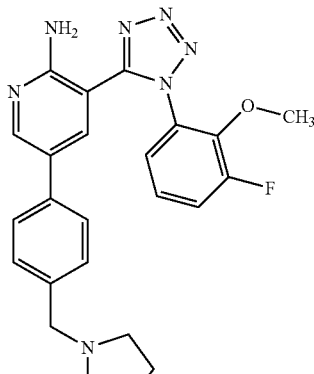
I-A-604
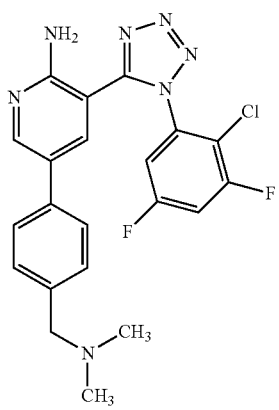
I-A-605
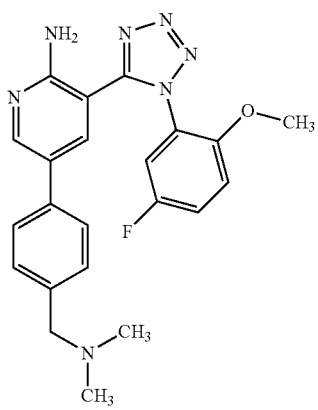
I-A-606
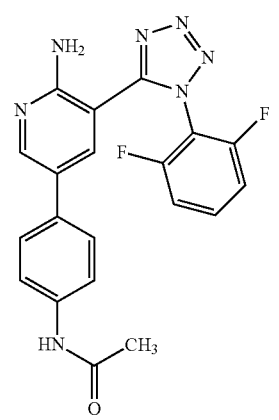
I-A-607
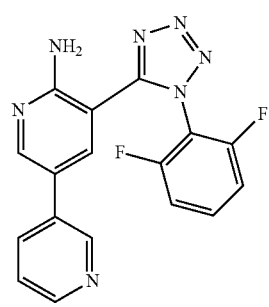
I-A-608

TABLE 1-continued
Compounds of Formula 1-A
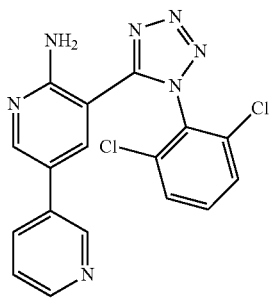
I-A-609
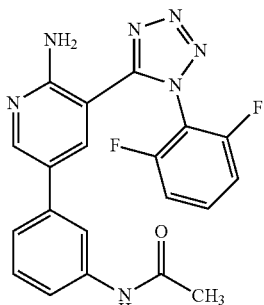
I-A-610
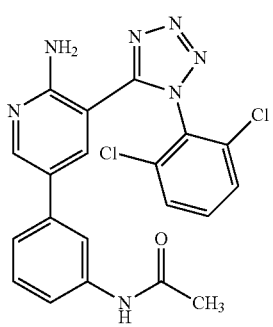
I-A-611
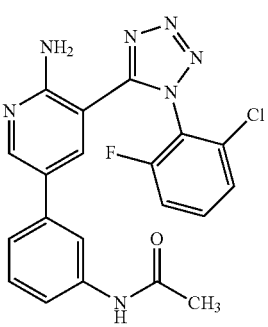
I-A-612
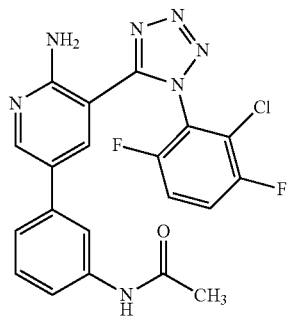
I-A-613
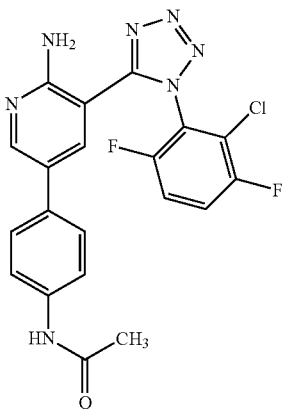
I-A-614
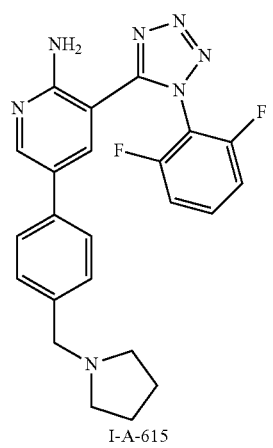
I-A-615
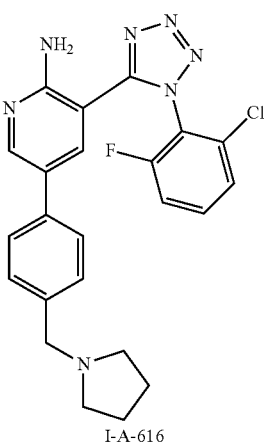
I-A-616

TABLE 1-continued
Compounds of Formula 1-A
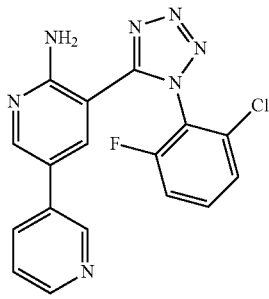
I-A-617
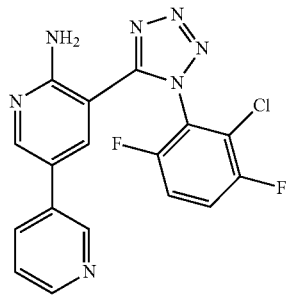
I-A-618
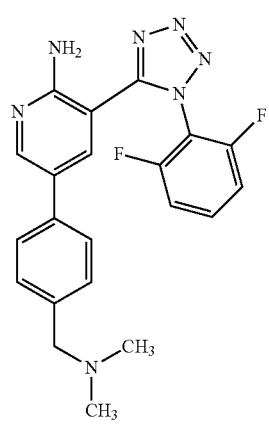
I-A-619
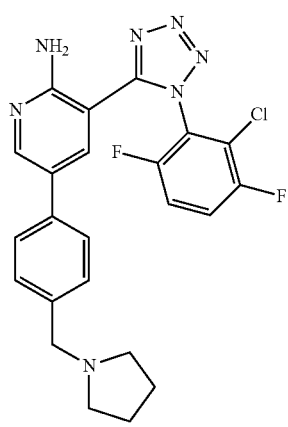
I-A-620
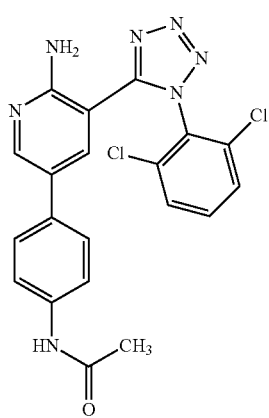
I-A-621
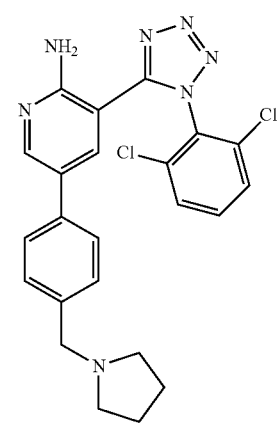
I-A-622

TABLE 1-continued
Compounds of Formula 1-A
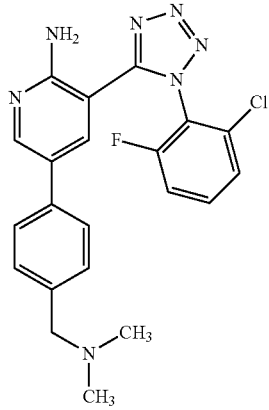
I-A-623
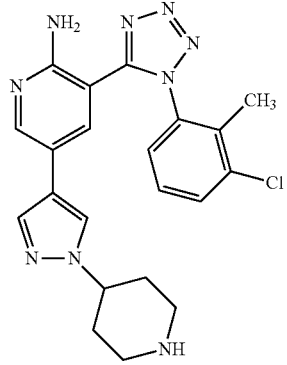
I-A-624
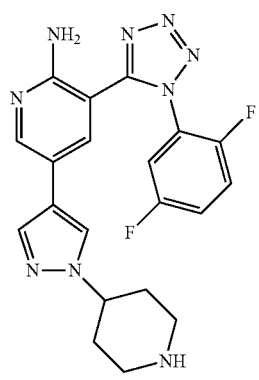
I-A-625
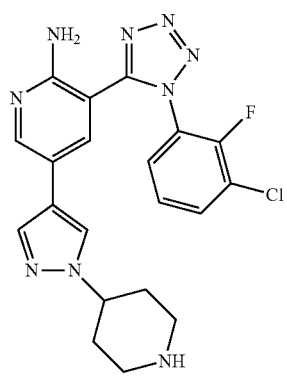
I-A-626
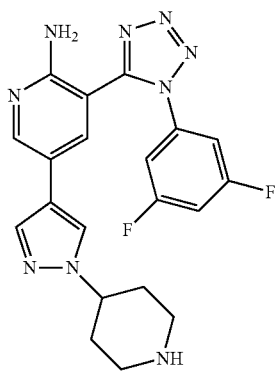
I-A-627
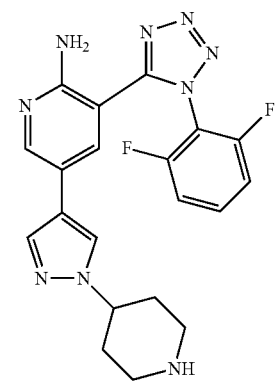
I-A-628

TABLE 1-continued
Compounds of Formula 1-A
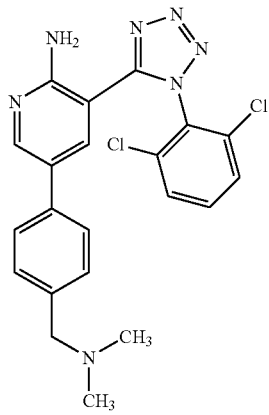
I-A-629
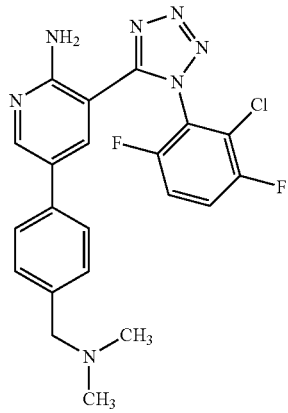
I-A-630
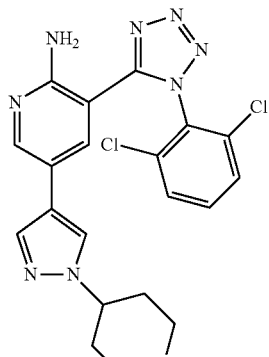
I-A-631
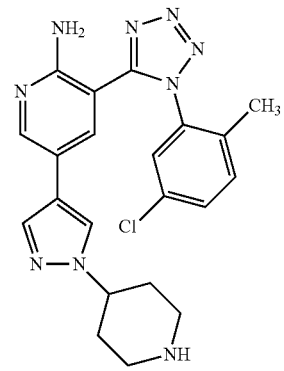
I-A-632
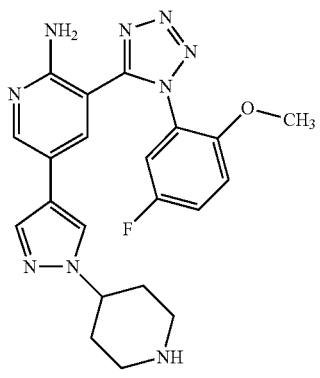
I-A-633
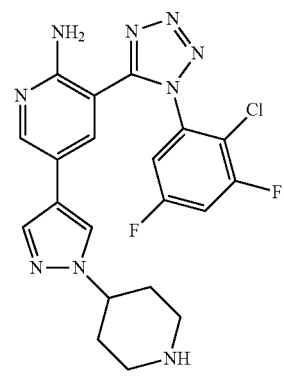
I-A-634

TABLE 1-continued
Compounds of Formula 1-A
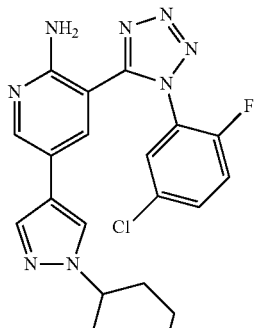
I-A-635
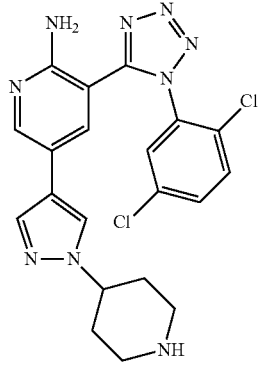
I-A-636
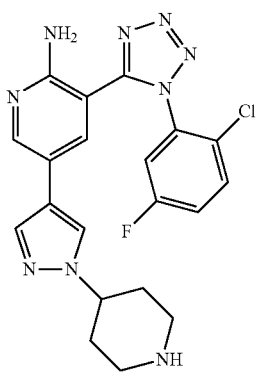
I-A-637
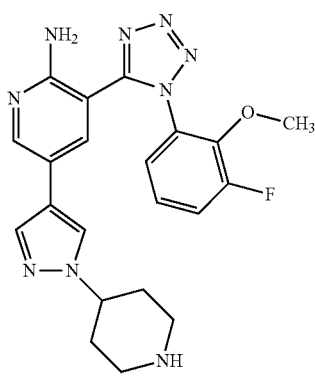
I-A-638
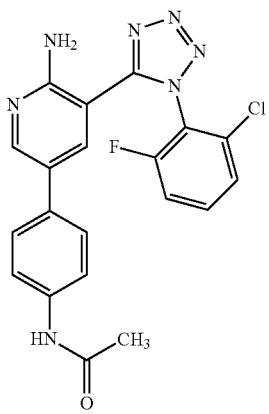
I-A-639
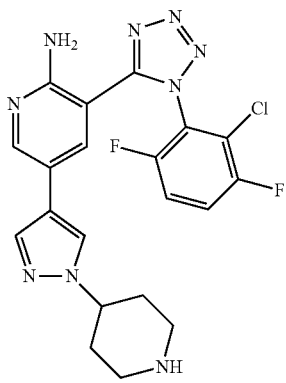
I-A-640

TABLE 1-continued
Compounds of Formula 1-A
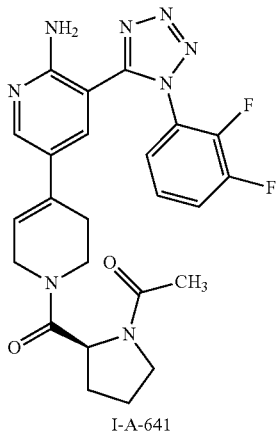
I-A-641
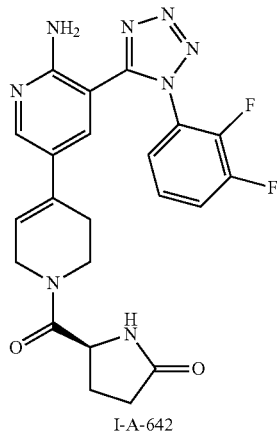
I-A-642
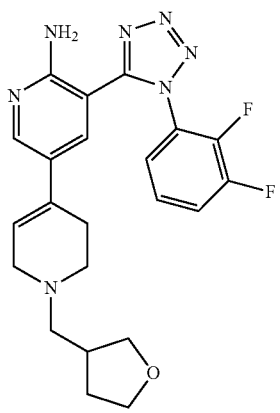
I-A-643
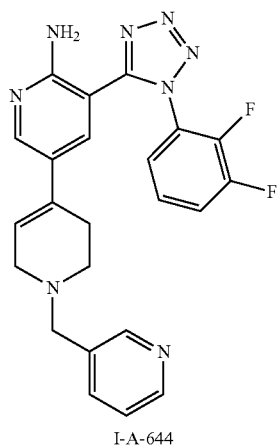
I-A-644
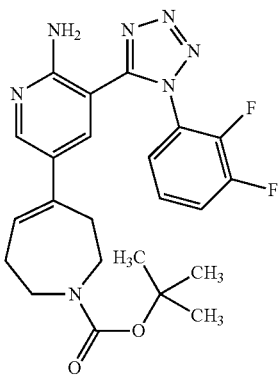
I-A-645
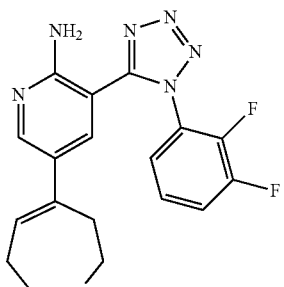
I-A-646

TABLE 1-continued
Compounds of Formula 1-A
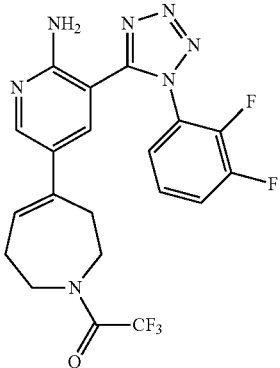
I-A-647
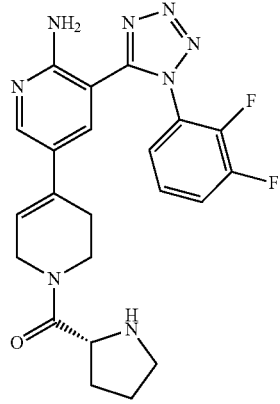
I-A-648
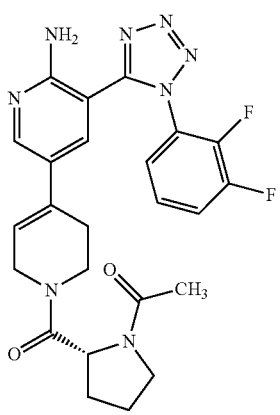
I-A-6493
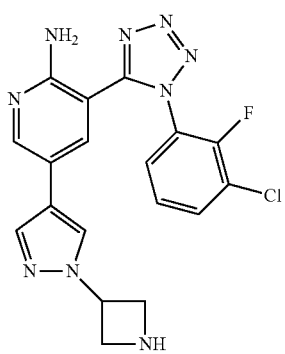
I-A-650
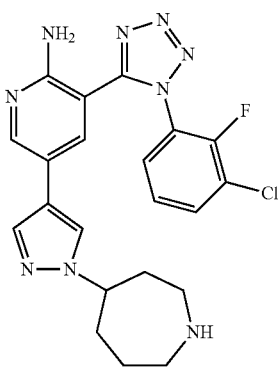
I-A-651
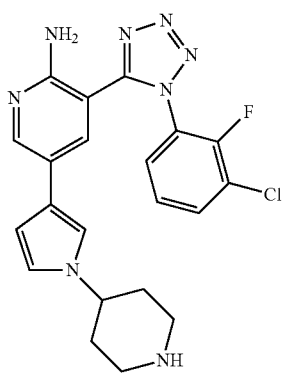
I-A-652

TABLE 1-continued
Compounds of Formula 1-A
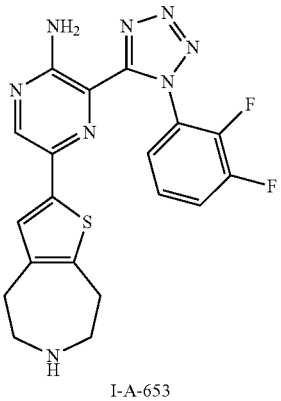
I-A-653
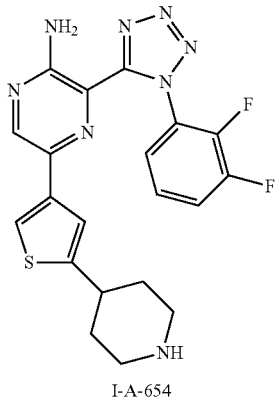
I-A-654
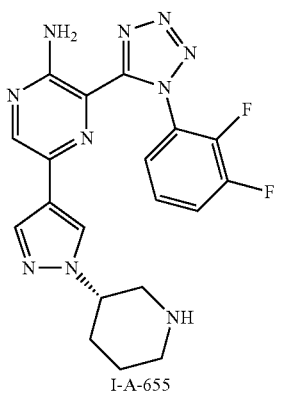
I-A-655
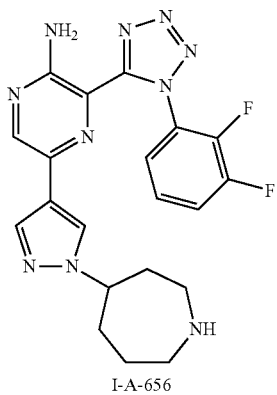
I-A-656
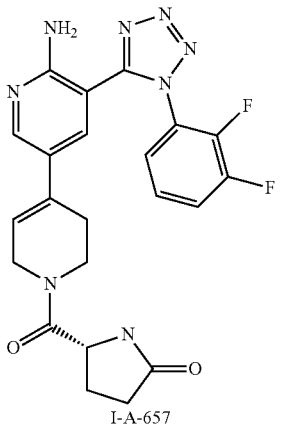
I-A-657
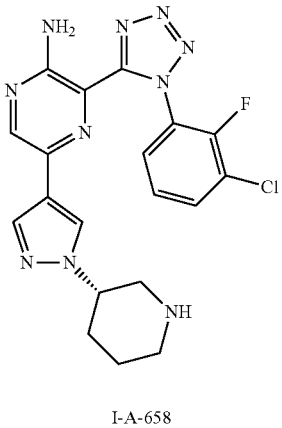
I-A-658
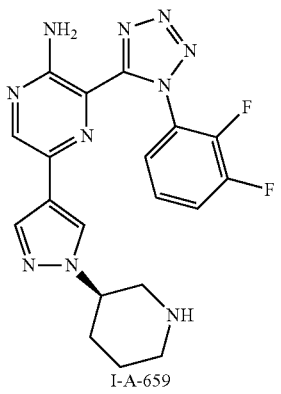
I-A-659
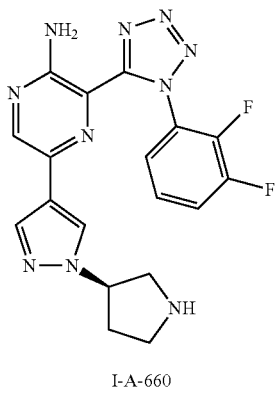
I-A-660

US 8,232,406 B2
217                                                                                                                                          218
TABLE 1-continued
Compounds of Formula 1-A
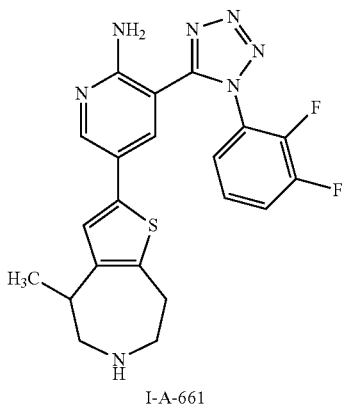
I-A-661
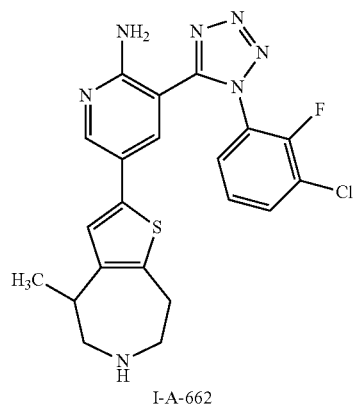
I-A-662
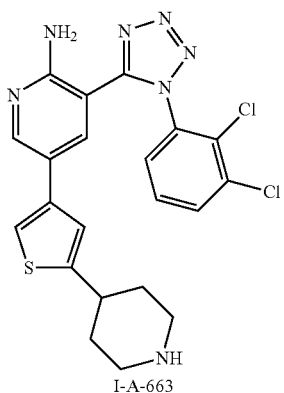
I-A-663
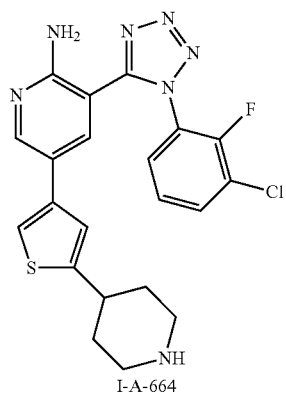
I-A-664
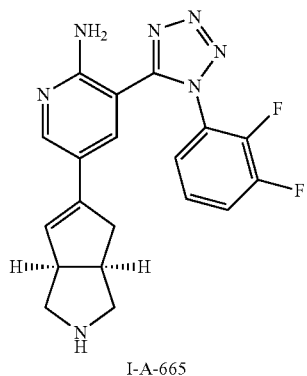
I-A-665
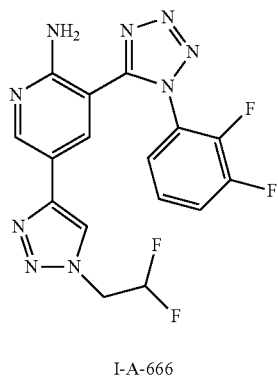
I-A-666
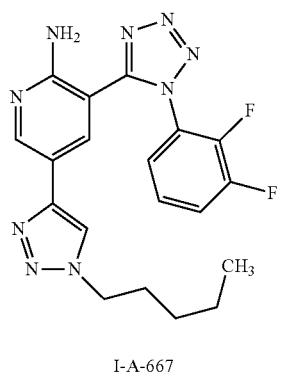
I-A-667
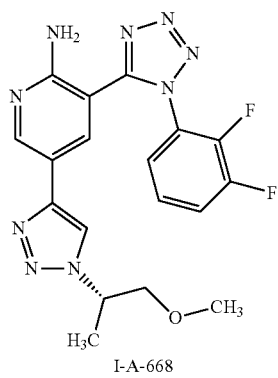
I-A-668

TABLE 1-continued
Compounds of Formula 1-A
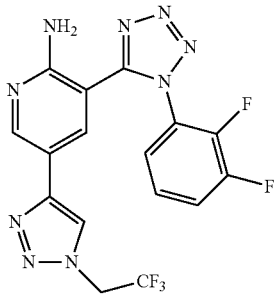
I-A-669
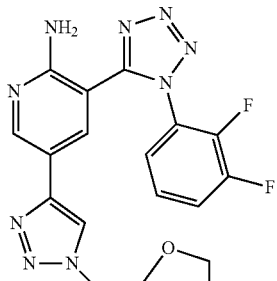
I-A-670
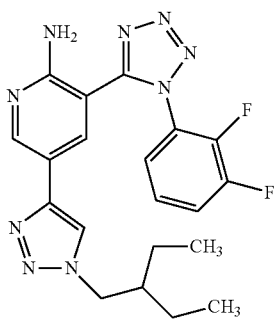
I-A-671
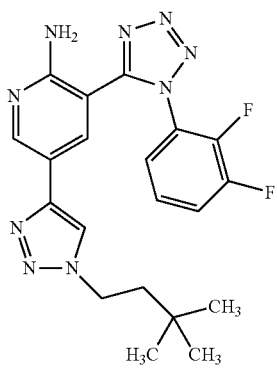
I-A-672
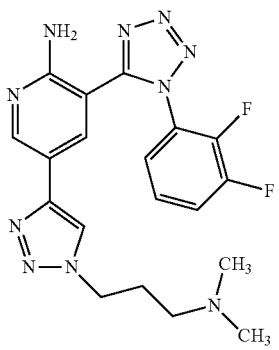
I-A-673
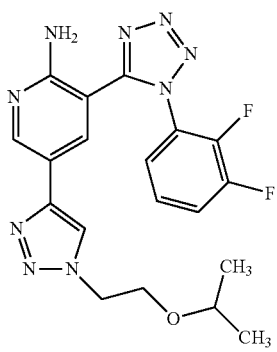
I-A-674
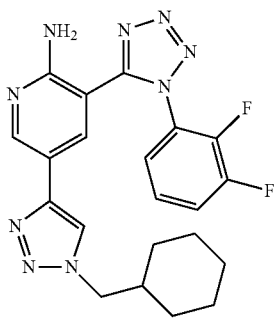
I-A-675
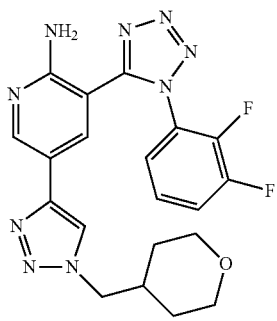
I-A-676

TABLE 1-continued
Compounds of Formula 1-A
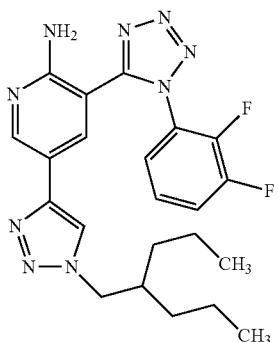
I-A-677
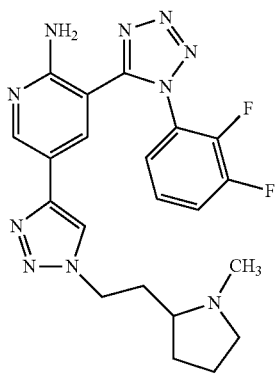
I-A-678
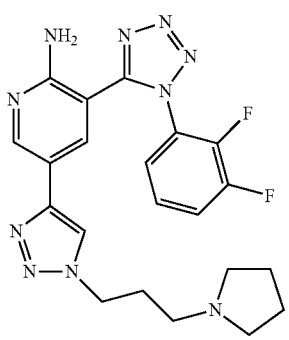
I-A-679
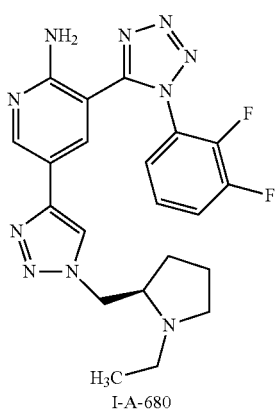
I-A-680
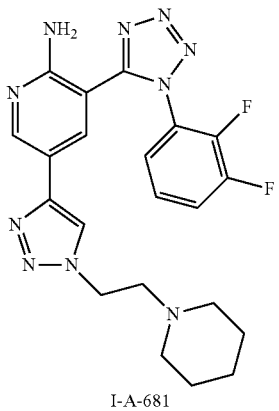
I-A-681
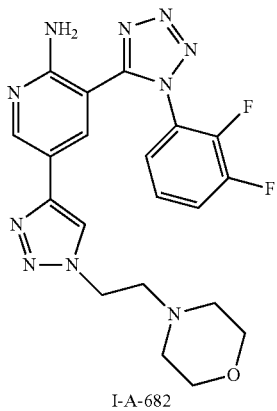
I-A-682
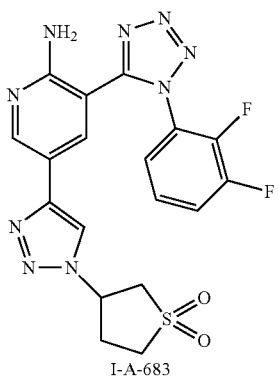
I-A-683
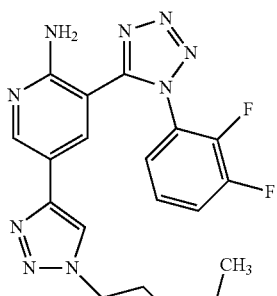
I-A-684

TABLE 1-continued
Compounds of Formula 1-A
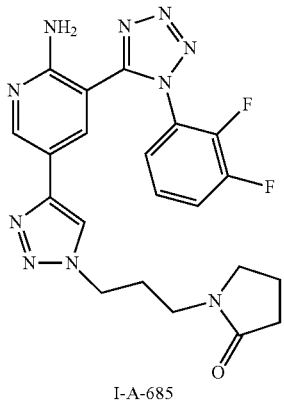
I-A-685
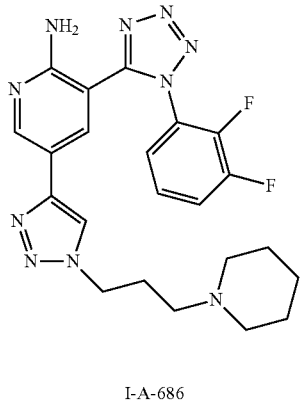
I-A-686
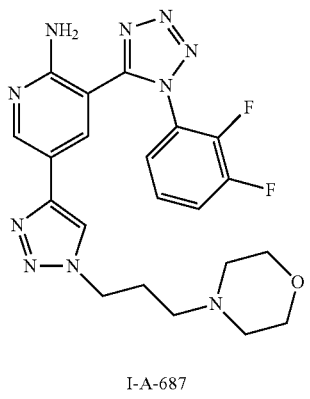
I-A-687
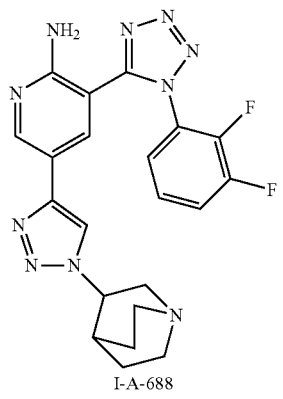
I-A-688
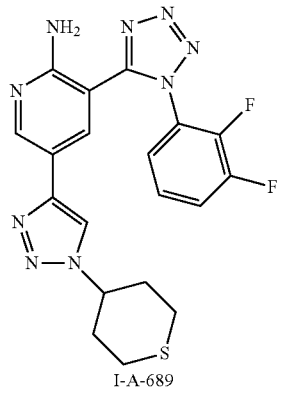
I-A-689
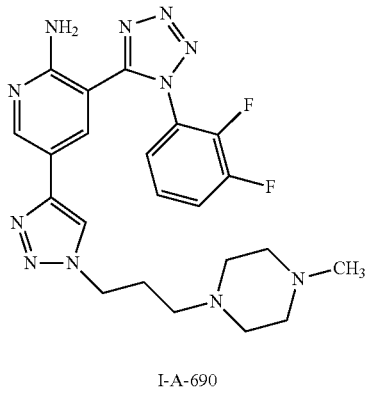
I-A-690
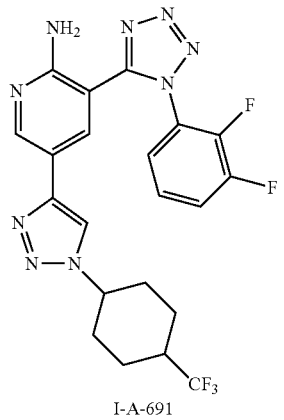
I-A-691
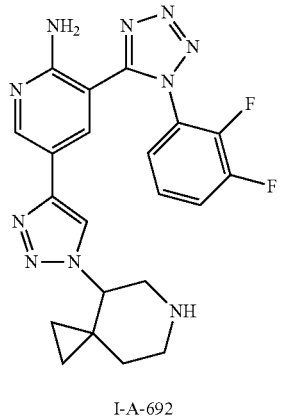
I-A-692

TABLE 1-continued
Compounds of Formula 1-A
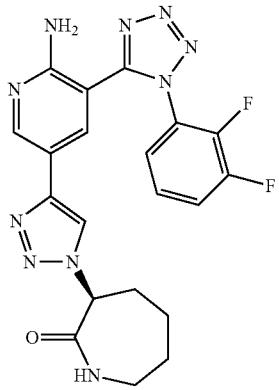
I-A-693
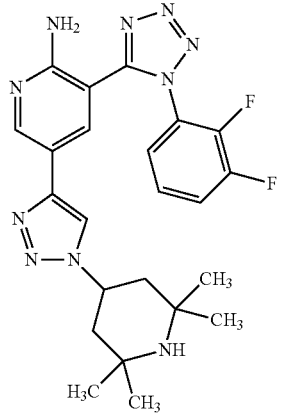
I-A-694
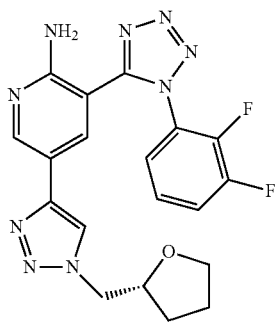
I-A-695
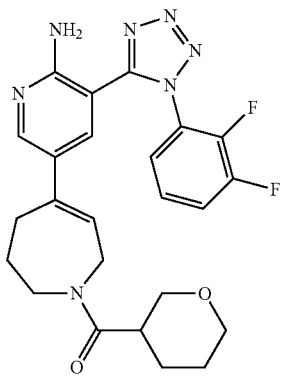
I-A-696
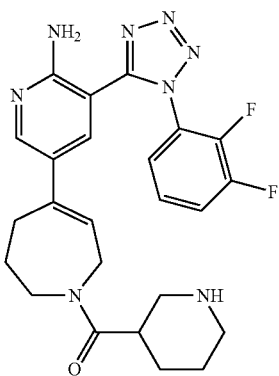
I-A-697
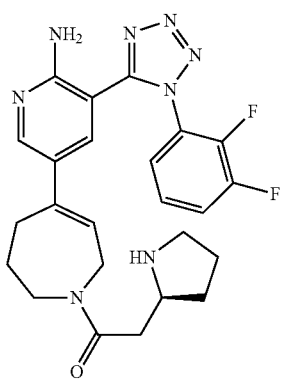
I-A-698

TABLE 1-continued
Compounds of Formula 1-A
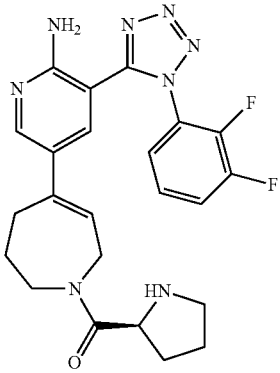
I-A-699
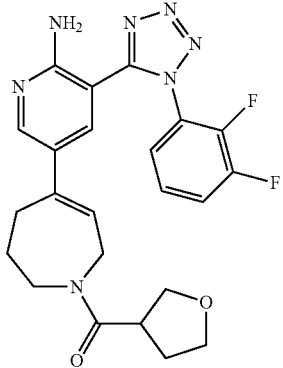
I-A-700
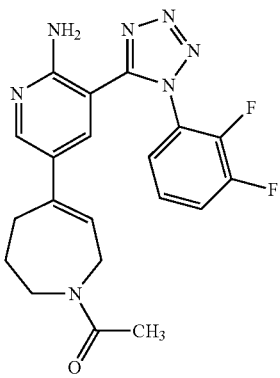
I-A-701
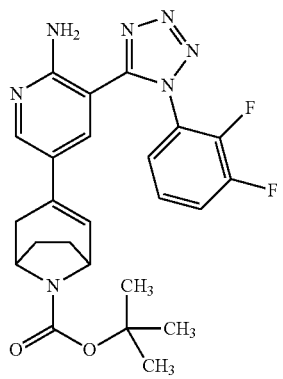
I-A-702
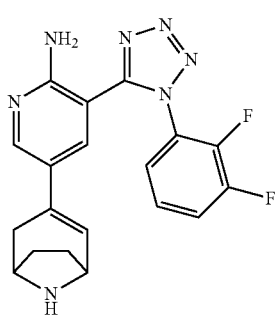
I-A-703
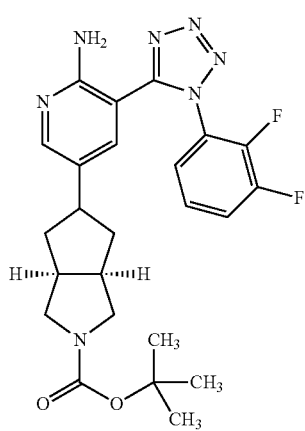
I-A-704

TABLE 1-continued
Compounds of Formula 1-A
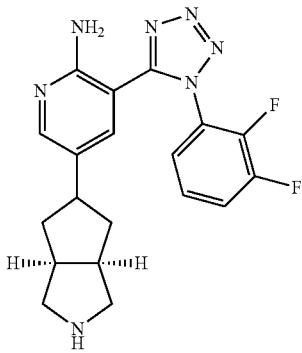
I-A-705
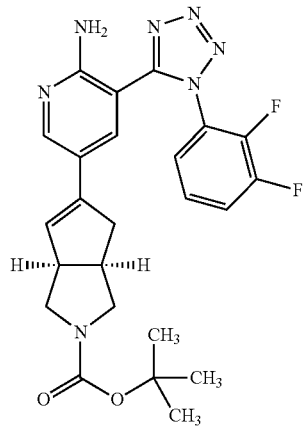
I-A-706
TABLE 2
Compounds of Formula I-B
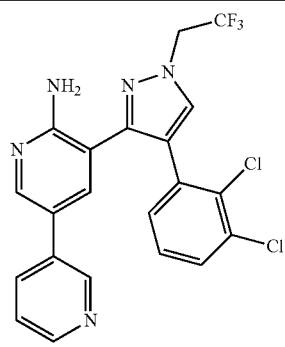
I-B-1
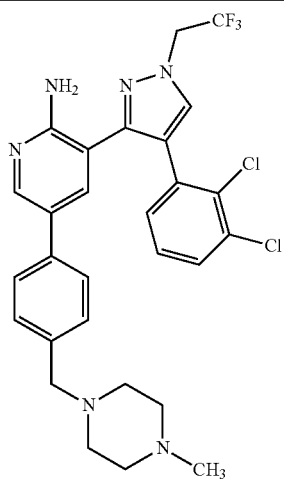
I-B-2
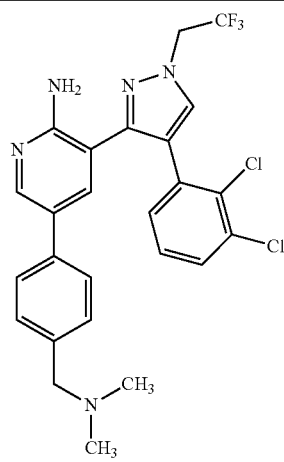
I-B-3
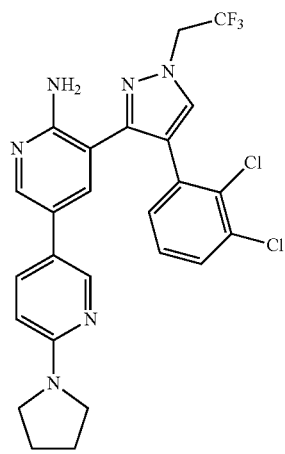
I-B-4
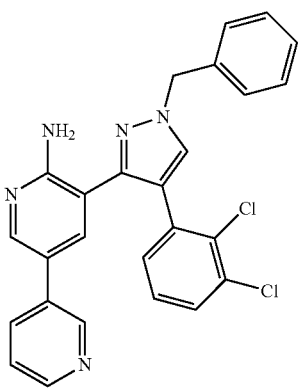
I-B-5
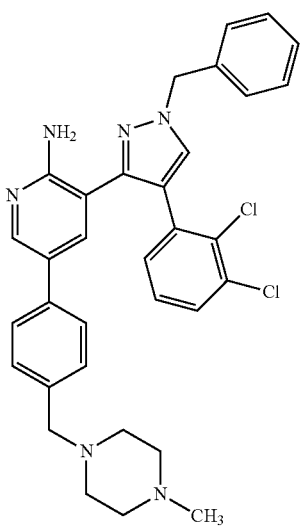
I-B-6

TABLE 2-continued
Compounds of Formula I-B
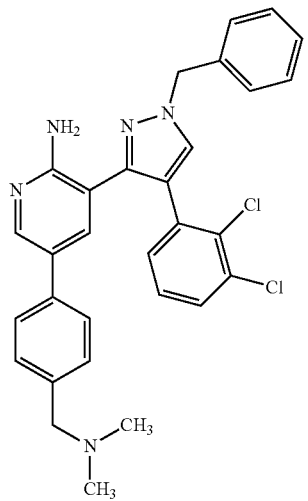
I-B-7
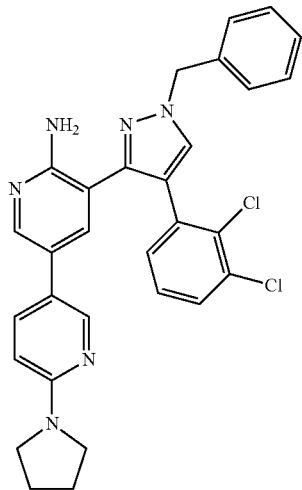
I-B-8
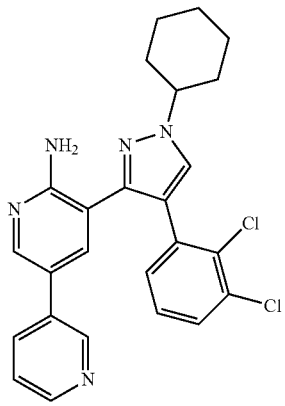
I-B-9
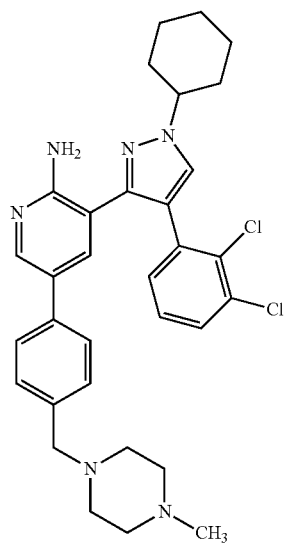
I-B-10
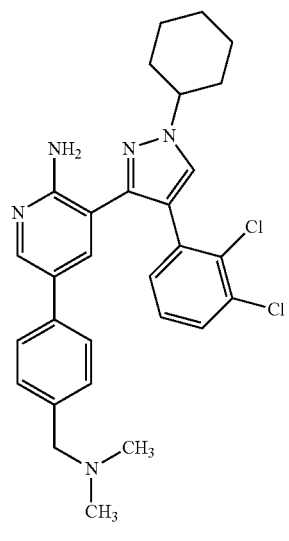
I-B-11
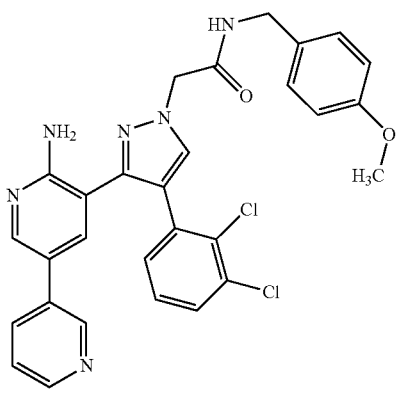
I-B-12
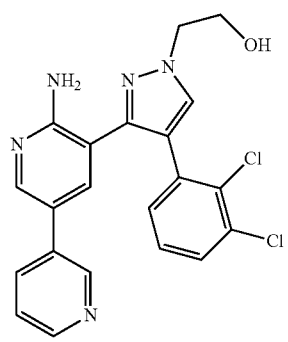
I-B-13
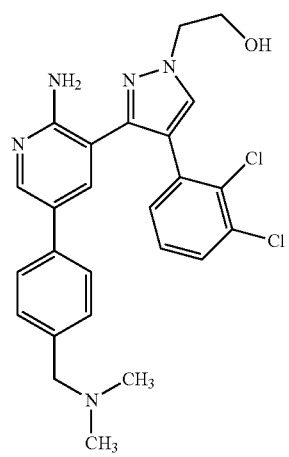
I-B-14
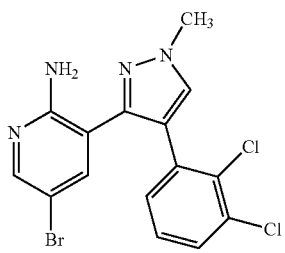
I-B-15

TABLE 2-continued
Compounds of Formula I-B
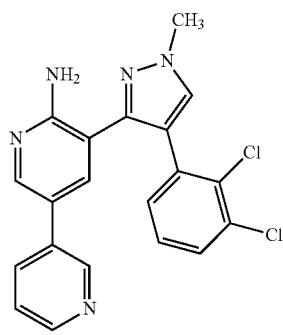
I-B-16
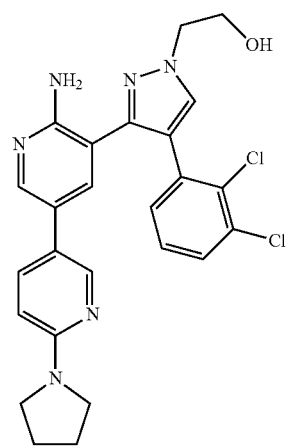
I-B-17
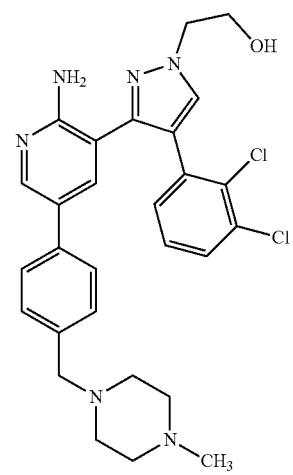
I-B-18
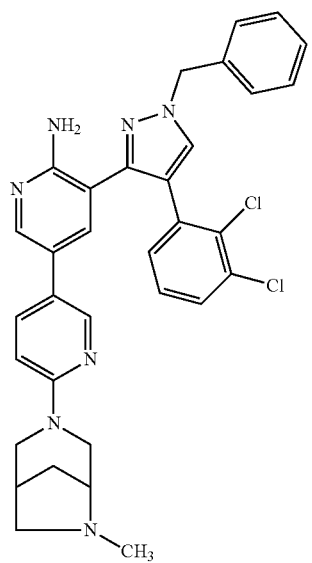
I-B-19
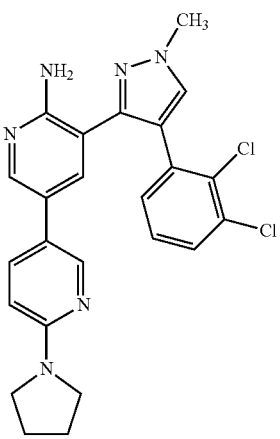
I-B-20
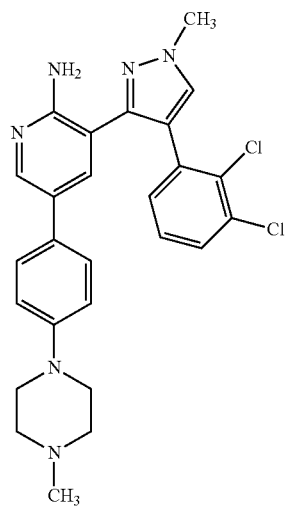
I-B-21
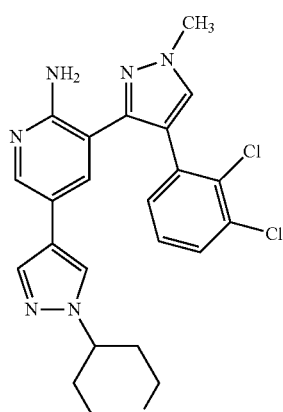
I-B-22

TABLE 3
Compounds of Formula I-C
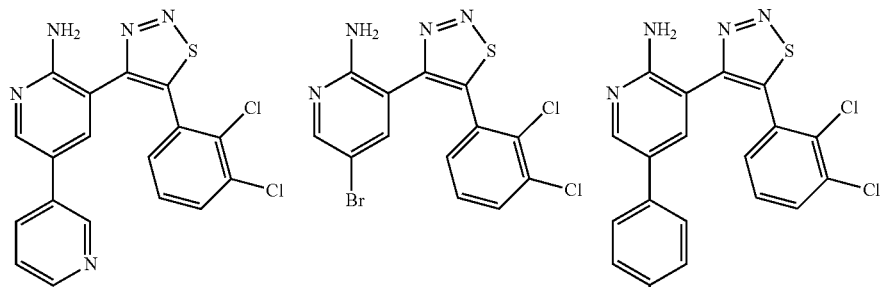
I-C-1    I-C-2    I-C-3
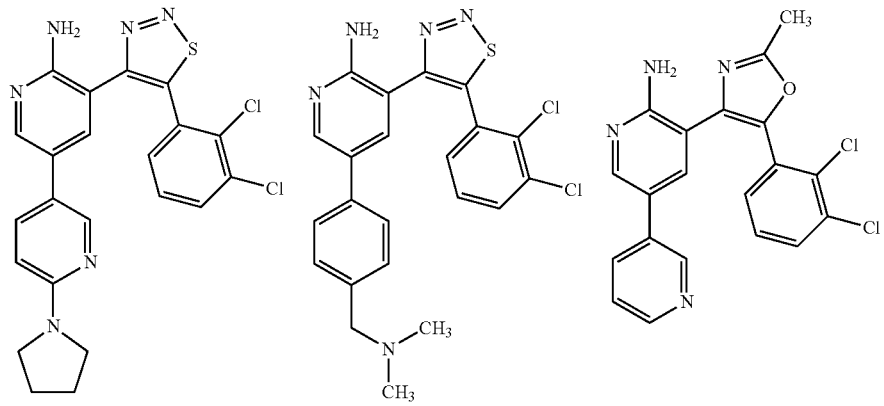
I-C-4    I-C-5    I-C-6
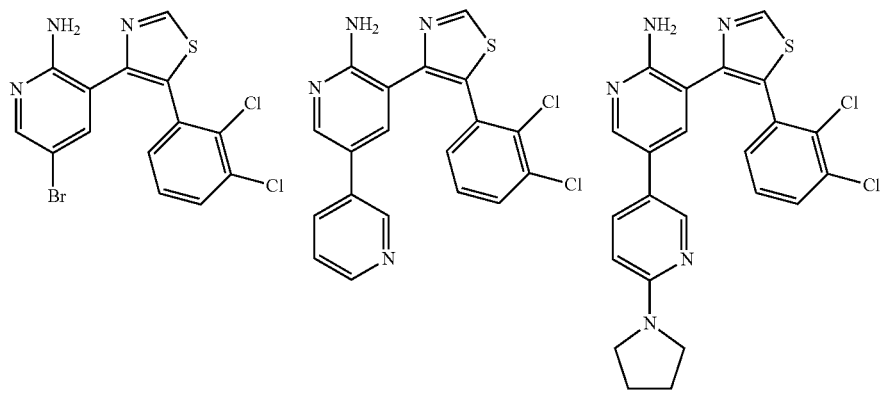
I-C-7    I-C-8    I-C-9

TABLE 3-continued
Compounds of Formula I-C
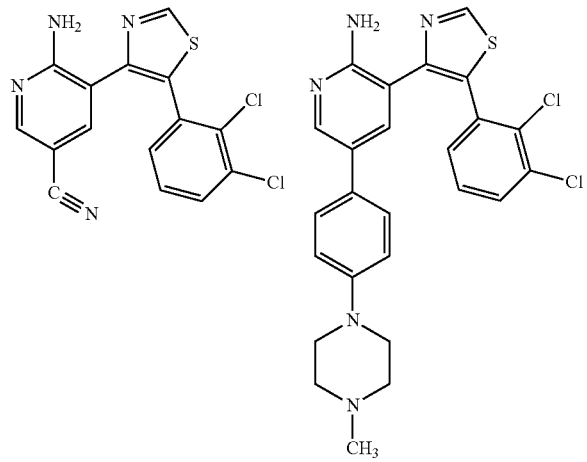
I-C-10     I-C-11
TABLE 4
Compounds of Formula I-D
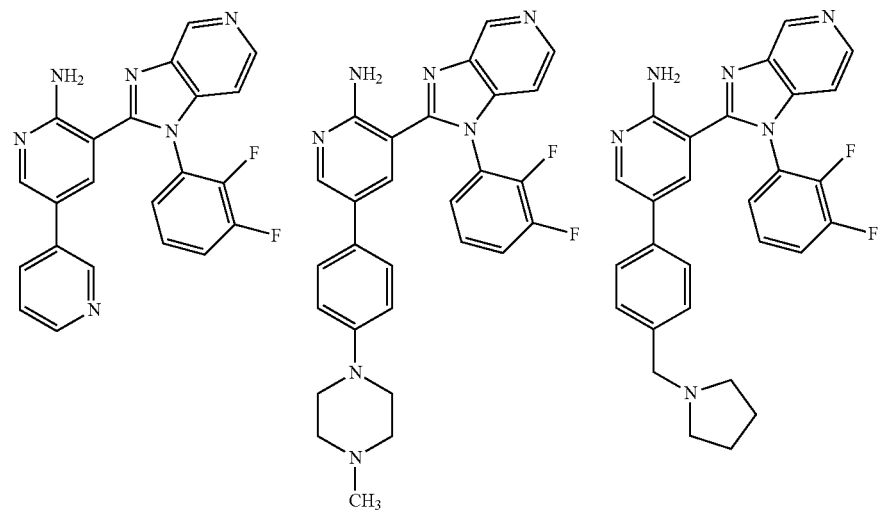
I-D-1     I-D-2     I-D-3

TABLE 4-continued
Compounds of Formula I-D
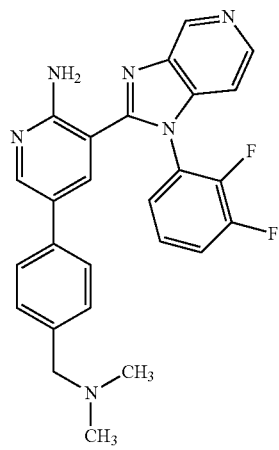
I-D-4
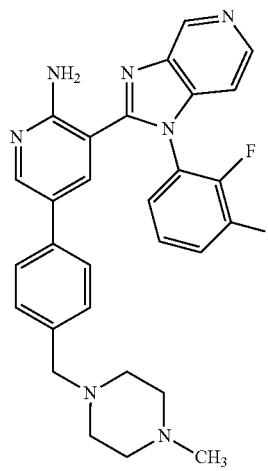
I-D-5
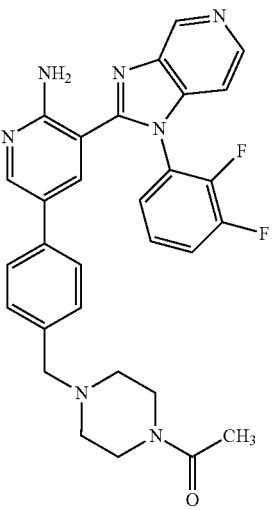
I-D-6
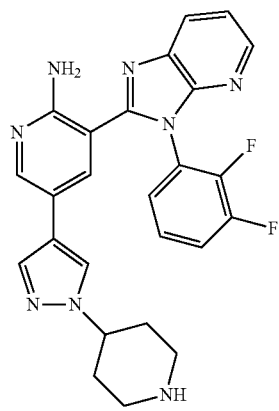
I-D-7
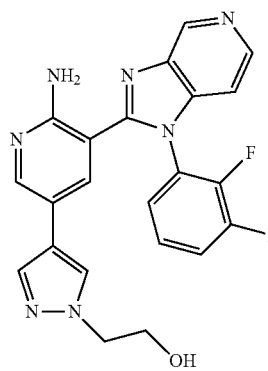
I-D-8
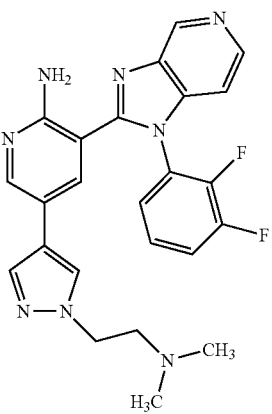
I-D-9
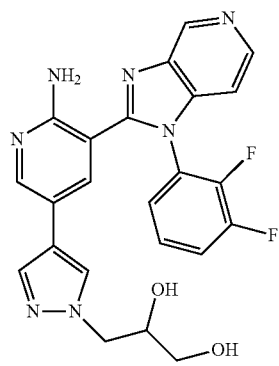
I-D-10
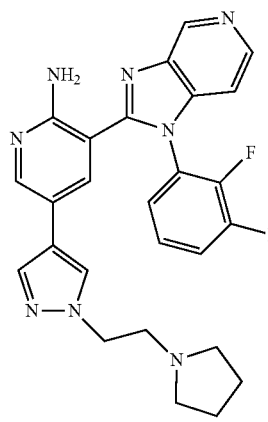
I-D-11
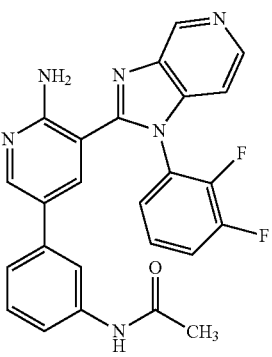
I-D-12

TABLE 4-continued
Compounds of Formula I-D
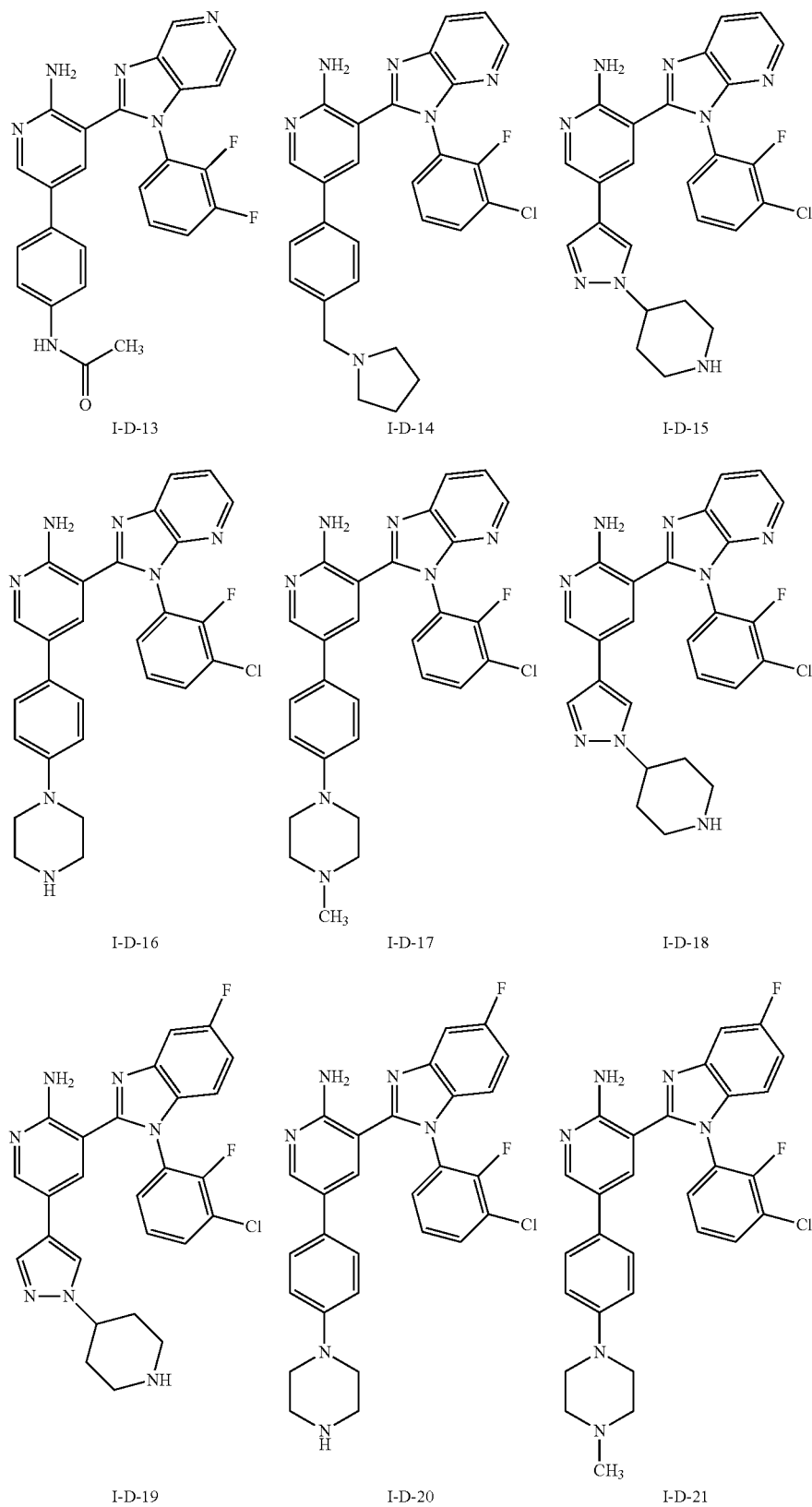

TABLE 4-continued
Compounds of Formula I-D
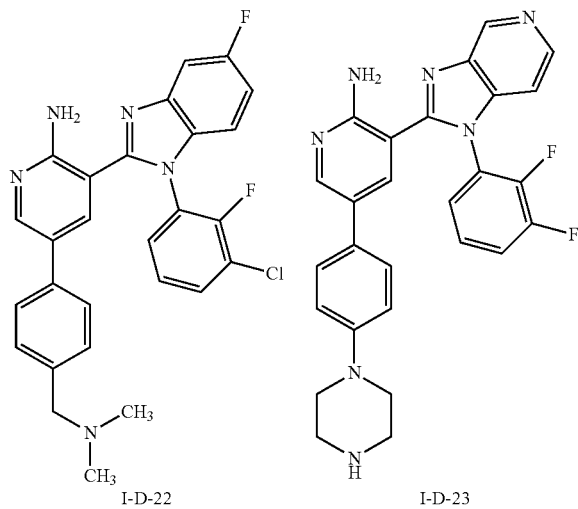
I-D-22   I-D-23
TABLE 5
Compounds of Formula I-E
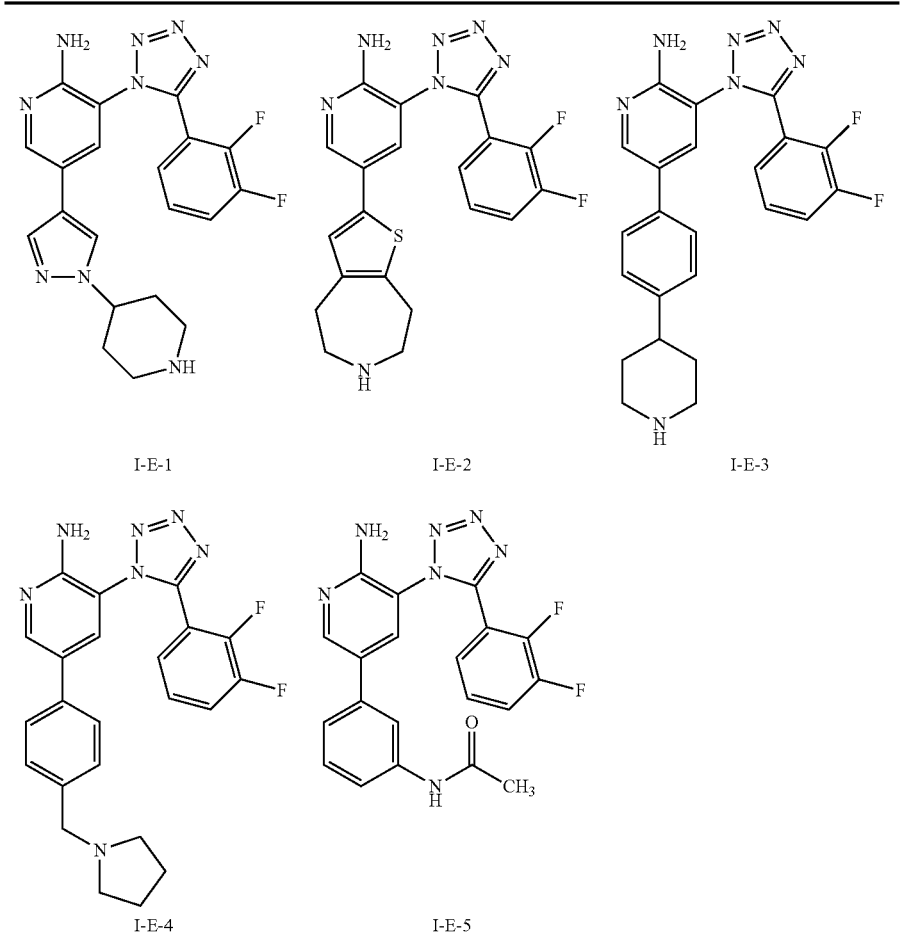
I-E-1   I-E-2   I-E-3
I-E-4   I-E-5

Compositions, Formulations, and Administration of Compounds of the Invention

In another aspect, the invention provides a pharmaceutical composition comprising a compound of any of the formulae or classes described herein. In a further embodiment, the invention provides a pharmaceutical composition comprising a compound of Tables 1, 2, 3, 4, or 5. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit c-MET in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions of the Invention

According to one embodiment, the invention relates to a method of inhibiting c-MET protein kinase activity in a biological sample comprising the step of contacting said biological sample with a compound of this invention, or a composition comprising said compound. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity in a biological sample is useful for a variety of purposes known to one of skill in the art. Examples of such purposes include, but are not limited to, biological specimen storage and biological assays. In one embodiment, the method of inhibiting kinase activity in a biological sample is limited to non-therapeutic methods.

The term "c-MET" is synonymous with "c-Met," "cMet", "MET", "Met" or other designations known to one skilled in the art.

According to another embodiment, the invention relates to a method of inhibiting c-MET kinase activity in a patient comprising the step of administering to said patient a compound of the present invention, or a composition comprising said compound.

The term "c-MET-mediated disease" or "c-MET-mediated condition", as used herein, means any disease state or other deleterious condition in which c-MET is known to play a role. The terms "c-MET-mediated disease" or "c-MET-mediated condition" also mean those diseases or conditions that are alleviated by treatment with a c-MET inhibitor. Such conditions include, without limitation, renal, gastric, colon, brain, breast, prostate, and lung cancer, glioblastoma, atherosclerosis, lung fibrosis, conditions associated with organ transplantation, allergic disorders, and autoimmune disorders.

In one aspect, the present invention features a method treating a proliferative disorder in a patient comprising the step of administering to the patient a therapeutically effective dose of any of the compounds or compositions of the invention.

According to one embodiment, the proliferative disorder is cancer, such as, for example, renal, gastric, colon, brain, breast, liver, prostate, and lung cancer, or a glioblastoma.

In another embodiment, the present invention relates to a method of treating or lessening the severity of brain cancer in a patient in need thereof, comprising administering to said patient a compound of the present invention or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient a compound of the present invention or composition thereof.

Depending upon the particular condition, or disease, to be treated, additional therapeutic agents, which are normally administered to treat that condition, may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with the compounds of this invention to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycinp, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCl), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), aza-epothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), O6 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Those additional agents may be administered separately from the compound-containing composition, as part of a multiple dosage regimen. Alternatively, those agents may be part of a single dosage form, mixed together with the compound of this invention in a single composition. If administered as part of a multiple dosage regime, the two active agents may be submitted simultaneously, sequentially or within a period of time from one another normally within five hours from one another.

The amount of both, the compound and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered.

In those compositions that comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of this invention are another embodiment of the present invention.

In order that the invention described herein may be more fully understood, the following examples are set forth. It should be understood that these examples are for illustrative purposes only and are not to be construed as limiting this invention in any manner.

Preparation of Compounds of the Invention

The following definitions describe terms and abbreviations used herein:

Ala alanine
ATP adenosine triphosphate
Boc t-butoxylcarbonyl
BSA bovine serum albumin
CDI carbonyl diimidazole
DCM dichloromethane
DIEA diisopropylethylamine
DMA dimethylacetamide
DMF dimethylformamide
DMSO methylsulfoxide
DTT dithiothreitol
EDC 1-ethyl-3-(3'-dimethylaminopropyl)carbodiimide hydrochloride
ES-MS electrospray mass spectrometry
$Et_2O$ ethyl ether
EtOAc ethyl acetate
EtOH ethyl alcohol
HBTU O-(benzotriazol-1-yl)-1,1,3,3-tetramethyluronium hexafluorophosphate
HEPES 4-(2-hydroxyethyl)-1-piperazineethanesulfonic acid
HOBT hydroxy benzotriazole hydrate
HPLC high performance liquid chromatography
J In some structures, "J" is used to represent an iodine atom.

Lawesson's Reagent 2,4-bis(4-methoxyphenyl)-1,3-dithia-2,4-diphosphetane-2,4-disulfide
LC-MS liquid chromatography-mass spectrometry
LiHMDS lithium hexamethyldisilazide
Me methyl
MeOH methanol
NBS N-bromosuccinimide
NMP N-methylpyrrolidine
$PdCl_2(dppf)$ 1,1'-bis(diphenylphosphino)ferrocene]dichloropalladium(II)
Ph phenyl
PyBOP benzotriazol-1-yl-oxytripyrrolidinophosphonium hexafluorophosphate
RT room temperature
tBu tertiary butyl
TCA trichloroacetic acid
THF tetrahydrofuran
TEA triethylamine
TFA trifluoacetic acid
TsOH p-toluenesulfonic acid As used herein, other abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

As used herein, the term "$R_t$(min)" refers to the HPLC retention time, in minutes, associated with the compound. Unless otherwise indicated, the HPLC method utilized to obtain the reported retention time is as follows: column: Zorbax SB C18 column, 3.0×150 mm; gradient: 10-90% acetonitrile/water (0.1% TFA), 5 minutes; flow rate: 1.0 mL/minute; and detection: 254 & 214 nm.

Purifications by reversed-phase HPLC were conducted on a Waters 20×100 mm YMC-Pack Pro C18 column using a linear water/acetonitrile (0.1% TFA) gradient at a flow rate of 28 mL/minute. Beginning and final composition of the gradient varied for each compound between 10-40 and 50-90% acetonitrile, respectively.

General Synthetic Procedures

In general, the compounds of this invention may be prepared by methods described herein or known to those skilled in the art for the preparation of analogous compounds. The following non-limiting schemes and examples are presented to further exemplify the invention. Physiochemical characterization of selected compounds of the invention is provided in Tables 6-10.

Compounds of the invention can, in general, be prepared as shown in Scheme 1. Accordingly, a compound of formula I-A-a, I-B-a, I-C-a, I-D-a, or I-E-a, or a protected derivative thereof, wherein $Z^1$, $Z^2$, U, V, $U^1$, $V^1$, Q, and Ring B, are as defined for a compound or formula I, is reacted with intermediate $R^A$-Metal in a catalyst-mediated cross coupling reaction to form a compound of formula I-A-b, I-B-b, I-C-b, I-D-b, or I-E-b, respectively. $R^A$ is as defined elsewhere herein or is a protected derivative thereof. Non-limiting examples of $R^A$ include optionally substituted $C_{6-10}$ aryls, 5-10 membered monocyclic or bicyclic heteroaryls, 5-10 membered monocyclic or bicyclic heterocyclyls, or 5-7 membered cycloaliphatics containing at least one point of unsaturation. The Metal group can be, for example, $-B(OAlkyl)_2$ or $-B(OH)_2$ (Suzuki reaction), $-Mg$-Hal (Kumada reaction), $-Zn$-Hal (Negishi reaction), $-Sn(Alkyl)_3$ (Stille reaction), $-Si(Alkyl)_3$ (Hiyama reaction), $-Cu$-Hal, $-ZrCp_2Cl$, or $-AlMe_2$. The catalyst for the cross-coupling reaction can be, for example, a palladium catalyst/ligand system (such as, for example, $Pd(PPh_3)_4$, $Pd(PtBu_3)_4$, $Pd[P(Me)(tBu_3)]_4$, $PdCl_2(PPh_3)_2$, $PdCl_2(dppf)_2$, $Pd_2(dba)_3BINAP$, or $Pd_2(dba)_3P(o-tol)_3$ (see Fu and Littke, *Angew. Chem. Int. Ed.* 41:4176-4211, 2002; Nicolaou et al., *Angew. Chem. Int. Ed.* 44:4442-4489, 2005; or Hassen et al., *Chemical Reviews* 102(5):1359-1469, 2002). The reaction is usually performed in the presence of a base.

Scheme 1

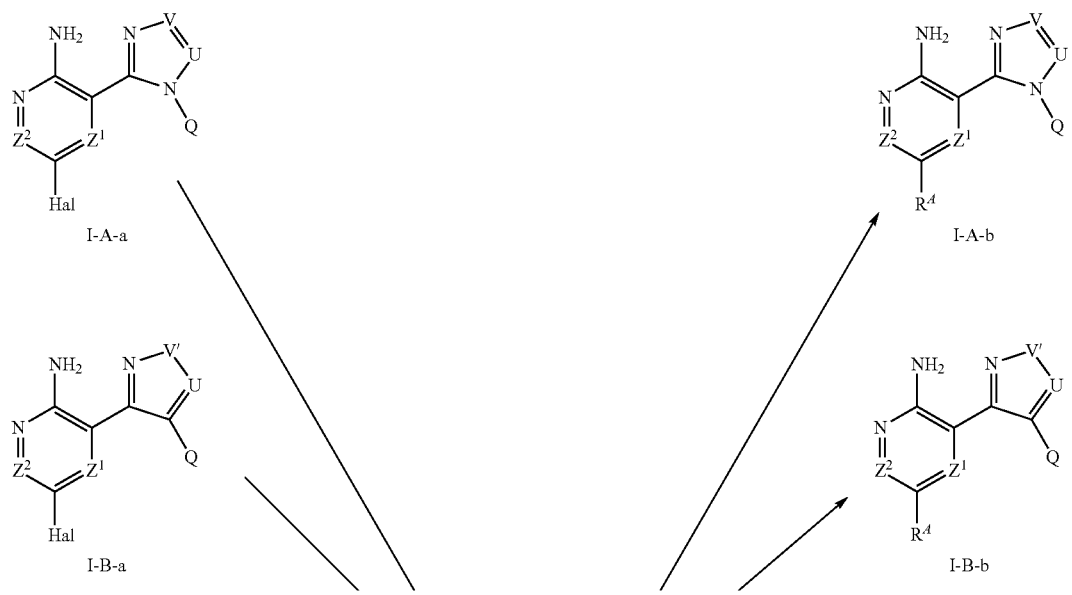

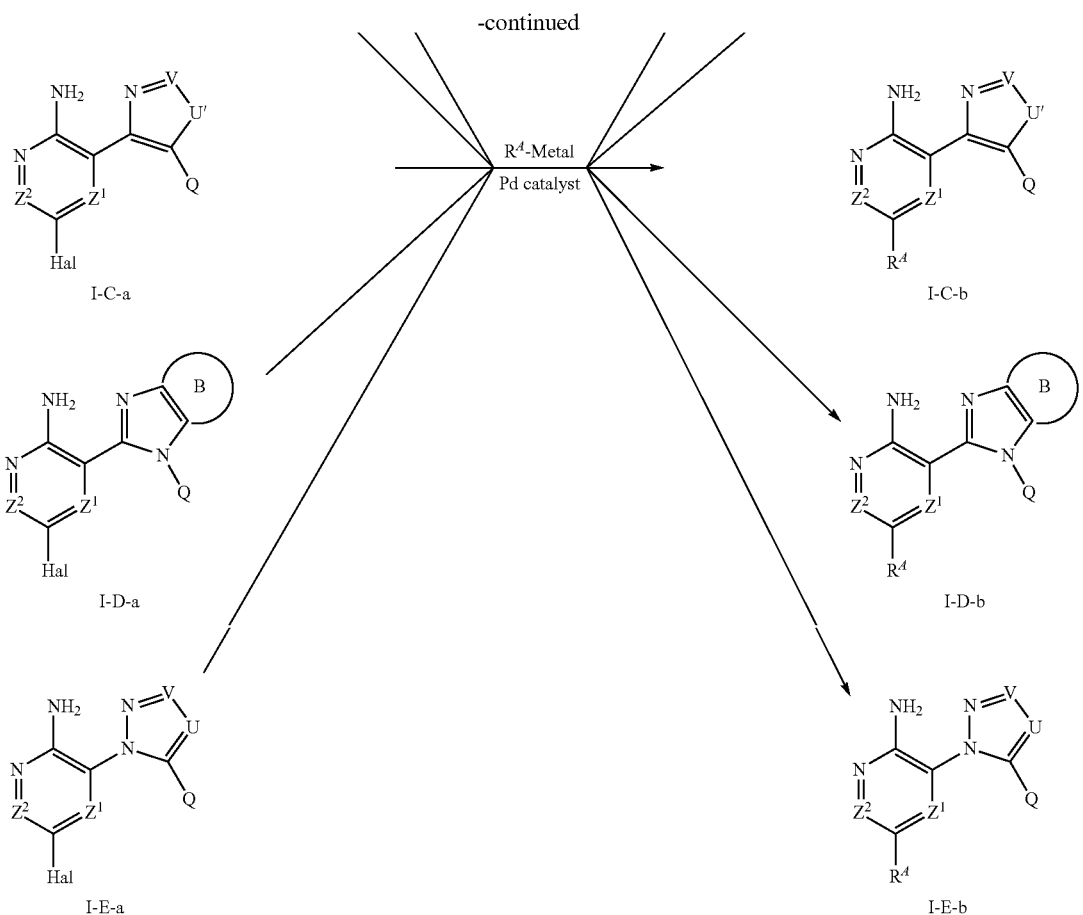

Alternatively, compound of formula I-a, wherein $Z^1$, $Z^2$, Q and Ring D are as defined for a compound of formula I, can be transformed into a boronate or boronic acid of formula I-b, as shown in Scheme 2. Subsequent reaction with an aryl, heteroaryl, or cycloalkenyl halide produces a compound of formula I-c (a compound of formula I, wherein $R^3$ is $R^A$).

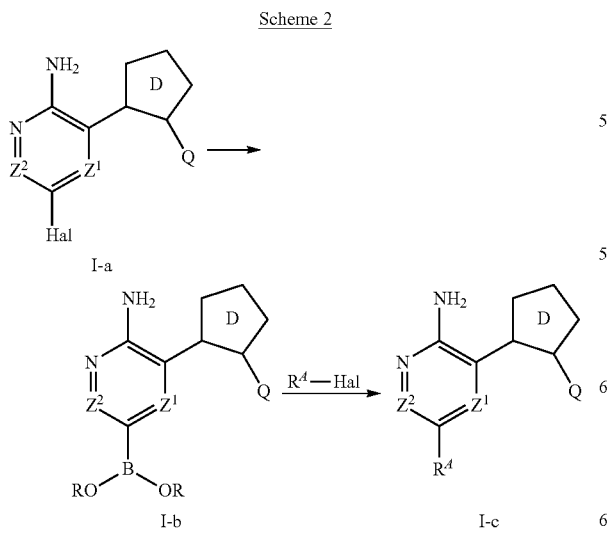

SYNTHETIC EXAMPLES

Example 1

3-Amino-N-(2,3-difluorophenyl)pyrazine-2-carboxamide

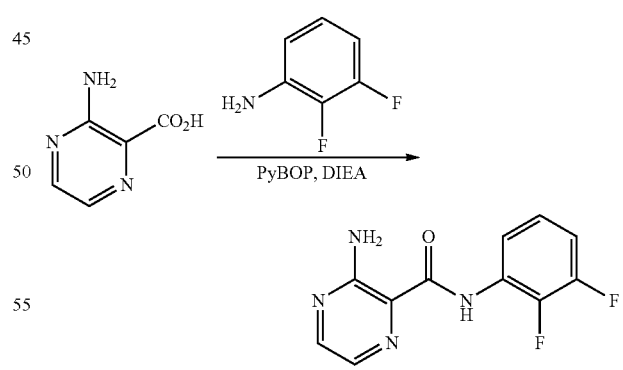

To a solution of 3-aminopyrazine-2-carboxylic acid (2.0 g, 14.38 mmol) in anhydrous DMF (20 mL) was added 2,3-difluoroaniline (2.2 g, 17.04 mmol) and DIEA (7.6 mL, 43.63 mmol). The mixture was stirred at room temperature while PyBOP (7.5 g, 14.41 mmol) was added. The stirring was continued for another 14 hours until HPLC detected no starting material. The reaction solution was then poured into saturated sodium bicarbonate solution. The crude product was collected by vacuum filtration and washed with water. After drying on vacuum pump for 24 hours, the off-white product (2.9 g, 80%) was used directly in the next reaction without further purification. LC-MS m/e=250.8 (M+H); $^1$H-NMR (500 MHZ, DMSO-$d_6$): 10.42 (s, 1H), 8.33 (d, 1H), 7.94 (d, 1H), 7.72 (m, 1H), 7.60 (br, 2H), 7.25 (m, 2H). Using the same procedure, 3-amino-N-(2,3-dichlorophenyl)pyrazine-2-carboxamide and 3-amino-N-(3-chloro-2-fluorophenyl)pyrazine-2-carboxamide can be produced by reacting 3-aminopyrazine-2-carboxylic acid with 2,3-dichloroaniline and 3-chloro-2-fluoroaniline, respectively. Analogously, this procedure can be used to produce 2-amino-N-(2,3-difluorophenyl)pyridine-3-carboxamide, 2-amino-N-(2,3-dichlorophenyl)pyridine-3-carboxamide, and 2-amino-N-(3-chloro-2-fluorophenyl)pyridiine-3-carboxamide by reacting 2-aminopyridine-3-carboxylic acid with 2,3-difluoroaniline, 2,3-dichloroaniline, and 3-chloro-2-fluoroaniline, respectively.

Example 2

3-Amino-N-(2,3-difluorophenyl)-N'-aminopyrazine-2-carboxamidine

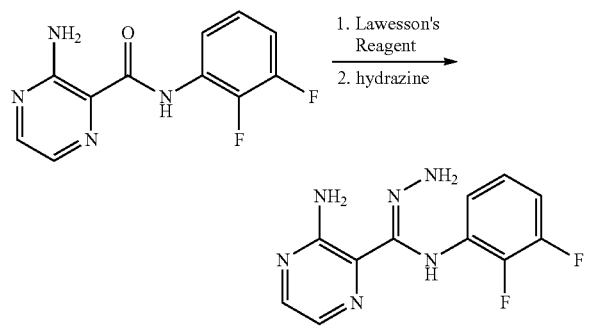

To a solution of 3-amino-N-(2,3-difluorophenyl)pyrazine-2-carboxamide (2.0 g, 8.0 mmol) in anhydrous 1,4-dioxane (50 mL) was added Lawesson's Reagent (2.3 g, 5.7 mmol). The solution was heated at 90° C. for 14 hours and cooled. The solvent was evaporated under vacuum, the residue was re-dissolved in ethanol (30 mL) and methylene chloride (30 mL), and hydrazine (2 mL) was added at RT. The mixture was then stirred for 3 hours and evaporated. The dark residue was poured into saturated NaHCO$_3$ solution and extracted with ethyl acetate. The combined organic layers were dried over MgSO$_4$, filtered, and removed under vacuum evaporation to give 3-amino-N-(2,3-difluorophenyl)-N'-aminopyrazine-2-carboxamidine (1.2 g, 57%), which was used directly in the next reaction without further purification. Using the same procedure, 3-amino-N-(2,3-dichlorophenyl)-N'-aminopyrazine-2-carboxamidine, 3-amino-N-(3-chloro-2-fluorophenyl)-N'-aminopyrazine-2-carboxamidine, 2-amino-N-(2,3-difluorophenyl)-N'-aminopyridine-3-carboxamidine, 2-amino-N-(2,3-dichlorophenyl)-N'-aminopyridine-3-carboxamidine, and 2-amino-N-(3-chloro-2-fluorophenyl)-N'-aminopyridine-3-carboxamidine can be produced from 3-amino-N-(2,3-dichlorophenyl)pyrazine-2-carboxamide, 3-amino-N-(3-chloro-2-fluorophenyl)pyrazine-2-carboxamide, 2-amino-N-(2,3-difluorophenyl)pyridine-3-carboxamide, 2-amino-N-(2,3-dichlorophenyl)pyridine-3-carboxamide, and 2-amino-N-(3-chloro-2-fluorophenyl)pyridine-3-carboxamide, respectively.

Example 3

3-(4-(2,3-Difluorophenyl)-4H-1,2,4-triazol-3-yl)pyrazin-2-amine

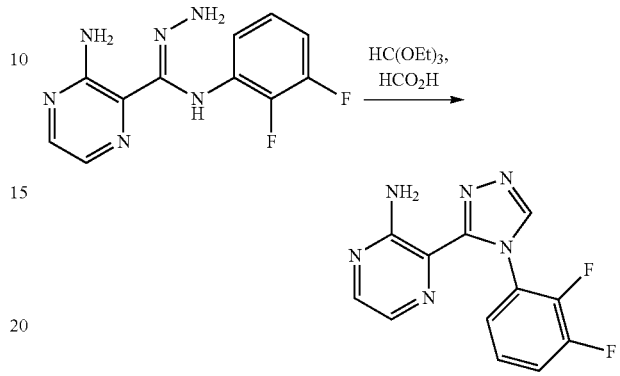

3-Amino-N-(2,3-difluorophenyl)-N'-aminopyrazine-2-carboxamidine (500 mg, 1.89 mmol) was dissolved in CH(OEt)$_3$ (20 mL) and HCOOH (5 mL) was added slowly at RT. The solution was kept at RT for 30 min and carefully neutralized with saturated NaHCO$_3$ and 6N NaOH until a pH of 10 was achieved. The resulting mixture was extracted with ethyl acetate. The combined organic layers were dried over MgSO$_4$ and evaporated to produce 3-(4-(2,3-Difluorophenyl)-4H-1,2,4-triazol-3-yl)pyrazin-2-amine as yellow solid (480 mg, 92%). A small amount of the crude product was purified by HPLC for characterization and the remainder used directly in the next reaction without further purification. LC-MS m/e=274.8 (M+H). Using the same procedure, 3-(4-(2,3-dichlorophenyl)-4H-1,2,4-triazol-3-yl)pyrazin-2-amine, 3-(4-(3-chloro-2-fluorophenyl)-4H-1,2,4-triazol-3-yl)pyrazin-2-amine, 3-(4-(2,3-difluorophenyl)-4H-1,2,4-triazol-3-yl)pyridin-2-amine, 3-(4-(2,3-dichlorophenyl)-4H-1,2,4-triazol-3-yl)pyridin-2-amine, and 3-(4-(3-chloro-2-fluorophenyl)-4H-1,2,4-triazol-3-yl)pyridin-2-amine can be produced from 3-amino-N-(2,3-dichlorophenyl)-N'-aminopyrazine-2-carboxamidine, 3-amino-N-(3-chloro-2-fluorophenyl)-N'-aminopyrazine-2-carboxamidine, 2-amino-N-(2,3-difluorophenyl)-N'-aminopyridine-3-carboxamidine, 2-amino-N-(2,3-dichlorophenyl)-N'-aminopyridine-3-carboxamidine, and 2-amino-N-(3-chloro-2-fluorophenyl)-N'-aminopyridine-3-carboxamidine, respectively.

Example 4

5-Bromo-3-(4-(2,3-difluorophenyl)-4H-1,2,4-triazol-3-yl)pyrazin-2-amine (compound I-A-1)

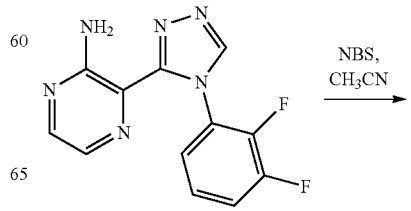

-continued

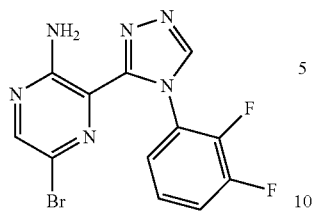

To a solution of 3-(4-(2,3-difluorophenyl)-4H-1,2,4-triazol-3-yl)pyrazin-2-amine (700 mg, 2.55 mmol) in dry CH₃CN (20 mL) was added NBS (550 mg, 3.09 (mmol). The solution was stirred at RT for 1 h and poured into saturated NaHCO₃ solution. The precipitate was collected by vacuum filtration and washed with water (700 mg, 78%) to produce 5-bromo-3-(4-(2,3-difluorophenyl)-4H-1,2,4-triazol-3-yl) pyrazin-2-amine [LC-MS m/e=353/354.6 (M+H)]. Using the same procedure, 5-bromo-3-(4-(2,3-dichlorophenyl)-4H-1, 2,4-triazol-3-yl)pyrazin-2-amine, 5-bromo-3-(4-(3-chloro-2-fluorophenyl)-4H-1,2,4-triazol-3-yl)pyrazin-2-amine, 5-bromo-3-(4-(2,3-difluorophenyl)-4H-1,2,4-triazol-3-yl) pyridin-2-amine, 5-bromo-3-(4-(2,3-dichlorophenyl)-4H-1, 2,4-triazol-3-yl)pyridin-2-amine, and 5-bromo-3-(4-(3-chloro-2-fluorophenyl)-4H-1,2,4-triazol-3-yl)pyridin-2-amine can be produced from 3-(4-(2,3-dichlorophenyl)-4H-1,2,4-triazol-3-yl)pyrazin-2-amine, 3-(4-(3-chloro-2-fluorophenyl)-4H-1,2,4-triazol-3-yl)pyrazin-2-amine, 3-(4-(2,3-difluorophenyl)-4H-1,2,4-triazol-3-yl)pyridin-2-amine, 3-(4-(2,3-dichlorophenyl)-4H-1,2,4-triazol-3-yl)pyridin-2-amine, and 3-(4-(3-chloro-2-fluorophenyl)-4H-1,2,4-triazol-3-yl)pyridin-2-amine, respectively.

Example 5

2-(tert-Butylamino)-N-(2,3-difluorophenyl)pyridine-3-carboxamide

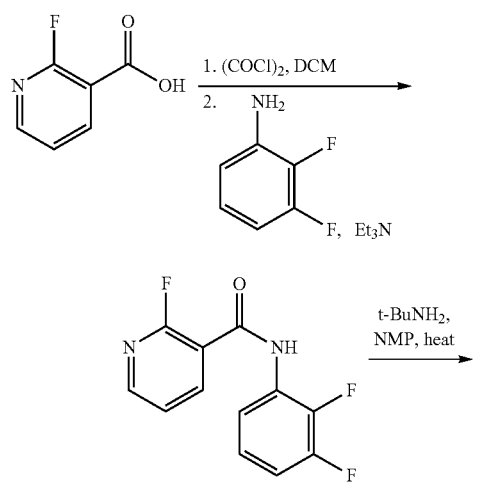

-continued

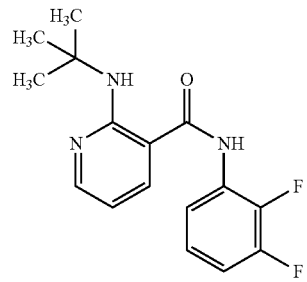

A room temperature solution of 2-fluoronicotinic acid (1 g) in DCM (20 mL) was sequentially treated with DMF (0.2 mL) and oxalyl chloride (0.62 mL, 1 eq). The resulting solution was stirred at RT for 1 hour and monitored by HPLC (analyte quenched with methanol) until the consumption of starting material was complete. The reaction mixture was cooled to 0° C. and sequentially treated with 2,3-difluoroaniline (1.4 g, 1.5 eq) and 2 mL of triethylamine. The reaction was warmed to RT and maintained for 3 additional hours, followed by washing the mixture with 2N HCl, saturated NaCl, and saturated NaHCO₃ solution. The organic extracts were dried over MgSO₄, filtered, and concentrated in vacuo. The resulting crude 2-fluoro-N-(2,3-difluorophenyl)pyridine-3-carboxamide was dissolved in NMP (20 mL) and reacted with excess t-butylamine at 80° C. for 14 hours. After cooling to RT, the solution was poured into sat NaHCO₃ solution. The resulting precipitate was collected by filtration and washed with water. The crude product, 2-(tert-butylamino)-N-(2,3-difluorophenyl)pyridine-3-carboxamide, was dried in vacuo and used directly in the next reaction without further purification. Using the same procedure, 2-(tert-butylamino)-N-(2,3-dichlorophenyl)pyridine-3-carboxamide and 2-(tert-butylamino)-N-(3-chloro-2-fluorophenyl)pyridine-3-carboxamide can be produced from the reaction of 2-fluoronicotinic acid with 2,3-dichloroaniline and 3-chloro-2-fluoroaniline, respectively.

Example 6

N-tert-Butyl-3-(1-(2,3-difluorophenyl)-1H-tetrazol-5-yl)pyridin-2-amine

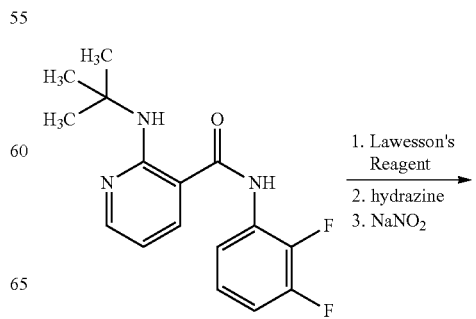

-continued

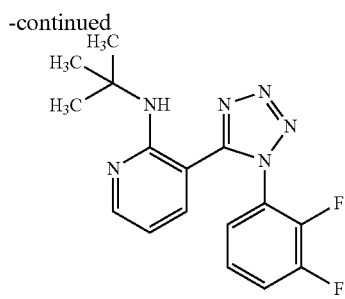

Crude 2-(tert-butylamino)-N-(2,3-difluorophenyl)pyridine-3-carboxamide (1.5 g) was dissolved in dry toluene (24 mL), combined with Lawesson's reagent (1.4 g, 0.7 eq), heated at 90° C. for 10 hours, then evaporated to near dryness. The residue was diluted DCM (20 mL) and EtOH (20 mL) and treated with $NH_2NH_2$. The mixture was stirred at RT for 2 hours then concentrated in vacuo. The residue was diluted with $Et_2O$ and washed with sat $NaHCO_3$ three times. The $Et_2O$ layer was washed with 6N HCl solution (2×20 mL), and the combined HCl extracts treated with $NaNO_2$ (3 eq) in water at RT for 30 min. The resulting mixture was neutralized with 6N NaOH (to pH 7-8) and extracted with EtOAc. The combined extracts were dried over $MgSO_4$, filtered, and concentrated in vacuo to afford crude N-tert-butyl-3-(1-(2,3-difluorophenyl)-1H-tetrazol-5-yl)pyridin-2-amine. Using the same procedure, N-tert-butyl-3-(1-(2,3-dichlorophenyl)-1H-tetrazol-5-yl)pyridin-2-amine and N-tert-butyl-3-(1-(3-chloro-2-fluorophenyl)-1H-tetrazol-5-yl)pyridin-2-amine can be produced from 2-(tert-butylamino)-N-(2,3-dichlorophenyl)pyridine-3-carboxamide and 2-(tert-butylamino)-N-(3-chloro-2-fluorophenyl)pyridine-3-carboxamide, respectively.

Example 7

3-(1-(2,3-Difluorophenyl)-1H-tetrazol-5-yl)pyridin-2-amine

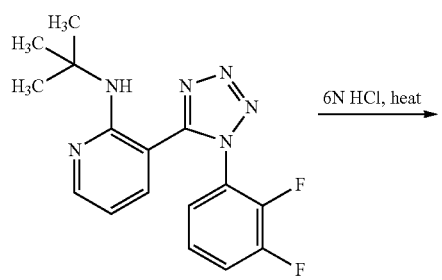

Crude N-tert-butyl-3-(1-(2,3-difluorophenyl)-1H-tetrazol-5-yl)pyridin-2-amine was dissolved in MeOH (10 mL), treated with 6N HCl (20 mL), and heated to reflux for 2 hours. The mixture was subsequently cooled to RT and neutralized with 6N NaOH. The resulting precipitate was collected, washed with water, and dried in vacuo to give 3-(1-(2,3-difluorophenyl)-1H-tetrazol-5-yl)pyridin-2-amine as white solid. Using the same procedure, 3-(1-(2,3-dichlorophenyl)-1H-tetrazol-5-yl)pyridin-2-amine and 3-(1-(3-chloro-2-fluorophenyl)-1H-tetrazol-5-yl)pyridin-2-amine can be produced from N-tert-butyl-3-(1-(2,3-dichlorophenyl)-1H-tetrazol-5-yl)pyridin-2-amine and N-tert-butyl-3-(1-(3-chloro-2-fluorophenyl)-1H-tetrazol-5-yl)pyridin-2-amine, respectively.

Example 8

5-Bromo-3-(1-(2,3-difluorophenyl)-1H-tetrazol-5-yl)pyridin-2-amine (compound I-A-61)

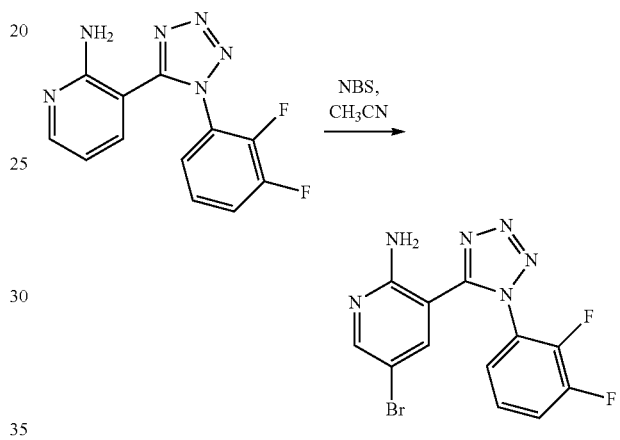

3-(1-(2,3-Difluorophenyl)-1H-tetrazol-5-yl)pyridin-2-amine was stirred in $CH_3CN$ (15 mL) and treated with NBS (2 eq). The reaction mixture was maintained at room temperature for 30 min. The reaction was subsequently poured into sat $NaHCO_3$ solution and treated sequentially with 5 mL $Na_2S_2O_3$ and 2 mL 6N NaOH. The solids were filtered, washed with water, and dried in vacuo to afford 5-bromo-3-(1-(2,3-difluorophenyl)-1H-tetrazol-5-yl)pyridin-2-amine, which was purified by silica gel chromatography. Using the same procedure, 5-bromo-3-(1-(2,3-dichlorophenyl)-1H-tetrazol-5-yl)pyridin-2-amine and 5-bromo-3-(1-(3-chloro-2-fluorophenyl)-1H-tetrazol-5-yl)pyridin-2-amine can be produced from 3-(1-(2,3-dichlorophenyl)-1H-tetrazol-5-yl)pyridin-2-amine and 3-(1-(3-chloro-2-fluorophenyl)-1H-tetrazol-5-yl)pyridin-2-amine, respectively.

Example 9

5-(3-Aminopyrazin-2-yl)-4-(2,3-difluorophenyl)-4H-1,2,4-triazol-3-ol

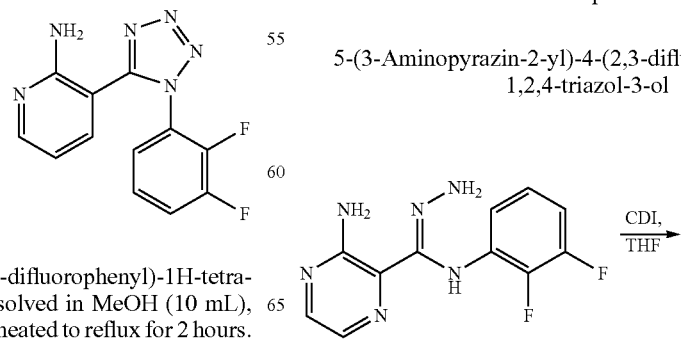

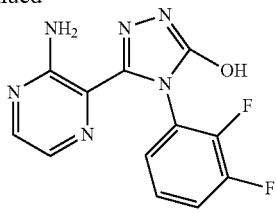

3-Amino-N-(2,3-difluorophenyl)-N'-aminopyrazine-2-carboxamidine (500 mg, 1.89 mmol) was dissolved in dry THF (10 mL) and CDI (340 mg, 2.10 mmol) was added at RT. The solution was kept at RT for overnight. After the solvent was removed by evaporation, the residue was added to saturated NaHCO$_3$ solution and filtered. After washing with water, the crude yellow solid product (500 mg, 91%) was obtained after drying under vacuum. LC-MS m/e=290.8 (M+H). Using the same procedure, 5-(3-aminopyrazin-2-yl)-4-(2,3-dichlorophenyl)-4H-1,2,4-triazol-3-ol, 5-(3-aminopyrazin-2-yl)-4-(3-chloro-2-fluorophenyl)-4H-1,2,4-triazol-3-ol, 5-(2-aminopyridin-3-yl)-4-(2,3-difluorophenyl)-4H-1,2,4-triazol-3-ol, 5-(2-aminopyridin-3-yl)-4-(2,3-dichlorophenyl)-4H-1,2,4-triazol-3-ol, and 5-(2-aminopyridin-3-yl)-4-(3-chloro-2-fluorophenyl)-4H-1,2,4-triazol-3-ol can be produced from 3-amino-N-(2,3-dichlorophenyl)-N'-aminopyrazine-2-carboxamidine, 3-amino-N-(3-chloro-2-fluorophenyl)-N'-aminopyrazine-2-carboxamidine, 2-amino-N-(2,3-difluorophenyl)-N'-aminopyridine-3-carboxamidine, 2-amino-N-(2,3-dichlorophenyl)-N'-aminopyridine-3-carboxamidine, and 2-amino-N-(3-chloro-2-fluorophenyl)-N'-aminopyridine-3-carboxamidine, respectively.

Example 10

5-(3-Amino-6-bromopyrazin-2-yl)-4-(2,3-difluorophenyl)-4H-1,2,4-triazol-3-ol (compound I-A-14)

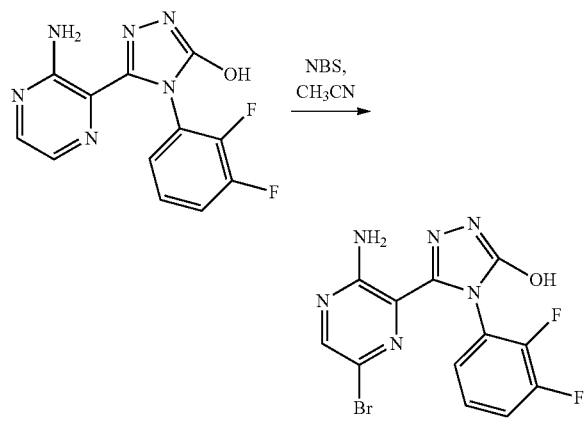

To a solution of 5-(3-aminopyrazin-2-yl)-4-(2,3-difluorophenyl)-4H-1,2,4-triazol-3-ol (400 mg, 1.38 mmol) in dry CH$_3$CN (15 mL) was added NBS (300 mg, 1.68 mmol). The solution was stirred at RT for 3 h and poured into saturated NaHCO$_3$ solution. The aqueous solution was extracted with ethyl acetate (2×20 mL). The combined organic layers were dried over MgSO4, filtered, and evaporated. The crude foam product was used directly in the next reaction without further purification (350 mg, 69%). LC-MS m/e=369/370.7 (M+H). Using the same procedure 5-(3-amino-6-bromopyrazin-2-yl)-4-(2,3-dichlorophenyl)-4H-1,2,4-triazol-3-ol, 5-(3-amino-6-bromopyrazin-2-yl)-4-(3-chloro-2-fluorophenyl)-4H-1,2,4-triazol-3-ol, 5-(2-amino-5-bromopyridin-3-yl)-4-(2,3-difluorophenyl)-4H-1,2,4-triazol-3-ol, 5-(2-amino-5-bromopyridin-3-yl)-4-(2,3-dichlorophenyl)-4H-1,2,4-triazol-3-ol, and 5-(2-amino-5-bromopyridin-3-yl)-4-(3-chloro-2-fluorophenyl)-4H-1,2,4-triazol-3-ol can be produced from 5-(3-aminopyrazin-2-yl)-4-(2,3-dichlorophenyl)-4H-1,2,4-triazol-3-ol, 5-(3-aminopyrazin-2-yl)-4-(3-chloro-2-fluorophenyl)-4H-1,2,4-triazol-3-ol, 5-(2-aminopyridin-3-yl)-4-(2,3-difluorophenyl)-4H-1,2,4-triazol-3-ol, 5-(2-aminopyridin-3-yl)-4-(2,3-dichlorophenyl)-4H-1,2,4-triazol-3-ol, and 5-(2-aminopyridin-3-yl)-4-(3-chloro-2-fluorophenyl)-4H-1,2,4-triazol-3-ol, respectively.

Example 11

5-Bromo-3-(4-(3-chloro-2-fluorophenyl)-5-methyl-4H-1,2,4-triazol-3-yl)pyridin-2-amine (compound I-A-437)

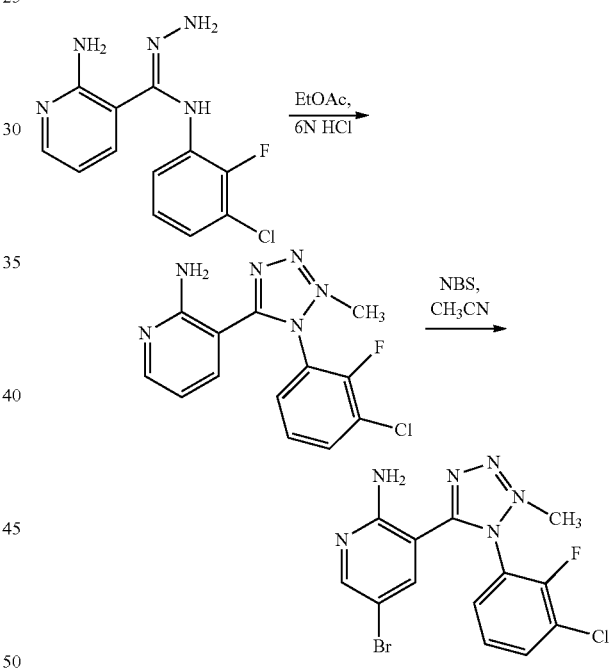

2-amino-N-(3-chloro-2-fluorophenyl)-N'-aminopyridine-3-carboxamidine (500 mg, 1.79 mmol) was dissolved in ethyl acetate (20 mL) and 6N HCl (1 mL) was added at RT. The solution was kept at RT for 14 hours and evaporated to 90% dryness. The residue was poured into saturated NaHCO$_3$ and an off-white solid was collected by filtration, which was dried in vacuo. The resulting 3-(4-(3-chloro-2-fluorophenyl)-5-methyl-4H-1,2,4-triazol-3-yl)pyridin-2-amine was used as is in the subsequent bromination reaction.

3-(4-(3-Chloro-2-fluorophenyl)-5-methyl-4H-1,2,4-triazol-3-yl)pyridin-2-amine was dissolved in CH$_3$CN (15 mL) and NBS (320 mg, 1.80 mmol) was added. The reaction mixture was stirred at RT for 30 min, and then poured into saturated NaHCO$_3$ solution. The precipitate was collected by filtration, washed with water, and purified by HPLC to 5-bromo-3-(4-(3-chloro-2-fluorophenyl)-5-methyl-4H-1,2, 4-triazol-3-yl)pyridin-2-amine as a yellow solid (400 mg, 1.05 mmol). LC-MS m/e=382.0 (M+H); $^1$H-NMR (300 MHz, DMSO) 8.06 (d, J=2.4 Hz, 1H), 7.89-7.84 (m, 1H), 7.79-7.74 (m, 1H), 7.49 (td, J=8.2, 3.2 Hz, 1H), 7.12 (d, J=2.4 Hz, 1H), 6.92 (s, 2H), 3.30 (s, 3H). Using the same procedure, 5-bromo-3-(4-(2,3-difluorophenyl)-5-methyl-4H-1,2,4-triazol-3-yl)pyrazin-2-amine, 5-bromo-3-(4-(2,3-dichlorophenyl)-5-methyl-4H-1,2,4-triazol-3-yl)pyrazin-2-amine, 5-bromo-3-(4-(3-chloro-2-fluorophenyl)-5-methyl-4H-1,2,4-triazol-3-yl)pyrazin-2-amine, 5-bromo-3-(4-(2,3-difluorophenyl)-5-methyl-4H-1,2,4-triazol-3-yl)pyridin-2-amine, and 3-(4-(2,3-dichlorophenyl)-5-methyl-4H-1,2,4-triazol-3-yl)pyridin-2-amine can be produced from 3-amino-N-(2,3-difluorophenyl)-N'-aminopyrazine-2-carboxamidine, 3-amino-N-(2,3-dichlorophenyl)-N'-aminopyrazine-2-carboxamidine, 3-amino-N-(3-chloro-2-fluorophenyl)-N'-aminopyrazine-2-carboxamidine, 2-amino-N-(2,3-difluorophenyl)-N'-aminopyridine-3-carboxamidine, and 2-amino-N-(2,3-dichlorophenyl)-N'-aminopyridine-3-carboxamidine, respectively.

Example 12

5-Bromo-2-chloro-N-(2,3-dichlorophenyl)pyridine-3-carboxamide

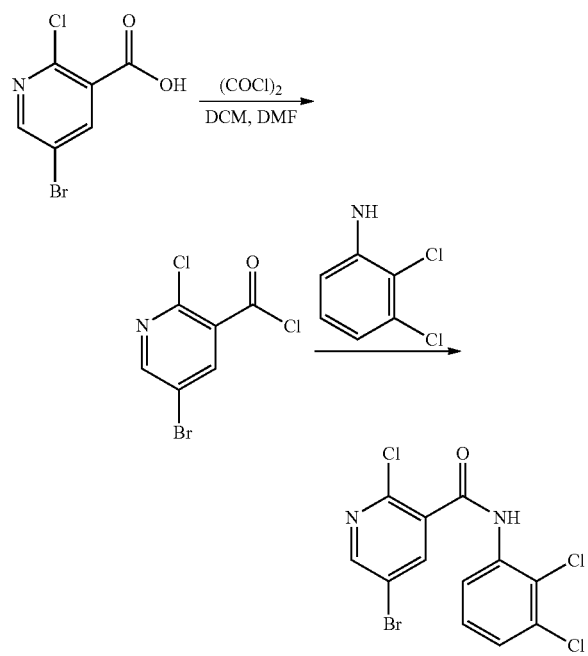

To a slurry of 5-bromo-2-chloronicotinic acid (2.063 g, 8.725 mmol) in methylene chloride (20 mL) was slowly added oxalyl chloride (1.11 g, 8.725 mmol) followed by the addition of dimethylformamide (5 drops). After 4H the mixture was concentrated in vacuo to provide 2.21 g of 5-bromo-2-chloropyridine-3-carbonyl chloride as a light brown solid, which was used as is in the next reaction.

To a solution of 2,3 dichloroaniline (3.875 g, 23.914 mmol) in diethyl ether (20 mL) was added 5-bromo-2-chloropyridine-3-carbonyl chloride (3.0 g, 11.96 mmol). The reaction was stirred overnight. The precipitated solids were collected and washed with diethyl ether to provide 3.6 g of 5-bromo-2-chloro-N-(2,3-dichlorophenyl)pyridine-3-carboxamide as a cream colored solid [LC-MS m/e=380.0 (M+H)]. Using the same procedure, 5-bromo-2-chloro-N-(2,3-fluorophenyl)pyridine-3-carboxamide and 5-bromo-2-chloro-N-(3-chloro-2-fluorophenyl)pyridine-3-carboxamide can be produced from reacting 5-bromo-2-chloropyridine-3-carbonyl chloride with 2,3 fluororoaniline and 3-chloro-2-fluoroaniline, respectively.

Example 13

5-Bromo-2-chloro-3-(1-(2,3-dichlorophenyl)-1H-imidazol-2-yl)pyridine

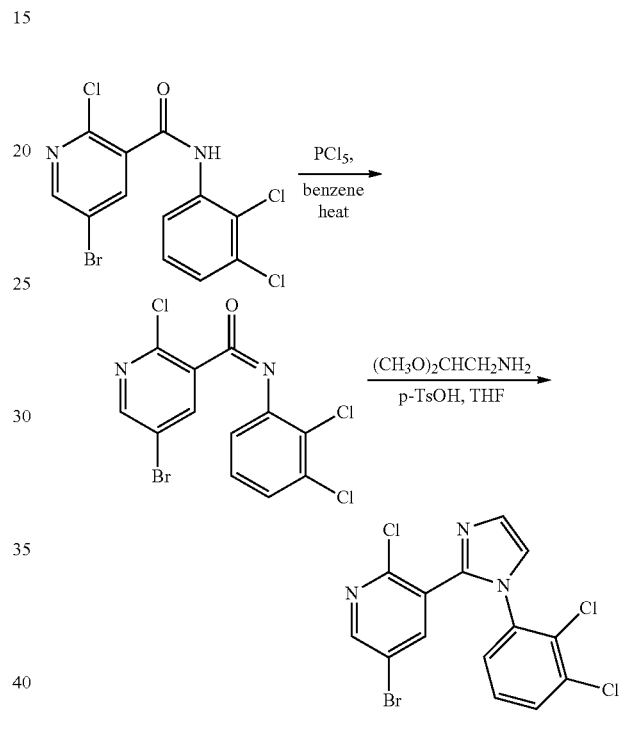

To a slurry of 5-bromo-2-chloro-N-(2,3-dichlorophenyl)pyridine-3-carboxamide (0.75 g, 1.97 mmol) in benzene was added phosphorous pentachloride (0.5 g, 2.365 mmol) and the mixture heated to reflux. After 1.5 hours, the resulting solution was concentrated to provide 0.76 g of N-((5-bromo-2-chloropyridin-3-yl)chloromethylene)-2,3-dichlorobenzenamine as an off white solid. This material was used directly in the next reaction as is.

To a solution of 2,2-dimethoxyethanamine (0.053 g, 0.505 mmol) in anhydrous tetrahydrofuran (5 mL) at 0-5° C. was added the N-((5-bromo-2-chloropyridin-3-yl)chloromethylene)-2,3-dichlorobenzenamine (0.1 g, 0.2526 mmol) as a solution in anhydrous tetrahydrofuran (5 mL). After stirring overnight, p-toluene sulfonic acid (0.05 g, 0.51 mmol) was added and the reaction mixture was stirred an additional 2 hours. After concentration to dryness the resulting solid purified by flash chromatography (0 to 30% ethyl acetate/methylene chloride) to provide 0.092 g of 5-bromo-2-chloro-3-(1-(2,3-dichlorophenyl)-1H-imidazol-2-yl)pyridine. Using the same procedure, 5-bromo-2-chloro-3-(1-(2,3-difluorophenyl)-1H-imidazol-2-yl)pyridine and 5-bromo-2-chloro-3-(1-(3-chloro-2-fluorophenyl)-1H-imidazol-2-yl)pyridine can be produced from 5-bromo-2-chloro-N-(2,3-difluorophenyl)

pyridine-3-carboxamide and 5-bromo-2-chloro-N-(3-chloro-2-fluorophenyl)pyridine-3-carboxamide, respectively.

Example 14

5 N-(4-Methoxybenzyl)-5-bromo-3-(1-(2,3-dichlorophenyl)-1H-imidazol-2-yl)pyridin-2-amine

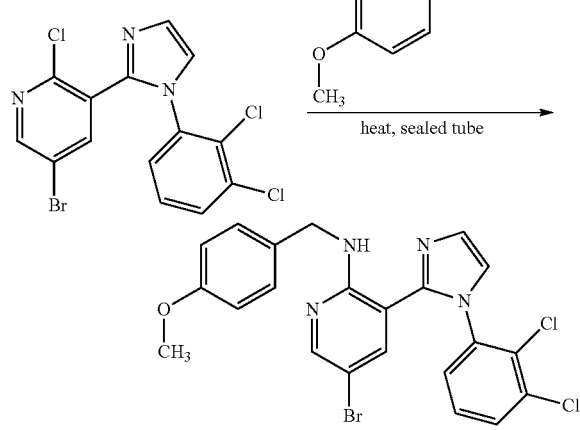

To a solution of excess (4-methoxyphenyl)methanamine (0.2 mL) in dioxane (2 mL) was added 5-bromo-2-chloro-3-(1-(2,3-dichlorophenyl)-1H-imidazol-2-yl)pyridine (0.089 g, 0.222 mmol). The mixture was heated at 100° C. for 16 hours in a sealed reaction vessel. The mixture was then cooled, diluted with ethyl acetate, washed with saturated aqueous sodium bicarbonate, and the combined organics dried over sodium sulfate. After filtration and concentration, the residue was purified by flash chromatography (20% hexanes/methylene chloride to 25% ethyl acetate/methylene chloride to provide 0.065 g of N-(4-methoxybenzyl)-5-bromo-3-(1-(2,3-dichlorophenyl)-1H-imidazol-2-yl)pyridin-2-amine [LC-MS m/e=505.0 (M+H)]. Using the same procedure, N-(4-methoxybenzyl)-5-bromo-3-(1-(2,3-difluorophenyl)-1H-imidazol-2-yl)pyridin-2-amine and N-(4-methoxybenzyl)-5-bromo-3-(1-(3-chloro-2-fluorophenyl)-1H-imidazol-2-yl)pyridin-2-amine can be produced from 5-bromo-2-chloro-3-(1-(2,3-difluorophenyl)-1H-imidazol-2-yl)pyridine and 5-bromo-2-chloro-3-(1-(3-chloro-2-fluorophenyl)-1H-imidazol-2-yl)pyridine, respectively

Example 15

N-(4-Methoxybenzyl)-5-bromo-3-(5-(2,3-dichlorophenyl)-2-methyloxazol-4-yl)pyridin-2-amine

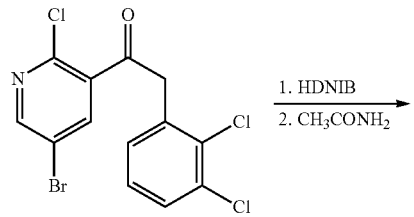

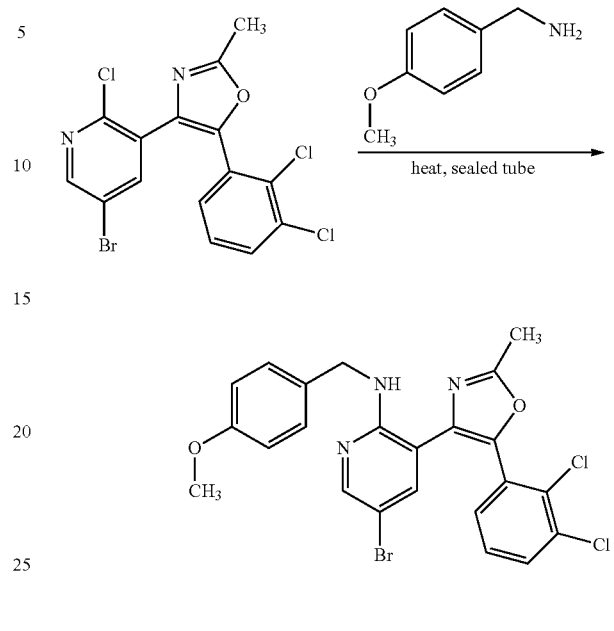

To a solution of 1-(5-bromo-2-chloropyridin-3-yl)-2-(2,3-dichlorophenyl)ethanone (0.315 g, 0.83 mmol) in THF (3 mL) was added HDNIB (0.585 g, 1.2 mmol, [hydroxy(2,4-dinitrobenzenesulfonyloxy)iodo]benzene, see Lee et al., Synlett, 10: 1563-1564, 2001) in 1,2-dichloroethane (3 mL). The reaction mixture was heated to reflux in a sealed tube for 2 hours, at which point a solution formed. The reaction was cooled to RT and acetamide (2 eq., 0.115 g, 1.9 mmol) was added. The reaction was then heated to reflux for 18 hours. After cooling, the mixture was dissolved in MeOH, adsorbed onto Celite™ and purified by silica gel chromatography (5 to 40% EtOAc/hexanes) to give 5-bromo-2-chloro-3-(5-(2,3-dichlorophenyl)-2-methyloxazol-4-yl)pyridine as a colorless oil [0.084 g, 24% yield; LC-MS m/e=418.8 (M+H)].

To a solution of -bromo-2-chloro-3-(5-(2,3-dichlorophenyl)-2-methyloxazol-4-yl)pyridine (0.08 g, 0.19 mmol) in dioxane (2 mL) was added 4-methoxybenzylamine (0.5 mL). The reaction mixture was heated to 120° C. in a sealed tube for 18 hours. After cooling, the mixture was diluted with EtOAc, washed with H$_2$O (2×5 mL), and the aqueous phase back-extracted with EtOAc (2×5 mL). The combined organics were adsorbed onto Celite and purified by silica gel chromatography (5-40% EtOAc/hexanes) to give N-(4-methoxybenzyl)-5-bromo-3-(5-(2,3-dichlorophenyl)-2-methyloxazol-4-yl)pyridin-2-amine as a yellow solid (82 mg, 83% yield). Using the same procedure, N-(4-methoxybenzyl)-5-bromo-3-(5-(2,3-difluorophenyl)-2-methyloxazol-4-yl)pyridin-2-amine and N-(4-methoxybenzyl)-5-bromo-3-(5-(3-chloro-2-fluorophenyl)-2-methyloxazol-4-yl)pyridin-2-amine can be produced from 1-(5-bromo-2-chloropyridin-3-yl)-2-(2,3-difluorophenyl)ethanone and 1-(5-bromo-2-chloropyridin-3-yl)-2-(3-chloro-2-fluorophenyl)ethanone, respectively.

Example 16

5-Bromo-3-(5-(2,3-dichlorophenyl)-1,2,3-thiadiazol-4-yl)pyridin-2-amine (compound I-C-2)

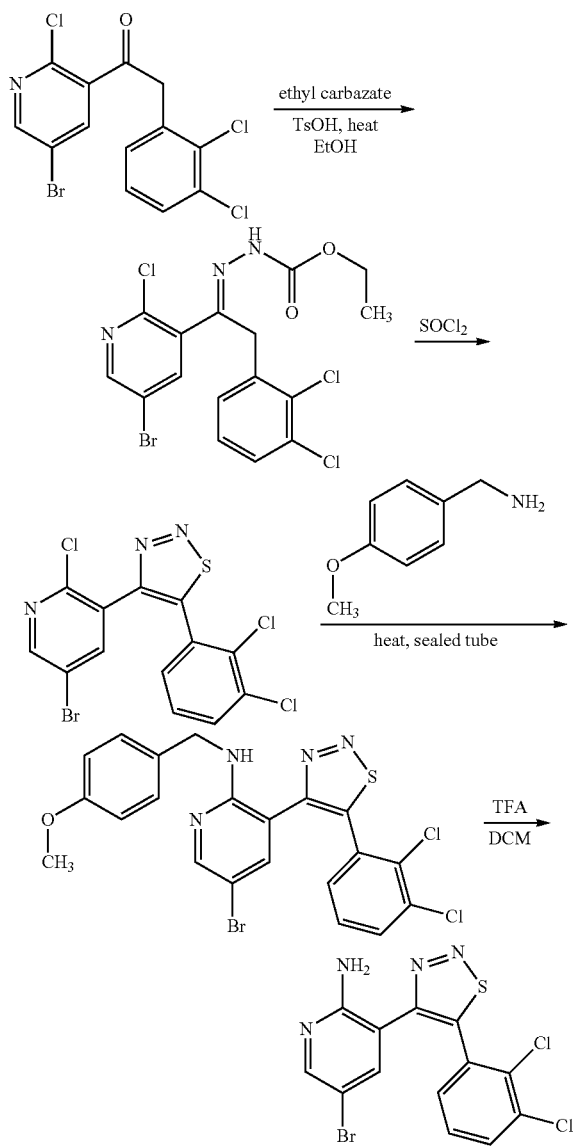

To a solution of 1-(5-bromo-2-chloropyridin-3-yl)-2-(2,3-dichlorophenyl)ethanone (1.14 g, 3.03 mmol) in EtOH (40 mL) was added ethyl carbazate (0.95 g, 9.09 mmol) and TsOH (2 mg). The reaction mixture was heated for 3 hours, followed by evaporated of the volatiles to give ethyl-2-(1-(5-bromo-2-chloropyridin-3-yl)-2-(2,3-dichlorophenyl)ethylidene)hydrazinecarboxylate as a yellow oil, which was used directly in the next step.

A solution of ethyl-2-(1-(5-bromo-2-chloropyridin-3-yl)-2-(2,3-dichlorophenyl)ethylidene)hydrazinecarboxylate (3.03 mmol) was stirred in thionyl chloride (20 mL). The solution was heated from 0° C. to RT and stirred for 3.5 hours. The solvent was evaporated to give a yellow oil which was adsorbed onto Celite™ and purified by silica gel chromatography (5-40% EtOAc/hexanes) to give 5-bromo-2-chloro-3-(5-(2,3-dichlorophenyl)-1,2,3-thiadiazol-4-yl)pyridine as a yellow solid (640 mg, 50% yield over 2 steps).

To a solution of 5-bromo-2-chloro-3-(5-(2,3-dichlorophenyl)-1,2,3-thiadiazol-4-yl)pyridine (0.37 g, 0.88 mmol) in dioxane (2 mL) was added 4-methoxybenzylamine (4 eq, 460 µL, 3.5 mmol). The solution was heated in a sealed tube at 120° C. for 18 h. After cooling, the mixture was filtered and the filtrate was reduced in vacuo. The resulting oil was purified by silica gel chromatography (5 to 70% EtOAc/hexanes) to provide N-(4-methoxybenzyl)-5-bromo-3-(5-(2,3-dichlorophenyl)-1,2,3-thiadiazol-4-yl)pyridin-2-amine as a yellow sticky solid (415 mg, 90% yield)

To a solution of N-(4-methoxybenzyl)-5-bromo-3-(5-(2,3-dichlorophenyl)-1,2,3-thiadiazol-4-yl)pyridin-2-amine (0.128 mmol) in $CH_2Cl_2$ (2 mL) was added TFA (3 mL). The mixture was heated at 40° C. for 20 hours then at RT for 3d. The volatiles were evaporated and the residue purified by preparative reversed-phase HPLC to afford 5-bromo-3-(5-(2,3-dichlorophenyl)-1,2,3-thiadiazol-4-yl)pyridin-2-amine as a colorless oil (0.019 g, 37% yield). Using the same procedure, 5-bromo-3-(5-(2,3-fluorophenyl)-1,2,3-thiadiazol-4-yl)pyridin-2-amine and 5-bromo-3-(5-(3-chloro-2-fluorophenyl)-1,2,3-thiadiazol-4-yl)pyridin-2-amine can be produced from 1-(5-bromo-2-chloropyridin-3-yl)-2-(2,3-difluorophenyl)ethanone and 1-(5-bromo-2-chloropyridin-3-yl)-2-(3-chloro-2-fluorophenyl)ethanone, respectively.

Example 17

5-Bromo-3-(5-(2,3-difluorophenyl)-1H-tetrazol-1-yl)pyridin-2-amine

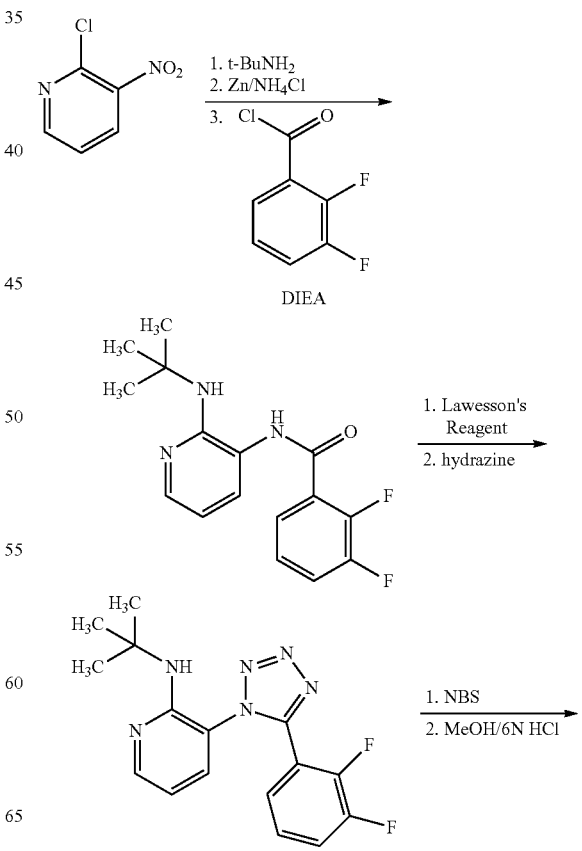

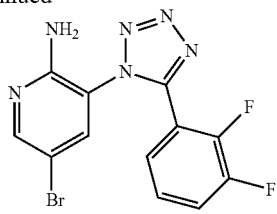

To a solution of 2-chloro-3-nitropyridine (5.0 g, 31.53 mmol) in anhydrous NMP (100 mL) was added tert-butylamine (10 mL, 94.52 mmol). The solution was heated at 60° C. for 14 hours and cooled. The mixture was poured into 1N HCl solution (400 mL) and extracted with EtOAc (3×150 mL). The combined organic layers were washed with saturated $NaHCO_3$ solution and dried over $MgSO_4$. After filtration, the solvent was evaporated under vacuum to afford N-tert-butyl-3-nitropyridin-2-amine as dark brown syrup.

To a solution of the N-tert-butyl-3-nitropyridin-2-amine in MeOH (200 mL), was added solid $NH_4Cl$ (16.4 g, 306.54 mmol) and zinc dust (10.0 g, 153 mmol). The suspension was heated under reflux for 3 hours and then cooled to RT. After filtration through Celite™, the solvent was removed by vacuum evaporation. The resulting black residue was taken up to EtOAc (300 mL) and filtered through Celite™ again to remove the remaining $NH_4Cl$. The solvent was again evaporated and the residue was dried on the high vacuum oil pump overnight to yield $N^2$-tert-butylpyridine-2,3-diamine.

To a solution of $N^2$-tert-butylpyridine-2,3-diamine in dry DCM (150 mL) was added DIEA (17 mL, 95.5 mmol). The solution was cooled to 0° C. and carefully added 2,3-difluorobenzoyl chloride (8.35 g, 47.30 mmol). The reaction was allowed to warm up to RT and stirred for 1 hr. The mixture was then washed with water, saturated NaHCO3, and dried over MgSO4. Removal of the solvent by evaporation, the residue was purified by silica gel chromatography (5%-60% EtOAc/hexane) to yield N-(2-(tert-butylamino)pyridin-3-yl)-2,3-difluorobenzamide (4.0 g, 13.10 mmol); LC-MS m/e=306.1 (M+H).

To a solution of N-(2-(tert-butylamino)pyridin-3-yl)-2,3-difluorobenzamide (4.0 g, 13.10 mmol) in anhydrous 1,4-dioxane (60 mL) was added Lawesson's reagent (3.7 g, 9.15 mmol). The solution was heated at 80° C. for 40 min and cooled to RT. To the cooled solution was added a solution of hydrazine (5 mL) in EtOH (60 mL). The mixture was stirred at RT for 14 hours and poured into saturated $NaHCO_3$ solution (300 mL). The aqueous solution was extracted with EtOAc (3×150 mL), the combined organic layers were then reverse-extracted with 2N HCl solution (2×150 mL). The combined acidic layers were treated with $NaNO_2$ (0.9 g, 13.1 mmol) at RT for 10 min. The reaction mixture was cooled to 0° C. and solid NaOH was added to a pH of 8. Filtration yielded N-tert-butyl-3-(5-(2,3-difluorophenyl)-1H-tetrazol-1-yl)pyridin-2-amine as a brownish solid; LC-MS m/e=303.1 (M+H—$N_2$).

To a solution of N-tert-butyl-3-(5-(2,3-difluorophenyl)-1H-tetrazol-1-yl)pyridin-2-amine (13.10 mmol) in $CH_3CN$ (150 mL) was added NBS (2.33 g, 13.10 mmol). The reaction was stirred at RT for 20 min and poured into a solution of $Na_2SO_3$ (150 mL) and 6N NaOH (5 mL). The mixture was stirred for an additional 30 min and filtered. The resulting dark colored solid was collected and washed with water. To this solid was added MeOH (100 mL) and 6N HCl (100 mL). The mixture was heated under reflux for 4 hours and cooled to 0° C. NaOH was added as a solid until a pH of 9 was achieved, at which time 5-bromo-3-(5-(2,3-difluorophenyl)-1H-tetrazol-1-yl)pyridin-2-amine was collected as a pinkish solid by filtration (3.8 g, 10.76 mmol); LC-MS m/e=325.1 (M+H—$N_2$). Using the same procedure, 5-bromo-3-(5-(2,3-dichlorophenyl)-1H-tetrazol-1-yl)pyridin-2-amine and 5-bromo-3-(5-(3-chloro-2-fluorophenyl)-1H-tetrazol-1-yl)pyridin-2-amine can be produced from 2,3-dichlorobenzoyl chloride and 3-chloro-2-fluorobenzoyl chloride, respectively.

Example 18

1-(5-Bromo-2-chloropyridin-3-yl)-2-(2,3-dichlorophenyl)-3-(dimethylamino)prop-2-en-1-one

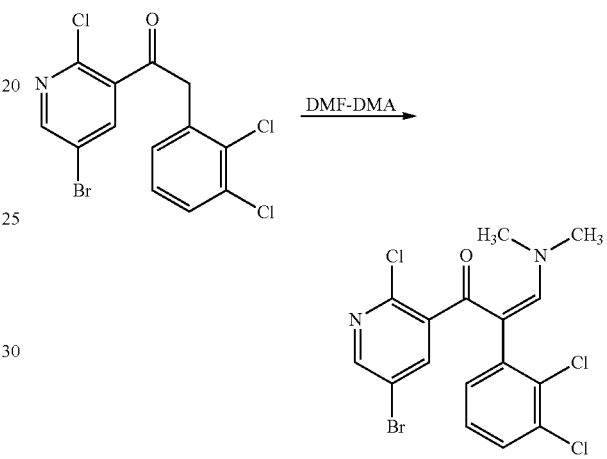

A solution of 1-(5-bromo-2-chloropyridin-3-yl)-2-(2,3-dichlorophenyl)ethanone in dry THF was slowly treated with DMF-DMA under $N_2$ atmosphere for 45 min and stirred at RT until completion of the reaction. The reaction mixture was concentrated under reduced pressure to obtain 1-(5-bromo-2-chloropyridin-3-yl)-2-(2,3-dichlorophenyl)-3-(dimethylamino)prop-2-en-1-one as semi solid. Washing the crude product with n-pentane and pet-ether resulted in a free flowing light brown solid (1.0 g, 58.8%) which was used as is in the next reaction without further purification.

Example 19

5-Bromo-2-chloro-3-(4-(2,3-dichlorophenyl)-1-cyclohexyl-1H-pyrazol-3-yl)pyridine and 5-bromo-2-chloro-3-(4-(2,3-dichlorophenyl)-1-cyclohexyl-1H-pyrazol-5-yl)pyridine

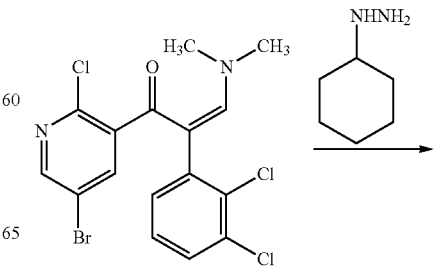

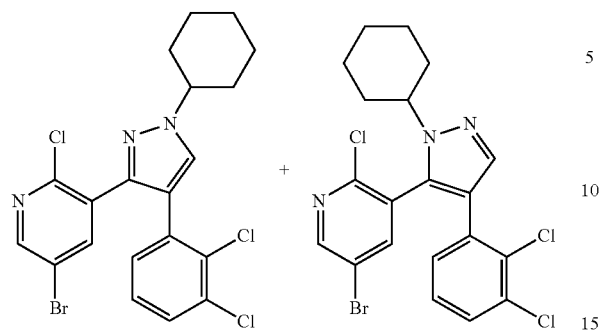
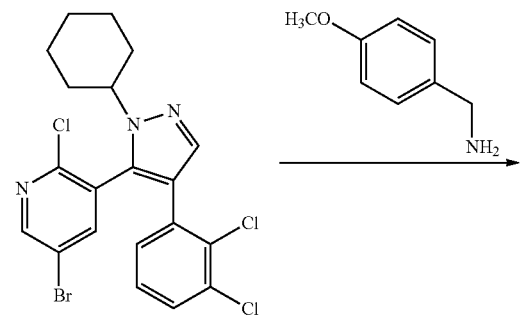

To a stirred solution of cyclohexyl hydrazine hydrochloride in toluene was added K$_2$CO$_3$. After stirring for 10 min at RT, the mixture was treated with 1-(5-bromo-2-chloropyridin-3-yl)-2-(2,3-dichlorophenyl)-3-(dimethylamino)prop-2-en-1-one followed by treatment with acetic acid. The reaction mixture was stirred for 10 min at RT and heated to 80° C. for 18 hr. The mixture was cooled to RT, concentrated to dryness under reduced pressure, diluted with water, extracted with ethyl acetate, washed with saturated aqueous NaHCO$_3$ solution, water, and brine solution, respectively, prior to drying over Na$_2$SO$_4$. Filtration and evaporation of solvent gave crude mixture of 5-bromo-2-chloro-3-(4-(2,3-dichlorophenyl)-1-cyclohexyl-1H-pyrazol-3-yl)pyridine and 5-bromo-2-chloro-3-(4-(2,3-dichlorophenyl)-1-cyclohexyl-1H-pyrazol-5-yl)pyridine as mixture of regioisomeric pyrazoles (700 mg, 52.2% yield; 80:20 as determined by LC-MS). The product mixture can be purified by column chromatography over silica gel 60-120 mesh size, 0→2% EtOAc in pet ether to obtain both regioisomeric products.

Example 20

N-(4-Methoxybenzyl)-5-bromo-3-(4-(2,3-dichlorophenyl)-1-cyclohexyl-1H-pyrazol-3-yl)pyridin-2-amine and N-(4-methoxybenzyl)-5-bromo-3-(4-(2,3-dichlorophenyl)-1-cyclohexyl-1H-pyrazol-5-yl)pyridin-2-amine

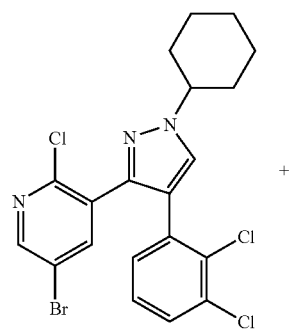

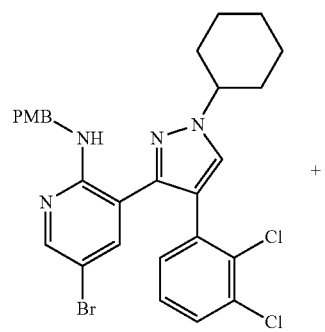

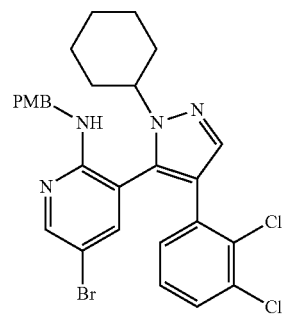

A solution of 5-bromo-2-chloro-3-(4-(2,3-dichlorophenyl)-1-cyclohexyl-1H-pyrazol-3-yl)pyridine and 5-bromo-2-chloro-3-(4-(2,3-dichlorophenyl)-1-cyclohexyl-1H-pyrazol-5-yl)pyridine (about a 4/1 mixture) in 1,4-dioxane was treated with p-methoxybenzyl amine at RT and the resulting mixture was heated to 120° C. for 24 hours until completion of reaction as monitored by LCMS. The reaction mixture was cooled to RT, evaporated to dryness, treated with saturated aqueous NaHCO$_3$ solution, and extracted with EtOAc. The combined organic. layer was washed with brine solution, dried over Na$_2$SO$_4$, and concentrated to obtain a mixture of N-(4-methoxybenzyl)-5-bromo-3-(4-(2,3-dichlorophenyl)-1-cyclohexyl-1H-pyrazol-3-yl)pyridin-2-amine and N-(4-methoxybenzyl)-5-bromo-3-(4-(2,3-dichlorophenyl)-1-cyclohexyl-1H-pyrazol-5-yl)pyridin-2-amine as brown oil (350 mg, 54.6% yield). Each regioisomeric product was obtained in pure form after purification by silica gel column chromatography (60-120 mesh silica gel, 3%→10% EtOAc/Pet ether).

Example 21

5-Bromo-3-(1-(2,3-difluorophenyl)-1H-imidazo[4,5-c]pyridin-2-yl)pyridin-2-amine

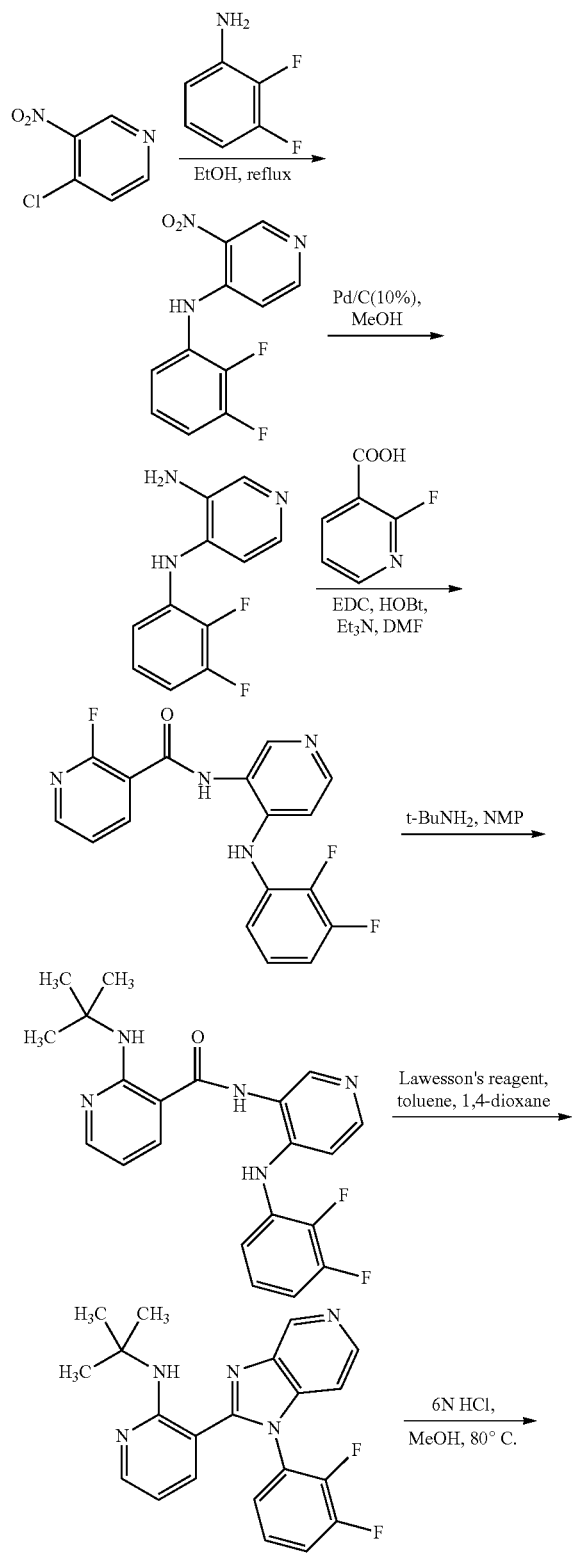

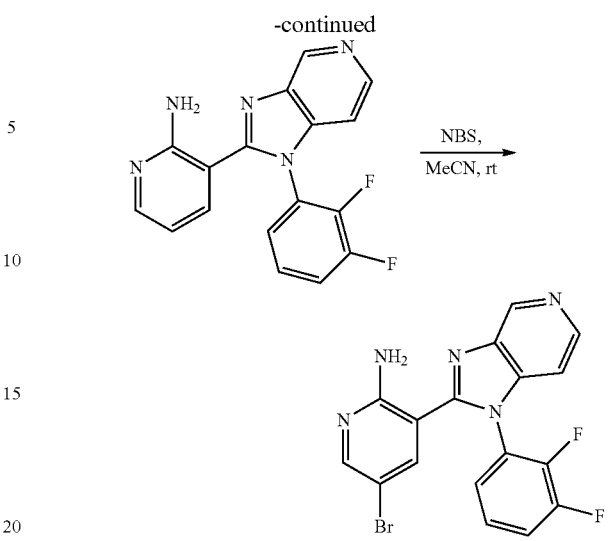

To a solution of 4-chloro-3-nitropyridine (3.0 g, 18.9 mmol) in dry ethanol as added 2,3-difluorobenzenamine (3.66 g, 28.3 mmol). The reaction mixture was refluxed for 30 min. After cooling and concentration in vacuo to give a brown solid, the crude product was taken up in water and the aqueous solution adjusted to a pH of 8-9 and the solution extracted with EtOAc (3×100 mL). The combined organics were washed with water (3×100 mL) and brine solution (1×100 mL), respectively, dried over $Na_2SO_4$, and evaporated in vacuo to give a light brown solid. The crude product was triturated with petroleum ether (3×30 mL) to afford N-(2,3-difluorophenyl)-3-nitropyridin-4-amine (3.7 g, 79% yield) as light yellow solid.

To a solution of N-(2,3-difluorophenyl)-3-nitropyridin-4-amine in 200 mL of methanol under an atmosphere of nitrogen was added 10% Pd/C (0.75 g). The atmosphere was replaced with hydrogen gas and the reaction mixture stirred under balloon pressure for 14 hours at RT. The reaction mixture was filtered over Celite which was washed with methanol (3×30 mL). The filtrate was concentrated in vacuo to give a brown solid. The crude product was triturated with petroleum ether (3×50 mL) to afford $N^4$-(2,3-difluorophenyl)pyridine-3,4-diamine (4.0 g, 90% yield) as light brown solid; LC-MS: 222.2 (M+H).

To a solution of 2-fluoropyridine-3-carboxylic acid (1.41 g, 10.00 mmol) in anhydrous DMF (15 mL) was added HOBT (2.56 g, 16.74 mmol) and $Et_3N$ (2.0 g, 20.09 mmol) at RT. The mixture was cooled to 0° C., treated with a solution of $N^4$-(2,3-difluorophenyl)pyridine-3,4-diamine in DMF (15 mL), stirred for 15 min at RT and EDC (3.2 g, 16.74 mmol) was added portion wise. The reaction mixture was warmed to RT and stirred for 16 hr. The reaction mixture was diluted with water (100 mL) and extracted with EtOAc (4×200 mL). The combined organics were washed with saturated aq. $NaHCO_3$ solution (2×100 mL), water (2×100 mL), brine solution (100 mL), and dried ($Na_2SO_4$). Filtration and evaporation of the solvent in vacuo gave a brown solid. Chromatographic purification (silica gel, 1% methanol in chloroform) provided N-(4-(2,3-difluorophenylamino)pyridin-3-yl)-2-fluoropyridine-3-carboxamide (1.05 g, 45% yield) as yellow solid; LC-MS: 345.2 (M+H).

To a solution of N-(4-(2,3-difluorophenylamino)pyridin-3-yl)-2-fluoropyridine-3-carboxamide (4.0 g, 11.6 mmol) in NMP (30 mL) was added t-butylamine (15.0 mL, 145.3 mmol) at RT. The reaction mixture was slowly heated to 100° C. and stirred at this temperature for 48 hr. The reaction mixture was diluted with water (150 mL) and extracted with EtOAc (3×200 mL). The combined organics were washed with water (4×100 mL), brine solution (100 mL), and dried (Na$_2$SO$_4$). Filtration and evaporation of solvent in vacuo gave N-(4-(2,3-difluorophenylamino)pyridin-3-yl)-2-(tert-butylamino)pyridine-3-carboxamide (4.1 g, 89% yield), which was used as is in subsequent reactions; LC-MS: 398.3 (M+H).

To a stirred solution of N-(4-(2,3-difluorophenylamino)pyridin-3-yl)-2-(tert-butylamino)pyridine-3-carboxamide (3.0 g, 7.55 mmol) in 1,4-dioxane (50 mL) was added 2,4-bis(4-methoxyphenyl)-1,3-dithia-2,4-diphosphetane-2,4-disulfide (Lawesson's reagent, 4.5 g, 11.3 mmol) at room temperature. The reaction mixture was heated at reflux (110° C.) for 10 hr. The reaction mixture was concentrated in vacuo and the resulting residue was taken in saturated aq. NaHCO$_3$ solution (100 mL) and extracted with CHCl$_3$ (200 mL). The organics were washed with water (3×100 mL), brine solution (1×100 mL), and dried (Na$_2$SO$_4$). Filtration and evaporation of solvent in vacuo, followed by silica gel chromatography (0.5% methanol/chloroform) gave N-tert-butyl-3-(1-(2,3-difluorophenyl)-1H-imidazo[4,5-c]pyridin-2-yl)pyridin-2-amine (1.2 g, 41.9% yield) as a light yellow solid; LC-MS: 380.2 (M+H).

To a stirred solution of N-tert-butyl-3-(1-(2,3-difluorophenyl)-1H-imidazo[4,5-c]pyridin-2-yl)pyridin-2-amine (1.5 g, 3.95 mmol) in methanol (7.0 mL) was added 6N aq. HCl at room temperature and the mixture heated at reflux for 5 hr. After cooling to 0° C., the pH of the solution was adjusted to pH 8-9 with 2N aq. NaOH solution (150 mL). The resulting precipitate was filtered off and dissolved in EtOAc (300 mL). The combined organics were washed with water (3×100 mL), brine (100 mL), and dried (Na$_2$SO$_4$). Filtration and evaporation of solvent in vacuo gave a solid, which was triturated with petroleum ether (3×20 mL) to give 3-(1-(2,3-difluorophenyl)-1H-imidazo[4,5-c]pyridin-2-yl)pyridin-2-amine (0.9 g, 75% yield) as a light yellow solid; LC-MS: 324.0 (M+H).

A solution of 3-(1-(2,3-difluorophenyl)-1H-imidazo[4,5-c]pyridin-2-yl)pyridin-2-amine (2.4 g, 7.43 mmol) in acetonitrile (70 mL) was treated with N-bromosuccinimide (1.45 g, 18.17 mmol) at 0° C. and the reaction mixture stirred for 30 min. reaction mixture was treated with saturated aq. NaHCO$_3$ solution (150 mL), stirred for 30 min, and the resulting precipitate filtered and dissolved in CHCl$_3$ (200 mL). The combined organics were washed with water (3×70 mL), brine (70 mL), and dried (Na$_2$SO$_4$). Filtration and evaporation of solvent in vacuo gave a solid, which was purified by silica gel chromatography (4% methanol/chloroform) to give 5-bromo-3-(1-(2,3-difluorophenyl)-1H-imidazo[4,5-c]pyridin-2-yl)pyridin-2-amine (2.2 g, 75% yield) as a light yellow solid; LC-MS: 402.0, 404.0 (M+H).

Example 22

5-Bromo-3-(5-(2,3-dichlorophenyl)thiazol-4-yl)pyridin-2-amine (compound I-C-7)

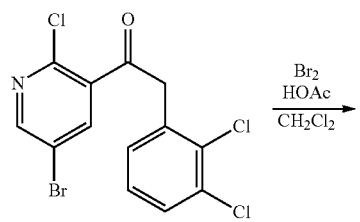

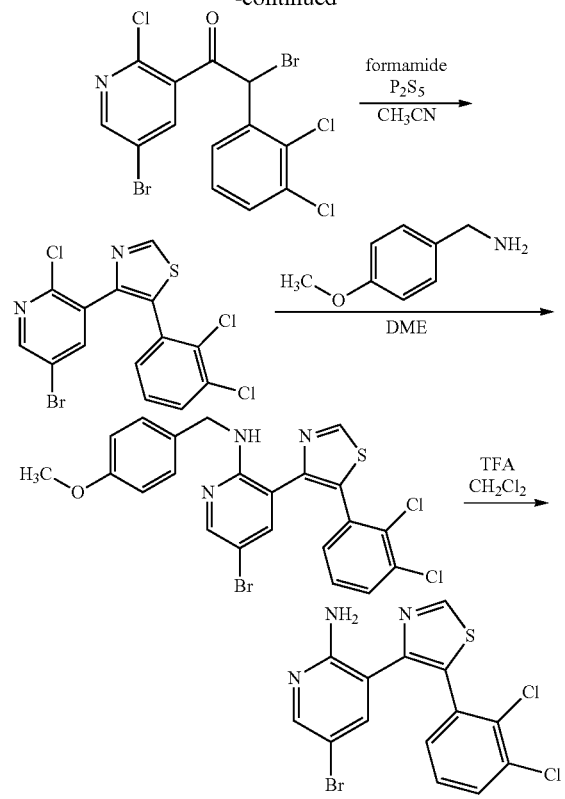

To a stirred solution of 1-(5-bromo-2-chloropyridin-3-yl)-2-(2,3-dichlorophenyl)ethanone (1.01 g, 2.66 mmol) in 1:1 methylene chloride/tetrahydrofuran (26 mL) was added bromine (136 µL, 2.66 mmol) and 3 mL acetic acid. The reaction mixture was stirred at room temperature overnight, at which point the orange color had dissipated. Concentration gave 2-bromo-1-(5-bromo-2-chloropyridin-3-yl)-2-(2,3-dichlorophenyl)ethanone as an orange oil (1.1 g, 95%), which was used in the next reaction without further purification.

Formamide (528 µL, 13.3 mmol) and P$_2$S$_5$ (6.5 g, 14.63 mmol) were stirred in acetonitrile for 30 minutes, until the suspension became an unstirrable paste. The supernatant was decanted and added to an acetonitrile solution of 2-bromo-1-(5-bromo-2-chloropyridin-3-yl)-2-(2,3-dichlorophenyl)ethanone (0.609 g, 1.33 mmol). The reaction mixture was stirred at room temperature overnight. The solids were removed by filtration, rinsed with methylene chloride, and the filtrate was concentrated and taken up in ethyl ether. The organics were filtered through silica, which was washed with diethyl ether. The filtrate was concentrated and the product obtained by crystallization from hexanes/ether to provide 5-bromo-2-chloro-3-(5-(2,3-dichlorophenyl)thiazol-4-yl)pyridine as a white solid [532 mg, 95% yield; LC-MS, M+H=419.0; $^1$H-NMR (300 MHz, CDCl$_3$) 8.51 (1H, s), 8.36 (1H, d), 7.78 (1H, d), 7.42 (1H, dd), 7.01-7.11 (2H, m)].

A solution of 5-bromo-2-chloro-3-(5-(2,3-dichlorophenyl)thiazol-4-yl)pyridine (520 mg, 1.24 mmol) and p-methoxybenzyl amine (373 mg, 2.72 mmol) in DME (12 mL) was stirred at 80° C. for 48 hours. The reaction mixture was concentrated and the residue purified by silica gel chromatography (0-25% EtOAc/hexanes) to give N-(4-methoxybenzyl)-5-bromo-3-(5-(2,3-dichlorophenyl)thiazol-4-yl)pyridin-2-amine as a pale yellow solid [631 mg, 85% yield; LC-MS, M+H=519.9; $^1$H-NMR (300 MHz, CDCl$_3$) 8.85 (1

H, s), 8.00 (1 H, d, J=2.3 Hz), 7.45 (1H, dd, J=1.9, 7.6 Hz), 7.10-7.17 (4 H, m), 7.01 (1 H, d, J=2.4 Hz), 6.77 (1 H, t, J=6.7 Hz)].

A solution of N-(4-methoxybenzyl)-5-bromo-3-(5-(2,3-dichlorophenyl)thiazol-4-yl)pyridin-2-amine (110 mg) and TFA (100 µL) in methylene chloride (2 mL) was stirred at 40° C. overnight. The reaction was concentrated and purified by reversed-phase HPLC to give 5-bromo-3-(5-(2,3-dichlorophenyl)thiazol-4-yl)pyridin-2-amine as a white solid [1.1 mg, 2% yield; LC-MS M+H=519.9; $^1$H-NMR (300 MHz, methanol-d4) 9.17 (1H, d), 7.95 (1H, d), 7.60-7.63 (2H, m), 7.34-7.35 (1H, m), 7.27 (1H, dd)].

Example 23

3-(5-(2,3-Dichlorophenyl)thiazol-4-yl)-5-(pyridin-3-yl)pyridin-2-amine (compound I-C-8)

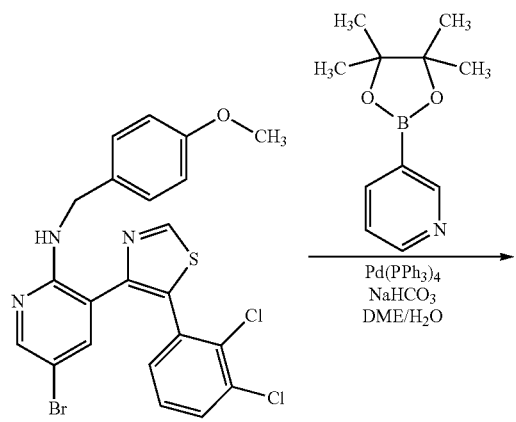

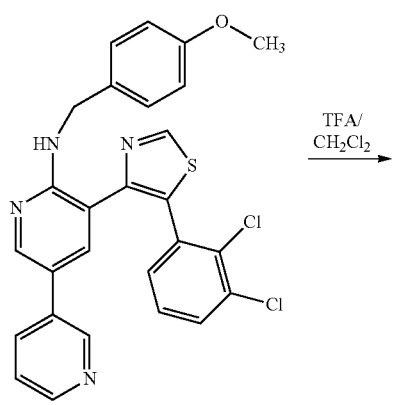

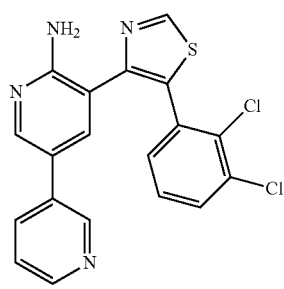

A solution of N-(4-methoxybenzyl)-5-bromo-3-(5-(2,3-dichlorophenyl)thiazol-4-yl)pyridin-2-amine (50 mg, 0.116 mmol) in dimethoxyethane (0.5 mL) and water (0.5 mL) was degassed with nitrogen while adding NaHCO$_3$ (30 mg, 0.347 mmol), and palladium tetrakis triphenylphosphine (13 mg, 0.012 mmol). 3-(4,4,5,5-Tetramethyl-1,3,2-dioxaborolan-2-yl)pyridine (28 mg, 174 mmol) was added under nitrogen and the mixture was heated to 120° C. overnight. The reaction mixture was concentrated and taken up in ethyl acetate, filtered through silica with ethyl acetate eluant, and the filtrate concentrated to provide N-(4-methoxybenzyl)-3-(5-(2,3-dichlorophenyl)thiazol-4-yl)-5-(pyridin-3-yl)pyridin-2-amine, which was used in the next reaction without further purification.

A solution of N-(4-methoxybenzyl)-3-(5-(2,3-dichlorophenyl)thiazol-4-yl)-5-(pyridin-3-yl)pyridin-2-amine (24 mg, 0.046 mmol) in TFA (1 mL) was heated to reflux overnight. The solvent was removed in vacuo and the compound was purified by reversed-phase HPLC to provide 3-(5-(2,3-dichlorophenyl)thiazol-4-yl)-5-(pyridin-3-yl)pyridin-2-amine as a while solid [2.2 mg, 9% yield; LC-MS M+H=399.2; $^1$H-NMR (300 MHz, methanol-d4) 9.34 (1H, s), 8.57 (1H, dd), 8.41 (1H, d), 8.28 (1H, d), 7.79 (1H, d), 7.71 (1H, dd), 7.58 (1H, dd), 7.57 (1H, t), 7.46 (1H, t), 2.64 (3H, s)].

Example 24 tert-Butyl 2-bromo-4,5-dihydrothieno[2,3-c]pyridine-6(7H)-carboxylate

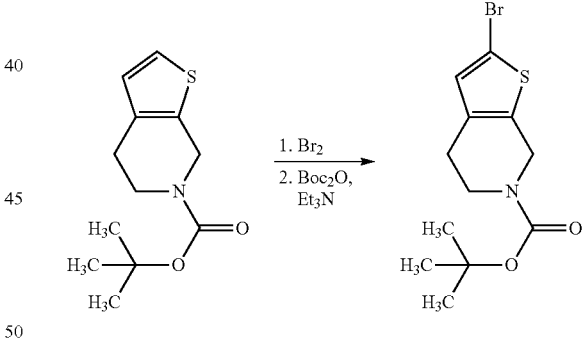

To tert-butyl 4,5-dihydrothieno[2,3-c]pyridine-6(7H)-carboxylate (2.0 g, 8.4 mmol) in chloroform (100 mL) at 0° C. was added dropwise bromine (430 µL, 8.4 mmol). The reaction was stirred 45 min with gradual warming to room temperature. The mixture was cooled to 0° C., and triethylamine (1.2 mL, 8.4 mmol) was added followed by di-tert-butyl dicarbonate (913 mg, 4.2 mmol). The reaction was stirred 1 hour, diluted with dichloromethane (50 mL), washed with 1.0 N HCl (1×50 mL), dried over MgSO$_4$, and concentrated under reduced pressure. The resulting crude residue was purified via silica gel chromatography to afford 2 g (77% yield) of tert-butyl 2-bromo-4,5-dihydrothieno[2,3-c]pyridine-6(7H)-carboxylate as a colorless oil; $^1$H NMR (CDCl$_3$) δ 6.78 (s, 1H), 4.50 (s, 2H), 3.67 (t, J=5.7 Hz, 2H), 2.65 (t, J=5.7 Hz, 2H), 1.50 (s, 9H); ES-MS: m/e=261.9 (M-55)$^+$.

Example 25 tert-Butyl 4-(5-bromothiazol-2-yl)piperidine-1-carboxylate

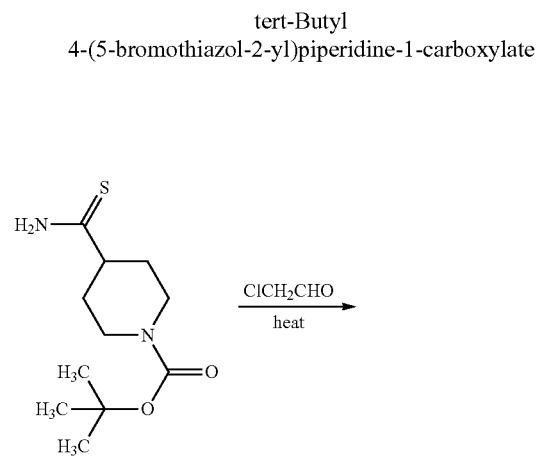

To a solution of tert-butyl 4-thiocarbamoylpiperidine-1-carboxylate (1 g, 4.09 mmol) in acetone (5 mL) was added 2-chloroacetaldehyde (0.32 g, 4.08 mmol). The mixture was heated under reflux for 4 hours. Additional 2-chloroacetaldehyde (0.32 g, 4.08 mmol) was added and heating was continued for another 14 hours. The solvent was removed by evaporation and the crude product was purified by silica gel chromatography to give tert-butyl 4-(thiazol-2-yl)piperidine-1-carboxylates an oil [530 mg (1.97 mmol); LC-MS=213.1 (M+H); $^1$H NMR (300 MHz, CDCl$_3$) 7.74 (d, J=3.3 Hz, 1H), 7.26 (d, J=3.3 Hz, 1H), 4.23 (brd, 2H), 3.22 (m, 1H), 2.91 (t, 2H), 2.14 (m, 2H), 1.77 (m, 2H), 1.48 (s, 9H)].

To a solution of tert-butyl 4-(thiazol-2-yl)piperidine-1-carboxylate (530 mg, 1.97 mmol) in acetonitrile (10 mL) was added NBS (1.40 g, 7.86 mmol). The mixture was stirred at RT for 14 hours and heated at 50° C. for 4 hours. The reaction mixture with some starting material recovered was poured into a solution of Na$_2$SO$_3$ (30 mL) and 6N NaOH (2 mL). The aqueous layer was extracted with EtOAc, dried over MgSO4, and the combined organics concentrated in vacuo. The residue was purified by silica gel chromatography to provide tert-butyl 4-(5-bromothiazol-2-yl)piperidine-1-carboxylate as a yellow oil [210 mg (0.61 mmol); $^1$H NMR (300 MHz, CDCl$_3$) 7.59 (s, 1H), 4.20 (brd, J=12.9 Hz, 2H), 3.13 (tt, J=3.8, 11.5 Hz, 1H), 2.89 (t, J=11.6 Hz, 2H), 2.08 (d, J=11.7 Hz, 2H), 1.72 (dq, J=4.3, 11.9 Hz, 2H), 1.49 (s, 9H)].

Example 26 tert-Butyl 2-bromo-4,5,7,8-tetrahydrofuro[3,2-d]azepine-6-carboxylate

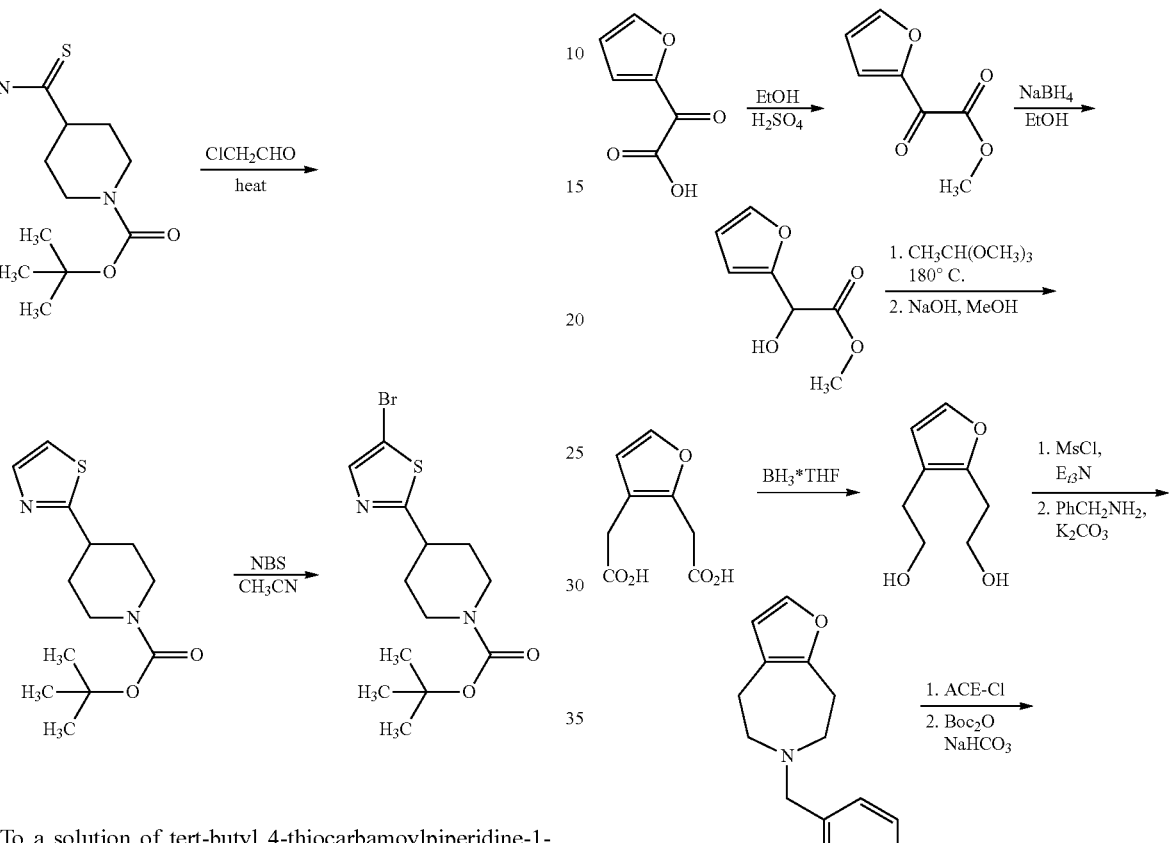

2-(Furan-2-yl)-2-oxoacetic acid (15.0 g, 107 mmol) was dissolved in chloroform (420 mL) and treated with EtOH (165 mmol) and H$_2$SO$_4$ (1 mL). The reaction was heated to 65° C. overnight, at which point LC-MS indicated disappearance of starting material and product formation. The crude reaction was cooled and washed with sat. aq. NaHCO$_3$ (3×100 mL) and brine (100 mL). The organics were concentrated to provide ethyl 2-(furan-2-yl)-2-oxoacetate (15.5 g, 64%) as a brown oil, which was used without further purification.

Ethyl 2-(furan-2-yl)-2-oxoacetate (15.5 g, 92.1 mmol) in ethanol (500 mL) and water (25 mL) at 0° C. was treated with sodium borohydride (1.74 g, 46.05 mmol). The mixture was stirred for 15 minutes, at which point acetic acid (10 mL) was slowly added. After the cessation of gas evolution, water (100 mL) was carefully added, and the reaction mixture was concentrated. The residue was dissolved in methylene chloride and washed with brine. The crude product was dried and concentrated to give ethyl 2-(furan-2-yl)-2-hydroxyacetate as a pale brown viscous oil (11.05 g, 71%) which was used without further purification.

A solution of ethyl 2-(furan-2-yl)-2-hydroxyacetate (11.05 g, 64.5 mmol), trimethylorthoacetate (29.8 mL, 387 mmol) and hexanoic acid (2 mL) in decalin (195 mL) is heated at 180° C. for 12 hours. The reaction is cooled and extracted with methanol to provide a mixture of diester and decalin. This mixture is dissolved in methanol (250 mL), cooled to 0° C., treated with 2 M NaOH (150 mL) and stirred for 12 hours. The methanol is removed and the crude reaction is extracted with ether, and the basic layer is acidified with 6 N HCl and extracted with ethyl acetate. The organic layer is washed with brine, dried and concentrated to give 2,3-di(carboxymethyl) furan.

A solution of 2,3-di(carboxymethyl)furan (35 mmol) in THF (400 mL) is cooled to 0° C. and treated with $BH_3 \cdot THF$ (174 mmol) over 10 minutes, and stirred for an additional 20 minutes at 0° C. before warming to room temperature overnight. The crude reaction is poured over saturated aqueous $NaHCO_3$ and extracted with ethyl acetate. The organic layer is dried and concentrated to give 2,3-di(2-hydroxyethyl)furan.

A solution of 2,3-di(2-hydroxyethyl)furan (23 mmol) in methylene chloride (114 mmol) is cooled to 0° C. and treated with triethylamine (69 mmol) followed by dropwise addition of methanesulfonyl chloride (50.4 mmol) over 10 minutes. After 1 hour the reaction mixture is transferred to a reparatory funnel and extracted with cold water, 10% citric acid, saturated aqueous $NaHCO_3$, and brine. The organic layer is dried and concentrated twice with the aid of dioxane to produce 2,3-di(2-methanesulfonyloxy-ethyl)furan, which is used crude without further purification.

A solution of 2,3-di(2-methanesulfonyloxyethyl)furan (114 mmol) in dioxane (168 mL) is treated with potassium carbonate (337 mmol) and benzyl amine (70.1 mmol) and heated to 102° C. for 18 hours. The reaction is cooled, the precipitate removed by filtration, and the mother liquor concentrated to give a crude oil which is purified by silica chromatography (EtOAc/hexanes eluant) to provide 6-benzyl-5,6,7,8-tetrahydro-4H-furo[3,2-d]azepine.

A solution of 6-benzyl-5,6,7,8-tetrahydro-4H-furo[3,2-d] azepine (11.3 mmol) in methylene chloride (56 mL) is cooled to ° C. and treated with 1-chloroethyl chloroformate (ACE-Cl) (56.4 mmol). The reaction is warmed to RT for 1 hour, diluted with methylene chloride (100 mL), washed with $NaHCO_3$ (50 mL), and extracted with methylene chloride (50 mL). The combined organic layers are washed with brine (50 mL), dried and concentrated to give an oily residue which was dissolved in methanol (150 mL) and refluxed for 1 hour. The solvent is removed in vacuo and the crude product is triturated in ether and filtered to give 5,6,7,8-tetrahydro-4H-furo[3,2-d]azepine, which is used without further purification.

A solution of 5,6,7,8-tetrahydro-4H-furo[3,2-d]azepine (2.88 mmol) in acetone (7.2 mL) and water (7.2 mL) is treated with $NaHCO_3$ (5.76 mmol) and di-t-butyl dicarbonate (3.17 mmol) for one hour. The reaction is diluted with water (10 mL) and extracted with ethyl acetate (2×50 mL). The organic layer is dried, concentrated, and purified by silica chromatography (EtOAc/hexanes eluant) to give tert-butyl 4,5,7,8-tetrahydrofuro[3,2-d]azepine-6-carboxylate.

A solution of tert-butyl 4,5,7,8-tetrahydrofuro[3,2-c] azepine-6-carboxylate (0.21 mmol) in chloroform (0.5 mL) and acetic acid (0.5 mL) is treated with N-bromosuccinimide (0.21 mmol) at RT. After 1 hour, the reaction is poured over saturated aqueous $NaHCO_3$, and extracted with ethyl acetate (2×5 mL). The organic layers are washed with brine, dried, and purified by silica chromatography (20% ethyl acetate/ hexanes) to give tert-butyl 2-bromo-4,5,7,8-tetrahydrofuro [3,2-c]azepine-6-carboxylate.

Example 27

Ethyl 2-bromo-4,5,7,8-tetrahydrothieno[3,2-d] azepine-6-carboxylate

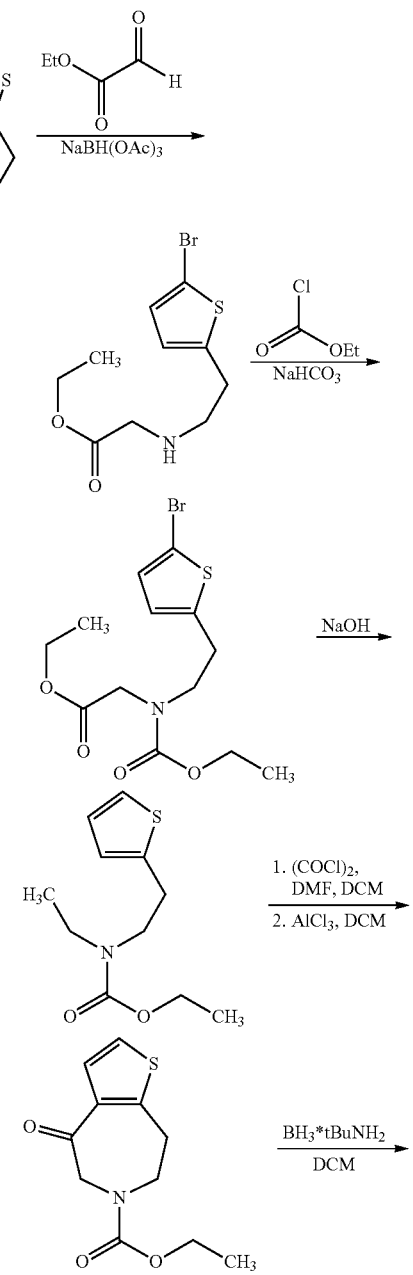

-continued

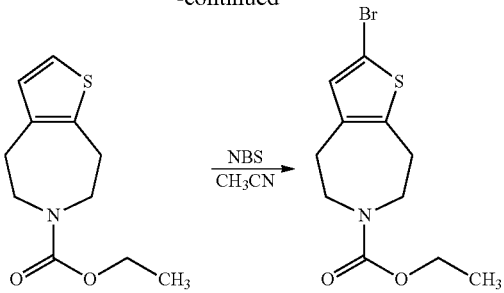

To a solution of 2-(thiophen-2-yl)ethanamine (20 g, 157.4 mmol) in CH$_2$Cl$_2$ at 0° C. was added ethyl glyoxylate followed by acetic acid (4 mL). The reaction mixture stirred for 15 minutes followed by the addition of NaBH(OAc)$_3$ (40 g, 204.7 mmol) in portions. The reaction mixture was stirred for an additional 1 hour and 7 mL of acetic acid was added. The reaction was warmed to RT and stirred until complete consumption of 2-(thiophen-2-yl)ethanamine was observed. The reaction mixture was concentrated in vacuo, the residue taken in THF (500 mL), and the mixture treated with solid NaHCO$_3$ (40 g, 472.2 mmol) at 0° C. This was followed by addition of ethyl chloroformate (19.5 mL, 157 mmol) and saturated aq. NaHCO$_3$ solution slowly until the gas evolution was minimal. The reaction mixture was stirred overnight and extracted with ethyl acetate. The combined organics were washed with brine solution and concentrated to obtain crude product, which was purified by silica gel chromatography to yield ethyl (ethoxycarbonyl)methyl2-(5-bromothiophen-2-yl)ethylcarbamate (15.0 g, 34% yield); ES-MS: 286.2 (M+H).

To solution of ethyl (ethoxycarbonyl)methyl-2-(5-bromothiophen-2-yl)ethylcarbamate (30.0 g, 105.26 mmol) in ethanol at 0° C. was added dropwise 200 mL of 1N NaOH. The reaction mixture was warmed to RT and stirred for 24 hours. The reaction mixture was extracted with Et$_2$O to remove unreacted starting material and the aqueous layer acidified to pH=1 with 1N HCl. The aqueous solution was extracted with ethyl acetate (2×500 mL) and the combined organics were washed with brine solution, dried (Na$_2$SO$_4$), filtered, and evaporated to obtain crude product. 2-(N-(Ethoxycarbonyl)-N-(2-(thiophen-2-yl)ethyl)amino)acetic acid (74% yield)was obtained as a colorless solid after washing the crude product with pentane; ES-MS: 258.2 (M+H).

2-(N-(Ethoxycarbonyl)-N-(2-(thiophen-2-yl)ethyl)amino)acetic acid (14 g, 54.41 mmol) was dissolved in dry dichloromethane (DCM) (300 mL). To this suspension was added 0.1 mL of DMF, followed by the careful addition of oxayl chloride (10.4 g, 81.93 mmol). The reaction mixture was stirred at room temperature for 1 hour, at which time 0.5 mL of additional oxalyl chloride was added. The solvent was evaporated under vacuum to give 2-(N-(ethoxycarbonyl)-N-(2-(thiophen-2-yl)ethyl)amino)acetyl chloride. This acid chloride was re-dissolved in dry DCM (300 mL) and AlCl$_3$ (18.1 g, 135.74 mmol) was added at room temperature. The reaction was kept at room temperature for 1 hour then quenched by the slow addition of ethanol (about 10 mL). The mixture was then poured into ice and stirred for 1 hr. The aqueous mixture was extracted with DCM (3×150 mL). The combined organic layers were dried over MgSO4, filtered, and evaporated to give a residue, which was purified by silica gel chromatography to produce ethyl 4,5,7,8-tetrahydro-4-oxothieno[3,2-d]azepine-6-carboxylate (7.4 g, 30.92 mmol).

A suspension of AlCl$_3$ (6.7 g, 50.25 mmol) in dry DCM (60 mL) was cooled to 0° C. and BH$_3$.tBuNH$_2$ solid (8.7 g, 100 mmol) was added. After stirring at 0° C. for 5 min, a solution of ethyl 2-(4,5,7,8-tetrahydro-4-oxothieno[3,2-d]azepin-6-yl)acetate (4 g, 16.72 mmol) in DCM was added. The reaction was stirred at room temperature for 14 hours, The reaction was monitored by TLC and, if necessary, more BH$_3$.tBuNH$_2$ was added to drive the reaction to completion. The mixture was carefully quenched by the addition of 2N HCl (gas evolution observed). When gas evolution stopped, more 2N HCl was added, and the mixture extracted with DCM (3×100 mL). The combined DCM layers were dried over MgSO4, filtered, and the filtrate evaporated under vacuum to afford ethyl 4,5,7,8-tetrahydrothieno[3,2-d]azepine-6-carboxylate as a crude white solid that was used directly without purification.

Ethyl 4,5,7,8-tetrahydrothieno[3,2-d]azepine-6-carboxylate (16.72 mmol) was dissolved in CH$_3$CN (150 mL) and NBS (4.74 g, 26.63 mmol) was added. The reaction was stirred at room temperature for 30 min, and poured into a solution of Na$_2$SO$_3$ (200 mL)/6N NaOH (5 mL). The aqueous layer was extracted with EtOAc (3×150 mL), dried over MgSO4, filtered, and evaporated. The residue was purified by silica gel chromatography to provide ethyl 2-(2-bromo-4,5,7,8-tetrahydrothieno[3,2-d]azepin-6-yl)acetate (3.1 g, 10.20 mmol).

Example 28 tert-Butyl 3-(4-iodo-1H-pyrazol-1-yl)azetidine-1-carboxylate

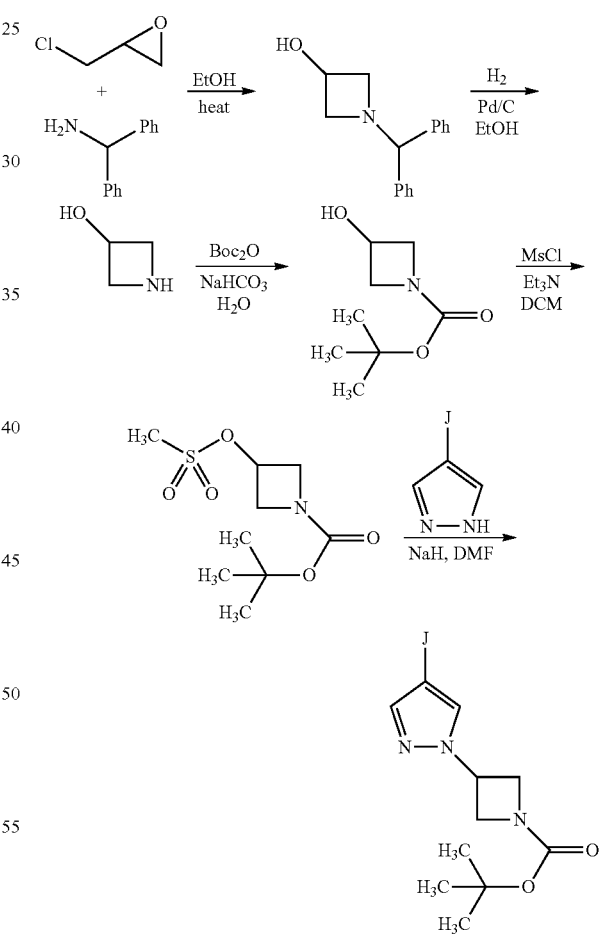

A solution of diphenylmethanamine (16.2 g, 88.5 mmol) and 2-(chloromethyl)oxirane (8.19 g, 88.5 mmol) in dry EtOH was stirred at RT for 48 hours and then heated at reflux for 48 hour. The reaction mixture was concentrated under reduced pressure and the residue was stirred in acetone (300 mL) for 30 min. The resulting off-white solid precipitate was filtered, washed with cold acetone (100 mL), and dried in vacuo to obtain 1-benzhydrylazetidin-3-ol as white crystalline solid (11.0 g, 51% yield); LC-MS: 240.3 (M+H).

A suspension of 1-benzhydrylazetidin-3-ol (11.0 g, 40 mmol) and 10% Pd/C (10 g) in ethanol (150 mL) was hydrogenated at 70 psi pressure for 18 hours. The reaction mixture was filtered through short Celite™ plug, washed with EtOH and the combined filtrates were concentrated to obtain crude product as pale yellow viscous liquid. The crude product was washed thoroughly with pet-ether to remove diphenylmethane and azetidin-3-ol was obtained as colorless solid (3.0 g, 90% yield); LC-MS: 74.2 (M+H).

A solution of azetidin-3-ol (5.0 g, 68.5 mmol) and NaHCO$_3$ (34.52 g, 410.9 mmol) in water at RT was treated with (Boc)$_2$O (16.43 g, 75.34 mmol) and the reaction mixture stirred at RT until complete consumption of compound azetidin-3-ol was indicated by TLC (EtOAc/hexanes, 1:1). The reaction mixture was extracted with EtOAc (3×50 mL). The combined organics were washed with brine solution (50 mL), dried over Na$_2$SO$_4$, filtered, and concentrated in vacuo to obtain tert-butyl 3-hydroxyazetidine-1-carboxylate (6.0 g, 51% yield); ES-MS: 172.11 (M+H).

To a solution of tert-butyl 3-hydroxyazetidine-1-carboxylate (6.0 g, 34.68 mmol) in DCM was added by Et$_3$N. The mixture was cooled to 0° C. and methanesulfonyl chloride was slowly added. After addition was complete, the reaction mixture was warmed to RT and stirred until starting material was completely consumed as indicated by TLC (40% EtOAc/hexanes). The reaction mixture was filtered and CH$_2$Cl$_2$ was added to the filtrate (100 mL). The organics were washed with water (2×30 mL), brine solution (30 mL), dried (Na$_2$SO$_4$), filtered, and concentrated to obtain crude product, which was purified by silica gel chromatography (5% EtOAc/hexanes, then 15% EtOAc/hexanes). 1-(tert-Butoxycarbonyl)azetidin-3-yl methanesulfonate was isolated as an off-while solid (2.2 g, 36% yield); ES-MS: 252.08 (M+H).

At 0° C., a solution of 4-iodopyrazole (3.0 g, 15.46 mmol) in DMF (40 mL) was treated with NaH (60% mineral oil dispersion, 1.11 g, 46.39 mmol) in portions. The mixture stirred for 30 minutes, followed by the slow addition of 1-(tert-butoxycarbonyl)azetidin-3-yl methanesulfonate (5.0 g, 20.1 mmol). The reaction mixture was warmed to RT and then heated at 100° C. for 5 hours. The reaction mixture was poured into ice cold water, stirred for 30 minutes, and resulting precipitate collected by filtration and dried. The resulting residue was washed with pentane and dried to obtain tert-butyl 3-(4-iodo-1H-pyrazol-1-yl)azetidine-1-carboxylate (3.3 g, 62% yield); $^1$H-NMR (400 MHz, CDCl$_3$): 7.58 (s, 1H), 7.57 (s, 1 H), 5.07-5.0 (m, 1 H), 4.39-4.34 (m, 2H), 4.29-4.25 (dd, 2 H), 1.45 (s, 9H).

Example 29 endo- and exo-3-(4-Iodo-pyrazol-1-yl)-8-aza-bicyclo[3.2.1]octane-8-carboxylic acid, tert-butyl ester

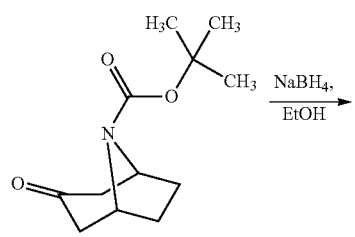

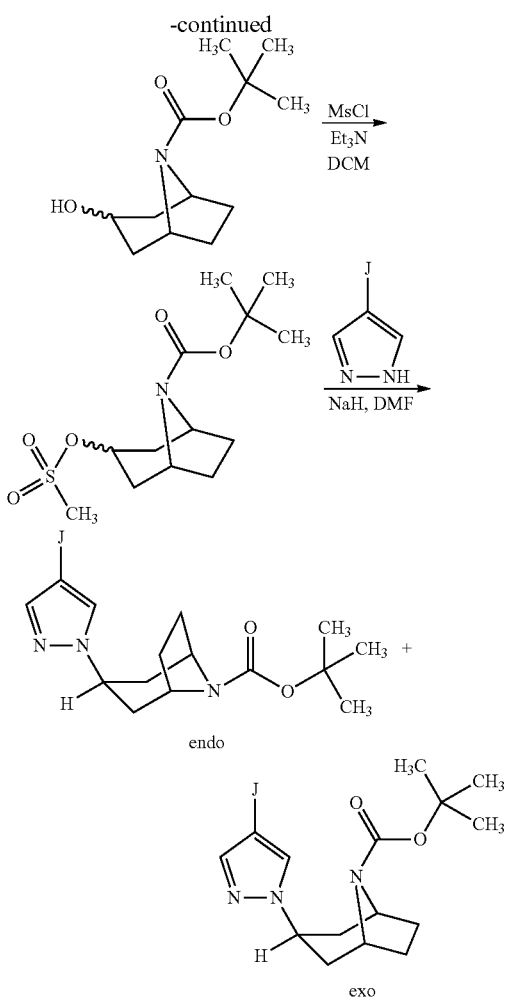

3-Oxo-8-aza-bicyclo[3.2.1]octane-8-carboxylic acid, tert-butyl ester (8 g, 35.5 mmol) was dissolved in 100 mL of ethanol. Sodium borohydride (2 g, 53.5 mmol) was added to the solution portionwise at room temperature. After stirring for 3 hours, the reaction was evaporated in vacuo to give clear viscous oil. The oil was dissolved in dichloromethane, washed with water and brine, dried over anhydrous sodium sulfate, filtered, and evaporated to afford 7.55 g of 3-hydroxy-8-aza-bicyclo[3.2.1]octane-8-carboxylic acid, tert-butyl ester as a white crystalline solid; $^1$H NMR (300 MHz, DMSO-d$_6$): 4.23 (dd, J=2.7, 4.6 Hz, 1 H), 4.18-4.06 (m, 2 H), 2.17-2.06 (m, 1 H), 1.99-1.91 (m, 3 H), 1.72-1.50 (m, 5H), 1.47 (s, 9H).

3-Hydroxy-8-aza-bicyclo[3.2.1]octane-8-carboxylic acid, tert-butyl ester (7.55 g, 33.2 mmol), triethylamine (5.1 mL, 37 mmol), and 4-dimethylaminopyridine (36 mg, 0.3 mmol) was dissolved in 100 mL of dichloromethane and cooled to 5° C. in an ice bath. Methanesulfonyl chloride (2.6 mL, 33.2 mmol) was added to the solution dropwise and the reaction warmed to room temperature and stirred at room temperature for 18 hours. The reaction was washed with water and brine, dried over anhydrous sodium sulfate, and the solvent removed to afford 3-methanesulfonyloxy-8-aza-bicyclo[3.2.1]octane-8-carboxylic acid, tert-butyl ester as a clear yellow oil (10.2 g); $^1$H NMR (300 MHz, DMSO-d$_6$): 5.09-5.01 (m, 1 H), 4.28 (s, 1 H), 4.22 (s, 1 H), 3.01 (s, 3 H), 2.20-1.97 (m, 6 H), 1.71-1.66 (m, 2 H), 1.46 (s, 9 H).

Sodium hydride (60% in mineral oil) (1.52 g, 38 mmol) was added slowly to a cooled solution (0° C.) of 4-iodopyrazole (6.6 g, 34 mmol) in anhydrous DMF (75 mL). After stirring for 1 hour, a solution of (3-methanesulfonyloxy-8-aza-bicyclo[3.2.1]octane-8-carboxylic acid, tert-butyl ester (10.2 g, 34 mmol) in 25 mL of anhydrous DMF was added to the reaction. The reaction was heated to 100° C. for 18 hours. The reaction was poured into 50 ml, of water and extracted with ethyl acetate. The combined ethyl acetate extracts were washed with water (2×50 mL) and brine (2×50 mL), dried over anhydrous sodium sulfate, and evaporated to give 12.82 g of product as a mixture of endo and exo isomers; 3.0 g which was purified by medium pressure chromatography ($SiO_2$) eluting with a gradient (hexane-10% ethyl acetate in hexane) over 30 minutes to afford 1.5 g of the front running spot (endo isomer) and 1.3 g of the $2^{nd}$ spot (exo isomer); endo isomer-H NMR (300 MHz, DMSO-$d_6$): 7.58 (s, 1 H), 7.52 (s, 1 H), 7.26 (s, 1 H), 4.34 (q, J=5.3 Hz, 1 H), 4.27 (s, 2 H), 2.44 (s, 4 H), 1.89-1.85 (m, 2 H), 1.60-1.53 (m, 2 H), 1.49 (s, 9 H); exo isomer-H NMR (300 MHz, DMSO-$d_6$): 7.48 (d, J=0.4 Hz, 1 H), 7.41 (s, 1 H), 7.26 (s, 1 H), 4.68 (m, 1 H), 4.37 (br s, 2 H), 2.08-2.05 (m, 6 H), 1.79-1.75 (m, 2 H), 1.49 (s, 9 H).

Example 30 tert-Butyl 4-(5-bromothiophen-2-yl)piperidine-1-carboxylate

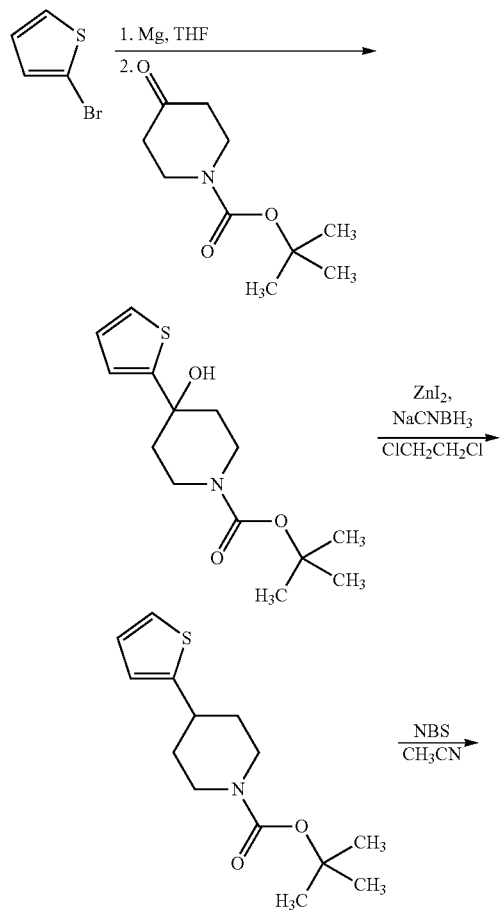

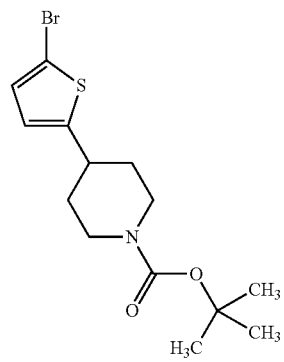

A solution of 2-bromothiophene in THF (25 ml) was added drop wise to a suspension of Mg turnings in THF (100 mL). The mixture was stirred for 30 minutes, cooled to 0° C., and a solution of tert-butyl 4-oxopiperidine-1-carboxylate (25.0 g, 125.4 mmol) in THF (25 mL) was added dropwise. The reaction mixture was slowly warmed to RT and stirred for 1 hour until complete consumption of 2-bromothiophene was indicated by TLC. The reaction was quenched with sat. aq. $NH_4Cl$ solution (50 mL), extracted with EtOAc (200 mL), washed with $H_2O$ (50 mL) and brine solution, dried ($Na_2SO_4$), filtered, and evaporated to afford crude product as light brown oil. Purification by silica gel chromatography (25% EtOAc/hexanes) yielded tert-butyl 4-hydroxy-4-(thiophen-2-yl)piperidine-1-carboxylate (14.0 g, 40% yield).

To a solution of tert-butyl 4-hydroxy-4-(thiophen-2-yl)piperidine-1-carboxylate (6.0 g, 21.2 mmol) in 1,2-dichloroethane at 0° C. was added $ZnI_2$ (10.15 g, 31.8 mmol) in portions. The reaction mixture was stirred for 30 minutes, followed by the addition of $NaCNBH_3$ (2.0 g, 31.8 mmol) in portions. The reaction mixture was slowly warmed to RT and stirred for 2 hours. The reaction was quenched with ice, extracted with $CH_2Cl_2$ (2×50 mL), washed with brine solution, dried ($Na_2SO_4$), filtered, and concentrated to obtain tert-butyl 4-(thiophen-2-yl)piperidine-1-carboxylate, which was used as is for subsequent reactions without further purification.

N-Bromosuccinimide (4.9 g, 28.08 mmol) was added in portions to a solution of tert-butyl 4-(thiophen-2-yl)piperidine-1-carboxylate (5.0 g, 18.72 mmol) in MeCN at −10° C. The reaction mixture was stirred for 30 minutes and treated with sat. aq. $NaHCO_3$ solution. The mixture was extracted with $CH_2Cl_2$ and the organics washed with water and brine solution, dried ($Na_2SO_4$), filtered, and evaporated to obtain crude product. Purification by silica gel chromatography (2% EtOAc/pet ether) yielded tert-Butyl 4-(5-bromothiophen-2-yl)piperidine-1-carboxylate (1.5 g, 21% from tert-butyl 4-hydroxy-4-(thiophen-2-yl)piperidine-1-carboxylate); $^1$H-NMR (400 MHz, $CHCl_3$): 6.85 (d, 1 H), 6.58 (d, 1 H), 4.22-4.10 (d, 2H), 3.90-3.78 (m, 3H), 1.98-1.90 (d, 2 H), 1.65-1.48 (m, 2 H), 1.45 (s, 9 H); ES-MS: 346.3, 348.3 (M+H).

Example 31 tert-Butyl 2-bromo-6,7-dihydrothiazolo[5,4-c]pyridine-5(4H)-carboxylate

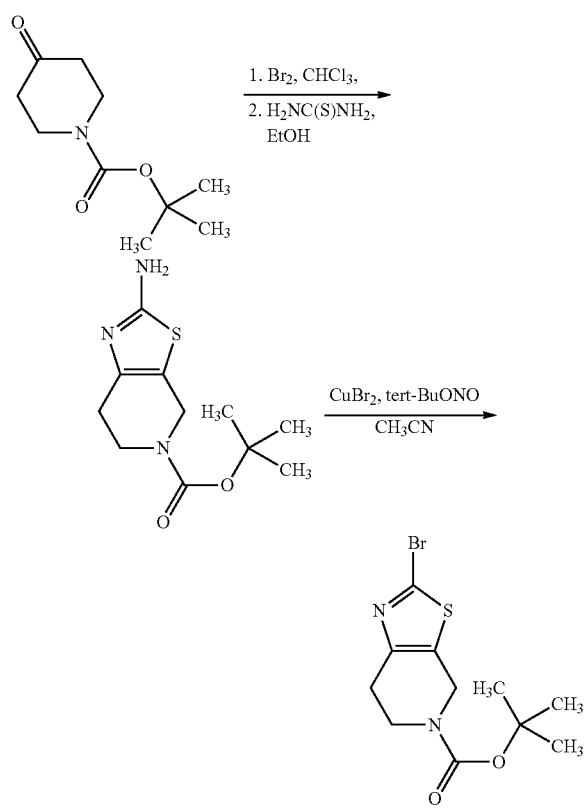

To a solution of compound tert-butyl 4-oxopiperidine-1-carboxylate (24.0 g, 120.6 mmol) in dry CHCl₃ (500 mL) at 0-5° C., was slowly added a solution of Br₂ in CHCl₃ (100 mL) over 1.5 hours. The reaction mixture was warmed to RT and stirred for 3 hours. The reaction mixture was concentrated to obtain solid, which was thoroughly washed with Et₂O. The resulting intermediate tert-butyl 3-bromo-4-oxopiperidine-1-carboxylate was used immediately in the next reaction. Accordingly, this intermediate (20 g, 72 mmol) was suspended in pentane, filtered, washed with pentane, and the solid so obtained dried in vacuo and dissolved in EtOH (100 mL). Thiourea (5.46 g, 72.0 mmol) was added and the reaction mixture heated for 4 hours at 70-75° C. The reaction mixture was concentrated to yield a residue, which was treated with aq. Na₂CO₃ solution, adjusted to pH=10, extracted with EtOAc, washed with water, washed with brine solution, dried (Na₂SO₄), filtered, and concentrated. The residue was washed with pentane to obtain tert-butyl 2-amino-6,7-dihydrothiazolo[5,4-c]pyridine-5(4H)-carboxylate (8.7 g, 28% yield)

tert-Butyl 2-amino-6,7-dihydrothiazolo[5,4-c]pyridine-5(4H)-carboxylate (8.5 g, 33.33 mmol) was added dropwise over 2 minutes to a suspension of t-butyl nitrite and CuBr₂ mixture in CH₃CN at 0° C. The reaction mixture was slowly warmed to RT over 30 min and stirred for 16 hours at RT. The reaction mixture was concentrated to obtain residue that was dissolved in EtOAc, filtered through a Celite™ plug, which was washed with EtOAc. The organics were washed with water and brine solution, dried (Na₂SO₄), filtered, and concentrated to obtain crude product as yellow solid. Purification by washings with pet ether and pentane yielded tert-butyl 2-bromo-6,7-dihydrothiazolo[5,4-c]pyridine-5(4H)-carboxylate (4.1 g, 38% yield); ¹H-NMR (400 MHz, CHCl₃): 4.56 (s, 2H), 3.73 (t, 2H), 2.85 (brt, 2H), 1.48 (s, 9H).

Example 32

4-Iodo-1-(2-(pyrrolidin-1-yl)ethyl)-1H-pyrazole

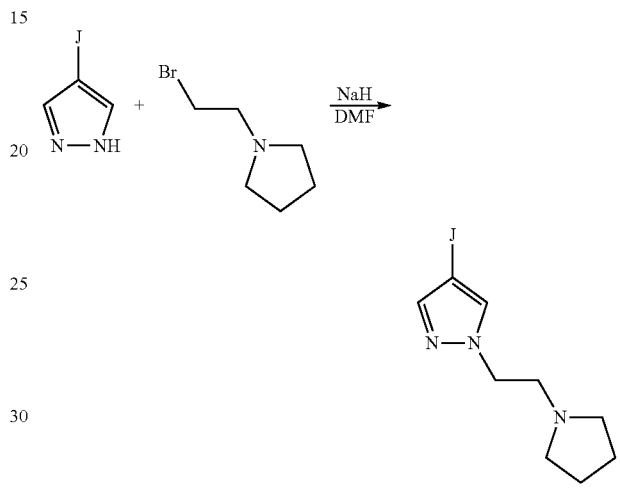

NaH (60% paraffin oil dispersion, 0.507 g, 21.13 mmol) was added portionwise to a solution of 4-iodopyrazole in DMF at 0° C. The reaction mixture was stirred for 1 hour, treated with solution of 1-(2-chloroethyl)pyrrolidine (1.40 g, 10.56 mmol) in DMF, slowly warmed to RT and stirred for additional 16 hours. The reaction mixture was cooled to 0° C. and ice cold water was added, followed by extraction with EtOAc (2×40 mL). The combined organics were washed with water (3×40 mL), brine solution (40 ml), dried (Na₂SO₄), filtered, and concentrated to obtain 4-iodo-1-(2-(pyrrolidin-1-yl)ethyl)-1H-pyrazole, which was used as is for subsequent reactions without further purification; ¹H-NMR (400 MHz, CHCl₃): 7.60 (1H, s), 7.52 (1H, s), 7.49 (1H, s), 4.25 (2H, t), 2.95 (2H, s), 2.57 (4H, m), 1.79 (4H, m); ES-MS: 292.0 (M+H).

Example 33

3-Bromo-1-(2-(pyrrolidin-1-yl)ethyl)-1H-pyrrole

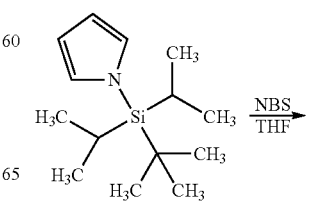

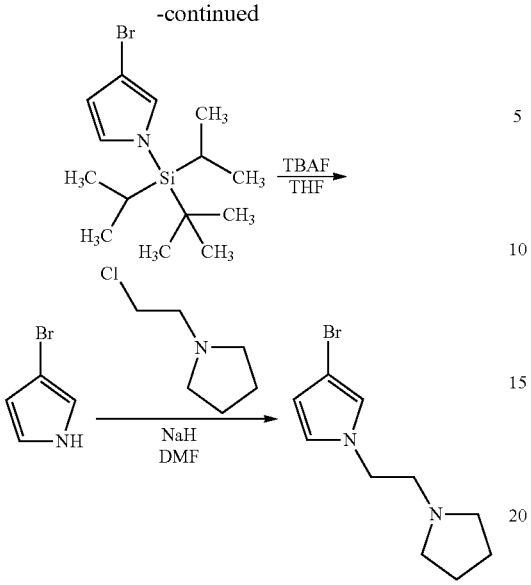

A solution of 1-(tert-butyldiisopropylsilyl)-1H-pyrrole (1.0 g, 4.48 mmol) in THF was added N-bromosuccinimde at −78° C. The reaction mixture was slowly warmed to RT and stirred for 24 hours. The reaction mixture was concentrated to obtain dark black residue, which was suspended in CCl$_4$ (100 mL) and stirred for 15 min and filtered. The filtrate was concentrated to obtain 1-(tert-butyldiisopropylsilyl)-3-bromo-1H-pyrrole as oily liquid (1.0 g).

A solution of 1-(tert-butyldiisopropylsilyl)-3-bromo-1H-pyrrole in THF at 0° C. was treated with tetrabutylammonium fluoride.3H$_2$O (0.81 g, 2.58 mmol). The reaction mixture was stirred for 1 hour and concentrated in vacuo to obtain 3-bromo-1H-pyrrole as an oil. The product was unstable upon standing and was used as is immediately in the next reaction.

To a solution of 3-bromo-1H-pyrrole (100 mg, 0.68 mmol) in DMF at 0° C. was added NaH (60% oil dispersion, 81 mg, 2.05 mmol). The reaction mixture was stirred for 1 hour, followed by the addition of 1-(2-chloroethyl)pyrrolidine (108 mg, 0.82 mmol). The reaction mixture was for 6 hours at 100° C. After cooling, the reaction mixture was treated with 20 mL of ice cold water, extracted with EtOAc (3×20 mL), washed with brine solution (20 mL), dried (Na$_2$SO$_4$), filtered, and concentrated under vacuum at 48° C. to obtain crude product. Purification by silica gel chromatography yielded 3-bromo-1-(2-(pyrrolidin-1-yl)ethyl)-1H-pyrrole (50 mg, 31% yield); $^1$H-NMR (400 MHz, CHCl$_3$): 6.69 (1H, s), 6.59 (1H, s), 6.12 (1H, s), 3.95 (2H, t), 2.80 (2H, t), 2.51 (4H, m), 1.81 (4H, m).

Example 34

1-(4-(4,4,5,5-Tetramethyl-1,3,2-dioxaborolan-2-yl)benzyl)-4-methylpiperazine

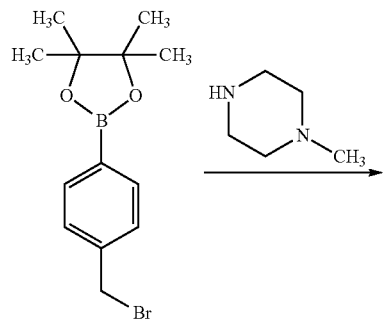

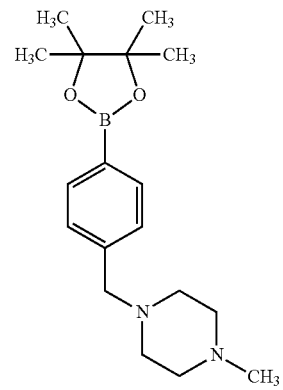

To a solution of 2-(4-(bromomethyl)phenyl)-4,4,5,5-tetramethyl-1,3,2-dioxaborolane product (1.0 g, 3.37 mmol) in anhydrous ether (30 mL) was added N-methylpiperizine (1.0 g, 10.1 mmol). The solution was stirred at RT for 14 hours and filtered through Celite™. The filtrate was evaporated under vacuum to give a crude product that was used directly without further purification.

Example 35 tert-Butyl 3,4-dihydro-5-(4,4,5,5-tetramethyl-1,3,2-dioxaborolan-2-yl)-2H-azepine-1(7H)-carboxylate

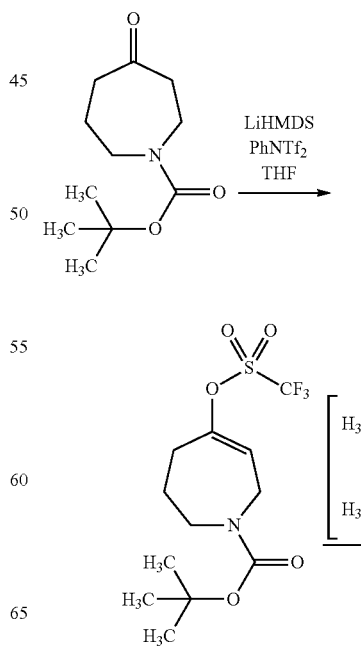

-continued

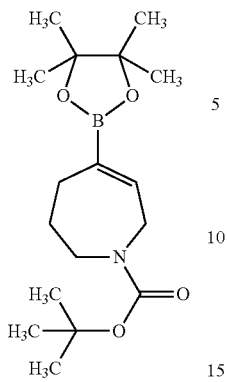

To a solution of tert-butyl 4-oxoazepane-1-carboxylate (3.0 g, 14 mmol, 1 eq.) in THF (20 mL) at −78° C. was added a 1N solution of LiHMDS (15.4 mL, 15.4 mmol, 1.1 eq.) dropwise under nitrogen. The mixture was stirred for 20 minutes, then a solution of (E)-1-(tert-butoxycarbonyl)-2,5, 6,7-tetrahydro-1H-azepin-4-yltrifluoromethanesulfonate (5.5 g, 15.4 mmol, 1.1 eq.) in THF (10 mL) was added. The mixture was warmed to 0° C. and stirred for 3 hours. The reaction was concentrated, diluted with DCM, filtered through neutral alumina and the product was eluted with 9:1 hexanes/EtOAc. Concentration of the eluant in vacuo gave (Z)-tert-butyl 3,4-dihydro-5-(4,4,5,5-tetramethyl-1,3,2-dioxaborolan-2-yl)-2H-azepine-1(7H)-carboxylate (3.6 g, 10.4 mmol); $^1$H NMR (300 MHz, CDCl$_3$): 5.9 (m, 1H); 4.05-3.9 (m, 2H); 3.55 (m, 2H); 2.55 (m, 2H); 1.95 (m, 2H); 1.45 (s, 9H). This product was used without further purification and contained up to 33% of the (E)-isomer.

(Z)-tert-butyl 3,4-dihydro-5-(4,4,5,5-tetramethyl-1,3,2-dioxaborolan-2-yl)-2H-azepine-1(7H)-carboxylate (3.6 g, 10.4 mmol, 1.0 eq.), bis(pinacolato)diboron (3.18 g, 12.5 mmol, 1.2 eq.) and potassium acetate (3.06 g, 21.2 mmol, 3 eq.) were combined and diluted with anhydrous 1,4-dioxane (100 mL). The mixture was degassed under nitrogen for 0.5 hours. PdCl$_2$(PPh$_3$)$_2$ (0.73 g, 1.04 mmol, 0.1 eq.) was added and the mixture degassed with nitrogen for an additional 15 minutes. The reaction was stirred at 80° C. overnight, concentrated, diluted with ethyl acetate and filtered through floricil, which was eluted with 2:1 hexanes:EtOAc. After concentration in vacuo, the residue was purified by silica gel chromatography (EtOAc/hexanes) to provide (Z)-tert-butyl 3,4-dihydro-5-(4,4,5,5-tetramethyl-1,3,2-dioxaborolan-2-yl)-2H-azepine-1(7H)-carboxylate (0.95 g, 2.95 mmol, 30% yield; $^1$H NMR (300 MHz, CDCl$_3$): 6.5 (m, 1H); 4.07-3.95 (m, 2H); 3.5 (m, 2H); 2.3 (m, 2H); 1.77 (m, 2H); 1.45 (s, 9H); 1.25 (s, 12H).

Example 36

3-(1-(2,3-Difluorophenyl)-1H-tetrazol-5-yl)-5-(4,4,5, 5-tetramethyl-1,3,2-dioxaborolan-2-yl)pyridin-2-amine

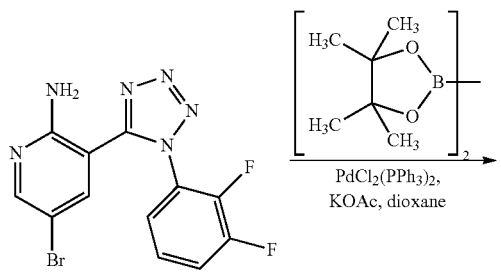

-continued

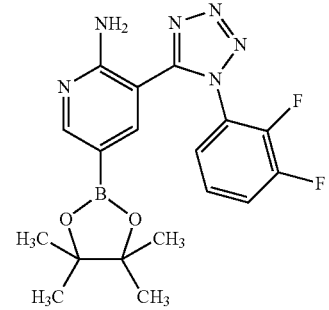

To 1,4-dioxane (450 mL) was added (15 g, 42.5 mmol), bis(pinacolato)diboron (12.95 g, 51.0 mmol) and potassium acetate (12.5 g, 127.5 mmol). The mixture was degassed with a nitrogen stream for 20 min., followed by the addition of bis(triphenylphosphine)palladium(II) dichloride (3.0 g, 4.3 mmol). The reaction was stirred at 80° C. for 14 hours under inert atmosphere. After cooling to room temperature, the mixture was concentrated under reduced pressure and the resulting crude solid treated with ethyl acetate (~250 mL) and filtered. The filtrate was concentrated, treated with 50% ethyl acetate in hexanes (~200 mL), and the resulting precipitate was filtered and dried to yield 9.64 g of 3-(1-(2,3-difluorophenyl)-1H-tetrazol-5-yl)-5-(4,4,5,5-tetramethyl-1,3,2-dioxaborolan-2-yl)pyridin-2-amine as a dark brown solid. The filtrate was concentrated again, treated with hexanes (200 mL), and filtered to provide an additional 6.2 g of product (93% overall yield) as a yellow solid: $^1$H NMR (CDCl$_3$) δ 7.54-7.32 (m, 5H), 6.71 (s, 2H), 1.24 (s, 12H); ES-MS: m/e=318 (M-82)$^+$. Using the same procedure, 3-(1-(2,3-chlorophenyl)-1H-tetrazol-5-yl)-5-(4,4,5,5-tetramethyl-1,3,2-dioxaborolan-2-yl)pyridin-2-amine and 3-(1-(3-chloro-2-fluorophenyl)-1H-tetrazol-5-yl)-5-(4,4,5,5-tetramethyl-1,3,2-dioxaborolan-2-yl)pyridin-2-amine can be produced from 5-bromo-3-(1-(2,3-chlorophenyl)-1H-tetrazol-5-yl)pyridin-2-amine and 5-bromo-3-(1-(3-chloro-2-fluorophenyl)-1H-tetrazol-5-yl)pyridin-2-amine, respectively.

Example 37

3-(1-(2,3-Difluorophenyl)-1H-tetrazol-5-yl)-5-(4,5,6, 7-tetrahydrothieno[2,3-c]pyridin-2-yl)pyridin-2-amine (compound I-A-492)

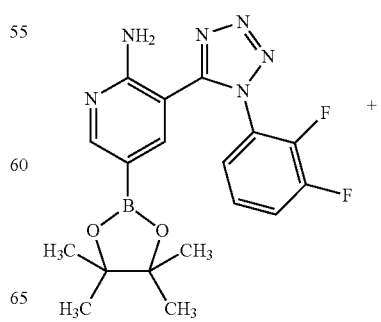

-continued

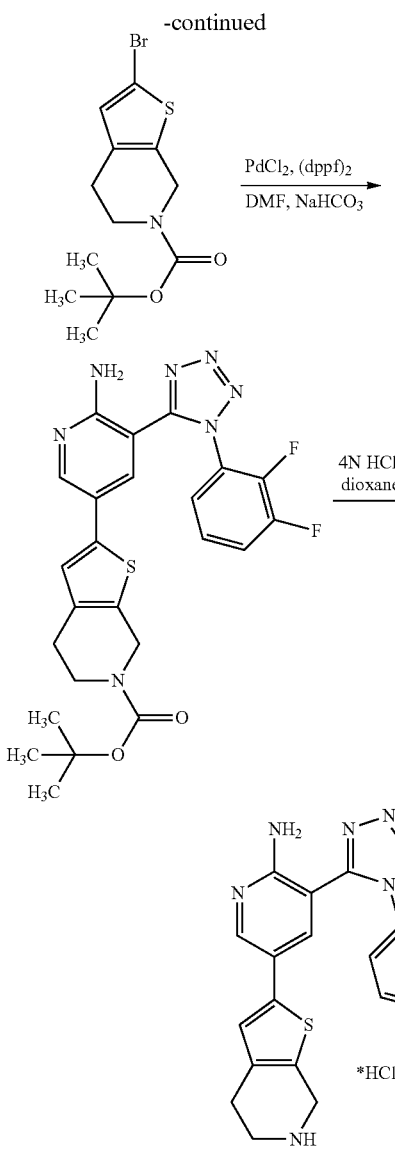

steps); $^1$H NMR (DMSO-$d_6$): 9.50 (s, 2H), 8.44 (d, J=2.4 Hz, 1H), 7.85-7.46 (m, 4H), 7.05 (s, 1H), 4.29 (s, 2H), 3.39-3.25 (m, 2H), 2.85-2.81 (m, 2H); ES-MS: m/e=412.2 (M+H).

Example 38

3-(1-(2,3-Difluorophenyl)-1H-tetrazol-5-yl)-5-(5,6,7,8-tetrahydro-4H-thieno[3,2-d]azepin-2-yl)pyridin-2-amine (compound I-A-430)

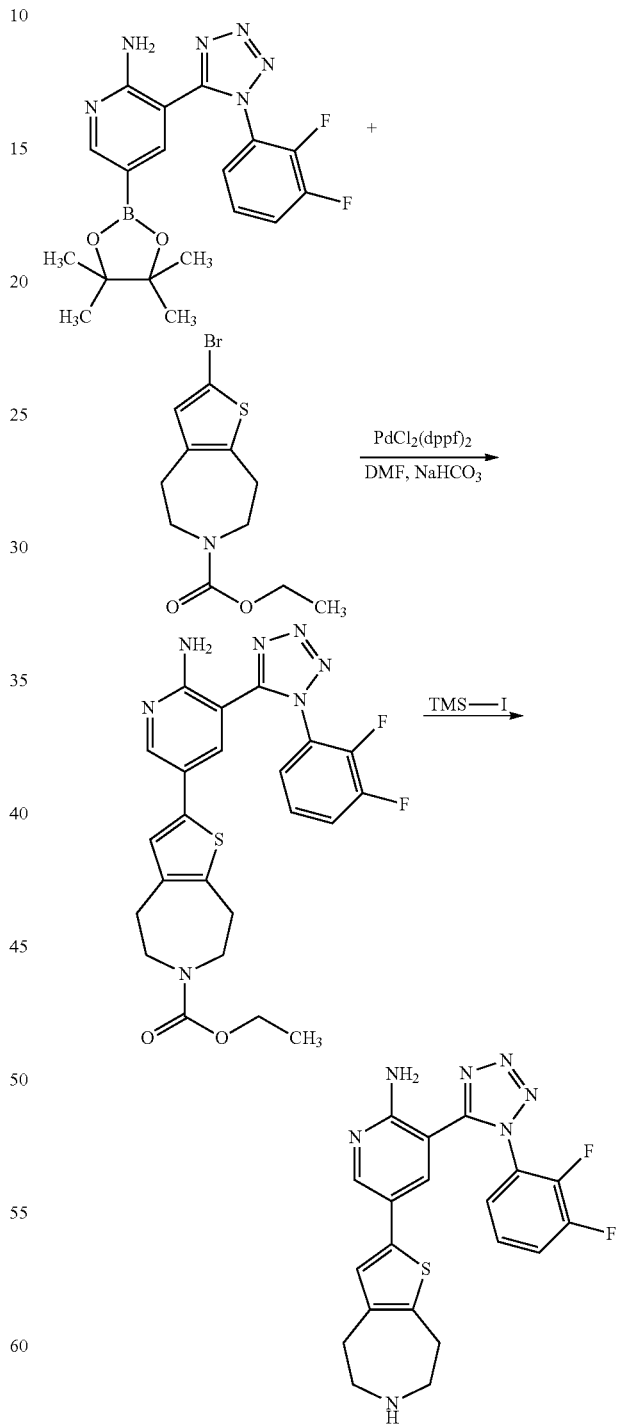

A mixture of 3-(1-(2,3-difluorophenyl)-1H-tetrazol-5-yl)-5-(4,4,5,5-tetramethyl-1,3,2-dioxaborolan-2-yl)pyridin-2-amine (250 mg, 0.63 mmol), tert-butyl 2-bromo-4,5-dihydrothieno[2,3-c]pyridine-6(7H)-carboxylate (198 mg, 0.63 mmol), and NaHCO$_3$ (1.56 mL, saturated solution in H$_2$O) in N,N-dimethylformamide (8.3 mL) was degassed with a nitrogen stream for 20 min. To this mixture was added [1,1'-bis(diphenylphosphino)-ferrocene]palladium (II) dichloride (46 mg, 0.06 mmol) and the reaction was stirred in a microwave for 10 min at 120° C. The resulting crude mixture was diluted with ethyl acetate (30 mL) and filtered. The filtrate was washed with H$_2$O (2×15 mL) and brine (1×15 mL), concentrated under reduced pressure, and purified via silica gel chromatography to provide tert-butyl 2-(6-amino-5-(1-(2,3-difluorophenyl)-1H-tetrazol-5-yl)pyridin-3-yl)-4,5-dihydrothieno[2,3-c]pyridine-6(7H)-carboxylate. This material (137 mg, 0.27 mmol) was treated with HCl (4 mL, 4.0 N in dioxane) for 1 hr, and solvent was removed under reduced pressure. The residue was dissolved in MeOH (500 mL) and treated with cold diethyl ether (~15 mL). The resulting precipitate was collected and dried in vacuo to provide the hydrochloride salt of 3-(1-(2,3-difluorophenyl)-1H-tetrazol-5-yl)-5-(4,5,6,7-tetrahydrothieno[2,3-c]pyridin-2-yl)pyridin-2-amine as a bright yellow solid (103 mg, 37% yield over two A mixture of 3-(1-(2,3-difluorophenyl)-1H-tetrazol-5-yl)-5-(4,4,5,5-tetramethyl-1,3,2-dioxaborolan-2- amine (2.50 g, 6.3 mmol), ethyl 2-bromo-4,5,7,8-tetrahydrothieno[3,2-d]azepine-6-carboxylate (1.91 g, 06.3 mmol), and NaHCO₃ (15.6 mL, saturated solution in H₂O) in N,N-dimethylformamide (83 mL) was degassed with a nitrogen stream for 20 min. To this mixture was added [1,1'-bis(diphenylphosphino)ferrocene]palladium (II) dichloride (460 mg, 0.6 mmol) and the reaction was stirred in a microwave for 10 min at 120° C. The resulting crude mixture was diluted with ethyl acetate (300 mL) and filtered. The filtrate was washed with H₂O (2×150 mL) and brine (1×150 mL), concentrated under reduced pressure, and purified via silica gel chromatography to provide ethyl 2-(6-amino-5-(1-(2,3-difluorophenyl)-1H-tetrazol-5-yl)pyridin-3-yl)-4,5,7,8-tetrahydrothieno[3,2-d]azepine-6-carboxylate.

Ethyl 2-(6-amino-5-(1-(2,3-difluorophenyl)-1H-tetrazol-5-yl)pyridin-3-yl)-4,5,7,8-tetrahydrothieno[3,2-d]azepine-6-carboxylate (2 g, 4.02 mmol) was dissolved in dry CHCl₃ (40 mL), followed by the addition of TMS-I (3.2 g, 16.0 mmol) at room temperature. The mixture was heated under reflux for 14 hours. After cooling, the reaction was carefully quenched by the addition of MeOH (10 mL), followed by 1N NaOH (30 mL). The mixture was stirred for 30 minutes and then extracted with DCM. The combined DCM layers were dried over MgSO₄ and evaporated. The residue was taken up in EtOAc (10 mL) and 4M HCl/dioxane solution was added. Isolation of the yellow precipitate provided 3-(1-(2,3-difluorophenyl)-1H-tetrazol-5-yl)-5-(5,6,7,8-tetrahydro-4H-thieno[3,2-d]azepin-2-yl)pyridin-2-amine as the HCl salt (1.8 g, 3.9 mmol).

Example 39 tert-Butyl 3-(6-amino-5-(1-(2,3-difluorophenyl)-1H-tetrazol-5-yl)pyridin-3-yl)-8-azabicyclo[3.2.1]oct-3-ene-8-carboxylate

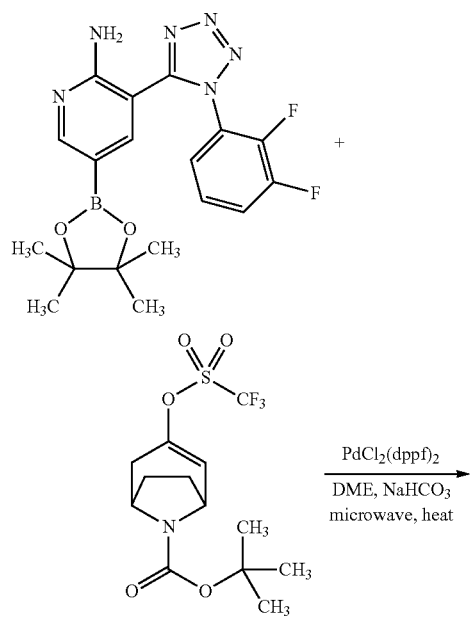

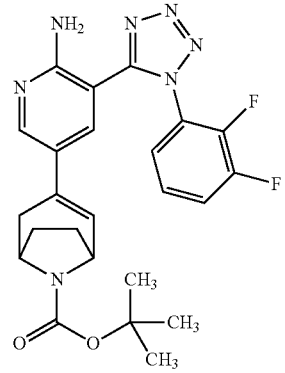

A solution of tert-butyl 3-(trifluoromethylsulfonyloxy)-8-azabicyclo[3.2.1]oct-3-ene-8-carboxylate (50 mg, 140 µmol, 1.0 eq.) in DME (2 mL) was degassed with nitrogen for 15 minutes. NaHCO₃ (1.2 mM solution, 350 µL, 420 µmol, 3 eq.) and 3-(1-(2,3-difluorophenyl)-1H-tetrazol-5-yl)-5-(4,4,5,5-tetramethyl-1,3,2-dioxaborolan-2-yl)pyridin-2-amine (56 mg, 140 µmol, 1.0 eq.) were added and degassing was continued for an additional 30 minutes. PdCl₂(dppf)₂ (10 mg, 14 µmol, 0.1 eq.) was added and degassing was continued for an additional 15 minutes. The reaction was sealed and microwaved at 90° C. for 15 minutes. After cooling, the organic layer was concentrated, NaHCO₃ was added, and the product was extracted with EtOAc. Silica gel chromatography (EtOAc/hexanes) provided tert-butyl 3-(6-amino-5-(1-(2,3-difluorophenyl)-1H-tetrazol-5-yl)pyridin-3-yl)-8-azabicyclo[3.2.1]oct-3-ene-8-carboxylate (34 mg, 51% yield); ¹H NMR (300 MHz, CDCl₃): 8.25 (m, 1H); 7.6-7.25 (m, 3H); 7.07 (s, 1H); 6.4 (br s, 2H); 6.0 (m, 1H); 4.38 (m, 2H); 2.65 (m, 1H); 2.15 (m, 1H); 2.14-1.5 (m, 4H); 1.44 (s, 9H).

Example 40

1-((E)-5-(6-Amino-5-(1-(2,3-difluorophenyl)-1H-tetrazol-5-yl)pyridin-3-yl)-3,4-dihydro-2H-azepin-1(7H)-yl)-2,2,2-trifluoroethanone

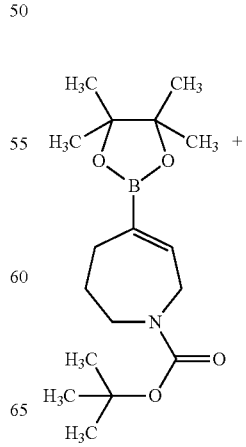

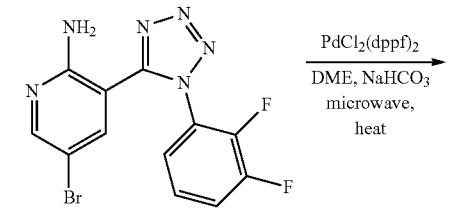

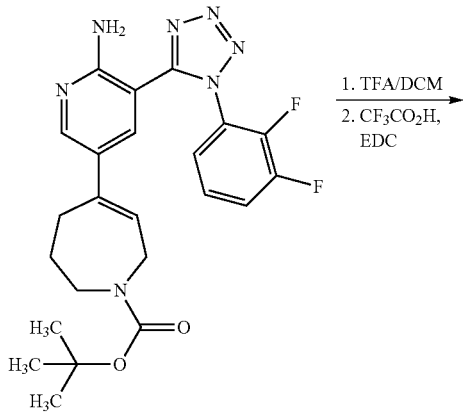

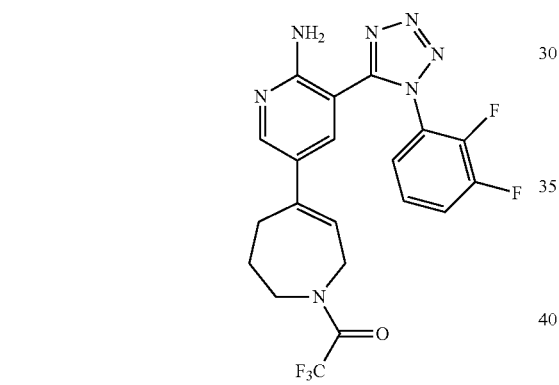

(Z)-tert-Butyl 3,4-dihydro-5-(4,4,5,5-tetramethyl-1,3,2-dioxaborolan-2-yl)-2H-azepine-1(7H)-carboxylate (510 mg, 1.44 mmol, 1.1 eq.) was dissolved in DME (14 mL) and degassed with nitrogen for 15 minutes. NaHCO$_3$ (1.2 M solution, 3.25 mL, 3.9 mmol, 3 eq.) and 5-bromo-3-(1-(2,3-difluorophenyl)-1H-tetrazol-5-yl)pyridin-2-amine (420 mg, 1.3 mmol, 1 eq.) were added and the mixture degassed with nitrogen for an additional 30 minutes. PdCl$_2$(dppf)$_2$ (95 mg, 0.13 mmol, 0.1 eq.) was added and the mixture degassed with nitrogen for an additional 15 minutes. The reaction was microwaved in a sealed tube for 20 min at 90° C. To drive the reaction to completion, additional PdCl$_2$(dppf)$_2$ (95 mg, 0.13 mmol, 0.1 eq.) was added under an atmosphere of nitrogen and the reaction microwaved for an additional 20 min at 90° C. The mixture was concentrated, NaHCO$_3$ was added, and the product was extracted with ethyl acetate. The organics were filtered through floricil and purified by silica gel chromatography (EtOAc/hexanes) to provide (E)-tert-butyl 5-(6-amino-5-(1-(2,3-difluorophenyl)-1H-tetrazol-5-yl)pyridin-3-yl)-3,4-dihydro-2H-azepine-1(7H)-carboxylate (360 mg, 0.76 mmol, 53% yield); $^1$H NMR (300 MHz, CDCl$_3$): 8.2 (m, 1H); 7.5 (m, 1H); 7.45-7.3 (m, 2H); 7.02 (s, 1H); 6.4 (br s, 2H); 5.6 (m, 1H); 3.8 (m, 2H); 3.55 (m, 2H); 2.2 (m, 2H); 1.7 (m, 2H) 1.45 (s, 9H).

(E)-tert-Butyl 5-(6-amino-5-(1-(2,3-difluorophenyl)-1H-tetrazol-5-yl)pyridin-3-yl)-3,4-dihydro-2H-azepine-1(7H)-carboxylate (14 mg, 29.9 µmol, 1 eq.) was diluted in 1:1 TFA:DCM (1.5 mL) and the mixture stirred at room temperature for 2 hours. The reaction was concentrated and purified by reversed-phase HPLC purification to give 3-(1-(2,3-difluorophenyl)-1H-tetrazol-5-yl)-5-((E)-2,5,6,7-tetrahydro-1H-azepin-4-yl)pyridin-2-amine in quantitative yield; $^1$H NMR (300 MHz, DMSO-d$_6$): 9.0 (br s, 2H); 8.25 (m, 1H); 7.87-7.77 (m, 1H); 7.75-7.6 (m, 2H); 7.6-4.5 (m, 1H); 5.85 (m, 1H); 3.7 (m, 2H); 3.25 (m, 2H); 2.5 (m, 2H); 1.78 (m, 2H).

3-(1-(2,3-Difluorophenyl)-1H-tetrazol-5-yl)-5-(E)-2,5,6,7-tetrahydro-1H-azepin-4-yl)pyridin-2-amine (37 mg, 100 µmol, 1 eq.) was diluted in DCM (1.5 mL). EDC (34.4 mg, 150 µmol, 1.5 eq.), trifluoroacetic acid (17.1 mg, 150 µmol, 1 eq.), and DIEA (53 µL, 300 µmol, 3 eq.) were added. The reaction was stirred at room temperature overnight then concentrated. The product was purified by reversed-phase HPLC purification to give 1-((E)-5-(6-amino-5-(1-(2,3-difluorophenyl)-1H-tetrazol-5-yl)pyridin-3-yl)-3,4-dihydro-2H-azepin-1(7H)-yl)-2,2,2-trifluoroethanone (13.6 mg, 30% yield); $^1$H NMR (300 MHz, DMSO-d$_6$): 8.25 (m, 1H); 7.87 (m, 1H); 7.77 (m, 1H); 7.55 (m, 1H); 7.37 (m, 1H); 5.95-5.7 (m, 1H); 4.12 (m, 2H); 3.75-3.6 (m, 2H); 2.4 (m, 2H); 1.75 (m, 2H).

Example 41

3-(1-(2,3-Difluorophenyl)-1H-tetrazol-5-yl)-5-(2-(piperidin-4-yl)thiazol-5-yl)pyridin-2-amine (compound I-A-549)

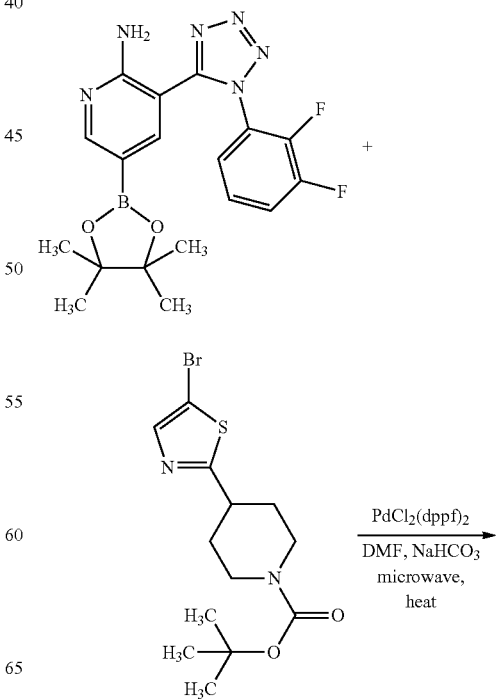

305
-continued

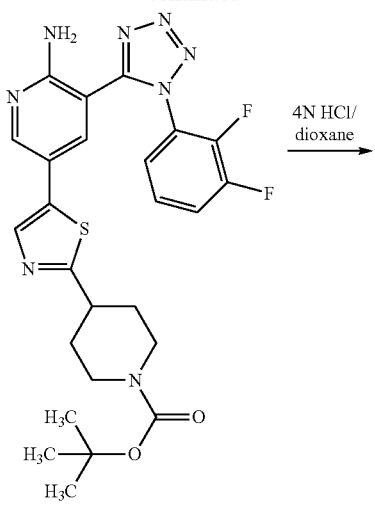

4N HCl/dioxane →

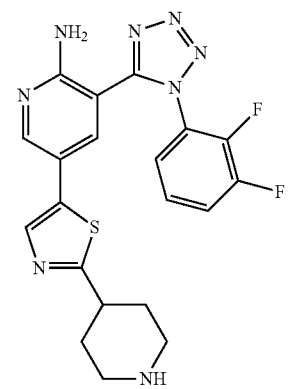

Using the same protocol used to prepare compound I-A-492, 3-(1-(2,3-difluorophenyl)-1H-tetrazol-5-yl)-5-(4,4,5,5-tetramethyl-1,3,2-dioxaborolan-2-yl)pyridin-2-amine and tert-butyl 4-(5-bromothiazol-2-yl)piperidine-1-carboxylate were reacted together in a PdCl$_2$(dppf)-2-mediated coupling to produce 3-(1-(2,3-difluorophenyl)-1H-tetrazol-5-yl)-5-(2-(piperidin-4-yl)thiazol-5-yl)pyridin-2-amine; $^1$H NMR (DMSO-d$_6$): 8.46 (d, J=2.3 Hz, 1H), 7.90-7.48 (m, 5H), 3.40-3.22 (m, 3H), 3.11-2.92 (m, 2H), 2.22-2.10 (m, 2H), 1.99-1.83 (m, 2H); ES-MS: m/e=441.1 (M+H).

Example 42

3-(1-(2,3-Difluorophenyl)-1H-tetrazol-5-yl)-5-(4-((4-methylpiperazin-1-yl)methyl)phenyl)pyridin-2-amine (compound I-A-62)

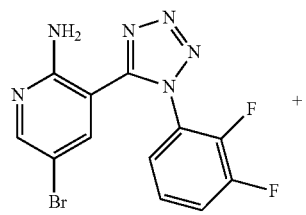 +

306
-continued

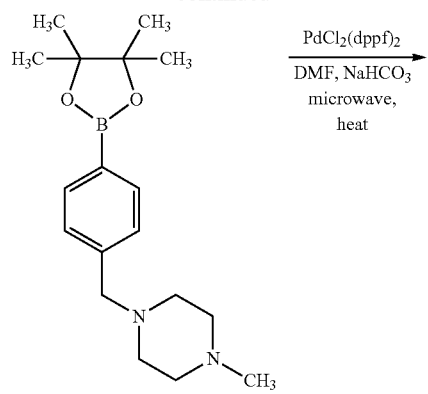

PdCl$_2$(dppf)$_2$
DMF, NaHCO$_3$
microwave, heat →

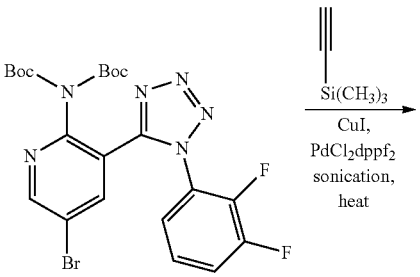

Using the same protocol used to prepare compound I-A-492, 5-bromo-3-(1-(2,3-difluorophenyl)-1H-tetrazol-5-yl)pyridin-2-amine and 1-(4-(4,4,5,5-tetramethyl-1,3,2-dioxaborolan-2-yl)benzyl)-4-methylpiperazine were reacted together in a PdCl$_2$(dppf)$_2$-mediated coupling to produce 3-(1-(2,3-difluorophenyl)-1H-tetrazol-5-yl)-5-(2-(piperidin-4-yl)thiazol-5-yl)pyridin-2-amine; $^1$H NMR (DMSO-d$_6$): 8.46 (d, J=2.3 Hz, 1H), 7.90-7.48 (m, 5H), 3.40-3.22 (m, 3H), 3.11-2.92 (m, 2H), 2.22-2.10 (m, 2H), 1.99-1.83 (m, 2H); ES-MS: m/e=441.1 (M+H).

Example 43

3-(1-(2,3-Difluorophenyl)-1H-tetrazol-5-yl)-5-(1-(piperidin-4-yl)-1H-1,2,3-triazol-4-yl)pyridin-2-amine (compound I-A-483)

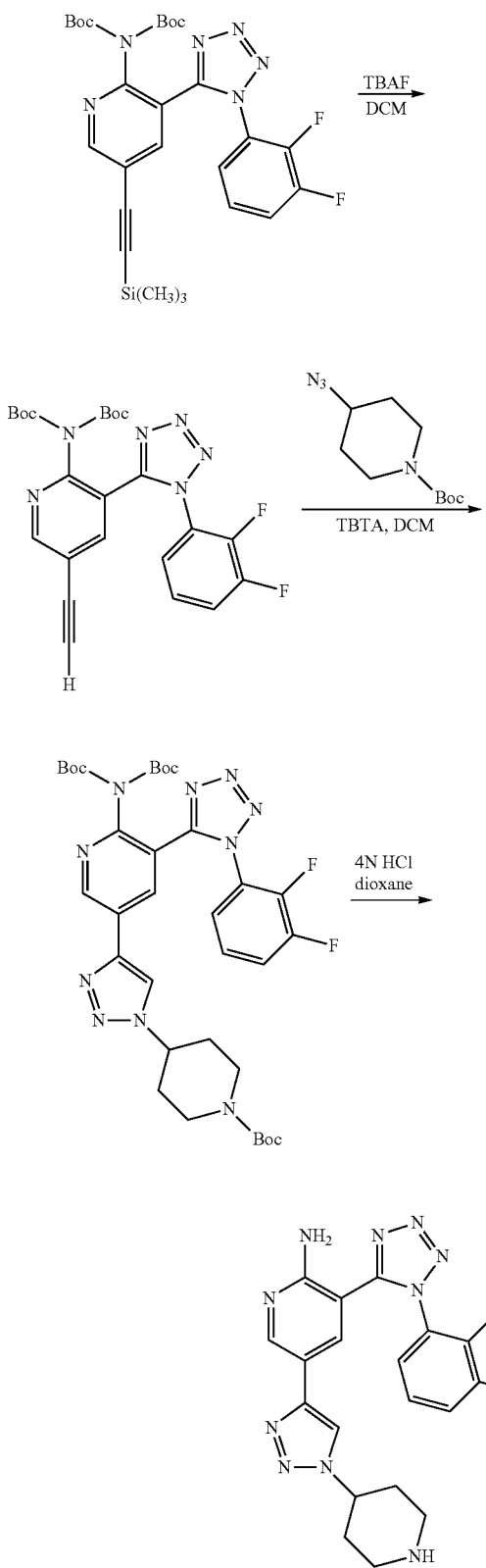

In a tube was placed N,N-di(1,1-dimethylethoxycarbonyl)-3-(1-(2,3-difluorophenyl)-1H-tetrazol-5-yl)-5-bromopyridin-2-amine (2.3 g, 4.1 mmol) in diethylamine (10 mL) with ethynyltrimethylsilane (1.5 g, 15.3 mmol) and the reaction was deoxygenated with a stream of nitrogen gas. To the mixture was added copper(I) iodide (554 mg, 2.9 mmol). The reaction vessel was sealed and warmed to 50° C. to achieve dissolution. To the mixture was added PdCl$_2$dppf$_2$.CH$_2$Cl$_2$ (190 mg, 0.06 eq). The reaction vessel was sealed and the mixture sonicated at 50° C. for 10 minutes. The reaction was diluted with methylene chloride, filtered through Celite™, concentrated, and purified by silica gel chromatography (10% ethyl acetate/hexane to 50% ethyl acetate/hexane) to give N,N-di(1,1-dimethylethoxycarbonyl)-3-(1-(2,3-difluorophenyl)-1H-tetrazol-5-yl)-5-(2-(trimethylsilyl)ethynyl)pyridin-2-amine (713 mg, 1.2 mmol, 30%) as a yellow solid; LC-MS: m/e=471.3 [M-Boc+H].

N,N-Di(1,1-dimethylethoxycarbonyl)-3-(1-(2,3-difluorophenyl)-1H-tetrazol-5-yl)-5-(2-(trimethylsilyl)ethynyl)pyridin-2-amine (713 mg, 1.2 mmol) was dissolved in methylene chloride (10 mL) and cooled to 0° C. To this was added tetrabutylammonium fluoride hydrate (163 mg, 625 µmol) in methylene chloride (1 mL). The reaction was loaded directly onto silica and chromatographed (10% ethyl acetate/hexane to 50% ethyl acetate/hexane) to give N,N-di(1,1-dimethylethoxycarbonyl)-3-(1-(2,3-difluorophenyl)-1H-tetrazol-5-yl)-5-ethynylpyridin-2-amine (496 mg, 1.0 mmol, 83%) as a yellow solid; $^1$H NMR (CDCl$_3$): 1.37 (s, 18H), 3.35 (s, 1H), 7.30 (m, 1H), 7.40 (m, 2H), 7.89 (s, 1H), 8.75 (s, 1H).

N,N-Di(1,1-dimethylethoxycarbonyl)-3-(1-(2,3-difluorophenyl)-1H-tetrazol-5-yl)-5-ethynylpyridin-2-amine (59 mg, 119 µmol) was dissolved in methylene chloride (1 mL) and to this was added tris((1-benzyl-1H-1,2,3-triazol-4-yl)methyl)amine (TBTA, 20 mg, 38 µmol, see Henning et al., *Organic Letters* 9(1): 1-4; 2007), sodium ascorbate (100 mg, 505 µmol), water (1 mL), and methanol (2 mL). To the reaction mixture was added tert-butyl 4-azidopiperidine-1-carboxylate (1 mmol) (prepared from tert-butyl 4-aminopiperidine-1-carboxylate, via the method described by Alper et al., *Tetrahedron Letters* 37(34): 6029-6032, 1996) in methylene chloride (2 mL). The reaction was left at room temperature for 30 minutes and concentrated to remove the volatile organics. The reaction was extracted with methylene chloride (2×10 mL) and saturated sodium bicarbonate (5 mL). The organics were dried over sodium sulfate, filtered and concentrated. The residue was purified by silica gel chromatography (CH$_2$Cl$_2$ to 8% MeOH/CH$_2$Cl$_2$) to give tert-butyl 4-(4-(6-N,N-di(1,1-dimethylethoxycarbonyl)amino-5-(1-(2,3-difluorophenyl)-1H-tetrazol-5-yl)pyridin-3-yl)-1H-1,2,3-triazol-1-yl)piperidine-1-carboxylate (57 mg, 79 µmol, 66% yield); $^1$H NMR (CDCl$_3$): 1.37 (s, 18H), 3.35 (s, 1H), 7.30 (m, 1H), 7.40 (m, 2H), 7.89 (s, 1H), 8.75 (s, 1H). LC-MS: m/e=625.4 [M-Boc+H].

tert-Butyl 4-(4-(6-N,N-di(1,1-dimethylethoxycarbonyl)amino-5-(1-(2,3-difluorophenyl)-1H-tetrazol-5-yl)pyridin-3-yl)-1H-1,2,3-triazol-1-yl)piperidine-1-carboxylate (57 mg, 79 µmol) was treated with 4N hydrochloric acid in dioxane (1 mL) at room temperature, overnight. The reaction was concentrated and purified via reversed-phase HPLC (10% to 40% acetonitrile water with 0.1% TFA, over 10 minutes) to give 3-(1-(2,3-difluorophenyl)-1H-tetrazol-5-O-5-(1-(piperidin-4-yl)-1H-1,2,3-triazol-4-yl)pyridin-2-amine (20.7 mg, 27 µmol, 34% yield); $^1$H NMR methanol-d$_4$: 8.55 (s, 1H); 8.3 (s, 1H); 8.0 (s, 1H); 7.6 (m, 2H); 7.5 (m, 1H); 3.6 (m, 2H); 3.2 (m, 3H); 2.4 (m, 2H); LC-MS: m/e=425.2 [M+H].

TABLE 6

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 1 | 353.00 | (500 MHz, DMSO-d₆): 9.03 (s, 1H), 8.19 (s, 1H), 7.91 (br, 2H), 7.68 (m, 1H), 7.46 (m, 1H), 7.37 (m, 1H) |
| 2 | 351.90 | (500 MHz, DMSO-d₆): 9.05 (s, 1H), 8.81 (s, 1H), 8.52 (dd, 1H), 8.45 (d, 1H), 8.05 (br, 2H), 7.73 (m, 1H), 7.60 (m, 1H), 7.53 (dt, 1H), 7.48 (m, 1H), 7.38 (dd, 1H) |
| 3 | 351.80 | (500 MHz, DMSO-d₆): 9.09 (s, 1H), 9.00 (s, 1H), 8.59 (d, 2H), 8.41 (br, 2H), 7.79 (q, 1H), 7.65 (dd, 1H), 7.51 (m, 1H), 7.35 (d, 2H) |
| 4 | 421.00 | (500 MHz, DMSO-d₆): 9.04 (s, 1H), 8.73 (s, 1H), 8.10 (d, 1H), 7.93 (br, 2H), 7.75 (q, 1H), 7.61 (dd, 1H), 7.48 (m, 1H), 7.09 (dd, 1H), 6.80 (d, 1H), 3.55 (tbr, 4H), 2.05 (tbr, 4H) |
| 5 | 449.90 | (500 MHz, DMSO-d₆): 9.96 (br, 1H), 9.03 (s, 1H), 8.77 (s, 1H), 7.97 (br, 2H), 7.71 (q, 1H), 7.60 (dd, 1H), 7.48 (m, 1H), 7.37 (d, 2H), 7.25 (d, 2H), 4.33 (s, 2H), 3.97 (br, 2H), 3.63 (tbr, 2H), 3.23 (br, 2H), 3.11 (br, 2H) |
| 6 | 463.00 | (500 MHz, DMSO-d₆): 9.02 (s, 1H), 8.72 (s, 1H), 7.90 (br, 2H), 7.74 (q, 1H), 7.59 (dd, 1H), 7.47 (m, 1H), 7.23 (d, 2H), 7.16 (d, 2H), 3.72 (s, 2H), 3.45-2.89 (br, 8H), 2.78 (s, 3H) |
| 7 | 449.0 | (500 MHz, DMSO-d₆): 9.77 (br, 1H), 9.00 (s, 1H), 8.64 (s, 1H), 7.75 (mbr, 3H), 7.58 (dd, 1H), 7.47 (m, 1H), 7.05 (d, 2H), 6.84 (d, 2H), 3.91 (br, 2H), 3.58-2.95 (br, complex, 8H), 2.88 (s, 3H) |
| 8 | 407.90 | (500 MHz, DMSO-d₆): 9.78 (br, 1H), 9.04 (s, 1H), 8.77 (s, 1H), 7.97 (br, 2H), 7.69 (dd, 1H), 7.61 (dd, 1H), 7.48 (m, 1H), 7.36 (d, 2H), 7.24 (d, 2H), 4.27 (s, 2H), 2.74 (s, 6H) |
| 9 | 461.90 | (500 MHz, DMSO-d₆): 9.73 (br, 1H), 9.01 (s, 1H), 8.65 (s, 1H), 8.17 (d, 1H), 7.78 (br, 2H), 7.72 (dd, 1H), 7.58 (dd, 1H), 7.46 (m, 1H), 7.06 (dd, 1H), 6.52 (d, 1H), 4.90 (s, 1H), 4.39 (s, 1H), 3.65 (dd, 2H), 2.90 (s, 3H), 2.40 (d, 1H), 2.15 (d, 1H) |
| 10 | 365.90 | (500 MHz, DMSO-d₆): 8.98 (s, 1H), 8.54 (s, 1H), 7.71 (dd, 1H), 7.65 (br, 2H), 7.57 (dd, 1H), 7.46 (m, 1H), 6.90 (d, 2H), 6.51 (d, 2H), 4.90 (s, 1H), 4.39 (s, 1H), 3.65 (dd, 2H), 2.90 (s, 3H), 2.40 (d, 1H), 2.15 (d, 1H) |
| 11 | 407.90 | (500 MHz, DMSO-d₆): 9.96 (s, 1H), 9.00 (s, 1H), 8.65 (s, 1H), 7.81 (br, 2H), 7.70 (dd, 1H), 7.57 (dd, 1H), 7.48 (m, 1H), 7.45 (d, 2H), 7.10 (d, 2H), 2.05 (s, 3H) |
| 12 | 365.90 | (500 MHz, DMSO-d₆): 8.99 (s, 1H), 8.51 (s, 1H), 7.81 (br, 2H), 7.70 (dd, 1H), 7.57 (dd, 1H), 7.48 (m, 1H), 6.88 (t, 1H), 6.56 (s, 1H), 6.51 (d, 1 H), 6.21 (d, 1H) |
| 13 | 390.90 | (500 MHz, DMSO-d₆): 11.68 (s, 1H), 9.02 (s, 1H), 9.76 (s, 1H), 8.20 (d, 1H), 7.78 (mbr, 3H), 7.62 (t, 1H), 7.48 (m, 3H), 6.42 (dd, 1H) |
| 14 | 370.70 | (500 MHz, DMSO-d₆): 12.75 (s, 1H), 8.14 (s, 1H), 7.58 (m, 1H), 7.48 (br, 2H), 7.30 (m, 2H) |
| 15 | 367.80 | (500 MHz, DMSO-d₆): 12.83 (s, 1H), 8.94 (s, 1H), 8.56 (d, 1H), 7.95 (br, 2H), 7.69 (m, 1H), 7.46 (m, 2H), 7.29 (d, 2H) |
| 16 | 465.90 | (500 MHz, DMSO-d₆): 12.75 (s, 1H), 8.73 (s, 1H), 7.62 (m, 1H), 7.52 (br, 2H), 7.45 (m, 2H), 7.36 (d, 2H), 7.21 (d, 2H), 4.33 (s, 2H), 3.98 (br, 2H), 3.64 (tbr, 2H), 3.25 (br, 2H), 3.13 (br, 2H) |
| 17 | 464.90 | (500 MHz, DMSO-d₆): 12.68 (s, 1H), 9.67 (br, 1H), 8.59 (s, 1H), 7.65 (m, 1H), 7.41 (m, 2H), 7.30 (s, 2H), 7.01 (d, 2H), 6.82 (d, 2H), 3.89 (br, 2H), 3.54 (br, 2H), 3.16 (br, 2H), 2.97 (br, 2H), 2.87 (s, 3H) |
| 18 | 436.90 | (500 MHz, DMSO-d₆): 12.75 (s, 1H), 8.68 (s, 1H), 8.09 (d, 1H), 7.65 (m, 1H), 7.48-7.39 (complex, 4H), 7.02 (dd, 1H), 6.75 (br, 1H), 3.50 (tbr, 4H), 1.99 (tbr, 4H) |
| 19 | 449.20 | (500 MHz, DMSO-d₆): 8.41 (d, 1H), 7.82 (q, 1H), 7.72 (t, 1H), 7.55 (m, 1H), 7.51 (d, 1H), 7.16 (d, 2H), 6.91 (d, 2H), 6.67 (s, 2H), 3.14 (tbr, 4H), 2.46 (tbr, 4H), 2.23 (s, 3H) |
| 20 | 352.10 | (500 MHz, DMSO-d₆): 8.57 (d, 1H), 8.54 (d, 1H), 8.47 (dd, 1H), 7.80 (m, 2H), 7.74 (d, 1H), 7.68 (m, 1H), 7.52 (m, 1H), 7.39 (dd, 1H), 6.83 (s, 2H) |
| 22 | 381.10 | |
| 24 | 385.10 | |
| 27 | 346.30 | (400 MHz, CDCl₃): 8.51 (s, 1H), 8.48 (br d, J = 4.8 Hz, 1H), 8.40 (br s, 1H), 8.32 (s, 1H), 7.47 (t, J = 8.0 Hz, 1H), 7.33-7.31 (m, 1H), 7.21-7.12 (m, 2H), 6.96 (br d, J = 7.6 Hz, 1H), 6.89 (m, 1H), 3.78 (s, 3H) |
| 28 | 356.30 | (400 MHz, CDCl₃): 8.49 (s, 1H), 8.48-8.47 (m, 1H), 8.31 (d, J = 1.2 Hz, 1H), 8.28 (s, 1H), 7.51 (d, J = 7.6 Hz, 1H), 7.35 (t, J = 8.0 Hz, 1H), 7.16-7.09 (m, 3H), 2.96 (br s, 2H), 2.51 (br s, 2H), 1.93 (br s, 2H) |
| 29 | 393.20 | (400 MHz, DMSO-d₆): 9.05 (s, 1H), 8.83 (s, 1H), 8.10 (s, 1H), 7.99 (br s), 1H), 7.85 (d, J = 7.6 Hz, 1H), 7.71 (dd, J = 16.4, 8.0 Hz, |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| | | 1H), 7.61 (t, J = 6.8 Hz, 1H), 7.48 (m, 1H), 7.35 (t, J = 8.0 Hz, 1H), 7.03 (d, J = 7.6 Hz, 1H), 6.74 (s, 1H), 2.61 (s, 3H) |
| 30 | 376.00 | (400 MHz, DMSO-$d_6$): 9.06 (s, 1H), 8.84 (s, 1H), 8.10 (br s), 7.74 (m, 2H), 7.64 (t, J = 7.6 Hz, 1H), 7.59 (d, J = 8.0 Hz, 1H), 7.52-7.45 (m, 2H), 7.41 (s, 1H) |
| 31 | 395.50 | (400 MHz, DMSO-$d_6$): 9.03 (s, 1H), 8.72 (s, 1H), 7.91 (br s, 2H), 7.71 (dd, J = 16.8, 8.0 Hz, 1H), 7.59 (t, J = 7.6 Hz, 1H), 7.45 (dd, J = 12.6, 6.8 Hz, 1H), 7.12 (t, J = 8.4 Hz, 1H), 6.82 (br d, J = 7.2 Hz, 1H), 6.80 (s, 1H), 6.67 (d, J = 7.6 Hz, 1H), 4.01 (q, J = 6.8 Hz, 2H), 1.37 (t, J = 6.8 Hz, 3H) |
| 32 | 429.00 | (400 MHz, DMSO-$d_6$): 9.07 (s, 1H), 8.86 (s, 1H), 8.15 (br s, 2H), 7.87 (dd, J = 17.2, 8.4 Hz, 1H), 7.74 (d, J = 7.6 Hz, 2H), 7.64 (t, J = 8.0 Hz, 1H), 7.53 (dd, J = 14.0, 7.2 Hz, 1H), 7.38 (d, J = 8.4 Hz, 2H), 3.23 (s, 3H) |
| 33 | 402.20 | (400 MHz, DMSO-$d_6$): 9.08 (s, 1H), 8.96 (s, 1H), 8.71 (d, J = 2.0 Hz, 1H), 8.09 (br s, 2H), 8.06 (br s, 1H), 8.02 (d, J = 8.0 Hz, 1H), 7.84 (d, J = 8.0 Hz, 1H), 7.78-7.73 (m, 2H), 7.70-7.64 (m, 3H) |
| 34 | 368.00 | (400 MHz, CDCl$_3$): 8.53 (d, J = 2.0 Hz, 1H), 8.52 (s, 1H), 8.42 (d, J = 2.0 Hz, 1H), 8.30 (s, 1H), 7.56 (dd. d, J = 8.8, 4.4, 2.8 Hz, 1H), 7.47 (dd, J = 6.4, 2.4 Hz, 1H), 7.41 (t, J = 8.4, 2.0 Hz, 1H), 7.23-7.18 (m, 2H) |
| 35 | 374.20 | (400 MHz, CDCl$_3$): 8.52 (s, 1H), 8.50-8.46 (m, 2H), 8.33 (s, 1H), 7.47 (t, J = 8.4 Hz, 1H), 7.28-7.23 (overlapped m, 1H), 7.15-7.04 (m, 2H), 6.93 (br d, J = 7.6 Hz, 1H), 6.84 (br s, 1H), 5.35-5.30 (m, 1H), 1.24 (d, J = 6.0 Hz, 6H) |
| 36 | 358.20 | (400 MHz, CDCl$_3$): 8.50 (s, 1H), 8.46 (br d, J = 3.6 Hz, 1H), 8.34 (br s, 1H), 8.33 (s, 1H), 7.48 (s, 2H), 7.26-7.07 (m, 4H), 3.55-3.45 (m, 1H), 1.16 (d, J = 6.8 Hz, 6H) |
| 37 | 350.30 | (400 MHz, CDCl$_3$): 8.51 (s, 1H), 8.50 (br s, 1H), 842 (br s, 1H), 8.32 (s, 1H), 7.62 (br d, J = 8.0 Hz, 1H), 7.52-7.47 (m, 2H), 7.43 (m, 1H), 7.33-7.15 (m, 2H) |
| 38 | 353.80 | (500 MHz, DMSO-$d_6$): 8.99 (s, 1H), 8.09 (d, 1H), 7.69 (q, 1H), 7.51 (t, 1H), 7.44 (ddd, 1H), 7.24 (d, 1H), 6.86 (br s, 2H) |
| 39 | 350.90 | (500 MHz, DMSO-$d_6$): 9.01 (s, 1H), 8.44 (m, 3H), 7.69 (m, 2H), 7.57 (t, 1H), 7.46 (m, 2H), 7.36 (dd, 1H), 6.98 (br s, 2H) |
| 40 | 419.90 | (500 MHz, DMSO-$d_6$): 9.05 (s, 1H), 8.41 (d, 1H), 7.93 (s, 1H), 7.91 (d, 1H), 7.65 (q, 1H), 7.60 (d, 1H), 7.52 (t, 1H), 7.40 (q, 1H), 7.2 (m, 2H), 7.05 (d, 1H), 3.52 (m, 4H), 2.02 (m, 4H) |
| 41 | 447.90 | (500 MHz, DMSO-$d_6$): 9.03 (s, 1H), 8.33 (d, 1H), 7.70 (q, 1H), 7.65 (t, 1H), 7.46 (t, 1H), 7.45 (s, 1H), 7.2 (m, 2H), 7.14 (d, 2H), 6.98 (d, 2H), 3.87 (d, 2H), 3.50 (d, 2H), 3.13 (m, 2H), 2.95 (t, 2H), 2.86 (t, 3H) |
| 42 | 478.90 | (500 MHz, DMSO-$d_6$): 12.75 (s, 1H), 8.68 (s, 1H), 7.63 (m, 1H), 7.41 (complex, 4H), 7.22 (d, 2H), 7.12 (d, 2H), 3.77 (br, 2H), 3.40 (br, 2H), 3.05 (br, 4H), 2.80 (s, 3H) |
| 43 | 421.10 | (500 MHz, DMSO-$d_6$): 9.18 (s, 1H), 8.22 (m, 2H), 7.73 (s, 1H), 7.67 (q, 1H), 7.52 (t, 1H), 7.46 (br, 2H), 7.40 (m, 1H), 7.01 (dbr, 1H), 3.54 (tbr, 4H), 2.02 (tbr, 4H) |
| 44 | 331.90 | (500 MHz, methanol-$d_4$): 8.78 (s, 1H), 8.77 (s, 1H), 8.65 (d, 1H), 8.55 (s, 1H), 8.27 (d, 1H), 7.98 (s, 1H), 7.89 (dd, 1H), 7.44 (t, 1H), 7.09 (d, 1H), 6.97 (d, 1H), 6.88 (s, 1H) |
| 45 | | (500 MHz, DMSO-$d_6$): 9.69 (br, 1H), 9.15 (s, 1H), 7.70 (q, 1H), 7.58 (dd, 1H), 7.55 (d, 2H), 7.48 (s, 1H), 7.45 (m, 1H), 7.27 (br, 2H), 7.04 (d, 2H), 3.95 (dbr, 2H), 3.52 (dbr, 2H), 3.14 (tbr, 2H), 3.01 (tbr, 2H), 2.86 (s, 3H) |
| 46 | 450.00 | (500 MHz, DMSO-$d_6$): 8.80 (1H), 7.96 (1H), 7.65 (complex, 4H), 7.08 (2H), 6.81 (2H), 3.28 (8H), 2.25 (3H) |
| 47 | 422.00 | (500 MHz, DMSO-$d_6$): 8.77 (s, 1H), 8.21 (s, 1H), 7.87 (dd, 1H), 7.70 (t, 1H), 7.56 (complex, 3H), 6.99 (d, 1H), 6.28 (d, 1H), 3.40 (tbr, 4H), 1.95 (tbr, 4H) |
| 48 | 409.00 | (500 MHz, DMSO-$d_6$): 8.88 (s, 1H), 7.91 (q, 1H), 7.78 (br, 2H), 7.72 (t, 1H), 7.57 (m, 1H), 7.19 (dd, 4H), 3.46 (s, 2H), 2.19 (s, 6H) |
| 49 | 330.00 | (500 MHz, methanol-$d_4$): 8.28 (s, 1H), 8.26 (s, 1H), 8.62 (d, 1H), 8.31 (s, 1H), 8.10 (d, 1H), 7.87 (dd, 1H), 7.11 (t, 1H), 7.50 (d, 1H), 7.48 (t, 1H), 7.42 (d, 1H), 2.01 (s, 3H) |
| 50 | 464.00 | (500 MHz, DMSO-$d_6$): 8.90 (s, 1H), 7.89 (q, 1H), 7.81 (br, 2H), 7.73 (dd, 1H), 7.57 (m, 1H), 7.28 (d, 2H), 7.23 (d, 2H), 3.80 (s, 2H), 3.50-2.95 (br, complex, 8H), 2.79 (s, 3H) |
| 51 | 451.00 | (500 MHz, DMSO-$d_6$): 9.95 (br, 1H), 8.94 (s, 1H), 7.86 (m, 3H), 7.73 (dd, 1H), 7.57 (m, 1H), 7.41 (d, 2H), 7.32 (d, 2H), 4.35 (s, 2H), 3.96 (br, 2H), 3.63 (br, 2H), 3.23 (br, 2H), 3.11 (br, 2H) |
| 52 | 424.90 | (500 MHz, DMSO-$d_6$): 12.75 (br, 2H), 8.57 (complex, 3H), 7.82 (s, 2H), 7.68 (m, 2H), 7.48 (m, 1H), 7.25 (d, 1H), 6.72 (d, 1H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 53 | 495.90 | (500 MHz, DMSO-d$_6$): 10.55 (br, 1H), 8.57 (d, 1H), 7.77 (sbr, 2H), 7.64 (m, 2H), 7.46 (m, 1H), 7.39 (br, 1H), 7.25 (d, 1H), 6.82 (d, 1H), 3.26 (m, 2H), 1.15 (t, 3H) |
| 54 | 436.90 | (500 MHz, DMSO-d$_6$): 12.52 (s, 2H), 8.63 (s, 1H), 8.40 (s, 2H), 7.67 (complex, 4H), 7.48 (m, 1H), 7.02 (s, 1H), 6.55 (s, 1H), 3.82 (s, 3H) |
| 55 | 507.90 | (500 MHz, DMSO-d$_6$): 11.00 (br, 1H), 8.64 (s, 1H), 7.66 (m, 3H), 7.57 (m, 3H), 7.45 (m, 1H), 7.17 (s, 1H), 6.80 (s, 1H), 3.81 (s, 3H), 3.26 9m, 2H), 1.16 (t, 3H) |
| 56 | 423.90 | (500 MHz, DMSO-d$_6$): 12.68 (br, 2H), 9.03 (s, 1H), 8.54 (s, 2H), 8.41 (d, 1H), 7.93 (br, 2H), 7.54 (m, 2H), 7.40 (m, 1H), 7.23 (d, 1H), 6.65 (d, 1H) |
| 57 | 494.90 | (500 MHz, DMSO-d$_6$): 10.98 (br, 1H), 9.03 (s, 1H), 8.42 (d, 1H), 7.92 (br, 2H), 7.54 (m, 2H), 7.47 (m, 1H), 7.37 (m, 1H), 7.30 (d, 1H), 6.83 (d, 1H), 3.26 (m, 2H), 1.15 (t, 3H) |
| 58 | 450.00 | (500 MHz, DMSO-d$_6$): 9.54 (br s, 1H), 9.01 (br s, 1H), 8.39 (d, 1H), 8.06 (d, 1H), 7.64 (q, 1H), 7.47 (t, 1H), 7.40 (m, 2H), 7.38 (m, 2H), 7.32 (m, 2H), 1.00 (s, 9H) |
| 59 | 365.90 | (500 MHz, DMSO-d$_6$): 9.04 (s, 1H), 8.17 (s, 1H), 7.96 (d, 1H), 7.71 (br s, 3H), 7.64 (q, 1H), 7.56 (m, 3H), 7.38 (m, 2H), 6.90 (t, 1H) |
| 60 | 363.00 | (500 MHz, methanol-d$_4$): 8.89 (m, 1H), 8.65 (d, 1H), 8.54 (m, 1H), 8.44 (d, 1H), 8.04 (m, 1H), 7.8 (t, 1H), 7.72 (d, 1H), 7.57 (m, 1H), 7.54 (m, 1H), 7.48 (t, 1H), 2.02 (s, 3H) |
| 61 | 353.00 | (500 MHz, DMSO-d$_6$): 8.20 (d, 1H), 7.79 (m, 1H), 7.61 (m, 1H), 7.56 (d, 1H), 7.52 (m, 1H), 6.73 (s, 2H) |
| 62 | 463.20 | (500 MHz, DMSO-d$_6$): 8.48 (d, 1H), 7.82 (q, 1H), 7.71 (t, 1H), 7.55 (m, 1H), 7.61 (d, 1H), 7.27 (s, 4H), 6.76 (s, 2H), 2.43 (s, 2H), 2.35-2.30 (complex, 8H), 2.14 (s, 3H) |
| 63 | 408.20 | (500 MHz, DMSO-d$_6$): 8.48 (d, 1H), 7.82 (q, 1H), 7.71 (t, 1H), 7.62 (d, 1H), 7.55 (m, 1H), 7.27 (s, 4H), 6.77 (s, 2H), 3.36 (s, 2H), 2.13 (s, 6H) |
| 64 | 421.20 | (500 MHz, DMSO-d$_6$): 8.39 (d, 1H), 8.05 (d, 1H), 7.80 (m, 1H), 7.70 (t, 1H), 7.55 (m, 1H), 7.52 (d, 1H), 7.46 (dd, 1H), 6.63 (s, 2H), 6.43 (d, 1H), 3.37 (br, 4H), 1.93 (br, 4H) |
| 65 | 382.00 | (500 MHz, methanol-d$_4$): 7.23 (s, 1H), 7.35 (m, 3H), 7.5 (m, 1H), 7.6 (d, 2H), 7.75 (d, 1H), 8.2 (s, 2H), 8.4 (d, 1H) |
| 66 | 436.30 | (500 MHz, DMSO-d$_6$): 9.56 (s, 1H), 8.57 (d, J = 2.4 Hz, 1H), 7.83-7.76 (m, 2H), 7.70 (dd, J = 6.5, 7.9 Hz, 1H), 7.55-7.49 (m, 4H), 6.92 (br, 2H), 4.31 (d, J = 5.3 Hz, 2H), 3.13-3.04 (m, 4H), 1.27-1.20 (m, 6H) |
| 67 | 434.20 | (500 MHz, DMSO-d$_6$): 9.71 (s, 1H), 8.54 (s, 1H), 7.80 (dd, J = 8.6, 17.5 Hz, 1H), 7.72-7.69 (m, 2H), 7.55-7.48 (m, 5H), 6.78 (s, 2H), 4.33 (s, 2H), 3.36 (sbr, 2H), 3.09 (brs, 2H), 2.30 (s, 3H), 2.03-1.86 (m, 4H) |
| 68 | 397.30 | (500 MHz, DMSO-d$_6$): 8.99 (1 H, s), 8.22 (1 H, s), 7.95 (1 H, d), 7.89 (1 H, d), 7.65 (1 H, t), 7.25 (2 H, m), 7.10 (1 H, t), 6.65 (1 H, br s), 6.41 (1 H, br s) |
| 69 | 412.30 | (500 MHz, DMSO-d$_6$): 8.99 (1 H, s), 8.30 (1 H, s), 7.95 (1 H, d), 7.89 (1 H, d), 7.65 (1 H, t), 7.25 (1 H, m), 7.10 (2 H, d), 6.95 (2 H, d), 3.71 (3 H, s) |
| 70 | 388.30 | (500 MHz, DMSO-d$_6$): 8.99 (1 H, s), 8.35 (1 H, s), 7.95 (2 H, m), 7.65 (2 H, m), 7.55 (1 H, s), 7.35 (2 H, m), 6.95 (1 H, s) |
| 71 | 383.30 | (500 MHz, DMSO-d$_6$): 8.99 (1 H, s), 8.65 (1 H, s), 8.10 (1 H, s), 7.95-7.85 (3 H, m), 7.80 (1 H, m), 7.55 (4 H, m), 7.55 |
| 72 | 425.40 | (500 MHz, methanol-d$_4$): 8.92 (1 H, s), 8.15 (1 H, s), 7.911 (1 H, d), 7.78 (1 H, d), 7.65 (2 H, m), 7.05 (2 H, m), 6.80 (2 H, d), 2.92 (6 H, s) |
| 73 | 439.40 | (500 MHz, methanol-d$_4$): 8.92 (1 H, s), 8.25 (1 H, s), 7.85 (1 H, d), 7.79 (1 H, d), 7.70 (1 H, d), 7.60 (2 H, m), 7.30 (2 H, m), 6.80 (1 H, m), 2.15 (3 H, s) |
| 74 | 382.30 | (500 MHz, methanol-d$_4$): 8.92 (1 H, s), 8.28 (1 H, s), 7.90 (1 H, d), 7.75 (1 H, d), 7.65 (3 H, m), 7.35 (3 H, m), 7.15 (2 H, m) |
| 75 | 398.30 | (500 MHz, methanol-d$_4$): 8.89 (1 H, s), 8.22 (1 H, s), 7.82 (2 H, m), 7.70 (1 H, d), 7.58 (1 H, m), 7.35 (3 H, m), 7.15 (1 H, m), 6.85 (3 H, m) |
| 76 | 439.40 | (500 MHz, methanol-d$_4$): 8.90 (1 H, s), 8.25 (1 H, s), 7.90 (1 H, m), 7.78 (1 H, d), 7.65-7.52 (5 H, m), 7.10 (2 H, d), 7.15 (1 H, m), 2.10 |
| 77 | 442.40 | (500 MHz, methanol-d$_4$): 8.89 (1 H, s), 8.23 (1 H, s), 7.89 (1 H, m), 7.75 (1 H, d), 7.60 (2 H, m), 6.92 (1 H, d), 6.70 (1 H, m), 3.83 (3 H, s), 3.80 (3 H, s) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 78 | 412.30 | (500 MHz, methanol-$d_4$): 8.90 (1 H, s), 8.29 (1 H, s), 7.90 (1 H, m), 7.79 (1 H, d), 7.62 (2 H, m), 7.39 (2 H, d), 7.12 (2 H, d), 4.60 (2 H, s) |
| 79 | 440.40 | (500 MHz, DMSO-$d_6$): 9.57 (br, 1H), 8.54 (d, J = 2.4 Hz, 1H), 8.06-8.02 (m, 2H), 7.74 (t, J = 8.1 Hz, 1H), 7.54 (d, J = 2.4 Hz, 1H), 7.48 (d, J = 8.2 Hz, 2H), 7.38 (d, J = 8.2 Hz, 2H), 7.00 (br, 2H), 4.27 (d, J = 5.2 Hz, 2H), 2.73 (d, J = 4.8 Hz, 6H) |
| 80 | 440.30 | (500 MHz, DMSO-$d_6$): 9.26 (br, 1H), 8.12 (d, J = 2.3 Hz, 1H), 7.99 (d, J = 8.1 Hz, 2H), 7.68 (t, J = 8.1 Hz, 1H), 7.63 (d, J = 7.4 Hz, 1H), 7.48-7.45 (m, 2H), 7.18 (d, J = 2.3 Hz, 1H), 6.97 (dd, J = 1.6, 7.3 Hz, 1H), 6.95 (sbr, 2H), 4.17 (d, J = 5.4 Hz, 2H) |
| 81 | 440.30 | (500 MHz, DMSO-$d_6$): 9.95 (s, 1H), 8.45 (d, J = 2.4 Hz, 2H), 8.07-8.04 (m, 2H), 7.76 (t, J = 8.1 Hz, 1H), 7.56 (d, J = 8.6 Hz, 2H), 7.42 (d, J = 2.4 Hz, 1H), 7.16 (d, J = 8.7 Hz, 2H), 6.98 (br, 2H), 2.04 (s, 3H) |
| 82 | 453.30 | (500 MHz, DMSO-$d_6$): 8.46 (d, J = 2.4 Hz, 1H), 8.03 (dd, 1H), 7.99 (dd, 1H), 7.96 (d, 1H), 7.85 (br, 1H), 7.70 (t, J = 8.1 Hz, 1H), 7.58 (s, 1H), 6.86 (br, 2H), 3.51 (tbr, 4H), 2.01 (tbr, 4H) |
| 83 | 384.30 | (500 MHz, DMSO-$d_6$): 8.62 (d, J = 1.7 Hz, 1H), 8.57 (d, 1H), 8.55 (dd, 1H), 8.05 (dd, 1H), 8.00 (dd, 1H), 7.94 (dbr, 1H), 7.73 (t, J = 8.1 Hz, 1H), 7.66 (d, J = 2.4 Hz, 1H), 7.55 (dd, 1H), 7.02 (br, 2H) |
| 84 | 384.30 | (500 MHz, DMSO-$d_6$): 8.81 (d, J = 2.4 Hz, 1H), 8.70 (d, J = 6.4 Hz, 2H), 8.05 (d, J = 8.0 Hz, 1H), 7.98 (d, 1H), 7.96 (s, 1H), 7.85 (br, 2H), 7.71 (t, 1H), 7.30 (br, 2H) |
| 85 | 481.40 | (500 MHz, DMSO-$d_6$): 9.58 (br, 1H), 8.43 (d, J = 2.4 Hz, 1H), 8.05-8.02 (m, 2H), 7.74 (d, J = 8.2 Hz, 1H), 7.39 (d, J = 2.4 Hz, 1H), 7.15 (d, J = 8.8 Hz, 2H), 6.99 (d, J = 8.8 Hz, 2H), 6.90 (br, 2H), 3.86 (d, 2H), 3.15 (q, 2H), 2.98 (d, 2H), 2.86 (d, 3H) |
| 86 | 398.30 | (500 MHz, DMSO-$d_6$): 8.40 (d, J = 2.4 Hz, 1H), 8.05 (d, J = 1.3 Hz, 1H), 8.03 (d, J = 1.3 Hz, 1H), 7.74 (t, J = 8.1 Hz, 1H), 7.40 (d, J = 2.3 Hz, 1H), 7.07 (d, J = 8.0 Hz, 1H), 7.00 (br, 2H), 6.82 (br, 2H) |
| 87 | 412.30 | (500 MHz, DMSO-$d_6$): 8.50 (d, J = 2.4 Hz, 1H), 8.11 (br, 2H), 8.04 (dd, 1H), 8.02 (dd, 1H), 7.73 (t, J = 8.1 Hz, 1H), 7.56 (d, J = 2.4 Hz, 1H), 7.52 (s, 1H), 7.42 (d, J = 7.7 Hz, 1H), 7.37 (d, 1H), 7.23 (d, 1H), 6.93 (br, 2H), 4.05 (q, J = 5.8 Hz, 2H) |
| 88 | 425.30 | (500 MHz, DMSO-$d_6$): 8.59 (d, J = 2.4 Hz, 1H), 8.07-8.05 (m, 2H), 7.94-7.92 (m, 2H), 7.75 (t, 1H), 7.57 (d, 1H), 7.41 (d, J = 8.4 Hz, 2H), 7.05 (br, 2H), 2.57 (s, 3H) |
| 89 | 408.40 | |
| 90 | 413.30 | (500 MHz, DMSO-$d_6$): 8.48 (d, J = 2.4 Hz, 1H), 8.07-8.04 (m, 2H), 7.75 (t, J = 8.1 Hz, 1H), 7.43 (d, J = 2.4 Hz, 1H), 7.30 (d, J = 8.2 Hz, 2H), 7.18 (d, J = 8.2 Hz, 2H), 7.01 (br, 2H), 4.48 (s, 2H) |
| 91 | 417.30 | |
| 92 | 423.30 | (500 MHz, DMSO-$d_6$): 11.67 (s, 1H), 8.51 (d, J = 2.4 Hz, 1H), 8.08-8.05 (m, 3H), 7.76 (t, J = 8.1 Hz, 1H), 7.76 (s, 1H), 7.51-7.47 (m, 2H), 7.00 (br, 2H), 6.44 (dd, J = 1.8, 3.3 Hz, 1H) |
| 93 | 527.40 | |
| 94 | 466.40 | (500 MHz, DMSO-$d_6$): 9.66 (br, 1H), 8.54 (d, J = 2.4 Hz, 1H), 8.04 (dt, 2H), 7.74 (t, 1H), 7.53 (d, 1H), 7.50 (d, 2H), 7.37 (d, J = 8.2 Hz, 2H), 7.00 (br, 2H), 4.34 (d, J = 5.7 Hz, 2H), 3.37 (mbr, 2H), 3.12 (mbr, 2H), 2.05 (mbr, 2H), 1.86 (mbr, 2H) |
| 95 | 511.50 | (500 MHz, DMSO-$d_6$): 8.55 (d, J = 2.4 Hz, 1H), 8.03 (m, 2H), 7.73 (t, J = 8.1 Hz, 1H), 7.56 (d, J = 2.4 Hz, 1H), 7.51 (d, J = 8.0 Hz, 2H), 7.41 (d, J = 8.1 Hz, 2H), 6.99 (s, 2H), 4.36 (d, 2H), 3.10 (m, 4H), 2.80 (d, J = 3.3 Hz, 6H), 2.71 (s, 3H), 2.15-2.00 (m, 2H) |
| 96 | 510.40 | (500 MHz, DMSO-$d_6$): 9.25 (br, 1H), 8.54 (d, J = 2.4 Hz, 1H), 8.05-8.02 (m, 2H), 7.75 (d, J = 8.1 Hz, 1H), 7.54 (d, J = 2.4 Hz, 1H), 7.48 (d, J = 8.2 Hz, 2H), 7.39-7.37 (m, 2H), 7.00 (br, 2H), 4.30-4.27 (m, 4H), 3.50 (m, 4H), 1.95 (m, 4H), 1.56 (m, 1H) |
| 97 | 496.40 | (500 MHz, DMSO-$d_6$): 9.20 (br, 1H), 8.54 (s, 1H), 8.04 (t, J = 7.9 Hz, 2H), 7.75 (d, J = 8.2 Hz, 1H), 7.54 (d, 1H), 7.52 (d, J = 8.2 Hz, 1H), 7.47 (d, 1H), 7.38 (d, J = 8.2 Hz, 2H), 7.00 (br, 2H), 4.31 (d, J = 4.7 Hz, 2H), 3.95 (s, 2H), 3.35 (m, 2H), 3.16 (m, 2H), 2.00 (m, 2H), 1.80 (m, 2H), 1.55 (m, 1H) |
| 98 | 563.50 | (500 MHz, DMSO-$d_6$): 8.54 (d, J = 2.2 Hz, 1H), 8.03 (t, J = 8.7 Hz, 2H), 7.74 (t, 1H), 7.55 (s, 1H), 7.48 (d, 2H), 7.41 (d, 2H), 6.99 (s, 2H), 4.32 (s, 2H), 3.35 (m, 4H), 2.95 (m, 4H), 2.25 (m, 2H), 1.88 (m, 4H), 1.71 (m, 2H), 1.55 (m, 1H) |
| 99 | 510.40 | (500 MHz, DMSO-$d_6$): 8.55 (dd, 1H), 8.05-8.02 (m, 2H), 7.74 (t, 1H), 7.55 (d, J = 2.4 Hz, 1H), 7.49 (d, J = 8.1 Hz, 2H), 7.39 (dd, J = 3.2, 8.2 Hz, 2H), 6.99 (br, 2H), 4.33-4.29 (m, 4H), 3.36 (m, 4H), 2.93 (m, 2H), 1.85 (m, 2H), 1.68 (m, 1H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 100 | 454.14 | (500 MHz, DMSO-d$_6$): 9.71 (s, 1H), 8.55 (d, J = 2.4 Hz, 1H), 8.06-8.02 (m, 2H), 7.74 (t, 1H), 7.55 (d, 1H), 7.51 (d, 2H), 7.39 (d, J = 8.3 Hz, 2H), 7.00 (br, 2H), 4.51-4.49 (m, 1H), 2.89 (s, H), 2.73 (d, 3H), 2.59 (d, 3H), 2.54 (s, H), 2.50 (qn, J = 1.8 1.61 (d, J = 6.9 Hz, 3H) |
| 101 | 528.40 | |
| 102 | 531.12 | (500 MHz, DMSO-d$_6$): 9.90 (br, 1H), 8.56-8.54 (m, 2H), 8.06 (dd, 1H), 8.01 (dd, 1H), 7.85 (td, J = 7.6, 1.6 Hz, 1H), 7.74 (t, J = 8.2 Hz, 1H), 7.56 (d, 1H), 7.53 (d, 2H), 7.41-7.35 (m, 4H), 7.05 (br, 2H), 4.40 (s, 2H), 3.51-3.48 (m, 2H), 3.28-3.25 (m, 2H), 2.82 (s, 3H) |
| 103 | 510.20 | (500 MHz, DMSO-d$_6$): 8.55 (d, J = 2.4 Hz, 1H), 8.06-8.02 (m, 2H), 7.75 (t, 1H), 7.56 (d, J = 2.4 Hz, 1H), 7.5 (d, 2H), 7.38 (d, 2H), 7.03 (br, 2H), 4.33 (s, 2H), 3.80 (dd, J = 6.3, 9.1 Hz, 2H), 3.28 (d, J = 11.8 Hz, 2H), 2.70-2.66 (m, 2H), 1.30 (d, J = 6.0 Hz, 6H) |
| 104 | | (500 MHz, DMSO-d$_6$): 8.52 (d, J = 2.4 Hz, 1H), 8.06-8.03 (m, 2H), 7.74 (t, J = 8.1 Hz, 1H), 7.52 (d, J = 2.4 Hz, 1H), 7.41 (d, J = 8.1 Hz, 2H), 7.31 (d, J = 8.1 Hz, 2H), 7.01 (br, 2H), 3.95 (s, 2H), 3.73-3.71 (m, 2H), 3.50-3.06 (br, 8H), 3.19 (s, 2H) |
| 105 | 572.20 | (500 MHz, DMSO-d$_6$): 8.79 (d, J = 6.3 Hz, 2H), 8.54 (d, J = 2.4 Hz, 1H), 8.06-8.01 (m, 2H), 7.80 (d, J = 5.8 Hz, 2H), 7.74 (t, J = 8.1 Hz, 1H), 7.56 (d, J = 2.4 Hz, 1H), 7.49 (d, J = 8.2 Hz, 2H), 7.38 (d, J = 8.3 Hz, 2H), 7.05 (br, 2H), 4.31 (s, 2H), 3.86 (s, 2H), 3.35-2.90 (complex, br, 8H) |
| 106 | 495.16 | (500 MHz, DMSO-d$_6$): 8.52 (d, J = 1.8 Hz, 1H), 8.04 (m, 2H), 7.75 (t, 1H), 7.52 (d, J = 2.0 Hz, 1H), 7.41 (d, J = 7.9 Hz, 2H), 7.30 (d, J = 7.9 Hz, 2H), 7.02 (br, 2H), 3.97 (s, 2H), 3.40 (d, J = 11.0 Hz, 2H), 3.16 (br, 3H), 2.74 (br, 2H), 1.20 (d, J = 6.4 Hz, 3H) |
| 107 | 517.20 | (500 MHz, DMSO-d$_6$): 10.20 (br, 1H), 8.77 (d, J = 1.8 Hz, 1H), 8.72 (dd, J = 1.3, 4.9 Hz, 1H), 8.56 (d, J = 2.4 Hz, 1H), 8.09-8.02 (m, 3H), 7.74 (t, J = 8.1 Hz, 1H), 7.61 (dd, 1H), 7.58 (d, 1H), 7.54 (d, 2H), 7.39 (d, J = 8.2 Hz, 2H), 7.10 (br, 2H), 7.35 (s, H), 7.24 (s, H), 7.14 (s, H), 7.04 4.45 (br, 4H), 2.54 (s, 3H) |
| 108 | 509.20 | |
| 109 | 466.11 | (500 MHz, DMSO-d$_6$): 8.48 (d, J = 2.0 Hz, 1H), 8.06 (d, J = 8.1 Hz, 2H), 7.76 (t, J = 8.2 Hz, 1H), 7.70 (d, J = 8.2 Hz, H), 7.46 7.39 (d, J = 1.9 Hz, 1H), 7.30 (t, J = 7.6 Hz, 1H), 7.22 (d, 1H), 7.18 (d, 1H), 7.07 (s, 2H), 6.95 (s, 1H), 3.53 (s, 2H), 2.42 (brs, 4H), 1.71 (br, 4H) |
| 110 | 381.40 | (500 MHz, DMSO-d$_6$): 9.0 (1 H, s), 8.34 (1 H, s), 8.05 (1 H, d), 7.70 (1 H, m), 7.55 (2 H, m), 7.45 (1 H, m), 6.80 (1 H, d), 3.80 (3 H, m) |
| 111 | 402.30 | (500 MHz, DMSO-d$_6$): 9.0 (1 H, s), 8.40 (1 H, s), 7.70 (1 H, m), 7.65 (1 H, m), 7.45-7.20 (5 H, m) |
| 112 | 368.40 | (500 MHz, DMSO-d$_6$): 9.0 (1 H, s), 8.35 (1 H, s), 7.70 (1 H, m), 7.58 (1 H, m), 7.40 (2 H, m), 7.25 (2 H, m), 7.18 (2 H, m) |
| 113 | 375.40 | (500 MHz, methanol-d$_4$): 8.35 (1 H, s), 7.90 (1 H, s), 7.20 (2 H, m), 7.05 (1 H, m), 6.90 (3 H, m) |
| 114 | 384.30 | (500 MHz, methanol-d$_4$): 9.0 (1 H, s), 8.30 (1 H, s), 7.80 (1 H, s), 7.60-7.30 (5 H, m), 7.20 (2 H, m) |
| 115 | 364.40 | (500 MHz, DMSO-d$_6$): 9.0 (1 H, s), 8.0 (1 H, s), 7.70 (1 H, m), 7.55 (1 H, m), 7.45 (1 H, m), 7.15 (3 H, m), 6.90 (2 H, d) |
| 116 | 418.40 | (500 MHz, DMSO-d$_6$): 9.0 (1 H, s), 8.45 (1 H, s), 8.10 (1 H, m), 7.75-7.55 (6 H, m), 7.45 (1 H, m), 7.30 (1 H, m) |
| 117 | 368.40 | (500 MHz, DMSO-d$_6$): 9.0 (1 H, s), 8.00 (1 H, s), 8.10 (1 H, m), 7.70 (1 H, m), 7.55 (1 H, m), 7.45 (1 H, m), 7.25 (1 H, s), 1.85 (6 H, s) |
| 118 | 549.23 | (500 MHz, DMSO-d$_6$): 10.25 (br, 1H), 8.54 (d, J = 2.4 Hz, 1H), 8.05 (dd, 1H), 8.02 (dd, 1H), 7.74 (t, J = 8.1 Hz, 1H), 7.54 (dbr, J = 3H), 7.37 (d, J = 7.5 Hz, 2H), 7.02 (brs, 2H), 4.80-4.30 (broad complex, 11 H), 1.96 (br, 8H) |
| 119 | 482.11 | (500 MHz, DMSO-d$_6$): 10.23 (br, 1H), 8.54 (d, J = 2.4 Hz, 1H), 8.06-8.02 (m, 2H), 7.74 (t, 1H), 7.54-7.48 (m, 3H), 7.40-7.35 (m, 2H), 7.03 (br, 2H), 4.45 (s, 2H), 4.41-4.39 (m, 1H), 3.52-3.46 (m, 2H), 3.19-3.17 (m, 2H), 2.32-2.24 (m, 1H), 2.02-1.95 (m, 1H) |
| 120 | 482.11 | (500 MHz, DMSO-d$_6$): 10.23 (br, 1H), 8.54 (d, J = 2.4 Hz, 1H), 8.04-8.02 (m, 2H), 7.74 (t, 1H), 7.54-7.51 (m, 3H), 7.37-7.35 (m, 2H), 7.02 (br, 2H), 4.46 (s, 2H), 4.41-4.39 (m, 1H), 3.52-3.46 (m, 2H), 3.19-3.11 (m, 2H), 2.30-2.26 (m, 1H), 2.02-1.95 (m, 1H) |
| 121 | 509.11 | (500 MHz, DMSO-d$_6$): 9.62 (br, 1H), 8.53 (d, J = 2.4 Hz, 1H), 8.06-8.03 (m, 2H), 7.90 (s, 1H), 7.75 (t, 1H), 7.62 (s, 1H), 7.52 (d, |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| | | 1H), 7.47 (d, 2H), 7.33 (d, J = 8.2 Hz, 2H), 7.02 (br, 2H), 4.36 (m, 3H), 4.09 (br, 1H), 3.49 (br, 1H), 2.89 (s, H), 2.73 (s, H), 2.54 (s, H), 2.45 (m, 1H), 2.07-2.05 (m, 1H), 1.89-1.83 (m, 2H) |
| 122 | 496.18 | (500 MHz, DMSO-$d_6$): 9.42 (s, 1H), 8.54 (d, J = 2.4 Hz, 1H), 8.06-8.02 (m, 2H), 7.75 (t, 1H), 7.53 (m, 3H), 7.36 (d, J = 8.2 Hz, 2H), 7.02 (sbr, 2H), 4.61-4.50 (m, 2H), 4.33-4.23 (m, 2H), 3.60 (m, 2H), 3.27 (m, 1H), 1.84-1.73 (m, 2H) |
| 123 | 440.08 | (500 MHz, DMSO-$d_6$): 10.63 (s, 1H), 8.57 (d, J = 2.4 Hz, 1H), 8.08 (dd, J = 1.3, 8.0 Hz, 1H), 8.03 (dd, J = 1.3, 8.3 Hz, 1H), 7.74 (t, 1H), 7.69 (m, 2H), 7.46 (d, 2H), 7.33-7.31 (m, 1H), 7.02 (br, 2H), 4.26 (d, J = 5.3 Hz, 2H), 2.71 (d, J = 4.8 Hz, 6H) |
| 124 | 497.14 | (500 MHz, DMSO-$d_6$): 9.51 (sbr, 1H), 8.71 (t, J = 5.6 Hz, 1H), 8.58 (d, J = 2.4 Hz, 1H), 8.07-8.03 (dt, 2H), 7.87 (d, J = 8.4 Hz, 2H), 7.75 (t, J = 8.1 Hz, 1H), 7.55 (d, J = 2.4 Hz, 1H), 7.39 (d, J = 8.4 Hz, 2H), 7.10 (sbr, 2H), 3.61 (q, J = 5.8 Hz, 2H), 3.27 (q, J = 5.8 Hz, 2H), 2.86-2.84 (d, 6H) |
| 125 | 511.16 | (500 MHz, DMSO-$d_6$): 9.65 (sbr, 1H), 8.63 (t, 1H), 8.57 (d, J = 2.4 Hz, 1H), 8.07-8.04 (m, 2H), 7.85 (d, 2H), 7.75 (t, 1H), 7.56 (d, J = 2.4 Hz, 1H), 7.37 (d, J = 8.4 Hz, 2H), 7.12 (sbr, 2H), 3.34 (dd, J = 6.4, 12.4 Hz, 2H), 3.11-3.07 (m, 2H), 2.79 (d, 6H), 1.93-1.87 (m, 2H) |
| 126 | 426.20 | (500 MHz, DMSO-$d_6$): 10.16 (s, 1H), 8.31 (d, J = 1.8 Hz, 1H), 7.82 (q, J = 8.4 Hz, 1H), 7.69 (t, 1H), 7.58 (d, 1H), 7.53 (m, 1H), 7.49 (s, 1H), 7.26 (m, 2H), 6.89 (s, 2H), 2.04 (s, 3H) |
| 127 | 426.20 | (500 MHz, DMSO-$d_6$): 9.72 (s, 1H), 8.51 (d, J = 2.4 Hz, 1H), 7.87 (t, J = 8.3 Hz, 1H), 7.80 (q, J = 7.9 Hz, 1H), 7.70-7.68 (m, 2H), 7.55-7.51 (m, 1H), 7.31 (dd, J = 2.0, 12.4 Hz, 1H), 7.13 (dd, J = 1.6, 8.5 Hz, 1H), 6.85 (br, 2H), 2.08 (s, 3H) |
| 128 | | (500 MHz, DMSO-$d_6$): 9.58 (s, 1H), 8.61 (d, J = 2.5 Hz, 1H), 8.27 (s, 1H), 7.86 (s, 1H), 7.82-7.77 (m, 4H), 7.71-7.67 (m, 3H), 7.53-7.51 (m, 1H), 6.84 (s, 2H) |
| 129 | | (500 MHz, DMSO-$d_6$): 8.52 (d, J = 2.4 Hz, 1H), 8.19 (s, 3H), 7.80 (q, J = 8.4 Hz, 1H), 7.72-7.69 (m, 2H), 7.53 (m, 1H), 7.48-7.44 (m, 4H), 6.80 (s, 2H), 4.43-4.41 (m, 1H), 1.50 (d, 3H) |
| 130 | 450.20 | (500 MHz, DMSO-$d_6$): 11.39 (s, 0.5H), 10.92 (s, 0.5H), 8.61 (d, J = 2.3 Hz, 1H), 8.02 (d, J = 5.2 Hz, 1H), 7.80 (q, J = 8.6 Hz, 1H), 7.71-7.63 (m, 3H), 7.55-7.50 (m, 3H), 4.40-4.29 (m, 3H), 3.52-3.45 (m, 1H), 3.38 (m, 0.5H), 3.26-3.11 (m, 2H), 2.94 (d, J = 11.9 Hz, 0.5H), 2.31-2.24 (m, 0.5H), 2.04-1.99 (m, 0.5H), 1.93-1.83 (m, 1H) |
| 131 | 450.20 | (500 MHz, DMSO-$d_6$): 11.50 (s, 0.5H), 11.01 (s, 0.5H), 8.62 (d, J = 2.2 Hz, 1H), 8.08 (d, J = 6.5 Hz, 1H), 7.81 (q, J = 8.7 Hz, 1H), 7.72-7.64 (m, 3H), 7.55-7.52 (m, 3H), 4.42-4.30 (m, 3H), 3.52-3.47 (m, 1H), 3.37 (m, 0.5H), 3.26-3.18 (m, 2H), 2.94 (d, J = 11.5 Hz, 0.5H), 2.31-2.24 (m, 0.5H), 2.03-1.99 (m, 0.5H), 1.96-1.83 (m, 1H) |
| 132 | 477.20 | (500 MHz, DMSO-$d_6$): 9.70 (s, 1H), 8.60 (d, J = 2.3 Hz, 1H), 8.05 (s, 1H), 7.96 (d, 1H), 7.82 (q, J = 8.6 Hz, 1H), 7.72 (t, 1H), 7.62 (s, 1H), 7.55-7.49 (m, 5H), 4.40 (d, J = 12.2 Hz, 1H), 4.33 (d, J = 9.8 Hz, 1H), 4.14 (q, J = 7.2 Hz, 1H), 3.49 (br, 1H), 3.27 (br, 1H), 2.09-2.02 (m, 1H), 1.91-1.82 (m, 2H) |
| 133 | 464.20 | (500 MHz, DMSO-$d_6$): 10.36 (s, 1H), 8.60 (d, J = 2.2 Hz, 1H), 7.99 (s, 1H), 7.82-7.77 (q, 1H), 7.69 (t, 1H), 7.65 (d, 2H), 7.53 (m, 3H), 4.55 (dd, 1H), 4.25 (dd, 1H), 3.75-3.63 (m, 2H), 3.56 (m, 1H), 3.25-3.22 (m, 1H), 3.15-3.08 (m, 1H), 2.50 (t, J = 1.5 Hz, H), 2.11 (q, J = 6.2 Hz, 2.15-1.75 (m, 4H) |
| 134 | 448.20 | (500 MHz, DMSO-$d_6$): 10.79 (s, 1H), 8.60 (d, J = 2.3 Hz, 1H), 7.99 (d, J = 1.5 Hz, 1H), 7.80 (q, J = 8.4 Hz, 1H), 7.71-7.64 (m, 3H), 7.55-7.50 (m, 3H), 4.23 (d, J = 5.1 Hz, 2H), 3.25 (d, J = 11.7 Hz, 2H), 2.84-2.78 (m, 2H), 1.82-1.77 (m, 5H), 1.38-1.31 (m, 1H) |
| 135 | 465.40 | |
| 136 | 479.29 | |
| 137 | 434.25 | |
| 138 | 408.21 | |
| 139 | 408.10 | (500 MHz, DMSO-$d_6$): 10.01 (s, 1 H), 8.44 (d, J = 2.1 Hz, 1 H), 8.03 (s, 1 H), 7.80 (d, J = 8.7 Hz, 1 H), 7.77 (s, 1 H), 7.71-7.68 (m, 1 H), 7.55-7.51 (m, 1 H), 7.47 (d, J = 8.0 Hz, 1 H), 7.33 (t, J = 7.9 Hz, 1 H), 7.05 (d, J = 7.6 Hz, 1 H), 2.42 (s, 3 H), 2.06 (s, 3 H) |
| 140 | 495.40 | |
| 141 | 424.30 | |
| 142 | 507.40 | |
| 143 | 357.14 | |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 144 | 367.30 | |
| 145 | 367.30 | |
| 146 | 452.30 | (500 MHz, DMSO-$d_6$): 10.36 (s, 1H), 8.61 (d, J = 2.3 Hz, 1H), 8.00 (d, J = 1.6 Hz, 1H), 7.79 (q, J = 8.3 Hz, 1H), 7.71-7.66 (m, 3H), 7.55-7.52 (m, 3H), 4.39-4.32 (m, 2H), 3.81-3.73 (m, 2H), 3.16-3.07 (m, 4H), 1.28 (t, J = 7.2 Hz, 3H) |
| 147 | 477.31 | |
| 148 | 447.24 | (500 MHz, DMSO-$d_6$): 11.37 (s, 1H), 8.60 (d, J = 2.3 Hz, 1H), 7.98 (d, J = 1.8 Hz, 1H), 7.79 (q, J = 8.6 Hz, 1H), 7.71-7.68 (m, 1H), 7.62 (d, 2H), 7.55-7.50 (m, 3H), 4.25 (d, J = 12.6 Hz, 2H), 3.47 (m, 2H), 3.23 (t, 2H), 2.68 (s, 3H) |
| 149 | 422.28 | (500 MHz, DMSO-$d_6$): 10.60 (s, 1H), 8.59 (d, J = 2.4 Hz, 1H), 7.94 (d, J = 1.8 Hz, 1H), 7.79 (q, 1H), 7.71-7.68 (m, 1H), 7.62 (d, J = 8.2 Hz, 2H), 7.55-7.51 (m, 3H), 4.33 (dd, 1H), 4.19 (dd, J = 6.2, 13.0 Hz, 1H), 3.16-3.12 (m, 1H), 3.02-2.97 (m, 1H), 2.61 (d, J = 4.9 Hz, 3H), 1.27 (t, J = 7.3 Hz, 3H) |
| 150 | 450.31 | (500 MHz, DMSO-$d_6$): 10.03 (s, 1H), 8.59 (d, J = 2.4 Hz, 1H), 7.91 (d, J = 2.0 Hz, 1H), 7.82-7.77 (m, 1H), 7.70 (dd, J = 6.5, 8.0 Hz, 1H), 7.63 (d, J = 8.3 Hz, 2H), 7.55-7.51 (m, 3H), 4.32-4.25 (m, 2H), 2.86-2.82 (m, 2H), 2.69 (d, 3H), 2.09 (qn, J = 6.7 Hz, 1H), 0.94 (d, 6H) |
| 151 | 434.40 | (500 MHz, DMSO-$d_6$): 9.53 (br, 1H), 8.58 (d, 1H), 7.92 (d, 1H), 7.81 (q, J = 8.6 Hz, 1H), 7.70 (dd, J = 6.4, 7.9 Hz, 1H), 7.55 (d, 2H), 7.52 (m, 1H), 7.48 (d, J = 8.3 Hz, 2H), 4.00 (t, J = 5.8 Hz, 2H), 3.67-3.61 (m, 1H), 2.28-2.19 (m, 2H), 2.16-2.11 (m, 2H), 1.83-1.72 (m, 2H) |
| 152 | 422.22 | (500 MHz, TFA salt, DMSO-$d_6$): 10.14 (s, 1H), 8.56 (d, J = 2.4 Hz, 1H), 7.82-7.79 (m, 2H), 7.69 (dd, J = 6.4, 8.0 Hz, 1H), 7.58-7.50 (m, 5H), 6.90 (br, 2H), 4.50-4.48 (m, 1H), 2.73 (d, J = 4.7 Hz, 3H), 2.58 (d, 3H), 1.62 (d, J = 6.9 Hz, 3H) |
| 153 | 394.30 | (500 MHz, DMSO-$d_6$): 10.55 (br, 1H), 8.53 (d, J = 2.4 Hz, 1H), 8.32 (sbr, 3H), 7.80 (q, 1H), 7.73 (d, J = 2.2 Hz, 1H), 7.70 (dd, 1H), 7.54-7.53 (m, 1H), 7.49 (d, J = 8.3 Hz, 2H), 7.45 (d, J = 8.4 Hz, 2H), 6.90 (br, 2H), 4.45 (m, 1H), 1.50 (d, J = 6.8 Hz, 3H) |
| 154 | 409.23 | (500 MHz, DMSO-$d_6$): 10.35 (s, 1H), 8.73 (d, J = 2.0 Hz, 1H), 8.63 (d, J = 2.3 Hz, 1H), 8.02 (dd, J = 2.3, 8.1 Hz, 1H), 7.94 (d, J = 2.1 Hz, 1H), 7.78 (q, J = 8.2 Hz, 1H), 7.69-7.61 (m, 2H), 7.53-7.51 (m, 1H), 7.05 (br, 2H), 4.43 (s, 2H), 2.79 (s, 6H) |
| 155 | 381.10 | (500 MHz, DMSO-$d_6$): 8.71 (d, J = 2.3, 1H), 8.69 (d, J = 2.3, 1H), 8.57 (sbr, 3H), 8.15 (d, J = 2.1 Hz, 1H), 8.03 (dd, J = 2.3, 8.2 Hz, 1H), 7.80 (q, J = 8.5 Hz, 1H), 7.69 (dd, J = 6.5, 7.9 Hz, 1H), 7.60 (d, J = 2.9 Hz, 1H), 7.52 (m, 1H), 4.23-4.18 (m, 2H) |
| 156 | 464.32 | (500 MHz, DMSO-$d_6$): 10.50 (s, 1H), 8.59 (d, J = 2.4 Hz, 1H), 7.93 (d, J = 1.9 Hz, 1H), 7.80 (q, J = 8.7 Hz, 1H), 7.69 (t, J = 8.3 Hz, 1H), 7.64 (d, 2H), 7.55-7.51 (m, 3H), 4.34 (d, J = 5.2 Hz, 2H), 2.96-2.88 (m, 4H), 2.50 (qn, J = 1.8 Hz, DMSO-d6), 1.79-1.67 (m, 4H), 0.86 (t, J = 7.4 Hz, 6H) |
| 157 | 450.20 | (500 MHz, DMSO-$d_6$): 9.06 (s, br, 1H), 8.93 (br, 1H), 8.55 (d, J = 2.3 Hz, 1H), 7.94 (d, J = 1.4 Hz, 1H), 7.84-7.79 (m, 1H), 7.71 (dd, J = 6.5, 7.9 Hz, 1H), 7.57-7.53 (m, 1H), 7.47 (d, J = 8.4 Hz, 2H), 3.17 (m, 4H), 2.26-2.20 (m, 2H), 1.74 (d, 2H) |
| 158 | 370.20 | (500 MHz, DMSO-$d_6$): 8.25 (d, J = 2.3 Hz, 1H), 8.19 (d, br, J = 3.2 Hz, 2H), 7.83-7.80 (m, 2H), 7.67 (dd, J = 6.5, 7.9 Hz, 1H), 7.55-7.51 (m, 1H), 5.86 (s, 1H), 3.23 (sbr, 1H), 2.47 (m, 3H), 2.05-2.01 (m, 1H), 1.73-1.66 (m, 1H) |
| 159 | 529.26 | (500 MHz, DMSO-$d_6$): 10.70 (s, 1H), 8.64 (d, J = 2.4 Hz, 1H), 7.98 (d, J = 2.2 Hz, 1H), 7.83-7.78 (m, 3H), 7.71-7.67 (m, 3H), 7.55-7.51 (m, 1H), 3.06-3.02 (m, 4H), 2.73 (d, J = 4.9 Hz, 6H), 2.70 (s, 3H), 1.96-1.90 (m, 2H) |
| 160 | 507.25 | (500 MHz, CDCl$_3$): 9.31 (1 H, s), 8.31 (1 H, s), 7.48 (3 H, m), 7.35 (2 H, m), 7.21 (1 H, m), 6.95 (2 H, d), 6.45 (2 H, s), 3.66 (1 H, dd), 3.55 (1 H, dd), 3.44 (1 H, m), 3.20 (1 H, m), 2.80 (1 H, m), 2.0 (2 H, s), 1.80 (3 H, m), 1.73 (1 H, m) |
| 161 | 476.16 | (500 MHz, DMSO-$d_6$): 10.3 (1 H, s), 8.50 (1 H, s), 8.05 (1 H, s), 7.95-7.80 (5 H, m), 7.51 (1 H, m), 7.4 (2 H, m), 7.20 (1 H, d) |
| 162 | 460.16 | (500 MHz, DMSO-$d_6$): 10.2 (1 H, s), 8.45 (1 H, s), 7.95 (1 H, s), 7.85-7.68 (5 H, m), 7.55 (1 H, m), 7.31 (3 H, m) |
| 163 | 493.24 | (500 MHz, DMSO-$d_6$): 9.80 (1 H, s), 8.45 (1 H, s), 7.85 (1 H, m), 7.75 (1 H, m), 7.61 (3 H, m), 7.55 (1 H, m), 7.25 (2 H, d), 6.71 (2 H, s) 3.70 (4 H, m) 3.61 (4 H, m), 3.0 (2 H, m) |
| 164 | 333.02 | (500 MHz, DMSO-$d_6$): 8.65 (d, J = 2.2 Hz, 1H), 7.84-7.79 (m, 2H), 7.67 (dd, J = 6.5, 8.0 Hz, 1H), 7.56-7.51 (m, 1H), 7.46 (s, 2H), 3.72 (s, 3H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 165 | 426.19 | (500 MHz, DMSO-d$_6$): 10.93 (s, 1H), 8.65 (d, J = 2.4 Hz, 1H), 8.01 (d, J = 2.2 Hz, 1H), 7.81-7.73 (m, 2H), 7.68 (dd, J = 6.5, 7.9 Hz, 1H), 7.57-7.46 (m, 2H), 7.42 (dd, J = 1.6, 8.1 Hz, 1H), 4.31 (d, J = 4.9 Hz, 2H), 2.75 (d, 6H) |
| 166 | 388.16 | (500 MHz, DMSO-d$_6$): 9.43 (s, 1H), 8.65 (d, J = 2.3 Hz, 1H), 8.52 (t, J = 5.6 Hz, 1H), 7.89 (d, J = 2.2 Hz, 1H), 7.80 (q, J = 8.4 Hz, 1H), 7.65 (dd, J = 6.5, 7.9 Hz, 1H), 7.54-7.49 (m, 1H), 7.15 (s, 2H), 3.53 (q, J = 5.8 Hz, 2H), 3.21 (t, J = 5.3 Hz, 2H), 2.82 (d, J = 4.0 Hz, 6H) |
| 167 | 417.23 | (500 MHz, DMSO-d$_6$): 9.44 (s, 1H), 8.28 (s, 1H), 7.78 (q, J = 8.7 Hz, 1H), 7.67-7.64 (m, 1H), 7.54-7.50 (m, 2H), 7.01 (s, 2H), 3.36 (s, 2H), 2.99 (s, 2H), 2.80 (s, 3H), 2.77 (d, J = 4.6 Hz, 6H), 1.87 (m, 2H) |
| 168 | 437.19 | (500 MHz, DMSO-d$_6$): 8.76 (d, J = 6.5 Hz, 2H), 8.31 (s, 1H), 7.81-7.74 (m, 3H), 7.64 (t, 1H), 7.55-7.49 (m, 2H), 7.02 (s, 2H), 4.75 (s, 2H), 3.24 (q, J = 7.0 Hz, 2H), 0.97 (t, J = 7.0 Hz, 3H) |
| 169 | 416.20 | (500 MHz, DMSO-d$_6$): 8.21 (t, J = 2.4 Hz, 1H), 7.79 (m, 1H), 7.67-7.63 (m, 1H), 7.54-7.50 (m, 1H), 7.41 (dd, J = 2.2, 8.7 Hz, 1H), 7.03 (br, 2H), 4.26 (d, J = 6.6 Hz, 1H), 3.24 (d, J = 5.9 Hz, 1H), 2.89-2.85 (m, 4H), 1.59 (br, 3H), 1.12-1.06 (m, 1H), 0.94 (m, 1H) |
| 170 | 388.18 | (500 MHz, DMSO-d$_6$): 8.36 (s, 1H), 7.95 (s, H), 7.78 (q, J = 8.8 Hz, 1H), 7.66 (t, 1H), 7.59 (s, 1H), 7.54-7.49 (m, 1H), 7.11-7.07 (br, 2H), 4.24 (dbr, 1H), 3.47-3.06 (br, 4H), 1.82 (br, 2H) |
| 171 | 434.18 | (500 MHz, DMSO-d$_6$): 8.21 (d, J = 2.2 Hz, 1H), 7.79 (q, J = 8.3 Hz, 1H), 7.65 (dd, J = 6.4, 7.9 Hz, 1H), 7.54-7.49 (m, 1H), 7.41 (d, J = 2.2 Hz, 1H), 7.00 (sbr, 2H), 3.44 (sbr, 8H), 3.31 (s, 6H) |
| 172 | 478.40 | (500 MHz, DMSO-d$_6$): 8.76 (d, J = 6.0 Hz, 2H), 8.26 (d, J = 2.2 Hz, 1H), 7.77 (q, J = 7.9 Hz, 1H), 7.64 (m, 3H), 7.51-7.49 (m, 2H), 7.06 (sbr, 2H), 4.25 (br, 2H), 3.50-2.85 (br, 8H) |
| 173 | 372.30 | (500 MHz, DMSO-d$_6$): 8.36 (d, J = 2.3 Hz, 1H), 7.83-7.78 (m, 1H), 7.67 (dd, J = 6.5, 8.0 Hz, 1H), 7.58 (d, J = 2.3 Hz, 1H), 7.55-7.51 (m, 1H), 7.06 (br, 2H), 3.35 (brs, 2H), 3.07 (brs, 2H), 1.75 (s, 4H) |
| 174 | 346.30 | (500 MHz, DMSO-d$_6$): 8.25 (d, J = 2.3 Hz, 1H), 7.81-7.76 (m, 1H), 7.65 (dd, J = 6.4, 8.0 Hz, 1H), 7.54-7.48 (m, 1H), 7.47 (d, 1H), 7.02 (br, 2H), 2.80 (s, 6H) |
| 175 | 389.40 | (500 MHz, DMSO-d$_6$): 8.25 (d, J = 2.3 Hz, 1H), 7.81-7.76 (m, 1H), 7.65 (dd, J = 6.4, 8.0 Hz, 1H), 7.54-7.48 (m, 1H), 7.47 (d, 1H), 7.02 (br, 2H), 2.80 (s, 6H) |
| 176 | 415.40 | (500 MHz, DMSO-d$_6$): 9.75 (br, 1H), 8.38 (d, J = 2.3 Hz, 1H), 7.79 (q, J = 8.2 Hz, 1H), 7.66 (t, 1H), 7.61 (d, 1H), 7.52-7.51 (m, 1H), 7.08 (sbr, 2H), 3.84-3.79 (m, 2H), 3.60 (dd, J = 6.2, 11.9 Hz, 1H), 3.48-3.21 (br, 2H), 2.81 (s, 6H), 2.28 (br, 1H), 2.04 (br, 1H) |
| 177 | 403.40 | (500 MHz, DMSO-d$_6$): 8.97 (br, 1H), 8.65 (d, J = 2.3 Hz, 1H), 8.22 (d, J = 8.6 Hz, 1H), 7.90 (d, J = 2.3 Hz, 1H), 7.79 (q, J = 8.8 Hz, 1H), 7.65 (dd, J = 6.5, 8.0 Hz, 1H), 7.52-7.51 (m, 1H), 7.12 (s, 2H), 4.44-4.35 (m, 1H), 3.17-3.14 (m, 2H), 2.82 (d, 3H), 2.78 (d, 3H), 1.14 (d, J = 6.7 Hz, 3H) |
| 178 | 387.40 | (500 MHz, DMSO-d$_6$): 10.75 (br, 1H), 8.61 (d, J = 2.2 Hz, 1H), 7.86 (d, J = 2.2 Hz, 1H), 7.80 (q, J = 8.9 Hz, 1H), 7.67-7.64 (m, 1H), 7.54-7.51 (m, 1H), 7.36 (s, 2H), 3.35 (s, 4H), 1.94 (s, 4H) |
| 179 | 399.17 | (500 MHz, DMSO-d$_6$): 8.60 (1 H, s), 7.86 (1 H, d), 7.80 (1 H, m), 7.70 (2 H, m), 7.51 (1 H, m), 7.32 (1 H, d), 7.01 (1 H, s), 2.5 (3 H, s) |
| 180 | 448.25 | (500 MHz, DMSO-d$_6$): 8.48 (s, 1H), 7.83 (dd, J = 8.3, 16.9 Hz, 1H), 7.72 (t, J = 6.5 Hz, 1H), 7.62 (s, 1H), 7.56 (d, J = 5.7 Hz, 1H), 7.27 (d, J = 15.8 Hz, 2H), 7.25 (d, J = 7.7 Hz, 2H), 6.75 (s, 2H), 3.19 (m, 1H), 2.45 (sbr, 2H), 2.28 (brs, 2H), 1.66 (brs, 4H), 1.28 (d, J = 6.1 Hz, 3H) |
| 181 | 448.26 | (500 MHz, DMSO-d$_6$): 10.94 (s, 1H), 8.55 (d, J = 2.3 Hz, 1H), 7.98 (s, 1H), 7.81 (q, J = 8.7 Hz, 1H), 7.72-7.62 (m, 1H), 7.56-7.47 (m, 1H), 7.39 (d, J = 8.1 Hz, 2H), 7.32 (d, J = 8.2 Hz, 2H), 3.51 (t, J = 5.1 Hz, 2H), 3.39-3.31 (m, 2H), 3.09-3.00 (m, 4H), 2.05-1.88 (m, 4H) |
| 182 | 434.18 | (500 MHz, DMSO-d$_6$): 8.47 (d, J = 2.3 Hz, 1H), 8.00 (d, J = 8.1 Hz, 1H), 7.86-7.81 (m, 1H), 7.74-7.70 (m, 2H), 7.55 (dd, J = 7.2, 13.8 Hz, 1H), 7.23 (s, 1H), 7.12 (d, J = 8.4 Hz, 1H), 4.10 (t, J = 8.3 Hz, 2H), 3.14 (t, J = 8.4 Hz, 2H), 2.16 (s, 3H) |
| 183 | 409.17 | (500 MHz, DMSO-d$_6$): 8.67 (s, 1H), 8.45 (d, J = 2.3 Hz, 1H), 7.82 (q, J = 8.4 Hz, 1H), 7.75-7.70 (m, 3H), 7.57-7.50 (m, 1H), 7.41 (d, J = 8.7 Hz, 2H), 7.22 (d, J = 8.6 Hz, 2H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 184 | 477.23 | (500 MHz, DMSO-$d_6$): 10.86 (s, 1H), 10.27 (s, 1H), 8.51 (d, J = 2.3 Hz, 1H), 7.82-7.78 (m, 2H), 7.72-7.69 (m, 1H), 7.64 (d, J = 8.5 Hz, 2H), 7.59-7.52 (m, 1H), 7.40 (d, J = 8.6 Hz, 2H), 4.26 (d, J = 5.1 Hz, 2H), 3.62 (br, 2H), 3.13 (br, 2H), 2.02-1.91 (m, 4H) |
| 185 | 401.10 | (500 MHz, DMSO-$d_6$): 8.55 (1 H, s), 8.10 (1 H, s), 7.80 (1 H, m), 7.69 (2 H, m), 7.50 (1 H, m), 7.45 (1 H, s) |
| 186 | 440.15 | (500 MHz, methanol-$d_4$): 8.35 (1 H, s), 7.65 (1 H, m), 7.60 (1 H, m), 7.51 (1 H, m), 7.45 (1 H, s), 6.85 (2 H, m), 3.85 (2 H, s), 2.55 (4 H, m), 1.80 (4 H, m) |
| 187 | 436.10 | (500 MHz, methanol-$d_4$): 8.55 (1 H, s), 7.95 (1 H, s), 7.65 (1 H, m), 7.60 (1 H, m), 7.55 (1 H, m), 7.50 (1 H, s), 6.95 (1 H, s) |
| 188 | 406.16 | (500 MHz, DMSO-$d_6$): 10.43 (s, 1H), 8.43 (d, J = 2.4 Hz, 1H), 7.83 (q, J = 8.6 Hz, 1H), 7.75 (s, 1H), 7.72-7.69 (m, 1H), 7.54 (dd, J = 8.3, 13.6 Hz, 1H), 7.20 (s, 1H), 7.17 (d, J = 8.0 Hz, 1H), 6.81 (d, J = 8.1 Hz, 1H), 3.48 (s, 2H) |
| 189 | 434.18 | (500 MHz, DMSO-$d_6$): 8.53 (s, 1H), 7.90-7.67 (m, 7H), 7.55-7.52 (m, 1H), 7.39 (d, J = 8.1 Hz, 2H), 3.84 (t, J = 6.8 Hz, 2H), 2.58 (t, J = 8.0 Hz, 2H), 2.12-2.04 (m, 2H) |
| 190 | 406.16 | (500 MHz, DMSO-$d_6$): 7.78 (s, 1H), 7.17-7.06 (m, 2H), 6.93-6.90 (m, 2H), 6.55 (d, J = 7.6 Hz, 1H), 6.21 (d, J = 7.7 Hz, 1H), 6.08 (s, 1H), 2.82 (s, 2H) |
| 191 | 451.20 | (500 MHz, DMSO-$d_6$): 11.17 (s, 1H), 10.14 (s, 1H), 8.54 (d, J = 2.2 Hz, 1H), 7.95 (s, 1H), 7.81 (q, J = 8.7 Hz, 1H), 7.72-7.67 (m, 3H), 7.56-7.52 (m, 1H), 7.42 (d, J = 8.6 Hz, 2H), 4.19 (s, 2H), 2.88 (s, 6H) |
| 192 | 458.18 | (500 MHz, DMSO-$d_6$): 8.50 (d, J = 2.4 Hz, 1H), 7.82 (dd, J = 8.6, 17.5 Hz, 1H), 7.71 (d, J = 8.5 Hz, 2H), 7.57-7.51 (m, 2H), 7.35 (s, 4H), 4.15 (d, J = 6.1 Hz, 2H), 2.86 (s, 3H) |
| 193 | 436.23 | (500 MHz, methanol-$d_4$): 8.35 (1 H, s), 8.10 (1 H, s), 7.70 (1 H, m), 7.63 (3 H, m), 7.53 (1 H, m), 7.25 (2 H, d), 2.60 (1 H, m), 1.20 (6 H, d) |
| 194 | 450.18 | (500 MHz, methanol-$d_4$): 8.39 (1 H, s), 8.08 (1 H, s), 7.70 (1 H, m), 7.60 (3 H, m), 7.51 (1 H, m), 7.25 (2 H, d), 1.30 (9 H, s) |
| 195 | 436.17 | (500 MHz, methanol-$d_4$): 8.39 (1 H, s), 8.13 (1 H, s), 7.70 (1 H, m), 7.65 (3 H, m), 7.55 (1 H, m), 7.25 (2 H, d), 2.35 (2 H, t), 1.72 (2 H, m), 1.0 (3 H, t) |
| 196 | 480.15 | (500 MHz, methanol-$d_4$): 8.39 (1 H, s), 8.12 (1 H, s), 7.65 (4 H, m), 7.52 (1 H, m), 7.22 (2 H, d), 4.20 (2 H, q), 3.45 (2 H, s), 1.25 (3 H, t) |
| 197 | 464.19 | (500 MHz, methanol-$d_4$): 8.40 (1 H, s), 7.75-7.45 (6 H, m), 7.15 (2 H, d), 2.20 (1 H, q), 1.70 (2 H, m), 1.55 (2 H, m), 0.95 (6 H, m) |
| 198 | 434.18 | (500 MHz, methanol-$d_4$): 8.35 (1 H, s), 7.65 (1 H, m), 7.60 (1 H, m), 7.52 (4 H, m), 7.10 (2 H, d), 1.75 (1 H, m), 0.95 (2 H, m), 0.85 (2 H, m) |
| 199 | 463.19 | (500 MHz, methanol-$d_4$): 8.35 (1 H, s), 7.65 (1 H, m), 7.60 (1 H, m), 7.52 (4 H, m), 7.12 (2 H, d), 2.20 (2 H, s), 0.95 (2 H, m), 1.05 (9 H, s) |
| 200 | 394.21 | (500 MHz, DMSO-$d_6$): 9.28 (s, 2H), 8.59 (d, J = 2.3 Hz, 1H), 7.98 (s, 1H), 7.80 (dd, J = 8.5, 17.5 Hz, 1H), 7.72-7.69 (m, 1H), 7.57-7.53 (m, 5H), 4.10 (t, J = 5.6 Hz, 2H) |
| 201 | 366.17 | (500 MHz, DMSO-$d_6$): 8.50 (d, J = 2.4 Hz, 1H), 7.94 (d, J = 1.8 Hz, 1H), 7.79 (q, J = 8.7 Hz, 1H), 7.71-7.68 (m, 1H), 7.56-7.52 (m, 1H), 7.48 (t, J = 7.9 Hz, 1H), 7.39-7.36 (m, 2H), 7.29 (d, J = 7.9 Hz, 1H) |
| 202 | 380.24 | (500 MHz, DMSO-$d_6$): 8.58 (d, J = 2.3 Hz, 1H), 8.42 (s, br, 3H), 7.94 (s, 1H), 7.80 (q, J = 8.6 Hz, 1H), 7.72-7.69 (m, 1H), 7.55-7.46 (m, 5H), 4.01 (q, J = 5.5 Hz, 2H) |
| 203 | 448.26 | (500 MHz, DMSO-$d_6$): 8.56 (d, J = 2.3 Hz, 1H), 8.06 (s, 1H), 7.81 (q, J = 8.7 Hz, 1H), 7.71-7.68 (m, 1H), 7.56-7.52 (m, 1H), 7.40 (d, J = 8.2 Hz, 2H), 7.26 (d, J = 8.1 Hz, 2H), 4.37 (s, 2H), 3.24-3.21 (m, 2H), 2.29 (t, J = 8.1 Hz, 2H), 1.91 (m, 2H) |
| 204 | 420.04 | (500 MHz, DMSO-$d_6$): 11.08 (s, 1H), 8.49 (d, J = 2.2 Hz, 1H), 7.80 (dd, J = 8.5, 8.2 Hz, 1H), 7.71-7.59 (m, 3H), 7.53-7.46 (m, 1H), 7.46 (s, 1H), 6.92 (d, J = 8.1 Hz, 1H) |
| 205 | 424.07 | (500 MHz, DMSO-$d_6$): 8.72 (s, 3H), 8.54 (d, J = 2.4 Hz, 1H), 7.79 (q, J = 8.7 Hz, 1H), 7.74 (d, J = 2.4 Hz, 1H), 7.71-7.64 (m, 1H), 7.55-7.45 (m, 5H), 6.85 (s, 2H), 5.13 (s, 1H) |
| 206 | 438.37 | (500 MHz, DMSO-$d_6$): 8.96 (s, 3H), 8.55 (d, J = 2.4 Hz, 1H), 7.81-7.77 (m, 2H), 7.70-7.68 (m, 1H), 7.58-7.44 (m, 5H), 5.31 (br, 1H), 3.73 (s, 3H) |
| 207 | 451.14 | (500 MHz, DMSO-$d_6$): 8.52 (d, J = 2.4 Hz, 1H), 7.89 (s, 1H), 7.81 (q, J = 8.7 Hz, 1H), 7.71-7.69 (m, 1H), 7.54 (dd, J = 8.2, 13.6 Hz, 1H), 7.36-7.31 (m, 4H), 3.59 (s, 3H), 1.50 (s, 6H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 208 | 492.10 | (500 MHz, DMSO-d$_6$): 11.30 (s, 1H), 8.57 (d, J = 2.3 Hz, 1H), 7.88 (s, 1H), 7.79 (q, J = 8.6 Hz, 1H), 7.69-7.67 (m, 1H), 7.60 (d, J = 8.2 Hz, 2H), 7.57-7.51 (m, 3H), 5.50 (d, J = 8.6 Hz, 1H), 3.73 (s, 4H), 3.25 (br, 1H), 2.95 (br, 2H), 2.09-1.80 (m, 4H) |
| 209 | 448.20 | (500 MHz, DMSO-d$_6$): 10.73 (s, 1H), 8.60 (d, J = 2.3 Hz, 1H), 7.99 (s, 1H), 7.80 (q, J = 8.7 Hz, 1H), 7.71 (m, 1H), 7.65 (d, J = 8.2 Hz, 2H), 7.53 (m, 3H), 4.49 (dd, J = 4.0, 13.0 Hz, 1H), 4.13 (dd, J = 7.2, 13.0 Hz, 1H), 3.44 (m, 1H), 3.24-3.20 (m, 1H), 3.10-3.03 (m, 1H), 2.22-2.17 (m, 1H), 1.94-1.84 (m, 2H), 1.71-1.63 (m, 1H), 1.37 (d, J = 6.4 Hz, 3H) |
| 210 | 462.22 | |
| 211 | 448.20 | (500 MHz, DMSO-d$_6$): 11.55 (s, 1H), 8.59 (s, 1H), 7.98 (s, 1H), 7.80 (q, J = 8.5 Hz, 1H), 7.71 (d, J = 7.6 Hz, 3H), 7.56-7.50 (m, 3H), 4.39 (t, J = 7.0 Hz, 1H), 3.67 (br, 1H), 3.10 (m, 1H), 2.90-2.79 (m, 2H), 2.00-1.76 (m, 4H), 1.63 (d, J = 6.5 Hz, 3H) |
| 212 | 448.20 | (500 MHz, DMSO-d$_6$): 11.37 (s, 1H), 8.57 (d, J = 2.3 Hz, 1H), 7.91 (s, 1H), 7.80 (q, J = 8.6 Hz, 1H), 7.71-7.67 (m, 3H), 7.55-7.48 (m, 3H), 4.40-4.36 (m, 1H), 3.66 (m, J = 5.4 Hz, 1H), 3.12-3.08 (m, 1H), 2.91-2.79 (m, 1H), 1.99-1.76 (m, 4H), 1.63 (d, J = 6.7 Hz, 3H) |
| 213 | 452.24 | (500 MHz, DMSO-d$_6$): 11.12 (s, 1H), 8.63 (d, J = 2.3 Hz, 1H), 7.97 (s, 1H), 7.81-7.77 (m, 2H), 7.69-7.67 (m, 1H), 7.54-7.50 (m, 1H), 7.44 (d, J = 11.5 Hz, 1H), 7.38 (d, J = 11.5 Hz, 1H), 3.41 (br, 2H), 3.05 (br, 2H), 2.01-1.88 (m, 4H) |
| 214 | 419.10 | |
| 215 | 419.10 | |
| 216 | 419.10 | |
| 217 | 393.10 | |
| 218 | 393.10 | |
| 219 | 393.10 | |
| 220 | 397.10 | |
| 221 | 381.10 | |
| 222 | 381.10 | |
| 223 | 369.10 | |
| 224 | 385.10 | |
| 225 | 385.10 | |
| 226 | 385.10 | |
| 227 | 376.00 | |
| 228 | 376.00 | |
| 229 | 375.00 | |
| 230 | 381.00 | |
| 231 | 381.00 | |
| 232 | 381.00 | |
| 233 | 351.10 | |
| 234 | 394.30 | |
| 235 | 409.00 | |
| 236 | 393.10 | |
| 237 | 393.10 | |
| 238 | 396.00 | |
| 239 | 396.00 | |
| 240 | 409.10 | |
| 241 | 365.10 | |
| 242 | 365.40 | |
| 243 | 419.00 | |
| 244 | 403.00 | |
| 245 | 394.00 | |
| 246 | 379.00 | |
| 247 | 367.00 | |
| 248 | 341.00 | |
| 249 | 355.00 | |
| 250 | 428.90 | |
| 251 | 397.00 | |
| 252 | 397.00 | |
| 253 | 444.00 | |
| 254 | 444.00 | |
| 255 | 365.10 | |
| 256 | 449.10 | (500 MHz, DMSO-d$_6$): 11.20 (s, 1H), 8.52 (d, J = 2.3 Hz, 1H), 7.84-7.80 (m, 2H), 7.73-7.70 (m, 1H), 7.61 (d, J = 8.7 Hz, 2H), 7.54 (dd, J = 8.5, 13.4 Hz, 1H), 7.39 (d, J = 8.8 Hz, 2H), 4.45 (s, 2H) |
| 257 | 449.10 | (500 MHz, DMSO-d$_6$): 10.79 (s, 1H), 8.56 (d, J = 2.3 Hz, 1H), 8.39 (s, 1H), 7.98 (s, 1H), 7.82 (dd, J = 8.7, 17.6 Hz, 1H), 7.71 (t, J = 6.5 Hz, 1H), 7.56-7.52 (m, 1H), 7.36 (d, J = 8.3 Hz, 2H), 7.44 (d, J = 8.4 Hz, 2H), 5.19 (s, 1H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 258 | 420.10 | (500 MHz, DMSO-$d_6$): 10.03 (brs, 1H), 8.94 (brs, 1H), 8.57 (d, J = 2.3 Hz, 1H), 7.90 (s, 1H), 7.83-7.78 (m, 1H), 7.72-7.69 (m, 1H), 7.58-7.53 (m, 3H), 7.48 (d, J = 8.3 Hz, 2H), 4.65-4.54 (m, 1H), 3.36-3.25 (m, 2H), 2.37-2.34 (m, 1H), 2.15-1.97 (m, 3H) |
| 259 | 477.10 | (500 MHz, DMSO-$d_6$): 10.92 (s, 1H), 10.41 (s, br, 1H), 8.44 (d, J = 2.3 Hz, 1H), 7.85 (s, 1H), 7.83-7.79 (m, 1H), 7.76 (s, 1H), 7.70 (dd, J = 6.5, 7.9 Hz, 1H), 7.57-7.55 (m, 1H), 7.52 (d, J = 8.3 Hz, 1H), 7.38 (t, J = 7.9 Hz, 1H), 7.12 (d, J = 7.6 Hz, 1H), 4.27 (d, J = 5.3 Hz, 2H), 3.65 (m, br, 2H), 3.17-3.15 (m, br, 2H), 2.07-1.92 (m, 4H) |
| 260 | 436.10 | (500 MHz, DMSO-$d_6$): 9.94 (s, 1H), 8.45 (d, J = 2.4 Hz, 1H), 7.88 (s, 1H), 7.80-7.75 (m, 2H), 7.69 (dd, J = 6.4, 7.9 Hz, 1H), 7.54-7.48 (m, 2H), 7.31 (t, J = 7.9 Hz, 1H), 7.02 (d, J = 7.7 Hz, 1H), 2.62 (qn, J = 6.8 Hz, 1H), 1.11 (d, J = 6.8 Hz, 6H) |
| 261 | 434.10 | (500 MHz, DMSO-$d_6$): 10.25 (s, 1H), 8.43 (d, J = 2.3 Hz, 1H), 7.80-7.74 (m, 3), 7.69-7.67 (m, 1H), 7.51 (dd, J = 8.4, 13.6 Hz, 1H), 7.44 (d, J = 8.0 Hz, 1H), 7.30 (t, J = 7.9 Hz, 1H), 7.00 (d, J = 7.7 Hz, 1H), 1.82-1.77 (m, 1H), 0.84-0.78 (m, 4H) |
| 262 | 454.15 | (500 MHz, CDCl$_3$): 8.44 (1 H, s), 7.53 (1 H, m), 7.41 (1 H, m), 7.37 (1 H, m), 7.29 (1 H, s), 6.85 (1 H, d), 6.61 (1 H, d), 6.50 (2 H, s), 3.61 (1 H, q), 2.60 (2 H, m), 2.50 (2 H, m), 1.80 (4 H, m), 1.41 (3 H, d) |
| 263 | 413.90 | (500 MHz, CDCl$_3$): 8.31 (1 H, s), 7.60 (1 H, m), 7.50 (1 H, m), 7.40 (1 H, m), 7.30 (1 H, s), 6.55 (1 H, d), 6.40 (1 H, d), 2.10 (3 H, s) |
| 264 | 478.20 | (500 MHz, DMSO-$d_6$): 10.78 (s, 1H), 8.61 (d, J = 2.3 Hz, 1H), 8.03 (d, J = 1.6 Hz, 1H), 7.80 (q, J = 8.8 Hz, 1H), 7.72-7.69 (m, 1H), 7.64 (d, J = 8.2 Hz, 2H), 7.55-7.51 (m, 3H), 4.53 (dd, J = 4.1, 13.0 Hz, 1H), 4.25 (dd, J = 6.9, 13.0 Hz, 1H), 3.78 (dd, J = 7.4, 10.6 Hz, 1H), 3.72-3.67 (m, 1H), 3.53 (dd, J = 4.1, 10.7 Hz, 1H), 3.28 (s, 3H), 3.28-3.22 (m, 1H), 3.14-3.03 (m, 1H), 2.19-2.05 (m, 1H), 2.02-1.82 (m, 2H), 1.76-1.64 (m, 1H) |
| 265 | 462.20 | |
| 266 | 418.20 | (500 MHz, DMSO-$d_6$): 8.51 (d, J = 2.4 Hz, 1H), 7.82 (dd, J = 8.7, 17.6 Hz, 1H), 7.72-7.69 (m, 2H), 7.57-7.51 (m, 3H), 7.41 (d, J = 8.4 Hz, 2H), 1.68 (s, 6H) |
| 267 | 462.20 | (500 MHz, DMSO-$d_6$): 10.44 (s, 1H), 8.58 (d, J = 2.4 Hz, 1H), 7.90 (s, 1H), 7.79 (q, J = 8.8 Hz, 1H), 7.74 (d, J = 8.3 Hz, 2H), 7.70 (dd, J = 6.5, 7.9 Hz, 1H), 7.55-7.49 (m, 3H), 4.28 (dd, J = 6.6, 13.5 Hz, 1H), 4.21 (dd, J = 6.1, 13.5 Hz, 1H), 3.79-3.76 (m, 1H), 3.63 (m, 1H), 2.32-2.09 (m, 2H), 1.76-1.59 (m, 2H), 1.28 (d, J = 6.8 Hz, 3H), 1.18 (d, J = 6.6 Hz, 3H) |
| 268 | 409.10 | (500 MHz, DMSO-$d_6$): 8.47 (d, J = 2.4 Hz, 1H), 7.83 (q, J = 8.8 Hz, 1H), 7.72 (dd, J = 6.4, 7.9 Hz, 1H), 7.63-7.50 (m, 2H), 7.44 (d, J = 8.4 Hz, 2H), 7.24 (d, J = 8.4 Hz, 2H), 6.76 (s, 2H), 4.97 (s, 1H), 1.41 (s, 6H) |
| 269 | 463.10 | |
| 270 | 492.10 | |
| 271 | 468.00 | |
| 272 | 486.10 | |
| 273 | 493.10 | |
| 274 | 499.10 | |
| 275 | 491.10 | |
| 276 | 463.10 | |
| 277 | 468.10 | |
| 278 | 486.10 | |
| 279 | 499.10 | |
| 280 | 471.10 | |
| 281 | 437.10 | |
| 282 | 491.10 | |
| 283 | 411.00 | |
| 284 | 426.10 | |
| 285 | 431.10 | |
| 286 | 384.00 | |
| 287 | 434.00 | |
| 288 | 387.00 | |
| 289 | 422.00 | |
| 290 | 399.10 | |
| 291 | 403.10 | |
| 292 | 385.00 | |
| 293 | 384.00 | |
| 294 | 387.10 | |
| 295 | 385.00 | |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 296 | 441.10 | |
| 297 | 402.10 | |
| 298 | 381.00 | |
| 299 | 397.00 | |
| 300 | 480.10 | |
| 301 | 387.00 | |
| 302 | 426.10 | |
| 303 | 402.00 | |
| 304 | 403.10 | |
| 305 | 395.10 | |
| 306 | 411.10 | |
| 307 | 405.00 | |
| 308 | 423.00 | |
| 309 | 411.10 | |
| 310 | 431.00 | |
| 311 | 384.00 | |
| 312 | 411.10 | |
| 313 | 369.00 | |
| 314 | 369.10 | |
| 315 | 395.10 | |
| 316 | 409.10 | |
| 317 | 409.10 | |
| 318 | 370.00 | |
| 319 | 370.10 | |
| 320 | 464.10 | |
| 321 | 402.10 | |
| 322 | 402.00 | |
| 323 | 377.10 | |
| 324 | 448.10 | (500 MHz, DMSO-$d_6$): 8.48 (d, J = 2.4 Hz, 1H), 7.80 (dd, J = 8.6, 17.6 Hz, 1H), 7.71-7.69 (m, 2H), 7.55-7.51 (m, 1H), 7.36 (d, J = 5.1 Hz, 2H), 7.19 (s, 1H), 7.08-7.06 (m, 1H), 3.50 (s, 2H), 1.32 (s, 6H) |
| 325 | 450.00 | (500 MHz, DMSO-$d_6$): 8.50 (d, J = 2.1 Hz, 1), 7.82 (q, J = 8.7 Hz, 1H), 7.73-7.70 (m, 1H), 7.67 (d, J = 2.0 Hz, 1H), 7.57-7.53 (m, 2H), 7.35 (d, J = 8.4 Hz, 2H), 7.32 (d, J = 8.3 Hz, 2H), 4.61 (t, J = 5.8 Hz, 1H), 4.20-4.16 (m, 1H), 4.09-4.05 (m, 1H), 2.19-2.07 (m, 1H), 1.82-1.77 (m, 1H) |
| 326 | 537.20 | (500 MHz, DMSO-$d_6$): 8.55 (s, 1 H), 8.40 (d, J = 2.4 Hz, 1 H), 7.76 (dd, J = 8.6, 16.4 Hz, 1 H), 7.69 (dd, J = 6.4, 8.1 Hz, H), 7.61 (d, J = 2.4 Hz, H), 7.54-7.49 (m, H), 7.24-7.20 (m, H), 6.90-6.84 (m, H), 6.57 (d, J = 8.0 Hz, H), 4.15 (dd, J = 8.2, 14.9 Hz, H), 3.61 (s, 3 H), 1.72-1.40 (m, 2 H), 0.93-0.85 (m, 6 H) |
| 327 | 495.10 | |
| 328 | 465.20 | (500 MHz, DMSO-$d_6$): 8.39 (d, J = 2.4 Hz, H), 8.25 (s, H), 7.77 (dd, J = 8.4, 16.5 Hz, H), 7.70 (dd, J = 6.5, 7.9 Hz, H), 7.62 (d, J = 2.3 Hz, H), 7.55-7.51 (m, H), 7.21-7.14 (m, H), 6.79 (d, J = 7.5 Hz, H), 6.00 (s, H), 1.30 (s, 9 H) |
| 329 | 477.20 | (500 MHz, DMSO-$d_6$): 8.40 (d, J = 2.4 Hz, H), 8.25 (s, H), 7.80-7.68 (m, H), 7.62 (d, J = 2.4 Hz, H), 7.55-7.50 (m, H), 7.20 (s, H), 7.19 (dd, J = 7.5, 20.4 Hz, H), 6.82 (s, H), 6.81 (td, J = 4.3, 2.1 Hz, H), 6.18 (d, J = 6.8 Hz, H), 3.98 (s, H), 3.94 (qn, J = 6.5 Hz, H), 1.88-1.82 (m, H), 1.70-1.50 (m, H), 1.44-1.29 (m, H) |
| 330 | 537.20 | (500 MHz, DMSO-$d_6$): 8.59 (s, H), 8.44 (d, J = 2.4 Hz, H), 7.82 (dd, J = 8.7, 16.4 Hz, H), 7.73-7.70 (m, H), 7.60 (d, J = 2.3 Hz, H), 7.57-7.53 (m, H), 7.38 (d, J = 8.7 Hz, H), 7.21 (d, J = 8.6 Hz, H), 6.31 (d, J = 8.3 Hz, H), 4.15 (dd, J = 8.2, 14.8 Hz, H), 3.61 (s, 3 H), 1.69-1.58 (m, H), 1.49-1.40 (m, H), 0.92-0.85 (m, 6 H) |
| 331 | 495.20 | |
| 332 | 465.10 | (500 MHz, DMSO-$d_6$): 8.43 (d, J = 2.4 Hz, H), 8.28 (s, H), 7.86 (s, H), 7.84 (dd, J = 8.6, 16.5 Hz, H), 7.72 (dd, J = 6.5, 7.9 Hz, H), 7.60-7.54 (m, H), 7.34 (d, J = 8.7 Hz, 2 H) 7.17 (d, J = 8.7 Hz, 2H), 5.98 (s, H), 1.29 (s, 9 H) |
| 333 | 477.20 | (500 MHz, DMSO-$d_6$): 8.43 (d, J = 2.4 Hz, H), 8.30 (s, H), 7.82 (d, J = 8.7, 16.5 Hz, H), 7.71 (dd, J = 6.5, 7.9 Hz, H), 7.63 (d, J = 2.3 Hz, H), 7.57-7.53 (m, H), 7.37 (d, J = 8.7 Hz, 2 H), 7.19 (d, J = 8.7 Hz, 2 H), 6.16 (d, J = 6.7 Hz, H), 3.94 (dd, J = 6.2, 12.7 Hz, H), 3.91 (s, H), 1.87-1.81 (m, 2 H), 1.68-1.49 (m, 4 H), 1.39-1.33 (m, 2 H) |
| 334 | 433.10 | |
| 335 | 462.10 | (500 MHz, DMSO-$d_6$): 8.53 (d, J = 2.3 Hz, 0.5), 8.51 (d, J = 2.4 Hz, 0.5H), 7.96 (s, 1H), 7.83-7.78 (m, 1H), 7.70 (t, J = 6.6 Hz, 1H), 7.54 (dd, J = 8.3, 13.6 Hz, 1H), 7.39 (d, J = 8.3 Hz, 1H), 7.31 (d, J = 8.3 Hz, 1H), 7.22 (d, J = 8.3 Hz, 1H), 7.17 (d, J = 8.3 Hz, |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| | | 1H), 5.04 (d, J = 8.0 Hz, 0.5H), 5.00 (dd, J = 2.6, 8.0 Hz, 0.5H), 3.77-3.50 (m, 1H), 2.40-2.15 (m, 1H), 2.02 (s, 1.5H), 1.92-1.70 (m, 3H), 1.69 (s, 1.5H) |
| 336 | 445.10 | (500 MHz, DMSO-$d_6$): 8.51 (d, J = 2.4 Hz, 1H), 7.94 (s, 1H), 7.79 (dd, J = 8.6, 16.4 Hz, 1H), 7.68 (dd, J = 6.4, 7.9 Hz, 1H), 7.55-7.48 (m, 3H), 6.80 (d, J = 9.1 Hz, 1H), 3.54 (t, J = 6.5 Hz, 4H), 1.95 (m, 4H) |
| 337 | 422.09 | (500 MHz, CDCl$_3$): 7.94 (s, H), 7.53-7.48 (m, H), 7.42-7.37 (m, 3 H), 7.12 (d, J = 7.9 Hz, H), 7.05 (d, J = 8.3 Hz, 2 H), 3.41 (s, 3 H), 1.97 (s, 3 H) |
| 338 | 424.00 | (500 MHz, methanol-$d_4$): 8.41-8.39 (m, H), 7.74 (s, H), 7.71 (dd, J = 8.7, 17.2 Hz, H), 7.65-7.61 (m, H), 7.57-7.50 (m, H), 7.23-7.21 (m, H), 3.39 (s, H) |
| 339 | 491.10 | (500 MHz, DMSO-$d_6$): 9.85 (s, 1H), 9.81 (s, 1H), 8.51 (d, J = 2.4 Hz, 1H), 7.78 (dd, J = 8.5, 16.4 Hz, 1H), 7.71-7.67 (m, 2H), 7.60 (d, J = 8.0 Hz, 1H), 7.54-7.50 (m, 1H), 7.38 (s, 2H), 6.88 (sbr, 2H), 4.31 (d, J = 5.7 Hz, 2H), 3.39-3.32 (m, 2H), 3.11-3.05 (m, 2H), 2.11 (d, J = 27.3 Hz, 3H), 2.04-2.01 (m, 2H), 1.89-1.87 (m, 2H) |
| 340 | 479.10 | (500 MHz, DMSO-$d_6$): 9.72 (s, 1H), 8.68 (d, J = 2.5 Hz, 1H), 8.17 (d, J = 1.9 Hz, 1H), 8.03 (dd, J = 1.9, 8.1 Hz, 1H), 7.92 (d, J = 2.5 Hz, 1H), 7.87 (d, J = 8.1 Hz, 1H), 7.81-7.76 (m, 1H), 7.68 (dd, J = 6.5, 7.9 Hz, 1H), 7.54-7.50 (m, 1H), 7.01 (s, 2H), 4.67 (d, J = 4.6 Hz, 2H), 3.51-3.26 (m, 4H), 2.08-1.90 (m, 4H) |
| 341 | 405.10 | (500 MHz, DMSO-$d_6$): 8.50 (d, J = 2.4 Hz, 1H), 7.99 (s, 1H), 7.82-7.72 (m, 2H), 7.69-7.66 (m, 1H), 7.57 (d, J = 2.2 Hz, 1H), 7.54-7.49 (m, 2H), 6.74 (d, J = 8.9 Hz, 1H), 2.79 (s, 3H) |
| 342 | 438.10 | (500 MHz, CDCl$_3$): d 8.31 (d, 1 H), 8.22 (1 H, br s), 7.52-7.40 (3 H, m), 7.39-7.25 (3 H, m), 6.96 (2 H, d), 6.85 (2 H, br s), 3.95 (2 H, s), 3.42 (3 H, s) |
| 343 | 450.10 | (500 MHz, DMSO-$d_6$): 10.99 (s, 1H), 8.58 (d, J = 2.4 Hz, 1H), 7.93 (dd, J = 1.5, 15.1 Hz, 1H), 7.93 (s, 1H), 7.87-7.84 (m, 1H), 7.64 (d, J = 8.3 Hz, 2H), 7.54 (td, J = 8.2, 3.1 Hz, 1H), 7.49 (d, J = 8.3 Hz, 2H), 4.32 (d, J = 5.9 Hz, 2H), 3.35-3.30 (m, 2H), 3.06-3.00 (m, 2H), 2.05-1.85 (m, 2H) |
| 344 | 424.00 | (500 MHz, DMSO-$d_6$): 10.00 (s, 1H), 8.42 (d, J = 2.3 Hz, 1H), 7.92 (dt, J = 1.5, 8.4 Hz, 1H), 7.85 (dt, J = 1.4, 8.1 Hz, 1H), 7.79 (d, J = 2.0 Hz, 1H), 7.72 (s, 1H), 7.53 (dt, J = 1.0, 8.2 Hz, 1H), 7.46 (d, J = 8.3 Hz, 1H), 7.30 (t, J = 7.9 Hz, 1H), 6.98 (d, J = 7.7 Hz, 1H), 2.06 (s, 3H) |
| 345 | 427.30 | |
| 346 | 464.40 | |
| 347 | 391.10 | |
| 348 | 413.50 | |
| 349 | 431.40 | |
| 350 | 399.30 | |
| 351 | 408.10 | (500 MHz, DMSO-$d_6$): 9.59 (brs, 1H), 9.16 (br, 1H), 8.57 (d, J = 2.4 Hz, 1H), 7.92 (d, J = 1.8 Hz, 1H), 7.83-7.78 (m, 1H), 7.71-7.68 (m, 1H), 7.57 (d, J = 8.4 Hz, 2H), 7.54-7.52 (m, 1H), 7.50 (d, J = 8.3 Hz, 2H), 4.33-4.26 (m, 1H), 2.38 (t, J = 5.4 Hz, 3H), 1.55 (d, J = 6.9 Hz, 3H) |
| 352 | 424.07 | (500 MHz, CDCl$_3$): 8.40 (d, J = 2.3 Hz, H), 7.41-7.37 (m, 2 H), 7.32 (d, J = 2.2 Hz, H), 7.02 (dd, J = 1.9, 6.7 Hz, 2 H), 6.80 (s, H), 6.71 (s, H), 3.80 (s, 3 H) |
| 353 | 444.10 | (500 MHz, methanol-$d_4$): 8.39 (s, H), 7.95 (s, H), 7.71-7.63 (m, 2 H), 7.53 (d, J = 4.7 Hz, 2 H), 7.28-7.25 (m, 3 H), 2.96 (s, 3 H) |
| 354 | 499.20 | (500 MHz, DMSO-$d_6$): 8.49 (d, J = 2.4 Hz, 1H), 7.81-7.77 (m, 1H), 7.70 (dd, J = 6.4, 8.0 Hz, 1H), 7.55 (s, H), 7.53 (dd, J = 1.7, 5.3 Hz, 1H), 6.99 (d, J = 8.3 Hz, 2H), 6.93-6.90 (m, 2H), 4.09 (dd, J = 5.7, 9.4 Hz, 4H), 3.69-3.64 (m, 4H), 3.34 (s, 3H), 3.32 (s, 3H) |
| 355 | 463.00 | (500 MHz, DMSO-$d_6$): 8.66 (s, 1H), 8.50 (d, J = 2.4 Hz, 1H), 7.81 (dd, J = 8.7, 16.6 Hz, 1H), 7.72-7.70 (m, 2H), 7.57-7.52 (m, 1H), 7.38 (d, J = 8.4 Hz, 2H), 7.34 (d, J = 8.4 Hz, 2H), 2.86 (s, 3H) |
| 356 | 432.10 | (500 MHz, DMSO-$d_6$): 10.93 (s, 1H), 8.57 (d, J = 2.4 Hz, 1H), 8.03 (d, J = 1.7 Hz, 1H), 7.81 (t, J = 1.9 Hz, 1H), 7.71-7.69 (m, 1H), 7.64-7.62 (m, 3H), 7.60-7.58 (m, 1), 7.55 (d, J = 8.3 Hz, 2H), 4.33 (d, J = 5.9 Hz, 2H), 3.34-3.32 (m, 2H), 3.07-3.00 (m, 2H), 2.05-1.88 (m, 4H) |
| 357 | 448.10 | (500 MHz, DMSO-$d_6$): 8.51 (d, J = 1.8 Hz, 1H), 7.87 (s, 1H), 7.81 (q, J = 8.7 Hz, 1H), 7.71 (t, J = 7.0 Hz, 1H), 7.56-7.52 (m, 1H), 7.41 (d, J = 8.5 Hz, 2H), 7.35 (d, J = 8.5 Hz, 2H), 3.51 (s, 2H), 1.30 (s, 6H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 358 | 406.00 | (500 MHz, DMSO-$d_6$): 9.79 (s, 1H), 8.55 (d, J = 2.4 Hz, 1H), 7.89 (d, J = 2.4 Hz, 1H), 7.81 (t, J = 1.8 Hz, 1H), 7.70-7.69 (m, 1H), 7.64-7.56 (m, 3H), 7.51 (d, J = 8.2 Hz, 2H), 4.28 (d, J = 4.7 Hz, 2H), 2.74 (d, J = 4.4 Hz, 6H) |
| 359 | 406.10 | (500 MHz, DMSO-$d_6$): 10.04 (s, 1H), 8.43 (d, J = 2.2 Hz, 1H), 8.05 (s, 1H), 7.80-7.79 (m, 2H), 7.69 (d, J = 8.0 Hz, 1H), 7.63-7.59 (m, 2H), 7.49 (d, J = 7.9 Hz, 1H), 7.34 (t, J = 7.9 Hz, 1H), 7.10 (d, J = 7.5 Hz, 1H), 2.06 (s, 3H) |
| 360 | 423.90 | (500 MHz, DMSO-$d_6$): 9.87 (s, 1H), 8.57 (d, J = 2.3 Hz, 1H), 7.93 (t, J = 7.0 Hz, 1H), 7.86 (t, J = 6.8 Hz, 1H), 7.80 (d, J = 2.3 Hz, 1H), 7.56-7.45 (m, 5H), 4.28 (d, J = 4.5 Hz, 2H), 2.74 (d, J = 4.0 Hz, 6H) |
| 361 | 422.90 | (500 MHz, DMSO-$d_6$): 12.53 (s, 1H), 10.00 (s, 1H), 8.29 (d, J = 2.1 Hz, 1H), 7.70 (d, J = 9.3 Hz, 2H), 7.58 (q, J = 8.5 Hz, 1H), 7.45 (t, J = 7.4 Hz, 2H), 7.39-7.34 (m, 1H), 7.30 (t, J = 7.9 Hz, 1H), 6.93 (d, J = 7.4 Hz, 1H), 2.06 (s, 3H) |
| 362 | 449.00 | |
| 363 | 413.50 | |
| 364 | 452.50 | |
| 365 | 583.50 | |
| 366 | 341.20 | (500 MHz, DMSO-$d_6$): 8.4 (s, 1H), 7.85-7.6 (m, 5H), 7.5 (m, 1H), 6.7 (bs, 2H) |
| 367 | 399.50 | |
| 368 | 415.50 | |
| 369 | 412.50 | |
| 370 | 424.30 | (500 MHz, DMSO-$d_6$): 9.05 (m, 1H), 8.85 (m, 1H), 8.50 (s, 1H), 8.10 (s, 1H), 7.9 (m, 1H), 7.85-7.45 (m, 3H), 4.45 (m, 1H), 3.70 (m, 1H), 3.5 (m, 1H), 3.35 (m, 2H), 3.00 (m, 2H), 2.15 (m, 4H) |
| 371 | 456.20 | (500 MHz, DMSO-$d_6$): 9.42 (br, 2H), 8.51 (d, 1H), 8.12 (s, 1H), 8.06 (d, 1H), 8.03 (d, 1H), 7.94 (d, 1H), 7.75 (t, 1H), 7.66 (s, 1H), 4.49 (m, 1H), 3.39 (d, 2H), 3.06 (m, 2H), 2.15 (m, 4H) |
| 372 | 466.00 | (300 MHz, DMSO-$d_6$): d 8.6 (s, 1H), 7.83 (q, 1H), 7.72 (q, 1H), 7.68 (d, 1H), 7.59 (d, 2H), 7.55 (q, 1H), 7.38 (d, 1H), 6.81 (bs, 2H), 4.72 (m, 1H), 4.2 (t, 2H), 3.8 (m, 2H) |
| 373 | | (400 MHz, CDCl$_3$): 8.86 (d, J = 2.4 Hz, 1H), 8.63 (dd, J = 4.4, 2.4 Hz, 1H), 8.48 (d, J = 2.0 Hz, 1H), 8.14 (d, J = 2.0 Hz, 1H), 7.88 (7t, J = 8.0, 2.4 Hz, 1H), 7.41 (dd, J = 7.2, 4.8 Hz, 1H), 7.35 (dd, J = 8.8, 4.0 Hz, 1H), 7.18 (t, J = 10.0 Hz, 1H), NH$_2$ protons were overlapped with CDCl$_3$ signal) |
| 374 | | (400 MHz, CDCl$_3$/DMSO-$d_6$): 9.75 (s, exchqnged with D$_2$O, 1H), 8.46 (d, J = 2.4 Hz, 1H), 8.1 (d, J = 2.4 Hz, 1H), 7.70 (d, J = 7.6 Hz, 2H), 7.48 (d, J = 7.6 Hz, 2H), 7.26-7.15 (m, 2H), 2.15 (s, 3H), NH$_2$ protons were not observed) |
| 375 | | (400 MHz, CDCl$_3$): 8.46 (br. s, 1H), 8.10 (br. s, 1H), 7.73 (s, 1H), 7.49-7.39 (m, 2H), 7.39-7.13 (m, 5H, addition of D$_2$O exchanged to m, 3H), 2.20 (s, 3H) |
| 376 | | (400 MHz, CDCl$_3$): 8.43 (d, J = 2.0 Hz, 1H), 8.09 (d, J = 2.0 Hz, 1H), 7.47 (d, J = 7.6 Hz, 2H), 7.41 (d, J = 7.6 Hz, 2H), 7.28 (dd, J = 8.4, 3.6 Hz, 1H), 7.12 (t, J = 9.6 Hz, 1H), 7.09 (br.s, exchanged with D$_2$O, 2H), 3.65 (s, 2H), 2.53 (br. s, 4H), 1.77 (br. s, 4H) |
| 377 | | (400 MHz, CDCl$_3$): 8.49 (d, J = 2.4 Hz, 1H), 8.14 (d, J = 2.4 Hz, 1H), 7.54 (d, J = 7.6 Hz, 2H), 7.43 (d, J = 8.0 Hz, 2H), 7.32 (dd, J = 9.6, 4.0 Hz, 1H), 3.49 (s, 2H), 7.17 (overlapped t, J = 9.6 Hz, 1H), 7.16 (br.s, exchanged D$_2$O, 2H), 2.29 (s, 6H) |
| 378 | | (400 MHz, CDCl$_3$): 8.86 (s, 1H), 8.66 (dd, J = 4.4, 1.6 Hz, 1H), 8.48 (d, J = 2.4 Hz, 1H), 8.13 (d, J = 2.0 Hz, 1H), 7.89 (tt, J = 8.0, 1.6 Hz, 1H), 7.36-7.30 (m, 1H), 7.26-7.21 (br. s overlapped with CDCl3 signal, exchanged with D$_2$O, 2H), 7.16 (td, J = 9.2, 4.0 Hz, 1H), 7.09 (td, J = 8.8, 3.2 Hz, 1H) |
| 379 | | (400 MHz, CDCl$_3$): 8.46 (br. s, 1H), 8.12 (br. s, 1H), 7.76 (s, 1H), 7.49 (br. d, J = 8.0 Hz, 1H), 7.92 (t, J = 8.0 Hz, 1H), 7.31 (d, J = 4.8 Hz, 1H), 7.18 (br. s, exchanged with D$_2$O, 2H), 7.15 (br. td, J = 9.6, 4.4 Hz, 1H), 7.06 (br. td, J = 9.2, 4.8 Hz, 1H), 2.23 (s, 3H) |
| 380 | | (400 MHz, CDCl$_3$): 8.48 (d, J = 2.4 Hz, 1H), 8.12 (d, J = 2.0 Hz, 1H), 7.53 (d, J = 8.0 Hz, 2H), 7.47 (d, J = 8.0 Hz, 2H), 7.15 (overlapped br.s, exchanged with D$_2$O, 2H), 7.14 (overlapped td, J = 9.2, 4.0 Hz, 1H), 7.08 (td, J = 8.8, 3.6 Hz, 1H), 3.72 (s, 2H), 2.60 (s, 4H), 1.83 (br. s, 4H) |
| 381 | | (400 MHz, CDCl$_3$): 8.49 (d, J = 2.0 Hz, 1H), 8.13 (d, J = 2.0 Hz, 1H), 7.53 (d, J = 8.8 Hz, 2H), 7.43 (d, J = 8.0 Hz, 2H), 7.14 (overlapped br. s, exchanged with D$_2$O, 2H), 7.12 (overlapped td, J = 9.2, 4.0 Hz, 1H), 7.06 (td, J = 8.8, 4.8 Hz, 1H), 3.49 (s, 2H), 2.29 (s, 6H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 382 | | (400 MHz, CDCl$_3$): 8.39 (d, J = 2.0 Hz, 1H), 8.07 (d, J = 2.0 Hz, 1H), 7.71 (s, 1H), 7.69 (s, 1H), 7.34 (dd, J = 8.4, 3.6 Hz, 1H), 7.18 (t, J = 8.8 Hz, 1H), 7.09 (s, exchanged with D$_2$O, 2H), 4.32-4.29 (m, 1H), 3.31-3.27 (m, 2H), 2.81 (br. td, J = 12.0 Hz, 2H), 2.29-2.20 (m, 2H), 2.01-1.95 (br. dq, J = 11.6, 4.0 Hz, 2H) |
| 383 | | (400 MHz, DMSO-d$_6$): 9.94 (s, exchanged with D$_2$O, 1H), 8.41 (d, J = 2.0 Hz, 1H), 7.67 (s, 1H), 7.58 (d, J = 2.0 Hz, 1H), 7.46 (d, J = 8.0 Hz, 1H), 7.31 (ddd, J = 14.4, 11.2, 5.2 Hz, 1H), 7.28 (t, J = 7.6 Hz, 1H), 7.06 (s, exchanged with D$_2$O, 2H), 6.84 (br. s, d, 7.2 Hz, 1H), 6.56 (td, J = 9.6, 3.6 Hz, 1H), 6.28 (s, exchanged with D20, 2H), 2.07 (s, 3H) |
| 384 | | (400 MHz, CDCl$_3$): 8.52 (dd, J = 5.2, 2.4 Hz, 1H), 8.43 (d, J = 2.4 Hz, 1H), 8.34 (d, J = 2.0 Hz, 1H), 7.50-7.47 (m, 2H), 7.31-7.25 (m, 2H), 6.64 (overlapped br. s, exchanged with D$_2$O, 2H), 6.62 (overlapped td, J = 8.8, 4.0 Hz, 1H), 4.16 (br. s, exchanged with D20, 2H) |
| 385 | 440.20 | (300 MHz, DMSO-d$_6$): 9.20 (br, 1H), 9.06 (br, 1H), 8.53 (d, J = 2.2 Hz, 1H), 8.24-8.22 (m, 2H), 7.90-7.84 (m, 2H), 7.79 (dd, J = 2.3, 9.5 Hz, 1H), 7.49 (dt, J = 8.7, 2.5 Hz, 1H), 4.50-4.46 (m, 1H), 3.39-3.06 (m, 4H), 2.16-2.09 (m, 4H) |
| 386 | 450.10 | (300 MHz, DMSO-d$_6$): 11.15 (brs, 1H), 8.61 (d, J = 2.3 Hz, 1H), 8.19 (d, J = 2.2 Hz, 1H), 7.89 (t, J = 8.3 Hz, 1H), 7.82 (dd, J = 2.3, 9.5 Hz, 1H), 7.69 (d, J = 8.3 Hz, 2H), 7.61 (d, J = 8.3 Hz, 2H), 7.52 (dd, J = 1.1, 7.6 Hz, 1H), 4.34 (d, J = 5.7 Hz, 2H), 3.32 (br, 2H), 3.06-3.01 (m, 2H), 2.01-1.87 (m, 4H) |
| 387 | 424.20 | (300 MHz, DMSO-d$_6$): 10.92 (br, 1H), 8.62 (d, J = 2.3 Hz, 1H), 8.20 (d, J = 2.2 Hz, 1H), 7.89 (t, J = 8.3 Hz, 1H), 7.82 (dd, J = 2.3, 9.5 Hz, 1H), 7.64 (s, 4H), 7.55-7.51 (m, 1H), 4.28 (d, J = 5.3 Hz, 2H), 2.68 (d, J = 4.8 Hz, 6H) |
| 388 | 463.20 | |
| 389 | 437.10 | |
| 390 | 453.20 | (300 MHz, DMSO-d$_6$): 9.23 (brs, 1H), 9.11 (brs, H), 8.42 (d, J = 2.2 Hz, 1H), 8.17 (s, 1H), 8.09 (d, J = 2.1 Hz, 1H), 7.86 (t, J = 8.4 Hz, 1H), 7.79 (dd, J = 2.3, 9.7 Hz, 1H), 7.72 (s, 1H), 7.46 (dt, J = 8.6, 2.4 Hz, 1H), 4.60-4.37 (m, 1H), 3.37 (brd, 2H), 3.08 (br, 2H), 2.36 (s, 3H), 2.18-1.93 (m, 4H) |
| 391 | 450.20 | (300 MHz, DMSO-d$_6$): 10.49 (br, 2H), 8.47 (d, J = 2.3 Hz, 1H), 7.95 (d, J = 2.0 Hz, 1H), 7.84-7.75 (m, 1H), 7.72-7.68 (m, 1H), 7.56 (dd, J = 1.8, 8.2 Hz, 1H), 7.52 (d, J = 7.9 Hz, 1H), 7.08 (s, 1H), 6.88 (d, J = 6.5 Hz, 1H), 4.26 (d, J = 5.3 Hz, 2H), 3.37-3.06 (m, 4H), 2.00-1.87 (m, 4H) |
| 392 | 482.20 | (300 MHz, DMSO-d$_6$): 8.50 (d, J = 2.1 Hz, 1H), 8.30-8.25 (m, 2H), 7.87 (t, J = 8.3 Hz, 1H), 7.81 (s, 1H), 7.79 (d, J = 2.3 Hz, 1H), 7.49 (d, J = 7.5 Hz, 1H), 4.45-4.39 (m, 2H), 3.91 (d, J = 13.8 Hz, 1H), 3.22 (t, 1H), 2.74 (t, 1H), 2.09-2.04 (m, 5H), 1.85-1.68 (m, 2H) |
| 393 | 464.00 | (300 MHz, DMSO-d$_6$): 10.5 (bs, 1H), 8.4 (s, 1H), 7.95 (dd, 1H), 7.8 (dd, 1H), 7.79 (d, 1H), 7.66 (t, 2H), 7.58 (m, 3H), 7.51 (s, 1H), 7.22 (d, 2H), 4.35 (s, 2H), 3.1-3.35 (m, 4H), 1.9-2.35 (m, 4H) |
| 394 | 454.00 | (300 MHz, DMSO-d$_6$): 8.31 (s, 1H), 7.97 (dd, 1H), 7.88 (dd, 1H), 7.78 (s, 1H), 7.71 (t, 2H), 7.57 (s, 1H), 7.51 (s, 1H), 7.42 (s, 1H), 4.39 (m, 1H), 3.1-3.4 (m, 4H), 2.0-2.3 (m, 4H) |
| 395 | 536.20 | (300 MHz, DMSO-d$_6$): 8.42 (d, J = 2.3 Hz, 1H), 8.16 (d, J = 16.5 Hz, 1H), 7.95 (d, J = 2.1 Hz, 1H), 7.86 (t, J = 8.3 Hz, 1H), 7.77 (d, J = 2.3 Hz, 1H), 7.74 (s, 1H), 7.46 (d, J = 8.6 Hz, 1H), 4.58-4.53 (m, 1H), 4.36 (d, J = 13.1 Hz, 1H), 3.96 (d, J = 12.8 Hz, 1H), 3.51-3.43 (m, 1H), 3.17-3.09 (m, 1H), 2.18-1.85 (m, 4H) |
| 396 | 425.20 | (300 MHz, DMSO-d$_6$): 8.54 (d, J = 2.1 Hz, 1H), 8.26-8.24 (m, 2H), 7.96 (br, 2H), 7.85-7.76 (m, 2H), 7.67 (dd, J = 6.4, 8.0 Hz, 1H), 7.56-7.48 (m, 1H), 4.42-4.38 (m, 1H), 3.95 (d, J = 11.6 Hz, 2H), 3.47-3.44 (m, 2H), 2.01-1.83 (m, 4H) |
| 397 | 441.20 | (300 MHz, DMSO-d$_6$): 8.49 (d, J = 1.5 Hz, 1H), 8.19 (s, 1H), 8.12 (s, 1H), 7.96-7.91 (m, 1H), 7.82 (t, J = 7.3 Hz, 1H), 7.70 (s, 1H), 7.53 (t, J = 8.2 Hz, 1H), 4.41-4.33 (m, 1H), 3.95 (d, J = 11.3 Hz, 2H), 3.51-3.43 (m, 2H), 2.01-1.82 (m, 4H) |
| 398 | 507.20 | (300 MHz, DMSO-d$_6$): 11.03 (brs, 1H), 10.19 (s, 1H), 8.60 (d, J = 2.0 Hz, 1H), 8.12 (d, J = 1.7 Hz, 1H), 7.94-7.74 (m, 4H), 7.55-7.42 (m, 4H), 4.33 (d, J = 5.7 Hz, 2H), 3.35 (br, 2H), 3.10 (br, 2H), 2.16 (s, 3H), 2.02-1.90 (m, 4H) |
| 399 | 482.30 | (300 MHz, CDCl$_3$): 8.24 (d, J = 2.2 Hz, 1 H), 7.72-7.67 (m, 1 H), 7.45-7.40 (m, 1 H), 7.34 (td, J = 8.1, 3.1 Hz, 1 H), 7.19 (s, 1 H), 7.12-7.06 (m, 2 H), 6.37 (s, 2 H), 4.67 (d, J = 11.9 Hz, 1 H), 4.29-4.18 (m, 1 H), 3.89 (d, J = 12.7 Hz, 1 H), 3.17 (dd, J = 2.6, 25.9 Hz, |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| | | 1 H), 2.74-2.65 (m, 1 H), 2.07 (s, 2 H), 1.95-1.76 (m, 2 H), 1.54-1.41 (m, 2 H), 1.20-1.07 (m, 2 H), 0.91-0.76 (m, 2 H) |
| 400 | 434.20 | (300 MHz, DMSO-d$_6$): 9.04 (brs, 2H), 8.54 (d, J = 2.0 Hz, 1H), 8.00 (s, 1H), 7.82 (dd, J = 8.4, 17.5 Hz, 1H), 7.73-7.68 (m, 1H), 7.55-7.50 (m, 1H), 7.39 (d, J = 8.0 Hz, 2H), 7.26 (d, J = 8.1 Hz, 2H), 3.34 (brd, J = 12.2 Hz, 2H), 2.99-2.84 (m, 3H), 1.91-1.70 (m, 4H) |
| 401 | 465.00 | (300 MHz, DMSO-d$_6$): 9.19 (bs.1H), 8.4 (s, 1H), 7.95 (d, 1H), 7.85 (d, 1H), 7.78 (s, 1H), 7.67 (t, 1H) 7.52 (s, 2H), 7.25 (t, 1H), 6.96 (d, 1H), 6.82 (s, 1H), 6.65 (d, 1H), 3.35 (s, 4H), 3.23 (s, 4H) |
| 402 | 479.00 | (300 MHz, DMSO-d$_6$): 10.85 (bs, 1H), 8.29 (s, 1H), 7.96 (d, 1H), 7.88 (d, 1H), 7.78 (s, 1H), 7.58 (t, 1H), 7.53 (d, 2H), 7.03 (q, 2H), 6.85 (d, 1H), 6.7 (d, 1H), 3.89 (d, 2H), 3.55 (d, 2H), 3.12 (m, 4H), 2.78 (s, 3H) |
| 403 | 423.20 | (300 MHz, DMSO-d$_6$): 8.45 (s, 1H), 8.13 (s, 1H), 8.01 (s, 1H), 7.84-7.76 (m, 1H), 7.64 (m, 2H), 7.52 (m, 1H), 4.09 (m, 1H), 2.08-2.00 (m, 2H), 1.82-1.60 (m, 5H), 1.45-1.17 (m, 3H) |
| 404 | | (400 MHz, DMSO-d$_6$): 8.41 (d, J = 2.0 Hz, 1H), 8.04 (s, 1H), 7.82 (q, J = 8.0 Hz, 1H), 7.67 (t, J = 7.2 Hz, 1H), 7.58 (d, J = 2.0 Hz, 1H), 7.58 (s, 1H), 7.51-7.50 (overlapped m, 1H), 6.51 (s, exchanged with D$_2$O, 2H), 4.85-4.80 (m, 1H), 3.40-2.95 (m, 4H), 2.21-2.15 (m, 1H), 2.05-2.00 (m, 1H) |
| 405 | | (400 MHz, DMSO-d$_6$): 8.40 (d, J = 2.0 Hz, 1H), 8.01 (s, 1H), 7.76 (q, J = 8.4 Hz, 1H), 7.66 (br. t, J = 5.6 Hz, 1H), 7.56 (d, J = 2.0 Hz, 1H), 7.53-7.50 (overlapped m, 1H), 7.50 (s, 1H), 6.51 (s, exchanged with D$_2$O, 2H), 4.1-4.05 (m, 1H), 3.15 (br. d, J = 12.4 Hz, 1H), 2.87 (br. dt, J = 12.0, <1.0 Hz, 1H), 2.69 (t, J = 10.2 Hz, 1H), 2.08 (br. d, J = 12.0, 4.0 Hz, 1H), 1.83 (dd, J = 12.0, 3.6 Hz, 1H), 1.78 (dd, J = 12.0, 4.0 Hz, 1H), 1.70-1.67 (m, 1H), 1.53-1.43 (m, 1H) |
| 406 | | (400 MHz, CDCl$_3$, addition of D$_2$O sharpend signals): 8.33 (d, J = 2.0 Hz, 1H), 7.65-7.55 (m, 1H), 7.50-7.35 (m, 3H) 7.18 (d, J = 2.4 Hz, 1H), 7.15 (s, 1H), 6.39 (s, exchanged with D$_2$O, 2H), 4.17 (t, J = 6.4 Hz, 2H), 2.74 (t, J = 6.4 Hz, 2H), 2.27 (s, 6H) |
| 407 | | (400 MHz, CDCl$_3$): 8.32 (d, J = 2.0 Hz, 1H), 7.58-7.52 (m, 1H), 7.46-7.37 (m, 3H), 7.18-7.17 (m, 2H), 6.38 (s, exchanged with D$_2$O, 2H), 4.46 (br. s, 2H), 3.10 (br. s, 2H), 2.94 (br. s, 4H), 2.54 (s, 4H) |
| 408 | | (400 MHz, DMSO-d$_6$): 8.39 (d, J = 2.0 Hz, 1H), 8.04 (d, J = 7.6 Hz, 2H), 7.93 (s, 1H), 7.74 (t, J = 8.0 Hz, 1H), 7.36 (br. s, 2H), 6.73 (s, exchanged with D$_2$O, 2H), 4.76-4.72 (m, 1H), 3.13 (dd, J = 11.6, 7.2 Hz, 1H), 3.04-3.00 (m, 1H), 2.92 (dd, J = 11.6, 3.6 Hz, 1H), 2.88-2.86 (m, 1H), 2.21-2.08 (m, 1H), 2.01-1.93 (m, 1H) |
| 409 | 456.20 | (400 MHz, DMSO-d$_6$): 8.39 (d, J = 2.4 Hz, 1H), 8.04 (d, J = 8.0 Hz, 2H), 7.92 (s, 1H), 7.74 (t, J = 7.6 Hz, 1H), 7.36 (s, 1H), 7.35 (d, J = 2.4 Hz, 1H), 6.74 (s, exchanged with D$_2$O, 2H), 4.10-4.05 (m, 1H), 3.14 (br. d, J = 12.0 Hz, 1H), 2.86 (br. d, J = 12.0 Hz, 1H), 2.69 (t, J = 10.6 Hz, 1H), 2.50-2.43 (overlapped m, 1H), 2.08-2.06 (m, 1H), 1.83 (dd, J = 12.0, 3.6 Hz, 1H), 1.77 (dd, J = 12.0, 4.0 Hz, 1H), 1.70-1.65 (m, 1H), 1.55-1.45 (m, 1H) |
| 410 | | (400 MHz, CDCl$_3$): 8.30 (d, J = 2.0 Hz, 1H), 7.82 (br. dd, J = 8.0, 1.2 Hz, 1H), 7.54 (t, J = 8.0 Hz, 1H), 7.50 (dd, J = 7.6, 1.6 Hz, 1H), 7.38 (s, 1H), 7.13 (s, 1H), 7.04 (d, J = 2.0 Hz, 1H), 6.49 (s, exchanged with D$_2$O, 2H), 4.21 (t, J = 6.8 Hz, 2H), 2.77 (t, J = 6.8 Hz, 2H), 2.29 (s, 6H) |
| 411 | | (400 MHz, CDCl$_3$): 8.30 (d, J = 2.0 Hz, 1H), 7.83 (dd, J = 8.0, 1.6 Hz, 1H), 7.54 (t, J = 8.0 Hz, 1H), 7.50 (dd, J = 7.6, 1.6 Hz, 1H), 7.38 (s, 1H), 7.13 (s, 1H), 7.09 (d, J = 2.4 Hz, 1H), 6.49 (br. s, exchanged with D$_2$O, 2H), 4.27 (t, J = 6.4 Hz, 2H), 2.99 (br. m, 2H), 2.58 (br. s, 4H), 1.81 (br. s, 4H) |
| 412 | | (400 MHz, DMSO-d$_6$): 8.40 (d, J = 2.0 Hz, 1H), 8.01 (s, 1H), 7.80-7.76 (q, J = 8.8 Hz, 1H), 7.64 (t, J = 8.0 Hz, 1H), 7.56 (d, J = 2.4 Hz, 1H), 7.55-7.51 (overlapped m, 1H), 7.52 (s, 1H), 6.51 (s, exchanged with D$_2$O, 2H), 4.77-4.71 (m, 1H), 3.11 (br. dd, J = 12.0, 6.4 Hz, 1H), 3.00 (m, 1H), 2.91 (dd, J = 12.4, 4.8 Hz, 1H), 2.87-2.81 (m, 1H), 2.20-2.11 (qd, J = 8.4, 7.2 Hz, 1H), 2.0-1.94 (m, 1H) |
| 413 | | (400 MHz, DMSO-d$_6$): 8.29 (d, J = 2.0 Hz, 1H), 8.04 (d, J = 8.0 Hz, 1H), 7.93 (s, 1H), 7.74 (t, J = 7.6 Hz, 1H), 7.36 (2 overlapped br. s, 2H), 6.73 (s, exchanged with D$_2$O, 2H), 4.80-4.70 (m, 1H), 3.14 (dd, J = 12.4, 9.6 Hz, 1H), 3.14 (dd, J = 12.4, 9.6 Hz, 1H), 3.05-2.95 (m, 1H), 2.98 (br. dd, J = 12.0, 3.6 Hz, 1H), 2.86-2.83 (m, 1H), 2.19-2.15 (m, 1H), 1.99-1.98 (m, 1H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 414 | 435.00 | (400 MHz, DMSO-d$_6$): 9.23 (bs, 2H), 8.58)s, 1H), 8.00 (s, 1H), 7.82 (q, 1H), 7.71 (t, 1H), 7.58 (q, 1H), 7.29 (t, 1H), 6.87-7.00 (m, 3H), 3.4 (bs, 4H), 3.22 (bs, 4H) |
| 415 | | (400 MHz, DMSO-d$_6$): 8.92 (d, J = 2.4 Hz, 1H), 7.84 (br.q, J = 8.0 Hz, 1H), 7.72-7.65 (m, 1H), 7.58-7.54 (m, 1H), 7.50 (d, J = 2.4 Hz, 1H), 6.99 (d, J = 4.0 Hz, 1H), 6.84 (s, exchanged with D$_2$O, 2H), 6.78 (d, J = 3.6 Hz, 1H), 3.0 (br. d, J = 12.0 Hz, 2H), 2.85-2.8 (m, 1H), 2.07-2.54 (br. d., J = 12.0 Hz, 2H), 1.84 (br. d, J = 11.6 Hz, 2H), 1.46 (br. ABq, J = 12.0, 4.0 Hz, 2H) |
| 416 | | (400 MHz, DMSO-d$_6$): 8.44 (d, J = 2.4 Hz, 1H), 8.05 (dd, J = 8.4, 1.2 Hz, 1H), 8.00 (dd, J = 8.0, 1.2 Hz, 1H), 7.75 (t, J = 8.0 Hz, 1H), 7.28 (d, J = 2.4 Hz, 1H), 7.09 (br. s, exchanged with D$_2$O, 2H), 6.95 (t, J = 3.6 Hz, 1H), 6.75 (d, J = 3.6 Hz, 1H), 3.0-2.95 (m, 2H), 2.83-2.75 (m, 1H), 2.58-2.50 (m, 2H), 1.85-1.81 (m, 2H), 1.47 (dd, J = 12.4, 4.0 Hz, 1H), 1.38 (dd, J = 12.4, 4.0 Hz, 1H) |
| 417 | | (400 MHz, DMSO-d$_6$): 8.39 (d, J = 2.4 Hz, 1H), 8.00 (s, 1H), 7.79 (br. q, J = 8.8 Hz, 1H), 7.65-7.63 (m, 1H), 7.55 (s, 1H), 7.54-7.51 (m, 1H), 7.49 (d, J = 2.4 Hz, 1H), 6.49 (s, exchanged with D$_2$O, 2H), 4.10-4.05 (m, 1H), 3.12-3.11 (m, 1H), 2.90-2.80 (m, 1H), 2.70-2.64 (m, 1H)), 2.53-2.39 (m, 1H), 2.06-2.00 (m, 1H), 1.85-1.76 (m, 1H), 1.69-1.62 (m, 1H), 1.48-1.46 (m, 1H) |
| 418 | | (400 MHz, DMSO-d$_6$): 8.37 (d, J = 2.4 Hz, 1H), 8.03 (d, J = 8.4 Hz, 2H), 7.91 (s, 1H), 7.73 (t, J = 8.0 Hz, 1H), 7.34 (s, 2H), 6.72 (s, exchanged with D$_2$O, 2H), 4.10-4.05 (m, 1H), 3.11 (dd, J = 11.6, 2.8 Hz, 1H), 2.84 (br. d, J = 12.0 Hz, 1H), 2.68 (t, J = 11.6 Hz, 1H), 2.50-2.40 (overlapped m, 1H), 2.10-2.04 (m, 1H), 1.82 (qd, J = 11.6, 4.0 Hz, 1H), 1.69-1.65 (m, 1H), 1.55-1.45 (m, 1H) |
| 419 | 411.20 | (300 MHz, DMSO-d$_6$): 8.43 (d, J = 2.2 Hz, 1H), 8.05 (s, 1H), 7.81-7.76 (m, 2H), 7.67-7.64 (m, 1H), 7.62 (s, 1H), 7.62-7.51 (m, 1H), 5.00-4.96 (m, 1H), 3.99-3.81 (m, 4H), 2.51-2.35 (m, 2H) |
| 420 | 427.20 | (300 MHz, DMSO-d$_6$): 8.42 (d, J = 2.3 Hz, 1H), 8.03 (s, 1H), 7.95-7.90 (m, 1H), 7.82 (t, J = 6.7 Hz, 1), 7.70 (d, J = 2.0 Hz, 1H), 7.58 (s, 1H), 7.53 (t, J = 8.2 Hz, 1H), 5.01-4.94 (m, 1H), 4.04-3.78 (m, 4H), 2.44-2.22 (m, 2H) |
| 421 | 529.30 | (300 MHz, DMSO-d$_6$): 8.40 (d, J = 2.3 Hz, 1H), 8.25 (d, J = 1.5 Hz, 1H), 8.07 (dt, J = 6.3, 7.9 Hz, 1H), 7.95 (d, J = 1.2 Hz, 1H), 7.91 (s, 1H), 7.72-7.67 (m, 1H), 7.62 (d, J = 2.3 Hz, 1H), 7.51 (t, J = 7.9 Hz, 1H), 7.46 (d, J = 0.5 Hz, 1H), 5.09-5.01 (m, 1H), 4.97-4.90 (m, 1H), 4.00-3.77 (m, 8H), 2.41-2.17 (m, 4H) |
| 422 | 454.00 | (300 MHz, DMSO-d$_6$): 8.29 (m, 1H), 7.79 (q, 1H), 7.67 (t, 1H), 7.53 (m, 1H), 7.39 (s, 1H), 6.18 (d, 1H), 5.88 (m, 1H), 4.13 (s, 1H), 4.05 (s, 1H), 3.88 (q, 1H), 3.55-3.75 (m, 5H), 3.39 (m, 1H), 2.27 (s, 1H), 2.11 (s, 1H), 2.0 (m, 2H) |
| 423 | 467.00 | (300 MHz, DMSO-d$_6$): 8.81 (bs, 1H), 8.65 (bs, 1H), 8.29 (m.1H), 7.8 (q, 1H), 7.68 (t, 1H), 7.6 (s, 1H), 7.53 (m, 1H), 7.0 (bs, 1H), 5.93 (d, 1H), 3.63 (m, 2H), 3.18 (m, 2H), 3.0 (m, 4H), 2.27 (m, 1H), 2.32 (bs, 1H), 2.18 (bs, 1H), 1.5-1.8 (m, 3H) |
| 424 | 439.00 | (300 MHz, DMSO-d$_6$): 8.23 (d, 1H), 7.8 (q, 1H), 7.19 (t, 1H), 7.55 (q, 1H), 7.31 (d, 1H), 6.68 (s, 1H), 5.82 (bs, 1H), 3.1 (s, 2H), 2.98 (d, 2H), 2.25-2.55 (m, 5H), 2.1 (bs, 1H), 1.69 (d, 2H), 1.29 (m, 3H) |
| 425 | 411.20 | (300 MHz, DMSO-d$_6$): 8.42 (d, J = 2.3 Hz, 1H), 8.04 (d, J = 0.4 Hz, 1H), 7.84-7.75 (m, 1H), 7.73 (d, J = 2.3 Hz, 1H), 7.69-7.63 (m, 1H), 7.60 (d, J = 0.5 Hz, 1H), 7.56-7.48 (m, 1H), 5.01-4.94 (m, 1H), 4.00-3.78 (m, 4H), 2.50 (qn, J = 1.8 Hz, DMSO), 2.44-2.22 (m, 2H) |
| 426 | | (400 MHz, DMSO-d$_6$): 8.41 (d, J = 2.0 Hz, 1H), 8.10 (s, 1H), 7.78 (br. q, J = 8.4 Hz, 1H), 7.66 (br. t, J = 6.4 Hz, 1H), 7.60 (s, 1H), 7.59 (overlapped d, J = 2.0 Hz, 1H), 7.54-7.50 (m, 1H), 6.51 (s, exchanged with D$_2$O, 2H), 5.14 (quintet, J = 7.2 Hz, 1H), 3.84 (t, J = 8.0 Hz, 2H), 3.71 (t, J = 7.6 Hz, 2H) |
| 427 | | (400 MHz, DMSO-d$_6$): 8.40 (d, J = 2.0 Hz, 1H), 8.03 (d, J = 7.6 Hz, 2H), 8.02 (overlapped s, 1H), 7.74 (t, J = 8.0 Hz, 1H), 7.44 (s, 1H), 7.39 (d, J = 1.6 Hz, 1H), 6.73 (br. s, exchanged with D$_2$O, 2H), 5.14 (quintet, J = 7.2 Hz, 1H), 3.84 (t, J = 8.0 Hz, 2H), 3.71 (t, J = 7.6 Hz, 2H) |
| 428 | | (400 MHz, DMSO-d$_6$): 8.40 (d, J = 2.4 Hz, 1H), 7.98 (s, 1H), 7.89-7.68 (m, 1H), 7.67-7.56 (m, 1H), 7.55 (d, J = 2.4 Hz, 1H), 7.52-7.49 (m, 1H), 7.48 (s, 1H), 6.50 (br. s, exchanged with D$_2$O, 2H), 4.42-4.34 (m, 1H), 2.92-2.85 (m, 2H), 2.80-2.71 (m, 2H), 2.05-1.95 (m, 4H), 1.75-1.70 (m, 1H), 1.62-1.53 (m, 1H) |
| 429 | | (400 MHz, DMSO-d$_6$): 8.40 (d, J = 2.4 Hz, 1H), 7.98 (s, 1H), 7.89-7.68 (m, 1H), 7.67-7.56 (m, 1H), 7.55 (d, J = 2.4 Hz, 1H), 7.52-7.49 (m, 1H), 7.48 (s, 1H), 6.50 (br. s, exchanged with D$_2$O, 2H), |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| | | 4.42-4.34 (m, 1H), 2.92-2.85 (m, 2H), 2.80-2.71 (m, 2H), 2.05-1.95 (m, 4H), 1.75-1.70 (m, 1H), 1.62-1.53 (m, 1H) |
| 430 | 426.20 | (300 MHz, DMSO-d$_6$): 9.41 (brs, 2H), 8.40 (d, J = 2.4 Hz, 1H), 7.82 (dd, J = 8.4, 16.4 Hz, 1H), 7.69 (dd, J = 6.4, 8.0 Hz, 1H), 7.58-7.51 (m, 2H), 7.00 (s, 1H), 3.21-3.12 (br, 6H), 2.99-2.96 (br, 2H) |
| 431 | | (400 MHz, DMSO-d$_6$): 8.38 (d, J = 2.4 Hz, 1H), 8.06 (d, J = 8.0 Hz, 1H), 7.98 (d, J = 8.0 Hz, 1H), 7.74 (t, J = 8.0 Hz, 1H), 7.23 (d, J = 2.4 Hz, 1H), 7.03 (s, exchanged with D$_2$O, 2H), 6.78 (s, 1H), 2.81-2.46 (m, 8H) |
| 432 | 427.20 | (300 MHz, DMSO-d$_6$): 8.44 (d, J = 2.3 Hz, 1H), 8.13 (s, 1H), 7.84-7.75 (m, 1H), 7.73 (d, J = 2.3 Hz, 1H), 7.71-7.65 (m, 2H), 7.56-7.48 (m, 1H), 4.92 (d, J = 6.2 Hz, 1H), 4.87 (d, J = 6.2 Hz, 1H), 4.41-4.35 (m, 1H), 4.22 (dd, J = 3.5, 11.7 Hz, 2H), 4.10 (dd, J = 5.4, 11.6 Hz, 2H) |
| 433 | 427.10 | (300 MHz, DMSO-d$_6$): 8.41 (d, J = 2.3 Hz, 1H), 7.93 (s, 1H), 7.81-7.78 (m, 1H), 7.71-7.65 (m, 1H), 7.58-7.51 (m, 3H), 6.54 (s, 2H), 4.90 (s, 1H), 4.80 (s, 1H), 4.37-4.33 (m, 1H), 4.23-4.20 (m, 2H), 3.93 (dd, J = 6.8, 8.3 Hz, 1H), 3.66 (dd, J = 5.6, 8.4 Hz, 1H) |
| 434 | 438.10 | (300 MHz, DMSO-d$_6$): 8.40 (d, J = 2.0 Hz, 1H), 8.02 (s, 1H), 7.84-7.75 (m, 1H), 7.69-7.64 (m, 1H), 7.57-7.51 (m, 3H), 6.50 (s, 2H), 4.06-4.03 (m, 1H), 2.83 (d, J = 10.9 Hz, 2H), 2.20 (s, 3H), 2.07-1.88 (m, 6H) |
| 435 | 452.20 | (300 MHz, DMSO-d$_6$): 10.70 (brs, 1H), 8.51 (d, J = 2.2 Hz, 1H), 8.13 (s, 1H), 8.05 (d, J = 1.6 Hz, 1H), 7.86-7.74 (m, 2H), 7.67 (dd, J = 6.4, 8.0 Hz, 1H), 7.57-7.50 (m, 1H), 4.47-4.39 (m, 1H), 3.58 (d, J = 12.2 Hz, 2H), 3.12-3.02 (m, 4H), 2.37-2.25 (m, 4H), 1.28 (t, J = 7.3 Hz, 3H) |
| 436 | 454.10 | (300 MHz, DMSO-d$_6$): 10.55 (brs, 1H), 8.47 (d, J = 2.3 Hz, 1H), 8.09 (s, 1H), 7.98-7.92 (m, 1H), 7.88 (s, 1H), 7.85-7.80 (m, 1H), 7.68 (s, H), 7.54 (td, J = 8.2, 3.2 Hz, 1H), 4.42-4.35 (m, 1H, covered by water), 3.53 (d, J = 12.2 Hz, 2H), 3.21-3.08 (m, 2H), 2.77 (d, J = 4.8 Hz, 3H), 2.28-2.18 (m, 4H) |
| 437 | 382.00 | (300 MHz, DMSO-d$_6$): 8.06 (d, J = 2.4 Hz, 1H), 7.89-7.84 (m, 1H), 7.79-7.74 (m, 1H), 7.49 (td, J = 8.2, 3.2 Hz, 1H), 7.12 (d, J = 2.4 Hz, 1H), 6.92 (s, 2H), 3.30 (s, 3H) |
| 438 | 439.10 | (300 MHz, DMSO-d$_6$): 9.26 (brs, 2H), 9.16 (d, J = 0.8 Hz, 1H), 8.48 (d, J = 2.1 Hz, 1H), 8.12 (s, 1H), 8.05 (d, J = 2.0 Hz, 1H), 7.89-7.84 (m, 1H), 7.74-7.68 (m, 1H), 7.68 (s, 1H), 7.47 (td, J = 8.2, 3.2 Hz, 1H), 4.52-4.42 (m, 1H), 3.41-3.34 (m, 2H), 3.13-3.03 (m, 2H), 2.28-2.05 (m, 4H) |
| 439 | | (300 MHz, DMSO-d$_6$): 8.98 (s, 1H), 8.31 (d, J = 2.3 Hz, 1H), 7.86-7.80 (m, 3H), 7.72 (t, J = 6.7 Hz, 1H), 7.46 (td, J = 8.2, 3.2 Hz, 1H), 7.40 (s, 1H), 7.29 (d, J = 2.2 Hz, 1H), 6.66 (s, 2H) |
| 440 | 542.10 | (300 MHz, DMSO-d$_6$): 7.34 (d, J = 1.9 Hz, H), 6.91-6.85 (m, 2 H), 6.83 (d, J = 2.2 Hz, 1 H), 6.78-6.73 (m, 1 H), 6.54 (dd, J = 1.6, 8.2 Hz, 1 H), 6.50 (d, J = 0.5 Hz, 1 H), 3.38 (s, 1 H), 3.28 (s, 2 H), 3.24 (dd, J = 3.2, 6.1 Hz, 2 H), 2.63 (dd, J = 3.2, 6.1 Hz, 2 H),, 2.39 (s, 3 H), 2.08-2.00 (m, 2 H), 1.10 (dd, J = 2.6, 12.3 Hz, 2 H), 0.96-0.85 (m, 2 H) |
| 441 | 510.10 | (300 MHz, DMSO-d$_6$): 8.41 (d, J = 2.3 Hz, 1 H), 8.09 (s, 1 H), 7.95-7.90 (m, 1 H), 7.84-7.79 (m, 1 H), 7.69 (d, J = 2.0 Hz, 1 H), 7.56 (s, 1 H), 7.56-7.50 (ddd, J = 6.8, 1.5, 1 H), 4.60-4.34 (m, 2 H), 4.04 (d, J = 11.5 Hz, 1 H), 3.21 (t, J = 13.1 Hz, 1 H), 2.92 (qn, J = 6.7 Hz, 1 H), 2.73 (t, J = 1.8 Hz, 1 H), 2.07 (s, 2 H), 1.84-1.68 (m, 2 H), 1.02 (d, J = 5.5 Hz, 6 H) |
| 442 | 547.10 | |
| 443 | 537.10 | (300 MHz, DMSO-d$_6$): 8.32 (d, J = 1.9 Hz, 1 H), 7.88 (d, J = 1.6 Hz, 1 H), 7.86 (t, J = 1.5 Hz, 1 H), 7.79 (d, J = 2.1 Hz, 1 H), 7.75-7.70 (m, 1 H), 7.53-7.47 (m, 1 H), 7.47 (d, J = 0.7 Hz, 1 H), 4.33 (dd, J = 7.2, 15.7 Hz, 1 H), 3.87 (d, J = 13.5 Hz, 2 H), 3.38 (t, J = 6.6 Hz, 4 H), 1.94 (dt, J = 2.4, 25.6 Hz, 2 H), 2.09-1.90 (m, 4 H), 1.84 (m, 4 H) |
| 444 | 525.10 | |
| 445 | 511.10 | |
| 446 | 546.10 | |
| 447 | 498.20 | |
| 448 | 466.10 | (300 MHz, DMSO-d$_6$): 10.54 (brs, 1H), 8.50 (d, J = 2.3 Hz, 1H), 8.08 (s, 1H), 7.97 (d, J = 1.9 Hz, 1H), 7.86-7.75 (m, 1H), 7.72 (s, 1H), 7.70-7.64 (m, 1H), 7.57-7.51 (m, 1H), 4.51-4.47 (m, 1H), 3.47 (m, 3H), 3.21-3.10 (m, 2H), 2.39-2.24 (m, 4H), 1.30 (d, J = 6.6 Hz, 6H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 449 | 478.10 | (300 MHz, DMSO-d$_6$): 10.72 (brs, 1), 8.50 (d, J = 2.2 Hz, 1H), 8.11 (s, 1H), 7.99 (d, J = 1.6 Hz, 1H), 7.88-7.77 (m, 1H), 7.73 (s, 1H), 7.67 (dd, J = 6.4, 8.0 Hz, 1H), 7.57-7.50 (m, 1H), 4.44-4.40 (m, 1H), 3.66 (brd, J = 12.3 Hz, 2H), 3.18-2.96 (m, 4H), 2.38-2.28 (m, 4H), 1.24-1.09 (m, 1H), 0.69-0.59 (m, 2H), 0.41 (dd, J = 5.0, 10.3 Hz, 2H) |
| 450 | 481.10 | (300 MHz, DMSO-d$_6$): 9.10 (s, 1H), 8.32 (d, J = 2.2 Hz, 1H), 8.07 (s, 1H), 7.86-7.78 (m, 2H), 7.72-7.66 (m, 1H), 7.53 (s, 1H), 7.45 (td, J = 8.2, 3.2 Hz, 1H), 4.40 (m, 1H), 3.9 (brd, 2H), 3.22 (tbr, 2H), 2.04 (s, 3H), 1.75 (m, 2H) |
| 451 | 478.20 | (300 MHz, DMSO-d$_6$): 11.45 (br, 1H), 8.53 (d, J = 2.2 Hz, 1H), 8.12 (s, 1H), 8.09 (d, J = 1.9 Hz, 1H), 7.87-7.78 (m, 1H), 7.75 (s, 1H), 7.68 (dd, J = 6.4, 8.0 Hz, 1H), 7.58-7.50 (m, 1H), 4.49-4.39 (m, 1H), 3.60 (q, J = 8.2 Hz, 1H), 3.44 (dbr, 2H), 2.98-2.88 (m, 2H), 2.44-2.07 (m, 8H), 1.77-1.65 (m, 2H) |
| 452 | 470.20 | (300 MHz, DMSO-d$_6$): 11.05 (br, 1H), 8.50 (d, J = 2.3 Hz, 1H), 8.12 (s, 1H), 8.01 (d, J = 1.6 Hz, 1H), 7.86-7.76 (m, 1H), 7.73 (s, 1H), 7.67 (td, J = 6.4, 2.7 Hz, 1H), 7.57-7.49 (m, 1H), 4.95 (td, J = 4.4, 47.43 Hz, 2H), 4.42-4.38 (m, 1H), 3.65-3.22 (m, 6H), 2.41-2.26 (m, 4H) |
| 453 | 488.10 | (300 MHz, DMSO-d$_6$): 11.05 (br, 1H), 8.50 (d, J = 2.3 Hz, 1H), 8.01 (d, J = 1.9 Hz, 1H), 8.14 (s, 1H), 7.85-7.76 (m, 1H), 7.74 (s, 1H), 7.67 (td, J = 6.5, 2.7 Hz, 1H), 7.56-7.49 (m, 1H), 6.68 (t, J = 53.8 Hz, 1H), 4.48 (m, 1H), 3.78-3.68 (m, 4H), 3.31 (br, 2H), 2.31-2.27 (m, 4H) |
| 454 | 453.10 | (300 MHz, DMSO-d$_6$): 9.30-9.13 (br, 2H), 8.43 (d, J = 2.1 Hz, 1H), 8.07 (s, 1H), 7.94-7.89 (m, 2H), 7.85-7.79 (m, 1H), 7.66 (d, J = 15.7 Hz, 1H), 7.54 (td, J = 8.2, 3.2 Hz, 1H), 4.53-4.43 (m, 1H), 3.37 (dbr, 2H), 3.13-3.03 (m, 2H), 2.36 (s, 3H), 2.22-2.05 (m, 4H) |
| 455 | 466.10 | (300 MHz, DMSO-d$_6$): 8.46 (d, J = 2.3 Hz, 1H), 8.16 (s, 1H), 7.98 (d, J = 1.9 Hz, 1H), 7.81-7.78 (m, 1H), 7.69-7.64 (m, 2H), 7.56-7.50 (m, 1H), 4.45-4.36 (m, 2H), 3.90 (brd, J = 14.2 Hz, 1H), 3.21 (t, 1H), 2.73 (t, 1H), 2.07-1.99 (m, 5H), 1.78 (m, 2H) |
| 456 | 406.00 | (300 MHz, DMSO-d$_6$): 9.38 (bs, 1H), 8.5 (s, 1H), 7.81 (m, 2H), 7.69 (m, 1H), 7.53 (m, 2H), 7.28 (m, 2H), 4.62 (bs, 1H), 4.22 (s, 2H), 3.38 (d, 2H), 3.0 (t, 2H) |
| 457 | 495.10 | |
| 458 | 467.20 | (300 MHz, DMSO-d$_6$): 9.36-9.20 (br, 1H), 9.01 (s, 1H), 8.32 (d, J = 2.3 Hz, 1H), 7.97 (s, 1H), 7.85-7.79 (m, 1H), 7.72-7.67 (m, 1H), 7.49-7.41 (m, 3H), 4.42-4.39 (m, 1H), 3.64-3.50 (m, 2H), 3.24-3.04 (m, 4H), 2.30-2.04 (m, 4H), 1.25 (t, J = 7.3 Hz, 3H) |
| 459 | 485.10 | |
| 460 | 503.10 | (300 MHz, DMSO-d$_6$): 9.02 (s, 1H), 8.32 (d, J = 2.2 Hz, 1H), 8.02 (s, 1H), 7.85-7.79 (m, 1H), 7.72-7.67 (m, 1H), 7.51-7.42 (m, 3H), 6.48 (t, J = 53.1 Hz, 1H), 4.33-4.21 (m, 1H), 3.73-3.34 (m, 4H), 3.34-3.12 (m, 2H), 2.37-2.20 (m, 4H) |
| 461 | 466.10 | (300 MHz, DMSO-d$_6$): 10.38 (brs, 1H), 8.47 (d, J = 2.1 Hz, 1H), 8.08 (s, 1H), 7.88 (s, 1H), 7.86-7.77 (m, 1H), 7.71-7.64 (m, 2H), 7.57-7.50 (m, 1H), 4.49-4.38 (m, 1H), 3.61-3.41 (m, 2H), 3.13-2.97 (m, 4H), 2.34-2.27 (m, 4H), 1.80-1.65 (m, 2H), 0.92 (t, J = 7.4 Hz, 3H) |
| 462 | 463.10 | (300 MHz, DMSO-d$_6$): 8.42 (d, J = 2.2 Hz, 1H), 8.09 (s, 1H), 7.84-7.75 (m, 2H), 7.66 (dd, J = 6.4, 8.0 Hz, 1H), 7.62 (s, 1H), 7.56-7.48 (m, 1H), 4.26-4.16 (m, 1H), 3.93 (s, 2H), 3.03 (d, J = 11.7 Hz, 2H), 2.54-2.51 (m, 2H), 2.13-1.92 (m, 4H) |
| 463 | 440.20 | (400 MHz, DMSO-d$_6$): 8.51 (d, J = 2.4 Hz, 1H), 7.80 (br. q, J = 8.8 Hz, 1H), 7.69 (t, J = 6.0 Hz, 1H), 7.63 (d, J = 2.4 Hz, 1H), 7.56-7.52 (m, 1H), 7.32 (d, J = 1.2 Hz, 1H), 6.89 (s, 1H), 6.70 (s, exchanged with D$_2$O, 2H), 3.0 (br. dt, J = 12.0, <1 Hz, 2H), 2.90-2.75 (m, 1H), 2.58-2.45 (m, 2H), 1.83 (br. d, J = 12.0 Hz, 2H), 1.44 (AB q, J = 12.0, 3.6 Hz, 2H) |
| 464 | 423.10 | (400 MHz, DMSO-d$_6$): 8.35 (d, J = 2.4 Hz, 1H), 7.82 (br. q, J = 8.0 Hz, 1H), 7.72 (br. t, J = 6.4 Hz, 1H), 7.58-7.55 (m, 1H), 7.41 (d, J = 2.0 Hz, 1H), 7.02 (t, J = 2.4 Hz, 1H), 6.80 (t, J = 2.8 Hz, 1H), 6.50 (br. s, exchanged with D$_2$O, 2H), 5.97 (dd, J = 2.0, 4.4 Hz, 1H), 3.89-3.83 (m, 1H), 3.04 (d, J = 12.4 Hz, 2H), 2.80-2.60 (m, 2H), 1.85 (d, J = 12.0 Hz, 2H), 1.63 (AB q, J = 12.0, 1.0 Hz, 2H) |
| 465 | 413.10 | (400 MHz, DMSO-d$_6$): 8.46 (d, J = 2.0 Hz, 1H), 7.81-7.75 (m, 1H), 7.78 (d, J = 2.4 Hz, 1H), 7.71-7.67 (m, 1H), 7.57-7.52 (m, 1H), 7.11 (s, exchanged with D$_2$O, 2H), 3.86 (br. s, 2H), 2.97 (t, J = 7.6 Hz, 2H), 2.68-2.60 (m, 2H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 466 | 437.20 | (400 MHz, DMSO-d$_6$): 8.33 (d, J = 2.0 Hz, 1H), 7.80 (br. d, J = 8.4 Hz, 1H), 7.71 (t, J = 8.0 Hz, 1H), 7.57-7.51 (m, 1H), 7.40 (d, J = 2.0 Hz, 1H), 6.96 (s, 1H), 6.75 (s, 1H), 6.48 (s, exchanged with D$_2$O, 2H), 5.97 (br. s, 1H), 3.93 (t, J = 6.4 Hz, 2H), 2.70-2.65 (m, 2H), 2.50-2.35 (m, 4H), 1.67 (br. s, 4H) |
| 467 | 445.00 | (400 MHz, DMSO-d$_6$): 8.61 (d, J = 2.0 Hz, 1H), 8.03-8.00 (m, 2H), 7.73 (t, J = 7.6 Hz, 1H), 7.62 (d, J = 2.4 Hz, 1H), 7.37 (s, exchanged with D$_2$O, 2H), 3.84 (s, 2H), 2.96 (t, J = 5.6 Hz, 2H), 2.61 (br. t, J = 5.6 Hz, 2H) |
| 468 | 425.10 | (300 MHz, DMSO-d$_6$): 8.70 (brs, 1H), 8.65 (s, 1H), 7.99 (dd, J = 8.7, 16.5 Hz, 1H), 7.74 (dd, J = 6.4, 8.1 Hz, 1H), 7.62-7.56 (m, 4H), 7.21 (s, 1H), 4.45-4.38 (m, 1H), 3.39 (dbr, 2H), 3.08-3.04 (m, 2H), 2.19-2.00 (m, 4H) |
| 469 | 484.10 | (300 MHz, DMSO-d$_6$): 10.13 (brs, 1H), 8.47 (d, J = 2.3 Hz, 1H), 8.09 (s, 1H), 7.97-7.91 (m, 1H), 7.89 (s, 1H), 7.85-7.80 (m, 1H), 7.68 (s, 1H), 7.54 (td, J = 8.2, 3.2 Hz, 1H), 4.54-4.40 (m, 1H), 3.82-3.78 (m, 2H), 3.65 (brd, J = 12.0 Hz, 2H), 3.25-3.17 (m, 4H), 2.32-2.25 (m, 4H) |
| 470 | 482.10 | (300 MHz, DMSO-d$_6$): 10.51 (brs, 1H), 8.48 (d, J = 2.3 Hz, 1H), 8.09 (s, 1H), 7.98-7.92 (m, 2H), 7.86-7.80 (m, 1H), 7.70 (s, 1H), 7.57-7.50 (m, 1H), 4.55-4.42 (m, 1H), 3.59 (d, J = 11.8 Hz, 2H), 3.15 (m, 4H), 2.35 (m, 4H), 1.67 (m, 2H), 0.95 (t, 3H) |
| 471 | 482.10 | (300 MHz, DMSO-d$_6$): 10.52 (brs, 1H), 8.51 (d, J = 2.2 Hz, 1H), 8.10 (s, 1H), 8.03 (d, J = 1.9 Hz, 1H), 7.98-7.92 (m, 1H), 7.86-7.80 (m, 1H), 7.73 (s, 1H), 7.55 (td, J = 8.2, 3.2 Hz, 1H), 4.53-4.43 (m, 1H), 3.48 (m, 3H), 3.21-3.10 (m, 2H), 2.39-2.28 (m, 4H), 1.30 (d, J = 6.6 Hz, 6H) |
| 472 | 494.20 | (300 MHz, DMSO-d$_6$): 10.64 (brs, 1H), 8.50 (d, J = 2.2 Hz, 1H), 8.12 (s, 1H), 8.00-7.92 (m, 2H), 7.83-7.80 (m, 1H), 7.72 (s, 1H), 7.57-7.50 (m, 1H), 4.47-4.40 (m, 1H), 3.66 (d, J = 11.9 Hz, 2H), 3.15-2.96 (m, 4H), 2.38-2.28 (m, 4H), 1.23-1.09 (m, 1H), 0.69-0.59 (m, 2H), 0.47-0.38 (m, 2H) |
| 473 | 494.20 | (300 MHz, DMSO-d$_6$): 11.15 (br, 1H), 8.49 (d, J = 2.3 Hz, 1H), 8.10 (s, 1H), 7.98-7.91 (m, 2H), 7.86-7.80 (m, 1H), 7.71 (s, 1H), 7.58-7.50 (m, 1H), 4.56-4.39 (m, 1H), 3.60 (q, J = 8.2 Hz, 1H), 3.45 (d, J = 11.7 Hz, 2H), 2.94-2.87 (m, 2H), 2.45-2.05 (m, 8H), 1.81-1.65 (m, 2H) |
| 474 | 508.20 | (300 MHz, DMSO-d$_6$): 10.62 (brs, 1H), 8.47 (d, J = 2.3 Hz, 1H), 8.08 (s, 1H), 7.98-7.92 (m, 1H), 7.89 (d, J = 1.7 Hz, 1H), 7.85-7.80 (m, 1H), 7.69 (s, 1H), 7.57-7.51 (m, 1H), 4.51-4.43 (m, 1H), 3.62-3.41 (m, 3H), 3.18-3.05 (m, 2H), 2.36-2.25 (m, 4H), 2.12-2.01 (m, 2H), 1.85-1.44 (m, 6H) |
| 475 | 496.20 | (300 MHz, DMSO-d$_6$): 9.83 (brs, 1H), 8.47 (d, J = 2.2 Hz, 1H), 8.10 (s, 1H), 7.97-7.94 (m, 2H), 7.85-7.80 (m, 1H), 7.70 (s, 1H), 7.57-7.50 (m, 1H), 4.43-4.39 (m, 1H), 3.61 (d, J = 11.5 Hz, 2H), 3.17-2.91 (m, 4H), 2.41-2.10 (m, 5H), 1.01 (d, J = 6.4 Hz, 6H) |
| 476 | 482.10 | (300 MHz, DMSO-d$_6$): 8.40 (d, J = 2.3 Hz, 1H), 8.05 (d, J = 3.7 Hz, 1H), 7.79 (q, J = 7.8 Hz, 1H), 7.67 (dd, J = 6.4, 8.0 Hz, 1H), 7.57-7.51 (m, 3H), 6.50 (s, 2H), 4.11 (m, 1H), 3.70 (t, J = 6.7 Hz, 1H), 3.30 (s, 3H), 3.27 (br, 1H), 2.97 (br, 2H), 2.71-2.51 (m, 2H), 2.21-1.88 (m, 6H) |
| 477 | 498.10 | |
| 478 | 452.20 | |
| 479 | 468.30 | (300 MHz, DMSO-d$_6$): 9.11 (br, 1H), 8.75 (br, 1H), 8.11 (d, J = 2.2 Hz, 1H), 7.96-7.83 (m, 2H), 7.54 (td, J = 8.2, 3.2 Hz, 2H), 4.42 (m, 1H), 3.37 (d, J = 12.6 Hz, 2H), 3.04 (m, 2H), 2.17 (m, 2H), 1.99 (s, 3H), 1.95-1.86 (m, 2H), 1.86 (s, 3H) |
| 480 | 498.20 | (300 MHz, DMSO-d$_6$): 8.37 (d, J = 2.4 Hz, 1H), 7.87-7.78 (m, 1H), 7.70 (dd, J = 6.3, 8.1 Hz, 1H), 7.59-7.51 (m, 1H), 7.45 (d, J = 2.4 Hz, 1H), 6.90 (s, 1H), 6.81 (s, 2H), 4.08 (q, J = 7.1 Hz, 2H), 3.54 (m, 4H), 2.87-2.72 (m, 4H), 1.20 (t, J = 7.0 Hz, 3H) |
| 481 | 442.20 | (300 MHz, DMSO-d$_6$): 9.33 (br, 2H), 8.40 (d, J = 2.4 Hz, 1H), 7.95 (m, 1H), 7.85 (m, 1H), 7.55 (dd, 1H), 7.53 (d, J = 2.4 Hz, 1H), 6.99 (s, 1H), 3.22 (brs, 4H), 3.12 (br, 2H), 2.97 (br, 2H) |
| 482 | 467.30 | |
| 483 | 425.20 | |
| 484 | 465.30 | |
| 485 | 426.20 | (300 MHz, methanol-d$_4$): 8.55 (s, 1H), 8.25 (s, 1H), 8.05 (s, 1H), 7.65 (m, 1H), 7.60 (m, 1H), 7.50 (m, 1H), 4.79 (m, 1H), 4.10 (m, 2H), 3.60 (m, 2H), 2.10 (m, 2H) |
| 486 | 457.10 | (400 MHz, CDCl$_3$): 8.34 (s, 1H), 7.85 (d, J = 8.0 Hz, 1H), 7.52 (t, J = 8.0 Hz, 1H), 7.44 (dd, J = 8.0, 1.2 Hz, 1H), 7.29 (s, 1H), 7.08 (s, |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| | | 1H), 4.23-4.17 (m, 1H), 3.35-3.30 (m, 2H), 2.84 (br. t, J = 11.6 Hz, 2H), 2.17 (br. d, J = 11.6 Hz, 2H), 1.90-1.70 (m, 2H) |
| 487 | 357.10 | (300 MHz, DMSO-d₆): 8.53 (s, 1H), 7.87-7.78 (m, 1H), 7.75-7.69 (m, 1H), 7.59-7.48 (m, 2H), 7.42 (dd, J = 1.1, 5.1 Hz, 1H), 7.20 (dd, J = 1.1, 3.6 Hz, 1H), 7.05 (dd, J = 3.6, 5.1 Hz, 1H), 6.89 (br s, 2H) |
| 488 | 341.00 | (300 MHz, DMSO-d₆): 8.51 (d, J = 2.3 Hz, 1H), 7.84-7.75 (m, 1H), 7.71-7.61 (m, 3H), 7.56-7.48 (m, 1H), 6.80 (br s, 2H), 6.62-6.57 (m, 1H), 6.51 (dd, J = 1.8, 3.4 Hz, 1H) |
| 489 | 353.20 | (300 MHz, DMSO-d₆): 9.08 (s, 1H), 8.88 (s, 2H), 8.62 (d, J = 2.4 Hz, 1H), 7.88 (d, J = 2.5 Hz, 1H), 7.83-7.74 (m, 1H), 7.68-7.62 (m, 1H), 7.54-7.47 (m, 1H), 6.91 (br s, 2H) |
| 490 | 352.20 | (300 MHz, DMSO-d₆): 8.82 (s, 1H), 8.68 (s, 2H), 8.10 (s, 1H), 7.90 (m, 2H), 7.81-7.72 (m, 1H), 7.68-7.62 (m, 1H), 7.53-7.47 (m, 1H), 7.17 (br s, 2H) |
| 491 | 457.20 | (300 MHz, DMSO-d₆): 9.05-8.91 (br, 2H), 8.47 (d, J = 2.4 Hz, 1H), 7.99-7.94 (m, 1H), 7.86-7.76 (m, 2H), 7.69 (d, J = 2.4 Hz, 1H), 7.55 (td, J = 8.2, 3.2 Hz, 1H), 3.35-3.31 (m, 3H), 3.08-2.96 (m, 2H), 2.16 (d, J = 11.9 Hz, 2H), 1.99-1.85 (m, 2H) |
| 492 | | |
| 493 | 352.20 | (300 MHz, DMSO-d₆): 8.87 (d, J = 2.3 Hz, 1H), 8.51 (d, J = 4.7 Hz, 1H), 8.17 (d, J = 2.1 Hz, 1H), 7.86-7.55 (m, 4H), 7.56-7.48 (m, 1H), 7.29 (m, 1H), 7.09 (br s, 2H) |
| 494 | 373.10 | (300 MHz, DMSO-d₆): 8.66 (d, J = 2.4 Hz, 1H), 7.90 (d, J = 2.3 Hz, 1H), 7.85-7.76 (m, 1H), 7.72-7.66 (m, 1H), 7.57-7.49 (m, 1H), 7.25 (br s, 2H), 2.72 (m, 3H) |
| 495 | 355.20 | (300 MHz, DMSO-d₆): 8.51 (d, J = 2.1 Hz, 1H), 7.78 (m, 1H), 7.73-7.65 (m, 2H), 7.55-7.48 (m, 2H), 7.34 (s, 1H), 6.55 (br s, 2H), 3.62 (s, 3H) |
| 496 | 355.20 | |
| 497 | 341.00 | (300 MHz, DMSO-d₆): 8.37 (d, J = 2.3 Hz, 1H), 7.86 (s, 1H), 7.76-7.67 (m, 1H), 7.63-7.57 (m, 3H), 7.49-7.41 (m, 1H), 6.59 (m, 3H) |
| 498 | 370.20 | (300 MHz, DMSO-d₆): 8.09 (d, J = 2.3 Hz, 1H), 7.77-7.68 (m, 1H), 7.64-7.58 (m, 1H), 7.49-7.41 (m, 1H), 7.35-7.33 (m, 1H), 6.85 (br s, 2H), 2.10 (s, 3H), 1.87 (s, 3H) |
| 499 | 484.20 | (300 MHz, CDCl₃): 8.24 (d, J = 2.2 Hz, 1 H), 7.76 (dd, J = 2.2, 7.5 Hz, 1 H), 7.49-7.40 (m, 2 H), 7.33 (s, 1 H), 7.06 (d, J = 0.7 Hz, 1 H), 7.02 (d, J = 2.2 Hz, 1 H), 6.44 (s, 2 H), 4.25 (d, J = 3.8 Hz, 1 H), 3.09 (dd, J = 3.8, 10.8 Hz, 1 H), 2.83-2.79 (m, 1 H), 2.48-2.40 (m, 2 H), 2.32 (s, 2 H), 2.08-2.01 (m, 2 H), 1.80-1.64 (m, 3 H), 1.04 (t, J = 7.2 Hz, 3 H) |
| 500 | 424.30 | |
| 501 | 424.30 | |
| 502 | 438.30 | |
| 503 | 467.00 | (300 MHz, DMSO-d₆): 9.52 (bs, 1H), 8.29 (d, 1H), 7.78 (q, 1H), 7.69 (t, 1H), 7.53 (q, 1H), 6.9 (bs, 1H) 5.95 (s, 1H), 4.6 (m, 1H), 4.15 (bs, 2H), 3.62 (m, 2H), 3.1 (m1H) 2.80 (s, 3H), 2.41 (m, 1H), 2.28 (bs, 1H), 2.11 (m, 2H), 1.85 (m, 2H) |
| 504 | 453.00 | (300 MHz, DMSO-d₆): 9.82 (bs, 1H), 8.49 (bs, 1H), 8.29 (d, 1H), 7.79 (q, 1H)<7.7 (m, 3H), 7.53 (q, 1H), 5.97 (s, 1H) 4.61 (m, 1H), 4.1 (m, 2H), 3.88 (m1H), 3.61 (bt, 2H) 3.5 (m, 1H), 3.2 (m3H), 2.38 (m, 1H), 2.25 (bs, 1H), 1.91 (m1H), 1.81 (m, 1H) |
| 505 | 466.00 | (300 MHz, DMSO-d₆): 9.07 (bs, 1H), 8.8 (bs, 1H), 8.39 (d, 1H), 7.82 (q, 1H), 7.77 (s, 1H), 7.68 (t, 1H), 7.55 (q, 1H), 5.98 (s, 1H), 4.08 (s, 2H), 3.73 (m, 1H), 3.68 (t, 1H), 3.58 (t, 1H), 3.11 (m2H), 2.9-3.0 (m, 2H), 2.34 (bs, 1H), 2.25 (bs, 1H0, 2.11 (m1H), 1.81-2.01 (m, 2H), 1.63 (m, 1H) |
| 506 | 456.00 | (300 MHz, CDCl₃): 8.19 (s, 1H), 7.55 (m, 1H), 7.42 (m2H), 7.22 (s, 1H), 7.08 (bs, 1H), 5.62 (bs, 1H), 3.98 (q, 2H), 3.54 (t, 2H), 2.08 (bs, 2H), 1.51 (s, 9H) |
| 507 | 461.00 | (300 MHz, CDCl₃): 8.75 (d, 1H), 8.71 (s, 1H), 8.27 (s, 1H), 7.79 (dt, 1H), 7.55 (m, 1H), 7.48 (m2H), 7.13 (bs, 1H), 6.50 (bs.2H), 5.6 (bs, 1H), 4.3 (bs, 1H), 4.1 (bs, 1H), 3.89 (bs, 1H) 3.58 (bs, 1H), 2.2 (bs, 2H) 1.28 (s, 1H) |
| 508 | 442.00 | (300 MHz, DMSO-d₆): 8.25 (d, 1H), 7.79 (q, 1H), 7.68 (t, 1H), 7.55 (q, 1H), 7.40 (d, 1H), 6.19 (bs, 1H), 5.88 (bs, 1H), 4.79 (pentet, 1H), 3.91 (bs, 1H), 3.5 (t, 1H), 3.38 (bs, 2H), 2.17 (bs, 1H), 1.20 (d, 6H) |
| 509 | 406.00 | (300 MHz, DMSO-d₆): 9.11 (bs, 1H), 8.12 (d, 1H), 7.78 (q, 1H), 7.63 (t, 1H), 7.58 (q, 1H), 7.42 (d, 1H), 7.2-7.35 (m, 2H), 6.89 (d, 1), 4.03 (bs, 2H), 3.32 (bs, 2H), 3.05 (t, 2H) |
| 510 | 398.30 | (400 MHz, methanol-d₄): 8.2 (m, 2H); 7.8-7.5 (m, 3H); 5.9 (bs, 1H); 4.1 (m, 2H); 3.7 (m, 2H); 2.45-2.3 (m, 2H); 2.1 (s, 3H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 511 | 412.20 | (400 MHz, methanol-d₄): 8.2 (m, 2H); 7.8-7.5 (m, 3H); 5.9 (bs, 1H); 4.1 (m, 2H); 3.7 (m, 2H); 2.5 (m, 2H); 2.45-2.3 (m, 2H); 1.2 (m, 3H) |
| 512 | 426.30 | (400 MHz, methanol-d₄): 8.2 (m, 2H); 7.8-7.5 (m, 3H); 5.9 (bs, 1H); 4.1 (m, 2H); 3.7 (m, 2H); 3.0 (m, 1H); 2.45-2.3 (m, 2H); 1.1 (m, 6H) |
| 513 | 440.30 | (400 MHz, methanol-d₄): 8.2 (m, 2H); 7.8-7.5 (m, 3H); 5.9 (bs, 1H); 4.1 (m, 2H); 3.7 (m, 2H); 2.45-2.3 (m, 4H); 2.05 (m, 1H); 1.0 (m, 6H) |
| 514 | 442.10 | (400 MHz, methanol-d₄): 8.2 (m, 2H); 7.8-7.5 (m, 3H); 5.9 (bs, 1H); 4.1 (m, 2H); 3.7 (m, 4H); 3.4 (s, 3H); 2.7 (m, 2H); 2.3 (m, 2H) |
| 515 | 496.10 | (400 MHz, methanol-d₄): 8.2 (m, 2H); 7.8-7.5 (m, 3H); 5.9 (bs, 1H); 4.3 (m, 2H); 3.7 (m, 4H); 3.2 (m, 2H); 2.4 (m, 2H); 1.6 (m, 4H); 1.4 (s, 3H); 1.2 (s, 3H) |
| 516 | 482.20 | (400 MHz, methanol-d₄): 8.2 (m, 2H); 7.8-7.5 (m, 3H); 5.9 (bs, 1H); 4.2 (m, 2H); 4.0 (m, 2H); 3.7 (m, 2H); 3.4 (m, 2H); 2.45-2.3 (m, 2H); 2.0 (m, 1H); 1.7 (m, 2H); 1.4 (m, 2H) |
| 517 | 495.20 | (400 MHz, methanol-d₄): 8.2 (m, 2H); 7.8-7.5 (m, 3H); 5.9 (bs, 1H); 5.2 (m, 1H); 4.3 (m, 2H); 3.7 (m, 2H); 3.7 (m, 2H); 3.5 (m, 2H); 3.4 (m, 2H); 2.4 (m, 3H); 2.0 (m, 1H); 1.4 (m, 3H) |
| 518 | 461.10 | (400 MHz, methanol-d₄): 9.0 (m, 2H); 8.1 (m, 5H); 7.6 (m, 3H); 6.0 (m, 1H); 4.4 (bs, 1H); 4.0 (m, 2H); 3.6 (m, 1H); 2.5 (bs, 2H) |
| 519 | | |
| 520 | 470.30 | (400 MHz, DMSO-d₆): 8.3 (s, 1H); 7.8 (m, 1H); 7.65 (m, 1H); 7.5 (m, 1H): 7.4 (s, 1H); 6.8 (bs, 2H); 5.9 (s, 1H); 5.1 (t, 1H); 4.0 (s, 2H); 3.7 (m, 4H); 3.4 (t, 2H); 2.2 (bs, 2H); 2.15 (m, 1H); 1.9 (m, 1H) |
| 521 | 468.30 | (400 MHz, DMSO-d₆): 8.3 (s, 1H); 7.8 (m, 1H); 7.65 (m, 1H); 7.5 (m, 1H): 7.5 (s, 1H); 6.8 (bs, 2H); 5.9 (s, 1H); 4.15 (s, 1H); 4.0 (s, 1H); 3.8 (m, 2H); 3.6 (m, 2H); 3.4 (m, 2H); 2.9 (m, 1H); 2.2 (m, 2H); 1.5 (m, 4H) |
| 522 | 468.10 | |
| 523 | 424.20 | (400 MHz, DMSO-d₆): 8.3 (s, 1H); 7.8 (m, 1H); 7.6 (m, 1H); 7.55 (m, 2H): 7.4 (s, 1H); 6.8 (bs, 2H); 5.9 (m, 1H); 4.3 (s, 1H); 4.0 (s, 1H); 3.8 (s, 1H); 3.6 (s, 1H); 2.25 (m, 2H); 1.9 (m, 1H); 0.75 (m, 4H) |
| 524 | 438.30 | (400 MHz, DMSO-d₆): 8.3 (s, 1H); 7.8 (m, 1H); 7.65 (m, 1H); 7.55 (m, 1H): 6.55 (s, 1H); 6.8 (bs, 2H); 5.9 (m, 1H); 4.3 (s, 1H); 4.0 (s, 1H); 3.55 (m, 2H); 2.3 (m, 2H); 2.2 (m, 2H); 0.95 (m, 1H); 0.45 (m, 2H); 0.1 (m, 2H) |
| 525 | | (400 MHz, DMSO-d₆): 9.35 (bs, 2H); 8.3 (s, 1H); 7.9 (s, 1H); 7.8 (m, 1H); 7.7 (m, 1H): 7.5 (m, 1H); 7.2 (m, 2H); 6.0 (s, 1H); 5.1 (t, 1H); 3.65 (m, 2H); 3.2 (bs, 2H); 3.4 (t, 2H); 2.5 (bs, 2H) |
| 526 | 470.30 | (400 MHz, DMSO-d₆): 8.3 (s, 1H); 7.8 (m, 1H); 7.65 (m, 1H); 7.5 (m, 1H): 7.4 (s, 1H); 6.8 (bs, 2H); 5.9 (s, 1H); 5.1 (t, 1H); 4.0 (s, 2H); 3.7 (m, 4H); 3.4 (t, 2H); 2.2 (bs, 2H); 2.15 (m, 1H); 1.9 (m, 1H) |
| 527 | 454.30 | |
| 528 | 466.20 | |
| 529 | 466.20 | |
| 530 | 426.20 | (400 MHz, CDCl₃): 8.31 (d, J = 2.0 Hz, 1H), 7.79-7.75 (m, 1H), 7.50-7.74 (m, 1H), 7.41 (br. d, J = 8.0 Hz, 1H), 7.38 (s, 1H), 7.18 (br. d, J = 1.6 Hz, 1H), 7.13 (s, 1H), 6.42 (br. s, exchanged with D₂O, 2H), 4.76-4.74 (m, 1H), 3.30-3.19 (m, 3H), 3.03-2.95 (m, 1H), 2.35-2.26 (m, 1H), 2.18-2.10 (m, 1H) |
| 531 | 440.20 | (400 MHz, DMSO-d₆): 8.32 (d, J = 2.0 Hz, 1H), 7.76 (br. td, J = 8.0, 1.2 Hz, 1H), 7.49 (br. t, J = 8.0 Hz, 1H), 7.39 (overlapped t, J = 8.0 Hz, 1H), 7.38 (br. s, 1H), 7.18 (d, J = 2.4 Hz, 1H), 7.15 (s, 1H), 6.43 (d, exchanged with D₂O, 2H), 4.20-4.14 (m, 1H), 3.34 (dd, J = 12.0, 3.6 Hz, 1H), 3.06-2.93 (m, 2H), 2.69 (br. td, J = 12.4, 3.2 Hz, 1H), 2.25-2.15 (m, 2H), 1.99-1.58 (series of m, 2H) |
| 532 | 456.20 | (400 MHz, DMSO-d₆): 8.42 (d, J = 2.4 Hz, 1H), 7.96 (br. t, J = 8.4 Hz, 1H), 7.85 (br. t, J = 8.0 Hz, 1H), 7.56 (t, J = 8.4 Hz, 1H), 7.47 (d, J = 2.4 Hz, 1H), 7.00 (d, J = 3.6 Hz, 1H), 6.88 (br. s, exchanged with D₂O, 2H), 6.78 (d, J = 3.2 Hz, 1H), 3.05 (br. d, J = 12.0 Hz, 2H), 2.89-2.82 (m, 1H), 2.62 (t, J = 12.0 Hz, 2H), 1.88 (br. t, J = 12.4 Hz, 2H), 1.51-1.43 (m, 2H) |
| 533 | | (400 MHz, CDCl₃): 8.71 (d, J = 2.4 Hz, 1H), 7.76 (ddd, J = 8.4, 6.4, 2.4 Hz, 1H), 7.67 (d, J = 2.4 Hz, 1H), 7.49 (ddd, J = 8.4, 6.0, 2.0 Hz, 1H), 7.40 (td, J = 8.4, 2.0 Hz, 1H), 6.75 (br. s, exchanged with D₂O, 2H), 4.02 (br. s, 2H), 3.18 (t, J = 6.0 Hz, 2H), 2.78-2.75 (m, 2H) |
| 534 | 424.20 | (400 MHz, CDCl₃): 8.35 (s, 1H), 7.55-7.45 (m, 1H), 7.40-7.32 (m, 2H), 6.63 (s, 1H), 6.54 (br. s, exchanged with D₂O, 2H), 6.52 (s, |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| | | 1H), 5.99 (s, 1H), 3.82-3.75 (m, 1H), 3.26 (br. d, J = 12.0 Hz, 2H), 2.74 (t, J = 12.4 Hz, 2H), 2.03 (br. d, J = 12.0 Hz, 2H), 1.80-1.72 (m, 2H) |
| 535 | 441.20 | (400 MHz, DMSO-d$_6$): 8.76 (s, 1H), 7.85-7.78 (m, 1H), 7.74 (br. s, exchanged with D$_2$O, 2H), 7.70-7.60 (m, 1H), 7.55-7.50 (m, 1H), 7.35 (d, J = 3.6 Hz, 1H), 6.72 (d, J = 3.6 Hz, 1H), 3.10-3.00 (m, 2H), 2.95-2.85 (m, 1H), 2.70-2.50 (m, 2H), 1.90-1.80 (m, 2H), 1.60-1.40 (m, 2H) |
| 536 | 411.20 | (400 MHz, CDCl$_3$): 8.35 (s, 1H), 7.58-7.48 (m, 1H), 7.40-7.30 (m, 2H), 7.26 (overlapped s, 1H), 7.22 (s, 1H), 6.68 (br. s, exchanged with D$_2$O, 2H), 4.74-4.72 (m, 1H), 3.31-3.20 (m, 3H), 3.05-3.00 (m, 1H), 2.36-2.27 (m, 1H), 2.15-2.06 (m, 1H) |
| 537 | 414.10 | (400 MHz, DMSO-d$_6$): 8.85 (s, 1H), 8.05 (br. hump, exchanged with D$_2$O, 2H), 7.85-7.79 (m, 1H), 7.67-7.54 (m, 1H), 7.54-7.49 (m, 1H), 3.85 (br. s, 2H), 2.98 (t, J = 5.6 Hz, 2H), 2.67-2.60 (m, 2H) |
| 538 | 426.20 | (400 MHz, CDCl$_3$): 8.31 (d, J = 2.0 Hz, 1H), 7.76 (br. td, J = 8.0, 2.0 Hz, 1H), 7.51-7.47 (m, 1H), 7.40 (dd, J = 8.0, 1.6 Hz, 1H), 7.38 (s, 1H), 7.18 (d, J = 2.0 Hz, 1H), 7.13 (s, 1H), 6.43 (br. s, exchanged with D$_2$O, 2H), 4.79-4.73 (m, 1H), 3.30-3.16 (m, 3H), 3.03-2.96 (m, 1H), 2.35-2.26 (m, 1H), 2.18-2.10 (m, 1H) |
| 539 | 358.10 | (300 MHz, DMSO-d$_6$): 8.7 (m, 1H); 7.9-7.75 (m, 3H); 7.7 (m, 1H); 7.65 (m, 1H); 7.53 (m, 1H); 7.15 (br s, 2H) |
| 540 | 358.10 | (300 MHz, DMSO-d$_6$): 9.0 (s, 1H), 8.5 (d, J = 2.4 Hz, 1H), 8.02 (s, 1H); 7.8 (m, 1H); 7.65 (m, 1H); 7.6 (m, 1H); 7.55 (m, 1H); 6.95 (br s, 2H) |
| 541 | 358.00 | (300 MHz, DMSO-d$_6$): 9.1 (m, 1H); 8.77 (m, 1H); 8.0 (m, 1H); 7.87 (m, 1H); 7.77 (m, 1H); 7.67 (m, 1H); 7.5 (m, 1H); 6.8 (br s, 2H) |
| 542 | 428.20 | (300 MHz, DMSO-d$_6$): 9.58 (brs, 2H), 8.45 (d, J = 2.3 Hz, 1H), 7.94 (t, J = 7.2 Hz, 1H), 7.85 (t, J = 6.9 Hz, 1H), 7.61 (d, J = 2.3 Hz, 1H), 7.57-7.52 (m, 1H), 7.05 (s, 1H), 4.29 (br, 2H), 3.34 (br, 2H), 2.83 (br, 2H) |
| 543 | 450.30 | |
| 544 | 450.30 | |
| 545 | 428.20 | (300 MHz, DMSO-d$_6$): 9.55 (s, 2H), 8.44 (d, J = 2.4 Hz, 1H), 7.95 (td, J = 6.8 Hz, 1.4 Hz, 1H), 7.85 (td, J = 6.6 Hz, 1.4 Hz, 1H), 7.61 (d, J = 2.3 Hz, 1H), 7.55 (td, J = 8.2, 3.2 Hz, 1H), 7.05 (s, 1H), 4.11 (brs, 2H), 3.38 (br, 2H), 3.01 (br, 2H), |
| 546 | | |
| 547 | 409.80 | |
| 548 | 438.10 | |
| 549 | | |
| 550 | | (400 MHz, CDCl$_3$): 8.55 (br. hump, addition of D$_2$O changed to s, 1H), 8.42 (s, 1H), 8.20 (br. hump, addition of D$_2$O changed to s, 1H), 7.53-7.38 (series of m, 3H), 7.26-7.20 (m, 3H), 6.75 (br. s, exchanged to D$_2$O, 2H), 1.93 (s, 3H) |
| 551 | | (400 MHz, CDCl$_3$): 8.53 (br. s, 1H), 8.42 (s, 1H), 8.23 (br. s, 1H), 7.76 (d, J = 8.0 Hz, 1H), 7.45 (t, J = 8.0 Hz, 1H), 7.36-7.21 (series of m, 4H), 6.77 (br. s, exchanged with D$_2$O, 2H), 2.03 (s, 3H) |
| 552 | | (400 MHz, CDCl$_3$): 8.52 (br. s, 1H), 8.42 (d, J = 2.0 Hz, 1H), 8.24 (br. s, 1H), 7.69 (br. d, J = 8.0 Hz, 1H), 7.46 (d, J = 8.0 Hz, 1H), 7.44-7.39 (m, 2H), 7.30-7.20 (m, 2H), 6.90 (br. s, exchanged with D$_2$O, 2H), 2.00 (s, 3H) |
| 553 | 400.40 | |
| 554 | | (400 MHz, CDCl$_3$): 8.54 (br. s, 1H), 8.42 (d, J = 2.4 Hz, 1H), 8.29 (br. s, 1H), 7.69-7.63 (m, 2H), 7.49 (br. dt, J = 8.0, <2.0 Hz, 1H), 7.37-7.27 (m, 3H), 6.59 (s, exchanged with D$_2$O, 2H) |
| 555 | | (400 MHz, CDCl$_3$): 8.52 (dd, J = 4.4, 1.2 Hz, 1H), 8.43 (d, J = 2.4 Hz, 1H), 8.25 (d, J = 2.0 Hz, 1H), 7.69 (dd, J = 8.0, 4.8 Hz, 1H), 7.47 (dt, J = 8.0, 2.0 Hz, 1H), 7.43 (ddd, J = 9.2, 7.6, 3.2 Hz, 1H), 7.37 (dd, J = 7.6, 3.2 Hz, 1H), 7.29 (dd, J = 9.2, 7.6 Hz, 1H), 7.26 (overlapped d, J = 2.4 Hz, 1H), 6.66 (br. s, exchanged with D$_2$O, 2H) |
| 556 | | (400 MHz, CDCl$_3$): 8.52 (d, J = 4.0 Hz, 1H), 8.45 (d, J = 2.0 Hz, 1H), 8.32 (br. s, 1H), 7.50 (br. dt, J = 8.0, <2 Hz, 1H), 7.35-7.24 (series of m, 4H), 6.61 (br. s, exchanged with D$_2$O, 2H) |
| 557 | | (400 MHz, CDCl$_3$): 8.53 (d, J = 3.6 Hz, 1H), 8.43 (d, J = 2.0 Hz, 1H), 8.26 (s, 1H), 7.78 (br. dt, J = 9.6, 1.6 Hz, 1H), 7.53 (br. t, J = 8.0, 7.6 Hz, 1H), 7.46 (dt, J = 8.0, <2 Hz, 1H), 7.24 (br. td, J = 8.0, <2 Hz, 1H), 7.32 (d, J = 2.0 Hz, 1H), 7.28 (dd, J = 8.0, 4.8 Hz, 1H), 6.59 (br. s, exchanged with D$_2$O, 2H) |
| 558 | | (400 MHz, CDCl$_3$): 8.53 (br. s, 1H), 8.41 (br. s, 1H), 8.27 (br. s, 1H), 7.47 (br. d, J = 7.6 Hz, 1H), 7.38-7.35 (m, 2H), |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| | | 7.32-7.26 (overlapped m, 2H), 7.08 (dd, J = 9.6, 3.6 Hz, 1H), 6.56 (br. s, 2H), 3.64 (s, 3H) |
| 559 | | (400 MHz, CDCl₃): 8.53 (br. s, 1H), 8.46 (d, J = 2.0 Hz, 1H), 8.39 (br. s, 1H), 7.53 (d, J = 8.0 Hz, 1H), 7.36 (d, J = 2.4 Hz, 1H), 7.32-7.28 (m, 1H), 7.15-7.10 (m, 3H), 6.40 (s, exchanged with D₂O, 2H) |
| 560 | | (400 MHz, CDCl₃): 8.58 (s, 1H), 8.47 (s, 1H), 8.41 (s, 1H), 7.69 (br. t, J = 1.6 Hz, 1H), 7.54 (d, J = 7.6 Hz, 1H), 7.48-7.46 (m, 2H), 7.29 (d, J = 2.0 Hz, 1H), 7.36-7.32 (m, 1H), 6.50 (s, exchanged with D₂O, 2H) |
| 561 | | (400 MHz, CDCl₃): 8.52 (br. dd, J = 4.4, 1.2 Hz, 1H), 8.42 (d, J = 2.4 Hz, 1H), 8.28 (d, J = 2.0 Hz, 1H), 7.48-7.43 (m, 2H), 7.36 (d, J = 2.0 Hz, 1H), 7.33-7.26 (overlapped m, 3H), 6.55 (s, exchanged with D₂O, 2H), 3.78 (d, J = 2.8 Hz, 3H) |
| 562 | | (400 MHz, CDCl₃): 8.40 (d, J = 1.6 Hz, 1H), 7.42-7.37 (series of m, 4H), 7.30-7.26 (series of m, 3H), 7.15 (s, exchanged with D₂O, 1H), 6.76 (d, J = 7.6 Hz, 1H), 6.49 (s, exchanged with D₂O, 2H), 3.77 (d, J = 3.2 Hz, 3H), 2.19 (s, 3H) |
| 563 | 375.40 | |
| 564 | | (400 MHz, DMSO-d₆): 9.92 (s, exchanged with D₂O, 1H), 8.36 (d, J = 2.0 Hz, 1H), 7.63 (s, 1H), 7.52-7.49 (m, 3H), 7.45 (d, J = 3.0 Hz, 1H), 7.40 (d, J = 8.0 Hz, 1H), 7.25 (t, J = 8.0 Hz, 1H), 6.92 (br. s, exchanged with D₂O, 2H), 6.81 (d, J = 7.6 Hz, 1H), 2.05 (s, 3H), 1.90 (d, J = 2.0 Hz, 3H) |
| 565 | | (400 MHz, DMSO-d₆): 9.90 (s, exchanged with D₂O, 1H), 8.36 (d, J = 1.6 Hz, 1H), 7.76 (d, J = 8.0 Hz, 1H), 7.65 (d, J = 8.0 Hz, 1H), 7.63 (s, 1H), 7.50 (t, J = 8.0 Hz, 1H), 7.42 (d, J = 2.0 Hz, 1H), 7.42 (d, J = 8.0 Hz, 1H), 7.25 (t, J = 7.6 Hz, 1H), 6.92 (br. s, exchanged with D₂O, 2H), 6.80 (d, J = 8.0 Hz, 1H), 2.05 (s, 3H), 1.99 (s, 3H) |
| 566 | | (400 MHz, DMSO-d₆): 9.92 (s, exchanged with D₂O, 1H), 8.37 (d, J = 2.4 Hz, 1H), 7.88 (d, J = 2.0 Hz, 1H), 7.66 (d, J = 2.4 Hz, 1H), 7.65-7.63 (m, 1H), 7.54 (d, J = 7.6 Hz, 1H), 7.47 (overlapped dd, J = 8.0, 2.4 Hz, 1H), 7.42 (d, J = 8.0 Hz, 1H), 7.26 (t, J = 8.0 Hz, 1H), 6.94 (s, exchanged with D₂O, 2H), 6.89 (d, J = 8.0 Hz, 1H), 2.05 (s, 3H), 1.94 (s, 3H) |
| 567 | | (400 MHz, DMSO-d₆): 9.90 (s, exchanged with D₂O, 1H), 8.40 (d, J = 2.0 Hz, 1H), 7.89-7.84 (m, 1H), 7.67 (s, 1H), 7.65-7.62 (m, 2H), 7.58 (d, J = 2.0 Hz, 1H), 7.42 (d, J = 8.0 Hz, 1H), 7.29 (t, J = 8.0 Hz, 1H), 6.77 (d, J = 8.0 Hz, 1H), 6.78 (s, exchanged with D₂O, 2H), 2.05 (s, 3H) |
| 568 | | (400 MHz, DMSO-d₆): 9.93 (s, exchanged with D₂O, 1H), 8.38 (d, J = 2.0 Hz, 1H), 8.05 (dd, J = 6.4, 2.8 Hz, 1H), 7.82-7.78 (m, 1H), 7.69 (br. s, 1H), 7.61 (overlapped t, J = 8.0 Hz, 1H), 7.58 (d, J = 2.4 Hz, 1H), 7.42 (d, J = 8.0 Hz, 1H), 7.27 (d, J = 7.6 Hz, 1H), 6.95 (d, J = 8.0 Hz, 1H), 6.74 (s, exchanged with D₂O, 2H), 2.03 (s, 3H) |
| 569 | | (400 MHz, CDCl₃): 8.40 (br. s, 1H), 7.70 (dd, J = 9.6, 4.8 Hz, 1H), 7.48 (br. s, 1H), 7.45-7.35 (m, 2H), 7.28-7.25 (m, 3H), 7.14 (br. s, 1H), 6.80-6.75 (m, 1H), 6.58 (br. s, exchanged with D₂O, 2H), 2.20 (s, 3H) |
| 570 | | (400 MHz, DMSO-d₆): 9.92 (s, exchanged with D₂O, 1H), 8.40 (d, J = 2.0 Hz, 1H), 7.98-7.95 (m, 1H), 7.64 (br. s, 1H), 7.48 (d, J = 2.0 Hz, 1H), 7.36 (d, J = 2.0 Hz, 1H), 7.38 (d, J = 8.4 Hz, 1H), 7.27 (t, J = 8.4 Hz, 1H), 6.94 (d, J = 7.6 Hz, 1H), 6.88 (br. s, exchanged with D₂O, 2H), 2.04 (s, 3H) |
| 571 | | (400 MHz, CDCl₃): 8.40 (br. s, 1H), 7.39-7.37 (m, 2H), 7.34-7.26 (series of m, 4H), 7.11 (dd, J = 8.0, 4.4 Hz, 1H), 6.80 (br. s, 1H), 6.47 (br. s, exchanged with D₂O, 2H), 3.69 (s, 3H), 2.4 (s, 3H) |
| 572 | | (400 MHz, CDCl₃): 8.46 (br. s, 1H), 7.50 (br. s, 1H), 7.37 (br. s, 1H), 7.30-7.26 (series of m, 3H), 7.20-7.10 (m, 3H), 6.87 (m, 1H), 6.29 (s, exchanged with D₂O, 2H), 2.19 (s, 3H) |
| 573 | | (400 MHz, CDCl₃): 8.47 (d, J = 2.0 Hz, 1H), 7.64 (br. s, 1H), 7.47-7.45 (m, 2H), 7.42-7.39 (m, 3H), 7.32 (t, J = 8.0 Hz, 1H), 7.13 (br. s, exchanged with D₂O, 1H), 6.88 (d, J = 7.6 Hz, 1H), 6.37 (br. s, exchanged with D₂O, 2H), 2.20 (s, 3H) |
| 574 | | (400 MHz, DMSO-d₆): 9.94 (s, exchanged with D₂O, 1H), 8.43 (d, J = 2.4 Hz, 1H), 7.56-7.53 (m, 4H), 7.41 (d, J = 2.0 Hz, 2H), 7.16 (d, J = 8.0 Hz, 2H), 6.92 (s, exchanged with D₂O, 2H), 2.03 (s, 3H), 1.88 (d, J = 1.6 Hz, 3H) |
| 575 | | (400 MHz, DMSO-d₆): 9.98 (s, exchanged with D₂O, 1H), 8.43 (d, J = 2.0 Hz, 1H), 7.82 (d, J = 7.6 Hz, 1H), 7.70 (d, J = 7.6 Hz, 1H), 7.56 (d, J = 8.0 Hz, 2H), 7.54 (overlapped t, J = 8.0 Hz, 1H), 7.40 (d, J = 2.4 Hz, 1H), 7.16 (d, J = 8.4 Hz, 2H), 6.95 (s, exchanged with D₂O, 2H), 2.04 (s, 3H), 1.98 (s, 3H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 576 | | (400 MHz, DMSO-d$_6$): 9.99 (s, exchanged with D$_2$O, 1H), 8.44 (d, J = 2.9 Hz, 1H), 7.96 (d, J = 2.0 Hz, 1H), 7.72 (dd, J = 8.4, 2.0 Hz, 1H), 7.57 (overlapped d, J = 8.4 Hz, 1H), 7.55 (d, J = 8.4 Hz, 2H), 7.46 (d, J = 2.0 Hz, 1H), 7.55 (d J = 8.4 Hz, 2H),, 6.96 (s, exchanged with D$_2$O, 2H), 2.04 (s, 3H), 1.91 (s, 3H) |
| 577 | | (400 MHz, CDCl$_3$): 8.43 (d, J = 2.0 Hz, 1H), 7.49 (dd, J = 14.4, 8.4 Hz, 1H), 7.31 (t, J = 8.8 Hz, 1H), 7.27 (overlapped d, J = 8.0 Hz, 2H), 7.26 (overlapped d, J = 2.0 Hz, 1H), 7.20 (d, J = 8.0 Hz, 1H), 6.94 (d, J = 7.6 Hz, 2H), 6.62 (s, exchanged with D$_2$O, 2H), 3.40 (s, 2H), 2.24 (s, 6H), 1.94 (br. s, 3H) |
| 578 | | (400 MHz, CDCl$_3$): 8.43 (d, J = 2.0 Hz, 1H), 7.74 (d, J = 7.6 Hz, 1H), 7.42 (t, J = 8.0 Hz, 1H), 7.31 (d, J = 7.6 Hz, 1H), 7.27 (d, J = 8.0 Hz, 2H), 7.24 (d, J = 2.0 Hz, 1H), 6.95 (d, J = 8.0 Hz, 2H), 6.64 (s, exchanged with D$_2$O, 2H), 3.41 (s, 2H), 2.24 (s, 6H), 2.04 (s, 3H) |
| 579 | | (400 MHz, CDCl$_3$): 8.44 (d, J = 2.0 Hz, 1H), 7.62 (dd, J = 8.8, 2.0 Hz, 1H), 7.44 (s, J = 2.0 Hz, 1H), 7.44 (d, J = 7.6 Hz, 1H), 7.28 (overlapped d, J = 8.0 Hz, 2H), 7.27 (d, J = 2.4 Hz, 1H), 6.98 (d, J = 8.4 Hz, 2H), 6.65 (s, exchanged with D$_2$O, 2H), 3.42 (s, 2H), 2.26 (s, 6H), 1.98 (s, 3H) |
| 580 | | (400 MHz, CDCl$_3$): 8.45 (d, J = 2.4 Hz, 1H), 7.41-7.35 (series of m, 4H), 7.34 (d, J = 8.4 Hz, 2H), 7.04 (d, J = 8.0 Hz, 2H), 6.47 (s, exchanged with D$_2$O, 2H), 3.42 (s, 2H), 2.25 (s, 6H) |
| 581 | | (400 MHz, DMSO-d$_6$): 9.94 (s, exchanged with D$_2$O, 1H), 8.44 (d, J = 1.6 Hz, 1H), 7.91-7.88 (m, 1H), 7.67-7.62 (m, 2H), 7.56 (overlapped d, J = 1.6 Hz, 1H), 7.55 (overlapped d, J = 8.4 Hz, 2H), 7.25 (d, J = 8.8 Hz, 2H), 6.74 (s, exchanged with D$_2$O, 2H), 2.02 (s, 3H) |
| 582 | | (400 MHz, DMSO-d$_6$): 9.94 (s, 1H), 8.44 (d, J = 2.0 Hz, 1H), 8.11 (dd, J = 6.4, 2.4 Hz, 1H), 7.85-7.80 (m, 1H), 7.63 (t, J = 9.2 Hz, 1H), 7.56 (overlapped br. s, 1H), 7.55 (overlapped d, J = 8.8 Hz, 2H), 7.26 (d, J = 8.8 Hz, 2H), 6.73 (s, exchanged with D$_2$O, 2H), 2.03 (s, 3H) |
| 583 | | (400 MHz, DMSO-d$_6$): 9.95 (s, 1H), 8.45 (d, J = 2.4 Hz, 1H), 8.06-8.00 (m, 2H), 7.58 (d, J = 8.4 Hz, 2H), 7.49 (d, J = 2.0 Hz, 1H), 7.24 (d, J = 8.4 Hz, 2H), 6.83 (s, exchanged with D$_2$O, 2H), 2.07 (s, 3H) |
| 584 | | (400 MHz, DMSO-d$_6$): 9.94 (s, exchanged with D$_2$O, 1H), 8.44 (d, J = 2 Hz, 1H), 7.96 (t, J = 7.2 Hz, 1H), 7.87 (t, J = 7.6 Hz, 1H), 7.56-7.52 (overlapped m, 1H), 7.56 (overlapped d, J = 8.0 Hz, 2H), 7.55 (br.s, 1H), 7.24 (d, J = 8.8 Hz, 2H), 6.73 (s, exchanged with D$_2$O, 2H), 2.04 (s, 3H) |
| 585 | | (400 MHz, DMSO-d$_6$): 9.93 (s, exchanged with D$_2$O, 1H), 8.40 (br. s, 1H), 7.78-7.74 (m, 1H), 7.60-7.53 (overlapped m, 1H), 7.55 (d, J = 7.6 Hz, 2H), 7.46 (br. s, 1H), 7.34-7.30 (m, 1H), 7.16 (d, J = 8.4 Hz, 2H), 6.81 (s, exchanged with D$_2$O, 2H), 3.59 (s, 3H), 2.48 (s, 3H) |
| 586 | | (400 MHz, DMSO-d$_6$): 9.95 (s, exchanged with D$_2$O, 1H), 8.44 (d, J = 1.6 Hz, 1H), 7.74 (br. s, 1H), 7.62-7.58 (overlapped m, 1H), 7.59 (d, J = 8.4 Hz, 2H), 7.46-744 (m, 2H), 7.38 (d, J = 8.4 Hz, 2H), 6.51 (s, exchanged with D$_2$O, 2H), 2.02 (s, 3H) |
| 587 | | (400 MHz, DMSO-d$_6$): 9.95 (s, exchanged with D$_2$O, 1H), 8.44 (br. s, 1H), 7.93 (br. s, 1H), 7.77 (s, 2H), 7.75 (s, 1H), 7.60 (d, J = 8.8 Hz, 2H), 7.38 (d, J = 8.0 Hz, 2H), 6.53 (s, exchanged with D$_2$O, 2H), 2.03 (s, 3H) |
| 588 | | (400 MHz, DMSO-d$_6$): 9.94 (s, exchanged with D$_2$O, 1H), 8.44 (d, J = 2.0 Hz, 1H), 7.68-7.63 ((m, 2H), 7.55 (d, J = 8.4 Hz, 2H), 7.46 (d, J = 2 Hz, 1H), 7.42 (overlapped dt, J = 8.0, 4.8 Hz, 1H), 7.18 (d, J = 8.4 Hz, 2H), 6.84 (s, exchanged with D$_2$O, 2H), 3.58 (d, J = 2.0 Hz, 3H), 2.03 (s, 3H) |
| 589 | | (400 MHz, CDCl$_3$): 8.43 (d, J = 2.4 Hz, 1H), 7.45 (ddd, J = 11.6, 8.0, 2.4 Hz, 1H), 7.37 (d, J = 2.4 Hz, 1H), 7.31-7.24 (series of m, 4H), 7.06 (d, J = 8.0 Hz, 2H), 6.45 (s, exchanged with D$_2$O, 2H), 3.75 (d, J = 3.2 Hz, 3H), 3.41 (s, 2H), 2.25 (s, 6H) |
| 590 | | (400 MHz, CDCl$_3$): 8.49 (d, J = 2.0 Hz, 1H), 7.69-7.67 (m, 1H), 7.49 (d, J = 1.6 Hz, 2H), 7.40 (d, J = 2.0 Hz, 1H), 7.34 (d, J = 7.6 Hz, 2H), 7.12 (d, J = 8.4 Hz, 2H), 6.42 (s, exchanged with D$_2$O, 2H), 3.44 (s, 2H), 2.27 (s, 6H) |
| 591 | | (400 MHz, CDCl$_3$): 8.50 (d, J = 2.4 Hz, 1H), 7.39 (d, J = 2.4 Hz, 1H), 7.33 (d, J = 8.0 Hz, 2H), 7.16-7.10 (series of m, 5H), 6.34 (s, exchanged with D$_2$O, 2H), 3.42 (s, 2H), 2.27 (s, 6H) |
| 592 | | (400 MHz, CDCl$_3$): 8.47 (d, J = 2.4 Hz, 1H), 7.68 (dd, J = 8.8, 4.8 Hz, 1H), 7.485-7.38 (overlapped m, 2H), 7.31-7.26 (2 overlapped d, 3H), 7.04 (d, J = 8.0 Hz, 2H), 6.57 (s, exchanged with D$_2$O, 2H), 3.43 (s, 2H), 2.27 (s, 6H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 593 | | (400 MHz, CDCl$_3$): 8.46 (d, J = 2.4 Hz, 1H), 7.66-7.64 (m, 1H), 7.64 (overlapped d, J = 5.2 Hz, 1H), 7.37 (d, J = 1.6 Hz, 1H), 7.32-7.26 (overlapped t, J = 9.2 Hz, 1H), 7.26 (overlapped d, J = 8.8 Hz, 2H), 7.05 (d, J = 8.4 Hz, 2H), 6.46 (s, exchanged with D$_2$O, 2H), 3.42 (s, 2H), 2.25 (s, 6H) |
| 594 | | (400 MHz, CDCl$_3$): 8.45 (d, J = 2.0 Hz, 1H), 7.40-7.32 (m, 4H), 7.31 (d, J = 7.6 Hz, 2H), 7.04 (d, J = 7.6 Hz, 2H), 6.45 (s, exchanged with D$_2$O, 2H), 3.62 (s, 2H), 2.53 (br. s, 4H), 1.85 (br. s, 4H) |
| 595 | | (400 MHz, CDCl$_3$): 8.44 (d, J = 2.0 Hz, 1H), 7.68-7.62 (m, J = 2.8 Hz, 2H), 7.38 (d, J = 7.6 Hz, 2H), 7.37 (br. s, 1H), 7.33 (overlapped t, J = 9.2 Hz, 1H), 7.07 (d, J = 7.6 Hz, 2H), 6.47 (s, exchanged with D$_2$O, 2H), 3.74 (s, 2H), 2.68 (br. s, 4H), 1.88 (br. s, 4H) |
| 596 | | (400 MHz, CDCl$_3$): 8.44 (d, J = 2.4 Hz, 1H), 7.69 (dd, J = 9.2, 5.2 Hz, 1H), 7.43-7.35 (m, 4H), 7.28 (m, J = 2.4 Hz, 1H), 7.04 (d, J = 7.6 Hz, 2H), 6.58 (s, exchanged with D$_2$O, 2H), 3.76 (br. s, 2H), 2.72 (br. s, 4H), 1.89 (br. s, 4H) |
| 597 | | (400 MHz, CDCl$_3$): 8.46 (br. s, 1H), 7.66 (s, 1H), 7.46 (s, 2H), 7.45-7.44 (m, 2H), 7.38 (br. s, 1H), 7.14 (d, J = 7.6 Hz, 2H), 6.38 (s, exchanged with D$_2$O, 2H), 3.82 (br. s, 2H), 2.75 (br. hump, 4H), 1.92 (br. s, 4H) |
| 598 | | (400 MHz, CDCl$_3$): 8.43 (d, J = 2.4 Hz, 1H), 7.51-7.45 (m, 1H), 7.39 (t, J = 8 Hz, 1H), 7.34 (br. d, J = 6.8 Hz, 1H), 7.25 (d, J = 2.0 Hz, 1H), 7.24 (d, J = 8 Hz, 2H), 6.98 (d, J = 8.4 Hz, 2H), 6.63 (s, exchanged with D$_2$O, 2H), 3.68 (br. s, 2H), 2.60 (br. s, 4H), 1.94 (d, J = 1.6 Hz, 3H), 1.85 (br. s, 4H) |
| 599 | | (400 MHz, CDCl$_3$): 8.43 (d, J = 2.0 Hz, 1H), 7.75 (d, J = 8.0 Hz, 1H), 7.45 (t, J = 7.6 Hz, 1H), 7.36 (d J = 8.4 Hz, 2H), 7.32 (d, J = 8.0 Hz, 1H), 7.24 (d, J = 2.4 Hz, 1H), 6.98 (d, J = 8.4 Hz, 2H), 6.66 (s, exchanged with D$_2$O, 2H), 3.74 (s, 2H), 2.68 (s, 4H), 2.04 (s, 3H), 1.88 (br. s, 4H) |
| 600 | | (400 MHz, CDCl$_3$): 8.44 (d, J = 2 Hz, 1H), 7.62 (dd, J = 8.0, 2.0 Hz, 1H), 7.45 (m, J = 7.6 Hz, 1H), 7.44 (d, J = 2.4 Hz, 1H), 7.34 (d, J = 8 Hz, 2H), 7.28 (d, J = 2.4 Hz, 1H), 6.99 (d, J = 7.6 Hz, 2H), 6.55 (s, exchanged with D$_2$O, 2H), 3.67 (br. s, 2H), 2.60 (br. s, 4H), 1.99 (s, 3H), 1.84 (br. s, 4H) |
| 601 | | (400 MHz, CDCl$_3$): 8.46 (d, J = 1.6 Hz, 1H), 7.39-7.33 (m, 2H), 7.30 (td, J = 8.0, 2.4 Hz, 1H), 7..26-7.24 (m, 2H), 7.07 (d, J = 7.6 Hz, 2H), 6.52 (s, exchanged with D$_2$O, 2H), 3.70 (s, 2H), 2.61 (s, 4H), 1.86 (s, 4H) |
| 602 | | (400 MHz, CDCl$_3$): 8.42 (d, J = 1.6 Hz, 1H), 7.40 (d, J = 2.4 Hz, 1H), 7.37-7.27 (series of m, 4H), 7.04 (d, J = 8.8, 4.4 Hz, 1H), 7.03 (d, J = 7.6 Hz, 2H), 6.44 (s, exchanged with D$_2$O, 2H), 3.64 (s, 2H), 3.62 (s, 3H), 2.55 (s, 4H), 1.82 (s, 4H), |
| 603 | | (400 MHz, CDCl$_3$): 8.46 (br. s, 1H), 7.39-7.36 (m, 3H), 7.12-7.10 (m, 5H), 6.30 (s, exchanged with D$_2$O, 2H), 3.72 (s, 2H), 2.64 (s, 4H), 1.86 (s, 4H) |
| 604 | | (400 MHz, CDCl$_3$): 8.41 (d, J = 2.0 Hz, 1H), 7.45-7.38 (m, 1H), 7.38-7.34 (m, 2H), 7.31-7.26 (m, 3H), 7.04 (d, J = 8.0 Hz, 2H), 6.44 (s, exchanged with D$_2$O, 2H), 3.75 (d, J = 2.8 Hz, 3H), 3.74 (br. s, 2H), 2.68 (s, 4H), 1.88 (s, 4H) |
| 605 | | (400 MHz, CDCl$_3$): 8.47 (d, J = 2.0 Hz, 1H), 7.32-7.25 (series of m, 5H), 7.07 (d, J = 8.0 Hz, 2H), 6.53 (s, exchanged with D$_2$O, 2H), 3.44 (s, 2H), 2.27 (s, 6H) |
| 606 | | (400 MHz, CDCl$_3$): 8.43 (d, J = 2.0 Hz, 1H), 7.41 (d, J = 2.0 Hz, 1H), 7.35 (m, 1H), 7.33 (dd, J = 7.6, 3.2 Hz, 1H), 7.28 (d, J = 8.4 Hz, 2H), 7.06 (dd, J = 8.8, 4.4 Hz, 1H), 7.03 (d, J = 8.4 Hz, 2H), 6.45 (s,, exchanged with D$_2$O, 2H), 3.62 (s, 3H), 3.41 (s, 2H), 2.25 (s, 6H) |
| 607 | | (400 MHz, CDCl$_3$): 8.41 (d, J = 2.0 Hz, 1H), 7.72-7.67 (m, 1H), 7.50 (d, J = 8.4 Hz, 2H), 7.35 (s, 1H), 7.25-7.22 (overlapped m, 2H), 7.14 (s, exchanged with D$_2$O, 1H), 7.02 (d, J = 8.0 Hz, 2H), 6.48 (s, exchanged with D$_2$O, 2H), 2.19 (s, 3H) |
| 608 | | (400 MHz, CDCl$_3$): 8.52 (d, J = 3.6 Hz, 1H), 8.43 (d, J = 2.0 Hz, 1H), 8.24 (s, 1H), 7.75-7.68 (m, 1H), 7.50 (d, J = 8.0 Hz, 1H), 7.38 (s, J = 1.6 Hz, 1H), 7.29-7.24 (overlapped m, 3H), 6.60 (br. s, exchanged with D$_2$O, 2H) |
| 609 | | (400 MHz, CDCl$_3$): 8.52 (br. s, 1H), 8.42 (d, J = 2.4 Hz, 1H), 8.21 (s, 1H), 7.66-7.59 (overlapped m, 3H), 7.51 (d, J = 7.6 Hz, 1H), 7.30-7.26 (overlapped m, 2H), 6.68 (br. s, exchanged with D$_2$O, 2H) |
| 610 | | (400 MHz, CDCl$_3$): 8.42 (d, J = 2.3 Hz, 1H), 7.69-7.65 (m, 1H), 7.46 (s, 1H), 7.38 (d, J = 2.3 Hz, 1H), 7.30-7.22 (m, 4H), 7.11 (s, exchanged with D$_2$O, 1H), 6.76 (d, J = 7.4 Hz, 1H), 6.47 (br. s, exchanged with D$_2$O, 2H), 2.17 (s, 3H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 611 | | (400 MHz, CDCl$_3$): 8.41 (d, J = 2.3 Hz, 1H), 7.64 (d, J = 1.8 Hz, 1H), 7.61 (s, 1H), 7.56-7.50 (m, 1H), 7.45 (br. s, 1H), 7.27 (overlapped m, 3H), 7.11 (br. s, exchanged with D$_2$O, 1H), 6.74 (d, J = 6.7 Hz, 1H), 6.57 (br. s, exchanged with D$_2$O, 2H), 2.20 (s, 3H) |
| 612 | | (400 MHz, CDCl$_3$): 8.42 (d, J = 1.9 Hz, 1H), 7.61-7.56 (m, 1H), 7.54-7.46 (m, 2H), 7.42-7.36 (overlapped m, 3H), 7.31 (d, J = 1.9 Hz, 1H), 7.12 (br. exchanged with D$_2$O, 1H), 6.75 (d, J = 7.0 Hz, 1H), 6.53 (br. s, exchanged with D$_2$O, 2H), 2.20 (s, 3H) |
| 613 | | (400 MHz, CDCl$_3$): 8.44 (d, J = 1.9 Hz, 1H), 7.59-7.50 (m, 2H), 7.40-7.34 (m, 2H), 7.28-7.25 (overlapped m, 2H), 7.12 (br. s, exchanged with D$_2$O, 1H), 6.84 (d, J = 7.0 Hz, 1H), 6.49 (br. exchanged with D$_2$O, 2H), 2.20 (s, 3H) |
| 614 | | (400 MHz, CDCl$_3$): 8.41 (d, J = 1.9 Hz, 1H), 7.50-7.48 (overlapped m, 3H), 7.32-7.28 (m, 2H), 7.14 (br. s, exchanged with D$_2$O, 1H), 7.05 (d, J = 8.6 Hz, 2H), 6.54 (br.s, exchanged with D$_2$O, 2H), 2.19 (s, 3H) |
| 615 | | (400 MHz, CDCl$_3$): 8.44 (d, J = 2.3 Hz, 1H), 7.68-7.65 (m, 1H), 7.39 (d, J = 2.3 Hz, 1H), 7.29 (d, J = 7.8 Hz, 2H), 7.26-7.21 (overlapped m, 2H), 7.01 (d, J = 8.3 Hz, 2H), 6.47 (br. s, exchanged with D$_2$O, 2H), 3.61 (br. s, 2H), 2.52 (br. s, 4H), 1.80 (br. s, 4H) |
| 616 | | (400 MHz, CDCl$_3$): 8.44 (d, J = 2.2 Hz, 1H), 7.70-7.51 (m, 2H), 7.32-7.27 (overlapped m, 3H), 7.27 (d, J = 2.2 Hz, 1H), 7.01 (d, J = 8.2 Hz, 2H), 6.56 (br. s, exchanged with D$_2$O, 2H), 3.64 (br. s, 2H), 2.57 (br. s, 4H), 1.82 (br. s, 4H) |
| 617 | | (400 MHz, CDCl$_3$): 8.51 (dd, J = 3.2, 2.0 Hz, 1H), 8.42 (d, J = 2.4 Hz, 1H), 8.21 (d, J = 2.0 Hz, 1H), 7.70-7.64 (m, 1H), 7.54-7.48 (m, 2H), 7.37-7.34 (m, 1H), 7.29 (d, J = 2.4 Hz, 1H), 7.28-7.26 (overlapped m, 1H), 6.61 (br. s, exchanged with D$_2$O, 2H) |
| 618 | | (400 MHz, CDCl$_3$): 8.54 (dd, J = 3.8, 1.9 Hz, 1H), 8.44 (d, J = 2.3 Hz, 1H), 8.28 (d, J = 1.9 Hz, 1H), 7.57-7.50 (m, 2H), 7.38-7.34 (m, 1H), 7.32-7.30 (overlapped m, 1H), 7.29 (d, J = 2.3 Hz, 1H), 6.59 (br.s, exchanged with D$_2$O, 2H) |
| 619 | | (400 MHz, CDCl$_3$): 8.45 (d, J = 1.9 Hz, 1H), 7.68-7.62 (m, 1H), 7.39 (d, J = 1.9 Hz, 1H), 7.29-7.25 (overlapped m, 3H), 7.24 (s, 1H), 7.02 (d, J = 8.2 Hz, 2H), 6.48 (br. s, exchanged with D$_2$O, 2H), 3.40 (s, 2H), 2.24 (s, 6H) |
| 620 | | (400 MHz, CDCl$_3$): 8.45 (d, J = 2.3 Hz, 1H), 7.54-7.50 (m, 1H), 7.36-7.30 (m, 3H), 7.29 (d, J = 2.3 Hz, 1H), 7.03 (d, J = 8.2 Hz, 2H), 6.53 (br. s, exchanged with D$_2$O, 2H), 3.61 (br. s, 2H), 2.53 (br. s, 4H), 1.80 (br. s, 4H) |
| 621 | | (400 MHz, CDCl$_3$): 8.40 (d, J = 1.9 Hz, 1H), 7.61-7.56 (m, 3H), 7.46 (d, J = 8.6 Hz, 2H), 7.23 (d, J = 1.9 Hz, 1H), 7.14 (sb, 1H), 7.01 (d, J = 8.6 Hz, 2H), 6.55 (br. s, exchanged with D$_2$O, 2H), 2.19 (s, 3H) |
| 622 | | (400 MHz, CDCl$_3$): 8.44 (d, J = 2.2 Hz, 1H), 7.61-7.58 (m, 3H), 7.30 (d, J = 8.2 Hz, 2H), 7.27 (d, J = 2.2 Hz, 1H), 7.01 (d, J = 8.2 Hz, 2H), 6.56 (br. s, exchanged with D$_2$O, 2H), 3.64 (br. s, 2H), 2.57 (br. sb 4H), 1.82 (br. s, 4H) |
| 623 | | (400 MHz, CDCl$_3$): 8.44 (br. s, 1H), 7.65-7.60 (m, 1H), 7.51 (d, J = 8.1 Hz, 1H), 7.36-7.28 (series of m, 4H), 7.01 (d, J = 8.1 Hz, 2H), 6.53 (br. s, exchanged with D$_2$O, 2H), 3.46 (br. s, 2H), 2.28 (s, 6H) |
| 624 | | (400 MHz, CDCl$_3$): 8.29 (d, J = 1.9 Hz, 1H), 7.75 (d, J = 8.2 Hz, 1H), 7.44 (t, J = 8.2 Hz, 1H), 7.31 (d, J = 7.8 Hz, 1H), 7.24 (s, 1H), 7.12 (s, 1H), 7.06 (d, J = 1.9 Hz, 1H), 6.59 (br. s, exchanged with D$_2$O, 2H), 4.18-4.13 (m, 1H), 3.26 (br. d, J = 12.5 Hz, 2H), 2.78-2.70 (m, 2H), 2.15 (br. d, J = 11.7 Hz, 2H), 2.03 (s, 3H), 1.88-1.70 (m, 2H) |
| 625 | | (400 MHz, CDCl$_3$): 8.41 (d, J = 1.9 Hz, 1H), 8.01 (s, 1H), 7.81 (m, 1H), 7.59 (overlapped m, 4H), 6.49 (br. s, exchanged with D$_2$O, 2H), 4.42-4.35 (m, 1H), 3.29 (br. d, J = 12.5 Hz, 2H), 3.08-3.03 (m, 2H), 2.20-2.15 (br. d, J = 11.6 Hz, 2H), 2.11-2.02 (m, 2H) |
| 626 | 440.20 | (400 MHz, CDCl$_3$): 8.25 (d, J = 2.2 Hz, 1 H), 7.72-7.67 (m, 1 H), 7.45-7.31 (m, 3 H), 7.11 (d, J = 2.0 Hz, 1 H), 7.08 (s, 1 H), 6.37 (s, 2 H), 4.15-4.05 (m, 1 H), 3.41 (s, 1 H), 3.17 (d, J = 12.5 Hz, 2 H), 2.74-2.65 (m, 2 H), 2.08-2.04 (m, 2 H), 1.84-1.71 (m, 2 H) |
| 627 | | (400 MHz, CDCl$_3$): 8.35 (d, J = 1.6 Hz, 1H), 7.40 (s, 1H), 7.25 (s, 1H), 7.23 (d, J = 1.6 Hz, 1H), 7.11 (m, 3H), 6.19 (br. s, exchanged with D$_2$O, 2H), 4.18-4.10 (m, 1H), 3.24 (br. d, J = 12.5, 2H), 2.77-2.70 (m, 2H), 2.14-2.10 (br. d, J = 11.7 Hz, 2H), 1.87-1.80 (m, 2H) |
| 628 | | (400 MHz, CDCl$_3$): 8.31 (d, J = 2.3 Hz, 1H), 7.74-7.67 (m, 1H), 7.38 (br. s, 1H), 7.27-7.22 (overlapped m, 3H), 7.12 (br. s, 1H), 6.44 (br. s, exchanged with D$_2$O, 2H), 4.21-4.14 (m, 1H), 3.23 (br. |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| | | d, J = 12.0 Hz, 2H), 2.79 (br. td, J = 12.0, 2.0 Hzm, 2H), 2.17-2.10 (m, 2H), 1.87 (dd, J = 12.0, 4.0 Hz, 1H), 1.84 (dd, J = 12.0, 4.0 Hz, 1H) |
| 629 | | (400 MHz, CDCl$_3$): 8.44 (d, J = 1.9 Hz, 1H), 7.63-7.58 (m, 3H), 7.27-7.24 (overlapped m, 3H), 7.00 (d, J = 7.8 Hz, 2H), 6.55 (br. s, exchanged with D$_2$O, 2H), 3.41 (br. s, 2H), 2.52 (s, 6H) |
| 630 | | (400 MHz, CDCl$_3$): 8.43 (d, J = 1.8 Hz, 1H), 7.52-7.48 (m, 1H), 7.34-30 (m, 2H), 7.28 (d, J = 8.2 Hz, 2H), 7.04 (d, J = 8.2 Hz, 2H), 6.51 (br. s, exchanged with D$_2$O, 2H), 3.43 (s, 2H), 2.26 (s, 6H) |
| 631 | | (400 MHz, CDCl$_3$): 8.32 (d, J = 1.9 Hz, 1H), 7.625-7.60 (m, 3H), 7.39 (br. s, 1H), 7.31 (d, J = 1.9 Hz, 1H), 7.69 (s, 1H), 6.47 (br. s, exchanged with D$_2$O, 2H), 4.19-4.17 (m, 1H), 3.26 (br. d, J = 12.4 Hz, 2H), 2.79-2.70 (m, 2H), 2.15 (br. d, J = 11.0 Hz, 2H), 1.85-1.80 (m, 2H) |
| 632 | | (400 MHz, CDCl$_3$): 8.30 (d, J = 1.9 Hz, 1H), 7.65-7.60 (m, 1H), 7.43-7.40 (m, 2H), 7.29-7.27 (overlapped m, 1H), 7.13 (d, J = 8.4 Hz, 2H), 6.59 (br. s exchanged with D$_2$O, 2H), 4.20-4.15 (m, 1H), 3.27 (br. d, J = 12.3 Hz, 2H), 2.79-2.72 (m, 2H), 2.18-2.15 (br. d, J = 11.3 Hz, 2H), 1.96 (s, 3H), 1.90 (m, 2H) |
| 633 | | (400 MHz, CDCl$_3$): 8.28 (d, J = 1.9 Hz, 1H), 7.38 (ddd, J = 10.0, 8.0, 3.2 Hz, 1H), 7.34 (s, 1H), 7.29-7.27 (overlapped m, 2H), 7.14 (s, 1H), 7.09 (dd, J = 9.6, 4.8 Hz, 1H), 6.43 (br. s, exchanged with D$_2$O, 2H), 4.19-4.15 (m, 1H), 3.62 (s, 3H), 3.25 (br. d, J = 11.9 Hz, 2H), 2.79-2.75 (m, 2H), 2.09 (br. d, J = 10.5 Hz, 2H), 1.93-1.85 (m, 2H) |
| 634 | | (400 MHz, CDCl$_3$): 8.31 (br. s, 1H), 7.39-7.30 (m, 2H), 7.26 (overlapped s, 1H), 7.17 (br. s, 1H), 7.13 (br. s, 1H), 6.51 (br. s, exchanged with D$_2$O, 2H), 4.25-4.20 (m, 1H), 3.39 (br. d, J = 12.4 Hz, 2H), 2.84-2.80 (m, 2H), 2.21 (br. d, J = 11.0 Hz, 2H), 2.01-1.90 (m, 2H) |
| 635 | | (400 MHz, CDCl$_3$): 8.32 (d, J = 2.4 Hz, 1H), 7.70 (br. ddd, J = 10.0, 8.0, 3.6 Hz, 1H), 7.63 (dd, J = 6.4, 2.8 Hz, 1H), 7.36 (s, 1H), 7.34 (t, J = 8.0 Hz, 1H), 7.23 (d, J = 2.3 Hz, 1H), 7.18 (s, 1H), 6.42 (br. s, exchanged with D$_2$O, 2H), 4.23-4.15 (m, 1H), 3.36 (br. d, J = 12.1 Hz, 2H), 2.85-2.80 (m, 2H), 2.22 (br. d, J = 11.3 Hz, 2H), 1.91-1.85 (m, 2H) |
| 636 | | (400 MHz, CDCl$_3$): 8.34 (d, J = 2.2 Hz, 1H), 7.66-7.63 (m, 1H), 7.45-7.42 (m, 2H), 7.39 (s, 1H), 7.26 (s, merged with solvent peak, 1H), 7.23 (d, J = 2.2 Hz, 1H), 6.29 (br. s, exchanged with D$_2$O, 2H), 4.20-4.15 (m, 1H), 3.26 (br. d, J = 12.1 Hz, 2H), 2.79 (br. t, J = 12.0, 2.0 Hz, 2H), 2.17 (br. d, J = 11.5 Hz, 2H), 1.86 (dd, J = 12.4, 4.0 Hz, 1H), 1.84 (dd, J = 12.0, 4.0 Hz, 1H) |
| 637 | | (400 MHz, CDCl$_3$): 8.30 (d, J = 1.9 Hz, 1H), 7.68-7.62 (m, 1H), 7.42-7.36 (m, 1H), 7.38-7.30 (m, 2H), 7.12-7.10 (m, 2H), 6.51 (br. s, exchanged with D$_2$O, 2H), 4.21-4.15 (m, 1H), 3.31 (br. d, J = 12.3 Hz, 2H), 2.80-2.75 (m, 2H), 2.19 (br. d, J = 11.1 Hz, 2H), 1.92-1.85 (m, 2H) |
| 638 | | (400 MHz, CDCl$_3$): 8.28 (d, J = 1.9 Hz, 1H), 7.44-7.40 (m, 1H), 7.34 (s, 1H), 7.29-7.26 (overlapped m, 2H), 7.22 (d, J = 1.9 Hz, 1H), 7.17 (s, 1H), 6.41 (br. s, exchanged with D$_2$O, 2H), 4.21-4.15 (m, 1H), 3.75 (d, J = 2.3 Hz, 3H), 3.34 (br. d, J = 12.2 Hz, 2H), 2.83 (br. t, J = 7.6 Hz, 2H), 2.19 (br. d, J = 10.2 Hz, 2H), 1.91-1.85 (m, 2H) |
| 639 | | (400 MHz, DMSO-d$_6$): 9.96 (s, exchanged D$_2$O, 1H), 8.48 (s, 1H), 7.88-7.71 (m, 3H), 7.49 (d, J = 8.0 Hz, 2H), 7.19 (s, 1H), 7.10 (d, J = 8.0 Hz, 2H), 7.09 (overlapped s, exchanged with D$_2$O, 2H), 2.01 (s, 3H) |
| 640 | | (400 MHz, CDCl$_3$): 8.35 (d, J = 2.0 Hz, 1H), 7.59-7.53 (m, 1H), 7.40 (s, 1H), 7.39-7.36 (m, 1H), 7.18 (s, 2H), 6.43 (s, exchanged with D$_2$O, 2H), 4.25-4.18 (m, 1H), 3.30 (br. d, J = 12.4 Hz, 2H), 2.81 (br. td, J = 12.0, 2.0 Hz, 2H), 2.18-21.4 (m, 2H), 1.93 (br. qd, J = 12.0, 3.6 Hz, 2H) |
| 641 | 495.30 | (400 MHz, DMSO-d$_6$): 8.3 (m, 1H); 7.8 (m, 1H); 7.8 (m, 1H); 7.6 (m, 1H); 7.55 (m, 1H); 5.9 (bs, 1H); 4.7 (m, 1H); 4.2 (m, 2H); 3.75-3.4 (m, 4H); 2.25 (m, 4H); 2.11 (s, 3H); 1.9 (m, 2H) |
| 642 | 467.30 | (400 MHz, DMSO-d$_6$): 8.3 (m, 1H); 7.8 (m, 1H); 7.8 (m, 1H); 7.6 (m, 1H); 7.55 (m, 1H); 5.95 (bs, 1H); 4.5 (m, 1H); 4.1 (m, 2H); 3.5 (m, 2H); 2.4-2.0 (m, 5H); 1.9 (m, 1H) |
| 643 | 440.30 | |
| 644 | 447.40 | |
| 645 | 470.30 | (400 MHz, DMSO-d$_6$): 8.2 (m, 1H); 7.6-7.45 (m, 1H); 7.44-7.3 (m, 2H); 7.03 (m, 1H); 6.4 (br s, 2H); 5.7-5.52 (m, 1H); 4.0-3.85 (m, 2H); 3.6-3.4 (m, 2H); 2.38-2.18 (m, 2H); 1.7 (m, 2H); 1.45 (m, 9H) |

TABLE 6-continued

Analytical Chararacterization Data for Compounds of Formula I-A (blank cells indicate that the test was not performed)

| Cmpnd. No. I-A- | MS (M + H) | ¹H-NMR NMR peaks given as δ values in ppm |
|---|---|---|
| 646 | 370.20 | (400 MHz, DMSO-$d_6$): 9.0 (br s, 2H); 8.25 (m, 1H); 7.87-7.77 (m, 1H); 7.75-7.6 (m, 2H); 7.58-7.5 (m, 1H); 5.85 (t, J = 6.3 Hz, 1H), 3.7 (m, 2H); 3.25 (m, 2H); 2.5 (m, 2H); 1.78 (m, 2H) |
| 647 | 466.20 | (400 MHz, DMSO-$d_6$): 8.2 (m, 1H); 7.8 (m, 1H); 7.7 (m, 1H); 7.55 (m, 1H); 7.37 (m, 1H); 7.1-6.8 (m, 2H); 5.95-5.7 (m, 1H); 4.12 (m, 2H); 3.75-3.6 (m, 2H); 2.4 (m, 2H); 1.75 (m, 2H) |
| 648 | 452.30 | (400 MHz, DMSO-$d_6$): 8.2 (m, 2H); 7.8-7.55 (m, 3H); 5.9 (bs, 1H); 4.6 (m, 1H); 4.1 (m, 2H); 3.7 (m, 2H); 3.25 (m, 2H); 2.23 (m, 4H); 1.9 (m, 2H) |
| 649 | 495.30 | (400 MHz, DMSO-$d_6$): 8.3 (m, 1H); 7.8 (m, 1H); 7.8 (m, 1H); 7.6 (m, 1H); 7.55 (m, 1H); 5.9 (bs, 1H); 4.7 (m, 1H); 4.2 (m, 2H); 3.75-3.4 (m, 4H); 2.25 (m, 4H); 2.11 (s, 3H); 1.9 (m, 2H) |
| 650 | 412.10 | (400 MHz, CDCl$_3$): 8.32 (d, J = 2.0 Hz, 1H), 7.77 (t, J = 7.6 Hz, 1H), 7.49 (br. t, J = 7.6 Hz, 1H), 7.47 (overlapped s, 1H), 7.41 (t, J = 8.0 Hz, 1H), 7.20 (s, 1H), 7.19 (d, J = 2.0 Hz, 1H), 6.43 (br. s, exchanged with D$_2$O, 2H), 5.12 (quintet, J = 7.2 Hz, 1H), 4.11 (t, J = 7.6 Hz, 2H), 3.98 (t, J = 7.6 Hz, 2H) |
| 651 | 454.20 | (400 MHz, DMSO-$d_6$): 8.39 (d, J = 2.4 Hz, 1H), 7.98 (s, 1H), 7.96-7.90 (m, 1H), 7.85-7.81 (m, 1H), 7.55-7.49 (m, 2H), 7.47 (s, 1H), 6.51 (s, exchanged with D$_2$O, 2H), 4.42-4.34 (m, 1H), 2.90-2.70 (m, 4H), 2.1-1.90 (m, 4H), 1.80-1.70 (m, 1H), 1.65-1.50 (m, 1H) |
| 652 | 439.20 | (400 MHz, CDCl$_3$): 8.35 (d, J = 2.4 Hz, 1H), 7.78-7.74 (m, 1H), 7.47-7.37 (m, 2H), 7.21 (d, J = 2.4 Hz, 1H), 6.67 (t, J = 2.0 Hz, 1H), 6.62 (t, J = 2.0 Hz, 1H), 6.28 (br. s, exchanged with D$_2$O, 2H), 5.84 (dd, J = 2.8, 2.0 Hz, 1H), 3.84 (tt, J = 12.4, 3.6 Hz, 1H), 3.25 (br. d, J = 11.2 Hz, 2H), 2.74 (br. td, J = 12.4, 2.0 Hz, 2H), 2.06-2.04 (m, 2H), 1.83 (dd, J = 12.4, 4.4 Hz, 1H), 1.76 (dd, J = 12.4, 4.0 Hz, 1H) |
| 653 | 427.10 | (400 MHz, CDCl$_3$): 8.43 (s, 1H), 7.45-7.41 (m, 1H), 7.40-7.26 (m, overlapped m, 2H), 6.77 (s, 1H), 6.77-6.70 (br. s, exchanged with D$_2$O, 2H), 3.00-2.92 (m, 4H), 2.84-2.82 (m, 2H), 2.75-2.70 (m, 2H) |
| 654 | 441.10 | (400 MHz, DMSO-$d_6$): 8.79 (s, 1H), 7.96 (br. q, J = 8.4 Hz, 1H), 7.80-7.70 (br. m, 1H), 7.74 (overlapped s, 1H), 7.65-7.52 (m, 1H), 7.42 (s, 1H), 6.40 (s, exchanged with D$_2$O, 2H), 3.30-3.15 (m, 2H), 2.97-2.91 (m, 2H), 2.60-2.50 (m overlapped with DMSO-d6, 1H), 1.99-1.90 (m, 2H), 1.66-1.58 (m, 2H) |
| 655 | 425.20 | (400 MHz, CDCl$_3$): 8.36 (s, 1H), 7.54-7.48 (m, 1H), 7.48-7.36 (m, 2H), 7.24 (s, 2H), 6.80 (br. s, exchanged with D$_2$O, 2H), 4.18-4.11 (m, 1H), 3.34 (br. dd, J = 12.0, 3.2 Hz, 1H), 3.08 (br. dt, J = 12.0, 3.6 Hz, 1H), 2.92 (dd, J = 12.4, 10.0 Hz, 1H), 2.73-2.66 (m, 1H), 2.25-2.17 (m, 1H), 1.95-1.82 (m, 2H), 1.60-1.58 (m, 1H) |
| 656 | 439.20 | (400 MHz, DMSO-$d_6$): 8.59 (s, 1H), 7.90-7.68 (m, 5H, addition of D$_2$O changed to m, 3H), 7.42 (overlapped s, 1H), 7.14 (s, 1H), 4.50-4.40 (m, 1H), 3.20-2.90 (m, 4H), 2.20-1.90 (m, 6H) |
| 657 | 467.30 | (400 MHz, DMSO-$d_6$): 8.3 (m, 1H); 7.8 (m, 1H); 7.8 (m, 1H); 7.6 (m, 1H); 7.55 (m, 1H); 5.95 (bs, 1H); 4.5 (m, 1H); 4.1 (m, 2H); 3.5 (m, 2H); 2.4-2.0 (m, 5H); 1.9 (m, 1H) |
| 658 | 440.10 | (400 MHz, CDCl$_3$): 8.32 (d, J = 2.0 Hz, 1H), 7.78-7.74 (m, 1H), 7.51-7.47 (m, 1H), 7.42-7.38 (m, 1H), 7.39 (overlapped s, 1H), 7.18 (d, J = 2.0 Hz, 1H), 7.15 (s, 1H), 6.42 (br. s, exchanged with D$_2$O, 2H), 4.22-4.17 (m, 1H), 3.38 (dd, J = 12.0, 3.6 Hz, 1H), 3.04 (tt, J = 12.4, 4.0 Hz, 1H), 2.95 (dd, J = 12.0, 9.2 Hz, 1H), 2.76-2.69 (m, 1H), 2.21-2.16 (m, 1H), 1.99-1.60 (m, 3H) |
| 659 | 425.20 | (400 MHz, DMSO-$d_6$): 8.62 (s, 1H), 7.93 (br. q, J = 8.4 Hz, 1H), 7.72 (br. t, J = 7.6 Hz, 1H), 7.62 (s, 1H), 7.60 (br. overlapped s, exchanged with D$_2$O, 2H), 7.65-7.62 (m, 1H), 7.15 (s, 1H), 4.07-4.02 (m, 1H), 3.14 (br. d, J = 12.4 Hz, 1H), 2.89 (br. d, J = 12.0 Hz, 1H), 2.63 (br. t, J = 12.4 Hz, 1H), 2.50-2.40 (m, 1H), 2.08-2.05 (m, 1H), 1.81-1.69 (m, 2H), 1.54-1.45 (m, 1H) |
| 660 | 411.10 | (400 MHz, CDCl$_3$): 8.35 (s, 1H), 7.55-7.48 (m, 1H), 7.41-7.36 (m, 3H), 7.22 (s, 1H), 6.68 (br. s, exchanged with D$_2$O, 2H), 4.80-4.70 (m, 1H), 3.27-3.22 (m, 3H), 3.10-2.95 (m, 1H), 2.34-2.27 (m, 1H), 2.13-2.12 (m, 1H) |
| 661 |  | (300 MHz, DMSO-$d_6$): 8.56-8.49 (m, 1H), 7.87-7.45 (m, 4H), 7.03 (s, 1H), 3.63-2.78 (m, 7H), 1.40-1.28 (m, 3H) |
| 662 | 456.20 | (300 MHz, DMSO-$d_6$): 9.60 (br, 1H), 9.41 (br, 1H), 8.44-8.43 (m, 1H), 7.99-7.96 (m, 1H), 7.88-7.86 (m, 1H), 7.64-7.53 (m, 2H), 7.01 (s, 1H), 3.55-2.88 (m, 7H), 1.32 (d, J = 7.1 Hz, 3H) |
| 663 | 472.10 | (400 MHz, CDCl$_3$): 8.41 (d, J = 1.6 Hz, 1H), 7.86 (dd, J = 7.6, 1.8 Hz, 1H), 7.56 (t, J = 8.4 Hz, 1H), 7.49 (dd, J = 8.0, 1.6 Hz, 1H), 7.20 (d, J = 2.0 Hz, 1H), 6.76-6.75 (d, J = 1.2 Hz, 1H), 6.57 (s, exchanged with D$_2$O, 2H), 6.47 (br. s, 1H), 3.24-3.21 (m, 2H), 2.89-2.85 (m, 1H), 2.80-2.74 (m, 2H), 2.01-1.98 (d, 2H), 1.68-1.58 (m, 2H) |

TABLE 6-continued

Analytical Chararacterization Data for Compounds of Formula I-A (blank cells indicate that the test was not performed)

| Cmpnd. No. I-A- | MS (M + H) | $^1$H-NMR NMR peaks given as δ values in ppm |
|---|---|---|
| 664 | 456.20 | (400 MHz, CDCl$_3$): 8.41 (s, 1H), 7.80-7.76 (br. t, J = 7.2 Hz, 1H), 7.49-7.40 (m, 2H), 7.27 (s, 1H), 6.76 (s, 1H), 6.51 (s, 1H), 6.48 (s, exchanged with D$_2$O, 2H), 3.24-3.21 (d, J = 12.4 Hz, 2H), 2.89-2.83 (m, 1H), 2.80-2.74 (t, J = 11.6 Hz, 2H), 2.01-1.98 (m, 2H), 1.69-1.60 (m, 2H) |
| 665 | 382.30 | (400 MHz, CDCl$_3$): 9.5 (bs, 1H); 9.1 (bs, 1H); 8.3 (s, 1H); 7.9 (m, 2H); 7.7 (m, 1H); 7.5 (m, 1H); 5.9 (s, 1H); 3.5 (m, 1H); 3.2 (m, 2H); 3.0 (m, 2H); 2.8 (m, 2H) |
| 666 | 406.00 | |
| 667 | 412.00 | |
| 668 | 414.00 | |
| 669 | 424.00 | |
| 670 | 426.00 | |
| 671 | 426.00 | |
| 672 | 426.00 | |
| 673 | 427.00 | |
| 674 | 428.00 | |
| 675 | 438.00 | |
| 676 | 440.00 | |
| 677 | 440.00 | |
| 678 | 453.00 | |
| 679 | 453.00 | |
| 680 | 453.00 | |
| 681 | 453.00 | |
| 682 | 455.00 | |
| 683 | 460.00 | |
| 684 | 430.00 | |
| 685 | 467.00 | |
| 686 | 467.00 | |
| 687 | 469.00 | |
| 688 | 451.00 | |
| 689 | 442.00 | |
| 690 | 482.00 | |
| 691 | 492.00 | |
| 692 | 451.00 | |
| 693 | 453.00 | |
| 694 | 481.00 | |
| 695 | 426.00 | |
| 696 | 482.30 | |
| 697 | 481.20 | (400 MHz, DMSO-d$_6$): 8.2 (m, 2H); 7.8 (m, 1H); 7.7 (m, 1H); 7.55 (m, 1H); 7.25 (m, 1H) 6.7 (br s, 2H); 5.8 (m, 1H); 4.1-3.9 (m, 2H); 3.7-3.5 (m, 2H); 3.1-2.7 (m, 5H); 2.45-2.2 (m, 2H); 1.7-1.5 (m, 6H). |
| 698 | 481.30 | |
| 699 | 467.30 | |
| 700 | 468.10 | |
| 701 | 382.30 | (400 MHz, CDCl$_3$): 9.5 (bs, 1H); 9.1 (bs, 1H); 8.3 (s, 1H); 7.9 (m, 2H); 7.7 (m, 1H); 7.5 (m, 1H); 5.9 (s, 1H); 3.5 (m, 1H); 3.2 (m, 2H); 3.0 (m, 2H); 2.8 (m, 2H) |
| 702 | 406.00 | |
| 703 | 412.00 | |
| 704 | 414.00 | |
| 705 | 424.00 | |
| 706 | 426.00 | |

TABLE 7

Analytical Chararacterization Data for Compounds of Formula I-B

| Cmpnd. No. I-B- | MS (M + 1) | $^1$H-NMR NMR peaks given as δ values in ppm |
|---|---|---|
| 1 | 464.00 | (400 MHZ, CDCl$_3$): 8.69 (br. s, 1H), 8.59 (br. s, 1H), 8.42 (d, J = 2.4 Hz, 1H), 7.90 (s, 1H), 7.74 (br. dt, J = 7.6, <1 Hz, 1H), 7.56 (d, J = 2.4 Hz, 1H), 7.42 (dd, J = 8.0, 2.0 Hz, 1H), 7.38-7.36 (m, 1H), 7.14 (t, J = 8.0 Hz, 1H), 7.09 (dd, J = 7.6, 2.0 Hz, 1H), 4.81-4.68 (m, 1H), 4.66-4.59 (m, 1H), 4.59 (br. s, exchanged with D$_2$O, 2H) |
| 2 | 575.00 | (400 MHZ, CDCl$_3$): 8.41 (d, J = 2.0 Hz, 1H), 7.89 (s, 1H), 7.55 (br. s, 1H), 7.39 (m, 5H), 7.12 (t, J = 7.6 Hz, 1H), 7.06 (br. d, J = 7.2 Hz, |

TABLE 7-continued

Analytical Chararacterization Data for Compounds of Formula I-B

| Cmpnd. No. I-B- | MS (M + 1) | $^1$H-NMR NMR peaks given as δ values in ppm |
|---|---|---|
| | | 1H), 4.77-4.59 (m, 2H), 4.46 (br. s, exchanged with D$_2$O, 2H), 3.54 (br. s, 2H), 2.5-2.35 (br hump, 8H), 2.32 (s, 3H) |
| 3 | 520.00 | (400 MHZ, CDCl$_3$): 8.42 (d, J = 2.0 Hz, 1H), 7.9 (s, 1H), 7.58 (d, J = 2.0 Hz, 1H), 7.41-7.38 (m, 5H), 7.12 (t, J = 7.6 Hz, 1H), 7.08 (dd, J = 7.6, 1.2 Hz, 1H), 4.79-4.61 (m, 2H), 4.48 (s, exchanged with D$_2$O, 2H), 3.49 (br. s, 2H), 2.29 (s, 6H) |
| 4 | 533.00 | (400 MHZ, CDCl$_3$): 8.33 (br. s, 1H), 8.24 (br. s, 1H), 7.89 (s, 1H), 7.52 (dd, J = 8.8, 1.2 Hz, 1H), 7.46 (br. s, 1H), 7.40 (br. d, J = 7.2 Hz, 1H), 7.18-7.08 (m, 2H), 6.44 (d, J = 8.8 Hz, 1H), 4.78-4.59 (m, 2H), 4.46 (s, exchanged with D$_2$O, 2H), 3.49 (br. s, 4H), 2.04 (br. s, 4H) |
| 5 | 472.20 | (400 MHZ, CDCl$_3$): 8.47 (s, 1H), 8.33 (br. s, 1H), 8.21 (br. s, 1H), 7.54 (s, 1H), 7.53-7.51 (m, 1H), 7.42-7.20 (m, 10 H), 5.42 (s, 2H) |
| 6 | 583.30 | (400 MHZ, CDCl$_3$): 8.21 (s, 1H), 7.53 (s, 1H), 7.49 (m, 1H), 7.42-7.18 (series of m, 11H), 7.02 (d, J = 7.6 Hz, 1H), 6.10 (br. s, exchanged with D$_2$O, 2H), 5.4 (s, 2H), 3.48 (s, 2H), 2.5-2.40 (br. hump, 6H), 2.30 (s, 3H), 1.59 (br. s, 2H) |
| 7 | 528.30 | (400 MHZ, CDCl$_3$): 8.34 (d, J = 2.0 Hz, 1H), 7.85 (s, 1H), 7.34-7.21 (m, 9H), 7.08-7.06 (m, 2H), 7.03-6.99 (m, 2H), 5.37 (1/2 ABq, J = 14.8 Hz, 1H), 5.18 (1/2ABq, J = 14.8 Hz, 1H), 4.38 (s, exchanged with D$_2$O, 2H), 3.45 (s, 2H), 2.27 (s, 6H) |
| 8 | 541.20 | (400 MHZ, CDCl$_3$): 8.09 (s, 1H), 8.03 (d, J = 2.0 Hz, 1H), 7.55 (s, 1H), 7.46 (t, J = 4.8 Hz, 1H), 7.41-7.31 (series of m, 4H), 7.24 (d, J = 2 Hz, 1H), 7.16 (d, J = 4.8 Hz, 2H), 7.10 (dd, J = 8.8, 2.4 Hz, 1H), 6.31 (d, J = 8.8 Hz, 1H), 5.41 (s, 2H), 3.50-3.40 (m, 4H), 2.05-1.95 (m, 4H) |
| 9 | 464.20 | (400 MHZ, CDCl$_3$): 8.70 (br. s, 1H), 8.58 (br.s, 1H), 8.36 (d, J = 2.0 Hz, 1H,) 7.80 (s, 1H), 7.75 (br. d, J = 7.6 Hz, 1H), 7.52 (d, J = 2.0 Hz, 1H), 7.37-7.34 (m, 1H), 7.35 (dd, J = 8.0, 2.0 Hz, 1H), 7.08 (t, J = 7.6 Hz, 1H), 7.04 (dd, J = 8.0, 2.0 Hz, 1H), 4.47 (s, 2H), 3.95-3.90 (m, 1H), 2.20-1.60 (series of m, 6H) 1.40-1.20 (m, 4 H) |
| 10 | 575.20 | (400 MHZ, CDCl$_3$): 8.39 (s, 1H), 7.82 (s, 1H), 7.54 (br. s, 1H), 7.40 (s, 4H), 7.34 (br. d, J = 6.0 Hz, 1H), 7.10-7.01 (m, 2H), 4.94 (br. s, exchanged with D$_2$O, 2H), 3.95-3.85 (m, 1H), 3.56 (s, 2H), 2.6-2.4 (m, 6H), 2.31 (s, 3H), 2.20-1.6 (m, 7H), 1.3-1.20 (m, 5H) |
| 11 | 520.20 | (400 MHZ, CDCl$_3$): 8.2 (s, 1H), 7.59 (s, 1H), 7.49 (s, 1H), 7.34 (s, 1 H) 7.25-7.20 (m, 4H), 7.05 (d, J = 7.2 Hz, 2H), 6.13 (br. s, exchanged with D$_2$O, 2H), 4.15-4.05 (m, 1H), 3.42 (s, 2H), 2.25 (s, 6H), 2.31-1.25 (m, 10H) |
| 12 | 559.00 | (400 MHZ, CDCl$_3$): 8.47 (d, J = 4.8 Hz, 1H), 8.30 (s, 1H), 8.21 (s, 1H), 7.67 (s, 1H), 7.55 (d, J = 8.0 Hz, 1H), 7.38 (d, J = 8.0 Hz, 1H), 7.28-7.14, series of m, 6H), 6.82 (d, J = 8.0 Hz, 2H), 6.3 (br. s, exchanged with D$_2$O, 1H), 6.10 (br. s, exchanged with D$_2$O, 2H), 4.97 (s, 2H), 4.16-4.11 (m, 2H), 3.78 (s, 3H). |
| 13 | 426.00 | (400 MHZ, CDCl$_3$): 8.47 (d, J = 4.0 Hz, 1H), 8.32 (br s, 1H), 8.1 (b, 1H), 7.67 (s, 1H), 7.92 (dd, J = 6.8, 2.8 Hz, 1H), 7.41 (br d, J = 8.0 Hz, 1H). 7.29-7.19 (series of m, 4H), 6.21 (s, exchanged with D$_2$O, 2H), 4.38 (t, J = 5.2 Hz, 2H), 4.13 (t, J = 5.2 Hz, 2H) |
| 14 | 482.50 | (400 MHZ, CDCl$_3$, data for major regioisomer): 8.25 (d, J = 2.4 Hz, 1H), 7.68 (s, 1H), 7.55-7.50 (m, 1H), 7.42-7.35 (m, 2H), 7.26-7.25 (overlapped m, 2H), 7.22-7.21 (d, J = 4.8 Hz, 2H), 7.08 (d, J = 8.0 Hz, 2H), 5.97 (s, exchanged with D$_2$O, 1H), 4.39 (t, J = 5.2 Hz, 2H), 4.14 (t, J = 5.2 Hz, 2H), 3.44 (s, 2H), 2.27 (s, 6H) |
| 15 | 397.00 | (300 MHz, DMSO-d$_6$): 8.03 (1H, s), 7.98 (1H, d), 7.69-7.67 (1H, m), 7.43-7.40 (1H, t), 7.34-7.33 (1H, dd), 7.02 (1H, d), 5.43 (1H, br s), 3.98 (3H, s) |
| 16 | 396.00 | (400 MHz, methanol-d$_4$): (1H, d), 8.52 (1H, s), 8.28 (1H, d), 7.94-7.96 (1H, m), 7.92 (1H, s), 7.75 (1H, d), 7.73-7.75 (1H, m), 7.64 (1H, dd), 7.44 (1H, dd), 7.40 (1H, t), 4.05 (3H, s) |
| 17 | 495.20 | (400 MHZ, CDCl$_3$, major regioisomer, assignment based on internal correlation): 8.07 (s, 1H), 7.98 (s, 1H), 7.69 (s, 1H), 7.49 (d, J = 8.0 Hz, 1H), 7.26-6.98 (m, 4H), 6.31 (d, J = 8.4 Hz, 1H), 6.24 (br; s, exchanged with D$_2$O, 2H), 4.51-4.38 (m, 2H), 4.35-4.14 (m, 2H), 3.47-3.30 (m, 4H), 2.84-2.01 (m, 4H) |
| 18 | 537.30 | (400 MHZ, CDCl$_3$, 1:4 mixture of regioisomers, structure refers to major regioisomer): 8.38 (s, 0.3H), 8.27 (s, 0.7H), 7.84 (s, 0.3H), 7.68 (s, 0.7H), 7.56-7.50 (m, 1H), 7.37-7.04 (series of m, 7H), 5.; 97 (br. s, exchanged with D$_2$O, 1.4H) 4.57 (br. s, exchanged with D$_2$O, 0.6H), 4.39-4.38 (m, 4H), 4.15-4.13 (m, 4H), 3.54 (s, 0.6H), 3.49 (s, 1.4H), 2.7-2.4 (br. s, 8H), 2.30 (s, 3H) |
| 19 | 582.50 | (400 MHZ, CDCl$_3$, 1:1 mixture of regioisomers): 8.25 (br. s, 1H), 8.16 (br. s, 1H), 8.0 (br. s, 1H), 7.85 (br. s, 1H), 7.56 (s, 1H), 7.48-7.00 (series of m, 21H), 6.38 (d, J = 8.4 Hz, 1H), 6.34 (d, J = ; 8.4 Hz, 1H), 5.42 (s, 2H), 5.39 (d, J = 15.2 Hz, 1H), 5.22 (d, J = 15.2 Hz, |

TABLE 7-continued

Analytical Chararacterization Data for Compounds of Formula I-B

| Cmpnd. No. I-B- | MS (M + 1) | $^1$H-NMR NMR peaks given as δ values in ppm |
|---|---|---|
|  |  | 1H), 4.95 (br. s, exchanged with D$_2$O, 2H), 4.74 (br. s, exchanged with D$_2$O, 2H), 3.8-3.6 (series of m, 4H), 2.8 (br. s, 6H);, 2.54 (s, 3H), 2.34-0.84 (series of m, 9H) |
| 20 | 465.00 | (300 MHz, DMSO-d$_6$): 8.2-8.21 (1H, d), 8.11 (1H, s), 7.88-7.90 (1H, m), 7.71-7.60 (2H, m), 7.47-7.40 (5H, m), 6.75 (1H, br s), 4.02 (3H, s), 3.55 (4H, br m), 1.99-1.96 4H, m). |
| 21 | 493.20 | (300 MHz, DMSO-d$_6$): 11.06 (s, 1 H), 8.37 (s, 2 H), 8.29 (d, J = 2.1 Hz, 1 H), 8.16 (s, 1 H), 7.80-7.74 (m, 1 H), 7.60-7.58 (m, 1 H), 7.52-7.39 (m, 2 H), 7.10-6.96 (m, 4H), 4.04 (s, 3 H), 3.89-3.86 (m, 2 H), 3.70-3.47 (m, 2H),, 3.14-3.11 (m, 5 H), 2.80 (s, 3 H), |
| 22 | 468.20 | (300 MHz, DMSO-d$_6$): 9.2-9.13 (m, 2H), 8.30 (d, J = 1.8 Hz, 1 H), 8.24 (s, 2 H), 8.16 (s, 1 H), 7.87 (s, 1 H), 7.84-7.76 (m, 1 H), 7.57 (d, J = 1.8 Hz, 1 H), 7.53-7.45 (m, 2 H), 7.38 (s, 1 H), 4.49-4.42 (m, 1 H), 4.03 (s, 3 H), 3.38 (q, J = 7.0 Hz, 3 H), 3.13-3.06 (m, 2H), 2.20-2.04 (m, 4H) |

TABLE 8

Analytical Chararacterization Data for Compounds of Formula I-C (blank cells indicate that the test was not performed)

| Cmpnd. No. I-C- | MS (M + 1) | $^1$H-NMR NMR peaks given as δ values in ppm |
|---|---|---|
| 1 | 399.00 | (400 MHz, DMSO-d$_6$): 8.75 (s, 1H), 8.58 (d, 1H), 8.49 (d, 1H), 8.14-8.03 (m, 1H), 7.84-7.80 (m, 1H), 7.76 (d, 1H), 7.64-7.56 (m, 2H), 7.47 (t, 1H), 7.95-7.7 (br s, 2H) |
| 2 | 400.90 | (400 MHz, DMSO-d$_6$): 8.08 (d, 1H), 7.79-7.75 (m, 1H), 7.56-7.50 (m, 1H), 7.50-7.44 (m, 1H), 7.36 (d, 1H), 6.39-6.19 (br s, 2H) |
| 3 | 497.10 |  |
| 4 | 469.00 |  |
| 5 | 456.10 | (400 MHz, CDCl$_3$): (d, 1H), 7.72 (dd, 1H), 7.65 (d, 1H), 7.47-7.36 (m, 3H), 7.28 (dd, 1H), 6.99 (d, 2H), 4.12 (s, 2H), 2.76 (s, 6H) |
| 6 | 397.00 |  |
| 7 | 399.80 | (400 MHz, methanol-d$_4$): 9.17 (1H, d), 7.95 (1H, d), 7.60-7.63 (2H, m), 7.34-7.35 (1H, m), 7.27 (1H, dd) |
| 8 | 398.90 | (400 MHz, methanol-d$_4$): 9.34 (1H, s), 8.57 (1H, dd), 8.41 (1H, d), 8.28 (1H, d), 7.79 (1H, d), 7.71 (1H, dd), 7.58 (1H, dd), 7.57 (1H, t), 7.46 (1H, t), 2.64 (3H, s) |
| 9 | 580.10 | (400 MHz, methanol-d$_4$): 9.21 (1H, s), 8.22 (1H, dd), 7.77 (1H, dd), 7.68-7.74 (3H, m), 7.63 (1H, t), 7.34 (1H, d), 7.08-7.13 (3H, m), 6.79 (1H, dd), 3.62 (4H, p), 3.54 (4H, m), 2.12 (8H, p) |
| 10 | 422.90 | (400 MHz, methanol-d$_4$): 9.32 (1H, s), 8.25 (1H, d), 7.70-7.72 (2H, m), 7.61-7.65 (2H, m), .53-7.56 (1H, m), 7.45 (1H, t), 7.32 (2H, dd) |
| 11 | 495.90 | (400 MHz, methanol-d$_4$): 9.38 (1H, s), 8.07 (1H, d), 7.75 (1H, d), 7.72 (1H, dd), 7.66 (2H, d), 7.55 (1H, dd), 7.46 (1H, t), 7.08 (2H, d), 3.94 (2H, bs), 3.58 (2H, bs), 3.26 (3H, bs), 3.10 (2H, bs), 2.96 (3H, s) |

TABLE 9

Analytical Chararacterization Data for Compounds of Formula I-D (blank cells indicate that the test was not performed)

| Cmpnd. No. I-D- | MS (M + 1) | $^1$H-NMR NMR peaks given as δ values in ppm |
|---|---|---|
| 1 |  | (400 MHz, CDCl$_3$): 9.21 (br. s, 1H), 8.51 (overlapped 2s, 2H), 8.35 (d, J = 1.9 Hz, 1H), 8.18 (s, 1H), 7.53-7.38 (m, 3H), 7.35 (d, J = 1.9 Hz, 1H), 7.30-7.26 (overlapped m, 2H), 7.15 (d, J = 5.1 Hz, 1H), 6.79 (br. s, exchanged with D$_2$O, 2H) |
| 2 |  | (400 MHz, CDCl$_3$): 9.19 (s, 1H), 8.49 (d, J = 5.4 Hz, 1H), 8.32 (d, J = 2.0 Hz, 1H), 7.47-7.38 (m, 1H), 7.37-7.34 (m, 1H), 7.30 (d, J = 2.0 Hz, 1H), 7.25-7.20 (m, 1H), 7.13 (d, J = 5.4 Hz, 1H), 6.93 (d, J = 8.6 Hz, 2H), 6.86 (d, J = 8.6 Hz, 2H), 6.59 (br. s, exchanged with D$_2$O, 2H), 3.23 (m, 4H), 2.58 (m, 4H), 2.36 (s, 3H) |

TABLE 9-continued

Analytical Chararacterization Data for Compounds of Formula I-D (blank cells indicate that the test was not performed)

| Cmpnd. No. I-D- | MS (M + 1) | $^1$H-NMR NMR peaks given as δ values in ppm |
|---|---|---|
| 3 | 498.20 | (400 MHz, CDCl$_3$): 9.20 (s, 1H), 8.50 (d, J = 5.4 Hz, 1H), 8.36 (d, J = 2.3 Hz, 1H), 7.47-7.45 (m, 1H), 7.39-7.35 (m, 1H), 7.36 (d, J = 1.9 Hz, 1H), 7.30 (d, J = 8.2 Hz, 2H), 7.26-7.23 (overlapped m, 1H), 7.14 (d, J = 5.4 Hz, 1H), 6.96 (d, J = 8.2 Hz, 2H), 6.67 (br. s, exchanged with D$_2$O, 2H), 3.64 (s, 2H), 2.56 (br. s, 4H), 1.82 (br. s, 4H) |
| 4 | | (400 MHz, CDCl$_3$): 9.20 (s, 1H), 8.50 (d, J = 5.4 Hz, 1H), 8.37 (d, J = 1.9 Hz, 1H), 7.48-7.45 (m, 1H), 7.38-7.36 (overlapped m, 1H), 7.36 (d, J = 1.9 Hz, 1H), 7.27 (d, merged with solvent peak, J = 8.0 Hz, 2H), 7.27-7.25 (m, 1H), 7.14 (d, J = 5.4 Hz, 1H), 6.97 (d, J = 8.2 Hz, 2H), 6.68 (br. s, exchanged with D$_2$O, 2H), 3.43 (s, 2H), 2.26 (s, 6H) |
| 5 | | (400 MHz, CDCl$_3$): 9.20 (s, 1H), 8.50 (d, J = 5.8 Hz, 1H), 8.36 (d, J = 2.3 Hz, 1H), 7.48-7.44 (m, 1H), 7.37-7.32 (m, 1H), 7.35 (d, J = 2.3 Hz, 1H), 7.27 (overlapped d, J = 8.0 Hz, 2H), 7.27-7.24 (m, 1H), 7.14 (d, J = 5.8 Hz, 1H), 6.96 (d, J = 8.2 Hz, 2H), 6.67 (br. s, exchanged with D$_2$O 2H), 3.49 (s, 2H), 3.48 (br. s, 8H), 2.30 (s, 3H) |
| 6 | | (400 MHz, CDCl$_3$): 9.21 (s, 1H), 8.51 (d, J = 5.2 Hz, 1H), 8.36 (d, J = 1.9 Hz, 1H), 7.47-7.44 (m, 1H), 7.36-7.32 (m, 1H), 7.35 (d, J = 2.0 Hz, 1H), 7.28 (overlapped d, J = 8.0 Hz, 2H), 7.27-7.24 (overlapped m, 1H), 7.15 (d, J = 5.2 Hz, 1H), 6.97 (d, J = 7.8 Hz, 2H), 6.67 (br. s, exchanged with D$_2$O, 2H), 3.62 (br. s, 2H), 3.50 (br. s, 2H), 3.46-3.40 (m, 2H), 2.42 (m, 4H), 2.08 (s, 3H) |
| 7 | | (400 MHz, CDCl$_3$): 9.19 (s, 1H), 8.50 (d, J = 5.6 Hz, 1H), 8.24 (d, J = 2.0 Hz, 1H), 7.50-7.46 (m, 1H), 7.40-7.35 (m, 1H), 7.34 (s, 1H), 7.26-7.22 (overlapped m, 1H), 7.20 (d, J = 2.0 Hz, 1H), 7.12 (d, J = 7.2 Hz, 1H), 7.11 (s, 1H), 6.60 (s, exchanged with D$_2$O, 2H), 4.20-4.15 (m, 1H), 3.27 (brd, J = 12.8, <2 Hz, 2H), 2.78 (td, J = 12.8, 2.0 Hz, 2H), 2.28-2.13 (m, 2H), 1.88 (qd, J = 13.2, 4.4 Hz, 2H) |
| 8 | | (400 MHz, CDCl$_3$): 9.15 (s, 1H), 8.48 (d, J = 5.6 Hz, 1H), 8.20 (d, J = 2.0 Hz, 1H), 7.50-7.44 (m, 1H), 7.40-7.35 (m, 1H), 7.34 (s, 1H), 7.26-7.20 (overlapped m, 1H), 7.18 (d, J = 2.0 Hz, 1H), 7.14 (s, 1H), 7.12 (d, J = 6.0 Hz, 1H), 6.65 (s, exchanged D$_2$O, 2H), 4.25 (t, J = 4.8 Hz, 2H), 4.01 (t, J = 4.8 Hz, 2H) |
| 9 | | (400 MHz, CDCl$_3$): 9.19 (s, 1H), 8.50 (d, J = 5.6 Hz, 1H), 8.24 (d, J = 2.8 Hz, 1H), 7.50-7.45 (m, 1H), 7.40-7.35 (m, 1H), 7.38 (br. s, 1H), 7.26-7.22 (overlapped m, 1H), 7.21 (d, J = 2.0 Hz, 1H), 7.15 (s, 1H), 7.13 (s, 1H), 6.60 (br. s, exchanged D$_2$O, 2H), 4.22 (br. t, J = 6.0 Hz, 2H), 2.85-2.75 (m, addition of D$_2$O changed to t, J = 6.0 Hz, 2H), 2.30 (s, 6H) |
| 10 | | (400 MHz, CDCl$_3$): 9.20 (s, 1H), 8.51 (d, J = 5.6 Hz 1H), 8.23 (d, J = 2.0 Hz, 1H), 7.52-7.45 (m, 1H), 7.41-7.32 (m, 2H), 7.31 (br. s, 1H), 7.20 (d, J = 2.0 Hz, 1H), 7.16 (br. s, 1H), 7.14 (d, J = 6.0 Hz, 1H), 6.63 (s, exchanged with D20, 2H), 4.23 (d, J = 4.8 Hz, 2H), 4.10-4.03 (m, 1H), 3.62 (t, J = 4.8 Hz, 2H), 3.12 (q, J = 7.6 Hz, exchanged with D$_2$O, 1H), 1.34 (t, J = 7.6 Hz, exchanged with D$_2$O, 1H) |
| 11 | | (400 MHz, CDCl$_3$): 9.20 (s, 1H), 8.50 (d, J = 5.6 Hz, 1H), 8.29 (d, J = 2.0 Hz, 1H), 7.50-7.45 (m, 1H), 7.40-7.35 (m, 1H), 7.38 (overlapped s, 1H), 7.26-7.24 (m, overlapped with CDCl3, 1H), 7.21 (d, J = 2.0 Hz, 1H), 7.15-7.11 (m, 2H), 6.65 (br. s, exchanged with D$_2$O, 2H), 4.28 (br. s, 2H) |
| 12 | 457.50 | |
| 13 | 457.50 | |
| 14 | 499.20 | (300 MHz, DMSO-d$_6$): 8.39 (s, 1H), 8.38 (d, J = 5.0 Hz, 1H), 8.29 (d, J = 8.0 Hz, 1H), 7.94-7.89 (m, 1H), 7.83-7.78 (m, 1H), 7.57-7.44 (m, 3H), 7.33 (s, 2H), 7.26 (d, J = 7.9 Hz, 2H), 7.07 (d, J = 8.0 Hz, 2H), 3.54 (s, 2H), 2.41 (brs, 4H), 1.69 (brs, 4H) |
| 15 | 489.20 | (300 MHz, DMSO-d$_6$): 9.21 (br, 2H), 8.49-8.46 (m, 2H), 8.37 (d, J = 7.0 Hz, 1H), 8.09 (d, J = 6.2 Hz, 2H), 7.92-7.87 (m, 1H), 7.80 (t, J = 6.7 Hz, 1H), 7.63 (s, 1H), 7.54-7.50 (m, 2H), 4.51-4.45 (m, 1H), 3.37 (brd, 2H), 3.08 (br, 2H), 2.22-2.08 (m, 4H) |
| 16 | 500.10 | (300 MHz, DMSO-d$_6$): 9.41 (s, 2H), 8.48-8.47 (m, 2H), 8.37 (d, J = 6.9 Hz, 1H), 8.07 (d, J = 1.7 Hz, 1H), 7.95-7.81 (m, 2H), 7.56-7.52 (m, 2H), 7.21 (d, J = 8.6 Hz, 2H), 7.02 (d, J = 8.6 Hz, 2H), 3.44 (d, J = 4.3 Hz, 4H), 3.19 (s, 4H) |
| 17 | 514.20 | (300 MHz, DMSO-d$_6$): 11.20 (s, 1H), 8.47 (dd, J = 1.3, 3.4 Hz, 2H), 8.37 (dd, J = 1.3, 8.0 Hz, 1H), 8.04 (d, J = 1.9 Hz, 1H), 7.92-7.81 (m, 2H), 7.56-7.51 (m, 2H), 7.21 (d, J = 8.7 Hz, 2H), 7.03 (d, J = 8.8 Hz, 2H), 3.90 (d, J = 10.0 Hz, 2H), 3.47 (d, J = 8.8 Hz, 2H), 3.21-3.13 (m, 4H), 2.79 (d, J = 4.1 Hz, 3H) |

TABLE 9-continued

Analytical Chararacterization Data for Compounds of Formula I-D (blank cells indicate that the test was not performed)

| Cmpnd. No. I-D- | MS (M + 1) | $^1$H-NMR NMR peaks given as δ values in ppm |
|---|---|---|
| 18 | 516.2 | (300 MHz, DMSO-$d_6$): 10.89 (s, 1H), 8.51 (d, J = 2.2 Hz, 1H), 7.97-7.81 (m, 3H), 7.76 (dd, J = 2.2, 9.3 Hz, 1H), 7.62 (d, J = 8.2 Hz, 2H), 7.55 (t, J = 8.1 Hz, 1H), 7.39-7.24 (m, 4H), 4.33 (d, J = 5.5 Hz, 2H), 3.33 (brd, 2H), 3.04-3.00 (m, 2H), 1.94-1.86 (m, 4H) |
| 19 | 506.2 | (300 MHz, DMSO-$d_6$): 9.05 (br, 2H), 8.43 (d, J = 1.9 Hz, 1H), 8.06 (s, 1H), 8.03 (d, J = 1.8 Hz, 1H), 7.90-7.74 (m, 3H), 7.60-7.55 (m, 2H), 7.39-7.31 (m, 2H), 4.48 (m, 1H), 3.38 (brd, 2H), 3.08 (br, 2H), 2.17-2.08 (m, 4H) |
| 20 | 517.2 | (300 MHz, DMSO-$d_6$): 9.27 (s, 2H), 8.43 (d, J = 2.0 Hz, 1H), 7.93-7.83 (m, 3H), 7.77 (d, J = 6.9 Hz, 1H), 7.55 (t, J = 8.2 Hz, 1H), 7.42-7.27 (m, 2H), 7.17 (d, J = 8.5 Hz, 2H), 7.01 (d, J = 8.6 Hz, 2H), 3.42 (brd, 4H), 3.20 (brs, 4H) |
| 21 | 531.2 | (300 MHz, DMSO-$d_6$): 11.35 (s, 1H), 8.48 (s, 1H), 8.02 (s, 1H), 7.89 (qn, J = 7.2 Hz, 2H), 7.77 (d, J = 1.8 Hz, 1H), 7.60-7.56 (m, 2H), 7.44-7.29 (m, 2H), 7.20 (d, J = 8.5 Hz, 2H), 7.03 (d, J = 8.6 Hz, 2H), 3.90 (d, J = 10.3 Hz, 2H), 3.47 (d, J = 9.7 Hz, 2H), 3.23-3.10 (m, 4H), 2.79 (d, J = 3.7 Hz, 3H) |
| 22 | 490.1 | |
| 23 | 484.4 | (300 MHz, DMSO-$d_6$): 9.67 (s, 1 H), 9.09 (s, 1 H), 8.77 (d, J = 6.5 Hz, 1 H), 8.45 (d, J = 2.3 Hz, 1 H), 8.26 (s, 1 H), 7.99 (d, J = 6.1 Hz, 1 H), 7.83-7.51 (m, 3 H), 7.16 (d, J = 8.7 Hz, 1 H), 6.99 (d, J = 8.8 Hz, 1 H), 3.41 (s, 2 H), 3.20 (d, J = 12.8 Hz, 2 H) |

TABLE 10

Analytical Chararacterization Data for Compounds of Formula I-E

| Cmpnd. No. I-E- | MS (M + 1) | $^1$H-NMR NMR peaks given as δ values in ppm |
|---|---|---|
| 1 | 424.30 | (300 MHz, DMSO-$d_6$): 9.37 (brd, 1H), 9.17 (brd, 1H), 8.56 (d, J = 1.9 Hz, 1H), 8.28 (d, J = 1.6 Hz, 1H), 8.21 (s, 1H), 7.88 (s, 1H), 7.76-7.66 (m, 1H), 7.49-7.31 (m, 2H), 4.48-4.45 (m, 1H), 3.34 (brd, J = 12.7 Hz, 2H), 3.06 (m, 2H), 2.28-2.08 (m, 4H) |
| 2 | 426.20 | (300 MHz, DMSO-$d_6$): 9.10 (brs, 2H), 8.37 (d, J = 2.3 Hz, 1H), 7.88 (d, J = 2.3 Hz, 1H), 7.74-7.64 (m, 1H), 7.44-7.38 (m, 2H), 7.11 (s, 1H), 4.67 (m, covered by water, 1H), 3.22-3.09 (m, 6H), 2.97-2.94 (m, 2H) |
| 3 | 434.30 | (300 MHz, DMSO-$d_6$): 8.81 (brs, 2H), 8.54 (d, J = 2.3 Hz, 1H), 8.14 (d, J = 2.2 Hz, 1H), 7.71-7.67 (m, 1H), 7.55 (d, J = 8.3 Hz, 2H), 7.47-7.38 (m, 2H), 7.26 (d, J = 8.3 Hz, 2H), 3.36 (brd, J = 12.4 Hz, 2H), 3.01-2.86 (m, 3H), 1.94-1.81 (m, 4H) |
| 4 | 434.30 | (300 MHz, DMSO-$d_6$): 11.05 (br, 1H), 8.61 (d, J = 2.3 Hz, 1H), 8.16 (d, J = 2.2 Hz, 1H), 7.73-7.62 (m, 5H), 7.47-7.36 (m, 2H), 4.32 (d, J = 5.8 Hz, 2H), 3.35-3.31 (m, 2H), 3.07-2.99 (m, 2H), 2.00-1.85 (m, 4H) |
| 5 | 408.20 | (300 MHz, DMSO-$d_6$): 10.22 (s, 1H), 8.52 (d, J = 2.2 Hz, 1H), 8.46 (d, J = 2.2 Hz, 1H), 7.85 (s, 1H), 7.76-7.67 (m, 1H), 7.56-7.33 (m, 3H), 7.35 (t, J = 7.9 Hz, 1H), 7.22 (d, J = 7.8 Hz, 1H), 2.06 (s, 3H) |

Biological Assay of Compounds of the Invention

Example 44

$K_i$ Determination for the Inhibition of c-MET

Compounds of the invention were screened for their ability to inhibit c-MET kinase activity using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 µL per well containing 1.0 nM c-Met, 100 mM HEPES (pH 7.5), 10 mM $MgCl_2$, 25 mM NaCl, 0.01% BSA, 1 mM DTT, 0.5 mg/mL polyE4Y, and 35 µM ATP. Accordingly, compounds of the invention were dissolved in DMSO to make 10 mM initial stock solutions. Serial dilutions in DMSO were then made to obtain the final solutions for the assay. A 1.5 µL aliquot of DMSO or inhibitor in DMSO was added to each well. The reaction was initiated by the addition of $^{33}$P-ATP and polyE4Y (obtained from Sigma). After 20 min, the reaction was quenched with 50 µL of 30% trichloroacetic acid (TCA) containing 4 mM ATP. The reaction mixture was transferred to the 0.66 mm GF filter plates (Corning) and washed three times with 5% TCA. Following the addition of 50 µL of Ultimate Gold™ high efficiency scintillant (Packard Bioscience), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition.

Compounds having a $K_i$ of less than or equal to 0.10 μM for the inhibition of c-MET include: I-A-5, I-A-6, I-A-7, I-A-8, I-A-9, I-A-10, I-A-11, I-A-12, I-A-13, I-A-19, I-A-22, I-A-32, I-A-46, I-A-48, I-A-50, I-A-51, I-A-52, I-A-54, I-A-56, I-A-57, I-A-62, I-A-63, I-A-64, I-A-65, I-A-66, I-A-67, I-A-79, I-A-81, I-A-85, I-A-86, I-A-87, I-A-90, I-A-92, I-A-94, I-A-95, I-A-96, I-A-97, I-A-98, I-A-99, I-A-100, I-A-104, I-A-106, I-A-108, I-A-109, I-A-118, I-A-119, I-A-120, I-A-121, I-A-122, I-A-123, I-A-124, I-A-125, I-A-126, I-A-127, I-A-128, I-A-129, I-A-130, I-A-131, I-A-132, I-A-133, I-A-134, I-A-135, I-A-136, I-A-137, I-A-138, I-A-139, I-A-141, I-A-143, I-A-144, I-A-145, I-A-146, I-A-147, I-A-148, I-A-149, I-A-150, I-A-151, I-A-152, I-A-153, I-A-156, I-A-157, I-A-158, I-A-159, I-A-165, I-A-180, I-A-181, I-A-182, I-A-183, I-A-184, I-A-186, I-A-187, I-A-188, I-A-189, I-A-190, I-A-191, I-A-192, I-A-193, I-A-197, I-A-198, I-A-199, I-A-200, I-A-201, I-A-202, I-A-203, I-A-204, I-A-206, I-A-207, I-A-208, I-A-209, I-A-210, I-A-211, I-A-212, I-A-213, I-A-218, I-A-219, I-A-220, I-A-221, I-A-222, I-A-223, I-A-231, I-A-232, I-A-233, I-A-234, I-A-235, I-A-239, I-A-242, I-A-245, I-A-247, I-A-249, I-A-250, I-A-251, I-A-254, I-A-256, I-A-257, I-A-258, I-A-259, I-A-261, I-A-262, I-A-263, I-A-264, I-A-265, I-A-266, I-A-267, I-A-268, I-A-272, I-A-273, I-A-276, I-A-277, I-A-280, I-A-281, I-A-283, I-A-286, I-A-287, I-A-290, I-A-292, I-A-295, I-A-298, I-A-299, I-A-303, I-A-305, I-A-308, I-A-309, I-A-312, I-A-313, I-A-314, I-A-321, I-A-325, I-A-328, I-A-329, I-A-331, I-A-332, I-A-334, I-A-335, I-A-337, I-A-338, I-A-339, I-A-340, I-A-341, I-A-342, I-A-343, I-A-344, I-A-345, I-A-346, I-A-347, I-A-348, I-A-349, I-A-351, I-A-354, I-A-355, I-A-360, I-A-363, I-A-366, I-A-367, I-A-368, I-A-370, I-A-371, I-A-372, I-A-376, I-A-377, I-A-380, I-A-381, I-A-382, I-A-385, I-A-391, I-A-393, I-A-394, I-A-396, I-A-397, I-A-398, I-A-399, I-A-400, I-A-401, I-A-403, I-A-404, I-A-405, I-A-406, I-A-407, I-A-408, I-A-409, I-A-410, I-A-411, I-A-412, I-A-413, I-A-414, I-A-415, I-A-416, I-A-417, I-A-418, I-A-419, I-A-420, I-A-422, I-A-423, I-A-425, I-A-426, I-A-427, I-A-428, I-A-429, I-A-430, I-A-431, I-A-432, I-A-433, I-A-434, I-A-435, I-A-436, I-A-438, I-A-440, I-A-441, I-A-442, I-A-443, I-A-444, I-A-445, I-A-446, I-A-447, I-A-448, I-A-449, I-A-450, I-A-451, I-A-452, I-A-453, I-A-455, I-A-456, I-A-457, I-A-458, I-A-459, I-A-460, I-A-461, I-A-462, I-A-463, I-A-464, I-A-466, I-A-468, I-A-469, I-A-470, I-A-471, I-A-472, I-A-473, I-A-474, I-A-475, I-A-476, I-A-477, I-A-480, I-A-481, I-A-482, I-A-483, I-A-484, I-A-485, I-A-486, I-A-487, I-A-491, I-A-492, I-A-497, I-A-499, I-A-500, I-A-501, I-A-502, I-A-503, I-A-504, I-A-505, I-A-506, I-A-507, I-A-508, I-A-510, I-A-511, I-A-512, I-A-513, I-A-514, I-A-515, I-A-516, I-A-518, I-A-519, I-A-520, I-A-521, I-A-522, I-A-523, I-A-524, I-A-526, I-A-527, I-A-528, I-A-529, I-A-530, I-A-531, I-A-532, I-A-534, I-A-535, I-A-536, I-A-538, I-A-540, I-A-542, I-A-584, I-A-589, I-A-599, I-A-601, I-A-615, I-A-616, I-A-619, I-A-620, I-A-622, I-A-623, I-A-624, I-A-626, I-A-628, I-A-629, I-A-630, I-A-631, I-A-635, I-A-640, I-A-642, I-A-650, I-A-651, I-A-652, I-A-653, I-A-655, I-A-656, I-A-657, I-A-658, I-A-659, I-A-660, I-B-22, I-C-3, I-C-5, I-C-6, I-D-1, I-D-2, I-D-3, I-D-4, I-D-5, I-D-6, I-D-7, I-D-8, I-D-9, I-D-10, I-D-11, I-D-12, I-D-13, I-D-19, and 1-D-23.

Compounds having a $K_i$ of greater than 0.10 μM and less than or equal to 1.0 μM the inhibition of c-MET include I-A-2, I-A-3, I-A-4, I-A-15, I-A-16, I-A-17, I-A-18, I-A-20, I-A-29, I-A-30, I-A-31, I-A-33, I-A-34, I-A-39, I-A-40, I-A-41, I-A-42, I-A-53, I-A-55, I-A-68, I-A-69, I-A-70, I-A-71, I-A-72, I-A-73, I-A-74, I-A-75, I-A-76, I-A-77, I-A-78, I-A-82, I-A-83, I-A-84, I-A-88, I-A-89, I-A-93, I-A-101, I-A-102, I-A-103, I-A-105, I-A-107, I-A-110, I-A-111, I-A-112, I-A-113, I-A-114, I-A-116, I-A-140, I-A-142, I-A-154, I-A-155, I-A-160, I-A-161, I-A-162, I-A-163, I-A-179, I-A-185, I-A-194, I-A-195, I-A-196, I-A-205, I-A-215, I-A-224, I-A-225, I-A-228, I-A-229, I-A-236, I-A-237, I-A-240, I-A-241, I-A-248, I-A-252, I-A-255, I-A-260, I-A-269, I-A-270, I-A-271, I-A-274, I-A-275, I-A-278, I-A-279, I-A-282, I-A-285, I-A-288, I-A-289, I-A-291, I-A-294, I-A-296, I-A-301, I-A-304, I-A-306, I-A-310, I-A-315, I-A-316, I-A-317, I-A-318, I-A-319, I-A-320, I-A-324, I-A-326, I-A-327, I-A-330, I-A-333, I-A-336, I-A-350, I-A-352, I-A-353, I-A-356, I-A-357, I-A-358, I-A-359, I-A-362, I-A-364, I-A-365, I-A-369, I-A-383, I-A-386, I-A-387, I-A-388, I-A-389, I-A-390, I-A-392, I-A-395, I-A-402, I-A-421, I-A-424, I-A-439, I-A-454, I-A-465, I-A-467, I-A-478, I-A-479, I-A-488, I-A-490, I-A-493, I-A-494, I-A-495, I-A-496, I-A-509, I-A-517, I-A-525, I-A-533, I-A-537, I-A-539, I-A-541, I-A-551, I-A-554, I-A-557, I-A-561, I-A-562, I-A-564, I-A-565, I-A-567, I-A-568, I-A-569, I-A-570, I-A-574, I-A-575, I-A-576, I-A-577, I-A-578, I-A-579, I-A-580, I-A-581, I-A-582, I-A-583, I-A-585, I-A-587, I-A-588, I-A-590, I-A-591, I-A-592, I-A-593, I-A-594, I-A-595, I-A-596, I-A-597, I-A-598, I-A-600, I-A-602, I-A-603, I-A-604, I-A-605, I-A-606, I-A-607, I-A-608, I-A-609, I-A-610, I-A-611, I-A-612, I-A-613, I-A-614, I-A-617, I-A-618, I-A-621, I-A-625, I-A-627, I-A-632, I-A-633, I-A-634, I-A-636, I-A-637, I-A-638, I-A-639, I-A-641, I-A-643, I-A-644, I-A-646, I-A-647, I-A-649, I-A-654, I-B-11, I-B-14, I-B-16, I-B-20, I-B-21, I-C-1, I-C-4, I-C-8, I-C-11, I-D-14, I-D-15, I-D-16, I-D-17, I-D-18, I-D-20, I-D-21, I-D-22, I-E-1, I-E-2, I-E-3, I-E-4, and I-E-5.

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of treating gastric carcinoma in a patient comprising administering a compound or a pharmaceutical composition comprising said compound to said patient, wherein said compound has the following formula:

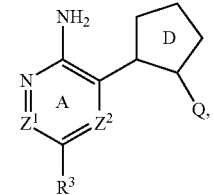

(I)

wherein:
$Z^1$ is $CR^4$;
$Z^2$ is CH;
Ring D is the selected from:

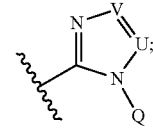

Q is a phenyl ring wherein each Q is optionally substituted with up to 5 occurrences of $J^Q$;

U is N;

V is N;

$R^3$ is halogen or $R^A$, wherein $R^A$ is $C_{6-10}$ aryl, 5-10 membered heteroaryl, 5-12 membered heterocyclyl, or $C_{3-8}$ cycloaliphatic, each of which is optionally substituted with 0-3 occurrences of $J^M$;

$R^4$ is hydrogen, —CN, $C_{1-4}$ aliphatic, halogen, or $C_{1-2}$ haloalkyl;

each $J^M$ is independently selected from halogen, —NO$_2$, —CN, $C_{1-4}$ aliphatic, $C_{1-2}$ haloalkyl, —(CH$_2$)$_{0-2}$CH(R')$_2$, —OH, —OR', —(CR'''$_2$)$_q$NH$_2$, —(CR'''$_2$)$_q$NHR', —(CR'''$_2$)$_q$N(R')$_2$, —(CR'''$_2$)$_q$NHS(O)$_2$R', —(CR'''$_2$)$_q$NHC(O)R', —(CR'''$_2$)$_q$NHC(O)OR', —(CR'''$_2$)$_q$NHC(O)NH$_2$, —(CR'''$_2$)$_q$NHC(O)NHR', —(CR'''$_2$)$_q$NHC(O)N(R')$_2$, —(CR'''$_2$)$_q$NHC(NH)NH$_2$, —(CR'''$_2$)$_q$NHC(NH)NHR', —(CR'''$_2$)$_q$NHC(NR)N(R')$_2$, —(CR'''$_2$)$_q$NHS(O)$_2$NH$_2$, —(CR'''$_2$)$_q$NHS(O)$_2$NHR', —(CR'''$_2$)$_q$NHS(O)$_2$N(R')$_2$, —SH, —SR', —(CR'''$_2$)$_q$CO$_2$H, —(CR'''$_2$)$_q$CO$_2$R', —C(O)H, —(CR'''$_2$)$_q$C(O)R', —(CR'''$_2$)$_q$—C(O)—(CH$_2$)$_{0-2}$CH(R')$_2$, —(CR'''$_2$)$_q$—C(O)—(CH$_2$)$_{0-2}$NHCH(R')$_2$, —(CR'''$_2$)$_q$—C(O)—(CH$_2$)$_{0-2}$NR'CH(R')$_2$, —(CR'''$_2$)$_q$C(O)NH$_2$, —(CR'''$_2$)$_q$—C(O)NHR', —(CR'''$_2$)$_q$—C(O)N(R')$_2$, —(CR'''$_2$)$_q$—C(O)N(OH)R', —(CR'''$_2$)$_q$—C(O)N(OR')R', —(CR'''$_2$)$_q$—C(O)N(OR')H, —(CR'''$_2$)$_q$—C(O)N(OH)H, —(CR'''$_2$)$_q$—C(=NOH)R', —(CR'''$_2$)$_q$—C(=NOR')H, —(CR'''$_2$)$_q$—C(NOR')R', —(CR'''$_2$)$_q$—S(O)$_2$R', —(CR'''$_2$)$_q$—S(O)$_2$OH, —(CR'''$_2$)$_q$—S(O)$_2$OR', —(CR'''$_2$)$_q$—S(O)$_2$NH$_2$, —(CR'''$_2$)$_q$—S(O)$_2$NHR', —(CR'''$_2$)$_q$—S(O)$_2$N(R')$_2$, —(CR'''$_2$)$_q$—S(O)R', —(CR'''$_2$)$_q$—C(=NR')—NH$_2$, —(CR'''$_2$)$_q$—C(=NR')—NHR', —(CR'''$_2$)$_q$—C(=NR')—N(R')$_2$, —(CR'''$_2$)$_q$—C(=NH)—NH$_2$, —(CR'''$_2$)$_q$—C(=NH)—NHR', —(CR'''$_2$)$_q$—C(=NH)—N(R')$_2$, $C_{6-10}$ aryl, 5-10 membered heteroaryl, 5-10 membered heterocyclyl, or $C_{3-8}$ cycloaliphatic, wherein q is selected from 0-4; or two $J^M$, together with the atom or atoms to which they are bound, form a 3-6 membered cycloaliphatic or heterocyclyl ring; wherein each of said cycloaliphatic or heterocyclyl is optionally substituted with up to 3 occurrences of $J^N$ or $J^R$;

each $J^N$ is independently selected from —(CR'''$_2$)$_q$C$_{1-4}$ aliphatic, —(CR'''$_2$)$_q$C$_{3-6}$cycloalkyl, —(CR'''$_2$)$_{q'}$ phenyl, —(CR'''$_2$)$_q$C(O)C$_{1-4}$aliphatic; —(CR'''$_2$)$_q$C(O)C$_{1-2}$haloalkyl; —C(O)O(C$_{1-4}$alkyl), —(CR'''$_2$)$_q$C(O)NH$_2$, —(CR'''$_2$)$_{q'}$C(O)NH(C$_{1-4}$aliphatic), —(CR'''$_2$)$_q$C(O)N(C$_{1-4}$aliphatic)$_2$, or —S(O)$_2$C$_{1-4}$aliphatic, wherein q' is 0-2 and each aliphatic or cycloaliphatic is optionally substituted with up to 2 occurrences of $J^R$;

each $J^Q$ is independently selected from halogen, $C_{1-4}$ aliphatic, $C_{1-4}$ haloalkyl, —OH, —OR", —NH$_2$, —NHR", —N(R")$_2$, or $C_{3-8}$ cycloaliphatic;

each $J^R$ is independently selected from halogen, —NO$_2$, —CN, $C_{1-4}$ aliphatic, $C_{1-4}$ haloalkyl, $C_{3-4}$ cycloalkyl, —OH, —NH$_2$, —O(C$_{1-4}$ aliphatic), —N(C$_{1-4}$ aliphatic)$_2$, or —NH(C$_{1-4}$ aliphatic);

each R' is independently selected from unsubstituted $C_{1-6}$ aliphatic; or two R' groups, together with the atom(s) to which they are bound, form a 3-6 membered cycloaliphatic or heterocyclyl, each optionally substituted with up to 2 occurrences of $J^R$;

each R" is independently selected from unsubstituted $C_{1-6}$ aliphatic; or two R" groups, together with the atom to which they are bound, form a 3-6 membered heterocyclyl, optionally substituted with up to 2 occurrences of $J^R$; and each R''' is independently selected from hydrogen or $C_{1-4}$ aliphatic, or an R''' group and an R' group, together with the atoms to which they are bound, form a 3-6 membered cycloaliphatic or heterocyclyl, each optionally substituted with up to 2 occurrences of $J^R$.

2. The method according to claim 1, wherein Ring A is

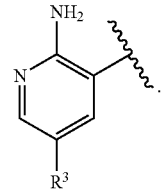

3. The method according to claim 1, wherein Q is

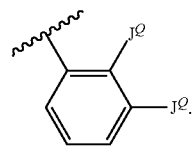

4. The method according to claim 1, wherein each $J^Q$ is, independently, fluoro or chloro.

5. The method according to claim 1, wherein Q is

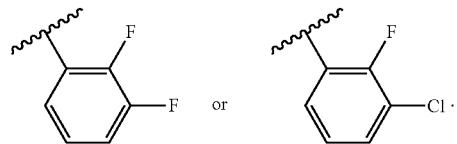

6. The method according to claim 1, wherein $R^3$ is a $C_{6-10}$ aryl, a $C_{3-8}$ cycloaliphatic, or a monocyclic or bicyclic 5-10 membered heteroaryl or heterocyclyl containing 1-4 heteroatoms independently selected from N, O, or S, wherein said aryl, cycloaliphatic, heteroaryl, or heterocyclyl is optionally substituted with up to 3 occurrences of $J^M$.

7. The method according to claim 1, wherein $R^A$ is a $C_{8-10}$ bicyclic heteroaryl selected from:

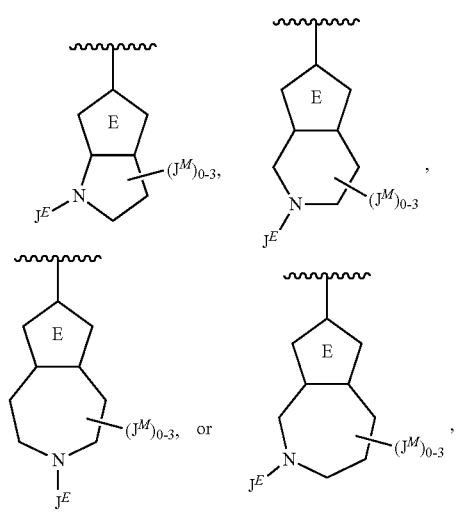

wherein
Ring E is a 5-membered heteroaryl ring with 1 to 2 heteroatoms selected from N, O, or S;
and $J^E$ is hydrogen or $J^N$.

8. The method according to claim 7, wherein Ring E is selected from thienyl, thiazolyl, pyrrolyl, imidazolyl, furanyl, or oxazolyl.

9. The method according to claim 1, wherein $R^A$ is

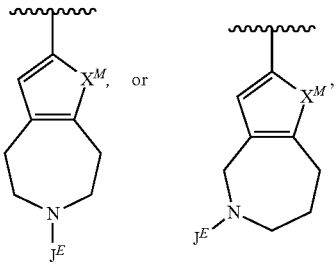

wherein $X^M$ is O or S.

10. The method according to claim 9, wherein $X^M$ is S.

11. The method according to claim 1, wherein said compound has the formula:

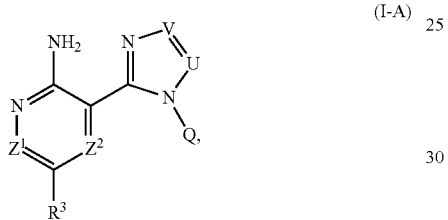

(I-A)

and is selected from 3-(1-(2,3-difluorophenyl)-1H-tetrazol-5-yl)-5-(4-(4-methylpiperazin-1-yl)phenyl)pyridin-2-amine (compound I-A-19), 3-(1-(2,3-difluorophenyl)-1H-tetrazol-5-yl)-5-(pyridin-3-yl)pyridin-2-amine (compound I-A-20), 3-(1-(2,3-difluorophenyl)-1H-tetrazol-5-yl)-5-(4-methoxyphenyl)pyridin-2-amine (compound I-A-22), 5-(4-chlorophenyl)-3-(1-(2,3-difluorophenyl)-1H-tetrazol-5-yl)pyridin-2-amine (compound I-A-24), 5-(1-(2,3-difluorophenyl)-1H-tetrazol-5-yl)-6'-(pyrrolidin-1-yl)-3,3'-bipyridin-6-amine (compound I-A-47), 5-bromo-3-(1-(2,3-difluorophenyl)-1H-tetrazol-5-yl)pyridin-2-amine (compound I-A-61), 3-(1-(2,3-difluorophenyl)-1H-tetrazol-5-yl)-5-(4-((4-methylpiperazin-1-yl)methyl)phenyl)pyridin-2-amine (compound I-A-62), 5-(4-((dimethylamino)methyl)phenyl)-3-(1-(2,3-difluorophenyl)-1H-tetrazol-5-yl)pyridin-2-amine (compound I-A-63), 3-(1-(2,3-difluorophenyl)-1H-tetrazol-5-yl)-5-(6-(pyrrolidin-1-yl)pyridin-3-yl)pyridin-2-amine (compound I-A-64), 5-(4-((diethylamino)methyl)phenyl)-3-(1-(2,3-difluorophenyl)-1H-tetrazol-5-yl)pyridin-2-amine (compound I-A-66), 3-(1-(2,3-difluorophenyl)-1H-tetrazol-5-yl)-5-(4-((pyrrolidin-1-yl)methyl)phenyl)pyridin-2-amine (compound I-A-67), 3-(1-(2,3-dichlorophenyl)-1H-tetrazol-5-yl)-5-(4-((dimethylamino)methyl)phenyl)pyridin-2-amine (compound I-A-79), 3-(1-(2,3-dichlorophenyl)-1H-tetrazol-5-yl)-5-(2-((dimethylamino)methyl)phenyl)pyridin-2-amine (compound I-A-80), N-(4-(6-amino-5-(1-(2,3-dichlorophenyl)-1H-tetrazol-5-yl)pyridin-3-yl)phenyl)acetamide (compound I-A-81), 3-(1-(2,3-dichlorophenyl)-1H-tetrazol-5-yl)-5-(6-(pyrrolidin-1-yl)pyridin-3-yl)pyridin-2-amine (compound I-A-82), 3-(1-(2,3-dichlorophenyl)-1H-tetrazol-5-yl)-5-(pyridin-3-yl)pyridin-2-amine (compound I-A-83), 3-(1-(2,3-dichlorophenyl)-1H-tetrazol-5-yl)-5-(pyridin-4-yl)pyridin-2-amine (compound I-A-84), 3-(1-(2,3-dichlorophenyl)-1H-tetrazol-5-yl)-5-(4-(4-methylpiperazin-1-yl)phenyl)pyridin-2-amine (compound I-A-85), 5-(4-aminophenyl)-3-(1-(2,3-dichlorophenyl)-1H-tetrazol-5-yl)pyridin-2-amine (compound I-A-86), 5-(3-(aminomethyl)phenyl)-3-(1-(2,3-dichlorophenyl)-1H-tetrazol-5-yl)pyridin-2-amine (compound I-A-87), 1-(4-(6-amino-5-(1-(2,3-dichlorophenyl)-1H-tetrazol-5-yl)pyridin-3-yl)phenyl)ethanone (compound I-A-88), 4-(6-amino-5-(1-(2,3-dichlorophenyl)-1H-tetrazol-5-yl)pyridin-3-yl)benzonitrile (compound I-A-89), (4-(6-amino-5-(1-(2,3-dichlorophenyl)-1H-tetrazol-5-yl)pyridin-3-yl)phenyl)methanol (compound I-A-90), 5-(4-chlorophenyl)-3-(1-(2,3-dichlorophenyl)-1H-tetrazol-5-yl)pyridin-2-amine (compound I-A-91), 3-(1-(2,3-dichlorophenyl)-1H-tetrazol-5-yl)-5-(1H-pyrrolo[2,3-b]pyridin-5-yl)pyridin-2-amine (compound I-A-92), 1-(5-(6-amino-5-(1-(2,3-dichlorophenyl)-1H-tetrazol-5-yl)pyridin-3-yl)-6-fluoro-1H-benzo[d]imidazol-2-yl)-3-ethylurea (compound I-A-93), 3-(1-(2,3-dichlorophenyl)-1H-tetrazol-5-yl)-5-(4-((pyrrolidin-1-yl)methyl)phenyl)pyridin-2-amine (compound I-A-94), 3-(1-(2,3-dichlorophenyl)-1H-tetrazol-5-yl)-5-(4-(($N^1,N^3,N^3$-trimethylpropane-1,3-diamino)methyl)phenyl)pyridin-2-amine (compound I-A-95), (1-(4-(6-amino-5-(1-(2,3-dichlorophenyl)-1H-tetrazol-5-yl)pyridin-3-yl)benzyl)piperidin-4-yl)methanol (compound I-A-96), 1-(4-(6-amino-5-(1-(2,3-dichlorophenyl)-1H-tetrazol-5-yl)pyridin-3-yl)benzyl)piperidin-4-ol (compound I-A-97), 3-(1-(2,3-dichlorophenyl)-1H-tetrazol-5-y1)-5-(4-((4-(piperidin-1-yl)piperidin-1-yl)methyl)phenyl)pyridin-2-amine (compound I-A-98), (1-(4-(6-amino-5-(1-(2,3-dichlorophenyl)-1H-tetrazol-5-yl)pyridin-3-yl)benzyl)piperidin-3-yl)methanol (compound I-A-99), 3-(1-(2,3-dichlorophenyl)-1H-tetrazol-5-yl)-5-(4-(1-(dimethylamino)ethyl)phenyl)pyridin-2-amine (compound I-A-100), 5-(4-((bis(2-methoxyethyl)amino)methyl)phenyl)-3-(1-(2,3-dichlorophenyl)-1H-tetrazol-5-yl)pyridin-2-amine (compound I-A-101), 3-(1-(2,3-dichlorophenyl)-1H-tetrazol-5-yl)-5-(4-((N-methyl-2-(pyridin-2-yl)ethanamino)methyl)phenyl)pyridin-2-amine (compound I-A-102), 3-(1-(2,3-dichlorophenyl)-1H-tetrazol-5-yl)-5-(4-(2,6-dimethylmorpholino)methyl)phenyl)pyridin-2-amine (compound I-A-103), 2-(4-(4-(6-amino-5-(1-(2,3-dichlorophenyl)-1H-tetrazol-5-yl)pyridin-3-yl)benzyl)piperazin-1-yl)ethanol (compound I-A-104), 3-(1-(2,3-dichlorophenyl)-1H-tetrazol-5-yl)-5-(4-((4-((pyridin-4-yl)methyl)piperazin-1-yl)methyl)phenyl)pyridin-2-amine (compound I-A-105), 3-(1-(2,3-dichlorophenyl)-1H-tetrazol-5-yl)-5-(4-((3-methylpiperazin-1-yl)methyl)phenyl)pyridin-2-amine (compound I-A-106), 3-(1-(2,3-dichlorophenyl)-1H-tetrazol-5-yl)-5-(4-((N-methyl(pyridin-3-yl)methanamino)methyl)phenyl)pyridin-2-amine (compound I-A-107), 5-(4-((4-(aminomethyl)piperazin-1-yl)methyl)phenyl)-3-(1-(2,3-dichlorophenyl)-1H-tetrazol-5-yl)pyridin-2-amine (compound I-A-108), 3-(1-(2,3-dichlorophenyl)-1H-tetrazol-5-yl)-5-(3-((pyrrolidin-1-yl)methyl)phenyl)pyridin-2-amine (compound I-A-109), 3-(1-(2,3-dichlorophenyl)-1H-tetrazol-5-yl)-5-(4-(((R)-2-((pyrrolidin-1-yl)methyl)pyrrolidin-1-yl)methyl)phenyl)pyridin-2-amine (compound I-A-118), (R)-1-(4-

(6-amino-5-(1-(2,3-dichlorophenyl)-1H-tetrazol-5-yl)pyridin-3-yl)benzyl)pyrrolidin-3-ol (compound I-A-119), (S)-1-(4-(6-amino-5-(1-(2,3-dichlorophenyl)-1H-tetrazol-5-yl)pyridin-3-yl)benzyl)pyrrolidin-3-ol (compound I-A-120), (S)-1-(4-(6-amino-5-(1-(2,3-dichlorophenyl)-1H-tetrazol-5-yl)pyridin-3-yl)benzyl)pyrrolidine-2-carboxamide (compound I-A-121), ((S)-1-(4-(6-amino-5-(1-(2,3-dichlorophenyl)-1H-tetrazol-5-yl)pyridin-3-yl)benzyl)pyrrolidin-2-yl)methanol (compound I-A-122), 3-(1-(2,3-dichlorophenyl)-1H-tetrazol-5-yl)-5-(3-((dimethylamino)methyl)phenyl)pyridin-2-amine (compound I-A-123), 4-(6-amino-5-(1-(2,3-dichlorophenyl)-1H-tetrazol-5-yl)pyridin-3-yl)-N-(2-(dimethylamino)ethyl)benzamide (compound I-A-124), 4-(6-amino-5-(1-(2,3-dichlorophenyl)-1H-tetrazol-5-yl)pyridin-3-yl)-N-(3-(dimethylamino)propyl)benzamide (compound I-A-125), N-(4-(6-amino-5-(1-(2,3-difluorophenyl)-1H-tetrazol-5-yl)pyridin-3-yl)-3-fluorophenyl)acetamide (compound I-A-126), N-(4-(6-amino-5-(1-(2,3-difluorophenyl)-1H-tetrazol-5-yl)pyridin-3-yl)-2-fluorophenyl)acetamide (compound I-A-127), 5-(6-(1H-imidazol-1-yl)pyridin-3-yl)-3-(1-(2,3-difluorophenyl)-1H-tetrazol-5-yl)pyridin-2-amine (compound I-A-128), 5-(6-(1-aminoethyl)pyridin-3-yl)-3-(1-(2,3-difluorophenyl)-1H-tetrazol-5-yl)pyridin-2-amine (compound I-A-129), (R)-1-(4-(6-amino-5-(1-(2,3-difluorophenyl)-1H-tetrazol-5-yl)pyridin-3-yl)benzyl)pyrrolidin-3-ol (compound I-A-130), (S)-1-(4-(6-amino-5-(1-(2,3-difluorophenyl)-1H-tetrazol-5-yl)pyridin-3-yl)benzyl)pyrrolidin-3-ol (compound I-A-131), (S)-1-(4-(6-amino-5-(1-(2,3-difluorophenyl)-1H-tetrazol-5-yl)pyridin-3-yl)benzyl)pyrrolidine-2-carboxamide (compound I-A-132), ((S)-1-(4-(6-amino-5-(1-(2,3-difluorophenyl)-1H-tetrazol-5-yl)pyridin-3-yl)benzyl)pyrrolidin-2-yl)methanol (compound I-A-133), 3-(1-(2,3-difluorophenyl)-1H-tetrazol-5-yl)-5-(4-((piperidin-1-yl)methyl)phenyl)pyridin-2-amine (compound I-A-134), 4-(6-amino-5-(1-(2,3-difluorophenyl)-1H-tetrazol-5-yl)pyridin-3-yl)-N-(2-(dimethylamino)ethyl)benzamide (compound I-A-135), 4-(6-amino-5-(1-(2,3-difluorophenyl)-1H-tetrazol-5-yl)pyridin-3-yl)-N-(3-(dimethylamino)propyl)benzamide (compound I-A-136), 4-(6-amino-5-(1-(2,3-difluorophenyl)-1H-tetrazol-5-yl)pyridin-3-yl)-N-cyclopropylbenzamide (compound I-A-137), N-(4-(6-amino-5-(1-(2,3-difluorophenyl)-1H-tetrazol-5-yl)pyridin-3-yl)phenyl)acetamide (compound I-A-138), N-(3-(6-amino-5-(1-(2,3-difluorophenyl)-1H-tetrazol-5-yl)pyridin-3-yl)phenyl)acetamide (compound I-A-139), 1-(5-(6-amino-5-(1-(2,3-difluorophenyl)-1H-tetrazol-5-yl)pyridin-3-yl)-6-fluoro-1H-benzo[d]imidazol-2-yl)-3-ethylurea (compound I-A-140), 5-(6-amino-5-(1-(2,3-difluorophenyl)-1H-tetrazol-5-yl)pyridin-3-yl)-6-fluoro-1H-benzo[d]imidazol-2-amine (compound I-A-141), 1-(5-(6-amino-5-(1-(2,3-difluorophenyl)-1H-tetrazol-5-yl)pyridin-3-yl)-6-methoxy-1H-benzo[d]imidazol-2-yl)-3-ethylurea (compound I-A-142), 3-(1-(2,3-difluorophenyl)-1H-tetrazol-5-yl)-5-(thiophen-3-yl)pyridin-2-amine (compound I-A-143), 4-(6-amino-5-(1-(2,3-difluorophenyl)-1H-tetrazol-5-yl)pyridin-3-yl)phenol (compound I-A-144), 2-(6-amino-5-(1-(2,3-difluorophenyl)-1H-tetrazol-5-yl)pyridin-3-yl)phenol (compound I-A-145), 2-(N-(4-(6-amino-5-(1-(2,3-difluorophenyl)-1H-tetrazol-5-yl)benzyl)-N-ethylamino)ethanol (compound I-A-146), 5-(4-((3-(dimethylamino)pyrrolidin-1-yl)methyl)phenyl)-3-(1-(2,3-difluorophenyl)-1H-tetrazol-5-yl)pyridin-2-amine (compound I-A-147), 3-(N-(4-(6-amino-5-(1-(2,3-difluorophenyl)-1H-tetrazol-5-yl)pyridin-3-yl)benzyl)-N-methylamino)propanenitrile (compound I-A-148), 5-(4-((N-methylethanamino)methyl)phenyl)-3-(1-(2,3-difluorophenyl)-1H-tetrazol-5-yl)pyridin-2-amine (compound I-A-149), 5-(4-((N,2-dimethylpropanamino)methyl)phenyl)-3-(1-(2,3-difluorophenyl)-1H-tetrazol-5-yl)pyridin-2-amine (compound I-A-150), 5-(4-((cyclobutylamino)methyl)phenyl)-3-(1-(2,3-difluorophenyl)-1H-tetrazol-5-yl)pyridin-2-amine (compound I-A-151), 5-(4-((R)-1-(dimethylamino)ethyl)phenyl)-3-(1-(2,3-difluorophenyl)-1H-tetrazol-5-yl)pyridin-2-amine (compound I-A-152), 5-(4-((R)-1-aminoethyl)phenyl)-3-(1-(2,3-difluorophenyl)-1H-tetrazol-5-yl)pyridin-2-amine (compound I-A-153), 5-(6-((dimethylamino)methyl)pyridin-3-yl)-3-(1-(2,3-difluorophenyl)-1H-tetrazol-5-yl)pyridin-2-amine (compound I-A-154), 5-(6-(aminomethyl)pyridin-3-yl)-3-(1-(2,3-difluorophenyl)-1H-tetrazol-5-yl)pyridin-2-amine (compound I-A-155), 5-(4-((dipropylamino)methyl)phenyl)-3-(1-(2,3-difluorophenyl)-1H-tetrazol-5-yl)pyridin-2-amine (compound I-A-156), 4-(4-(6-amino-5-(1-(2,3-difluorophenyl)-1H-tetrazol-5-yl)pyridin-3-yl)benzyl)piperidin-4-ol (compound I-A-157), 5-(4-aminocyclohex-1-enyl)-3-(1-(2,3-difluorophenyl)-1H-tetrazol-5-yl)pyridin-2-amine (compound I-A-158), 4-(6-amino-5-(1-(2,3-difluorophenyl)-1H-tetrazol-5-yl)pyridin-3-yl)-N-(3-(dimethylamino)propyl)-N-methylsulfonamide (compound I-A-159), N-(4-(6-amino-5-(1-(2,3-difluorophenyl)-1H-tetrazol-5-yl)pyridin-3-yl)phenyl)-2-((S)-2-(hydroxymethyl)pyrrolidin-1-yl)acetamide (compound I-A-160), N-(4-(6-amino-5-(1-(2,3-difluorophenyl)-1H-tetrazol-5-yl)pyridin-3-yl)phenyl)thiophene-2-carboxamide (compound I-A-161), N-(4-(6-amino-5-(1-(2,3-difluorophenyl)-1H-tetrazol-5-yl)pyridin-3-yl)phenyl)furan-2-carboxamide (compound I-A-162), N-(4-(6-amino-5-(1-(2,3-difluorophenyl)-1H-tetrazol-5-yl)pyridin-3-yl)phenyl)-2-morpholinoacetamide (compound I-A-163), methyl 6-amino-5-(1-(2,3-difluorophenyl)-1H-tetrazol-5-yl)pyridine-3-carboxylate (compound I-A-164), 5-(4-((dimethylamino)methyl)-3-fluorophenyl)-3-(1-(2,3-difluorophenyl)-1H-tetrazol-5-yl)pyridin-2-amine (compound I-A-165), 4-(6-amino-5-(1-(2,3-difluorophenyl)-1H-tetrazol-5-yl)pyridin-3-yl)-N-(2-(dimethylamino)ethyl)benzamide (compound I-A-166), 6-amino-N-(3-(dimethylamino)propyl)-5-(1-(2,3-difluorophenyl)-1H-tetrazol-5-yl)-N-methylpyridine-3-carboxamide (compound I-A-167), 6-amino-N-ethyl-5-(1-(2,3-difluorophenyl)-1H-tetrazol-5-yl)-N-((pyridin-4-yl)methyl)pyridine-3-carboxamide (compound I-A-168), (6-amino-5-(1-(2,3-difluorophenyl)-1H-tetrazol-5-yl)pyridin-3-yl)(4-(hydroxymethyl)piperidin-1-yl)methanone (compound I-A-169), (6-amino-5-(1-(2,3-difluorophenyl)-1H-tetrazol-5-yl)pyridin-3-yl)((R)-3-hydroxypyrrolidin-1-yl)methanone (compound I-A-170), 6-amino-5-(1-(2,3-difluorophenyl)-1H-tetrazol-5-yl)-N,N-bis(2-methoxyethyl)pyridine-3-carboxamide (compound I-A-171), (6-amino-5-(1-(2,3-difluorophenyl)-1H-tetrazol-5-yl)pyridin-3-yl)(4-((pyridin-4-yl)methyl)piperazin-1-yl)methanone (compound I-A-172), (6-amino-5-(1-(2,3-difluorophenyl)-1H-tetrazol-5-yl)pyridin-3-yl)(pyrrolidin-1-yl)methanone (compound I-A-173), 6-amino-5-(1-(2,3-difluorophenyl)-1H-tetrazol-5-yl)-N,N-dimethylpyridine-3-carboxamide (compound I-A-174), 6-amino-5-(1-(2,3-difluorophenyl)-1H-tetrazol-5-yl)-N-methyl-N-(2-(methylamino)ethyl)pyridine-3-carboxamide (compound I-A-175), (6-amino-5-(1-(2,3-difluorophenyl)-1H-tetrazol-5-yl)pyridin-3-yl)(3-(dimethylamino)pyrrolidin-1yl)methanone (compound I-A-176), 6-amino-N-(1-(dimethylamino)propan-2-yl)-5-(1-(2,3-difluorophenyl)-1H-tetrazol-5-yl)pyridine-3-carboxamide (compound I-A-177), 6-amino-5-(1-(2,3-difluorophenyl)-1H-tetrazol-5-yl)-N-(pyrrolidin-1-yl)pyridine-3-carboxamide (compound I-A-178), 1-(5-(6-amino-5-(1-(2,3-difluorophenyl)-1H-tetrazol-5-yl)pyridin-3-yl)thiophen-2-yl)ethanone (compound I-A-179), 3-(1-(2,3-difluorophenyl)-1H-tetrazol-5-yl)-5-(4-(1-(pyrrolidin-1-yl)ethyl)phenyl)pyridin-2-amine (compound I-A-180), 3-(1-(2,3-difluorophenyl)-1H-tetrazol-5-yl)-5-(4-(2-(pyrrolidin-1-yl)ethyl)phenyl)pyridin-2-amine (compound I-A-181), 1-(5-(6-amino-5-(1-(2,3-difluorophenyl)-1H-tetrazol-5-yl)pyridin-3-yl)indolin-1-yl)ethanone (compound I-A-182), 1-(4-(6-amino-5-(1-(2,3-difluorophenyl)-1H-tetrazol-5-yl)pyridin-3-yl)phenyl)urea (compound I-A-183), N-(4-(6-amino-5-(1-(2,3-difluorophenyl)-1H-tetrazol-5-yl)pyridin-3-yl)phenyl)-2-(pyrrolidin-1-yl)acetamide (compound I-A-184), 5-(6-amino-5-(1-(2,3-difluorophenyl)-1H-tetrazol-5-yl)pyridin-3-yl)thiophene-3-carboxylic acid (compound I-A-185), 3-(1-(2,3-difluorophenyl)-1H-tetrazol-5-yl)-5-(5-((pyrrolidin-1-yl)methyl)thiophen-2-yl)pyridin-2-amine (compound I-A-186), 5-(6-amino-5-(1-(2,3-difluorophenyl)-1H-tetrazol-5-yl)pyridin-3-yl)thiophene-2-sulfonamide (compound I-A-187), 5-(6-amino-5-(1-(2,3-difluorophenyl)-1H-tetrazol-5-yl)pyridin-3-yl)indolin-2-one (compound I-A-188), 1-(4-(6-amino-5-(1-(2,3-difluorophenyl)-1H-tetrazol-5-yl)pyridin-3-yl)phenyl)pyrrolidin-2-one (compound I-A-189), 6-(6-amino-5-(1-(2,3-difluorophenyl)-1H-tetrazol-5-yl)pyridin-3-yl)indolin-2-one (compound I-A-190), N-(4-(6-amino-5-(1-(2,3-difluorophenyl)-1H-tetrazol-5-yl)pyridin-3-yl)phenyl)-2-(dimethylamino)acetamide (compound I-A-191), N-(4-(6-amino-5-(1-(2,3-difluorophenyl)-1H-tetrazol-5-yl)pyridin-3-yl)benzyl)methylsulfonamide (compound I-A-192), N-(4-(6-amino-5-(1-(2,3-difluorophenyl)-1H-tetrazol-5-yl)pyridin-3-yl)phenyl) isobutyramide (compound I-A-193), N-(4-(6-amino-5-(1-(2,3-difluorophenyl)-1H-tetrazol-5-yl)pyridin-3-yl) phenyl)pivalamide (compound I-A-194), N-(4-(6-amino-5-(1-(2,3-difluorophenyl)-1H-tetrazol-5-yl)pyridin-3-yl)phenyl)butyramide (compound I-A-195), ethyl 2-(4-(6-amino-5-(1-(2,3-difluorophenyl)-1H-tetrazol-5-yl)pyridin-3-yl)phenylcarbamoyl)acetate (compound I-A-196), N-(4-(6-amino-5-(1-(2,3-difluorophenyl)-1H-tetrazol-5-yl)pyridin-3-yl)phenyl)-2-ethylbutanamide (compound I-A-197), 4-(6-amino -5-(1-(2,3-difluorophenyl)-1H-tetrazol-5-yl)pyridin-3-yl)-N-cyclopropylbenzamide (compound I-A-198), N-(4-(6-amino-5-(1-(2,3-difluorophenyl)-1H-tetrazol-5-yl)pyridin-3-yl)phenyl)-3,3-dimethylbutanamide (compound I-A-199), 3-(1-(2,3-difluorophenyl)-1H-tetrazol-5-yl)-5-(4-((methylamino)methyl)phenyl)pyridin-2-amine (compound I-A-200), 5-(3-aminophenyl)-3-(1-(2,3-difluorophenyl)-1H-tetrazol-5-yl)pyridin-2-amine (compound I-A-201), 5-(4-(aminomethyl)phenyl)-3-(1-(2,3-difluorophenyl)-1H-tetrazol-5-yl)pyridin-2-amine (compound I-A-202), 1-(4-(6-amino-5-(1-(2,3-difluorophenyl)-1H-tetrazol-5-yl)pyridin-3-yl)benzyl)pyrrolidin-2-one (compound I-A-203), 5-(6-amino-5-(1-(2,3-difluorophenyl)-1H-tetrazol-5-yl)pyridin-3-yl)indoline-2,3-dione (compound I-A-204), 2-amino-2-(4-(6-amino-5-(1-(2,3-difluorophenyl)-1H-tetrazol-5-yl)pyridin-3-yl)phenyl)acetic acid (compound I-A-205), methyl 2-amino-2-(4-(6-amino-5-(1-(2,3-difluorophenyl)-1H-tetrazol-5-yl)pyridin-3-yl) phenyl)acetate (compound I-A-206), methyl 2-(4-(6-amino-5-(1-(2,3-difluorophenyl)-1H-tetrazol-5-yl) pyridin-3-yl)phenyl)-2-methylpropanoate (compound I-A-207), methyl 2-(4-(6-amino-5-(1-(2,3-difluorophenyl)-1H-tetrazol-5-yl)pyridin-3-yl)phenyl)-2-(pyrrolidin-1-yl)acetate (compound I-A-208), 3-(1-(2,3-difluorophenyl)-1H-tetrazol-5-yl)-5-(4((2-methylpyrrolidin-1-yl)methyl)phenyl)pyridin-2-amine (compound I-A-209), 3-(1-(2,3-difluorophenyl)-1H-tetrazol-5-yl)-5-(4-((2,5-dimethylpyrrolidin-1-yl)methyl)phenyl)pyridin-2-amine (compound I-A-210), 3-(1-(2,3-difluorophenyl)-1H-tetrazol-5-yl)-5-(4-((S)-1-(pyrrolidin-1-yl)ethyl)phenyl)pyridin-2-amine (compound I-A-211), 3-(1-(2,3-difluorophenyl)-1H-tetrazol-5-yl)-5-(4-((R)-1-(pyrrolidin-1-yl)ethyl)phenyl)pyridin-2-amine (compound I-A-212), 5-(3-fluoro-4-((pyrrolidin-1-yl)methyl)phenyl)-3-(1-(2,3-difluorophenyl)-1H-tetrazol-5-yl)pyridin-2-amine (compound I-A-213), 5-(2-(trifluoromethyl)phenyl)-3-(1-(2,3-difluorophenyl)-1H-tetrazol-5-yl)pyridin-2-amine (compound I-A-214), 5-(3-(trifluoromethyl)phenyl)-3-(1-(2,3-difluorophenyl)-1H-tetrazol-5-yl)pyridin-2-amine (compound I-A-215), 5-(4-(trifluoromethyl)phenyl)-3-(1-(2,3-difluorophenyl)-1H-tetrazol-5-yl)pyridin-2-amine (compound I-A-216), 1-(2-(6-amino-5-(1-(2,3-difluorophenyl)-1H-tetrazol-5-yl)pyridin-3-yl)phenyl)ethanone (compound I-A-217), 1-(3-(6-amino-5-(1-(2,3-difluorophenyl)-1H-tetrazol-5-yl)pyridin-3-yl)phenyl)ethanone (compound I-A-218), 1-(4-(6-amino-5-(1-(2,3-difluorophenyl)-1H-tetrazol-5-yl)pyridin-3-yl)phenyl)ethanone (compound I-A-219), 4-(6-amino-5-(1-(2,3-difluorophenyl)-1H-tetrazol-5-yl)pyridin-3-yl)-3-methoxyphenol (compound I-A-220), 3-(1-(2,3-difluorophenyl)-1H-tetrazol-5-yl)-5-(3-methoxyphenyl)pyridin-2-amine (compound I-A-221), 3-(1-(2,3-difluorophenyl)-1H-tetrazol-5-yl)-5-(4-methoxyphenyl)pyridin-2-amine (compound I-A-222), 5-(4-fluorophenyl)-3-(1-(2,3-difluorophenyl)-1H-tetrazol-5-yl)pyridin-2-amine (compound I-A-223), 5-(2-chlorophenyl)-3-(1-(2,3-difluorophenyl)-1H-tetrazol-5-yl)pyridin-2-amine (compound I-A-224), 5-(3-chlorophenyl)-3-(1-(2,3-difluorophenyl)-1H-tetrazol-5-yl)pyridin-2-amine (compound I-A-225), 5-(4-chlorophenyl)-3-(1-(2,3-difluorophenyl)-1H-tetrazol-5-yl)pyridin-2-amine (compound I-A-226), 2-(6-amino-5-(1-(2,3-difluorophenyl)-1H-tetrazol-5-yl)pyridin-3-yl)benzonitrile (compound I-A-227), 3-(6-amino-5-(1-(2,3-difluorophenyl)-1H-tetrazol-5-yl)pyridin-3-yl)benzonitrile (compound I-A-228), 4-(6-amino-5-(1-(2,3-difluorophenyl)-1H-tetrazol-5-yl)pyridin-3-yl)benzonitrile (compound I-A-229), (2-(6-amino-5-(1-(2,3-difluorophenyl)-1H-tetrazol-5-yl)pyridin-3-yl)phenyl) methanol (compound I-A-230), (3-(6-amino-5-(1-(2,3-difluorophenyl)-1H-tetrazol-5-yl)pyridin-3-yl)phenyl) methanol (compound I-A-231), (4-(6-amino-5-(1-(2,3-difluorophenyl)-1H-tetrazol-5-yl)pyridin-3-yl)phenyl) methanol (compound I-A-232), 3-(1-(2,3-difluorophenyl)-1H-tetrazol-5-yl)-5-phenylpyridin-2-amine (compound I-A-233), 5-(4-(dimethylamino) phenyl)-3-(1-(2,3-difluorophenyl)-1H-tetrazol-5-yl) pyridin-2-amine (compound I-A-234), 3-(1-(2,3- difluorophenyl)-1H-tetrazol-5-yl)-5-(2,3-dihydrobenzo[b][1,4]dioxin-6-yl)pyridin-2-amine (compound I-A-235), 3-(1-(2,3-difluorophenyl)-1H-tetrazol-5-yl)-5-(3-isopropylphenyl)pyridin-2-amine (compound I-A-236), 3-(1-(2,3-difluorophenyl)-1H-tetrazol-5-yl)-5-(4-isopropylphenyl)pyridin-2-amine (compound I-A-237), 3-(1-(2,3-difluorophenyl)-1H-tetrazol-5-yl)-5-(2-nitrophenyl)pyridin-2-amine (compound I-A-238), 3-(1-(2,3-difluorophenyl)-1H-tetrazol-5-yl)-5-(3-nitrophenyl)pyridin-2-amine (compound I-A-239), 3-(1-(2,3-difluorophenyl)-1H-tetrazol-5-yl)-5-(4-isopropoxyphenyl)pyridin-2-amine (compound I-A-240), 3-(1-(2,3-difluorophenyl)-1H-tetrazol-5-yl)-5-o-tolylpyridin-2-amine (compound I-A-241), 3-(1-(2,3-difluorophenyl)-1H-tetrazol-5-yl)-5-m-tolylpyridin-2-amine (compound I-A-242), 5-(3,4-dichlorophenyl)-3-(1-(2,3-difluorophenyl)-1H-tetrazol-5-yl)pyridin-2-amine (compound I-A-243), 5-(3-chloro-4-fluorophenyl)-3-(1-(2,3-difluorophenyl)-1H-tetrazol-5-yl)pyridin-2-amine (compound I-A-244), 4-(6-amino-5-(1-(2,3-difluorophenyl)-1H-tetrazol-5-yl)pyridin-3-yl)benzamide (compound I-A-245), 5-(2-ethylphenyl)-3-(1-(2,3-difluorophenyl)-1H-tetrazol-5-yl)pyridin-2-amine (compound I-A-246), 3-(6-amino-5-(1-(2,3-difluorophenyl)-1H-tetrazol-5-yl)pyridin-3-yl)phenol (compound I-A-247), 3-(1-(2,3-difluorophenyl)-1H-tetrazol-5-yl)-5-(1H-pyrazol-5-yl)pyridin-2-amine (compound I-A-248), 3-(1-(2,3-difluorophenyl)-1H-tetrazol-5-yl)-5-(1-methyl-1H-pyrazol-4-yl)pyridin-2-amine (compound I-A-249), 3-(1-(2,3-difluorophenyl)-1H-tetrazol-5-yl)-5-(4-(methylsulfonyl)phenyl)pyridin-2-amine (compound I-A-250), 3-(1-(2,3-difluorophenyl)-1H-tetrazol-5-yl)-5-(4-(methylthio)phenyl)pyridin-2-amine (compound I-A-251), 3-(1-(2,3-difluorophenyl)-1H-tetrazol-5-yl)-5-(2-(methylthio)phenyl)pyridin-2-amine (compound I-A-252), N-(2-(6-amino-5-(1-(2,3-difluorophenyl)-1H-tetrazol-5-yl)pyridin-3-yl)phenyl)methylsulfonamide (compound I-A-253), N-(3-(6-amino-5-(1-(2,3-difluorophenyl)-1H-tetrazol-5-yl)pyridin-3-yl)phenyl)methylsulfonamide (compound I-A-254), 3-(1-(2,3-difluorophenyl)-1H-tetrazol-5-yl)-5-p-tolylpyridin-2-amine (compound I-A-255), 1-(4-(6-amino-5-(1-(2,3-difluorophenyl)-1H-tetrazol-5-yl)pyridin-3-yl)phenyl)imidazolidine-2,4-dione (compound I-A-256), 5-(4-(6-amino-5-(1-(2,3-difluorophenyl)-1H-tetrazol-5-yl)pyridin-3-yl)phenyl)imidazolidine-2,4-dione (compound I-A-257), 3-(1-(2,3-difluorophenyl)-1H-tetrazol-5-yl)-5-(4-(pyrrolidin-2-yl)phenyl)pyridin-2-amine (compound I-A-258), N-(3-(6-amino-5-(1-(2,3-difluorophenyl)-1H-tetrazol-5-yl)pyridin-3-yl)phenyl)-2-(pyrrolidin-1-yl)acetamide (compound I-A-259), N-(3-(6-amino-5-(1-(2,3-difluorophenyl)-1H-tetrazol-5-yl)pyridin-3-yl)phenyl)isobutyramide (compound I-A-260), N-(3-(6-amino-5-(1-(2,3-difluorophenyl)-1H-tetrazol-5-yl)pyridin-3-yl)phenyl)cyclopropanecarboxamide (compound I-A-261), 3-(1-(2,3-difluorophenyl)-1H-tetrazol-5-yl)-5-(5-(1-(pyrrolidin-1-yl)ethyl)thiophen-2-yl)pyridin-2-amine (compound I-A-262), N-(5-(6-amino-5-(1-(2,3-difluorophenyl)-1H-tetrazol-5-yl)pyridin-3-yl)thiophen-2-yl)acetamide (compound I-A-263), 3-(1-(2,3-difluorophenyl)-1H-tetrazol-5-yl)-5-(4-(((R)-2-(methoxymethyl)pyrrolidin-1-yl)methyl)phenyl)pyridin-2-amine (compound I-A-264), 5-(4-((5-oxa-2-aza-bicyclo[2.2.1]heptan-2-yl)methyl)phenyl)-3-(1-(2,3-difluorophenyl)-1H-tetrazol-5-yl)pyridin-2-amine (compound I-A-265), 2-(4-(6-amino-5-(1-(2,3-difluorophenyl)-1H-tetrazol-5-yl)pyridin-3-yl)phenyl)-2-methylpropanenitrile (compound I-A-266), 3-(1-(2,3-difluorophenyl)-1H-tetrazol-5-yl)-5-(4-(((2R,5R)-2,5-dimethylpyrrolidin-1-yl)methyl)phenyl)pyridin-2-amine (compound I-A-267), 2-(4-(6-amino-5-(1-(2,3-difluorophenyl)-1H-tetrazol-5-yl)pyridin-3-yl)phenyl)propan-2-ol (compound I-A-268), N-(3-(6-amino-5-(1-(2,3-difluorophenyl)-1H-tetrazol-5-yl)pyridin-3-yl)phenyl)pyrrolidine-1-carboxamide (compound I-A-269), N-(3-(6-amino-5-(1-(2,3-difluorophenyl)-1H-tetrazol-5-yl)pyridin-3-yl)phenyl)-4-methylpiperazine-1-carboxamide (compound I-A-270), 2-methoxyethyl 3-(6-amino-5-(1-(2,3-difluorophenyl)-1H-tetrazol-5-yl)pyridin-3-yl)phenylcarbamate (compound I-A-271), 1-(3-(6-amino-5-(1-(2,3-difluorophenyl)-1H-tetrazol-5-yl)pyridin-3-yl)phenyl)-3-(pyridin-3-yl)urea (compound I-A-272), 1-(3-(6-amino-5-(1-(2,3-difluorophenyl)-1H-tetrazol-5-yl)pyridin-3-yl)phenyl)-3-(tetrahydro-2H-pyran-2-yOurea (compound I-A-273), 3-(3-(6-amino-5-(1-(2,3-difluorophenyl)-1H-tetrazol-5-yl)pyridin-3-yl)phenyl)-1-methyl-1-phenylurea (compound I-A-274), 1-(3-(6-amino-5-(1-(2,3-difluorophenyl)-1H-tetrazol-5-yl)pyridin-3-yl)phenyl)-3-(thiophen-2-yl)urea (compound I-A-275), N-(4-(6-amino-5-(1-(2,3-difluorophenyl)-1H-tetrazol-5-yl)pyridin-3-yl)phenyl)pyrrolidine-1-carboxamide (compound I-A-276), 2-methoxyethyl 4-(6-amino-5-(1-(2,3-difluorophenyl)-1H-tetrazol-5-yl)pyridin-3-yl)phenylcarbamate (compound I-A-277), 1-(4-(6-amino-5-(1-(2,3-difluorophenyl)-1H-tetrazol-5-yl)pyridin-3-yl)phenyl)-3-(pyridin-3-yl)urea (compound I-A-278), 3-(4-(6-amino-5-(1-(2,3-difluorophenyl)-1H-tetrazol-5-yl)pyridin-3-yl)phenyl)-1-methyl-1-phenylurea (compound I-A-279), N-(4-(6-amino-5-(1-(2,3-difluorophenyl)-1H-tetrazol-5-yl)pyridin-3-yl)phenyl)isonicotinamide (compound I-A-280), 1-(4-(6-amino-5-(1-(2,3-difluorophenyl)-1H-tetrazol-5-yl)pyridin-3-yl)phenyl)-3-ethylurea (compound I-A-281), 1-(4-(6-amino-5-(1-(2,3-difluorophenyl)-1H-tetrazol-5-yl)pyridin-3-yl)phenyl)-3-(thiophen-2-yl)urea (compound I-A-282), 2-(4-(6-amino-5-(1-(2,3-difluorophenyl)-1H-tetrazol-5-yl)pyridin-3-yl)phenoxy)ethanol (compound I-A-283), N-(2-(6-amino-5-(1-(2,3-difluorophenyl)-1H-tetrazol-5-yl)pyridin-3-yl)-5-fluorophenyl)acetamide (compound I-A-284), 5-(2,2-difluorobenzo[d][1,3]dioxol-5-yl)-3-(1-(2,3-difluorophenyl)-1H-tetrazol-5-yl)pyridin-2-amine (compound I-A-285), 5-(4-amino-3-fluorophenyl)-3-(1-(2,3-difluorophenyl)-1H-tetrazol-5-yl)pyridin-2-amine (compound I-A-286), 5-(4-amino-3,5-dichlorophenyl)-3-(1-(2,3-difluorophenyl)-1H-tetrazol-5-yl)pyridin-2-amine (compound I-A-287), 5-(3,5-difluorophenyl)-3-(1-(2,3-difluorophenyl)-1H-tetrazol-5-yl)pyridin-2-amine (compound I-A-288), 3-(1-(2,3-difluorophenyl)-1H-tetrazol-5-yl)-5-(3,4-dihydro-4-methyl-2H-benzo[b][1,4]oxazin-7-yl)pyridin-2-amine (compound I-A-289), 5-(3-fluoro-4-methoxyphenyl)-3-(1-(2,3-difluorophenyl)-1H-tetrazol-5-yl)pyridin-2-amine (compound I-A-290), 5-(6-amino-5-(1-(2,3-difluorophenyl)-1H-tetrazol-5-yl)pyridin-3-yl)-2,3-difluorophenol (compound I-A-291), 2-(6-amino-5-(1-(2,3-difluorophenyl)-1H-tetrazol-5-yl)pyridin-3-yl)-4-fluorophenol (compound I-A-292), 5-(2-amino-3-fluorophenyl)-3-(1-(2,3-difluorophenyl)-1H-tetrazol-5-yl)pyridin-2-amine (compound I-A-293), 5-(2,5-difluorophenyl)-3-(1-(2,3-difluorophenyl)-1H-tetrazol-5-yl)pyridin-2-amine (compound I-A-294), 4-(6- amino-5-(1-(2,3-difluorophenyl)-1H-tetrazol-5-yl)pyridin-3-yl)-2-fluorophenol (compound I-A-295), 3-(1-(2,3-difluorophenyl)-1H-tetrazol-5-yl)-5-(3,4,5-trimethoxyphenyl)pyridin-2-amine (compound I-A-296), 5-(2-amino-3,5-difluorophenyl)-3-(1-(2,3-difluorophenyl)-1H-tetrazol-5-yl)pyridin-2-amine (compound I-A-297), 4-(6-amino-5-(1-(2,3-difluorophenyl)-1H-tetrazol-5-yl)pyridin-3-yl)benzene-1,2-diamine (compound I-A-298), 4-(6-amino-5-(1-(2,3-difluorophenyl)-1H-tetrazol-5-yl)pyridin-3-yl)-2-methoxyphenol (compound I-A-299), 5-(2,2,3,3-tetrafluoro-2,3-dihydrobenzo[b][1,4]dioxin-6-yl)-3-(1-(2,3-difluorophenyl)-1H-tetrazol-5-yl)pyridin-2-amine (compound I-A-300), 5-(2,3-difluorophenyl)-3-(1-(2,3-difluorophenyl)-1H-tetrazol-5-yl)pyridin-2-amine (compound I-A-301), N-(2-(6-amino-5-(1-(2,3-difluorophenyl)-1H-tetrazol-5-yl)pyridin-3-yl)-6-fluorophenyl)acetamide (compound I-A-302), 5-(4-amino-3,5-difluorophenyl)-3-(1-(2,3-difluorophenyl)-1H-tetrazol-5-yl)pyridin-2-amine (compound I-A-303), 3-(1-(2,3-difluorophenyl)-1H-tetrazol-5-yl)-5-(quinoxalin-6-yl)pyridin-2-amine (compound I-A-304), 5-(benzo [d][1,3]dioxol-4-yl)-3-(1-(2,3-difluorophenyl)-1H-tetrazol-5-yl)pyridin-2-amine (compound I-A-305), 3-(1-(2,3-difluorophenyl)-1H-tetrazol-5-yl)-5-(2,5-dimethoxyphenyl)pyridin-2-amine (compound I-A-306), 5-(3,4,5-trifluorophenyl)-3-(1-(2,3-difluorophenyl)-1H-tetrazol-5-yl)pyridin-2-amine (compound I-A-307), 6-(6-amino-5-(1-(2,3-difluorophenyl)-1H-tetrazol-5-yl)pyridin-3-yl)benzo[d]thiazol-2-amine (compound I-A-308), 3-(1-(2,3-difluorophenyl)-1H-tetrazol-5-yl)-5-(3,4-dimethoxyphenyl)pyridin-2-amine (compound I-A-309), 5-(2,2-difluorobenzo [d][1,3]dioxol-4-yl)-3-(1-(2,3-difluorophenyl)-1H-tetrazol-5-yl)pyridin-2-amine (compound I-A-310), 5-(2-amino-5-fluorophenyl)-3-(1-(2,3-difluorophenyl)-1H-tetrazol-5-yl)pyridin-2-amine (compound I-A-311), 5-(4-amino-3-nitrophenyl)-3-(1-(2,3-difluorophenyl)-1H-tetrazol-5-yl)pyridin-2-amine (compound I-A-312), 5-(2-fluorophenyl)-3-(1-(2,3-difluorophenyl)-1H-tetrazol-5-yl)pyridin-2-amine (compound I-A-313), 5-(3-fluorophenyl)-3-(1-(2,3-difluorophenyl)-1H-tetrazol-5-yl)pyridin-2-amine (compound I-A-314), 5-(3-ethoxyphenyl)-3-(1-(2,3-difluorophenyl)-1H-tetrazol-5-yl)pyridin-2-amine (compound I-A-315), methyl 4-(6-amino-5-(1-(2,3-difluorophenyl)-1H-tetrazol-5-yl)pyridin-3-yl)benzoate (compound I-A-316), methyl 3-(6-amino-5-(1-(2,3-difluorophenyl)-1H-tetrazol-5-yl)pyridin-3-yl)benzoate (compound I-A-317), 3-(1-(2,3-difluorophenyl)-1H-tetrazol-5-yl)-5-(6-fluoropyridin-3-yl)pyridin-2-amine (compound I-A-318), 3-(1-(2,3-difluorophenyl)-1H-tetrazol-5-yl)-5-(2-fluoropyridin-4-yl)pyridin-2-amine (compound I-A-319), (3-(6-amino-5-(1-(2,3-difluorophenyl)-1H-tetrazol-5-yl)pyridin-3-yl)phenyl)(morpholino)methanone (compound I-A-320), 3-(1-(2,3-difluorophenyl)-1H-tetrazol-5-yl)-5-(quinolin-6-yl)pyridin-2-amine (compound I-A-321), 3-(1-(2,3-difluorophenyl)-1H-tetrazol-5-yl)-5-(quinolin-8-yl)pyridin-2-amine (compound I-A-322), 3-(1-(2,3-difluorophenyl)-1H-tetrazol-5-yl)-5-styrylpyridin-2-amine (compound I-A-323), 1-(3-(6-amino-5-(1-(2,3-difluorophenyl)-1H-tetrazol-5-yl)pyridin-3-yl)phenyl)-3,3-dimethylazetidin-2-one (compound I-A-324), 4-(4-(6-amino-5-(1-(2,3-difluorophenyl)-1H-tetrazol-5-yl)pyridin-3-yl)phenyl)-1,3-oxazinan-2-one (compound I-A-325), 1-(3-(6-amino-5-(1-(2,3-difluorophenyl)-1H-tetrazol-5-yl)pyridin-3-yl)phenyl)-3-((S)-3-methyl-(1-methylcarboxy)butyl)urea (compound I-A-326), 1-(3-(6-amino-5-(1-(2,3-difluorophenyl)-1H-tetrazol-5-yl)pyridin-3-yl)phenyl)-3-((1-methylcarboxy)ethyl)urea (compound I-A-327), 1-tert-butyl-3-(3-(6-amino-5-(1-(2,3-difluorophenyl)-1H-tetrazol-5-yl)pyridin-3-yl)phenyl)urea (compound I-A-328), 1-(3-(6-amino-5-(1-(2,3-difluorophenyl)-1H-tetrazol-5-yl)pyridin-3-yl)phenyl)-3-cyclopentylurea (compound I-A-329), 1-(4-(6-amino-5-(1-(2,3-difluorophenyl)-1H-tetrazol-5-yl)pyridin-3-yl)phenyl)-3-((S)-3-methyl-(1-methylcarboxy)butyl)urea (compound I-A-330), 1-(4-(6-amino-5-(1-(2,3-difluorophenyl)-1H-tetrazol-5-yl)pyridin-3-yl)phenyl)-3-((1-methylcarboxy)ethyl)urea (compound I-A-331), 1-tert-butyl-3-(4-(6-amino-5-(1-(2,3-difluorophenyl)-1H-tetrazol-5-yl)pyridin-3-yl)phenyl)urea (compound I-A-332), 1-(4-(6-amino-5-(1-(2,3-difluorophenyl)-1H-tetrazol-5-yl)pyridin-3-yl)phenyl)-3-cyclopentylurea (compound I-A-333), N-(4-(6-amino-5-(1-(2,3-difluorophenyl)-1H-tetrazol-5-yl)pyridin-3-yl)phenyl)-2-cyanoacetamide (compound I-A-334), 1-(2-(4-(6-amino-5-(1-(2,3-difluorophenyl)-1H-tetrazol-5-yl)pyridin-3-yl)phenyl)pyrrolidin-1-yl)ethanone (compound I-A-335), 5-(6-amino-5-(1-(2,3-difluorophenyl)-1H-tetrazol-5-yl)pyridin-3-yl)-2-(pyrrolidin-1-yl)benzonitrile (compound I-A-336), N-(4-(6-amino-5-(1-(2,3-difluorophenyl)-1H-tetrazol-5-yl)pyridin-3-yl)phenyl)-N-methylacetamide (compound I-A-337), N-(4-(6-amino-5-(1-(2,3-difluorophenyl)-1H-tetrazol-5-yl)pyridin-3-yl)phenyl)-2-hydroxyacetamide (compound I-A-338), N-(5-(6-amino-5-(1-(2,3-difluorophenyl)-1H-tetrazol-5-yl)pyridin-3-yl)-2-((pyrrolidin-1-yl)methyl)phenyl)acetamide (compound I-A-339), 3-(1-(2,3-difluorophenyl)-1H-tetrazol-5-yl)-5-(3-nitro-4-((pyrrolidin-1-yl)methyl)phenyl)pyridin-2-amine (compound I-A-340), 5-(6-amino-5-(1-(2,3-difluorophenyl)-1H-tetrazol-5-yl)pyridin-3-yl)-2-(methylamino)benzonitrile (compound I-A-341), N-(4-(6-amino-5-(1-(2,3-difluorophenyl)-1H-tetrazol-5-yl)pyridin-3-yl)phenyl)-2-methoxyacetamide (compound I-A-342), 3-(1-(3-chloro-2-fluorophenyl)-1H-tetrazol-5-yl)-5-(4-((pyrrolidin-1-yl)methyl)phenyl)pyridin-2-amine (compound I-A-343), N-(3-(6-amino-5-(1-(3-chloro-2-fluorophenyl)-1H-tetrazol-5-yl)pyridin-3-yl)phenyl)acetamide (compound I-A-344), ethyl 2-(4-(6-amino-5-(1-(2,3-difluorophenyl)-1H-tetrazol-5-yl)pyridin-3-yl)-1H-pyrazol-1-yl)acetate (compound I-A-345), 5-(4-(2-(pyrrolidin-1-yl)ethoxy)phenyl)-3-(1-(2,3-difluorophenyl)-1H-tetrazol-5-yl)pyridin-2-amine (compound I-A-346), 3-(1-(2,3-difluorophenyl)-1H-tetrazol-5-yl)-5-(1H-indazol-5-yl)pyridin-2-amine (compound I-A-347), 1-(4-(6-amino-5-(1-(2,3-difluorophenyl)-1H-tetrazol-5-yl)pyridin-3-yl)-1H-pyrazol-1-yl)-2-methylpropan-2-ol (compound I-A-348), 5-(1-benzyl-1H-pyrazol-4-yl)-3-(1-(2,3-difluorophenyl)-1H-tetrazol-5-yl)pyridin-2-amine (compound I-A-349), 2-(4-(6-amino-5-(1-(2,3-difluorophenyl)-1H-tetrazol-5-yl)pyridin-3-yl)-1H-pyrazol-1-yl)acetic acid (compound I-A-350), 3-(1-(2,3-difluorophenyl)-1H-tetrazol-5-yl)-5-(4-((S)-1-(methylamino)ethyl)phenyl)pyridin-2-amine (compound I-A-351), methyl 4-(6-amino-5-(1-(2,3-difluorophenyl)-1H-tetrazol-5-yl)pyridin-3-yl)phenylcarbamate (compound I-A-352), N-(4-(6-amino-5-(1-(2,3-difluorophenyl)-1H-tetrazol-5-yl)pyridin-3-yl)phenyl)methylsulfonamide (compound I-A-353), 5-(3,4-bis(2-methoxyethoxy)phenyl)-3-(1-(2,3-difluorophenyl)-1H-tetrazol-5-yl)pyridin-2-amine (compound I-A-354), 5-(4-(6-amino-5-(1-(2,3-difluorophenyl)-1H-tetrazol-5-yl)pyridin-3-yl)phenyl)imidazolidine-2,4-dione (compound I-A-355), 3-(1-(3-chlorophenyl)-1H-tetrazol-5-yl)-5-(4-((pyrrolidin-1-yl)methyl)phenyl)pyridin-2-amine (compound I-A-356), 1-(4-(6-amino-5-(1-(2,3-difluorophenyl)-1H-tetrazol-5-yl)pyridin-3-yl)phenyl)-3,3-dimethylazetidin-2-one (compound I-A-357), 3-(1-(3-chlorophenyl)-1H-tetrazol-5-yl)-5-(4-((dimethylamino)methyl)phenyl)pyridin-2-amine (compound I-A-358), N-(3-(6-amino-5-(1-(3-chlorophenyl)-1H-tetrazol-5-yl)pyridin-3-yl)phenyl)acetamide (compound I-A-359), 3-(1-(3-chloro-2-fluorophenyl)-1H-tetrazol-5-yl)-5-(4-((dimethylamino)methyl)phenyl)pyridin-2-amine (compound I-A-360), ethyl 2-(4-(6-amino-5-(1-(2,3-difluorophenyl)-1H-tetrazol-5-yl)pyridin-3-yl)-1H-pyrazol-1-yl)acetate (compound I-A-363), 2-(4-(6-amino-5-(1-(2,3-difluorophenyl)-1H-tetrazol-5-yl)pyridin-3-yl)-1H-pyrazol-1-yl)-1-(pyrrolidin-1-yl)ethanone (compound I-A-364), 3-(1-(2,3-difluorophenyl)-1H-tetrazol-5-yl)-5-(1-trityl-1H-pyrazol-4-yl)pyridin-2-amine (compound I-A-365), 3-(1-(2,3-difluorophenyl)-1H-tetrazol-5-yl)-5-(1H-pyrazol-4-yl)pyridin-2-amine (compound I-A-366), 3-(1-(2,3-difluorophenyl)-1H-tetrazol-5-yl)-5-(1-(2-methoxyethyl)-1H-pyrazol-4-yl)pyridin-2-amine (compound I-A-367), 3-(4-(6-amino-5-(1-(2,3-difluorophenyl)-1H-tetrazol-5-yl)pyridin-3-yl)-1H-pyrazol-1-yl)propane-1,2-diol (compound I-A-368), 2-(4-(6-amino-5-(1-(2,3-difluorophenyl)-1H-tetrazol-5-yl)pyridin-3-yl)-1H-pyrazol-1-yl)-N-methylacetamide (compound I-A-369), 3-(1-(2,3-difluorophenyl)-1H-tetrazol-5-yl)-5-(1-(piperidin-4-yl)-1H-pyrazol-4-yl)pyridin-2-amine (compound I-A-370), 3-(1-(2,3-dichlorophenyl)-1H-tetrazol-5-yl)-5-(1-(piperidin-4-yl)-1H-pyrazol-4-yl)pyridin-2-amine (compound I-A-371), 3-(4-(6-amino-5-(1-(2,3-difluorophenyl)-1H-tetrazol-5-yl)pyridin-3-yl)phenyl)-5-(hydroxymethyl)oxazolidin-2-one (compound I-A-372), 3-(1-(3-chloro-2,6-difluorophenyl)-1H-tetrazol-5-yl)-5-(pyridin-3-yl)pyridin-2-amine (compound I-A-373), N-(4-(6-amino-5-(1-(2,3,6-trifluorophenyl)-1H-tetrazol-5-yl)pyridin-3-yl)phenyl)acetamide (compound I-A-374), N-(3-(6-amino-5-(1-(3-chloro-2,6-difluorophenyl)-1H-tetrazol-5-yl)pyridin-3-yl)phenyl)acetamide (compound I-A-375), 3-(1-(3-chloro-2,6-difluorophenyl)-1H-tetrazol-5-yl)-5-(4-((pyrrolidin-1-yl)methyl)phenyl)pyridin-2-amine (compound I-A-376), 3-(1-(3-chloro-2,6-difluorophenyl)-1H-tetrazol-5-yl)-5-(4-((dimethylamino)methyl)phenyl)pyridin-2-amine (compound I-A-377), 3-(1-(2,3,6-trifluorophenyl)-1H-tetrazol-5-yl)-5-(pyridin-3-yl)pyridin-2-amine (compound I-A-378), N-(3-(6-amino-5-(1-(2,3,6-trifluorophenyl)-1H-tetrazol-5-yl)pyridin-3-yl)phenyl)acetamide (compound I-A-379), 3-(1-(2,3,6-trifluorophenyl)-1H-tetrazol-5-yl)-5-(4-((pyrrolidin-1-yl)methyl)phenyl)pyridin-2-amine (compound I-A-380), 5-(4-((dimethylamino)methyl)phenyl)-3-(1-(2,3,6-trifluorophenyl)-1H-tetrazol-5-yl)pyridin-2-amine (compound I-A-381), 3-(1-(3-chloro-2,6-difluorophenyl)-1H-tetrazol-5-yl)-5-(1-(piperidin-4-yl)-1H-pyrazol-4-yl)pyridin-2-amine (compound I-A-382), N-(3-(6-amino-5-(1-(2-amino-3,6-difluorophenyl)-1H-tetrazol-5-yl)pyridin-3-yl)phenyl)acetamide (compound I-A-383), 3-(1-(2-amino-3,6-difluorophenyl)-1H-tetrazol-5-yl)-5-(pyridin-3-yl)pyridin-2-amine (compound I-A-384), 3-(1-(2-chloro-3-fluorophenyl)-1H-tetrazol-5-yl)-5-(1-(piperidin-4-yl)-1H-pyrazol-4-yl)pyridin-2-amine (compound I-A-385), 3-(1-(2-chloro-3-fluorophenyl)-1H-tetrazol-5-yl)-5-(4-((pyrrolidin-1-yl)methyl)phenyl)pyridin-2-amine (compound I-A-386), 3-(1-(2-chloro-3-fluorophenyl)-1H-tetrazol-5-yl)-5-(4-((dimethylamino)methyl)phenyl)pyridin-2-amine (compound I-A-387), 5-(6-amino-5-(1-(2,3-difluorophenyl)-1H-tetrazol-5-yl)pyridin-3-yl)-2-((pyrrolidin-1-yl)methyl)phenol (compound I-A-391), 1-(4-(4-(6-amino-5-(1-(2-chloro-3-fluorophenyl)-1H-tetrazol-5-yl)pyridin-3-yl)-1H-pyrazol-1-yl)piperidin-1-yl)ethanone (compound I-A-392), 1-(4-(4-(6-amino-5-(1-(2-chloro-3-fluorophenyl)-1H-tetrazol-5-yl)pyridin-3-yl)-1H-pyrazol-1-yl)piperidin-1-yl)-2,2,2-trifluoroethanone (compound I-A-395), 3-(1-(2,3-difluorophenyl)-1H-tetrazol-5-yl)-5-(1-(tetrahydro-2H-pyran-4-yl)-1H-pyrazol-4-yl)pyridin-2-amine (compound I-A-396), 3-(1-(3-chloro-2-fluorophenyl)-1H-tetrazol-5-yl)-5-(1-(tetrahydro-2H-pyran-4-yl)-1H-pyrazol-4-yl)pyridin-2-amine (compound I-A-397), N-(5-(6-amino-5-(1-(3-chloro-2-fluorophenyl)-1H-tetrazol-5-yl)pyridin-3-yl)-2-((pyrrolidin-1-yl)methyl)phenyl)acetamide (compound I-A-398), 1-(4-(4-(6-amino-5-(1-(3-chloro-2-fluorophenyl)-1H-tetrazol-5-yl)pyridin-3-yl)-1H-pyrazol-1-yl)piperidin-1-yl)ethanone (compound I-A-399), 3-(1-(2,3-difluorophenyl)-1H-tetrazol-5-yl)-5-(4-(piperidin-4-yl)phenyl)pyridin-2-amine (compound I-A-400), 5-(1-cyclohexyl-1H-pyrazol-4-yl)-3-(1-(2,3-difluorophenyl)-1H-tetrazol-5-yl)pyridin-2-amine (compound I-A-403), 3-(1-(2,3-difluorophenyl)-1H-tetrazol-5-yl)-5-(1-((R)-pyrrolidin-3-yl)-1H-pyrazol-4-yl)pyridin-2-amine (compound I-A-404), 3-(1-(2,3-difluorophenyl)-1H-tetrazol-5-yl)-5-(1-((S)-piperidin-3-yl)-1H-pyrazol-4-yl)pyridin-2-amine (compound I-A-405), 5-(1-(2-(dimethylamino)ethyl)-1H-pyrazol-4-yl)-3-(1-(2,3-difluorophenyl)-1H-tetrazol-5-yl)pyridin-2-amine (compound I-A-406), 3-(1-(2,3-difluorophenyl)-1H-tetrazol-5-yl)-5-(1-(2-(pyrrolidin-1-yl)ethyl)-1H-pyrazol-4-yl)pyridin-2-amine (compound I-A-407), 3-(1-(2,3-dichlorophenyl)-1H-tetrazol-5-yl)-5-(1-((R)-pyrrolidin-3-yl)-1H-pyrazol-4-yl)pyridin-2-amine (compound I-A-408), 3-(1-(2,3-dichlorophenyl)-1H-tetrazol-5-yl)-5-(1-((S)-piperidin-3-yl)-1H-pyrazol-4-yl)pyridin-2-amine (compound I-A-409), 3-(1-(2,3-dichlorophenyl)-1H-tetrazol-5-yl)-5-(1-(2-(dimethylamino)ethyl)-1H-pyrazol-4-yl)pyridin-2-amine (compound I-A-410), 3-(1-(2,3-dichlorophenyl)-1H-tetrazol-5-yl)-5-(1-(2-(pyrrolidin-1-yl)ethyl)-1H-pyrazol-4-yl)pyridin-2-amine (compound I-A-411), 3-(1-(2,3-difluorophenyl)-1H-tetrazol-5-yl)-5-(1-((S)-pyrrolidin-3-yl)-1H-pyrazol-4-yl)pyridin-2-amine (compound I-A-412), 3-(1-(2,3-dichlorophenyl)-1H-tetrazol-5-yl)-5-(1-((S)-pyrrolidin-3-yl)-1H-pyrazol-4-yl)pyridin-2-amine (compound I-A-413), 3-(1-(2,3-difluorophenyl)-1H-tetrazol-5-yl)-5-(3-(piperazin-1-yl)phenyl)pyridin-2-amine (compound I-A-414), 3-(1-(2,3-difluorophenyl)-1H-tetrazol-5-yl)-5-(5-(piperidin-4-yl)thiophen-2-yl)pyridin-2-amine (compound I-A-415), 3-(1-(2,3-dichlorophenyl)-1H-tetrazol-5-yl)-5-(5-(piperidin-4-yl)thiophen-2-yl)pyridin-2-amine (compound I-A-416), 3-(1-(2,3-difluorophenyl)-1H-tetrazol-5-yl)-5-(1-((R)-piperidin-3-yl)-1H-pyrazol-4-yl)pyridin-2-amine (compound I-A-417), 3-(1-(2,3-dichlorophenyl)-1H-tetrazol-5-yl)-5-(1-((R)-piperidin- 3-yl)-1H-pyrazol-4-yl)pyridin-2-amine (compound I-A-418), 3-(1-(2,3-difluorophenyl)-1H-tetrazol-5-yl)-5-(1-((R)-tetrahydrofuran-3-yl)-1H-pyrazol-4-yl)pyridin-2-amine (compound I-A-419), 3-(1-(3-chloro-2-fluorophenyl)-1H-tetrazol-5-yl)-5-(1-((R)-tetrahydrofuran-3-yl)-1H-pyrazol-4-yl)pyridin-2-amine (compound I-A-420), 3-(1-(2-fluoro-3-(1-((R)-tetrahydrofuran-3-yl)-1H-pyrazol-4-yl)phenyl)-1H-tetrazol-5-yl)-5-(1-((R)-tetrahydrofuran-3-yl)-1H-pyrazol-4-yl)pyridin-2-amine (compound I-A-421), (4-(6-amino-5-(1-(2,3-difluorophenyl)-1H-tetrazol-5-yl)pyridin-3-yl)-5,6-dihydropyridin-1(2H)-yl)(tetrahydrofuran-3-yl)methanone (compound I-A-422), (4-(6-amino-5-(1-(2,3-difluorophenyl)-1H-tetrazol-5-yl)pyridin-3-yl)-5,6-dihydropyridin-1(2H)-yl)(piperidin-3-yl)methanone (compound I-A-423), 3-(1-(2,3-difluorophenyl)-1H-tetrazol-5-yl)-5-(1,2,3,6-tetrahydro-1-(piperidin-4-yl)pyridin-4-yl)pyridin-2-amine (compound I-A-424), 3-(1-(2,3-difluorophenyl)-1H-tetrazol-5-yl)-5-(1-((S)-tetrahydrofuran-3-yl)-1H-pyrazol-4-yl)pyridin-2-amine (compound I-A-425), 5-(1-(azetidin-3-yl)-1H-pyrazol-4-yl)-3-(1-(2,3-difluorophenyl)-1H-tetrazol-5-yl)pyridin-2-amine (compound I-A-426), 5-(1-(azetidin-3-yl)-1H-pyrazol-4-yl)-3-(1-(2,3-dichlorophenyl)-1H-tetrazol-5-yl)pyridin-2-amine (compound I-A-427), 5-(1-(azepan-4-yl)-1H-pyrazol-4-yl)-3-(1-(2,3-difluorophenyl)-1H-tetrazol-5-yl)pyridin-2-amine (compound I-A-428), 5-(1-(azepan-4-yl)-1H-pyrazol-4-yl)-3-(1-(2,3-dichlorophenyl)-1H-tetrazol-5-yl)pyridin-2-amine (compound I-A-429), 3-(1-(2,3-difluorophenyl)-1H-tetrazol-5-yl)-5-(5,6,7,8-tetrahydro-4H-thieno[3,2-d]azepin-2-yl)pyridin-2-amine (compound I-A-430), 3-(1-(2,3-dichlorophenyl)-1H-tetrazol-5-yl)-5-(5,6,7,8-tetrahydro-4H-thieno[3,2-d]azepin-2-yl)pyridin-2-amine (compound I-A-431), 5-(1-(1,3-dioxan-5-yl)-1H-pyrazol-4-yl)-3-(1-(2,3-difluorophenyl)-1H-tetrazol-5-yl)pyridin-2-amine (compound I-A-432), 5-(1-((1,3-dioxolan-4-yl)methyl)-1H-pyrazol-4-yl)-3-(1-(2,3-difluorophenyl)-1H-tetrazol-5-yl)pyridin-2-amine (compound I-A-433), 3-(1-(2,3-difluorophenyl)-1H-tetrazol-5-yl)-5-(1-(1-methylpiperidin-4-yl)-1H-pyrazol-4-yl)pyridin-2-amine (compound I-A-434), 5-(1-(1-ethylpiperidin-4-yl)-1H-pyrazol-4-yl)-3-(1-(2,3-difluorophenyl)-1H-tetrazol-5-yl)pyridin-2-amine (compound I-A-435), 3-(1-(3-chloro-2-fluorophenyl)-1H-tetrazol-5-yl)-5-(1-(1-methylpiperidin-4-yl)-1H-pyrazol-4-yl)pyridin-2-amine (compound I-A-436), 2-methoxyethyl 4-(4-(6-amino-5-(1-(3-chloro-2-fluorophenyl)-1H-tetrazol-5-yl)pyridin-3-yl)-1H-pyrazol-1-yl)piperidine-1-carboxylate (compound I-A-440), 1-(4-(4-(6-amino-5-(1-(3-chloro-2-fluorophenyl)-1H-tetrazol-5-yl)pyridin-3-yl)-1H-pyrazol-1-yl)piperidin-1-yl)-2-methylpropan-1-one (compound I-A-441), 4-(4-(6-amino-5-(1-(3-chloro-2-fluorophenyl)-1H-tetrazol-5-yl)pyridin-3-yl)-1H-pyrazol-1-yl)-N,N-dimethylpiperidine-1-sulfonamide (compound I-A-442), (4-(4-(6-amino-5-(1-(3-chloro-2-fluorophenyl)-1H-tetrazol-5-yl)pyridin-3-yl)-1H-pyrazol-1-yl)piperidin-1-yl)(pyrrolidin-1-yl)methanone (compound I-A-443), 1-(4-(4-(6-amino-5-(1-(3-chloro-2-fluorophenyl)-1H-tetrazol-5-yl)pyridin-3-yl)-1H-pyrazol-1-yl)piperidin-1-yl)-2-(dimethylamino)ethanone (compound I-A-444), 4-(4-(6-amino-5-(1-(3-chloro-2-fluorophenyl)-1H-tetrazol-5-yl)pyridin-3-yl)-1H-pyrazol-1-yl)-N,N-dimethylpiperidine-1-carboxamide (compound I-A-445), 4-(4-(6-amino-5-(1-(3-chloro-2-fluorophenyl)-1H-tetrazol-5-yl)pyridin-3-yl)-1H-pyrazol-1-yl)-1-propylsulfonylpiperidine (compound I-A-446), 1-(4-(4-(6-amino-5-(1-(3-chloro-2-fluorophenyl)-1H-tetrazol-5-yl)pyridin-3-yl)-1H-pyrazol-1-yl)piperidin-1-yl)-2-hydroxyethanone (compound I-A-447), 3-(1-(2,3-difluorophenyl)-1H-tetrazol-5-yl)-5-(1-(1-isopropylpiperidin-4-yl)-1H-pyrazol-4-yl)pyridin-2-amine (compound I-A-448), 5-(1-(1-(cyclopropylmethyl)piperidin-4-yl)-1H-pyrazol-4-yl)-3-(1-(2,3-difluorophenyl)-1H-tetrazol-5-yl)pyridin-2-amine (compound I-A-449), 5-(1-(1-cyclobutylpiperidin-4-yl)-1H-pyrazol-4-yl)-3-(1-(2,3-difluorophenyl)-1H-tetrazol-5-yl)pyridin-2-amine (compound I-A-451), 5-(1-(1-(2-fluoroethyl)piperidin-4-yl)-1H-pyrazol-4-yl)-3-(1-(2,3-difluorophenyl)-1H-tetrazol-5-yl)pyridin-2-amine (compound I-A-452), 5-(1-(1-(2,2-difluoroethyl)piperidin-4-yl)-1H-pyrazol-4-yl)-3-(1-(2,3-difluorophenyl)-1H-tetrazol-5-yl)pyridin-2-amine (compound I-A-453), 1-(4-(4-(6-amino-5-(1-(2,3-difluorophenyl)-1H-tetrazol-5-yl)pyridin-3-yl)-1H-pyrazol-1-yl)piperidin-1-yl)ethanone (compound I-A-455), 3-(1-(2,3-difluorophenyl)-1H-tetrazol-5-yl)-5-(1,2,3,4-tetrahydroisoquinolin-7-yl)pyridin-2-amine (compound I-A-456), 3-(1-(2,3-difluorophenyl)-1H-tetrazol-5-yl)-5-(1-(1-propylpiperidin-4-yl)-1H-pyrazol-4-yl)pyridin-2-amine (compound I-A-461), 2-(4-(4-(6-amino-5-(1-(2,3-difluorophenyl)-1H-tetrazol-5-yl)pyridin-3-yl)-1H-pyrazol-1-yl)piperidin-1-yl)acetonitrile (compound I-A-462), 3-(1-(2,3-difluorophenyl)-1H-tetrazol-5-yl)-5-(5-(piperidin-4-yl)thiophen-3-yl)pyridin-2-amine (compound I-A-463), 3-(1-(2,3-difluorophenyl)-1H-tetrazol-5-yl)-5-(1-(piperidin-4-yl)-1H-pyrrol-3-yl)pyridin-2-amine (compound I-A-464), 3-(1-(2,3-difluorophenyl)-1H-tetrazol-5-yl)-5-(4,5,6,7-tetrahydrothiazolo[5,4-c]pyridin-2-yl)pyridin-2-amine (compound I-A-465), 3-(1-(2,3-difluorophenyl)-1H-tetrazol-5-yl)-5-(1-(2-(pyrrolidin-1-yl)ethyl)-1H-pyrrol-3-yl)pyridin-2-amine (compound I-A-466), 3-(1-(2,3-dichlorophenyl)-1H-tetrazol-5-yl)-5-(4,5,6,7-tetrahydrothiazolo[5,4-c]pyridin-2-yl)pyridin-2-amine (compound I-A-467), 2-(4-(4-(6-amino-5-(1-(3-chloro-2-fluorophenyl)-1H-tetrazol-5-yl)pyridin-3-yl)-1H-pyrazol-1-yl)piperidin-1-yl)ethanol (compound I-A-469), 3-(1-(3-chloro-2-fluorophenyl)-1H-tetrazol-5-yl)-5-(1-(1-propylpiperidin-4-yl)-1H-pyrazol-4-yl)pyridin-2-amine (compound I-A-470), 3-(1-(3-chloro-2-fluorophenyl)-1H-tetrazol-5-yl)-5-(1-(1-(cyclopropylmethyl)piperidin-4-yl)-1H-pyrazol-4-yl)pyridin-2-amine (compound I-A-472), 3-(1-(3-chloro-2-fluorophenyl)-1H-tetrazol-5-yl)-5-(1-(1-(cyclobutylmethyl)piperidin-4-yl)-1H-pyrazol-4-yl)pyridin-2-amine (compound I-A-473), 3-(1-(3-chloro-2-fluorophenyl)-1H-tetrazol-5-yl)-5-(1-(1-(cyclopentylmethyl)piperidin-4-yl)-1H-pyrazol-4-yl)pyridin-2-amine (compound I-A-474), 3-(1-(3-chloro-2-fluorophenyl)-1H-tetrazol-5-yl)-5-(1-(1-isobutylpiperidin-4-yl)-1H-pyrazol-4-yl)pyridin-2-amine (compound I-A-475), 3-(1-(2,3-difluorophenyl)-1H-tetrazol-5-yl)-5-(3,5-dimethyl-1-(piperidin-4-yl)-1H-pyrazol-4-yl)pyridin-2-amine (compound I-A-478), 3-(1-(3-chloro-2-fluorophenyl)-1H-tetrazol-5-yl)-5-(3,5-dimethyl-1-(piperidin-4-yl)-1H-pyrazol-4-yl)pyridin-2-amine (compound I-A-479), ethyl 2-(6-amino-5-(1-(2,3-difluorophenyl)-1H-tetrazol-5-yl)pyridin-3-yl)-4,5,7,8-tetrahydrothieno[3,2-d]azepine-6-carboxylate (compound I-A-480), 3-(1-(3-chloro-2-fluorophenyl)-

1H-tetrazol-5-yl)-5-(5,6,7,8-tetrahydro-4H-thieno[3,2-d]azepin-2-yl)pyridin-2-amine (compound I-A-481), 3-(1-(2,3-difluorophenyl)-1H-tetrazol-5-yl)-5-(1-(1-propylpiperidin-4-yl)-1H-1,2,3-triazol-4-yl)pyridin-2-amine (compound I-A-482), 3-(1-(2,3-difluorophenyl)-1H-tetrazol-5-yl)-5-(1-(piperidin-4-yl)-1H-1,2,3-triazol-4-yl)pyridin-2-amine (compound I-A-483), 3-(1-(2,3-difluorophenyl)-1H-tetrazol-5-yl)-5-(1-(8-methyl-8-aza-bicyclo[3.2.1]octan-3-yl)-1H-1,2,3-triazol-4-yl)pyridin-2-amine (compound I-A-484), 3-(1-(2,3-difluorophenyl)-1H-tetrazol-5-yl)-5-(1-(tetrahydro-2H-pyran-4-yl)-1H-1,2,3-triazol-4-yl)pyridin-2-amine (compound I-A-485), 3-(1-(2,3-dichlorophenyl)-1H-tetrazol-5-yl)-5-(1-(piperidin-4-yl)-1H-pyrazol-4-yl)pyrazin-2-amine (compound I-A-486), 3-(1-(2,3-difluorophenyl)-1H-tetrazol-5-yl)-5-(thiophen-2-yl)pyridin-2-amine (compound I-A-487), 3-(1-(2,3-difluorophenyl)-1H-tetrazol-5-yl)-5-(furan-2-yl)pyridin-2-amine (compound I-A-488), 3-(1-(2,3-difluorophenyl)-1H-tetrazol-5-yl)-5-(pyrimidin-5-yl)pyridin-2-amine (compound I-A-489), 3-(1-(2,3-difluorophenyl)-1H-tetrazol-5-yl)-5-(pyridin-4-yl)pyridin-2-amine (compound I-A-490), 3-(1-(3-chloro-2-fluorophenyl)-1H-tetrazol-5-yl)-5-(2-(piperidin-4-yl)thiazol-5-yl)pyridin-2-amine (compound I-A-491), 3-(1-(2,3-difluorophenyl)-1H-tetrazol-5-yl)-5-(4,5,6,7-tetrahydrothieno[2,3-c]pyridin-2-yl)pyridin-2-amine (compound I-A-492), 3-(1-(2,3-difluorophenyl)-1H-tetrazol-5-yl)-5-(pyridin-2-yl)pyridin-2-amine (compound I-A-493), 3-(1-(2,3-difluorophenyl)-1H-tetrazol-5-yl)-5-(5-methyl-1,3,4-thiadiazol-2-yl)pyridin-2-amine (compound I-A-494), 3-(1-(2,3-difluorophenyl)-1H-tetrazol-5-yl)-5-(1-methyl-1H-imidazol-4-yl)pyridin-2-amine (compound I-A-495), 3-(1-(2,3-difluorophenyl)-1H-tetrazol-5-yl)-5-(1-methyl-1H-imidazol-5-yl)pyridin-2-amine (compound I-A-496), 3-(1-(2,3-difluorophenyl)-1H-tetrazol-5-yl)-5-(furan-3-yl)pyridin-2-amine (compound I-A-497), 3-(1-(2,3-difluorophenyl)-1H-tetrazol-5-yl)-5-(3,5-dimethylisoxazol-4-yl)pyridin-2-amine (compound I-A-498), 3-(1-(2,3-dichlorophenyl)-1H-tetrazol-5-yl)-5-(1-((R)-1-ethylpiperidin-3-yl)-1H-pyrazol-4-yl)pyridin-2-amine (compound I-A-499), 3-(1-(2,3-difluorophenyl)-1H-tetrazol-5-yl)-5-(1-(((S)-pyrrolidin-2-yl)methyl)-1H-pyrazol-4-yl)pyridin-2-amine (compound I-A-500), 3-(1-(2,3-difluorophenyl)-1H-tetrazol-5-yl)-5-(1-((pyrrolidin-3-yl)methyl)-1H-pyrazol-4-yl)pyridin-2-amine (compound I-A-501), 3-(1-(2,3-difluorophenyl)-1H-tetrazol-5-yl)-5-(1-((piperidin-4-yl)methyl)-1H-pyrazol-4-yl)pyridin-2-amine (compound I-A-502), (4-(6-amino-5-(1-(2,3-difluorophenyl)-1H-tetrazol-5-yl)pyridin-3-yl)-5,6-dihydropyridin-1(2H)-yl)((S)-1-methylpyrrolidin-2-yl)methanone (compound I-A-503), (4-(6-amino-5-(1-(2,3-difluorophenyl)-1H-tetrazol-5-yl)pyridin-3-yl)-5,6-dihydropyridin-1(2H)-yl)((S)-pyrrolidin-2-yl)methanone (compound I-A-504), 1-(4-(6-amino-5-(1-(2,3-difluorophenyl)-1H-tetrazol-5-yl)pyridin-3-yl)-5,6-dihydropyridin-1(2H)-yl)-2-((S)-pyrrolidin-2-yl)ethanone (compound I-A-505), tert-butyl 4-(6-amino-5-(1-(2,3-difluorophenyl)-1H-tetrazol-5-yl)pyridin-3-yl)-5,6-dihydropyridine-1(2H)-carboxylate (compound I-A-506), (4-(6-amino-5-(1-(2,3-difluorophenyl)-1H-tetrazol-5-yl)pyridin-3-yl)-5,6-dihydropyridin-1(2H)-yl)(pyridin-3-yl)methanone (compound I-A-507), isopropyl 4-(6-amino-5-(1-(2,3-difluorophenyl)-1H-tetrazol-5-yl)pyridin-3-yl)-5,6-dihydropyridine-1(2H)-carboxylate (compound I-A-508), 3-(1-(2,3-difluorophenyl)-1H-tetrazol-5-yl)-5-(1,2,3,4-tetrahydroisoquinolin-6-yl)pyridin-2-amine (compound I-A-509), 1-(4-(6-amino-5-(1-(2,3-difluorophenyl)-1H-tetrazol-5-yl)pyridin-3-yl)-5,6-dihydropyridin-1(2H)-yl)ethanone (compound I-A-510), 1-(4-(6-amino-5-(1-(2,3-difluorophenyl)-1H-tetrazol-5-yl)pyridin-3-yl)-5,6-dihydropyridin-1(2H)-yl)propan-1-one (compound I-A-511), 1-(4-(6-amino-5-(1-(2,3-difluorophenyl)-1H-tetrazol-5-yl)pyridin-3-yl)-5,6-dihydropyridin-1(2H)-yl)-2-methylpropan-1-one (compound I-A-512), 1-(4-(6-amino-5-(1-(2,3-difluorophenyl)-1H-tetrazol-5-yl)pyridin-3-yl)-5,6-dihydropyridin-1(2H)-yl)-3-methylbutan-1-one (compound I-A-513), 1-(4-(6-amino-5-(1-(2,3-difluorophenyl)-1H-tetrazol-5-yl)pyridin-3-yl)-5,6-dihydropyridin-1(2H)-yl)-3-methoxypropan-1-one (compound I-A-514), (4-(6-amino-5-(1-(2,3-difluorophenyl)-1H-tetrazol-5-yl)pyridin-3-yl)-5,6-dihydropyridin-1(2H)-yl)(tetrahydro-2,2-dimethyl-2H-pyran-4-yl)methanone (compound I-A-515), 1-(4-(6-amino-5-(1-(2,3-difluorophenyl)-1H-tetrazol-5-yl)pyridin-3-yl)-5,6-dihydropyridin-1(2H)-yl)-2-(tetrahydro-2H-pyran-4-yl)ethanone (compound I-A-516), 1-((S)-1-(4-(6-amino-5-(1-(2,3-difluorophenyl)-1H-tetrazol-5-yl)pyridin-3-yl)-5,6-dihydropyridin-1(2H)-yl)-1-oxopropan-2-yl)pyrrolidin-2-one (compound I-A-517), (4-(6-amino-5-(1-(2,3-difluorophenyl)-1H-tetrazol-5-yl)pyridin-3-yl)-5,6-dihydropyridin-1(2H)-yl) (pyridin-4-yl)methanone (compound I-A-518), 3-(1-(2,3-difluorophenyl)-1H-tetrazol-5-yl)-5-(5,6,7,8-tetrahydro-6-propyl-4H-thieno[3,2-d]azepin-2-yl)pyridin-2-amine (compound I-A-519), tetrahydrofuran-3-yl 4-(6-amino-5-(1-(2,3-difluorophenyl)-1H-tetrazol-5-yl)pyridin-3-yl)-5,6-dihydropyridine-1(2H)-carboxylate (compound I-A-520), (4-(6-amino-5-(1-(2,3-difluorophenyl)-1H-tetrazol-5-yl)pyridin-3-yl)-5,6-dihydropyridin-1(2H)-yl)(tetrahydro-2H-pyran-4-yl)methanone (compound I-A-521), (4-(6-amino-5-(1-(2,3-difluorophenyl)-1H-tetrazol-5-yl)pyridin-3-yl)-5,6-dihydropyridin-1(2H)-yl)(tetrahydro-2H-pyran-3-yl)methanone (compound I-A-522), (4-(6-amino-5-(1-(2,3-difluorophenyl)-1H-tetrazol-5-yl)pyridin-3-yl)-5,6-dihydropyridin-1(2H)-yl)(cyclopropyl)methanone (compound I-A-523), 1-(4-(6-amino-5-(1-(2,3-difluorophenyl)-1H-tetrazol-5-yl)pyridin-3-yl)-5,6-dihydropyridin-1(2H)-yl)-2-cyclopropylethanone (compound I-A-524), 3-(1-(2,3-difluorophenyl)-1H-tetrazol-5-yl)-5-(1,2,3,6-tetrahydropyridin-4-yl)pyridin-2-amine (compound I-A-525), (S)-tetrahydrofuran-3-yl 4-(6-amino-5-(1-(2,3-difluorophenyl)-1H-tetrazol-5-yl)pyridin-3-yl)-5,6-dihydropyridine-1(2H)-carboxylate (compound I-A-526), (4-(6-amino-5-(1-(2,3-difluorophenyl)-1H-tetrazol-5-yl)pyridin-3-yl)-5,6-dihydropyridin-1(2H)-yl)((R)-tetrahydrofuran-3-yl)methanone (compound I-A-527), 5-(1-(endo-8-aza-bicyclo[3.2.1]octan-3-yl)-1H-pyrazol-4-yl)-3-(1-(3-chloro-2-fluorophenyl)-1H-tetrazol-5-yl)pyridin-2-amine (compound I-A-528), 5-(1-(exo-8-aza-bicyclo[3.2.1]octan-3-yl)-1H-pyrazol-4-yl)-3-(1-(3-chloro-2-fluorophenyl)-1H-tetrazol-5-yl)pyridin-2-amine (compound I-A-529), 3-(1-(2,3-difluorophenyl)-1H-tetrazol-5-yl)-5-(1-((R)-pyrrolidin-3-yl)-1H-pyrazol-4-yl)pyridin-2-amine (compound I-A-530), 3-(1-(2,3-difluorophenyl)-1H-tetrazol-5-yl)-5-(1-((R)-piperidin-3-yl)-1H-pyrazol-4-yl)pyridin-2-amine (compound I-A-531), 3-(1-(3-chloro-2-fluorophenyl)-1H-tetrazol-5-yl)-5-(5-(piperidin-4-yl)thiophen-2-yl)pyridin-2-amine (compound I-A-532), 3-(1-(3-chloro- 2-fluorophenyl)-1H-tetrazol-5-yl)-5-(4,5,6,7-tetrahydrothiazolo[5,4-c]pyridin-2-yl)pyridin-2-amine (compound I-A-533), 3-(1-(2,3-difluorophenyl)-1H-tetrazol-5-yl)-5-(5-(piperidin-4-yl)thiophen-2-yl)pyridin-2-amine (compound I-A-535), 3-(1-(3-chloro-2-fluorophenyl)-1H-tetrazol-5-yl)-5-(1-((R)-pyrrolidin-3-yl)-1H-pyrazol-4-yl)pyridin-2-amine (compound I-A-538), 3-(1-(2,3-difluorophenyl)-1H-tetrazol-5-yl)-5-(thiazol-2-yl)pyridin-2-amine (compound I-A-539), 3-(1-(2,3-difluorophenyl)-1H-tetrazol-5-yl)-5-(thiazol-5-yl)pyridin-2-amine (compound I-A-540), 5-(1-(endo-8-aza-bicyclo[3.2.1]octan-3-yl)-1H-pyrazol-4-yl)-3-(1-(2,3-difluorophenyl)-1H-tetrazol-5-yl)pyridin-2-amine (compound I-A-543), 5-(1-(exo-8-aza-bicyclo[3.2.1]octan-3-yl)-1H-pyrazol-4-yl)-3-(1-(2,3-difluorophenyl)-1H-tetrazol-5-yl)pyridin-2-amine (compound I-A-544), 3-(1-(2,3-difluorophenyl)-1H-tetrazol-5-yl)-5-(2-(piperidin-4-yl)thiazol-5-yl)pyridin-2-amine (compound I-A-549), 3-(1-(3-fluoro-2-methylphenyl)-1H-tetrazol-5-yl)-5-(pyridin-3-yl)pyridin-2-amine (compound I-A-550), 3-(1-(3-chloro-2-methylphenyl)-1H-tetrazol-5-yl)-5-(pyridin-3-yl)pyridin-2-amine (compound I-A-551), 3-(1-(5-chloro-2-methylphenyl)-1H-tetrazol-5-yl)-5-(pyridin-3-yl)pyridin-2-amine (compound I-A-552), 3-(1-(2,5-difluorophenyl)-1H-tetrazol-5-yl)-5-(pyridin-3-yl)pyridin-2-amine (compound I-A-553), 3-(1-(5-chloro-2-fluorophenyl)-1H-tetrazol-5-yl)-5-(pyridin-3-yl)pyridin-2-amine (compound I-A-554), 3-(1-(2-chloro-5-fluorophenyl)-1H-tetrazol-5-yl)-5-(pyridin-3-yl)pyridin-2-amine (compound I-A-555), 3-(1-(2-chloro-3,5-difluorophenyl)-1H-tetrazol-5-yl)-5-(pyridin-3-yl)pyridin-2-amine (compound I-A-556), 3-(1-(3-chloro-2-fluorophenyl)-1H-tetrazol-5-yl)-5-(pyridin-3-yl)pyridin-2-amine (compound I-A-557), 3-(1-(5-fluoro-2-methoxyphenyl)-1H-tetrazol-5-yl)-5-(pyridin-3-yl)pyridin-2-amine (compound I-A-558), 3-(1-(3,5-difluorophenyl)-1H-tetrazol-5-yl)-5-(pyridin-3-yl)pyridin-2-amine (compound I-A-559), 3-(1-(3,5-dichlorophenyl)-1H-tetrazol-5-yl)-5-(pyridin-3-yl)pyridin-2-amine (compound I-A-560), 3-(1-(3-fluoro-2-methoxyphenyl)-1H-tetrazol-5-yl)-5-(pyridin-3-yl)pyridin-2-amine (compound I-A-561), N-(3-(6-amino-5-(1-(3-fluoro-2-methoxyphenyl)-1H-tetrazol-5-yl)pyridin-3-yl)phenyl)acetamide (compound I-A-562), N-(4-(6-amino-5-(1-(2-chloro-5-fluorophenyl)-1H-tetrazol-5-yl)pyridin-3-yl)phenyl)acetamide (compound I-A-563), N-(3-(6-amino-5-(1-(3-fluoro-2-methylphenyl)-1H-tetrazol-5-yl)pyridin-3-yl)phenyl)acetamide (compound I-A-564), N-(3-(6-amino-5-(1-(3-chloro-2-methylphenyl)-1H-tetrazol-5-yl)pyridin-3-yl)phenyl)acetamide (compound I-A-565), N-(3-(6-amino-5-(1-(5-chloro-2-methylphenyl)-1H-tetrazol-5-yl)pyridin-3-yl)phenyl)acetamide (compound I-A-566), N-(3-(6-amino-5-(1-(2,5-difluorophenyl)-1H-tetrazol-5-yl)pyridin-3-yl)phenyl)acetamide (compound I-A-567), N-(3-(6-amino-5-(1-(5-chloro-2-fluorophenyl)-1H-tetrazol-5-yl)pyridin-3-yl)phenyl)acetamide (compound I-A-568), N-(3-(6-amino-5-(1-(2-chloro-5-fluorophenyl)-1H-tetrazol-5-yl)pyridin-3-yl)phenyl)acetamide (compound I-A-569), N-(3-(6-amino-5-(1-(2-chloro-3,5-difluorophenyl)-1H-tetrazol-5-yl)pyridin-3-yl)phenyl)acetamide (compound I-A-570), N-(3-(6-amino-5-(1-(5-fluoro-2-methoxyphenyl)-1H-tetrazol-5-yl)pyridin-3-yl)phenyl)acetamide (compound I-A-571), N-(3-(6-amino-5-(1-(3,5-difluorophenyl)-1H-tetrazol-5-yl)pyridin-3-yl)phenyl)acetamide (compound I-A-572), N-(3-(6-amino-5-(1-(3,5-dichlorophenyl)-1H-tetrazol-5-yl)pyridin-3-yl)phenyl)acetamide (compound I-A-573), N-(4-(6-amino-5-(1-(3-fluoro-2-methylphenyl)-1H-tetrazol-5-yl)pyridin-3-yl)phenyl)acetamide (compound I-A-574), N-(4-(6-amino-5-(1-(3-chloro-2-methylphenyl)-1H-tetrazol-5-yl)pyridin-3-yl)phenyl)acetamide (compound I-A-575), N-(4-(6-amino-5-(1-(5-chloro-2-methylphenyl)-1H-tetrazol-5-yl)pyridin-3-yl)phenyl)acetamide (compound I-A-576), 5-(4-((dimethylamino)methyl)phenyl)-3-(1-(3-fluoro-2-methylphenyl)-1H-tetrazol-5-yl)pyridin-2-amine (compound I-A-577), 3-(1-(3-chloro-2-methylphenyl)-1H-tetrazol-5-yl)-5-(4-((dimethylamino)methyl)phenyl)pyridin-2-amine (compound I-A-578), 3-(1-(5-chloro-2-methylphenyl)-1H-tetrazol-5-yl)-5-(4-((dimethylamino)methyl)phenyl)pyridin-2-amine (compound I-A-579), 5-(4-((dimethylamino)methyl)phenyl)-3-(1-(2,5-difluorophenyl)-1H-tetrazol-5-yl)pyridin-2-amine (compound I-A-580), N-(4-(6-amino-5-(1-(2,5-difluorophenyl)-1H-tetrazol-5-yl)pyridin-3-yl)phenyl)acetamide (compound I-A-581), N-(4-(6-amino-5-(1-(5-chloro-2-fluorophenyl)-1H-tetrazol-5-yl)pyridin-3-yl)phenyl)acetamide (compound I-A-582), N-(4-(6-amino-5-(1-(2-chloro-3,5-difluorophenyl)-1H-tetrazol-5-yl)pyridin-3-yl)phenyl)acetamide (compound I-A-583), N-(4-(6-amino-5-(1-(3-chloro-2-fluorophenyl)-1H-tetrazol-5-yl)pyridin-3-yl)phenyl)acetamide (compound I-A-584), N-(4-(6-amino-5-(1-(5-fluoro-2-methoxyphenyl)-1H-tetrazol-5-yl)pyridin-3-yl)phenyl)acetamide (compound I-A-585), N-(4-(6-amino-5-(1-(3,5-difluorophenyl)-1H-tetrazol-5-yl)pyridin-3-yl)phenyl)acetamide (compound I-A-586), N-(4-(6-amino-5-(1-(3,5-dichlorophenyl)-1H-tetrazol-5-yl)pyridin-3-yl)phenyl)acetamide (compound I-A-587), N-(4-(6-amino-5-(1-(3-fluoro-2-methoxyphenyl)-1H-tetrazol-5-yl)pyridin-3-yl)phenyl)acetamide (compound I-A-588), 5-(4-((dimethylamino)methyl)phenyl)-3-(1-(3-fluoro-2-methoxyphenyl)-1H-tetrazol-5-yl)pyridin-2-amine (compound I-A-589), 3-(1-(3,5-dichlorophenyl)-1H-tetrazol-5-yl)-5-(4-((dimethylamino)methyl)phenyl)pyridin-2-amine (compound I-A-590), 5-(4-((dimethylamino)methyl)phenyl)-3-(1-(3,5-difluorophenyl)-1H-tetrazol-5-yl)pyridin-2-amine (compound I-A-591), 3-(1-(2-chloro-5-fluorophenyl)-1H-tetrazol-5-yl)-5-(4-((dimethylamino)methyl)phenyl)pyridin-2-amine (compound I-A-592), 3-(1-(5-chloro-2-fluorophenyl)-1H-tetrazol-5-yl)-5-(4-((dimethylamino)methyl)phenyl)pyridin-2-amine (compound I-A-593), 3-(1-(2,5-difluorophenyl)-1H-tetrazol-5-yl)-5-(4-((pyrrolidin-1-yl)methyl)phenyl)pyridin-2-amine (compound I-A-594), 3-(1-(5-chloro-2-fluorophenyl)-1H-tetrazol-5-yl)-5-(4-((pyrrolidin-1-yl)methyl)phenyl)pyridin-2-amine (compound I-A-595), 3-(1-(2-chloro-5-fluorophenyl)-1H-tetrazol-5-yl)-5-(4-((pyrrolidin-1-yl)methyl)phenyl)pyridin-2-amine (compound I-A-596), 3-(1-(3,5-dichlorophenyl)-1H-tetrazol-5-yl)-5-(4-((pyrrolidin-1-yl)methyl)phenyl)pyridin-2-amine (compound I-A-597), 3-(1-(3-fluoro-2-methylphenyl)-1H-tetrazol-5-yl)-5-(4-((pyrrolidin-1-yl)methyl)phenyl)pyridin-2-amine (compound I-A-598), 3-(1-(3-chloro-2-methylphenyl)-1H-tetrazol-5-yl)-5-(4-((pyrrolidin-1-yl)methyl)phenyl)pyridin-2-amine (compound I-A-599), 3-(1-(5-chloro-2-methylphenyl)-1H-tetrazol-5-yl)-5-(4-((pyrrolidin-1-yl)methyl)phenyl)pyridin-2-amine (compound I-A-600), 3-(1-(2-chloro-3,5-difluorophenyl)-1H-tetrazol-5-yl)-5-(4-((pyrrolidin-1- yl)methyl)phenyl)pyridin-2-amine (compound I-A-601), 3-(1-(5-fluoro-2-methoxyphenyl)-1H-tetrazol-5-yl)-5-(4-((pyrrolidin-1-yl)methyl)phenyl)pyridin-2-amine (compound I-A-602), 3-(1-(3,5-difluorophenyl)-1H-tetrazol-5-yl)-5-(4-((pyrrolidin-1-yl)methyl) phenyl)pyridin-2-amine (compound I-A-603), 3-(1-(3-fluoro-2-methoxyphenyl)-1H-tetrazol-5-yl)-5-(4-((pyrrolidin-1-yl)methyl)phenyl)pyridin-2-amine (compound I-A-604), 3-(1-(2-chloro-3,5-difluorophenyl)-1H-tetrazol-5-yl)-5-(4-((dimethylamino)methyl) phenyl)pyridin-2-amine (compound I-A-605), 5-(4-((dimethylamino)methyl)phenyl)-3-(1-(5-fluoro-2-methoxyphenyl)-1H-tetrazol-5-yl)pyridin-2-amine (compound I-A-606), N-(4-(6-amino-5-(1-(2,6-difluorophenyl)-1H-tetrazol-5-yl)pyridin-3-yl)phenyl)acetamide (compound I-A-607), 3-(1-(2,6-difluorophenyl)-1H-tetrazol-5-yl)-5-(pyridin-3-yl)pyridin-2-amine (compound I-A-608), 3-(1-(2,6-dichlorophenyl)-1H-tetrazol-5-yl)-5-(pyridin-3-yl)pyridin-2-amine (compound I-A-609), N-(3-(6-amino-5-(1-(2,6-difluorophenyl)-1H-tetrazol-5-yl)pyridin-3-yl)phenyl)acetamide (compound I-A-610), N-(3-(6-amino-5-(1-(2,6-dichlorophenyl)-1H-tetrazol-5-yl)pyridin-3-yl)phenyl)acetamide (compound I-A-611), N-(3-(6-amino-5-(1-(2-chloro-6-fluorophenyl)-1H-tetrazol-5-yl)pyridin-3-yl) phenyl)acetamide (compound I-A-612), N-(3-(6-amino-5-(1-(2-chloro-3,6-difluorophenyl)-1H-tetrazol-5-yl)pyridin-3-yl)phenyl)acetamide (compound I-A-613), N-(4-(6-amino-5-(1-(2-chloro-3,6-difluorophenyl)-1H-tetrazol-5-yl)pyridin-3-yl)phenyl) acetamide (compound I-A-614), 3-(1-(2,6-difluorophenyl)-1H-tetrazol-5-yl)-5-(4-((pyrrolidin-1-yl)methyl)phenyl)pyridin-2-amine (compound I-A-615), 3-(1-(2-chloro-6-fluorophenyl)-1H-tetrazol-5-yl)-5-(4-((pyrrolidin-1-yl)methyl)phenyl)pyridin-2-amine (compound I-A-616), 3-(1-(2-chloro-6-fluorophenyl)-1H-tetrazol-5-yl)-5-(pyridin-3-yl) pyridin-2-amine (compound I-A-617), 3-(1-(2-chloro-3,6-difluorophenyl)-1H-tetrazol-5-yl)-5-(pyridin-3-yl) pyridin-2-amine (compound I-A-618), 5-(4-((dimethylamino)methyl)phenyl)-3-(1-(2,6-difluorophenyl)-1H-tetrazol-5-yl)pyridin-2-amine (compound I-A-619), 3-(1-(2-chloro-3,6-difluorophenyl)-1H-tetrazol-5-yl)-5-(4-((pyrrolidin-1-yl)methyl) phenyl)pyridin-2-amine (compound I-A-620), N-(4-(6-amino-5-(1-(2,6-dichlorophenyl)-1H-tetrazol-5-yl) pyridin-3-yl)phenyl)acetamide (compound I-A-621), 3-(1-(2,6-dichlorophenyl)-1H-tetrazol-5-yl)-5-(4-((pyrrolidin-1-yl)methyl)phenyl)pyridin-2-amine (compound I-A-622), 3-(1-(2-chloro-6-fluorophenyl)-1H-tetrazol-5-yl)-5-(4-((dimethylamino)methyl)phenyl)pyridin-2-amine (compound I-A-623), 3-(1-(3-chloro-2-methylphenyl)-1H-tetrazol-5-yl)-5-(1-(piperidin-4-yl)-1H-pyrazol-4-yl)pyridin-2-amine (compound I-A-624), 3-(1-(2,5-difluorophenyl)-1H-tetrazol-5-yl)-5-(1-(piperidin-4-yl)-1H-pyrazol-4-yl) pyridin-2-amine (compound I-A-625), 3-(1-(3-chloro-2-fluorophenyl)-1H-tetrazol-5-yl)-5-(1-(piperidin-4-yl)-1H-pyrazol-4-yl)pyridin-2-amine (compound I-A-626), 3-(1-(3,5-difluorophenyl)-1H-tetrazol-5-yl)-5-(1-(piperidin-4-yl)-1H-pyrazol-4-yl)pyridin-2-amine (compound I-A-627), 3-(1-(2,6-difluorophenyl)-1H-tetrazol-5-yl)-5-(1-(piperidin-4-yl)-1H-pyrazol-4-yl) pyridin-2-amine (compound I-A-628), 3-(1-(2,6-dichlorophenyl)-1H-tetrazol-5-yl)-5-(4-((dimethylamino)methyl)phenyl)pyridin-2-amine (compound I-A-629), 3-(1-(2-chloro-3,6-difluorophenyl)-1H-tetrazol-5-yl)-5-(4-((dimethylamino)methyl) phenyl)pyridin-2-amine (compound I-A-630), 3-(1-(2,6-dichlorophenyl)-1H-tetrazol-5-yl)-5-(1-(piperidin-4-yl)-1H-pyrazol-4-yl)pyridin-2-amine (compound I-A-631), 3-(1-(5-chloro-2-methylphenyl)-1H-tetrazol-5-yl)-5-(1-(piperidin-4-yl)-1H-pyrazol-4-yl)pyridin-2-amine (compound I-A-632), 3-(1-(5-fluoro-2-methoxyphenyl)-1H-tetrazol-5-yl)-5-(1-(piperidin-4-yl)-1H-pyrazol-4-yl)pyridin-2-amine (compound I-A-633), 3-(1-(2-chloro-3,5-difluorophenyl)-1H-tetrazol-5-yl)-5-(1-(piperidin-4-yl)-1H-pyrazol-4-yl)pyridin-2-amine (compound I-A-634), 3-(1-(5-chloro-2-fluorophenyl)-1H-tetrazol-5-yl)-5-(1-(piperidin-4-yl)-1H-pyrazol-4-yl)pyridin-2-amine (compound I-A-635), 3-(1-(2,5-dichlorophenyl)-1H-tetrazol-5-yl)-5-(1-(piperidin-4-yl)-1H-pyrazol-4-yl)pyridin-2-amine (compound I-A-636), 3-(1-(2-chloro-5-fluorophenyl)-1H-tetrazol-5-yl)-5-(1-(piperidin-4-yl)-1H-pyrazol-4-yl) pyridin-2-amine (compound I-A-637), 3-(1-(3-fluoro-2-methoxyphenyl)-1H-tetrazol-5-yl)-5-(1-(piperidin-4-yl)-1H-pyrazol-4-yl)pyridin-2-amine (compound I-A-638), N-(4-(6-amino-5-(1-(2-chloro-6-fluorophenyl)-1H-tetrazol-5-yl)pyridin-3-yl)phenyl)acetamide (compound I-A-639), 3-(1-(2-chloro-3,6-difluorophenyl)-1H-tetrazol-5-yl)-5-(1-(piperidin-4-yl)-1H-pyrazol-4-yl)pyridin-2-amine (compound I-A-640), (4-(6-amino-5-(1-(2,3-difluorophenyl)-1H-tetrazol-5-yl) pyridin-3-yl)-5,6-dihydropyridin-1(2H)-yl)((S)-1-acetylpyrrolidin-2-yl)methanone (compound I-A-641), (4-(6-amino-5-(1-(2,3-difluorophenyl)-1H-tetrazol-5-yl)pyridin-3-yl)-5,6-dihydropyridin-1(2H)-yl)((S)-5-oxo-pyrrolidin-2-yl)methanone (compound I-A-642), 3-(1-(2,3-difluorophenyl)-1H-tetrazol-5-yl)-5-(1,2,3,6-tetrahydro-1-((tetrahydrofuran-3-yl)methyl)pyridin-4-yl)pyridin-2-amine (compound I-A-643), 3-(1-(2,3-difluorophenyl)-1H-tetrazol-5-yl)-5-(1,2,3,6-tetrahydro-1-((pyridin-3-yl)methyl)pyridin-4-yl)pyridin-2-amine (compound I-A-644), (E)-tert-butyl 4-(6-amino-5-(1-(2,3-difluorophenyl)-1H-tetrazol-5-yl)pyridin-3-yl)-2,3,6,7-tetrahydroazepine-1-carboxylate (compound I-A-645), 3-(1-(2,3-difluorophenyl)-1H-tetrazol-5-yl)-5-((E)-2,3,6,7-tetrahydro-1H-azepin-4-yl)pyridin-2-amine (compound I-A-646), 1-((E)-4-(6-amino-5-(1-(2,3-difluorophenyl)-1H-tetrazol-5-yl)pyridin-3-yl)-2,3,6,7-tetrahydroazepin-1-yl)-2,2,2-trifluoroethanone (compound I-A-647), (4-(6-amino-5-(1-(2,3-difluorophenyl)-1H-tetrazol-5-yl)pyridin-3-yl)-5,6-dihydropyridin-1(2H)-yl)((R)-pyrrolidin-2-yl)methanone (compound I-A-648), (4-(6-amino-5-(1-(2,3-difluorophenyl)-1H-tetrazol-5-yl)pyridin-3-yl)-5,6-dihydropyridin-1(2H)-yl)((R)-1-acetyl-pyrrolidin-2-yl)methanone (compound I-A-649), 5-(1-(azetidin-3-yl)-1H-pyrazol-4-yl)-3-(1-(3-chloro-2-fluorophenyl)-1H-tetrazol-5-yl)pyridin-2-amine (compound I-A-650), 5-(1-(azepan-4-yl)-1H-pyrazol-4-yl)-3-(1-(3-chloro-2-fluorophenyl)-1H-tetrazol-5-yl)pyridin-2-amine (compound I-A-651), 3-(1-(3-chloro-2-fluorophenyl)-1H-tetrazol-5-yl)-5-(1-(piperidin-4-yl)-1H-pyrazol-4-yl) pyridin-2-amine (compound I-A-652), (4-(6-amino-5-(1-(2,3-difluorophenyl)-1H-tetrazol-5-yl)pyridin-3-yl)-5,6-dihydropyridin-1(2H)-yl)((R)-5-oxo-pyrrolidin-2-yl)methanone (compound I-A-657), 3-(1-(2,3-difluorophenyl)-1H-tetrazol-5-yl)-5-(5,6,7,8-tetrahydro-4-methyl-4H-thieno[3,2-d]azepin-2-yl) pyridin-2-amine (compound I-A-661), 3-(1-(3-chloro-2-fluorophenyl)-1H-tetrazol-5-yl)-5-(5,6,7,8-tetrahydro-4-methyl-4H-thieno[3,2-d] azepin-2-yl)

pyridin-2-amine (compound I-A-662), 3-(1-(2,3-dichlorophenyl)-1H-tetrazol-5-yl)-5-(5-(piperidin-4-yl)thiophen-3-yl)pyridin-2-amine (compound I-A-663), 3-(1-(3-chloro-2-fluorophenyl)-1H-tetrazol-5-yl)-5-(5-(piperidin-4-yl)thiophen-3-yl)pyridin-2-amine (compound I-A-664), 3-(1-(2,3-difluorophenyl)-1H-tetrazol-5-yl)-5-((3aR,6aS)-1,2,3,3a,4,6a-hexahydro-cyclopenta[c]pyrrol-5-yl)pyridin-2-amine (compound I-A-665), 5-(1-(2,2-difluoroethyl)-1H-1,2,3-triazol-4-yl)-3-(1-(2,3-difluorophenyl)-1H-tetrazol-5-yl)pyridin-2-amine (compound I-A-666), 3-(1-(2,3-difluorophenyl)-1H-tetrazol-5-yl)-5-(1-pentyl-1H-1,2,3-triazol-4-yl)pyridin-2-amine (compound I-A-667), 3-(1-(2,3-difluorophenyl)-1H-tetrazol-5-yl)-5-(1-((S)-1-methoxypropan-2-yl)-1H-1,2,3-triazol-4-yl)pyridin-2-amine (compound I-A-668), 5-(1-(2,2,2-trifluoroethyl)-1H-1,2,3-triazol-4-yl)-3-(1-(2,3-difluorophenyl)-1H-tetrazol-5-yl)pyridin-2-amine (compound I-A-669), 3-(1-(2,3-difluorophenyl)-1H-tetrazol-5-yl)-5-(1-(((S)-tetrahydrofuran-2-yl)methyl)-1H-1,2,3-triazol-4-yl)pyridin-2-amine (compound I-A-670), 5-(1-(2-ethylbutyl)-1H-1,2,3-triazol-4-yl)-3-(1-(2,3-difluorophenyl)-1H-tetrazol-5-yl)pyridin-2-amine (compound I-A-671), 3-(1-(2,3-difluorophenyl)-1H-tetrazol-5-yl)-5-(1-(3,3-dimethylbutyl)-1H-1,2,3-triazol-4-yl)pyridin-2-amine (compound I-A-672), 5-(1-(3-(dimethylamino)propyl)-1H-1,2,3-triazol-4-yl)-3-(1-(2,3-difluorophenyl)-1H-tetrazol-5-yl)pyridin-2-amine (compound I-A-673), 3-(1-(2,3-difluorophenyl)-1H-tetrazol-5-yl)-5-(1-(2-isopropoxyethyl)-1H-1,2,3-triazol-4-yl)pyridin-2-amine (compound I-A-674), 5-(1-(cyclohexylmethyl)-1H-1,2,3-triazol-4-yl)-3-(1-(2,3-difluorophenyl)-1H-tetrazol-5-yl)pyridin-2-amine (compound I-A-675), 3-(1-(2,3-difluorophenyl)-1H-tetrazol-5-yl)-5-(1-((tetrahydro-2H-pyran-4-yl)methyl)-1H-1,2,3-triazol-4-yl)pyridin-2-amine (compound I-A-676), 3-(1-(2,3-difluorophenyl)-1H-tetrazol-5-yl)-5-(1-(2-propylpentyl)-1H-1,2,3-triazol-4-yl)pyridin-2-amine (compound I-A-677), 3-(1-(2,3-difluorophenyl)-1H-tetrazol-5-yl)-5-(1-(2-(1-methylpyrrolidin-2-yl)ethyl)-1H-1,2,3-triazol-4-yl)pyridin-2-amine (compound I-A-678), 3-(1-(2,3-difluorophenyl)-1H-tetrazol-5-yl)-5-(1-(3-(pyrrolidin-1-yl)propyl)-1H-1,2,3-triazol-4-yl)pyridin-2-amine (compound I-A-679), 5-(1-(((R)-1-ethylpyrrolidin-2-yl)methyl)-1H-1,2,3-triazol-4-yl)-3-(1-(2,3-difluorophenyl)-1H-tetrazol-5-yl)pyridin-2-amine (compound I-A-680), 3-(1-(2,3-difluorophenyl)-1H-tetrazol-5-yl)-5-(1-(2-(piperidin-1-yl)ethyl)-1H-1,2,3-triazol-4-yl)pyridin-2-amine (compound I-A-681), 3-(1-(2,3-difluorophenyl)-1H-tetrazol-5-yl)-5-(1-(2-morpholinoethyl)-1H-1,2,3-triazol-4-yl)pyridin-2-amine (compound I-A-682), 3-(1-(2,3-difluorophenyl)-1H-tetrazol-5-yl)-5-(1-(S,S-dioxo-tetrahydrothiophen-3-yl)-1H-1,2,3-triazol-4-yl)pyridin-2-amine (compound I-A-683), 5-(1-(2-(ethylthio)ethyl)-1H-1,2,3-triazol-4-yl)-3-(1-(2,3-difluorophenyl)-1H-tetrazol-5-yl)pyridin-2-amine (compound I-A-684), 1-(3-(4-(6-amino-5-(1-(2,3-difluorophenyl)-1H-tetrazol-5-yl)pyridin-3-yl)-1H-1,2,3-triazol-1-yl)propyl)pyrrolidin-2-one (compound I-A-685), 3-(1-(2,3-difluorophenyl)-1H-tetrazol-5-yl)-5-(1-(3-(piperidin-1-yl)propyl)-1H-1,2,3-triazol-4-yl)pyridin-2-amine (compound I-A-686), 3-(1-(2,3-difluorophenyl)-1H-tetrazol-5-yl)-5-(1-(3-morpholinopropyl)-1H-1,2,3-triazol-4-yl)pyridin-2-amine (compound I-A-687), 3-(1-(2,3-difluorophenyl)-1H-tetrazol-5-yl)-5-(1-(quinuclidin-3-yl)-1H-1,2,3-triazol-4-yl)pyridin-2-amine (compound I-A-688), 3-(1-(2,3-difluorophenyl)-1H-tetrazol-5-yl)-5-(1-(tetrahydro-2H-thiopyran-4-yl)-1H-1,2,3-triazol-4-yl)pyridin-2-amine (compound I-A-689), 3-(1-(2,3-difluorophenyl)-1H-tetrazol-5-yl)-5-(1-(3-(4-methylpiperazin-1-yl)propyl)-1H-1,2,3-triazol-4-yl)pyridin-2-amine (compound I-A-690), 5-(1-(4-(trifluoromethyl)cyclohexyl)-1H-1,2,3-triazol-4-yl)-3-(1-(2,3-difluorophenyl)-1H-tetrazol-5-yl)pyridin-2-amine (compound I-A-691), 3-(1-(2,3-difluorophenyl)-1H-tetrazol-5-yl)-5-(1-(6-azaspiro[2.5]octan-4-yl)-1H-1,2,3-triazol-4-yl)pyridin-2-amine (compound I-A-692), (S)-3-(4-(6-amino-5-(1-(2,3-difluorophenyl)-1H-tetrazol-5-yl)pyridin-3-yl)-1H-1,2,3-triazol-1-yl)azepan-2-one (compound I-A-693), 3-(1-(2,3-difluorophenyl)-1H-tetrazol-5-yl)-5-(1-(2,2,6,6-tetramethylpiperidin-4-yl)-1H-1,2,3-triazol-4-yl)pyridin-2-amine (compound I-A-694), 3-(1-(2,3-difluorophenyl)-1H-tetrazol-5-yl)-5-(1-(((R)-tetrahydrofuran-2-yl)methyl)-1H-1,2,3-triazol-4-yl)pyridin-2-amine (compound I-A-695), ((E)-5-(6-amino-5-(1-(2,3-difluorophenyl)-1H-tetrazol-5-yl)pyridin-3-yl)-3,4-dihydro-2H-azepin-1(7H)-yl)(tetrahydro-2H-pyran-3-yl)methanone (compound I-A-696), ((E)-5-(6-amino-5-(1-(2,3-difluorophenyl)-1H-tetrazol-5-yl)pyridin-3-yl)-3,4-dihydro-2H-azepin-1(7H)-yl)(piperidin-3-yl)methanone (compound I-A-697), 1-((E)-5-(6-amino- 5-(1-(2,3-difluorophenyl)-1H-tetrazol-5-yl)pyridin-3-yl)-3,4-dihydro-2H-azepin-1(7H)-yl)-2-((S)-pyrrolidin-2-yl)ethanone (compound I-A-698), ((E)-5-(6-amino-5-(1-(2,3-difluorophenyl)-1H-tetrazol-5-yl)pyridin-3-yl)-3,4-dihydro-2H-azepin-1(7H)-yl)((S)-pyrrolidin-2-yl)methanone (compound I-A-699), ((E)- 5-(6-amino-5-(1-(2,3-difluorophenyl)-1H-tetrazol-5-yl)pyridin-3-yl)-3,4-dihydro-2H-azepin-1(7H)-yl)(tetrahydrofuran-3-yl)methanone (compound I-A-700), 1-((E)-5-(6-amino-5-(1-(2,3-difluorophenyl)-1H-tetrazol-5-yl)pyridin-3-yl)-3,4-dihydro-2H-azepin-1(7H)-yl)ethanone (compound I-A-701), 3-(6-amino-5-(1-(2,3-difluorophenyl)-1H-tetrazol-5-yl)pyridin-3-yl)-8-carbo-tert-butoxy-8-aza-bicyclo[3.2.1]oct-2-ene (compound I-A-702), 3-(6-amino-5-(1-(2,3-difluorophenyl)-1H-tetrazol-5-yl)pyridin-3-yl)-8-carbo-tert-butoxy-8-aza-bicyclo[3.2.1]oct-2-ene (compound I-A-703), (3aS,6aR)-tert-butyl 5-(6-amino-5-(1-(2,3-difluorophenyl)-1H-tetrazol-5-yl)pyridin-3-yl)-hexahydrocyclopenta[c]pyrrole-2(1H)-carboxylate (compound I-A-704), 3-(1-(2,3-difluorophenyl)-1H-tetrazol-5-yl)-5-((3aR,6aS)-octahydrocyclopenta[c]pyrrol-5-yl)pyridin-2-amine (compound I-A-705), or (3aS,6aR)-tert-butyl 5-(6-amino-5-(1-(2,3-difluorophenyl)-1H-tetrazol-5-yl)pyridin-3-yl)-3,3a,6,6a-tetrahydrocyclopenta[c]pyrrole-2(1H)-carboxylate (compound I-A-706).

* * * * *